(12) United States Patent
Sidhu et al.

(10) Patent No.: US 8,957,187 B2
(45) Date of Patent: Feb. 17, 2015

(54) BINDING POLYPEPTIDES AND USES THEREOF

(75) Inventors: Sachdev S. Sidhu, San Francisco, CA (US); Sara C. Birtalan, Menlo Park, CA (US); Frederic A. Fellouse, Toronto (CA)

(73) Assignee: Genentech, Inc., South San Francisco, CA (US)

( * ) Notice: Subject to any disclaimer, the term of this patent is extended or adjusted under 35 U.S.C. 154(b) by 1422 days.

(21) Appl. No.: 11/566,120

(22) Filed: Dec. 1, 2006

(65) Prior Publication Data

US 2007/0202552 A1 Aug. 30, 2007

Related U.S. Application Data

(60) Provisional application No. 60/805,553, filed on Jun. 22, 2006, provisional application No. 60/742,185, filed on Dec. 2, 2005.

(51) Int. Cl.
| | | |
|---|---|---|
| C07K 16/00 | (2006.01) | |
| C07K 16/32 | (2006.01) | |
| C07K 16/28 | (2006.01) | |
| G01N 33/574 | (2006.01) | |
| G01N 33/68 | (2006.01) | |

(52) U.S. Cl.
CPC ............... *C07K 16/32* (2013.01); *C07K 16/005* (2013.01); *C07K 16/2878* (2013.01); *G01N 33/574* (2013.01); *G01N 33/6857* (2013.01); *C07K 2317/24* (2013.01); *C07K 2317/55* (2013.01); *C07K 2317/565* (2013.01); *C07K 2317/92* (2013.01); *G01N 2333/70539* (2013.01); *G01N 2333/71* (2013.01)
USPC .................................. 530/387.3; 530/388.25

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |
| 4,670,393 A | 6/1987 | Seeburg |
| 4,755,465 A | 7/1988 | Gray et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 4,970,198 A | 11/1990 | Lee et al. |
| 4,975,278 A | 12/1990 | Senter et al. |
| 5,053,394 A | 10/1991 | Ellestad et al. |
| 5,079,233 A | 1/1992 | Lee |
| 5,122,469 A | 6/1992 | Mather et al. |
| 5,208,020 A | 5/1993 | Chari et al. |
| 5,264,365 A | 11/1993 | Georgiou et al. |
| 5,362,852 A | 11/1994 | Geoghegan |
| 5,416,064 A | 5/1995 | Chari et al. |
| 5,427,908 A | 6/1995 | Dower et al. |
| 5,432,018 A | 7/1995 | Dower et al. |
| 5,498,530 A | 3/1996 | Schatz et al. |
| 5,500,362 A | 3/1996 | Robinson et al. |
| 5,508,192 A | 4/1996 | Georgiou et al. |
| 5,534,615 A | 7/1996 | Baker et al. |
| 5,580,717 A | 12/1996 | Dower et al. |
| 5,585,089 A | 12/1996 | Queen et al. |

(Continued)

FOREIGN PATENT DOCUMENTS

| | | |
|---|---|---|
| EP | 0 128 733 A1 | 12/1984 |
| EP | 0 230 869 A2 | 8/1987 |

(Continued)

OTHER PUBLICATIONS

Rudikoff et al (Proc Natl Acad Sci USA 1982 vol. 79 p. 1979).*

(Continued)

*Primary Examiner* — Sheela J Huff
(74) *Attorney, Agent, or Firm* — Gates & Cooper LLP

(57) ABSTRACT

The invention provides antibodies or antigen binding fragments thereof to DR5 and HER-2. The antibodies and/or antigen binding fragments thereof comprise variant CDRs comprising highly restricted amino acid sequence diversity. The invention also provides these polypeptides as fusion polypeptides to heterologous polypeptides such as at least a portion of phage or viral coat proteins, tags and linkers. In addition, compositions and methods of use for treatment of cancer and immune related conditions are provided.

18 Claims, 48 Drawing Sheets

(56) References Cited

U.S. PATENT DOCUMENTS

| | | | |
|---|---|---|---|
| 5,606,040 A | 2/1997 | McGahren et al. |
| 5,624,821 A | 4/1997 | Winter et al. |
| 5,639,635 A | 6/1997 | Joly et al. |
| 5,648,237 A | 7/1997 | Carter |
| 5,648,260 A | 7/1997 | Winter et al. |
| 5,658,727 A | 8/1997 | Barbas et al. |
| 5,667,780 A | 9/1997 | Ho et al. |
| 5,693,762 A | 12/1997 | Queen et al. |
| 5,712,374 A | 1/1998 | Kuntsmann et al. |
| 5,714,586 A | 2/1998 | Kunstmann et al. |
| 5,723,286 A | 3/1998 | Dower et al. |
| 5,731,168 A | 3/1998 | Carter et al. |
| 5,733,743 A | 3/1998 | Johnson et al. |
| 5,739,116 A | 4/1998 | Hamann et al. |
| 5,739,277 A | 4/1998 | Presta et al. |
| 5,750,373 A | 5/1998 | Garrard et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,821,337 A | 10/1998 | Carter et al. |
| 5,837,242 A | 11/1998 | Holliger et al. |
| 5,840,523 A | 11/1998 | Simmons et al. |
| 5,877,296 A | 3/1999 | Hamann et al. |
| 5,969,108 A | 10/1999 | McCafferty et al. |
| 6,027,888 A | 2/2000 | Georgiou et al. |
| 6,054,297 A | 4/2000 | Carter et al. |
| 6,083,715 A | 7/2000 | Georgiou et al. |
| 6,172,197 B1 | 1/2001 | McCafferty et al. |
| 6,387,371 B1 | 5/2002 | Hudziak et al. |
| 2002/0081300 A1 | 6/2002 | McMichael |
| 2005/0119455 A1 | 6/2005 | Fuh et al. |

FOREIGN PATENT DOCUMENTS

| | | |
|---|---|---|
| EP | 0 266 032 A1 | 5/1988 |
| EP | 0 288 451 A2 | 10/1988 |
| EP | 0 404 097 A2 | 12/1990 |
| EP | 0 425 235 A2 | 5/1991 |
| EP | 0 368 684 B1 | 3/1994 |
| EP | 1 391 213 | 2/2004 |
| WO | WO 87/00195 | 1/1987 |
| WO | WO 90/03430 | 4/1990 |
| WO | WO 90/04788 | 5/1990 |
| WO | WO 92/01047 | 1/1992 |
| WO | WO 92/09690 | 6/1992 |
| WO | WO 92/20791 | 11/1992 |
| WO | WO 93/06213 | 4/1993 |
| WO | WO 93/11161 | 6/1993 |
| WO | WO 93/11236 | 6/1993 |
| WO | WO 93/19172 | 9/1993 |
| WO | WO 93/21232 | 10/1993 |
| WO | WO 94/11026 | 5/1994 |
| WO | WO 94/29351 | 12/1994 |
| WO | WO 98/17797 | 4/1998 |
| WO | WO 98/35986 | 8/1998 |
| WO | WO 98/51793 | 11/1998 |
| WO | WO 99/51642 | 10/1999 |
| WO | WO 00/42072 | 7/2000 |
| WO | WO 01/19861 | 3/2001 |
| WO | WO 01/45746 | 6/2001 |
| WO | 02/061071 | 8/2002 |
| WO | WO 02/060919 | 8/2002 |
| WO | 2004/065416 | 8/2004 |
| WO | 2005/012359 | 2/2005 |
| WO | 2005/012531 | 2/2005 |
| WO | WO 2005/100399 | 10/2005 |
| WO | 2007/056441 | 5/2007 |

OTHER PUBLICATIONS

MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. Journal of Molecular Biology, (2002) 320, 415-428.*
Holm et al. Molecular Immunology, (2007) 44, 1075-1084.*
Chen et al. J. Mol. Bio. (1999) 293, 865-881.*
Wu et al. J. Mol. Biol. (1999) 294, 151-162.*
Buchsbaum et al. (Clinical Cancer Research, vol. 9, pp. 3731-3741, 2003).*
EP Office Action dated Dec. 7, 2010 (EP Application No. 06849911.0).
Spiridon, Camelia I. et al., "Targeting Multiple Her-2 epitopes with Monoclonal Antibodies Results in Improved Antigrowth Activity of a Human Breast Cancer Cell Line in Vitro and in Vivo", Clinical Cancer Research, The American Association for Cancer Research, US, vol. 8, No. 6, Jun. 1, 2002, pp. 1720-1730, XP002389218, ISSN: 1078-0432.
Culler, S. et al., "Cluster and information entropy patterns in immunoglobulin complementarity determining regions," BioSystems (2004) pp. 195-212, vol. 77.
Fellouse, F.A. et al., "High-throughput Generation of Synthetic Antibodies from Highly Functional Minimalist Phage-displayed Libraries," J. Mol. Biol. (2007), pp. 924-940, vol. 373, XP-002457179.
Fellouse, F.A. et al., "Molecular Recognition by a Binary Code," J. Mol. Biol. (2005), pp. 1153-1162, vol. 348.
Hoet, R.M. et al., "Generation of high-affinity human antibodies by combining donor-derived and synthetic complementarity-determining-region diversity," Nature Biotechnology, Mar. 2005, pp. 344-348, vol. 23, No. 3, XP-002421213.
Hoogenboom, H.R., "Selecting and screening recombinant antibody libraries," Nature Biotechnology, Sep. 2005, pp. 1105-1116, vol. 23, No. 9, XP-002348401.
Akanuma et al., "Combinatorial mutagenesis to restrict amino acid usage in an enzyme to a reduced set", Proc. Natl. Acad. Sci., 99(21):13549-13553 (2002).
Arie et al., "Chaperone function of FkpA, a heat shock prolyl isomerase, in the periplasm of Escherichi coli", Mol. Microbiol., 39:199-210 (2001).
Bachmann, "Derivations and Genotypes of Some Mutant Derivatives of Escherichia coli K-12", Cellular and Molecular Biology, (Washington, D.C.: American Society for Microbiology), vol. 2, pp. 1190-1219 (1987).
Baldwin et al., "Monoclonal Antibodies in Cancer Treatment", The Lancet, pp. 603-605 (1986).
Barbas et al., "Selection and evolution of high-affinity human antiviral antibodies", Trends Biotech., 14:230-234 (1996).
Barbas et al., "In vitro Evolution of a Neutralizing Human Antibody to Human Immunodeficiency Virus Type 1 to Enhance Affinity and Broaden Strain Cross-Reactivity", Proc Nat. Acad. Sci. USA, 91(9):3809-3813 (1994).
Barnes et al., "Methods for Growth of Cultured Cells in Serum-Free Medium", Anal. Biochem., 102:255-270 (1980).
Bass et al., "Hormone Phage: An Enrichment Method for Variant Proteins with Altered Binding Properties", Proteins, 8:309-314 (1990).
Bothmann et al., "The Periplasmic Escherichia coli Peptidylprolyl cis,trans-Isomerase FkpA", J. Biol. Chem., 275(22):17100-17105 (2000).
Brown et al., "Tolerance of Arc repressor to multiple-alanine substitutions", Proc. Natl. Acad. Sci. USA, 96:1983-1988 (1999).
Bullock et al., "XL1-Blue: A High Efficiency Plasmid Transforming recA Escherichia coli Strain With Beta-Galactosidase Selection", BioTechniques, 5(4):376-379 (1987).
Cannata et al., "Simplifying amino acids alphabets by means of a branch and bound algorithm and substitution matrices", Bioinformatics, 18(8):1102-1108 (2002).
Carlsson et al., "Protein Thiolation and Reversible Protein-Protein Conjugation", Biochem. J., 173:723-737 (1978).
Carter et al., "Humanization of an anti-p185$^{HER2}$ antibody for human cancer therapy", Proc. Natl. Acad. Sci. USA, 89:4285-4289 (1992).
Chan, "Folding Alphabets", Nat. Struct. Biol., 6(11):994-996 (1999).
Chang et al., "High-level secretion of human growth hormone by Escherichia coli", Gene, 55:189-196 (1987).

(56) References Cited

OTHER PUBLICATIONS

Chari et al., "Immunoconjugates Containing Novel Maytansinoids: Promising Anticancer Drugs", *Cancer Research*, 52:127-131 (1992).
Chen et al., "Chaperone Activity of DsbC", *J. Bio. Chem.*, 274(28):19601-19605 (1999).
Chen et al., "Selection and Analysis of an Optimized Anti-VEGF Antibody: Crystal Structure of an Affinity-matured Fab in Complex with Antigen", *J Mol. Biol.*, 293: 865-881 (1999).
Chothia et al., "Canonical Structures for the Hypervariable Regions of Immunoglobulins", *J. Mol. Biol.*, 196:901-917 (1987).
Clackson et al., "Making antibody fragments using phage display libraries", *Nature*, 352:624-628 (1991).
Clynes et al., "Fc receptors are required in passive and active immunity to melanoma", *Proc Nat. Acad. Sci. USA*, 95:652-656 (1998).
Connolly, "Analytical Molecular Surface Calculation", *J. Appl. Cryst.*, 16:548-558 (1983).
Crea et al., "Chemical synthesis of genes for human insulin", *Proc. Natl. Acad. Sci. USA*, 75(12):5765-5769 (1978).
Cunningham et al., "High-Resolution Epitope Mapping of hGH-Receptor Interactions by Alanine-Scanning Mutagensis", *Science*, 244:1081-1085 (1989).
Davidson et al., "Cooperatively folded proteins in random sequence libraries", *Nat. Struct. Biol.*, 2(10):856-863 (1995).
Davis et al., *Microbiology: Including Immunology and Molecular Genetics*, Third Edition, Harper & Row, New York, pp. 237, 245-247 and 374 (1980).
Deng et al., "Selection of Antibody Single-chain Variable Fragments with Improved Carbohydrate Binding by Phage Display", *J. Biol. Chem.*, 269:9533-9538 (1994).
Dennis et al., "Albumin Binding as a General Strategy for Improving the Pharmacokinetics of Proteins", *J. Biol. Chem.*, 277(38):35035-35043 (2002).
deWildt et al., "Antibody arrays for high-throughput screening of antibody-antigen interactions", *Nature Biotechnology*, 18:989-994 (2000).
Doronina et al., "Development of potent monoclonal antibody auristatin conjugates for cancer therapy", *Nature Biotechnology*, 21(7):778-784 (2003).
*Drugs of the Future*, 25(7):686 (2000).
Duncan et al., "The binding site for Clq on IgG", *Nature*, 332:738-740 (1988).
Eigenbrot et al., "X-ray Structures of the Antigen-binding Domains from Three Variants of Humanized anti-p185$^{HER2}$ Antibody 4D5 and Comparison with Molecular Modeling", *J. Mol. Biol.*, 229:969-995 (1993).
Engels et al., *Agnew. Chem. Int. Ed. Engl.*, 28:716-734 (1989).
Enshell-Seijffers et al., "The rational design of a 'type 88' genetically stable peptide display vector in the filamentous bacteriophage fd", *Nucleic Acids Research*, 29(10):e50 (2001).
Evan et al., "Isolation of Monoclonal Antibodies Specific for Human c-myc Proto-Oncogene Product", *Mol. Cell. Biol.*, 5(12):3610-3616 (1985).
Ferrara et al., "Clinical applications of angiogenic growth factors and their inhibitors", *Nature Medicine*, 5(12):1359-1364 (1999).
Field et al., "Purification of a RAS-Responsive Adenylyl Cyclase Complex from *Saccharomyces cerevisiae* by Use of an Epitope Addition Method", *Mol. Cell. Biol.*, 8(5):2159-2165 (1988).
Forsberg et al., "Identification of Framework Residues in a Secreted Recombinant Antibody Fragment that Control Production Level and Localization in *Escherichia coli*", *J. Biol. Chem.*, 272(19):12430-12436 (1997).
Fraker et al., *Biochem. Biophys. Res. Commun.*, 80(4):849-857 (1978).
Franklin et al., *Cancer Cell.*, 5(4):317-328 (2004).
Froehler et al., "Synthesis of DNA via deoxynucleoside H-phosphonate intermediates", *Nucl. Acids Res.*, 14(13):5399-5407 (1986).
Garrard et al., "Selection of an anti-IGF-I Fab from a Fab phage library created by mutagenesis of multiple CDR loops", *Gene*, 128:103-109 (1993).

Gazzano-Santoro et al., "A non-radioactive complement-dependent cytotoxicity assay for anti-CD20 monoclonal antibody", *J. Immunol. Methods*, 202:163-171 (1997).
Geoghegan et al., "Site-Directed Conjugation of Nonpeptide Groups to Peptides and Proteins via Periodate Oxidation of a 2-Amino Alcohol. Application to Modification at N-Terminal Serine", *Bioconjugate Chem.*, 3:138-146 (1992).
Ghetie et al., "Multiple Roles for the Major Histocompatibility Complex Class I-Related Receptor FcRn", *Ann. Rev. Immunol.*, 18:739-766 (2000).
Goeddel et al., "Direct expression in *Escherichia coli* of a DNA sequence coding for human growth hormone", *Nature*, 281:544-548 (1979).
Graham et al., "Characteristics of a Human Cell Line Transformed by DNA from Human Adenovirus Type 5", *J. Gen Virol.*, 36:59-72 (1977).
Gray et al., "*Pseudomonas aeruginosa* Secretes and Correctly Processes Human Growth Hormone", *Biotechnology*, 2:161-165 (1984).
Griffiths et al., "Isolation of high affinity human antibodies directly from large synthetic repertoires", *EMBO J.*, 13(14):3245-3260 (1994).
"Guidelines for the Management of Rheumatoid Arthritis", *Arthritis & Rheumatism*, 46(2):328-346 (2002).
Guss et al., "Structure of the IgG-binding regions of streptococcal protein G", *EMBO J.*, 5(7):1567-1575 (1986).
Ham et al., "Media and Growth Requirements", *Meth. Enz.*, 58:44-93 (1979).
Hara et al., *Microbial Drug Resistance*, 2:63-72 (1996).
Hawkins et al., "Selection of Phage Antibodies by Binding Affinity: Mimicking Affinity Maturation", *J. Mol. Biol.*, 226:889-896 (1992).
Heinz et al., "Folding and function of T4 lysozyme containing 10 consecutive alanines illustrate the redundancy of information in an amino acid sequence", *Proc. Natl. Acad. Sci. USA*, 89:3751-3755 (1992).
Hinman et al., "Preparation and Characterization of Monoclonal Antibody Conjugates of the Calicheamicins: A Novel and Potent Family of Antitumor Antibiotics", *Cancer Research*, 53:3336-3342 (1993).
Hinton et al., "Engineered Human IgG Antibodies with Longer Serum Half-lives in Primates", *J. Biol. Chem.*, 279(8):6213-6216 (2004).
Hollinger et al., "Diabodies: Small bivalent and bispecific antibody fragments", *Proc. Natl. Acad. Sci. USA*, 90:6444-6448 (1993).
Hoogenboom et al., "Antibody phage display technology and its applications", *Immunotechnology*, 4:1-20 (1998).
Hoogenboom et al., *J. Mol. Biol.*, 227:381-388 (1992).
Houck et al., "The Vascular Endothelial Growth Factor Family: Identification of a Fourth Molecular Species and Characterization of Alternative Splicing of RNA", *Mol. Endocrin.*, 5:1806-1814 (1991).
Hufton et al., "Phage display of cDNA repertoires: the pVI display system and its applications for the selection of immunogenic ligands", *J Immunol Methods*, 231(1-2):39-51 (1999).
Hymowitz et al., *Molecular Cell*, 4:564 (1999).
Jackson et al., "In Vitro Antibody Maturation: Improvement of a High Affinity, Neutralizing Antibody Against IL-1β", *J. Immunol.*, 154(7):3310-3319 (1995).
Jones et al., "Replacing the complementarity-determining regions in a human antibody with those from a mouse", *Nature*, 321:522-525 (1986).
Kamteker et al., "Protein Design by Binary Patterning of Polar and Nonpolar Amino Acids", *Science*, 262:1680-1685 (1993).
Klagsbrun et al., "Regulators of Angiogenesis", *Annu. Rev. Physiol.*, 53:217-239 (1991).
Knappik et al., "Fully Synthetic Human Combinatorial Antibody Libraries (HuCAL) Based on Modular Consensus Frameworks and CDRs Randomized with Trinucleotides", *J. Mol. Biol.*, 296:57-86 (2000).
Köhler et al., "Continuous cultures of fused cells secreting antibody of predefined specificity", *Nature* 256:495-497 (1975).
Kunkel et al., "Rapid and Efficient Site-Specific Mutagenesis without Phenotype Selection", *Methods Enzymol.*, 154:367-382 (1987).
Lee et al., "The Interpretation of Protein Structures: Estimation of Static Accessibility", *J. Mol. Biol.*, 55:379-400 (1971).

(56) References Cited

OTHER PUBLICATIONS

Lee et al., "Bivalent antibody phage display mimics natural immunoglobulin", *J. Immunol. Meth.*, 284:119-132 (2004).
Leung et al., "Vascular Endothelial Growth Factor is a Secreted Angiogenic Mitogen", *Science*, 246:1306-1309 (1989).
Lindmark et al., "Binding of Immunoglobulins to Protein A and Immunoglobulin Levels in Mammalian Sera", *J. Immunol. Meth.*, 62:1-13 (1983).
Liu et al., "Eradication of large colon tumor xenografts by targeted delivery of maytansinoids", *Proc. Natl. Acad. Sci. USA*, 93:8618-8623 (1996).
Lode et al., "Targeted Therapy with a Novel Enediyene Antibiotic Calicheamicin $\theta^1_1$ Effectively Suppresses Growth and Dissemination of Liver Metastases in a Syngeneic Model of Murine Neuroblastoma", *Cancer Research*, 58:2925-2928 (1998).
Lowman and Wells, "Monovalent Phage Display: A Method for Selecting Variant Proteins from Random Libraries", *Methods: A companion to Methods in Enzymology*, 3:205-216 (1991).
Mandler et al., "Modifications in Synthesis Strategy Imprve the Yield and Efficacy of Geldanamycin-Herceptin Immunoconjugates", *Bioconjugate Chem.*, 13:786-791 (2002).
Mandler et al., "Synthesis and Evaluation of Antiproliferative Activity of a Geldanamycin-Herceptin™ Immunoconjugate", *Bioorganic & Med. Chem. Letters*, 10:1025-1028 (2000).
Mandler et al., "Immunoconjugates of Geldanamycin and Anti-HER2 Monoclonal Antibodies: Antiproliferative Activity on Human Breast Carcinoma Cell Lines", *Jour. of the Nat. Cancer Inst.*, 92(19):1573-1581 (2000).
Marks et al., "By-passing Immunization Human Antibodies from V-gene Libraries Displayed on Phage", *J. Mol. Biol.*, 222:581-597 (1991).
Marks et al., "By-Passing Immunization: Building High Affinity Human Antibodies by Chain Shuffling", *Bio/Technology*, 10:779-783 (1992).
Marsters et al., *Current Biology*, 6:1669 (1996).
Mather et al., "Culture of Testicular Cells in Hormone-Supplemented Serum-Free Medium", *Annals N.Y. Acad. Sci.*, 383:44-68 (1982).
Mather, "Establishment and Characterization of Two Distinct Mouse Testicular Epithelial Cell Lines", *Biol. Reprod.*, 23:243-252 (1980).
Moore et al., *Endocrinology*, 122:2920-2926 (1988).
Morrison et al., "Chimeric human antibody molecules: Mouse antigen-binding domains with human constant region domains", *Proc. Natl. Acad. Sci. USA*, 81:6851-6855 (1984).
Murphy et al., "Simplified amino acid alphabets for protein fold recognition and implications for folding", *Prot. Eng.*, 13(3):149-152 (2000).
Nicolaou et al., "Calicheamicin $\theta^1_1$: A Rationally Designed Molecule with Extremely Potent and Selective DNA Cleaving Properties and Apoptosis Inducing Activity", *Agnew Chem Intl. Ed. Engl.*, 33:183-186 (1994).
Nicoletti et al., *J. Immunol. Methods*, 139:271-279 (1991).
Niculescu-Duvaz et al., "Antibody-directed enzyme prodrug therapy (ADEPT): a review", *Adv. Drg Del. Rev.*, 26:151-172 (1997).
Paborsky et al., "Mammalian cell transient expression of tissue factor for the production of antigen", *Protein Engineering*, 3(6):547-553 (1990).
Pacios, "ARVOMOL/CONTOUR: Molecular Surface Areas and Volumes on Personal Computers", *Comput. Chem.*, 18(4):377-385 (1994).
Pacios, "Variations of Surface Areas and Volumes in Distinct Molecular Surfaces of Biomolecules", *J. Mol. Model.*, 1:46-53 (1995).
Pereboev et al., "Phage Display of Adenovirus Type 5 Fiber Knob as a Tool for Specific Ligand Selection and Validation", *Journal of Virology*, 75(15):7107-7113 (2001).
Pluckthun, "Antibodies from *Escherichia coli*", *The Pharmacology of Monoclonal Antibodies*, Rosenburg and Moore eds. Springer-Verlag, New York, Ch. 11, vol. 113, pp. 269-315 (1994).
Presta, "Antibody Engineering", *Curr. Op. Struct. Biol.*, 2:593-596 (1992).
Presta et al., "Humanization of an Antibody Directed Against IgE", *J. Immunol.*, 151:2623-2632 (1993).
Presta et al., "Humanization of an Anti-Vascular Endothelial Growth Factor Monoclonal Antibody for the Therapy of Solid Tumors and Other Disorders", *Cancer Res.*, 57:4593-4599 (1997).
Proba et al., "Functional antibody single-chain fragments from the cytoplasm of *Escherichia coli*: influence of thioredoxin reductase (TrxB)", *Gene*, 159:203-207 (1995).
Ramm et al., "The Periplasmic *Escherichia coli* Peptidylprolyl *cis,trans*-Isomerase FkpA", *J. Biol. Chem.*, 275:17106-17113 (2000).
Ravetch et al., "Fc Receptors", *Annu. Rev. Immunol.*, 9:457-492 (1991).
Regan & Degrado, *Science*, 241:976-978 (1988).
Reyes et al., "Expression of human β-interferon cDNA under the control of a thymidine kinase promoter from herpes simplex virus", *Nature*, 297:598-601 (1982).
Riddle et al., "Functional rapidly folding proteins from simplified amino acid sequences", *Nat. Struct. Biol.*, 4(10):805-809 (1997).
Riechmann et al., "Reshaping human antibodies for therapy", *Nature*, 332:323-329 (1988).
Rondot et al., "A helper phage to improve single-chain antibody presentation in phage display", *Nat. Biotechnology*, 19:75-78 (2001).
Rowland et al., *Cancer Immunol. Immunother.*, 21:183-187 (1986).
Sato, "Molecular diagnosis of tumor angiogenesis and anti-angiogenic cancer therapy", *Int. J. Clin. Oncol.*, 8:200-206 (2003).
Schier et al., "Identification of functional and structural amino-acid residues by parsimonious mutagenesis", *Gene*, 169:147-155 (1996).
Shang et al., "Design of a "minimA1" homeodomain: The N-terminal arm modulates DNA binding affinity and stabilizes homeodomain structure", *Proc. Natl. Acad. Sci. USA*, 91:8373-8377 (1994).
Shields et al., "High Resolution Mapping of the Binding Site on Human IgG1 for FcγRI, FcγRII, FcγIII, and FcRn and Design of IgG1 Variants with Improved Binding to the FcγR", *J. Biol. Chem.*, 276(9):6591-6604 (2001).
Sidhu et al., "Phage Display for Selection of Novel binding Peptides", *Methods Enzymol.*, 328:333-363 (2000).
Siebenlist et al., "*E. coli* RNA Polymerase Interacts Homologously with Two Different Promoters", *Cell*, 20:269-281 (1980).
Simmons et al., "Expression of full-length immunoglobulins in *Escherichia coli*: rapid and efficient production of aglycosylated antibodies", *J. Immunol. Methods*, 263:133-147 (2002).
Sims et al., "A Humanized CD18 Antibody Can Block Function without Cell Destruction", *J. Immunol.* 151(4):2296-2308 (1993).
Skerra et al., "Assembly of a Functional Immunoglobulin $F_v$ Fragment in *Escherichia coli*", *Science*, 240:1038-1041 (1988).
Smith et al., "Filamentous Fusion Phage: Novel Expression Vectors That Display Cloned Antigens on the Virion Surface", *Science*, 228:1315-1317 (1985).
Stella et al., "Prodrugs: A Chemical Approach to Targeted Drug Delivery", *Directed Drug Delivery*, Borchardt et al., (ed.), pp. 247-267, Humana Press (1985).
Streit et al., "Angiogenesis, lymphangiogenesis, and melanoma metastasis", *Oncogene*, 22:3172-3179 (2003).
Syrigos et al., "Antibody Directed Enzyme Prodrug Therapy (ADEPT): A Review of the Experimental and Clinical Considerations", *Anticancer Research*, 19:605-614 (1999).
Tonini et al., "Molecular basis of angiogenesis and cancer", *Oncogene*, 22:6549-6556 (2003).
Ulrich et al., "Expression studies of catalytic antibodies", *Proc. Natl. Acad. Sci. USA*, 92:11907-11911 (1995).
Urlaub et al., "Isolation of Chinese hamster cell mutants deficient in dihydrofolate reductase activity", *Proc. Natl. Acad. Sci. USA*, 77:4216-4220 (1980).
Vaughan et al., "Human Antibodies with Sub-nanomolar Affinities Isolated from a Large Non-immunized Phage Display Library", *Nat. Biotech.*, 14:309-314 (1996).
Verhoeyen et al., "Reshaping Human Antibodies: Grafting an Antilysozyme Activity", *Science*, 239:1534-1536 (1988).
Vieira et al., "Production of Single-Stranded Plasmid DNA", *Meth. Enzymol.*, 153:3-11 (1987).
Vitetta et al., "Redesigning Nature's Poisons to Create Anti-Tumor Reagents", *Science*, 238:1098-1104 (1987).

(56) References Cited

OTHER PUBLICATIONS

Wang et al., "A computational approach to simplifying the protein folding alphabet", *Nat. Struct. Biol.*, 6(11):1033-1038 (1999).

Weiss et al., "Mutational analysis of the major coat protein of M13 identifies residues that control protein display", *Protein Science*, 9:647-654 (2000).

Wells et al., "Rapid evolution of peptide and protein binding properties in vitro", *Curr. Opin. Struct. Biol.*, 3:355-362 (1992).

Wilman, "Prodrugs in Cancer Chemotherapy", *Biochemical Society Transactions*, 14:375-382, 615th Meeting Belfast (1986).

Wiseman et al., "Ibritumomab tiuxetan radioimmunotherapy for patients with relapsed or refractory non-Hodgkin lymphoma and mild thrombocytopenia: a phase II multicenter trial", *Blood*, 99(12):4336-4342 (2002).

Wiseman et al., *Eur. Jour. Nucl. Med.*, 27(7):766-77 (2000).

Witzig et al., "Randomized Controlled Trial of Yttrium-90-Labeled Ibritumomab Tiuxetan Radioimmunotherapy Versus Rituximab Immunotherapy for Patients with Relapsed or Refractory Low-Grade, Follicular, or Transformed B-Cell Non-Hodgkin's Lymphoma", *J. Clin. Oncol.*, 20(10):2453-2463 (2002).

Witzig et al., "Treatment with Ibritumomab Tiuxetan Radioimmunotherapy in Patients with Rituximab-Refractory Follicular Non-Hodgkin's Lymphoma", *J. Clin. Oncol.*, 20(15):3262-3269 (2002).

Wong et al., "Expression of secreted insulin-like growth factor-1 in *Escherichia coli*", *Gene*, 68:193-203 (1988).

Xiong et al., "Periodicity of polar and nonpolar amino acids is the major determinant of secondary structure in self-assembling oligomeric peptides", *Proc. Natl. Acad. Sci. USA*, 92:6349-6353 (1995).

Yaniv, "Enhancing elements for activation of eukaryotic promoters", *Nature* 297:17-18 (1982).

Yansura et al., *METHODS: A Companion to Methods in Enzymol.* 4:151-158 (1992).

Yelton et al., "Affinity Maturation of the BR96 Anti-Carcinoma Antibody by Codon-Based Mutagenesis", *J. Immunol.*, 155:1994-2004 (1995).

Zapata et al., "Engineering linear F(ab')$_2$ fragments for efficient production in *Escherichia coli* and enhanced antiproliferative activity", *Protein Eng.*, 8(10):1057-1062 (1995).

Zoller et al., "Oligonucleotide-directed mutagenesis using M13-derived vectors: an efficient and general procedure for the production of point mutations in any fragment of DNA", *Nucleic Acids Res.*, 10(20):6487-6504 (1982).

\* cited by examiner

FIG. 1

Asp Ile Gln Met Thr Gln Ser Pro Ser Ser Leu Ser Ala Ser Val Gly Asp Arg Val Thr Ile Thr Cys
Arg Ala Ser Gln Asp Val Asn Thr Ala Val Ala Trp Tyr Gln Gln Lys Pro Gly Lys Ala Pro Lys
Leu Leu Ile Tyr Ser Ala Ser Ser Leu Tyr Ser Gly Val Pro Ser Arg Phe Ser Gly Ser Arg Ser Gly
Thr Asp Phe Thr Leu Thr Ile Ser Ser Leu Gln Pro Glu Asp Phe Ala Thr Tyr Tyr Cys Gln Gln His
Tyr Thr Thr Pro Pro Thr Phe Gly Gln Gly Thr Lys Val Glu Ile Lys Arg Thr (SEQ ID NO:1)

Glu Val Gln Leu Val Glu Ser Gly Gly Gly Leu Val Gln Pro Gly Gly Ser Leu Arg Leu Ser Cys
Ala Ala Ser Gly Phe Asn Ile Lys Asp Thr Tyr Ile His Trp Val Arg Gln Ala Pro Gly Lys Gly Leu
Glu Trp Val Ala Arg Ile Tyr Pro Thr Asn Gly Tyr Thr Arg Tyr Ala Asp Ser Val Lys Gly Arg Phe
Thr Ile Ser Ala Asp Thr Ser Lys Asn Thr Ala Tyr Leu Gln Met Asn Ser Leu Arg Ala Glu Asp
Thr Ala Val Tyr Tyr Cys Ser Arg Trp Gly Gly Asp Gly Phe Tyr Ala Met Asp Tyr Trp Gly Gln
Gly Thr Leu Val Thr Val Ser Ser (SEQ ID NO:2)

LC frequency

| | | | | | | | | | | |
|---|---|---|---|---|---|---|---|---|---|---|
| 28 | S 511 | N 262 | V 258 | D 186 | G 178 | I 44 | T 39 | L 16 | X 35 | | |
| 29 | I | S | V | G | N | X 70 | | | | | |
| 30 | S 612 | S 272 | V 254 | G 192 | R 147 | Y 63 | T 29 | D 28 | A 17 | X 45 | |
| 31 | S 849 | N 176 | K 169 | G 86 | I 81 | D 28 | K 25 | G 18 | X 53 | | |
| 32 | S 676 | N 496 | T 170 | R 47 | I 29 | D 28 | R 25 | X 69 | | | |
| | Y 1055 | N 128 | W 97 | F 77 | S 61 | D 40 | R 25 | | | | |
| 50 | G 386 | A 341 | D 294 | W 151 | K 116 | L 91 | E 39 | S 30 | X 82 | | |
| 53 | S 545 | N 438 | T 407 | K 41 | I 23 | R 23 | X 58 | | | | |
| 91 | Y 849 | S 196 | R 169 | A 118 | G 61 | H 41 | X 148 | | | | |
| 92 | Y 362 | G 356 | N 248 | S 193 | D 114 | L 94 | T 64 | H 43 | I 38 | X 91 | |
| 93 | S 738 | N 346 | Q 117 | T 101 | H 66 | G 51 | D 47 | R 35 | X 112 | | |
| 94 | S | T | W | Y | L | F | A | P | V | I | N |
| | 386 | 365 | 288 | 172 | 114 | 79 | 46 | 43 | 33 | 24 | 18 |
| 96 | L 264 | Y 205 | W 176 | F 140 | I 117 | R 115 | P 46 | X 121 | | | |



Framework sequences of huMAb4D5-8 light chain

LC-FR1       $^{1}$Asp Ile Gln Met Thr Gln Ser Pro Ser Ser Leu Ser Ala Ser Val Gly Asp Arg Val Thr Ile Thr Cys$^{23}$  (SEQ ID NO:6)

LC-FR2       $^{35}$Trp Tyr Gln Gln Lys Pro Gly Lys Ala Pro Lys Leu Leu Ile Tyr$^{49}$   (SEQ ID NO:7)

LC-FR3       $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$   (SEQ ID NO:8)

LC-FR4       $^{98}$Phe Gly Gln Gly Thr Lys Val Glu Ile Lys$^{107}$   (SEQ ID NO:9)

Framework sequences of huMAb4D5-8 heavy chain

HC-FR1       $^{1}$Glu Val Gln Leu Val Glu Ser Gly Gly Gly Leu Val Gln Pro Gly Gly Ser Leu Arg Leu Ser Cys Ala Ala Ser$^{25}$   (SEQ ID NO:10)

HC-FR2       $^{36}$Trp Val Arg Gln Ala Pro Gly Lys Gly Leu Glu Trp Val$^{48}$   (SEQ ID NO:11)

HC-FR3       $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$   (SEQ ID NO:12)

HC-FR4       $^{103}$Trp Gly Gln Gly Thr Leu Val Thr Val Ser Ser$^{113}$   (SEQ ID NO: 13)

FIG. 6

Framework sequences of huMAb4D5-8 light chain modified at position 66 (underlined)

LC-FR1    $^1$Asp Ile Gln Met Thr Gln Ser Pro Ser Ser Leu Ser Ala Ser Val Gly Asp Arg Val Thr Ile Thr Cys$^{23}$    (SEQ ID NO:14)

LC-FR2    $^{35}$Trp Tyr Gln Gln Lys Pro Gly Lys Ala Pro Lys Leu Leu Ile Tyr$^{49}$    (SEQ ID NO:15)

LC-FR3    $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$    (SEQ ID NO:16)

LC-FR4    $^{98}$Phe Gly Gln Gly Thr Lys Val Glu Ile Lys$^{107}$    (SEQ ID NO:17)

Framework sequences of huMAb4D5-8 heavy chain modified at positions 71, 73 and 78 (underlined)

HC-FR1    $^1$Glu Val Gln Leu Val Glu Ser Gly Gly Gly Leu Val Gln Pro Gly Gly Ser Leu Arg Leu Ser Cys Ala Ala Ser$^{25}$    (SEQ ID NO:18)

HC-FR2    $^{36}$Trp Val Arg Gln Ala Pro Gly Lys Gly Leu Glu Trp Val$^{48}$    (SEQ ID NO:19)

HC-FR3    $^{66}$Arg Phe Thr Ile Ser <u>Arg</u> Asp <u>Asn</u> Ser Lys Asn Thr <u>Leu</u> Tyr Leu Gln Met Asn$^{83}$ Ser$^{83a}$ Leu$^{83b}$ Arg$^{83c}$ Ala Glu Asp Thr Ala Val Tyr Tyr Cys$^{92}$    (SEQ ID NO:20)

HC-FR4    $^{103}$Trp Gly Gln Gly Thr Leu Val Thr Val Ser Ser$^{113}$    (SEQ ID NO:21)

FIG. 7

| CDR | Position | YSGR-A library | | YSGR-B library | | YSGR-C library | | YSGR-D library | |
|---|---|---|---|---|---|---|---|---|---|
| | | amino acid type | amino acid molar ratio | amino acid type | amino acid molar ratio | amino acid type | amino acid molar ratio | amino acid type | amino acid molar ratio |
| L3 | 91 | Y, S | 50, 50 | Y, S | 50, 50 | Y, S | 50, 50 | Y, S | 50, 50 |
| | 92 | Y, S | 50, 50 | Y, S | 50, 50 | Y, S | 50, 50 | Y, S | 50, 50 |
| | 93 | Y, S | 50, 50 | Y, S | 50, 50 | Y, S | 50, 50 | Y, S | 50, 50 |
| | 94 | Y, S | 50, 50 | Y, S | 50, 50 | Y, S | 50, 50 | Y, S | 50, 50 |
| | 96 | Y, S | 50, 50 | Y, S | 50, 50 | Y, S | 50, 50 | Y, S | 50, 50 |
| H1 | 28 | Y, S | 50, 50 | Y, S | 50, 50 | Y, S | 50, 50 | Y, S | 50, 50 |
| | 30 | Y, S | 50, 50 | Y, S | 50, 50 | Y, S | 50, 50 | Y, S | 50, 50 |
| | 31 | Y, S | 50, 50 | Y, S | 50, 50 | Y, S | 50, 50 | Y, S | 50, 50 |
| | 32 | Y, S | 50, 50 | Y, S | 50, 50 | Y, S | 50, 50 | Y, S | 50, 50 |
| | 33 | Y, S | 50, 50 | Y, S | 50, 50 | Y, S | 50, 50 | Y, S | 50, 50 |
| H2 | 50 | Y, S | 50, 50 | Y, S | 50, 50 | Y, S | 50, 50 | Y, S | 50, 50 |
| | 52 | Y, S | 50, 50 | Y, S | 50, 50 | Y, S | 50, 50 | Y, S | 50, 50 |
| | 53 | Y, S | 50, 50 | Y, S | 50, 50 | Y, S | 50, 50 | Y, S | 50, 50 |
| | 54 | Y, S | 50, 50 | Y, S | 50, 50 | Y, S | 50, 50 | Y, S | 50, 50 |
| | 56 | Y, S | 50, 50 | Y, S | 50, 50 | Y, S | 50, 50 | Y, S | 50, 50 |
| | 58 | Y, S | 50, 50 | Y, S | 50, 50 | Y, S | 50, 50 | Y, S | 50, 50 |
| H3 | 95 | | | | | | | | |
| | 96 | | | | | | | | |
| | 97 | Y, S, G | 50, 25, 25 | Y, S, R | 25, 50, 25 | Y, S, G, R | 38, 25, 25, 12 | Y, S, G, R, A, D, E, F, H, I, K, L, M, N, P, Q, T, V, W | 20, 26, 26, 13, 1, 1, 1, 1, 1, 1, 1, 1, 1, 1, 1, 1, 1, 1, 1 |
| | 98 | | | | | | | | |
| | 99 | | | | | | | | |
| | 100 | | | | | | | | |
| | 100a | | | | | | | | |
| | 100b | G, A | 50, 50 | G, A | 50, 50 | G, A | 50, 50 | G, A | 50, 50 |
| | 100c | I, M, L, F | 25, 25, 25, 25 | I, M, L, F | 25, 25, 25, 25 | I, M, L, F | 25, 25, 25, 25 | I, M, L, F | 25, 25, 25, 25 |

FIG. 8

FIG. 9A: Mutagenic oligonucleotides used in the construction of libraries YSGR-A, YSGR-B, YSGR-C and YSGR-D. Equimolar DNA degeneracies are represented in the IUB code (W = A/T, K = G/T, M = A/C, S = G/C, Y=T/C, R=A/G, and N=A/T/G/C). The notation "XXX" represents Tyr/Ser/Gly-encoding codons at a molar ratio of 50/25/25, respectively.

H1
GCA GCT TCT GGC TTC TMT ATT TMT TMT TMT TMT ATA CAC TGG GTG CGT  (SEQ ID NO:32)

H2
CTG GAA TGG GTT GCA TMT ATT TMT CCA TMT TMT GGT TMT ACT TMT TAT GCC GAT AGC GTC  (SEQ ID NO:33)

L3
ACT TAT TAC TGT CAG CAA TMT TMT TMT TMT CCA TMT ACG TTC GGA CAG GGT ACC  (SEQ ID NO:34)

H3-A6
GTC TAT TAT TGT GCT CGC XXX XXX XXX XXX XXX XXX GST WTK GAC TAC TGG GGT CAA GGA  (SEQ ID NO:35)

H3-A7
GTC TAT TAT TGT GCT CGC XXX XXX XXX XXX XXX XXX XXX GST WTK GAC TAC TGG GGT CAA GGA  (SEQ ID NO:36)

H3-A8
GTC TAT TAT TGT GCT CGC XXX XXX XXX XXX XXX XXX XXX XXX GST WTK GAC TAC TGG GGT CAA GGA  (SEQ ID NO:37)

H3-A9
GTC TAT TAT TGT GCT CGC XXX XXX XXX XXX XXX XXX XXX XXX XXX GST WTK GAC TAC TGG GGT CAA GGA  (SEQ ID NO:38)

H3-A10
GTC TAT TAT TGT GCT CGC XXX XXX XXX XXX XXX XXX XXX XXX XXX XXX GST WTK GAC TAC TGG GGT CAA GGA  (SEQ ID NO:39)

H3-A11
GTC TAT TAT TGT GCT CGC XXX XXX XXX XXX XXX XXX XXX XXX XXX XXX XXX GST WTK GAC TAC TGG GGT CAA GGA  (SEQ ID NO:40)

H3-A12
GTC TAT TAT TGT GCT CGC XXX XXX XXX XXX XXX XXX XXX XXX XXX XXX XXX XXX GST WTK GAC TAC TGG GGT CAA GGA  (SEQ ID NO:41)

H3-A13
GTC TAT TAT TGT GCT CGC XXX XXX XXX XXX XXX XXX XXX XXX XXX XXX XXX XXX XXX GST WTK GAC TAC TGG GGT CAA GGA  (SEQ ID NO:42)

H3-A14
GTC TAT TAT TGT GCT CGC XXX XXX XXX XXX XXX XXX XXX XXX XXX XXX XXX XXX XXX XXX GST WTK GAC TAC TGG GGT CAA GGA  (SEQ ID NO:43)

H3-A15
GTC TAT TAT TGT GCT CGC XXX XXX XXX XXX XXX XXX XXX XXX XXX XXX XXX XXX XXX XXX XXX GST WTK GAC TAC TGG GGT CAA GGA  (SEQ ID NO:44)

H3-A16
GTC TAT TAT TGT GCT CGC XXX XXX XXX XXX XXX XXX XXX XXX XXX XXX XXX XXX XXX XXX XXX XXX GST WTK GAC TAC TGG GGT CAA GGA  (SEQ ID NO:45)

H3-A17
GTC TAT TAT TGT GCT CGC XXX XXX XXX XXX XXX XXX XXX XXX XXX XXX XXX XXX XXX XXX XXX XXX XXX GST WTK GAC TAC TGG GGT CAA GGA  (SEQ ID NO:46)

FIG. 9B: Mutagenic oligonucleotides used in the construction of library YSGR-B. Equimolar DNA degeneracies are represented in the IUB code (W = A/T, K = G/T, M = A/C, S = G/C, Y=T/C, R=A/G, and N=A/T/G/C). The notation "XXX" represents Tyr/Ser/Arg-encoding codons at a molar ratio of 25/50/25, respectively.

H3-B6
GTC TAT TAT TGT GCT CGC XXX XXX XXX XXX XXX XXX GST WTK GAC TAC TGG GGT CAA GGA (SEQ ID NO:47)

H3-B7
GTC TAT TAT TGT GCT CGC XXX XXX XXX XXX XXX XXX XXX GST WTK GAC TAC TGG GGT CAA GGA (SEQ ID NO:48)

H3-B8
GTC TAT TAT TGT GCT CGC XXX XXX XXX XXX XXX XXX XXX XXX GST WTK GAC TAC TGG GGT CAA GGA (SEQ ID NO:49)

H3-B9
GTC TAT TAT TGT GCT CGC XXX XXX XXX XXX XXX XXX XXX XXX XXX GST WTK GAC TAC TGG GGT CAA GGA (SEQ ID NO:50)

H3-B10
GTC TAT TAT TGT GCT CGC XXX XXX XXX XXX XXX XXX XXX XXX XXX XXX GST WTK GAC TAC TGG GGT CAA GGA (SEQ ID NO:51)

H3-B11
GTC TAT TAT TGT GCT CGC XXX XXX XXX XXX XXX XXX XXX XXX XXX XXX XXX GST WTK GAC TAC TGG GGT CAA GGA (SEQ ID NO:52)

H3-B12
GTC TAT TAT TGT GCT CGC XXX XXX XXX XXX XXX XXX XXX XXX XXX XXX XXX XXX GST WTK GAC TAC TGG GGT CAA GGA (SEQ ID NO:53)

H3-B13
GTC TAT TAT TGT GCT CGC XXX XXX XXX XXX XXX XXX XXX XXX XXX XXX XXX XXX XXX GST WTK GAC TAC TGG GGT CAA GGA (SEQ ID NO:54)

H3-B14
GTC TAT TAT TGT GCT CGC XXX XXX XXX XXX XXX XXX XXX XXX XXX XXX XXX XXX XXX XXX GST WTK GAC TAC TGG GGT CAA GGA (SEQ ID NO:55)

H3-B15
GTC TAT TAT TGT GCT CGC XXX XXX XXX XXX XXX XXX XXX XXX XXX XXX XXX XXX XXX XXX XXX GST WTK GAC TAC TGG GGT CAA GGA (SEQ ID NO:56)

H3-B16
GTC TAT TAT TGT GCT CGC XXX XXX XXX XXX XXX XXX XXX XXX XXX XXX XXX XXX XXX XXX XXX XXX GST WTK GAC TAC TGG GGT CAA GGA (SEQ ID NO:57)

H3-B17
GTC TAT TAT TGT GCT CGC XXX XXX XXX XXX XXX XXX XXX XXX XXX XXX XXX XXX XXX XXX XXX XXX XXX GST WTK GAC TAC TGG GGT CAA GGA (SEQ ID NO:58)

FIG. 9C: Mutagenic oligonucleotides used in the construction of library YSGR-C. Equimolar DNA degeneracies are represented in the IUB code (W = A/T, K = G/T, M = A/C, S = G/C, Y=T/C, R=A/G, and N=A/T/G/C). The notation "XXX" represents Tyr/Ser/Gly/Arg-encoding codons at a molar ratio of 38/25/25/12, respectively.

H3-C6
GTC TAT TAT TGT GCT CGC XXX XXX XXX XXX XXX XXX GST WTK GAC TAC TGG GGT CAA GGA  (SEQ ID NO:59)
H3-C7
GTC TAT TAT TGT GCT CGC XXX XXX XXX XXX XXX XXX XXX GST WTK GAC TAC TGG GGT CAA GGA  (SEQ ID NO:60)
H3-C8
GTC TAT TAT TGT GCT CGC XXX XXX XXX XXX XXX XXX XXX XXX GST WTK GAC TAC TGG GGT CAA GGA  (SEQ ID NO:61)
H3-C9
GTC TAT TAT TGT GCT CGC XXX XXX XXX XXX XXX XXX XXX XXX XXX GST WTK GAC TAC TGG GGT CAA GGA  (SEQ ID NO:62)
H3-C10
GTC TAT TAT TGT GCT CGC XXX XXX XXX XXX XXX XXX XXX XXX XXX XXX GST WTK GAC TAC TGG GGT CAA GGA  (SEQ ID NO:63)
H3-C11
GTC TAT TAT TGT GCT CGC XXX XXX XXX XXX XXX XXX XXX XXX XXX XXX XXX GST WTK GAC TAC TGG GGT CAA GGA  (SEQ ID NO:64)
H3-C12
GTC TAT TAT TGT GCT CGC XXX XXX XXX XXX XXX XXX XXX XXX XXX XXX XXX XXX GST WTK GAC TAC TGG GGT CAA GGA  (SEQ ID NO:65)
H3-C13
GTC TAT TAT TGT GCT CGC XXX XXX XXX XXX XXX XXX XXX XXX XXX XXX XXX XXX XXX GST WTK GAC TAC TGG GGT CAA GGA  (SEQ ID NO:66)
H3-C14
GTC TAT TAT TGT GCT CGC XXX XXX XXX XXX XXX XXX XXX XXX XXX XXX XXX XXX XXX XXX GST WTK GAC TAC TGG GGT CAA GGA  (SEQ ID NO:67)
H3-C15
GTC TAT TAT TGT GCT CGC XXX XXX XXX XXX XXX XXX XXX XXX XXX XXX XXX XXX XXX XXX XXX GST WTK GAC TAC TGG GGT CAA GGA  (SEQ ID NO:68)
H3-C16
GTC TAT TAT TGT GCT CGC XXX XXX XXX XXX XXX XXX XXX XXX XXX XXX XXX XXX XXX XXX XXX XXX GST WTK GAC TAC TGG GGT CAA GGA  (SEQ ID NO:69)
H3-C17
GTC TAT TAT TGT GCT CGC XXX XXX XXX XXX XXX XXX XXX XXX XXX XXX XXX XXX XXX XXX XXX XXX XXX GST WTK GAC TAC TGG GGT CAA GGA  (SEQ ID NO:70)

FIG. 9D: Mutagenic oligonucleotides used in the construction of library YSGR-D. Equimolar DNA degeneracies are represented in the IUB code (W = A/T, K = G/T, M = A/C, S = G/C, Y=T/C, R=A/G, and N=A/T/G/C). The notation "XXX" represents Tyr/Ser/Gly/Arg/Ala/Asp/Glu/Phe/His/Ile/Lys/Leu/Met/Asn/Pro/Gln/Thr/Val/Trp–encoding codons at a molar ratio of 20/26/26/13/1/1/1/1/1/1/1/1/1/1/1/1/1/1/1, respectively.

H3-D6
GTC TAT TAT TGT GCT CGC XXX XXX XXX XXX XXX XXX GST WTK GAC TAC TGG GGT CAA GGA  (SEQ ID NO:71)
H3-D7
GTC TAT TAT TGT GCT CGC XXX XXX XXX XXX XXX XXX XXX GST WTK GAC TAC TGG GGT CAA GGA  (SEQ ID NO:72)
H3-D8
GTC TAT TAT TGT GCT CGC XXX XXX XXX XXX XXX XXX XXX XXX GST WTK GAC TAC TGG GGT CAA GGA  (SEQ ID NO:73)
H3-D9
GTC TAT TAT TGT GCT CGC XXX XXX XXX XXX XXX XXX XXX XXX XXX GST WTK GAC TAC TGG GGT CAA GGA  (SEQ ID NO:74)
H3-D10
GTC TAT TAT TGT GCT CGC XXX XXX XXX XXX XXX XXX XXX XXX XXX XXX GST WTK GAC TAC TGG GGT CAA GGA  (SEQ ID NO:75)
H3-D11
GTC TAT TAT TGT GCT CGC XXX XXX XXX XXX XXX XXX XXX XXX XXX XXX XXX GST WTK GAC TAC TGG GGT CAA GGA  (SEQ ID NO:76)
H3-D12
GTC TAT TAT TGT GCT CGC XXX XXX XXX XXX XXX XXX XXX XXX XXX XXX XXX XXX GST WTK GAC TAC TGG GGT CAA GGA  (SEQ ID NO:77)
H3-D13
GTC TAT TAT TGT GCT CGC XXX XXX XXX XXX XXX XXX XXX XXX XXX XXX XXX XXX XXX GST WTK GAC TAC TGG GGT CAA GGA  (SEQ ID NO:78)
H3-D14
GTC TAT TAT TGT GCT CGC XXX XXX XXX XXX XXX XXX XXX XXX XXX XXX XXX XXX XXX XXX GST WTK GAC TAC TGG GGT CAA GGA  (SEQ ID NO:79)
H3-D15
GTC TAT TAT TGT GCT CGC XXX XXX XXX XXX XXX XXX XXX XXX XXX XXX XXX XXX XXX XXX XXX GST WTK GAC TAC TGG GGT CAA GGA  (SEQ ID NO:80)
H3-D16
GTC TAT TAT TGT GCT CGC XXX XXX XXX XXX XXX XXX XXX XXX XXX XXX XXX XXX XXX XXX XXX XXX GST WTK GAC TAC TGG GGT CAA GGA  (SEQ ID NO:81)
H3-D17
GTC TAT TAT TGT GCT CGC XXX XXX XXX XXX XXX XXX XXX XXX XXX XXX XXX XXX XXX XXX XXX XXX XXX GST WTK GAC TAC TGG GGT CAA GGA  (SEQ ID NO:82)

FIG. 10. Number of specific binders observed by phage ELISA. (unique clones / specific binders).

|  | Library YSGR-A-D |
|---|---|
| Human HER-2 binders | 106/240 |
| Human DR5 binders | 18/144 |

FIGURE 11A

| binds with <100 nM affinity | | # in italics 0.25 to 2 | | # in bold 2 to 10 | | | | | | | |
|---|---|---|---|---|---|---|---|---|---|---|---|
| Spot Affinity ELISA | | | Specificity ELISA | | | | | | | Binding affinity of Fab-phage | |
| w/ 100 nM HER2 | w/o HER2 | ratio | Human VEGF | Human HER2 | Human DR5 | Human Insulin | Neutravidin | Human Growth Hormone | Human IGF-1 | Bovine serum albumin | IC50 (nM) | error +/- |
| 0.20 | 1.80 | 0.15 | 0.10 | 4.40 | -0.07 | -0.05 | 0.07 | 0.04 | 0.07 | -0.02 | | |
| 0.18 | 1.49 | 0.17 | 0.15 | 3.74 | 0.01 | 0.04 | 0.13 | 0.12 | 0.19 | -0.02 | 6.34 | 1.03 |
| 0.17 | 1.81 | 0.14 | 0.39 | 3.89 | -0.02 | -0.01 | 0.11 | 0.08 | 0.16 | -0.03 | | |
| 0.28 | 2.53 | 0.14 | 0.24 | 5.76 | 0.02 | 0.10 | 0.21 | 0.23 | 0.39 | 0.03 | | |
| 0.14 | 2.58 | 0.08 | 0.14 | 4.23 | -0.04 | 0.01 | 0.08 | 0.08 | 0.17 | -0.04 | 1.58 | 0.07 |
| 0.27 | 2.30 | 0.15 | 0.21 | 4.04 | -0.03 | 0.01 | 0.11 | 0.11 | 0.18 | -0.02 | | |
| 0.38 | 2.54 | 0.18 | 0.25 | 4.35 | 0.05 | 0.25 | 0.19 | 0.30 | 0.40 | 0.01 | | |
| 0.49 | 3.16 | 0.18 | 0.21 | 3.56 | 0.02 | 0.06 | 0.16 | 0.14 | 0.23 | -0.01 | 2.38 | 0.13 |
| 0.49 | 2.88 | 0.20 | 0.41 | 5.10 | 0.10 | 3.27 | 0.28 | 0.84 | 1.00 | 0.05 | | |
| 0.39 | 3.12 | 0.15 | 0.27 | 4.57 | 0.03 | 0.12 | 0.20 | 0.28 | 0.36 | 0.00 | | |
| N/D | N/D | N/D | N/D | N/D | N/D | N/D | N/D | N/D | N/D | N/D | | |
| N/D | N/D | N/D | N/D | N/D | N/D | N/D | N/D | N/D | N/D | N/D | | |
| 2.55 | 2.60 | 0.98 | 0.19 | 4.40 | 0.01 | 0.15 | 0.15 | 0.29 | 0.34 | 0.04 | | |
| 2.07 | 2.00 | 1.03 | 0.28 | 3.64 | 0.25 | 0.14 | 0.15 | 0.30 | 0.41 | 0.06 | | |
| 1.87 | 2.00 | 0.94 | 0.20 | 4.90 | 0.19 | 0.12 | 0.14 | 0.27 | 0.33 | 0.00 | | |
| 2.03 | 2.47 | 0.83 | 0.12 | 3.40 | 0.02 | 0.00 | 0.07 | 0.11 | 0.19 | -0.01 | | |
| 2.94 | 3.84 | 0.77 | 0.38 | 5.76 | 0.12 | 0.48 | 0.24 | 0.70 | 0.87 | 0.09 | | |
| 2.99 | 3.42 | 0.88 | 0.28 | 5.76 | 0.06 | 0.24 | 0.17 | 0.47 | 0.52 | 0.05 | | |
| 2.82 | 2.95 | 0.95 | 0.18 | 4.16 | -0.01 | 0.04 | 0.10 | 0.14 | 0.23 | 0.01 | | |
| 3.03 | 3.80 | 0.80 | 0.23 | 3.73 | 0.05 | 0.12 | 0.14 | 3.25 | 0.41 | 0.03 | | |
| 2.79 | 3.17 | 0.88 | 0.22 | 5.76 | 0.03 | 0.11 | 0.15 | 0.39 | 0.40 | 0.08 | | |
| 3.36 | 3.30 | 1.02 | 3.00 | 3.62 | 2.40 | 4.33 | 2.27 | 3.77 | 3.88 | 1.18 | | |
| 2.73 | 2.93 | 0.93 | 0.18 | 5.76 | -0.01 | 0.06 | 0.10 | 2.24 | 0.30 | 0.03 | | |
| 3.33 | 3.65 | 0.91 | 0.19 | 4.19 | 0.02 | 0.14 | 0.15 | 3.48 | 0.37 | 0.06 | | |
| 3.03 | 3.23 | 0.94 | 0.23 | 4.20 | 0.05 | 0.32 | 0.20 | 0.43 | 0.46 | 0.02 | | |
| 3.43 | 3.18 | 1.07 | 0.95 | 3.60 | 0.41 | 2.01 | 0.63 | 2.04 | 1.78 | 0.27 | | |
| 3.26 | 3.58 | 0.91 | 0.17 | 3.71 | -0.03 | 0.02 | 0.11 | 0.21 | 0.23 | -0.01 | | |
| 1.95 | 2.09 | 0.94 | 0.17 | 3.91 | -0.02 | -0.02 | 0.10 | 0.09 | 0.18 | -0.01 | | |
| N/D | N/D | N/D | N/D | N/D | N/D | N/D | N/D | N/D | N/D | N/D | | |
| N/D | N/D | N/D | N/D | N/D | N/D | N/D | N/D | N/D | N/D | N/D | | |
| 1.73 | 2.20 | 0.80 | 0.24 | 3.86 | 0.01 | 0.16 | 0.20 | 0.34 | 0.48 | 0.01 | | |
| 0.41 | 2.28 | 0.21 | 0.21 | 5.76 | 0.00 | 0.08 | 0.15 | 0.13 | 0.25 | 0.00 | 3.12 | 0.37 |
| 0.10 | 2.39 | 0.07 | 0.20 | 4.26 | -0.02 | 0.03 | 0.16 | 0.11 | 0.17 | -0.01 | | |
| 0.30 | 2.39 | 0.16 | 0.20 | 3.72 | 0.00 | 0.03 | 0.14 | 0.20 | 0.23 | -0.01 | 1.61 | 0.33 |
| 0.34 | 1.59 | 0.25 | 0.23 | 4.13 | 0.00 | 0.05 | 0.17 | 0.17 | 0.27 | 0.01 | | |
| 0.27 | 2.31 | 0.15 | 0.18 | 3.80 | -0.03 | 0.03 | 0.14 | 0.15 | 0.19 | 0.00 | | |
| 0.66 | 2.93 | 0.25 | 0.18 | 5.76 | -0.01 | 0.02 | 0.10 | 0.12 | 0.20 | 0.01 | 2.44 | 0.24 |
| 0.71 | 2.65 | 0.29 | 0.20 | 3.86 | -0.02 | 0.03 | 0.12 | 0.18 | 0.18 | 0.00 | | |
| 0.44 | 2.89 | 0.18 | 0.14 | 3.82 | -0.04 | -0.01 | 0.09 | 0.11 | 0.18 | -0.03 | 2.34 | 0.20 |
| 0.23 | 2.78 | 0.11 | 0.22 | 4.00 | -0.02 | 0.00 | 0.14 | 0.15 | 0.21 | -0.01 | | |
| 0.27 | 2.63 | 0.13 | 0.20 | 5.76 | -0.04 | 0.52 | 0.09 | 0.10 | 0.14 | -0.03 | | |
| 0.11 | 2.29 | 0.08 | 0.16 | 4.35 | -0.02 | 0.01 | 0.12 | 0.14 | 0.18 | 0.03 | 0.32 | 0.01 |
| 0.30 | 2.61 | 0.14 | 0.16 | 4.16 | -0.01 | 0.02 | 0.12 | 0.13 | 0.21 | -0.03 | | |
| 0.18 | 1.93 | 0.13 | 0.11 | 5.76 | 0.16 | 0.00 | 0.09 | 0.09 | 0.18 | -0.01 | 2.41 | 0.22 |
| 0.27 | 2.60 | 0.13 | 0.19 | 5.76 | -0.02 | -0.01 | 0.11 | 0.12 | 0.17 | -0.02 | 2.78 | 0.26 |
| 0.30 | 2.00 | 0.18 | 0.17 | 3.31 | -0.03 | -0.01 | 0.11 | 0.10 | 0.18 | -0.02 | 3.46 | 0.40 |
| 0.32 | 2.46 | 0.16 | 0.32 | 4.30 | 0.01 | 0.02 | 0.11 | 0.12 | 0.19 | -0.01 | | |
| 0.34 | 1.90 | 0.21 | 0.14 | 3.74 | -0.03 | 0.02 | 0.10 | 0.10 | 0.15 | -0.01 | 4.97 | 0.37 |
| 0.50 | 2.92 | 0.20 | 0.15 | 5.76 | -0.03 | 0.03 | 0.11 | 0.12 | 0.15 | 0.00 | 1.62 | 0.28 |
| 0.37 | 2.93 | 0.15 | 0.17 | 5.76 | 0.40 | 0.65 | 0.12 | 0.12 | 0.21 | 0.01 | | |
| 0.62 | 2.78 | 0.25 | 0.12 | 4.45 | -0.05 | -0.02 | 0.10 | 0.12 | 0.15 | 0.00 | 3.70 | 0.28 |
| 0.58 | 2.58 | 0.25 | 0.22 | 4.51 | 0.04 | 0.11 | 0.21 | 0.21 | 0.34 | 0.04 | | |
| 0.35 | 2.40 | 0.18 | 0.16 | 5.76 | -0.04 | 0.01 | 0.13 | 0.10 | 0.16 | -0.01 | 3.42 | 0.15 |
| 0.15 | 2.21 | 0.10 | 0.52 | 5.76 | -0.03 | 0.03 | 0.15 | 0.14 | 0.17 | 0.01 | | |
| 0.32 | 2.78 | 0.14 | 0.16 | 3.94 | -0.04 | 0.22 | 0.10 | 0.06 | 0.14 | -0.04 | | |
| 0.38 | 2.51 | 0.18 | 0.29 | 4.04 | -0.02 | 0.03 | 0.15 | 0.11 | 0.20 | -0.01 | | |
| 0.34 | 2.98 | 0.14 | 0.15 | 3.71 | -0.05 | 0.02 | 0.11 | 0.08 | 0.21 | -0.01 | | |
| 0.35 | 2.67 | 0.16 | 0.15 | 5.76 | -0.06 | 0.05 | 0.13 | 0.09 | 0.13 | -0.02 | 1.39 | 0.09 |
| 0.25 | 2.46 | 0.13 | 0.14 | 3.92 | -0.05 | 0.05 | 0.14 | 0.07 | 0.14 | -0.03 | 1.69 | 0.13 |
| 0.34 | 2.56 | 0.16 | 1.04 | 4.39 | -0.02 | 0.05 | 0.12 | 0.12 | 0.21 | 0.00 | | |
| 0.64 | 3.12 | 0.23 | 0.11 | 5.76 | -0.03 | 0.49 | 0.11 | 0.12 | 0.15 | 0.00 | | |
| 0.64 | 2.96 | 0.24 | 0.17 | 4.17 | 0.00 | 0.07 | 0.17 | 0.23 | 0.38 | 0.04 | | |
| 0.65 | 2.97 | 0.24 | 0.18 | 3.76 | 0.00 | 0.07 | 0.17 | 0.24 | 0.28 | 0.04 | | |
| 0.53 | 2.10 | 0.28 | 0.12 | 5.10 | -0.02 | 0.01 | 0.10 | 0.09 | 0.17 | -0.01 | | |
| 0.64 | 2.65 | 0.27 | 0.17 | 3.89 | -0.04 | 0.00 | 0.11 | 0.10 | 0.19 | -0.01 | | |
| 0.31 | 1.85 | 0.20 | 0.44 | 4.04 | -0.04 | 0.03 | 0.11 | 0.12 | 0.18 | -0.01 | | |
| 0.38 | 2.03 | 0.22 | 0.13 | 5.76 | -0.03 | -0.01 | 0.11 | 0.11 | 0.17 | -0.01 | 3.15 | 0.16 |
| 1.99 | 2.28 | 0.88 | 0.36 | 4.34 | -0.01 | 0.03 | 0.12 | 0.15 | 0.26 | 0.00 | | |
| 0.63 | 2.67 | 0.26 | 0.15 | 5.76 | -0.01 | 0.02 | 0.13 | 0.11 | 0.18 | -0.01 | | |
| 0.08 | 1.21 | 0.12 | 0.58 | 5.76 | 0.32 | 1.39 | 0.45 | 1.13 | 3.00 | 0.17 | | |
| 0.34 | 2.67 | 0.15 | 0.16 | 5.48 | -0.02 | 0.03 | 0.12 | 0.18 | 0.24 | 0.00 | 2.25 | 0.18 |
| 0.41 | 2.91 | 0.17 | 0.18 | 5.76 | -0.03 | 0.06 | 0.12 | 0.13 | 0.19 | 0.00 | | |
| 0.78 | 2.83 | 0.30 | 0.15 | 5.76 | 0.06 | 0.08 | 0.12 | 0.15 | 0.26 | 0.00 | | |
| 0.61 | 2.88 | 0.24 | 0.13 | 5.76 | -0.02 | 0.02 | 0.10 | 0.11 | 0.21 | -0.03 | | |
| 0.20 | 1.93 | 0.14 | 3.18 | 4.90 | 2.74 | 5.79 | 3.13 | 4.99 | 5.86 | 1.57 | | |
| 0.36 | 2.38 | 0.18 | 0.55 | 3.45 | 0.31 | 0.86 | 0.41 | 1.19 | 3.84 | 0.12 | | |
| 0.21 | 2.04 | 0.14 | 0.45 | 5.76 | -0.01 | 0.04 | 0.14 | 0.15 | 0.28 | 0.03 | | |
| 0.22 | 2.35 | 0.12 | 0.21 | 3.68 | 0.01 | 0.05 | 0.18 | 0.14 | 0.24 | 0.01 | | |
| 0.23 | 2.79 | 0.11 | 0.18 | 4.35 | 0.00 | 0.03 | 0.15 | 0.11 | 0.24 | 0.00 | 0.38 | 0.05 |
| 1.57 | 1.98 | 0.80 | 0.20 | 3.46 | 0.00 | 0.06 | 0.17 | 0.15 | 0.29 | 0.01 | | |
| 0.21 | 1.25 | 0.22 | 0.19 | 5.76 | -0.02 | 0.02 | 0.15 | 0.11 | 0.18 | 0.00 | | |
| 3.14 | 3.57 | 0.88 | 0.27 | 3.67 | 0.05 | 0.27 | 0.19 | 0.25 | 0.38 | 0.05 | | |
| 0.13 | 2.71 | 0.08 | 0.16 | 4.57 | 0.25 | 0.35 | 0.16 | 0.18 | 0.30 | 0.02 | | |
| 0.13 | 2.15 | 0.10 | 0.35 | 4.06 | 0.44 | 0.10 | 0.17 | 0.22 | 0.33 | 0.03 | | |
| 0.29 | 2.66 | 0.14 | 0.12 | 5.76 | -0.05 | 0.34 | 0.12 | 0.16 | 0.23 | 0.00 | | |
| 0.28 | 2.91 | 0.12 | 0.15 | 5.76 | 0.03 | 0.15 | 0.17 | 0.19 | 0.33 | 0.02 | 0.41 | 0.02 |
| 3.48 | 3.38 | 1.03 | 0.18 | 5.76 | 0.07 | 0.15 | 0.16 | 0.27 | 0.35 | 0.02 | | |
| 0.77 | 3.33 | 0.25 | 0.20 | 5.76 | 0.04 | 0.10 | 0.18 | 0.22 | 0.31 | 0.04 | | |
| 0.39 | 1.93 | 0.23 | 0.20 | 3.57 | 0.07 | 0.16 | 0.20 | 0.29 | 0.43 | 0.07 | | |
| 0.08 | 2.47 | 0.07 | 0.47 | 5.76 | 0.08 | 0.07 | 0.14 | 0.17 | 0.35 | 0.02 | | |
| 0.27 | 1.89 | 0.18 | 0.18 | 4.04 | 0.10 | 0.11 | 0.16 | 0.23 | 0.30 | 0.03 | | |
| 0.09 | 2.52 | 0.07 | 1.37 | 5.76 | 0.63 | 2.41 | 0.88 | 5.86 | 5.86 | 0.44 | | |
| 0.20 | 1.63 | 0.17 | 0.12 | 3.99 | 0.08 | 0.01 | 0.09 | 0.11 | 0.17 | 0.00 | 5.44 | 0.22 |
| N/D | N/D | N/D | 3.53 | 3.37 | 5.79 | 3.42 | 3.91 | 3.34 | 3.57 | 3.34 | | |
| 0.37 | 2.35 | 0.16 | 0.23 | 4.13 | -0.14 | 0.13 | 0.06 | 0.06 | 0.18 | 0.01 | 2.54 | 0.21 |
| 0.24 | 2.24 | 0.11 | 0.08 | 5.92 | -0.08 | 0.14 | 0.07 | 0.07 | 0.19 | 0.02 | 2.25 | 0.24 |
| 2.59 | 3.02 | 0.86 | 0.18 | 5.92 | -0.11 | 0.17 | 0.12 | 0.16 | 0.33 | 0.05 | | |
| 1.55 | 1.83 | 0.85 | 0.30 | 4.04 | -0.05 | 0.51 | 0.16 | 0.40 | 0.65 | 0.05 | | |
| 2.33 | 2.65 | 0.88 | 0.19 | 4.30 | -0.08 | 0.21 | 0.18 | 0.19 | 0.32 | 0.07 | | |
| 2.24 | 2.76 | 0.81 | 0.16 | 4.06 | -0.13 | 0.22 | 0.06 | 0.10 | 0.26 | 0.03 | | |
| 2.30 | 2.67 | 0.86 | 0.14 | 4.12 | -0.15 | 0.07 | 0.03 | 0.07 | 0.10 | 0.01 | | |
| 1.62 | 1.91 | 0.85 | 0.18 | 5.24 | -0.10 | 0.21 | 0.12 | 0.18 | 0.29 | 0.05 | | |
| 2.58 | 3.19 | 0.81 | 0.20 | 3.72 | -0.07 | 0.27 | 0.10 | 0.16 | 0.33 | 0.04 | | |
| 2.01 | 3.02 | 0.67 | 0.08 | 5.92 | -0.14 | 0.06 | 0.04 | 0.04 | 0.10 | 0.00 | | |
| 1.61 | 1.70 | 0.95 | 0.13 | 5.92 | -0.13 | 0.10 | 0.05 | 0.08 | 0.13 | 0.03 | | |
| 1.18 | 1.32 | 0.89 | 0.06 | 4.37 | -0.15 | 0.06 | 0.05 | 0.05 | 0.12 | 0.01 | | |

FIGURE 11B

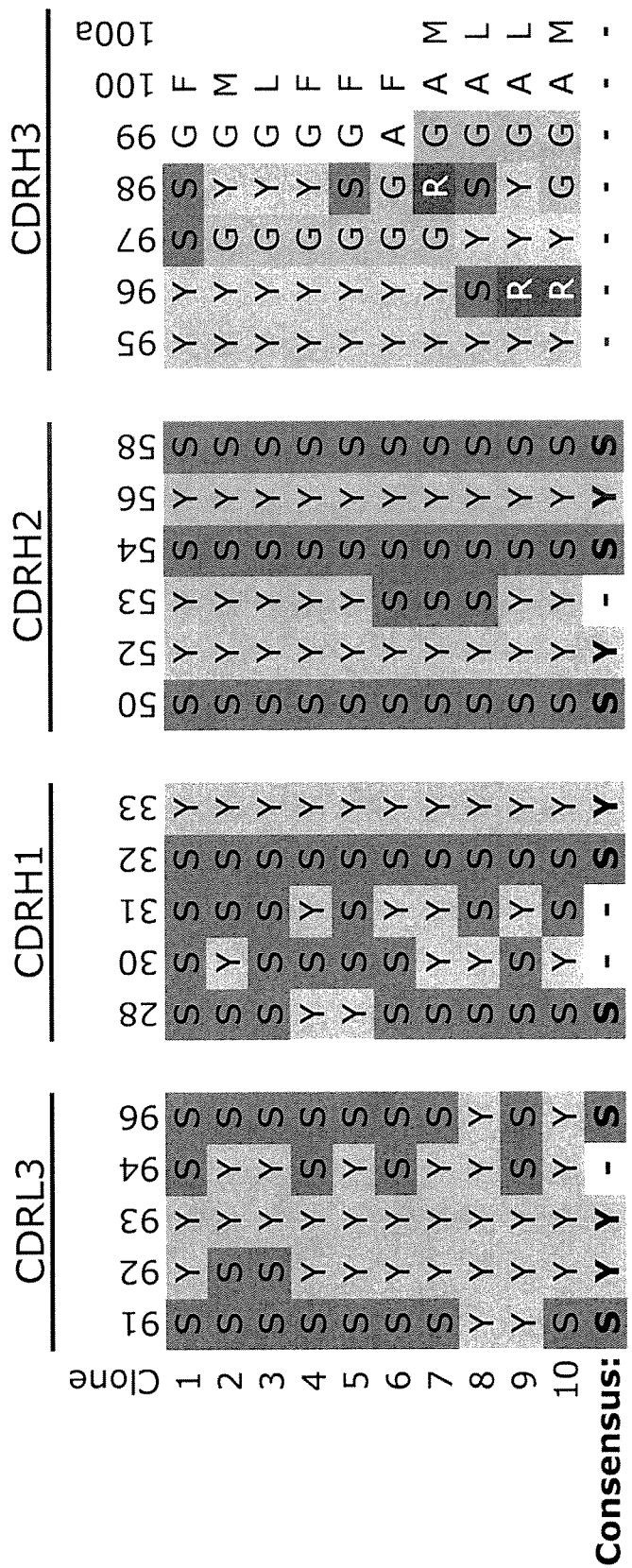
Figure 12: α-HER2 Fabs contain short CDRH3 sequences.

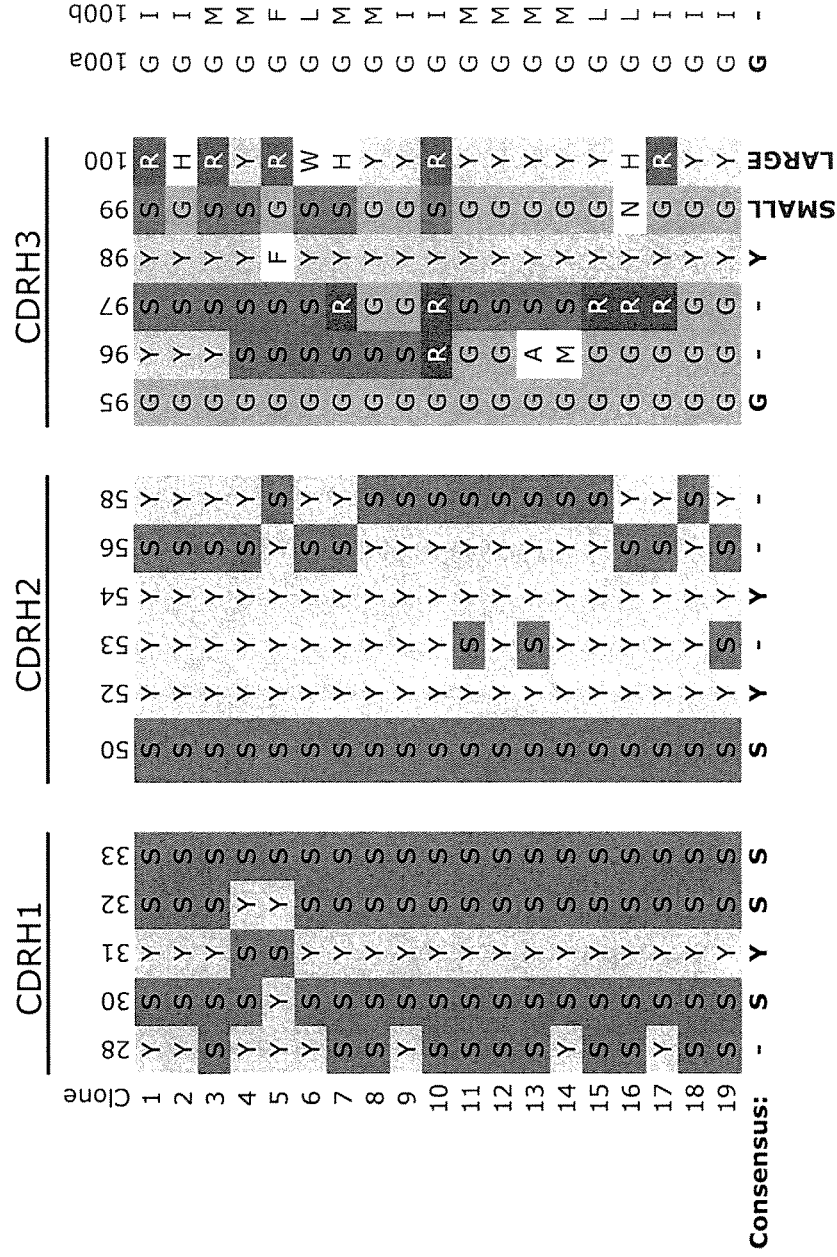
Figure 13: Anti-HER2 short, eight residue CDRH3

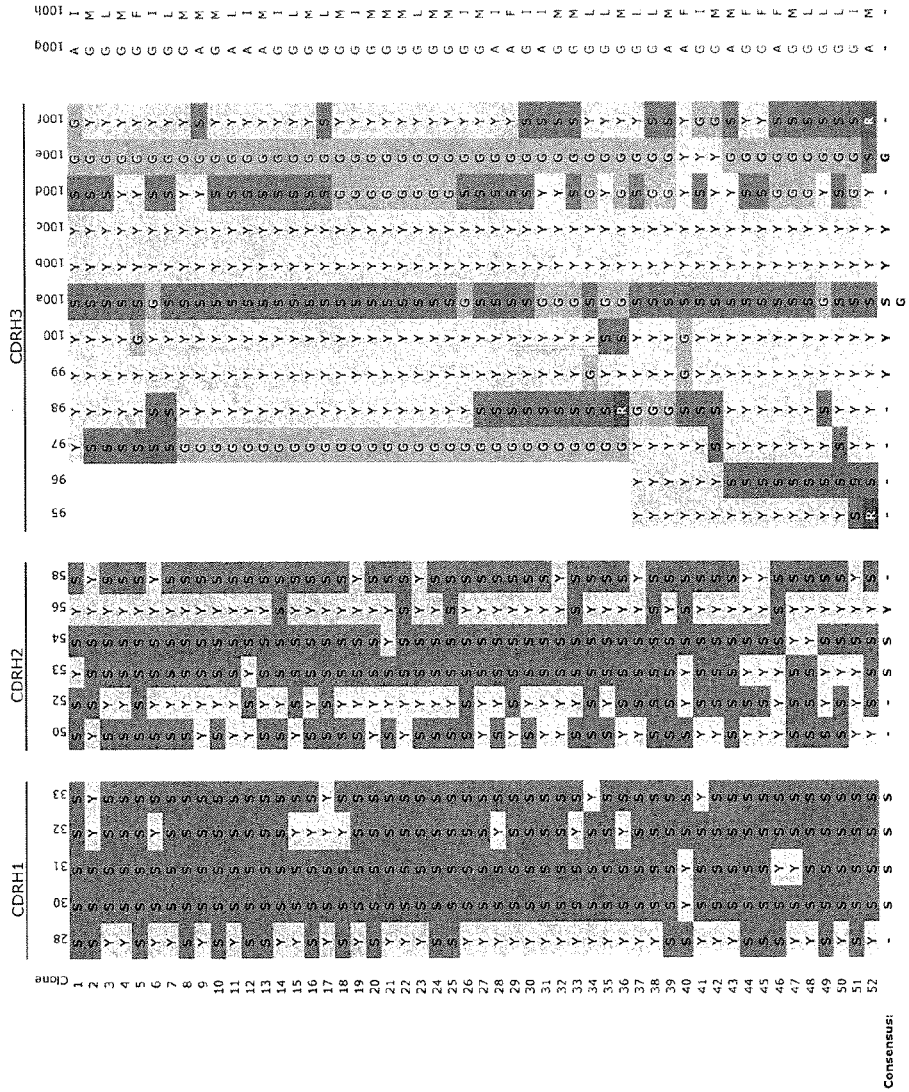
Figure 14: Anti-HER2 YSG medium length

FIG. 15

DR5 binding clones — CDRL3, CDRH1, CDRH2, CDRH3 sequences with SEQ ID NOs, IC50 (nM), and cross-reactivity with murine DR5.

ND is not-determined

Figure 17: DR5 Binding to Human and Murine DR5

| Binary H3 library | | SAH3 | | SCH3 | | SFH3 | | SGH3 | | SIH3 | | SLH3 | |
|---|---|---|---|---|---|---|---|---|---|---|---|---|---|
| CDR | Position | amino acid type | amino acid molar ratio | amino acid type | amino acid molar ratio | amino acid type | amino acid molar ratio | amino acid type | amino acid molar ratio | amino acid type | amino acid molar ratio | amino acid type | amino acid molar ratio |
| L3 | 91 | S,Y | 50, 50 | S,Y | 50, 50 | S,Y | 50, 50 | S,Y | 50, 50 | S,Y | 50, 50 | S,Y | 50, 50 |
| | 92 | S,Y | 50, 50 | S,Y | 50, 50 | S,Y | 50, 50 | S,Y | 50, 50 | S,Y | 50, 50 | S,Y | 50, 50 |
| | 93 | S,Y | 50, 50 | S,Y | 50, 50 | S,Y | 50, 50 | S,Y | 50, 50 | S,Y | 50, 50 | S,Y | 50, 50 |
| | 94 | S,Y | 50, 50 | S,Y | 50, 50 | S,Y | 50, 50 | S,Y | 50, 50 | S,Y | 50, 50 | S,Y | 50, 50 |
| | 96 | S,Y | 50, 50 | S,Y | 50, 50 | S,Y | 50, 50 | S,Y | 50, 50 | S,Y | 50, 50 | S,Y | 50, 50 |
| H1 | 28 | S,Y | 50, 50 | S,Y | 50, 50 | S,Y | 50, 50 | S,Y | 50, 50 | S,Y | 50, 50 | S,Y | 50, 50 |
| | 30 | S,Y | 50, 50 | S,Y | 50, 50 | S,Y | 50, 50 | S,Y | 50, 50 | S,Y | 50, 50 | S,Y | 50, 50 |
| | 31 | S,Y | 50, 50 | S,Y | 50, 50 | S,Y | 50, 50 | S,Y | 50, 50 | S,Y | 50, 50 | S,Y | 50, 50 |
| | 32 | S,Y | 50, 50 | S,Y | 50, 50 | S,Y | 50, 50 | S,Y | 50, 50 | S,Y | 50, 50 | S,Y | 50, 50 |
| | 33 | S,Y | 50, 50 | S,Y | 50, 50 | S,Y | 50, 50 | S,Y | 50, 50 | S,Y | 50, 50 | S,Y | 50, 50 |
| H2 | 50 | S,Y | 50, 50 | S,Y | 50, 50 | S,Y | 50, 50 | S,Y | 50, 50 | S,Y | 50, 50 | S,Y | 50, 50 |
| | 52 | S,Y | 50, 50 | S,Y | 50, 50 | S,Y | 50, 50 | S,Y | 50, 50 | S,Y | 50, 50 | S,Y | 50, 50 |
| | 53 | S,Y | 50, 50 | S,Y | 50, 50 | S,Y | 50, 50 | S,Y | 50, 50 | S,Y | 50, 50 | S,Y | 50, 50 |
| | 54 | S,Y | 50, 50 | S,Y | 50, 50 | S,Y | 50, 50 | S,Y | 50, 50 | S,Y | 50, 50 | S,Y | 50, 50 |
| | 56 | S,Y | 50, 50 | S,Y | 50, 50 | S,Y | 50, 50 | S,Y | 50, 50 | S,Y | 50, 50 | S,Y | 50, 50 |
| | 58 | S,Y | 50, 50 | S,Y | 50, 50 | S,Y | 50, 50 | S,Y | 50, 50 | S,Y | 50, 50 | S,Y | 50, 50 |
| H3 | 95 | | | | | | | | | | | | |
| | 96 | | | | | | | | | | | | |
| | 97 | | | | | | | | | | | | |
| | 98 | S,A | 50, 50 | S,C | 50, 50 | S,F | 50, 50 | S,G | 50, 50 | S,I | 50, 50 | S,L | 50, 50 |
| | 99 | | | | | | | | | | | | |
| | 100 | | | | | | | | | | | | |
| | 100x | | | | | | | | | | | | |
| | 100x | G,A I,M,L,F | 50, 50 25, 25, 25, 25 | G,A I,M,L,F | 50, 50 25, 25, 25, 25 | G,A I,M,L,F | 50, 50 25, 25, 25, 25 | G,A I,M,L,F | 50, 50 25, 25, 25, 25 | G,A I,M,L,F | 50, 50 25, 25, 25, 25 | G,A I,M,L,F | 50, 50 25, 25, 25, 25 |

FIGURE 19A

Binary H3 library

| CDR | Position | SNH3 amino acid type | SNH3 amino acid molar ratio | SPH3 amino acid type | SPH3 amino acid molar ratio | SRH3 amino acid type | SRH3 amino acid molar ratio | STH3 amino acid type | STH3 amino acid molar ratio | SWH3 amino acid type | SWH3 amino acid molar ratio | SYH3 amino acid type | SYH3 amino acid molar ratio |
|---|---|---|---|---|---|---|---|---|---|---|---|---|---|
| L3 | 91 | S,Y | 50, 50 | S,Y | 50, 50 | S,Y | 50, 50 | S,Y | 50, 50 | S,Y | 50, 50 | S,Y | 50, 50 |
|    | 92 | S,Y | 50, 50 | S,Y | 50, 50 | S,Y | 50, 50 | S,Y | 50, 50 | S,Y | 50, 50 | S,Y | 50, 50 |
|    | 93 | S,Y | 50, 50 | S,Y | 50, 50 | S,Y | 50, 50 | S,Y | 50, 50 | S,Y | 50, 50 | S,Y | 50, 50 |
|    | 94 | S,Y | 50, 50 | S,Y | 50, 50 | S,Y | 50, 50 | S,Y | 50, 50 | S,Y | 50, 50 | S,Y | 50, 50 |
|    | 96 | S,Y | 50, 50 | S,Y | 50, 50 | S,Y | 50, 50 | S,Y | 50, 50 | S,Y | 50, 50 | S,Y | 50, 50 |
| H1 | 28 | S,Y | 50, 50 | S,Y | 50, 50 | S,Y | 50, 50 | S,Y | 50, 50 | S,Y | 50, 50 | S,Y | 50, 50 |
|    | 30 | S,Y | 50, 50 | S,Y | 50, 50 | S,Y | 50, 50 | S,Y | 50, 50 | S,Y | 50, 50 | S,Y | 50, 50 |
|    | 31 | S,Y | 50, 50 | S,Y | 50, 50 | S,Y | 50, 50 | S,Y | 50, 50 | S,Y | 50, 50 | S,Y | 50, 50 |
|    | 32 | S,Y | 50, 50 | S,Y | 50, 50 | S,Y | 50, 50 | S,Y | 50, 50 | S,Y | 50, 50 | S,Y | 50, 50 |
|    | 33 | S,Y | 50, 50 | S,Y | 50, 50 | S,Y | 50, 50 | S,Y | 50, 50 | S,Y | 50, 50 | S,Y | 50, 50 |
| H2 | 50 | S,Y | 50, 50 | S,Y | 50, 50 | S,Y | 50, 50 | S,Y | 50, 50 | S,Y | 50, 50 | S,Y | 50, 50 |
|    | 52 | S,Y | 50, 50 | S,Y | 50, 50 | S,Y | 50, 50 | S,Y | 50, 50 | S,Y | 50, 50 | S,Y | 50, 50 |
|    | 53 | S,Y | 50, 50 | S,Y | 50, 50 | S,Y | 50, 50 | S,Y | 50, 50 | S,Y | 50, 50 | S,Y | 50, 50 |
|    | 54 | S,Y | 50, 50 | S,Y | 50, 50 | S,Y | 50, 50 | S,Y | 50, 50 | S,Y | 50, 50 | S,Y | 50, 50 |
|    | 56 | S,Y | 50, 50 | S,Y | 50, 50 | S,Y | 50, 50 | S,Y | 50, 50 | S,Y | 50, 50 | S,Y | 50, 50 |
|    | 58 | S,Y | 50, 50 | S,Y | 50, 50 | S,Y | 50, 50 | S,Y | 50, 50 | S,Y | 50, 50 | S,Y | 50, 50 |
| H3 | 95 | | | | | | | | | | | | |
|    | 96 | | | | | | | | | | | | |
|    | 97 | S,N | 50, 50 | S,P | 50, 50 | S,R | 50, 50 | S,T | 50, 50 | S,W | 50, 50 | S,Y | 50, 50 |
|    | 98 | | | | | | | | | | | | |
|    | 99 | | | | | | | | | | | | |
|    | 100 | G, A | 50, 50 | G, A | 50, 50 | G, A | 50, 50 | G, A | 50, 50 | G, A | 50, 50 | G, A | 50, 50 |
|    | 100x | I, M, L, F | 25, 25, 25, 25 | I, M, L, F | 25, 25, 25, 25 | I, M, L, F | 25, 25, 25, 25 | I, M, L, F | 25, 25, 25, 25 | I, M, L, F | 25, 25, 25, 25 | I, M, L, F | 25, 25, 25, 25 |

FIGURE 19B

FIG. 20A: Mutagenic oligonucleotides used in the construction of libraries SAH3, SCH3, SFH3, SGH3, SIH3, SLH3, SNH3, SPH3, SRH3, STH3, SWH3 and SYH3. Equimolar DNA degeneracies are represented in the IUB code (W = A/T, K = G/T, M = A/C, S = G/C, Y = C/T, R = A/G).

H1
GCA GCT TCT GGC TTC TMT ATT TMT TMT TMT TMT ATA CAC TGG GTG CGT (SEQ ID NO: 618)
H2
CTG GAA TGG GTT GCA TMT ATT TMT CCA TMT TMT GGT TMT ACT TMT TAT GCC GAT AGC GTC (SEQ ID NO: 619)
L3
ACT TAT TAC TGT CAG CAA TMT TMT TMT TMT CCA TMT ACG TTC GGA CAG GGT ACC (SEQ ID NO: 620)
H3-SA4
GTC TAT TAT TGT GCT CGC KCT KCT KCT KCT GST WTK GAC TAC TGG GGT CAA GGA (SEQ ID NO: 621)
H3-SA5
GTC TAT TAT TGT GCT CGC KCT KCT KCT KCT KCT GST WTK GAC TAC TGG GGT CAA GGA (SEQ ID NO: 622)
H3-SA6
GTC TAT TAT TGT GCT CGC KCT KCT KCT KCT KCT KCT GST WTK GAC TAC TGG GGT CAA GGA (SEQ ID NO: 623)
H3-SA7
GTC TAT TAT TGT GCT CGC KCT KCT KCT KCT KCT KCT KCT GST WTK GAC TAC TGG GGT CAA GGA (SEQ ID NO: 624)
H3-SA8
GTC TAT TAT TGT GCT CGC KCT KCT KCT KCT KCT KCT KCT KCT GST WTK GAC TAC TGG GGT CAA GGA (SEQ ID NO: 625)
H3-SA9
GTC TAT TAT TGT GCT CGC KCT KCT KCT KCT KCT KCT KCT KCT KCT GST WTK GAC TAC TGG GGT CAA GGA (SEQ ID NO: 626)
H3-sA10
GTC TAT TAT TGT GCT CGC KCT KCT KCT KCT KCT KCT KCT KCT KCT KCT GST WTK GAC TAC TGG GGT CAA GGA (SEQ ID NO: 627)
H3-SA11
GTC TAT TAT TGT GCT CGC KCT KCT KCT KCT KCT KCT KCT KCT KCT KCT KCT GST WTK GAC TAC TGG GGT CAA GGA (SEQ ID NO: 628)
H3-SA12
GTC TAT TAT TGT GCT CGC KCT KCT KCT KCT KCT KCT KCT KCT KCT KCT KCT KCT GST WTK GAC TAC TGG GGT CAA GGA (SEQ ID NO: 629)
H3-SA13
GTC TAT TAT TGT GCT CGC KCT KCT KCT KCT KCT KCT KCT KCT KCT KCT KCT KCT KCT GST WTK GAC TAC TGG GGT CAA GGA (SEQ ID NO: 630)
H3-SA14
GTC TAT TAT TGT GCT CGC KCT KCT KCT KCT KCT KCT KCT KCT KCT KCT KCT KCT KCT KCT GST WTK GAC TAC TGG GGT CAA GGA (SEQ ID NO: 631)
H3-SA15
GTC TAT TAT TGT GCT CGC KCT KCT KCT KCT KCT KCT KCT KCT KCT KCT KCT KCT KCT KCT KCT GST WTK GAC TAC TGG GGT CAA GGA (SEQ ID NO: 632)
H3-SA16
GTC TAT TAT TGT GCT CGC KCT KCT KCT KCT KCT KCT KCT KCT KCT KCT KCT KCT KCT KCT KCT KCT GST WTK GAC TAC TGG GGT CAA GGA (SEQ ID NO: 633)
H3-SA17
GTC TAT TAT TGT GCT CGC KCT KCT KCT KCT KCT KCT KCT KCT KCT KCT KCT KCT KCT KCT KCT KCT KCT GST WTK GAC TAC TGG GGT CAA GGA (SEQ ID NO: 634)

FIG. 20B: Mutagenic oligonucleotides used in the construction of libraries SCH3. Equimolar DNA degeneracies are represented in the IUB code (W = A/T, K = G/T, M = A/C, S = G/C, Y = C/T, R = A/G).

H3-SC4
GTC TAT TAT TGT GCT CGC TSC TSC TSC TSC GST WTK GAC TAC TGG GGT CAA GGA  (SEQ ID NO: 635)

H3-SC5
GTC TAT TAT TGT GCT CGC TSC TSC TSC TSC TSC GST WTK GAC TAC TGG GGT CAA GGA  (SEQ ID NO: 636)

H3-SC6
GTC TAT TAT TGT GCT CGC TSC TSC TSC TSC TSC TSC GST WTK GAC TAC TGG GGT CAA GGA  (SEQ ID NO: 637)

H3-SC7
GTC TAT TAT TGT GCT CGC TSC TSC TSC TSC TSC TSC TSC GST WTK GAC TAC TGG GGT CAA GGA  (SEQ ID NO: 638)

H3-SC8
GTC TAT TAT TGT GCT CGC TSC TSC TSC TSC TSC TSC TSC TSC GST WTK GAC TAC TGG GGT CAA GGA  (SEQ ID NO: 639)

H3-SC9
GTC TAT TAT TGT GCT CGC TSC TSC TSC TSC TSC TSC TSC TSC TSC GST WTK GAC TAC TGG GGT CAA GGA  (SEQ ID NO: 640)

H3-SC10
GTC TAT TAT TGT GCT CGC TSC TSC TSC TSC TSC TSC TSC TSC TSC TSC GST WTK GAC TAC TGG GGT CAA GGA  (SEQ ID NO: 641)

H3-SC11
GTC TAT TAT TGT GCT CGC TSC TSC TSC TSC TSC TSC TSC TSC TSC TSC TSC GST WTK GAC TAC TGG GGT CAA GGA  (SEQ ID NO: 642)

H3-SC12
GTC TAT TAT TGT GCT CGC TSC TSC TSC TSC TSC TSC TSC TSC TSC TSC TSC TSC GST WTK GAC TAC TGG GGT CAA GGA  (SEQ ID NO: 643)

H3-SC13
GTC TAT TAT TGT GCT CGC TSC TSC TSC TSC TSC TSC TSC TSC TSC TSC TSC TSC TSC GST WTK GAC TAC TGG GGT CAA GGA  (SEQ ID NO: 644)

H3-SC14
GTC TAT TAT TGT GCT CGC TSC TSC TSC TSC TSC TSC TSC TSC TSC TSC TSC TSC TSC TSC GST WTK GAC TAC TGG GGT CAA GGA  (SEQ ID NO: 645)

H3-SC15
GTC TAT TAT TGT GCT CGC TSC TSC TSC TSC TSC TSC TSC TSC TSC TSC TSC TSC TSC TSC TSC GST WTK GAC TAC TGG GGT CAA GGA  (SEQ ID NO: 646)

H3-SC16
GTC TAT TAT TGT GCT CGC TSC TSC TSC TSC TSC TSC TSC TSC TSC TSC TSC TSC TSC TSC TSC TSC GST WTK GAC TAC TGG GGT CAA GGA  (SEQ ID NO: 647)

H3-SC17
GTC TAT TAT TGT GCT CGC TSC TSC TSC TSC TSC TSC TSC TSC TSC TSC TSC TSC TSC TSC TSC TSC TSC GST WTK GAC TAC TGG GGT CAA GGA  (SEQ ID NO: 648)

FIG. 20C: Mutagenic oligonucleotides used in the construction of libraries SFH3. Equimolar DNA degeneracies are represented in the IUB code (W = A/T, K = G/T, M = A/C, S = G/C, Y = C/T, R = A/G).

H3-SF4
GTC TAT TAT TGT GCT CGC TYC TYC TYC TYC GST WTK GAC TAC TGG GGT CAA GGA (SEQ ID NO: 649)

H3-SF5
GTC TAT TAT TGT GCT CGC TYC TYC TYC TYC TYC GST WTK GAC TAC TGG GGT CAA GGA (SEQ ID NO: 650)

H3-SF6
GTC TAT TAT TGT GCT CGC TYC TYC TYC TYC TYC TYC GST WTK GAC TAC TGG GGT CAA GGA (SEQ ID NO: 651)

H3-SF7
GTC TAT TAT TGT GCT CGC TYC TYC TYC TYC TYC TYC TYC GST WTK GAC TAC TGG GGT CAA GGA (SEQ ID NO: 652)

H3-SF8
GTC TAT TAT TGT GCT CGC TYC TYC TYC TYC TYC TYC TYC TYC GST WTK GAC TAC TGG GGT CAA GGA (SEQ ID NO: 653)

H3-SF9
GTC TAT TAT TGT GCT CGC TYC TYC TYC TYC TYC TYC TYC TYC TYC GST WTK GAC TAC TGG GGT CAA GGA (SEQ ID NO: 654)

H3-SF10
GTC TAT TAT TGT GCT CGC TYC TYC TYC TYC TYC TYC TYC TYC TYC TYC GST WTK GAC TAC TGG GGT CAA GGA (SEQ ID NO: 655)

H3-SF11
GTC TAT TAT TGT GCT CGC TYC TYC TYC TYC TYC TYC TYC TYC TYC TYC TYC GST WTK GAC TAC TGG GGT CAA GGA (SEQ ID NO: 656)

H3-SF12
GTC TAT TAT TGT GCT CGC TYC TYC TYC TYC TYC TYC TYC TYC TYC TYC TYC TYC GST WTK GAC TAC TGG GGT CAA GGA (SEQ ID NO: 657)

H3-SF13
GTC TAT TAT TGT GCT CGC TYC TYC TYC TYC TYC TYC TYC TYC TYC TYC TYC TYC TYC GST WTK GAC TAC TGG GGT CAA GGA (SEQ ID NO: 658)

H3-SF14
GTC TAT TAT TGT GCT CGC TYC TYC TYC TYC TYC TYC TYC TYC TYC TYC TYC TYC TYC TYC GST WTK GAC TAC TGG GGT CAA GGA (SEQ ID NO: 659)

H3-SF15
GTC TAT TAT TGT GCT CGC TYC TYC TYC TYC TYC TYC TYC TYC TYC TYC TYC TYC TYC TYC TYC GST WTK GAC TAC TGG GGT CAA GGA (SEQ ID NO: 660)

H3-SF16
GTC TAT TAT TGT GCT CGC TYC TYC TYC TYC TYC TYC TYC TYC TYC TYC TYC TYC TYC TYC TYC TYC GST WTK GAC TAC TGG GGT CAA GGA (SEQ ID NO: 661)

H3-SF17
GTC TAT TAT TGT GCT CGC TYC TYC TYC TYC TYC TYC TYC TYC TYC TYC TYC TYC TYC TYC TYC TYC TYC GST WTK GAC TAC TGG GGT CAA GGA (SEQ ID NO: 662)

FIG. 20D: Mutagenic oligonucleotides used in the construction of libraries SGH3. Equimolar DNA degeneracies are represented in the IUB code (W = A/T, K = G/T, M = A/C, S = G/C, Y = C/T, R = A/G).

H3-SG4
GTC TAT TAT TGT GCT CGC RGC RGC RGC RGC GST WTK GAC TAC TGG GGT CAA GGA (SEQ ID NO: 663)
H3-SG5
GTC TAT TAT TGT GCT CGC RGC RGC RGC RGC RGC GST WTK GAC TAC TGG GGT CAA GGA (SEQ ID NO: 664)
H3-SG6
GTC TAT TAT TGT GCT CGC RGC RGC RGC RGC RGC RGC GST WTK GAC TAC TGG GGT CAA GGA (SEQ ID NO: 665)
H3-SG7
GTC TAT TAT TGT GCT CGC RGC RGC RGC RGC RGC RGC RGC GST WTK GAC TAC TGG GGT CAA GGA (SEQ ID NO: 666)
H3-SG8
GTC TAT TAT TGT GCT CGC RGC RGC RGC RGC RGC RGC RGC RGC GST WTK GAC TAC TGG GGT CAA GGA (SEQ ID NO: 667)
H3-SG9
GTC TAT TAT TGT GCT CGC RGC RGC RGC RGC RGC RGC RGC RGC RGC GST WTK GAC TAC TGG GGT CAA GGA (SEQ ID NO: 668)
H3-SG10
GTC TAT TAT TGT GCT CGC RGC RGC RGC RGC RGC RGC RGC RGC RGC RGC GST WTK GAC TAC TGG GGT CAA GGA (SEQ ID NO: 669)
H3-SG11
GTC TAT TAT TGT GCT CGC RGC RGC RGC RGC RGC RGC RGC RGC RGC RGC RGC GST WTK GAC TAC TGG GGT CAA GGA (SEQ ID NO: 670)
H3-SG12
GTC TAT TAT TGT GCT CGC RGC RGC RGC RGC RGC RGC RGC RGC RGC RGC RGC RGC GST WTK GAC TAC TGG GGT CAA GGA (SEQ ID NO: 671)
H3-SG13
GTC TAT TAT TGT GCT CGC RGC RGC RGC RGC RGC RGC RGC RGC RGC RGC RGC RGC RGC GST WTK GAC TAC TGG GGT CAA GGA (SEQ ID NO: 672)
H3-SG14
GTC TAT TAT TGT GCT CGC RGC RGC RGC RGC RGC RGC RGC RGC RGC RGC RGC RGC RGC RGC GST WTK GAC TAC TGG GGT CAA GGA (SEQ ID NO: 673)
H3-SG15
GTC TAT TAT TGT GCT CGC RGC RGC RGC RGC RGC RGC RGC RGC RGC RGC RGC RGC RGC RGC RGC GST WTK GAC TAC TGG GGT CAA GGA (SEQ ID NO: 674)
H3-SG16
GTC TAT TAT TGT GCT CGC RGC RGC RGC RGC RGC RGC RGC RGC RGC RGC RGC RGC RGC RGC RGC RGC GST WTK GAC TAC TGG GGT CAA GGA (SEQ ID NO: 675)
H3-SG17
GTC TAT TAT TGT GCT CGC RGC RGC RGC RGC RGC RGC RGC RGC RGC RGC RGC RGC RGC RGC RGC RGC RGC GST WTK GAC TAC TGG GGT CAA GGA (SEQ ID NO: 676)

FIG. 20E: Mutagenic oligonucleotides used in the construction of libraries SIH3. Equimolar DNA degeneracies are represented in the IUB code (W = A/T, K = G/T, M = A/C, S = G/C, Y = C/T, R = A/G).

H3-SI4
GTC TAT TAT TGT GCT CGC AKC AKC AKC AKC GST WTK GAC TAC TGG GGT CAA GGA (SEQ ID NO: 677)

H3-SI5
GTC TAT TAT TGT GCT CGC AKC AKC AKC AKC AKC GST WTK GAC TAC TGG GGT CAA GGA (SEQ ID NO: 678)

H3-SI6
GTC TAT TAT TGT GCT CGC AKC AKC AKC AKC AKC AKC GST WTK GAC TAC TGG GGT CAA GGA (SEQ ID NO: 679)

H3-SI7
GTC TAT TAT TGT GCT CGC AKC AKC AKC AKC AKC AKC AKC GST WTK GAC TAC TGG GGT CAA GGA (SEQ ID NO: 680)

H3-SI8
GTC TAT TAT TGT GCT CGC AKC AKC AKC AKC AKC AKC AKC AKC GST WTK GAC TAC TGG GGT CAA GGA (SEQ ID NO: 681)

H3-SI9
GTC TAT TAT TGT GCT CGC AKC AKC AKC AKC AKC AKC AKC AKC AKC GST WTK GAC TAC TGG GGT CAA GGA (SEQ ID NO: 682)

H3-SI10
GTC TAT TAT TGT GCT CGC AKC AKC AKC AKC AKC AKC AKC AKC AKC AKC GST WTK GAC TAC TGG GGT CAA GGA (SEQ ID NO: 683)

H3-SI11
GTC TAT TAT TGT GCT CGC AKC AKC AKC AKC AKC AKC AKC AKC AKC AKC AKC GST WTK GAC TAC TGG GGT CAA GGA (SEQ ID NO: 684)

H3-SI12
GTC TAT TAT TGT GCT CGC AKC AKC AKC AKC AKC AKC AKC AKC AKC AKC AKC AKC GST WTK GAC TAC TGG GGT CAA GGA (SEQ ID NO: 685)

H3-SI13
GTC TAT TAT TGT GCT CGC AKC AKC AKC AKC AKC AKC AKC AKC AKC AKC AKC AKC AKC GST WTK GAC TAC TGG GGT CAA GGA (SEQ ID NO: 686)

H3-SI14
GTC TAT TAT TGT GCT CGC AKC AKC AKC AKC AKC AKC AKC AKC AKC AKC AKC AKC AKC AKC GST WTK GAC TAC TGG GGT CAA GGA (SEQ ID NO: 687)

H3-SI15
GTC TAT TAT TGT GCT CGC AKC AKC AKC AKC AKC AKC AKC AKC AKC AKC AKC AKC AKC AKC AKC GST WTK GAC TAC TGG GGT CAA GGA (SEQ ID NO: 688)

H3-SI16
GTC TAT TAT TGT GCT CGC AKC AKC AKC AKC AKC AKC AKC AKC AKC AKC AKC AKC AKC AKC AKC AKC GST WTK GAC TAC TGG GGT CAA GGA (SEQ ID NO: 689)

H3-SI17
GTC TAT TAT TGT GCT CGC AKC AKC AKC AKC AKC AKC AKC AKC AKC AKC AKC AKC AKC AKC AKC AKC AKC GST WTK GAC TAC TGG GGT CAA GGA (SEQ ID NO: 690)

FIG. 20F: Mutagenic oligonucleotides used in the construction of libraries SLH3. Equimolar DNA degeneracies are represented in the IUB code (W = A/T, K = G/T, M = A/C, S = G/C, Y = C/T, R = A/G).

H3-SL4
GTC TAT TAT TGT GCT CGC TYA TYA TYA TYA GST WTK GAC TAC TGG GGT CAA GGA  (SEQ ID NO: 691)
H3-SL5
GTC TAT TAT TGT GCT CGC TYA TYA TYA TYA TYA GST WTK GAC TAC TGG GGT CAA GGA  (SEQ ID NO: 692)
H3-SL6
GTC TAT TAT TGT GCT CGC TYA TYA TYA TYA TYA TYA GST WTK GAC TAC TGG GGT CAA GGA  (SEQ ID NO: 693)
H3-SL7
GTC TAT TAT TGT GCT CGC TYA TYA TYA TYA TYA TYA TYA GST WTK GAC TAC TGG GGT CAA GGA  (SEQ ID NO: 694)
H3-SL8
GTC TAT TAT TGT GCT CGC TYA TYA TYA TYA TYA TYA TYA TYA GST WTK GAC TAC TGG GGT CAA GGA  (SEQ ID NO: 695)
H3-SL9
GTC TAT TAT TGT GCT CGC TYA TYA TYA TYA TYA TYA TYA TYA TYA GST WTK GAC TAC TGG GGT CAA GGA  (SEQ ID NO: 696)
H3-SL10
GTC TAT TAT TGT GCT CGC TYA TYA TYA TYA TYA TYA TYA TYA TYA TYA GST WTK GAC TAC TGG GGT CAA GGA  (SEQ ID NO: 697)
H3-SL11
GTC TAT TAT TGT GCT CGC TYA TYA TYA TYA TYA TYA TYA TYA TYA TYA TYA GST WTK GAC TAC TGG GGT CAA GGA  (SEQ ID NO: 698)
H3-SL12
GTC TAT TAT TGT GCT CGC TYA TYA TYA TYA TYA TYA TYA TYA TYA TYA TYA TYA GST WTK GAC TAC TGG GGT CAA GGA  (SEQ ID NO: 699)
H3-SL13
GTC TAT TAT TGT GCT CGC TYA TYA TYA TYA TYA TYA TYA TYA TYA TYA TYA TYA TYA GST WTK GAC TAC TGG GGT CAA GGA  (SEQ ID NO: 700)
H3-SL14
GTC TAT TAT TGT GCT CGC TYA TYA TYA TYA TYA TYA TYA TYA TYA TYA TYA TYA TYA TYA GST WTK GAC TAC TGG GGT CAA GGA  (SEQ ID NO: 701)
H3-SL15
GTC TAT TAT TGT GCT CGC TYA TYA TYA TYA TYA TYA TYA TYA TYA TYA TYA TYA TYA TYA TYA GST WTK GAC TAC TGG GGT CAA GGA  (SEQ ID NO: 702)
H3-SL16
GTC TAT TAT TGT GCT CGC TYA TYA TYA TYA TYA TYA TYA TYA TYA TYA TYA TYA TYA TYA TYA TYA GST WTK GAC TAC TGG GGT CAA GGA  (SEQ ID NO: 703)
H3-SL17
GTC TAT TAT TGT GCT CGC TYA TYA TYA TYA TYA TYA TYA TYA TYA TYA TYA TYA TYA TYA TYA TYA TYA GST WTK GAC TAC TGG GGT CAA GGA  (SEQ ID NO: 704)

FIG. 20G: Mutagenic oligonucleotides used in the construction of libraries SNH3. Equimolar DNA degeneracies are represented in the IUB code (W = A/T, K = G/T, M = A/C, S = G/C, Y = C/T, R = A/G).

H3-SN4
GTC TAT TAT TGT GCT CGC ARC ARC ARC ARC GST WTK GAC TAC TGG GGT CAA GGA  (SEQ ID NO: 705)

H3-SN5
GTC TAT TAT TGT GCT CGC ARC ARC ARC ARC ARC GST WTK GAC TAC TGG GGT CAA GGA  (SEQ ID NO: 706)

H3-SN6
GTC TAT TAT TGT GCT CGC ARC ARC ARC ARC ARC ARC GST WTK GAC TAC TGG GGT CAA GGA  (SEQ ID NO: 707)

H3-SN7
GTC TAT TAT TGT GCT CGC ARC ARC ARC ARC ARC ARC ARC GST WTK GAC TAC TGG GGT CAA GGA  (SEQ ID NO: 708)

H3-SN8
GTC TAT TAT TGT GCT CGC ARC ARC ARC ARC ARC ARC ARC ARC GST WTK GAC TAC TGG GGT CAA GGA  (SEQ ID NO: 709)

H3-SN9
GTC TAT TAT TGT GCT CGC ARC ARC ARC ARC ARC ARC ARC ARC ARC GST WTK GAC TAC TGG GGT CAA GGA  (SEQ ID NO: 710)

H3-SN10
GTC TAT TAT TGT GCT CGC ARC ARC ARC ARC ARC ARC ARC ARC ARC ARC GST WTK GAC TAC TGG GGT CAA GGA  (SEQ ID NO: 711)

H3-SN11
GTC TAT TAT TGT GCT CGC ARC ARC ARC ARC ARC ARC ARC ARC ARC ARC ARC GST WTK GAC TAC TGG GGT CAA GGA  (SEQ ID NO: 712)

H3-SN12
GTC TAT TAT TGT GCT CGC ARC ARC ARC ARC ARC ARC ARC ARC ARC ARC ARC ARC GST WTK GAC TAC TGG GGT CAA GGA  (SEQ ID NO: 713)

H3-SN13
GTC TAT TAT TGT GCT CGC ARC ARC ARC ARC ARC ARC ARC ARC ARC ARC ARC ARC ARC GST WTK GAC TAC TGG GGT CAA GGA  (SEQ ID NO: 714)

H3-SN14
GTC TAT TAT TGT GCT CGC ARC ARC ARC ARC ARC ARC ARC ARC ARC ARC ARC ARC ARC ARC GST WTK GAC TAC TGG GGT CAA GGA  (SEQ ID NO: 715)

H3-SN15
GTC TAT TAT TGT GCT CGC ARC ARC ARC ARC ARC ARC ARC ARC ARC ARC ARC ARC ARC ARC ARC GST WTK GAC TAC TGG GGT CAA GGA  (SEQ ID NO: 716)

H3-SN16
GTC TAT TAT TGT GCT CGC ARC ARC ARC ARC ARC ARC ARC ARC ARC ARC ARC ARC ARC ARC ARC ARC GST WTK GAC TAC TGG GGT CAA GGA  (SEQ ID NO: 717)

H3-SN17
GTC TAT TAT TGT GCT CGC ARC ARC ARC ARC ARC ARC ARC ARC ARC ARC ARC ARC ARC ARC ARC ARC ARC GST WTK GAC TAC TGG GGT CAA GGA  (SEQ ID NO: 718)

FIG. 20H: Mutagenic oligonucleotides used in the construction of libraries SPH3. Equimolar DNA degeneracies are represented in the IUB code (W = A/T, K = G/T, M = A/C, S = G/C, Y = C/T, R = A/G).

H3-SP4
GTC TAT TAT TGT GCT CGC YCT YCT YCT YCT GST WTK GAC TAC TGG GGT CAA GGA  (SEQ ID NO: 719)

H3-SP5
GTC TAT TAT TGT GCT CGC YCT YCT YCT YCT YCT GST WTK GAC TAC TGG GGT CAA GGA  (SEQ ID NO: 720)

H3-SP6
GTC TAT TAT TGT GCT CGC YCT YCT YCT YCT YCT YCT GST WTK GAC TAC TGG GGT CAA GGA  (SEQ ID NO: 721)

H3-SP7
GTC TAT TAT TGT GCT CGC YCT YCT YCT YCT YCT YCT YCT GST WTK GAC TAC TGG GGT CAA GGA  (SEQ ID NO: 722)

H3-SP8
GTC TAT TAT TGT GCT CGC YCT YCT YCT YCT YCT YCT YCT YCT GST WTK GAC TAC TGG GGT CAA GGA  (SEQ ID NO: 723)

H3-SP9
GTC TAT TAT TGT GCT CGC YCT YCT YCT YCT YCT YCT YCT YCT YCT GST WTK GAC TAC TGG GGT CAA GGA  (SEQ ID NO: 724)

H3-SP10
GTC TAT TAT TGT GCT CGC YCT YCT YCT YCT YCT YCT YCT YCT YCT YCT GST WTK GAC TAC TGG GGT CAA GGA  (SEQ ID NO: 725)

H3-SP11
GTC TAT TAT TGT GCT CGC YCT YCT YCT YCT YCT YCT YCT YCT YCT YCT YCT GST WTK GAC TAC TGG GGT CAA GGA  (SEQ ID NO: 726)

H3-SP12
GTC TAT TAT TGT GCT CGC YCT YCT YCT YCT YCT YCT YCT YCT YCT YCT YCT YCT GST WTK GAC TAC TGG GGT CAA GGA  (SEQ ID NO: 727)

H3-SP13
GTC TAT TAT TGT GCT CGC YCT YCT YCT YCT YCT YCT YCT YCT YCT YCT YCT YCT YCT GST WTK GAC TAC TGG GGT CAA GGA  (SEQ ID NO: 728)

H3-SP14
GTC TAT TAT TGT GCT CGC YCT YCT YCT YCT YCT YCT YCT YCT YCT YCT YCT YCT YCT YCT GST WTK GAC TAC TGG GGT CAA GGA  (SEQ ID NO: 729)

H3-SP15
GTC TAT TAT TGT GCT CGC YCT YCT YCT YCT YCT YCT YCT YCT YCT YCT YCT YCT YCT YCT YCT GST WTK GAC TAC TGG GGT CAA GGA  (SEQ ID NO: 730)

H3-SP16
GTC TAT TAT TGT GCT CGC YCT YCT YCT YCT YCT YCT YCT YCT YCT YCT YCT YCT YCT YCT YCT YCT GST WTK GAC TAC TGG GGT CAA GGA  (SEQ ID NO: 731)

H3-SP17
GTC TAT TAT TGT GCT CGC YCT YCT YCT YCT YCT YCT YCT YCT YCT YCT YCT YCT YCT YCT YCT YCT YCT GST WTK GAC TAC TGG GGT CAA GGA  (SEQ ID NO: 732)

FIG. 20I: Mutagenic oligonucleotides used in the construction of libraries SRH3. Equimolar DNA degeneracies are represented in the IUB code (W = A/T, K = G/T, M = A/C, S = G/C, Y = C/T, R = A/G).

H3-SR4
GTC TAT TAT TGT GCT CGC MGC MGC MGC MGC GST WTK GAC TAC TGG GGT CAA GGA (SEQ ID NO: 733)
H3-SR5
GTC TAT TAT TGT GCT CGC MGC MGC MGC MGC MGC GST WTK GAC TAC TGG GGT CAA GGA (SEQ ID NO: 734)
H3-SR6
GTC TAT TAT TGT GCT CGC MGC MGC MGC MGC MGC MGC GST WTK GAC TAC TGG GGT CAA GGA (SEQ ID NO: 735)
H3-SR7
GTC TAT TAT TGT GCT CGC MGC MGC MGC MGC MGC MGC MGC GST WTK GAC TAC TGG GGT CAA GGA (SEQ ID NO: 736)
H3-SR8
GTC TAT TAT TGT GCT CGC MGC MGC MGC MGC MGC MGC MGC MGC GST WTK GAC TAC TGG GGT CAA GGA (SEQ ID NO: 737)
H3-SR9
GTC TAT TAT TGT GCT CGC MGC MGC MGC MGC MGC MGC MGC MGC MGC GST WTK GAC TAC TGG GGT CAA GGA (SEQ ID NO: 738)
H3-SR10
GTC TAT TAT TGT GCT CGC MGC MGC MGC MGC MGC MGC MGC MGC MGC MGC GST WTK GAC TAC TGG GGT CAA GGA (SEQ ID NO: 739)
H3-SR11
GTC TAT TAT TGT GCT CGC MGC MGC MGC MGC MGC MGC MGC MGC MGC MGC MGC GST WTK GAC TAC TGG GGT CAA GGA (SEQ ID NO: 740)
H3-SR12
GTC TAT TAT TGT GCT CGC MGC MGC MGC MGC MGC MGC MGC MGC MGC MGC MGC MGC GST WTK GAC TAC TGG GGT CAA GGA (SEQ ID NO: 741)
H3-SR13
GTC TAT TAT TGT GCT CGC MGC MGC MGC MGC MGC MGC MGC MGC MGC MGC MGC MGC MGC GST WTK GAC TAC TGG GGT CAA GGA (SEQ ID NO: 742)
H3-SR14
GTC TAT TAT TGT GCT CGC MGC MGC MGC MGC MGC MGC MGC MGC MGC MGC MGC MGC MGC MGC GST WTK GAC TAC TGG GGT CAA GGA (SEQ ID NO: 743)
H3-SR15
GTC TAT TAT TGT GCT CGC MGC MGC MGC MGC MGC MGC MGC MGC MGC MGC MGC MGC MGC MGC MGC GST WTK GAC TAC TGG GGT CAA GGA (SEQ ID NO: 744)
H3-SR16
GTC TAT TAT TGT GCT CGC MGC MGC MGC MGC MGC MGC MGC MGC MGC MGC MGC MGC MGC MGC MGC MGC GST WTK GAC TAC TGG GGT CAA GGA (SEQ ID NO: 745)
H3-SR17
GTC TAT TAT TGT GCT CGC MGC MGC MGC MGC MGC MGC MGC MGC MGC MGC MGC MGC MGC MGC MGC MGC MGC GST WTK GAC TAC TGG GGT CAA GGA (SEQ ID NO: 746)

FIG. 20J: Mutagenic oligonucleotides used in the construction of libraries STH3. Equimolar DNA degeneracies are represented in the IUB code (W = A/T, K = G/T, M = A/C, S = G/C, Y = C/T, R = A/G).

H3-ST4
GTC TAT TAT TGT GCT CGC ASC ASC ASC ASC GST WTK GAC TAC TGG GGT CAA GGA (SEQ ID NO: 747)
H3-ST5
GTC TAT TAT TGT GCT CGC ASC ASC ASC ASC ASC GST WTK GAC TAC TGG GGT CAA GGA (SEQ ID NO: 748)
H3-ST6
GTC TAT TAT TGT GCT CGC ASC ASC ASC ASC ASC ASC GST WTK GAC TAC TGG GGT CAA GGA (SEQ ID NO: 749)
H3-ST7
GTC TAT TAT TGT GCT CGC ASC ASC ASC ASC ASC ASC ASC GST WTK GAC TAC TGG GGT CAA GGA (SEQ ID NO: 750)
H3-ST8
GTC TAT TAT TGT GCT CGC ASC ASC ASC ASC ASC ASC ASC ASC GST WTK GAC TAC TGG GGT CAA GGA (SEQ ID NO: 751)
H3-ST9
GTC TAT TAT TGT GCT CGC ASC ASC ASC ASC ASC ASC ASC ASC ASC GST WTK GAC TAC TGG GGT CAA GGA (SEQ ID NO: 752)
H3-ST10
GTC TAT TAT TGT GCT CGC ASC ASC ASC ASC ASC ASC ASC ASC ASC ASC GST WTK GAC TAC TGG GGT CAA GGA (SEQ ID NO: 753)
H3-ST11
GTC TAT TAT TGT GCT CGC ASC ASC ASC ASC ASC ASC ASC ASC ASC ASC ASC GST WTK GAC TAC TGG GGT CAA GGA (SEQ ID NO: 754)
H3-ST12
GTC TAT TAT TGT GCT CGC ASC ASC ASC ASC ASC ASC ASC ASC ASC ASC ASC ASC GST WTK GAC TAC TGG GGT CAA GGA (SEQ ID NO: 755)
H3-ST13
GTC TAT TAT TGT GCT CGC ASC ASC ASC ASC ASC ASC ASC ASC ASC ASC ASC ASC ASC GST WTK GAC TAC TGG GGT CAA GGA (SEQ ID NO: 756)
H3-ST14
GTC TAT TAT TGT GCT CGC ASC ASC ASC ASC ASC ASC ASC ASC ASC ASC ASC ASC ASC ASC GST WTK GAC TAC TGG GGT CAA GGA (SEQ ID NO: 757)
H3-ST15
GTC TAT TAT TGT GCT CGC ASC ASC ASC ASC ASC ASC ASC ASC ASC ASC ASC ASC ASC ASC ASC GST WTK GAC TAC TGG GGT CAA GGA (SEQ ID NO: 758)
H3-ST16
GTC TAT TAT TGT GCT CGC ASC ASC ASC ASC ASC ASC ASC ASC ASC ASC ASC ASC ASC ASC ASC ASC GST WTK GAC TAC TGG GGT CAA GGA (SEQ ID NO: 759)
H3-ST17
GTC TAT TAT TGT GCT CGC ASC ASC ASC ASC ASC ASC ASC ASC ASC ASC ASC ASC ASC ASC ASC ASC ASC GST WTK GAC TAC TGG GGT CAA GGA (SEQ ID NO: 760)

FIG. 20K: Mutagenic oligonucleotides used in the construction of libraries SWH3. Equimolar DNA degeneracies are represented in the IUB code (W = A/T, K = G/T, M = A/C, S = G/C, Y = C/T, R = A/G).

H3-SW4
GTC TAT TAT TGT GCT CGC TSG TSG TSG TSG GST WTK GAC TAC TGG GGT CAA GGA  (SEQ ID NO: 761)
H3-SW5
GTC TAT TAT TGT GCT CGC TSG TSG TSG TSG TSG GST WTK GAC TAC TGG GGT CAA GGA (SEQ ID NO: 762)
H3-SW6
GTC TAT TAT TGT GCT CGC TSG TSG TSG TSG TSG TSG GST WTK GAC TAC TGG GGT CAA GGA (SEQ ID NO: 763)
H3-SW7
GTC TAT TAT TGT GCT CGC TSG TSG TSG TSG TSG TSG TSG GST WTK GAC TAC TGG GGT CAA GGA  (SEQ ID NO: 764)
H3-SW8
GTC TAT TAT TGT GCT CGC TSG TSG TSG TSG TSG TSG TSG TSG GST WTK GAC TAC TGG GGT CAA GGA  (SEQ ID NO: 765)
H3-SW9
GTC TAT TAT TGT GCT CGC TSG TSG TSG TSG TSG TSG TSG TSG TSG GST WTK GAC TAC TGG GGT CAA GGA  (SEQ ID NO: 766)
H3-SW10
GTC TAT TAT TGT GCT CGC TSG TSG TSG TSG TSG TSG TSG TSG TSG TSG GST WTK GAC TAC TGG GGT CAA GGA  (SEQ ID NO: 767)
H3-SW11
GTC TAT TAT TGT GCT CGC TSG TSG TSG TSG TSG TSG TSG TSG TSG TSG TSG GST WTK GAC TAC TGG GGT CAA GGA  (SEQ ID NO: 768)
H3-SW12
GTC TAT TAT TGT GCT CGC TSG TSG TSG TSG TSG TSG TSG TSG TSG TSG TSG TSG GST WTK GAC TAC TGG GGT CAA GGA  (SEQ ID NO: 769)
H3-SW13
GTC TAT TAT TGT GCT CGC TSG TSG TSG TSG TSG TSG TSG TSG TSG TSG TSG TSG TSG GST WTK GAC TAC TGG GGT CAA GGA  (SEQ ID NO: 770)
H3-SW14
GTC TAT TAT TGT GCT CGC TSG TSG TSG TSG TSG TSG TSG TSG TSG TSG TSG TSG TSG TSG GST WTK GAC TAC TGG GGT CAA GGA  (SEQ ID NO: 771)
H3-SW15
GTC TAT TAT TGT GCT CGC TSG TSG TSG TSG TSG TSG TSG TSG TSG TSG TSG TSG TSG TSG TSG GST WTK GAC TAC TGG GGT CAA GGA  (SEQ ID NO: 772)
H3-SW16
GTC TAT TAT TGT GCT CGC TSG TSG TSG TSG TSG TSG TSG TSG TSG TSG TSG TSG TSG TSG TSG TSG GST WTK GAC TAC TGG GGT CAA GGA  (SEQ ID NO: 773)
H3-SW17
GTC TAT TAT TGT GCT CGC TSG TSG TSG TSG TSG TSG TSG TSG TSG TSG TSG TSG TSG TSG TSG TSG TSG GST WTK GAC TAC TGG GGT CAA GGA  (SEQ ID NO: 774)

FIG. 20L: Mutagenic oligonucleotides used in the construction of libraries SYH3. Equimolar DNA degeneracies are represented in the IUB code (W = A/T, K = G/T, M = A/C, S = G/C, Y = C/T, R = A/G).

H3-SY4
GTC TAT TAT TGT GCT CGC TMT TMT TMT TMT GST WTK GAC TAC TGG GGT CAA GGA  (SEQ ID NO: 775)
H3-SY5
GTC TAT TAT TGT GCT CGC TMT TMT TMT TMT TMT GST WTK GAC TAC TGG GGT CAA GGA  (SEQ ID NO: 776)
H3-SY6
GTC TAT TAT TGT GCT CGC TMT TMT TMT TMT TMT TMT GST WTK GAC TAC TGG GGT CAA GGA  (SEQ ID NO: 777)
H3-SY7
GTC TAT TAT TGT GCT CGC TMT TMT TMT TMT TMT TMT TMT GST WTK GAC TAC TGG GGT CAA GGA  (SEQ ID NO: 778)
H3-SY8
GTC TAT TAT TGT GCT CGC TMT TMT TMT TMT TMT TMT TMT TMT GST WTK GAC TAC TGG GGT CAA GGA  (SEQ ID NO: 779)
H3-SY9
GTC TAT TAT TGT GCT CGC TMT TMT TMT TMT TMT TMT TMT TMT TMT GST WTK GAC TAC TGG GGT CAA GGA  (SEQ ID NO: 780)
H3-SY10
GTC TAT TAT TGT GCT CGC TMT TMT TMT TMT TMT TMT TMT TMT TMT TMT GST WTK GAC TAC TGG GGT CAA GGA  (SEQ ID NO: 781)
H3-SY11
GTC TAT TAT TGT GCT CGC TMT TMT TMT TMT TMT TMT TMT TMT TMT TMT TMT GST WTK GAC TAC TGG GGT CAA GGA  (SEQ ID NO: 782)
H3-SY12
GTC TAT TAT TGT GCT CGC TMT TMT TMT TMT TMT TMT TMT TMT TMT TMT TMT TMT GST WTK GAC TAC TGG GGT CAA GGA  (SEQ ID NO: 783)
H3-SY13
GTC TAT TAT TGT GCT CGC TMT TMT TMT TMT TMT TMT TMT TMT TMT TMT TMT TMT TMT GST WTK GAC TAC TGG GGT CAA GGA  (SEQ ID NO: 784)
H3-SY14
GTC TAT TAT TGT GCT CGC TMT TMT TMT TMT TMT TMT TMT TMT TMT TMT TMT TMT TMT TMT GST WTK GAC TAC TGG GGT CAA GGA  (SEQ ID NO: 785)
H3-SY15
GTC TAT TAT TGT GCT CGC TMT TMT TMT TMT TMT TMT TMT TMT TMT TMT TMT TMT TMT TMT TMT GST WTK GAC TAC TGG GGT CAA GGA  (SEQ ID NO: 786)
H3-SY16
GTC TAT TAT TGT GCT CGC TMT TMT TMT TMT TMT TMT TMT TMT TMT TMT TMT TMT TMT TMT TMT TMT GST WTK GAC TAC TGG GGT CAA GGA  (SEQ ID NO: 787)
H3-SY17
GTC TAT TAT TGT GCT CGC TMT TMT TMT TMT TMT TMT TMT TMT TMT TMT TMT TMT TMT TMT TMT TMT TMT GST WTK GAC TAC TGG GGT CAA GGA  (SEQ ID NO: 788)

FIGURE 21A

|  | ELISA signal at 450 nm | | | | | | | Fab-phage IC50 (nM) | |
| --- | --- | --- | --- | --- | --- | --- | --- | --- | --- |
| Clone | Human VEGF | Human HER2 | Human DR5 | Human Insulin | Neutravidin | Human IGF-1 | Bovine serum albumin | IC50 (nM) | error +/- |
| B1 | 0.03 | 4.10 | 0.01 | 0.08 | 0.01 | 0.02 | 0.00 | 6.28 | 0.38 |
| B2 | 0.01 | 5.92 | 0.00 | 0.05 | 0.01 | 0.02 | -0.01 | 4.40 | 0.42 |
| B3 | 0.01 | 4.67 | -0.01 | 0.05 | 0.00 | 0.02 | -0.01 | 5.77 | 0.47 |
| B4 | 0.05 | 5.92 | 0.01 | 0.08 | 0.00 | 0.01 | -0.02 | 14.64 | 1.04 |
| B5 | 0.00 | 3.96 | 0.00 | 0.08 | -0.01 | 0.00 | -0.02 | 9.26 | 0.80 |
| B6 | 0.05 | 5.92 | 0.00 | 0.06 | 0.02 | 0.02 | -0.02 | 0.82 | 0.09 |
| B7 | 0.05 | 4.32 | 0.00 | 0.05 | 0.05 | 0.01 | -0.03 | 2.54 | 0.48 |
| B8 | 0.10 | 4.46 | 0.01 | 0.07 | 0.04 | 0.07 | -0.03 | 2.10 | 0.30 |
| B9 | 0.04 | 4.15 | 0.00 | 0.02 | 0.04 | 0.02 | -0.02 | 0.72 | 0.10 |
| B10 | 0.03 | 3.91 | 0.00 | 0.04 | 0.02 | 0.03 | -0.02 | 3.76 | 0.50 |
| B11 | 0.07 | 5.92 | -0.02 | 0.12 | 0.08 | 0.05 | -0.02 | 0.85 | 0.03 |
| B12 | 0.09 | 4.26 | 0.00 | 0.06 | 0.09 | 0.10 | 0.00 | 6.66 | 0.42 |
| B13 | 0.01 | 5.92 | 0.01 | 0.12 | 0.03 | 0.04 | -0.01 | 1.10 | 0.07 |
| B14 | 0.13 | 4.74 | 0.02 | 0.09 | 0.07 | 0.03 | 0.01 | 1.36 | 0.32 |
| B15 | 0.03 | 3.87 | 0.01 | 0.05 | 0.02 | 0.02 | 0.01 | 1.75 | 0.24 |
| B16 | 0.03 | 5.92 | 0.01 | 0.06 | 0.02 | 0.01 | 0.01 | 1.77 | 0.10 |
| B17 | 0.03 | 5.92 | 0.01 | 0.04 | 0.04 | 0.02 | 0.01 | 5.76 | 0.32 |
| B18 | 0.01 | 3.84 | 0.01 | 0.04 | 0.02 | 0.03 | 0.01 | 0.93 | 0.37 |
| B20 | 0.04 | 5.92 | 0.06 | 0.03 | 0.01 | 0.05 | -0.03 | 1.56 | 0.39 |
| B21 | 0.01 | 5.92 | 0.01 | 0.08 | 0.02 | 0.03 | 0.00 | 1.64 | 0.04 |
| B22 | 0.00 | 5.92 | 0.03 | 0.02 | 0.03 | 0.02 | 0.03 | 2.72 | 0.29 |
| B23 | 0.03 | 5.92 | 0.06 | 0.03 | 0.03 | 0.01 | -0.01 | 1.46 | 0.07 |
| B24 | 0.03 | 4.42 | 0.04 | 0.01 | 0.00 | -0.02 | -0.02 | 2.03 | 0.21 |
| B25 | 0.04 | 5.92 | 0.03 | 0.08 | 0.03 | -0.01 | 0.02 | 70.40 | 6.80 |
| B26 | 0.01 | 5.92 | 0.02 | 0.04 | 0.02 | -0.01 | 0.00 | >100 | N/D |
| B27 | 0.03 | 4.67 | 0.00 | 0.06 | 0.01 | -0.02 | 0.01 | 71.70 | 6.50 |
| B28 | 0.00 | 4.10 | -0.01 | 0.07 | 0.03 | -0.01 | 0.01 | N/D | N/D |

FIGURE 21B

| Binary surface library | | SY | | SW | | SR | | SF | |
|---|---|---|---|---|---|---|---|---|---|
| CDR | Position | amino acid type | amino acid molar ratio | amino acid type | amino acid molar ratio | amino acid type | amino acid molar ratio | amino acid type | amino acid molar ratio |
| L3 | 91 | S,Y | 50, 50 | S,W | 50, 50 | S,R | 50, 50 | S,F | 50, 50 |
|  | 92 | S,Y | 50, 50 | S,W | 50, 50 | S,R | 50, 50 | S,F | 50, 50 |
|  | 93 | S,Y | 50, 50 | S,W | 50, 50 | S,R | 50, 50 | S,F | 50, 50 |
|  | 94 | S,Y | 50, 50 | S,W | 50, 50 | S,R | 50, 50 | S,F | 50, 50 |
|  | 96 | S,Y | 50, 50 | S,W | 50, 50 | S,R | 50, 50 | S,F | 50, 50 |
| H1 | 28 | S,Y | 50, 50 | S,W | 50, 50 | S,R | 50, 50 | S,F | 50, 50 |
|  | 30 | S,Y | 50, 50 | S,W | 50, 50 | S,R | 50, 50 | S,F | 50, 50 |
|  | 31 | S,Y | 50, 50 | S,W | 50, 50 | S,R | 50, 50 | S,F | 50, 50 |
|  | 32 | S,Y | 50, 50 | S,W | 50, 50 | S,R | 50, 50 | S,F | 50, 50 |
|  | 33 | S,Y | 50, 50 | S,W | 50, 50 | S,R | 50, 50 | S,F | 50, 50 |
| H2 | 50 | S,Y | 50, 50 | S,W | 50, 50 | S,R | 50, 50 | S,F | 50, 50 |
|  | 52 | S,Y | 50, 50 | S,W | 50, 50 | S,R | 50, 50 | S,F | 50, 50 |
|  | 53 | S,Y | 50, 50 | S,W | 50, 50 | S,R | 50, 50 | S,F | 50, 50 |
|  | 54 | S,Y | 50, 50 | S,W | 50, 50 | S,R | 50, 50 | S,F | 50, 50 |
|  | 56 | S,Y | 50, 50 | S,W | 50, 50 | S,R | 50, 50 | S,F | 50, 50 |
|  | 58 | S,Y | 50, 50 | S,W | 50, 50 | S,R | 50, 50 | S,F | 50, 50 |
| H3 | 95 |  |  |  |  |  |  |  |  |
|  | 96 |  |  |  |  |  |  |  |  |
|  | 97 | S,Y | 50, 50 | S,W | 50, 50 | S,R | 50, 50 | S,F | 50, 50 |
|  | 98 |  |  |  |  |  |  |  |  |
|  | 99 |  |  |  |  |  |  |  |  |
|  | 100 |  |  |  |  |  |  |  |  |
|  | 100x | G, A | 50, 50 | G, A | 50, 50 | G, A | 50, 50 | G, A | 50, 50 |
|  | 100x | I, M, L, F | 25, 25, 25, 25 | I, M, L, F | 25, 25, 25, 25 | I, M, L, F | 25, 25, 25, 25 | I, M, L, F | 25, 25, 25, 25 |

FIGURE 22

FIG. 23: Mutagenic oligonucleotides used in the construction of libraries SF, SR, SW. Equimolar DNA degeneracies are represented in the IUB code (M = A/C, S = G/C, Y = C/T).

H1-SF
GCA GCT TCT GGC TTC TYC ATT TYC TYC TYC TYC ATA CAC TGG GTG CGT  (SEQ ID NO: 1005)
H2-SF
CTG GAA TGG GTT GCA TYC ATT TYC CCA TYC TYC GGT TYC ACT TYC TAT GCC GAT AGC GTC  (SEQ ID NO: 1006)
L3-SF
ACT TAT TAC TGT CAG CAA TYC TYC TYC TYC CCA TYC ACG TTC GGA CAG GGT ACC  (SEQ ID NO: 1007)
H1-SR
GCA GCT TCT GGC TTC MGC ATT MGC MGC MGC MGC ATA CAC TGG GTG CGT  (SEQ ID NO: 1008)
H2-SR
CTG GAA TGG GTT GCA MGC ATT MGC CCA MGC MGC GGT MGC ACT MGC TAT GCC GAT AGC GTC  (SEQ ID NO: 1009)
L3-SR
ACT TAT TAC TGT CAG CAA MGC MGC MGC MGC CCA MGC ACG TTC GGA CAG GGT ACC  (SEQ ID NO: 1010)
H1-SW
GCA GCT TCT GGC TTC TSG ATT TSG TSG TSG TSG ATA CAC TGG GTG CGT  (SEQ ID NO: 1011)
H2-SW
CTG GAA TGG GTT GCA TSG ATT TSG CCA TSG TSG GGT TSG ACT TSG TAT GCC GAT AGC GTC  (SEQ ID NO: 1012)
L3-SW
ACT TAT TAC TGT CAG CAA TSG TSG TSG TSG CCA TSG ACG TTC GGA CAG GGT ACC  (SEQ ID NO: 1013)

FIGURE 24A

|  | ELISA signal at 450 nm | | | | | | | Fab-phage IC50 | |
|---|---|---|---|---|---|---|---|---|---|
| Clone | Human VEGF | Human HER2 | Human DR5 | Human Insulin | Neutra vidin | Human IGF-1 | Bovine serum albumin | IC50 (nM) | error +/- |
| G29 | 0.33 | 4.67 | 0.06 | 0.26 | 0.26 | 0.32 | 0.02 | 1.96 | 0.22 |
| G30 | 0.13 | 3.73 | 0.04 | 0.19 | 0.17 | 0.29 | 0.01 | 1.26 | 0.21 |
| G31 | 0.09 | 3.70 | 0.07 | 0.22 | 0.12 | 0.26 | -0.01 | 1.66 | 0.07 |
| G32 | 0.35 | 3.82 | 0.13 | 0.48 | 0.33 | 0.52 | 0.08 | 1.12 | 0.14 |
| G33 | 0.09 | 4.14 | 0.11 | 0.10 | 0.06 | 0.15 | 0.00 | 1.70 | 0.10 |
| G34 | 0.16 | 3.52 | 0.13 | 0.18 | 0.18 | 0.35 | 0.01 | 1.06 | 0.27 |
| G35 | 0.31 | 5.92 | 0.12 | 0.37 | 0.29 | 0.25 | 0.03 | 0.65 | 0.14 |
| G36 | 0.38 | 3.86 | 0.14 | 0.29 | 0.26 | 0.30 | 0.01 | 1.20 | 0.19 |
| G37 | 0.23 | 4.04 | 0.21 | 0.45 | 0.32 | 0.32 | 0.03 | 0.31 | 0.09 |
| G40 | 0.31 | 3.88 | 0.10 | 2.64 | 0.45 | 0.85 | 0.03 | 1.80 | 0.30 |
| G41 | 0.04 | 5.92 | 0.04 | 0.08 | 0.08 | 0.07 | 0.01 | 51.00 | 6.00 |
| G42 | 0.02 | 3.63 | 0.17 | 0.14 | 0.06 | 0.07 | 0.03 | 43.00 | 7.00 |
| G43 | 0.13 | 4.67 | 0.06 | 0.14 | 0.29 | 0.37 | 0.03 | 22.00 | 3.00 |
| G44 | 0.04 | 4.67 | 0.06 | 0.11 | 0.13 | 0.29 | -0.02 | 29.00 | 3.00 |
| G46 | 0.02 | 4.13 | 0.03 | 0.07 | 0.07 | 0.10 | 0.00 | 73.00 | 11.00 |
| G48 | 0.09 | 3.69 | 0.04 | 0.04 | 0.01 | 0.01 | 0.01 | 67.00 | 11.00 |
| G49 | 0.02 | 3.50 | 0.04 | 0.04 | 0.00 | 0.05 | 0.01 | 3.13 | 0.37 |
| G50 | 0.12 | 5.92 | 0.11 | 0.05 | 0.10 | 0.10 | 0.02 | 7.94 | 0.42 |
| G51 | 0.05 | 4.13 | 0.10 | 0.03 | 0.04 | 0.08 | -0.01 | 3.28 | 0.24 |
| G53 | 0.00 | 3.93 | 0.02 | 0.02 | 0.08 | 0.08 | -0.03 | 9.75 | 1.76 |
| G54 | 0.05 | 5.92 | 0.06 | 0.05 | 0.03 | 0.05 | -0.02 | 2.44 | 0.73 |
| G55 | 0.05 | 3.99 | 0.06 | 0.04 | 0.06 | 0.05 | -0.03 | 6.52 | 0.73 |
| G56 | 0.01 | 5.92 | 0.08 | 0.11 | 0.05 | 0.07 | -0.01 | 7.13 | 0.88 |
| G58 | 0.05 | 3.73 | 0.08 | 0.08 | 0.06 | 0.36 | 0.00 | 15.10 | 0.82 |
| G59 | 0.02 | 3.45 | 0.05 | 0.02 | 0.05 | 0.04 | 0.00 | 6.80 | 0.99 |
| G60 | 0.07 | 4.24 | 0.08 | 0.07 | 0.03 | 0.09 | -0.01 | 79.80 | 17.20 |
| G61 | 0.09 | 3.73 | 0.09 | 0.07 | 0.12 | 0.09 | -0.02 | 145.00 | 42.00 |

FIGURE 24B

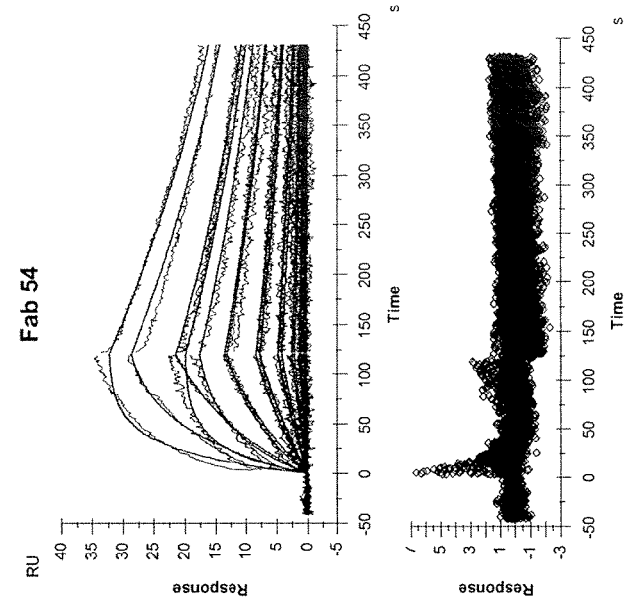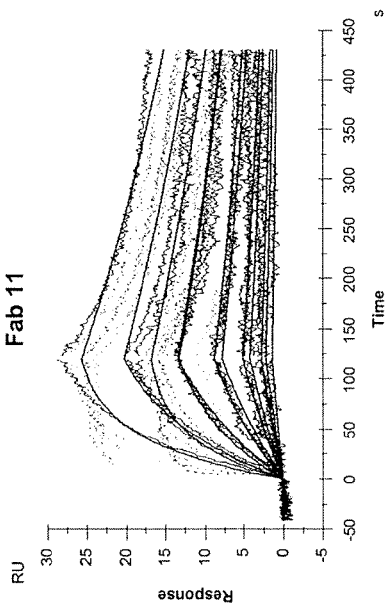
FIGURE 26A

FIG. 27
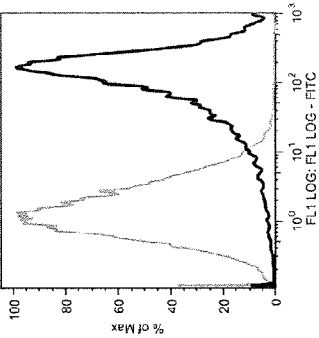
4D5 Fab positive control
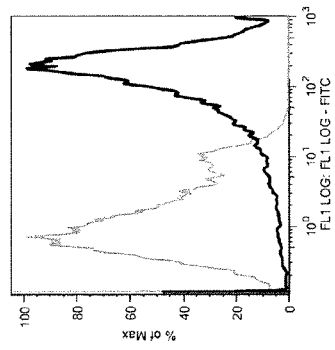
SXH3-B11
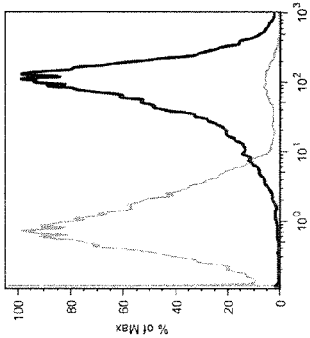
SX-surface-G54
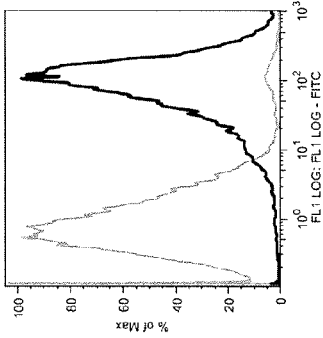
YSGR-A-42
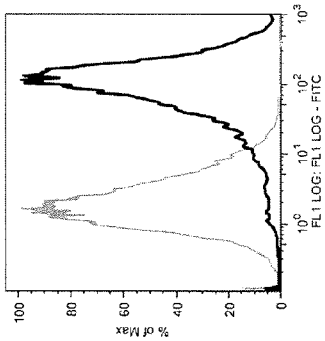
SX-surface-G37

ELISA signal @ 450 nm

Coated IgG

| | SXH3-B11 | SX-surface-G37 | YSGR-A-42 | SX-surface-G54 | YSGR-A-27 | SXH3-B27 | SX-surface-G43 | YSGR-D-104 | Omnitarg | Herceptin |
|---|---|---|---|---|---|---|---|---|---|---|
| SXH3-B11 | 0.10 | 0.06 | 0.07 | 0.06 | 1.54 | 0.24 | 1.22 | 0.96 | 1.60 | 1.55 |
| SX-surface-G37 | 0.11 | 0.06 | 0.08 | 0.06 | 1.73 | 0.49 | 1.58 | 1.22 | 1.72 | 1.68 |
| YSGR-A-42 | 0.09 | 0.06 | 0.06 | 0.05 | 1.87 | 1.18 | 1.57 | 1.40 | 1.53 | 1.45 |
| Incubated IgG @ 100 nM SX-surface-G54 | 0.32 | 0.16 | 0.30 | 0.13 | 1.55 | 0.27 | 1.37 | 1.23 | 1.48 | 1.15 |
| YSGR-A-27 | 2.10 | 1.17 | 1.90 | 2.02 | 0.06 | 0.08 | 0.05 | 0.16 | 1.28 | 1.13 |
| SXH3-B27 | 1.97 | 1.12 | 1.95 | 1.70 | 0.11 | 0.06 | 0.05 | 0.16 | 1.33 | 1.16 |
| SX-surface-G43 | 2.02 | 1.20 | 1.93 | 1.76 | 0.12 | 0.07 | 0.04 | 0.20 | 1.30 | 1.14 |
| YSGR-D-104 | 2.25 | 1.32 | 2.28 | 1.83 | 0.10 | 0.07 | 0.06 | 0.14 | 1.78 | 1.02 |

| | |
|---|---|
| (shaded) | positive control for blocking binding |
| # in bold | binding competition |

FIGURE 29

SEQUENCE LISTING

<160> NUMBER OF SEQ ID NOS: 1013

<210> SEQ ID NO 1
<211> LENGTH: 109
<212> TYPE: PRT
<213> ORGANISM: Artificial
<220> FEATURE:
<223> OTHER INFORMATION: synthetic 4D5 light chain variable domain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala

```
                    20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 2
<211> LENGTH: 120
<212> TYPE: PRT
<213> ORGANISM: Artificial
<220> FEATURE:
<223> OTHER INFORMATION: synthetic 4D5 heavy chain variable domain

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 3
<211> LENGTH: 35
<212> TYPE: PRT
<213> ORGANISM: Artificial
<220> FEATURE:
<223> OTHER INFORMATION: synthetic CDRL3

<400> SEQUENCE: 3

Gly Arg Met Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Arg Gly
        35

<210> SEQ ID NO 4
<211> LENGTH: 11
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
```

```
<222> LOCATION: (1)..(1)
<223> OTHER INFORMATION: X is independently either Y, G, S, R, A, D, E,
      F, H, I, K, L, M, N, P, Q, T, V, or W
<220> FEATURE:
<221> NAME/KEY: MISC_FEATURE
<222> LOCATION: (2)..(2)
<223> OTHER INFORMATION: X is independently either Y, G, S, R, A, D, E,
      F, H, I, K, L, M, N, P, Q, T, V, or W
<220> FEATURE:
<221> NAME/KEY: MISC_FEATURE
<222> LOCATION: (3)..(3)
<223> OTHER INFORMATION: X is independently either Y, G, S, R, A, D, E,
      F, H, I, K, L, M, N, P, Q, T, V, or W
<220> FEATURE:
<221> NAME/KEY: MISC_FEATURE
<222> LOCATION: (4)..(4)
<223> OTHER INFORMATION: X is independently either Y, G, S, R, A, D, E,
      F, H, I, K, L, M, N, P, Q, T, V, or W
<220> FEATURE:
<221> NAME/KEY: MISC_FEATURE
<222> LOCATION: (5)..(5)
<223> OTHER INFORMATION: X is independently either Y, G, S, R, A, D, E,
      F, H, I, K, L, M, N, P, Q, T, V, or W
<220> FEATURE:
<221> NAME/KEY: MISC_FEATURE
<222> LOCATION: (6)..(6)
<223> OTHER INFORMATION: X is independently either Y, G, S, R, A, D, E,
      F, H, I, K, L, M, N, P, Q, T, V, or W
<220> FEATURE:
<221> NAME/KEY: MISC_FEATURE
<222> LOCATION: (7)..(7)
<223> OTHER INFORMATION: X is independently either Y, G, S, R, A, D, E,
      F, H, I, K, L, M, N, P, Q, T, V, or W
<220> FEATURE:
<221> NAME/KEY: MISC_FEATURE
<222> LOCATION: (8)..(8)
<223> OTHER INFORMATION: X is independently either Y, G, S, R, A, D, E,
      F, H, I, K, L, M, N, P, Q, T, V, or W
<220> FEATURE:
<221> NAME/KEY: MISC_FEATURE
<222> LOCATION: (9)..(9)
<223> OTHER INFORMATION: X is independently either Y, G, S, R, A, D, E,
      F, H, I, K, L, M, N, P, Q, T, V, or W

<400> SEQUENCE: 4

Xaa Xaa Xaa Xaa Xaa Xaa Xaa Xaa Xaa Asp Tyr
1               5                   10

<210> SEQ ID NO 5
<211> LENGTH: 12
<212> TYPE: PRT
<213> ORGANISM: Artificial
<220> FEATURE:
<223> OTHER INFORMATION: synthetic heavy chain hinge sequence

<400> SEQUENCE: 5

Thr Cys Pro Pro Cys Pro Ala Pro Glu Leu Leu Gly
1               5                   10

<210> SEQ ID NO 6
<211> LENGTH: 23
<212> TYPE: PRT
<213> ORGANISM: Artificial
<220> FEATURE:
<223> OTHER INFORMATION: synthetic huMAb4D5-8 LC-FR1

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys
            20
```

```
<210> SEQ ID NO 7
<211> LENGTH: 15
<212> TYPE: PRT
<213> ORGANISM: Artificial
<220> FEATURE:
<223> OTHER INFORMATION: synthetic huMAb4D5 LC-FR2

<400> SEQUENCE: 7

Trp Tyr Gln Gln Lys Pro Gly Lys Ala Pro Lys Leu Leu Ile Tyr
1               5                   10                  15

<210> SEQ ID NO 8
<211> LENGTH: 32
<212> TYPE: PRT
<213> ORGANISM: Artificial
<220> FEATURE:
<223> OTHER INFORMATION: synthetic huMAb4D5 LC-FR3

<400> SEQUENCE: 8

Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 9
<211> LENGTH: 10
<212> TYPE: PRT
<213> ORGANISM: Artificial
<220> FEATURE:
<223> OTHER INFORMATION: synthetic huMAb4D5 LC-FR4

<400> SEQUENCE: 9

Phe Gly Gln Gly Thr Lys Val Glu Ile Lys
1               5                   10

<210> SEQ ID NO 10
<211> LENGTH: 25
<212> TYPE: PRT
<213> ORGANISM: Artificial
<220> FEATURE:
<223> OTHER INFORMATION: synthetic huMAb4D5-8 HC-FR1

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 11
<211> LENGTH: 13
<212> TYPE: PRT
<213> ORGANISM: Artificial
<220> FEATURE:
<223> OTHER INFORMATION: synthetic huMAb4D5 HC-FR2

<400> SEQUENCE: 11

Trp Val Arg Gln Ala Pro Gly Lys Gly Leu Glu Trp Val
1               5                   10

<210> SEQ ID NO 12
<211> LENGTH: 30
<212> TYPE: PRT
<213> ORGANISM: Artificial
<220> FEATURE:
<223> OTHER INFORMATION: synthetic huMAb4D5 HC-FR3

<400> SEQUENCE: 12
```

```
Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 13
<211> LENGTH: 11
<212> TYPE: PRT
<213> ORGANISM: Artificial
<220> FEATURE:
<223> OTHER INFORMATION: synthetic huMAb4D5 HC-FR4

<400> SEQUENCE: 13

Trp Gly Gln Gly Thr Leu Val Thr Val Ser Ser
1               5                   10

<210> SEQ ID NO 14
<211> LENGTH: 23
<212> TYPE: PRT
<213> ORGANISM: Artificial
<220> FEATURE:
<223> OTHER INFORMATION: synthetic huMAb4D5-8 LC-FR1

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 15
<211> LENGTH: 15
<212> TYPE: PRT
<213> ORGANISM: Artificial
<220> FEATURE:
<223> OTHER INFORMATION: synthetic huMAb4D5-8 LC-FR2

<400> SEQUENCE: 15

Trp Tyr Gln Gln Lys Pro Gly Lys Ala Pro Lys Leu Leu Ile Tyr
1               5                   10                  15

<210> SEQ ID NO 16
<211> LENGTH: 32
<212> TYPE: PRT
<213> ORGANISM: Artificial
<220> FEATURE:
<223> OTHER INFORMATION: synthetic huMAb4D5 LC-FR3

<400> SEQUENCE: 16

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 17
<211> LENGTH: 10
<212> TYPE: PRT
<213> ORGANISM: Artificial
<220> FEATURE:
<223> OTHER INFORMATION: synthetic huMAb4D5 LC-FR4

<400> SEQUENCE: 17

Phe Gly Gln Gly Thr Lys Val Glu Ile Lys
1               5                   10
```

```
<210> SEQ ID NO 18
<211> LENGTH: 25
<212> TYPE: PRT
<213> ORGANISM: Artificial
<220> FEATURE:
<223> OTHER INFORMATION: synthetic huMAb4D5-8 HC-FR1

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 19
<211> LENGTH: 13
<212> TYPE: PRT
<213> ORGANISM: Artificial
<220> FEATURE:
<223> OTHER INFORMATION: synthetic huMAb4D5 HC-FR2

<400> SEQUENCE: 19

Trp Val Arg Gln Ala Pro Gly Lys Gly Leu Glu Trp Val
1               5                   10

<210> SEQ ID NO 20
<211> LENGTH: 30
<212> TYPE: PRT
<213> ORGANISM: Artificial
<220> FEATURE:
<223> OTHER INFORMATION: synthetic huMAb4D5 HC-FR3

<400> SEQUENCE: 20

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 21
<211> LENGTH: 11
<212> TYPE: PRT
<213> ORGANISM: Artificial
<220> FEATURE:
<223> OTHER INFORMATION: synthetic huMAb4D5 HC-FR4

<400> SEQUENCE: 21

Trp Gly Gln Gly Thr Leu Val Thr Val Ser Ser
1               5                   10

<210> SEQ ID NO 22
<211> LENGTH: 10
<212> TYPE: PRT
<213> ORGANISM: Artificial
<220> FEATURE:
<223> OTHER INFORMATION: synthetic CDRH1
<220> FEATURE:
<221> NAME/KEY: MISC_FEATURE
<222> LOCATION: (3)..(3)
<223> OTHER INFORMATION: X is either Y or S
<220> FEATURE:
<221> NAME/KEY: MISC_FEATURE
<222> LOCATION: (5)..(5)
<223> OTHER INFORMATION: X is either Y or S
<220> FEATURE:
<221> NAME/KEY: MISC_FEATURE
<222> LOCATION: (6)..(6)
<223> OTHER INFORMATION: X is either Y or S
<220> FEATURE:
<221> NAME/KEY: MISC_FEATURE
<222> LOCATION: (7)..(7)
```

```
<223> OTHER INFORMATION: X is either Y or S
<220> FEATURE:
<221> NAME/KEY: MISC_FEATURE
<222> LOCATION: (8)..(8)
<223> OTHER INFORMATION: X is either Y or S

<400> SEQUENCE: 22

Gly Phe Xaa Ile Xaa Xaa Xaa Xaa Ile His
1               5                   10

<210> SEQ ID NO 23
<211> LENGTH: 17
<212> TYPE: PRT
<213> ORGANISM: Artificial
<220> FEATURE:
<223> OTHER INFORMATION: synthetic CDRH2
<220> FEATURE:
<221> NAME/KEY: MISC_FEATURE
<222> LOCATION: (1)..(1)
<223> OTHER INFORMATION: X is either Y or S
<220> FEATURE:
<221> NAME/KEY: MISC_FEATURE
<222> LOCATION: (3)..(3)
<223> OTHER INFORMATION: X is either Y or S
<220> FEATURE:
<221> NAME/KEY: MISC_FEATURE
<222> LOCATION: (5)..(5)
<223> OTHER INFORMATION: X is either Y or S
<220> FEATURE:
<221> NAME/KEY: MISC_FEATURE
<222> LOCATION: (6)..(6)
<223> OTHER INFORMATION: X is either Y or S
<220> FEATURE:
<221> NAME/KEY: MISC_FEATURE
<222> LOCATION: (8)..(8)
<223> OTHER INFORMATION: X is either Y or S
<220> FEATURE:
<221> NAME/KEY: MISC_FEATURE
<222> LOCATION: (10)..(10)
<223> OTHER INFORMATION: X is either Y or S

<400> SEQUENCE: 23

Xaa Ile Xaa Pro Xaa Xaa Gly Xaa Thr Xaa Tyr Ala Asp Ser Val Lys
1               5                   10                  15

Gly

<210> SEQ ID NO 24
<211> LENGTH: 21
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either Y, G, or S
<220> FEATURE:
<221> NAME/KEY: MISC_FEATURE
<222> LOCATION: (2)..(2)
<223> OTHER INFORMATION: X is either Y, G, or S
<220> FEATURE:
<221> NAME/KEY: MISC_FEATURE
<222> LOCATION: (3)..(3)
<223> OTHER INFORMATION: X is either Y, G, or S
<220> FEATURE:
<221> NAME/KEY: MISC_FEATURE
<222> LOCATION: (4)..(4)
<223> OTHER INFORMATION: X is either Y, G, or S
<220> FEATURE:
<221> NAME/KEY: MISC_FEATURE
<222> LOCATION: (5)..(5)
<223> OTHER INFORMATION: X is either Y, G, or S
<220> FEATURE:
<221> NAME/KEY: MISC_FEATURE
```

```
<222> LOCATION: (6)..(6)
<223> OTHER INFORMATION: X is either Y, G, or S
<220> FEATURE:
<221> NAME/KEY: MISC_FEATURE
<222> LOCATION: (7)..(7)
<223> OTHER INFORMATION: X is either Y, G, or S, or no amino acid
<220> FEATURE:
<221> NAME/KEY: MISC_FEATURE
<222> LOCATION: (8)..(8)
<223> OTHER INFORMATION: X is either Y, G, or S, or no amino acid
<220> FEATURE:
<221> NAME/KEY: MISC_FEATURE
<222> LOCATION: (9)..(9)
<223> OTHER INFORMATION: X is either Y, G, or S, or no amino acid
<220> FEATURE:
<221> NAME/KEY: MISC_FEATURE
<222> LOCATION: (10)..(10)
<223> OTHER INFORMATION: X is either Y, G, or S, or no amino acid
<220> FEATURE:
<221> NAME/KEY: MISC_FEATURE
<222> LOCATION: (11)..(11)
<223> OTHER INFORMATION: X is either Y, G, or S, or no amino acid
<220> FEATURE:
<221> NAME/KEY: MISC_FEATURE
<222> LOCATION: (12)..(12)
<223> OTHER INFORMATION: X is either Y, G, or S, or no amino acid
<220> FEATURE:
<221> NAME/KEY: MISC_FEATURE
<222> LOCATION: (13)..(13)
<223> OTHER INFORMATION: X is either Y, G, or S, or no amino acid
<220> FEATURE:
<221> NAME/KEY: MISC_FEATURE
<222> LOCATION: (14)..(14)
<223> OTHER INFORMATION: X is either Y, G, or S, or no amino acid
<220> FEATURE:
<221> NAME/KEY: MISC_FEATURE
<222> LOCATION: (15)..(15)
<223> OTHER INFORMATION: X is either Y, G, or S, or no amino acid
<220> FEATURE:
<221> NAME/KEY: MISC_FEATURE
<222> LOCATION: (16)..(16)
<223> OTHER INFORMATION: X is either Y, G, or S, or no amino acid
<220> FEATURE:
<221> NAME/KEY: MISC_FEATURE
<222> LOCATION: (17)..(17)
<223> OTHER INFORMATION: X is either Y, G, or S, or no amino acid
<220> FEATURE:
<221> NAME/KEY: MISC_FEATURE
<222> LOCATION: (18)..(18)
<223> OTHER INFORMATION: X is either G or A
<220> FEATURE:
<221> NAME/KEY: MISC_FEATURE
<222> LOCATION: (19)..(19)
<223> OTHER INFORMATION: X is either I, M, L, or F

<400> SEQUENCE: 24

Xaa Xaa Xaa Xaa Xaa Xaa Xaa Xaa Xaa Xaa Xaa Xaa Xaa Xaa Xaa
1               5                   10                  15

Xaa Xaa Xaa Asp Tyr
            20

<210> SEQ ID NO 25
<211> LENGTH: 9
<212> TYPE: PRT
<213> ORGANISM: Artificial
<220> FEATURE:
<223> OTHER INFORMATION: synthetic CDRL3
<220> FEATURE:
<221> NAME/KEY: MISC_FEATURE
<222> LOCATION: (3)..(3)
<223> OTHER INFORMATION: X is either Y or S
<220> FEATURE:
<221> NAME/KEY: MISC_FEATURE
<222> LOCATION: (4)..(4)
<223> OTHER INFORMATION: X is either Y or S
<220> FEATURE:
```

-continued

```
<221> NAME/KEY: MISC_FEATURE
<222> LOCATION: (5)..(5)
<223> OTHER INFORMATION: X is either Y or S
<220> FEATURE:
<221> NAME/KEY: MISC_FEATURE
<222> LOCATION: (6)..(6)
<223> OTHER INFORMATION: X is either Y or S
<220> FEATURE:
<221> NAME/KEY: MISC_FEATURE
<222> LOCATION: (8)..(8)
<223> OTHER INFORMATION: X is either Y or S

<400> SEQUENCE: 25

Gln Gln Xaa Xaa Xaa Xaa Pro Xaa Thr
1               5

<210> SEQ ID NO 26
<211> LENGTH: 21
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either Y, R, or S
<220> FEATURE:
<221> NAME/KEY: MISC_FEATURE
<222> LOCATION: (2)..(2)
<223> OTHER INFORMATION: X is either Y, R, or S
<220> FEATURE:
<221> NAME/KEY: MISC_FEATURE
<222> LOCATION: (3)..(3)
<223> OTHER INFORMATION: X is either Y, R, or S
<220> FEATURE:
<221> NAME/KEY: MISC_FEATURE
<222> LOCATION: (4)..(4)
<223> OTHER INFORMATION: X is either Y, R, or S
<220> FEATURE:
<221> NAME/KEY: MISC_FEATURE
<222> LOCATION: (5)..(5)
<223> OTHER INFORMATION: X is either Y, R, or S
<220> FEATURE:
<221> NAME/KEY: MISC_FEATURE
<222> LOCATION: (6)..(6)
<223> OTHER INFORMATION: X is either Y, R, or S
<220> FEATURE:
<221> NAME/KEY: MISC_FEATURE
<222> LOCATION: (7)..(7)
<223> OTHER INFORMATION: X is either Y, S, or R, or is not present
<220> FEATURE:
<221> NAME/KEY: MISC_FEATURE
<222> LOCATION: (8)..(8)
<223> OTHER INFORMATION: X is either Y, S, or R, or is not present
<220> FEATURE:
<221> NAME/KEY: MISC_FEATURE
<222> LOCATION: (9)..(9)
<223> OTHER INFORMATION: X is either Y, S, or R, or is not present
<220> FEATURE:
<221> NAME/KEY: MISC_FEATURE
<222> LOCATION: (10)..(10)
<223> OTHER INFORMATION: X is either Y, S, or R, or is not present
<220> FEATURE:
<221> NAME/KEY: MISC_FEATURE
<222> LOCATION: (11)..(11)
<223> OTHER INFORMATION: X is either Y, S, or R, or is not present
<220> FEATURE:
<221> NAME/KEY: MISC_FEATURE
<222> LOCATION: (12)..(12)
<223> OTHER INFORMATION: X is either Y, S, or R, or is not present
<220> FEATURE:
<221> NAME/KEY: MISC_FEATURE
<222> LOCATION: (13)..(13)
<223> OTHER INFORMATION: X is either Y, S, or R, or is not present
<220> FEATURE:
<221> NAME/KEY: MISC_FEATURE
<222> LOCATION: (14)..(14)
```

-continued

```
<223> OTHER INFORMATION: X is either Y, S, or R, or is not present
<220> FEATURE:
<221> NAME/KEY: MISC_FEATURE
<222> LOCATION: (15)..(15)
<223> OTHER INFORMATION: X is either Y, S, or R, or is not present
<220> FEATURE:
<221> NAME/KEY: MISC_FEATURE
<222> LOCATION: (16)..(16)
<223> OTHER INFORMATION: X is either Y, S, or R, or is not present
<220> FEATURE:
<221> NAME/KEY: MISC_FEATURE
<222> LOCATION: (17)..(17)
<223> OTHER INFORMATION: X is either Y, S, or R, or is not present
<220> FEATURE:
<221> NAME/KEY: MISC_FEATURE
<222> LOCATION: (18)..(18)
<223> OTHER INFORMATION: X is either G or A
<220> FEATURE:
<221> NAME/KEY: MISC_FEATURE
<222> LOCATION: (19)..(19)
<223> OTHER INFORMATION: X is either I, M, L, or F

<400> SEQUENCE: 26

Xaa Xaa Xaa Xaa Xaa Xaa Xaa Xaa Xaa Xaa Xaa Xaa Xaa Xaa Xaa
1               5                   10                  15

Xaa Xaa Xaa Asp Tyr
            20

<210> SEQ ID NO 27
<211> LENGTH: 21
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either Y, G, R, or S
<220> FEATURE:
<221> NAME/KEY: MISC_FEATURE
<222> LOCATION: (2)..(2)
<223> OTHER INFORMATION: X is either Y, G, R, or S
<220> FEATURE:
<221> NAME/KEY: MISC_FEATURE
<222> LOCATION: (3)..(3)
<223> OTHER INFORMATION: X is either Y, G, R, or S
<220> FEATURE:
<221> NAME/KEY: MISC_FEATURE
<222> LOCATION: (4)..(4)
<223> OTHER INFORMATION: X is either Y, G, R, or S
<220> FEATURE:
<221> NAME/KEY: MISC_FEATURE
<222> LOCATION: (5)..(5)
<223> OTHER INFORMATION: X is either Y, G, R, or S
<220> FEATURE:
<221> NAME/KEY: MISC_FEATURE
<222> LOCATION: (6)..(6)
<223> OTHER INFORMATION: X is either Y, G, R, or S
<220> FEATURE:
<221> NAME/KEY: MISC_FEATURE
<222> LOCATION: (7)..(7)
<223> OTHER INFORMATION: X is either Y, S, G, R, or no amino acid
<220> FEATURE:
<221> NAME/KEY: MISC_FEATURE
<222> LOCATION: (8)..(8)
<223> OTHER INFORMATION: X is either Y, S, G, R, or no amino acid
<220> FEATURE:
<221> NAME/KEY: MISC_FEATURE
<222> LOCATION: (9)..(9)
<223> OTHER INFORMATION: X is either Y, S, G, R, or no amino acid
<220> FEATURE:
<221> NAME/KEY: MISC_FEATURE
<222> LOCATION: (10)..(10)
<223> OTHER INFORMATION: X is either Y, S, G, R, or no amino acid
<220> FEATURE:
<221> NAME/KEY: MISC_FEATURE
```

```
<222> LOCATION: (11)..(11)
<223> OTHER INFORMATION: X is either Y, S, G, R, or no amino acid
<220> FEATURE:
<221> NAME/KEY: MISC_FEATURE
<222> LOCATION: (12)..(12)
<223> OTHER INFORMATION: X is either Y, S, G, R, or no amino acid
<220> FEATURE:
<221> NAME/KEY: MISC_FEATURE
<222> LOCATION: (13)..(13)
<223> OTHER INFORMATION: X is either Y, S, G, R, or no amino acid
<220> FEATURE:
<221> NAME/KEY: MISC_FEATURE
<222> LOCATION: (14)..(14)
<223> OTHER INFORMATION: X is either Y, S, G, R, or no amino acid
<220> FEATURE:
<221> NAME/KEY: MISC_FEATURE
<222> LOCATION: (15)..(15)
<223> OTHER INFORMATION: X is either Y, S, G, R, or no amino acid
<220> FEATURE:
<221> NAME/KEY: MISC_FEATURE
<222> LOCATION: (16)..(16)
<223> OTHER INFORMATION: X is either Y, S, G, R, or no amino acid
<220> FEATURE:
<221> NAME/KEY: MISC_FEATURE
<222> LOCATION: (17)..(17)
<223> OTHER INFORMATION: X is either Y, S, G, R, or no amino acid
<220> FEATURE:
<221> NAME/KEY: MISC_FEATURE
<222> LOCATION: (18)..(18)
<223> OTHER INFORMATION: X is either G or A
<220> FEATURE:
<221> NAME/KEY: MISC_FEATURE
<222> LOCATION: (19)..(19)
<223> OTHER INFORMATION: X is either I, M, L, or F

<400> SEQUENCE: 27

Xaa Xaa Xaa Xaa Xaa Xaa Xaa Xaa Xaa Xaa Xaa Xaa Xaa Xaa Xaa Xaa
1               5                   10                  15

Xaa Xaa Xaa Asp Tyr
            20

<210> SEQ ID NO 28
<211> LENGTH: 21
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either Y, G, S, R, A, D, E, F, H, I, K, L,
      M, N, P, Q, T, V, or W
<220> FEATURE:
<221> NAME/KEY: MISC_FEATURE
<222> LOCATION: (2)..(2)
<223> OTHER INFORMATION: X is either Y, G, S, R, A, D, E, F, H, I, K, L,
      M, N, P, Q, T, V, or W
<220> FEATURE:
<221> NAME/KEY: MISC_FEATURE
<222> LOCATION: (3)..(3)
<223> OTHER INFORMATION: X is either Y, G, S, R, A, D, E, F, H, I, K, L,
      M, N, P, Q, T, V, or W
<220> FEATURE:
<221> NAME/KEY: MISC_FEATURE
<222> LOCATION: (4)..(4)
<223> OTHER INFORMATION: X is either Y, G, S, R, A, D, E, F, H, I, K, L,
      M, N, P, Q, T, V, or W
<220> FEATURE:
<221> NAME/KEY: MISC_FEATURE
<222> LOCATION: (5)..(5)
<223> OTHER INFORMATION: X is either Y, G, S, R, A, D, E, F, H, I, K, L,
      M, N, P, Q, T, V, or W
<220> FEATURE:
<221> NAME/KEY: MISC_FEATURE
<222> LOCATION: (6)..(6)
<223> OTHER INFORMATION: X is either Y, G, S, R, A, D, E, F, H, I, K, L,
```

```
      M, N, P, Q, T, V, or W
<220> FEATURE:
<221> NAME/KEY: MISC_FEATURE
<222> LOCATION: (7)..(7)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (8)..(8)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (9)..(9)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (10)..(10)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (11)..(11)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (12)..(12)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (13)..(13)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (14)..(14)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (15)..(15)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (16)..(16)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (17)..(17)
<223> OTHER INFORMATION: X is either Y, G, S, R, A, D, E, F, H, I, K, L,
      M, N, P, Q, T, V, W, or no amino acid
<220> FEATURE:
<221> NAME/KEY: MISC_FEATURE
<222> LOCATION: (18)..(18)
<223> OTHER INFORMATION: X is either G or A
<220> FEATURE:
<221> NAME/KEY: MISC_FEATURE
<222> LOCATION: (19)..(19)
<223> OTHER INFORMATION: X is either I, M, L, or F

<400> SEQUENCE: 28

Xaa Xaa Xaa Xaa Xaa Xaa Xaa Xaa Xaa Xaa Xaa Xaa Xaa Xaa Xaa Xaa
1               5                   10                  15

Xaa Xaa Xaa Asp Tyr
            20

<210> SEQ ID NO 29
<211> LENGTH: 11
<212> TYPE: PRT
<213> ORGANISM: Artificial
<220> FEATURE:
```

<223> OTHER INFORMATION: synthetic Kabat consensus CDRL1

<400> SEQUENCE: 29

Arg Ala Ser Gln Asp Val Asn Thr Ala Val Ala
1               5                   10

<210> SEQ ID NO 30
<211> LENGTH: 7
<212> TYPE: PRT
<213> ORGANISM: Artificial
<220> FEATURE:
<223> OTHER INFORMATION: synthetic Kabat consensus CDRL2

<400> SEQUENCE: 30

Ser Ala Ser Ser Leu Tyr Ser
1               5

<210> SEQ ID NO 31
<211> LENGTH: 18
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either R, Y, or M
<220> FEATURE:
<221> NAME/KEY: MISC_FEATURE
<222> LOCATION: (2)..(2)
<223> OTHER INFORMATION: X is either Y or R
<220> FEATURE:
<221> NAME/KEY: MISC_FEATURE
<222> LOCATION: (3)..(3)
<223> OTHER INFORMATION: X is either Y, S, R, P, or G
<220> FEATURE:
<221> NAME/KEY: MISC_FEATURE
<222> LOCATION: (4)..(4)
<223> OTHER INFORMATION: X is either Y or S
<220> FEATURE:
<221> NAME/KEY: MISC_FEATURE
<222> LOCATION: (5)..(5)
<223> OTHER INFORMATION: X ix either Y, S, R, or H
<220> FEATURE:
<221> NAME/KEY: MISC_FEATURE
<222> LOCATION: (6)..(6)
<223> OTHER INFORMATION: X is either R, Y, or S
<220> FEATURE:
<221> NAME/KEY: MISC_FEATURE
<222> LOCATION: (7)..(7)
<223> OTHER INFORMATION: X is either G, Y, or S
<220> FEATURE:
<221> NAME/KEY: MISC_FEATURE
<222> LOCATION: (8)..(8)
<223> OTHER INFORMATION: X is either R, Y, or S
<220> FEATURE:
<221> NAME/KEY: MISC_FEATURE
<222> LOCATION: (9)..(9)
<223> OTHER INFORMATION: X is either G, Y, or S
<220> FEATURE:
<221> NAME/KEY: MISC_FEATURE
<222> LOCATION: (10)..(10)
<223> OTHER INFORMATION: X is either R, Y, or S
<220> FEATURE:
<221> NAME/KEY: MISC_FEATURE
<222> LOCATION: (11)..(11)
<223> OTHER INFORMATION: X is either G, Y, or S
<220> FEATURE:
<221> NAME/KEY: MISC_FEATURE
<222> LOCATION: (12)..(12)
<223> OTHER INFORMATION: X is either S, Y, R, G, or A
<220> FEATURE:
<221> NAME/KEY: MISC_FEATURE
<222> LOCATION: (13)..(13)
<223> OTHER INFORMATION: X is either G or Y

```
<220> FEATURE:
<221> NAME/KEY: MISC_FEATURE
<222> LOCATION: (14)..(14)
<223> OTHER INFORMATION: X is either L, M, R, G, or A
<220> FEATURE:
<221> NAME/KEY: MISC_FEATURE
<222> LOCATION: (15)..(15)
<223> OTHER INFORMATION: X is either G, F, L, or no amino acid
<220> FEATURE:
<221> NAME/KEY: MISC_FEATURE
<222> LOCATION: (16)..(16)
<223> OTHER INFORMATION: X is either F or no amino acid

<400> SEQUENCE: 31

Xaa Xaa Xaa Xaa Xaa Xaa Xaa Xaa Xaa Xaa Xaa Xaa Xaa Xaa Xaa Xaa
1               5                   10                  15

Asp Tyr

<210> SEQ ID NO 32
<211> LENGTH: 45
<212> TYPE: DNA
<213> ORGANISM: Artificial
<220> FEATURE:
<223> OTHER INFORMATION: synthetic H1

<400> SEQUENCE: 32
gcagcttctg gcttctmatt tmttmtmtmt atacactggg tgcgt                45

<210> SEQ ID NO 33
<211> LENGTH: 58
<212> TYPE: DNA
<213> ORGANISM: Artificial
<220> FEATURE:
<223> OTHER INFORMATION: synthetic H2

<400> SEQUENCE: 33
ctggaatggg ttgcatmtat ttmtccatmt tggttmtact tmttatgccg atagcgtc    58

<210> SEQ ID NO 34
<211> LENGTH: 54
<212> TYPE: DNA
<213> ORGANISM: Artificial
<220> FEATURE:
<223> OTHER INFORMATION: synthetic L3

<400> SEQUENCE: 34
acttattact gtcagcaatm ttmttmttmt ccatmtacgt tcggacaggg tacc        54

<210> SEQ ID NO 35
<211> LENGTH: 60
<212> TYPE: DNA
<213> ORGANISM: Artificial
<220> FEATURE:
<223> OTHER INFORMATION: synthetic H3-A6
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
```

```
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, or GGG

<400> SEQUENCE: 35
gtctattatt gtgctcgcnn nnnnnnnnnn nnnnnngstw tkgactactg gggtcaagga      60

<210> SEQ ID NO 36
<211> LENGTH: 63
<212> TYPE: DNA
<213> ORGANISM: Artificial
<220> FEATURE:
<223> OTHER INFORMATION: synthetic H3-A7
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, or GGG

<400> SEQUENCE: 36
gtctattatt gtgctcgcnn nnnnnnnnnn nnnnnnnnng stwtkgacta ctgggggtcaa     60 gga                                                                   63

<210> SEQ ID NO 37
<211> LENGTH: 66
<212> TYPE: DNA
<213> ORGANISM: Artificial
<220> FEATURE:
<223> OTHER INFORMATION: synthetic H3-A8
<220> FEATURE:
<221> NAME/KEY: misc_feature
<222> LOCATION: (19)..(21)
<223> OTHER INFORMATION: N19 to N21 are independently either TAT, TAC,
```

```
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, or GGG

<400> SEQUENCE: 37
gtctattatt gtgctcgcnn nnnnnnnnnn nnnnnnnnnn nngstwtkga ctactggggt      60
caagga                                                                66

<210> SEQ ID NO 38
<211> LENGTH: 69
<212> TYPE: DNA
<213> ORGANISM: Artificial
<220> FEATURE:
<223> OTHER INFORMATION: synthetic H3-A9
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
```

TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (40)..(42)
<223> OTHER INFORMATION: N40 to N42 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (43)..(45)
<223> OTHER INFORMATION: N43 to N45 are independently either TAT, TAC,
        TCA, TCT, TCC, TCG, AGT, AGC, GGA, GGT, GGC, or GGG

<400> SEQUENCE: 38
gtctattatt gtgctcgcnn nnnnnnnnnn nnnnnnnnnn nnnnngstwt kgactactgg     60
ggtcaagga                                                             69

<210> SEQ ID NO 39
<211> LENGTH: 72
<212> TYPE: DNA
<213> ORGANISM: Artificial
<220> FEATURE:
<223> OTHER INFORMATION: synthetic H3-A10
<220> FEATURE:
<221> NAME/KEY: misc_feature
<222> LOCATION: (19)..(21)
<223> OTHER INFORMATION: N19 to N21 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (40)..(42)
<223> OTHER INFORMATION: N40 to N42 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (43)..(45)
<223> OTHER INFORMATION: N43 to N45 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (46)..(48)
<223> OTHER INFORMATION: N46 to N48 are independently either TAT, TAC, TCA, TCT, TCC, TCG, AGT, AGC, GGA, GGT, GGC, or GGG

<400> SEQUENCE: 39
gtctattatt gtgctcgcnn nnnnnnnnnn nnnnnnnnnn nnnnnnnngs twtkgactac    60
tggggtcaag ga    72

<210> SEQ ID NO 40
<211> LENGTH: 75
<212> TYPE: DNA
<213> ORGANISM: Artificial
<220> FEATURE:
<223> OTHER INFORMATION: synthetic H3-A11
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, or GGG

<400> SEQUENCE: 40
gtctattatt gtgctcgcnn nnnnnnnnnn nnnnnnnnnn nnnnnnnnnn ngstwtkgac    60
tactggggtc aagga    75

<210> SEQ ID NO 41

```
<211> LENGTH: 78
<212> TYPE: DNA
<213> ORGANISM: Artificial
<220> FEATURE:
<223> OTHER INFORMATION: synthetic H3-A12
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, GGA, GGT, GGC, or GGG

<400> SEQUENCE: 41
gtctattatt gtgctcgcnn nnnnnnnnnn nnnnnnnnnn nnnnnnnnnn nnnngstwtk      60
gactactggg gtcaagga                                                    78

<210> SEQ ID NO 42
<211> LENGTH: 81
<212> TYPE: DNA
<213> ORGANISM: Artificial
<220> FEATURE:
<223> OTHER INFORMATION: synthetic H3-A13
```

```
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, GGA, GGT, GGC, or GGG

<400> SEQUENCE: 42
gtctattatt gtgctcgcnn nnnnnnnnnn nnnnnnnnn nnnnnnnnn nnnnnngst       60 wtkgactact ggggtcaagg a                                              81

<210> SEQ ID NO 43
<211> LENGTH: 84
<212> TYPE: DNA
<213> ORGANISM: Artificial
<220> FEATURE:
<223> OTHER INFORMATION: synthetic H3-A14
```

```
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (58)..(60)
<223> OTHER INFORMATION: N58 to N60 are independently either TAT, TAC,
      TCA, TCT, TCC, TCG, AGT, AGC, GGA, GGT, GGC, or GGG

<400> SEQUENCE: 43
gtctattatt gtgctcgcnn nnnnnnnnnn nnnnnnnnnn nnnnnnnnnn nnnnnnnnnn      60
gstwtkgact actggggtca agga                                             84

<210> SEQ ID NO 44
```

```
<211> LENGTH: 87
<212> TYPE: DNA
<213> ORGANISM: Artificial
<220> FEATURE:
<223> OTHER INFORMATION: synthetic H3-A15
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (58)..(60)
<223> OTHER INFORMATION: N58 to N60 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (61)..(63)
<223> OTHER INFORMATION: N61 to N63 are independently either TAT, TAC,
```

TCA, TCT, TCC, TCG, AGT, AGC, GGA, GGT, GGC, or GGG

<400> SEQUENCE: 44
gtctattatt gtgctcgcnn nnnnnnnnnn nnnnnnnnnn nnnnnnnnnn nnnnnnnnnn    60
nnngstwtkg actactgggg tcaagga                                        87

<210> SEQ ID NO 45
<211> LENGTH: 90
<212> TYPE: DNA
<213> ORGANISM: Artificial
<220> FEATURE:
<223> OTHER INFORMATION: synthetic H3-A16
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (55)..(57)
<223> OTHER INFORMATION: N55 to N57 are independently either TAT, TAC, TCA, TCT, TCC, TCG, AGT, AGC, GGA, GGT, GGC, or GGG
<220> FEATURE:
<221> NAME/KEY: misc_feature
<222> LOCATION: (58)..(60)
<223> OTHER INFORMATION: N58 to N60 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (61)..(63)
<223> OTHER INFORMATION: N61 to N63 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (64)..(66)
<223> OTHER INFORMATION: N64 to N66 are independently either TAT, TAC,
      TCA, TCT, TCC, TCG, AGT, AGC, GGA, GGT, GGC, or GGG

<400> SEQUENCE: 45
gtctattatt gtgctcgcnn nnnnnnnnnn nnnnnnnnnn nnnnnnnnnn nnnnnnnnnn    60
nnnnnngstw tkgactactg gggtcaagga                                     90

<210> SEQ ID NO 46
<211> LENGTH: 93
<212> TYPE: DNA
<213> ORGANISM: Artificial
<220> FEATURE:
<223> OTHER INFORMATION: synthetic H3-A17
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, or GGG
<220> FEATURE:
<221> NAME/KEY: misc_feature
<222> LOCATION: (46)..(48)
<223> OTHER INFORMATION: N46 to N48 are independently either TAT, TAC,

```
        TCA, TCT, TCC, TCG, AGT, AGC, GGA, GGT, GGC, or GGG
<220> FEATURE:
<221> NAME/KEY: misc_feature
<222> LOCATION: (49)..(51)
<223> OTHER INFORMATION: N49 to N51 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (52)..(54)
<223> OTHER INFORMATION: N52 to N54 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (55)..(57)
<223> OTHER INFORMATION: N55 to N57 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (58)..(60)
<223> OTHER INFORMATION: N58 to N60 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (61)..(63)
<223> OTHER INFORMATION: N61 to N63 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (64)..(66)
<223> OTHER INFORMATION: N64 to N66 are independently either TAT, TAC,
        TCA, TCT, TCC, TCG, AGT, AGC, GGA, GGT, GGC, or GGG
<220> FEATURE:
<221> NAME/KEY: misc_feature
<222> LOCATION: (67)..(69)
<223> OTHER INFORMATION: N67 to N69 are independently either TAT, TAC,
        TCA, TCT, TCC, TCG, AGT, AGC, GGA, GGT, GGC, or GGG

<400> SEQUENCE: 46
gtctattatt gtgctcgcnn nnnnnnnnnn nnnnnnnnnn nnnnnnnnnn nnnnnnnnnn      60
nnnnnnnnng stwtkgacta ctggggtcaa gga                                   93

<210> SEQ ID NO 47
<211> LENGTH: 60
<212> TYPE: DNA
<213> ORGANISM: Artificial
<220> FEATURE:
<223> OTHER INFORMATION: synthetic H3-B6
<220> FEATURE:
<221> NAME/KEY: misc_feature
<222> LOCATION: (19)..(21)
<223> OTHER INFORMATION: N19 to N21 are independently either TAT, TAC,
        TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
        TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
        TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N19 to N21 are independently either TAT, TAC,
        TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
        TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
```

TCA, TCT, TCC, TCG, AGT, AGC, CGA, CGT, CGC, CGG, AGA, or AGG

<400> SEQUENCE: 47
gtctattatt gtgctcgcnn nnnnnnnnnn nnnnnngstw tkgactactg gggtcaagga      60

<210> SEQ ID NO 48
<211> LENGTH: 63
<212> TYPE: DNA
<213> ORGANISM: Artificial
<220> FEATURE:
<223> OTHER INFORMATION: synthetic H3-B7
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG

<400> SEQUENCE: 48
gtctattatt gtgctcgcnn nnnnnnnnnn nnnnnnnnng stwtkgacta ctggggtcaa      60
gga                                                                   63

<210> SEQ ID NO 49
<211> LENGTH: 66
<212> TYPE: DNA
<213> ORGANISM: Artificial
<220> FEATURE:
<223> OTHER INFORMATION: synthetic H3-B8
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature

```
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, CGA, CGT, CGC, CGG, AGA, or AGG

<400> SEQUENCE: 49
gtctattatt gtgctcgcnn nnnnnnnnnn nnnnnnnnnn nngstwtkga ctactggggt     60
caagga                                                               66

<210> SEQ ID NO 50
<211> LENGTH: 69
<212> TYPE: DNA
<213> ORGANISM: Artificial
<220> FEATURE:
<223> OTHER INFORMATION: synthetic H3-B9
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
```

```
<222> LOCATION: (43)..(45)
<223> OTHER INFORMATION: N43 to N45 are independently either TAT, TAC,
      TCA, TCT, TCC, TCG, AGT, AGC, CGA, CGT, CGC, CGG, AGA, or AGG

<400> SEQUENCE: 50
gtctattatt gtgctcgcnn nnnnnnnnnn nnnnnnnnnn nnnnngstwt kgactactgg    60
ggtcaagga                                                           69

<210> SEQ ID NO 51
<211> LENGTH: 72
<212> TYPE: DNA
<213> ORGANISM: Artificial
<220> FEATURE:
<223> OTHER INFORMATION: synthetic H3-B10
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, CGA, CGT, CGC, CGG, AGA, or AGG

<400> SEQUENCE: 51
gtctattatt gtgctcgcnn nnnnnnnnnn nnnnnnnnnn nnnnnnnngs twtkgactac    60
tggggtcaag ga                                                       72

<210> SEQ ID NO 52
<211> LENGTH: 75
<212> TYPE: DNA
<213> ORGANISM: Artificial
```

```
<220> FEATURE:
<223> OTHER INFORMATION: synthetic H3-B11
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, CGA, CGT, CGC, CGG, AGA, or AGG

<400> SEQUENCE: 52
gtctattatt gtgctcgcnn nnnnnnnnnn nnnnnnnnnn nnnnnnnnnn ngstwtkgac      60
tactggggtc aagga                                                      75

<210> SEQ ID NO 53
<211> LENGTH: 78
<212> TYPE: DNA
<213> ORGANISM: Artificial
<220> FEATURE:
<223> OTHER INFORMATION: synthetic H3-B12
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
```

```
<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, CGA, CGT, CGC, CGG, AGA, or AGG

<400> SEQUENCE: 53
gtctattatt gtgctcgcnn nnnnnnnnnn nnnnnnnnnn nnnnnnnnnn nnnngstwtk      60
gactactggg gtcaagga                                                    78

<210> SEQ ID NO 54
<211> LENGTH: 81
<212> TYPE: DNA
<213> ORGANISM: Artificial
<220> FEATURE:
<223> OTHER INFORMATION: synthetic H3-B13
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
```

-continued

```
<223> OTHER INFORMATION: N25 to N27 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, CGA, CGT, CGC, CGG, AGA, or AGG

<400> SEQUENCE: 54
gtctattatt gtgctcgcnn nnnnnnnnnn nnnnnnnnnn nnnnnnnnnn nnnnnnngst      60
wtkgactact ggggtcaagg a                                                81

<210> SEQ ID NO 55
<211> LENGTH: 84
<212> TYPE: DNA
<213> ORGANISM: Artificial
<220> FEATURE:
<223> OTHER INFORMATION: synthetic H3-B14
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
```

```
<223> OTHER INFORMATION: N25 to N27 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (58)..(60)
<223> OTHER INFORMATION: N58 to N60 are independently either TAT, TAC,
      TCA, TCT, TCC, TCG, AGT, AGC, CGA, CGT, CGC, CGG, AGA, or AGG

<400> SEQUENCE: 55
gtctattatt gtgctcgcnn nnnnnnnnnn nnnnnnnnnn nnnnnnnnnn nnnnnnnnnn      60
gstwtkgact actggggtca agga                                              84

<210> SEQ ID NO 56
<211> LENGTH: 87
<212> TYPE: DNA
<213> ORGANISM: Artificial
<220> FEATURE:
<223> OTHER INFORMATION: synthetic H3-B15
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
```

<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (58)..(60)
<223> OTHER INFORMATION: N58 to N60 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (61)..(63)
<223> OTHER INFORMATION: N61 to N63 are independently either TAT, TAC,
      TCA, TCT, TCC, TCG, AGT, AGC, CGA, CGT, CGC, CGG, AGA, or AGG

<400> SEQUENCE: 56
gtctattatt gtgctcgcnn nnnnnnnnnn nnnnnnnnnn nnnnnnnnnn nnnnnnnnnn      60
nnngstwtkg actactgggg tcaagga                                          87

<210> SEQ ID NO 57
<211> LENGTH: 90
<212> TYPE: DNA
<213> ORGANISM: Artificial

```
<220> FEATURE:
<223> OTHER INFORMATION: synthetic H3-B16
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (58)..(60)
<223> OTHER INFORMATION: N58 to N60 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (61)..(63)
<223> OTHER INFORMATION: N61 to N63 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
```

<222> LOCATION: (64)..(66)
<223> OTHER INFORMATION: N64 to N66 are independently either TAT, TAC,
      TCA, TCT, TCC, TCG, AGT, AGC, CGA, CGT, CGC, CGG, AGA, or AGG

<400> SEQUENCE: 57
gtctattatt gtgctcgcnn nnnnnnnnnn nnnnnnnnnn nnnnnnnnnn nnnnnnnnnn    60
nnnnnngstw tkgactactg gggtcaagga                                    90

<210> SEQ ID NO 58
<211> LENGTH: 93
<212> TYPE: DNA
<213> ORGANISM: Artificial
<220> FEATURE:
<223> OTHER INFORMATION: synthetic H3-B17
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (58)..(60)
<223> OTHER INFORMATION: N58 to N60 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (61)..(63)
<223> OTHER INFORMATION: N61 to N63 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (64)..(66)
<223> OTHER INFORMATION: N64 to N66 are independently either TAT, TAC,
      TCA, TCT, TCC, TCG, AGT, AGC, CGA, CGT, CGC, CGG, AGA, or AGG
<220> FEATURE:
<221> NAME/KEY: misc_feature
<222> LOCATION: (67)..(69)
<223> OTHER INFORMATION: N67 to N69 are independently either TAT, TAC,
      TCA, TCT, TCC, TCG, AGT, AGC, CGA, CGT, CGC, CGG, AGA, or AGG

<400> SEQUENCE: 58
gtctattatt gtgctcgcnn nnnnnnnnnn nnnnnnnnnn nnnnnnnnnn nnnnnnnnnn      60
nnnnnnnnng stwtkgacta ctggggtcaa gga                                   93

<210> SEQ ID NO 59
<211> LENGTH: 60
<212> TYPE: DNA
<213> ORGANISM: Artificial
<220> FEATURE:
<223> OTHER INFORMATION: synthetic H3-C6
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, GGA, GGT, GGC, GGG, AGT, AGC, CGA, CGT, CGC,
      CGG, AGA, or AGG

<400> SEQUENCE: 59
gtctattatt gtgctcgcnn nnnnnnnnnn nnnnnngstw tkgactactg gggtcaagga       60

-continued

```
<210> SEQ ID NO 60
<211> LENGTH: 63
<212> TYPE: DNA
<213> ORGANISM: Artificial
<220> FEATURE:
<223> OTHER INFORMATION: synthetic H3-C7
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, GGA, GGT, GGC, GGG, AGT, AGC, CGA, CGT, CGC,
      CGG, AGA, or AGG

<400> SEQUENCE: 60
gtctattatt gtgctcgcnn nnnnnnnnnn nnnnnnnnng stwtkgacta ctggggtcaa      60
gga                                                                   63

<210> SEQ ID NO 61
<211> LENGTH: 66
<212> TYPE: DNA
<213> ORGANISM: Artificial
<220> FEATURE:
<223> OTHER INFORMATION: synthetic H3-C8
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, GGA, GGT, GGC, GGG, AGT, AGC, CGA, CGT, CGC,
```

```
          CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, GGA, GGT, GGC, GGG, AGT, AGC, CGA, CGT, CGC,
      CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, GGA, GGT, GGC, GGG, AGT, AGC, CGA, CGT, CGC,
      CGG, AGA, or AGG

<400> SEQUENCE: 61
gtctattatt gtgctcgcnn nnnnnnnnnn nnnnnnnnnn nngstwtkga ctactggggt    60
caagga                                                              66

<210> SEQ ID NO 62
<211> LENGTH: 69
<212> TYPE: DNA
<213> ORGANISM: Artificial
<220> FEATURE:
<223> OTHER INFORMATION: synthetic H3-C9
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
```

```
        TCA, TCT, TCC, TCG, AGT, AGC, GGA, GGT, GGC, GGG, CGA, CGT, CGC,
        CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
        TCA, TCT, TCC, TCG, AGT, AGC, GGA, GGT, GGC, GGG, CGA, CGT, CGC,
        CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
        TCA, TCT, TCC, TCG, AGT, AGC, GGA, GGT, GGC, GGG, CGA, CGT, CGC,
        CGG, AGA, or AGG
<220> FEATURE:
<221> NAME/KEY: misc_feature
<222> LOCATION: (43)..(45)
<223> OTHER INFORMATION: N43 to N45 are independently either TAT, TAC,
        TCA, TCT, TCC, TCG, AGT, AGC, GGA, GGT, GGC, GGG, CGA, CGT, CGC,
        CGG, AGA, or AGG

<400> SEQUENCE: 62
gtctattatt gtgctcgcnn nnnnnnnnnn nnnnnnnnnn nnnnngstwt kgactactgg    60
ggtcaagga                                                           69

<210> SEQ ID NO 63
<211> LENGTH: 72
<212> TYPE: DNA
<213> ORGANISM: Artificial
<220> FEATURE:
<223> OTHER INFORMATION: synthetic H3-C10
<220> FEATURE:
<221> NAME/KEY: misc_feature
<222> LOCATION: (19)..(21)
<223> OTHER INFORMATION: N19 to N21 are independently either TAT, TAC,
        TCA, TCT, TCC, TCG, AGT, AGC, GGA, GGT, GGC, GGG, CGA, CGT, CGC,
        CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
        TCA, TCT, TCC, TCG, AGT, AGC, GGA, GGT, GGC, GGG, CGA, CGT, CGC,
        CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
        TCA, TCT, TCC, TCG, AGT, AGC, GGA, GGT, GGC, GGG, CGA, CGT, CGC,
        CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
        TCA, TCT, TCC, TCG, AGT, AGC, GGA, GGT, GGC, GGG, CGA, CGT, CGC,
        CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
        TCA, TCT, TCC, TCG, AGT, AGC, GGA, GGT, GGC, GGG, CGA, CGT, CGC,
        CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
        TCA, TCT, TCC, TCG, AGT, AGC, GGA, GGT, GGC, GGG, CGA, CGT, CGC,
        CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
        TCA, TCT, TCC, TCG, AGT, AGC, GGA, GGT, GGC, GGG, CGA, CGT, CGC,
        CGG, AGA, or AGG
<220> FEATURE:
<221> NAME/KEY: misc_feature
<222> LOCATION: (40)..(42)
```

-continued

```
<223> OTHER INFORMATION: N40 to N42 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, GGG, CGA, CGT, CGC,
      CGG, AGA, or AGG

<400> SEQUENCE: 63
gtctattatt gtgctcgcnn nnnnnnnnnn nnnnnnnnnn nnnnnnnngs twtkgactac    60
tggggtcaag ga                                                        72

<210> SEQ ID NO 64
<211> LENGTH: 75
<212> TYPE: DNA
<213> ORGANISM: Artificial
<220> FEATURE:
<223> OTHER INFORMATION: synthetic H3-C11
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
```

```
<222> LOCATION: (43)..(45)
<223> OTHER INFORMATION: N43 to N45 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, GGG, CGA, CGT, CGC,
      CGG, AGA, or AGG

<400> SEQUENCE: 64
gtctattatt gtgctcgcnn nnnnnnnnnn nnnnnnnnnn nnnnnnnnnn ngstwtkgac      60
tactggggtc aagga                                                      75

<210> SEQ ID NO 65
<211> LENGTH: 78
<212> TYPE: DNA
<213> ORGANISM: Artificial
<220> FEATURE:
<223> OTHER INFORMATION: synthetic H3-C12
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
```

```
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, GGG, CGA, CGT, CGC,
      CGG, AGA, or AGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, GGA, GGT, GGC, GGG, CGA, CGT, CGC,
      CGG, AGA, or AGG

<400> SEQUENCE: 65
gtctattatt gtgctcgcnn nnnnnnnnnn nnnnnnnnnn nnnnnnnnnn nnnngstwtk    60
gactactggg gtcaagga                                                  78

<210> SEQ ID NO 66
<211> LENGTH: 81
<212> TYPE: DNA
<213> ORGANISM: Artificial
<220> FEATURE:
<223> OTHER INFORMATION: synthetic H3-C13
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (25)..(27)
<223> OTHER INFORMATION: N19 to N21 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, GGG, CGA, CGT, CGC,
      CGG. AGA, or AGG
```

```
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, GGA, GGT, GGC, GGG, CGA, CGT, CGC,
      CGG. AGA, or AGG

<400> SEQUENCE: 66
gtctattatt gtgctcgcnn nnnnnnnnnn nnnnnnnnnn nnnnnnnnnn nnnnnnngst      60
wtkgactact ggggtcaagg a                                                81

<210> SEQ ID NO 67
<211> LENGTH: 84
<212> TYPE: DNA
<213> ORGANISM: Artificial
<220> FEATURE:
<223> OTHER INFORMATION: synthetic H3-C14
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, GGG, CGA, CGT, CGC,
```

CGG. AGA, or AGG
<220> FEATURE:
<221> NAME/KEY: misc_feature
<222> LOCATION: (34)..(36)
<223> OTHER INFORMATION: N34 to N36 are independently either TAT, TAC, TCA, TCT, TCC, TCG, AGT, AGC, GGA, GGT, GGC, GGG, CGA, CGT, CGC, CGG. AGA, or AGG
<220> FEATURE:
<221> NAME/KEY: misc_feature
<222> LOCATION: (37)..(39)
<223> OTHER INFORMATION: N37 to N39 are independently either TAT, TAC, TCA, TCT, TCC, TCG, AGT, AGC, GGA, GGT, GGC, GGG, CGA, CGT, CGC, CGG. AGA, or AGG
<220> FEATURE:
<221> NAME/KEY: misc_feature
<222> LOCATION: (40)..(42)
<223> OTHER INFORMATION: N40 to N42 are independently either TAT, TAC, TCA, TCT, TCC, TCG, AGT, AGC, GGA, GGT, GGC, GGG, CGA, CGT, CGC, CGG. AGA, or AGG
<220> FEATURE:
<221> NAME/KEY: misc_feature
<222> LOCATION: (43)..(45)
<223> OTHER INFORMATION: N43 to N45 are independently either TAT, TAC, TCA, TCT, TCC, TCG, AGT, AGC, GGA, GGT, GGC, GGG, CGA, CGT, CGC, CGG. AGA, or AGG
<220> FEATURE:
<221> NAME/KEY: misc_feature
<222> LOCATION: (46)..(48)
<223> OTHER INFORMATION: N46 to N48 are independently either TAT, TAC, TCA, TCT, TCC, TCG, AGT, AGC, GGA, GGT, GGC, GGG, CGA, CGT, CGC, CGG. AGA, or AGG
<220> FEATURE:
<221> NAME/KEY: misc_feature
<222> LOCATION: (49)..(51)
<223> OTHER INFORMATION: N49 to N51 are independently either TAT, TAC, TCA, TCT, TCC, TCG, AGT, AGC, GGA, GGT, GGC, GGG, CGA, CGT, CGC, CGG. AGA, or AGG
<220> FEATURE:
<221> NAME/KEY: misc_feature
<222> LOCATION: (52)..(54)
<223> OTHER INFORMATION: N52 to N54 are independently either TAT, TAC, TCA, TCT, TCC, TCG, AGT, AGC, GGA, GGT, GGC, GGG, CGA, CGT, CGC, CGG. AGA, or AGG
<220> FEATURE:
<221> NAME/KEY: misc_feature
<222> LOCATION: (55)..(57)
<223> OTHER INFORMATION: N55 to N57 are independently either TAT, TAC, TCA, TCT, TCC, TCG, AGT, AGC, GGA, GGT, GGC, GGG, CGA, CGT, CGC, CGG. AGA, or AGG
<220> FEATURE:
<221> NAME/KEY: misc_feature
<222> LOCATION: (58)..(60)
<223> OTHER INFORMATION: N58 to N60 are independently either TAT, TAC, TCA, TCT, TCC, TCG, AGT, AGC, GGA, GGT, GGC, GGG, CGA, CGT, CGC, CGG. AGA, or AGG

<400> SEQUENCE: 67
gtctattatt gtgctcgcnn nnnnnnnnnn nnnnnnnnnn nnnnnnnnnn nnnnnnnnnn    60
gstwtkgact actggggtca agga                                            84

<210> SEQ ID NO 68
<211> LENGTH: 87
<212> TYPE: DNA
<213> ORGANISM: Artificial
<220> FEATURE:
<223> OTHER INFORMATION: synthetic H3-C15
<220> FEATURE:
<221> NAME/KEY: misc_feature
<222> LOCATION: (19)..(21)
<223> OTHER INFORMATION: N19 to N21 are independently either TAT, TAC, TCA, TCT, TCC, TCG, AGT, AGC, GGA, GGT, GGC, GGG, CGA, CGT, CGC, CGG. AGA, or AGG
<220> FEATURE:
<221> NAME/KEY: misc_feature
<222> LOCATION: (22)..(24)
<223> OTHER INFORMATION: N22 to N24 are independently either TAT, TAC,

```
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (58)..(60)
<223> OTHER INFORMATION: N58 to N60 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (61)..(63)
<223> OTHER INFORMATION: N61 to N63 are independently either TAT, TAC,
      TCA, TCT, TCC, TCG, AGT, AGC, GGA, GGT, GGC, GGG, CGA, CGT, CGC,
```

CGG. AGA, or AGG

<400> SEQUENCE: 68
gtctattatt gtgctcgcnn nnnnnnnnnn nnnnnnnnnn nnnnnnnnnn nnnnnnnnnn    60
nnngstwtkg actactgggg tcaagga                                        87

<210> SEQ ID NO 69
<211> LENGTH: 90
<212> TYPE: DNA
<213> ORGANISM: Artificial
<220> FEATURE:
<223> OTHER INFORMATION: synthetic H3-C16
<220> FEATURE:
<221> NAME/KEY: misc_feature
<222> LOCATION: (19)..(21)
<223> OTHER INFORMATION: N19 to N21 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (22)..(24)
<223> OTHER INFORMATION: N22 to N24 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (25)..(27)
<223> OTHER INFORMATION: N25 to N27 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (28)..(30)
<223> OTHER INFORMATION: N28 to N30 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (31)..(33)
<223> OTHER INFORMATION: N31 to N33 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (34)..(36)
<223> OTHER INFORMATION: N34 to N36 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (49)..(51)
<223> OTHER INFORMATION: N49 to N51 are independently either TAT, TAC, TCA, TCT, TCC, TCG, AGT, AGC, GGA, GGT, GGC, GGG, CGA, CGT, CGC,
        CGG. AGA, or AGG
<220> FEATURE:
<221> NAME/KEY: misc_feature
<222> LOCATION: (52)..(54)
<223> OTHER INFORMATION: N52 to N54 are independently either TAT, TAC,
        TCA, TCT, TCC, TCG, AGT, AGC, GGA, GGT, GGC, GGG, CGA, CGT, CGC,
        CGG. AGA, or AGG
<220> FEATURE:
<221> NAME/KEY: misc_feature
<222> LOCATION: (55)..(57)
<223> OTHER INFORMATION: N55 to N57 are independently either TAT, TAC,
        TCA, TCT, TCC, TCG, AGT, AGC, GGA, GGT, GGC, GGG, CGA, CGT, CGC,
        CGG. AGA, or AGG
<220> FEATURE:
<221> NAME/KEY: misc_feature
<222> LOCATION: (58)..(60)
<223> OTHER INFORMATION: N58 to N60 are independently either TAT, TAC,
        TCA, TCT, TCC, TCG, AGT, AGC, GGA, GGT, GGC, GGG, CGA, CGT, CGC,
        CGG. AGA, or AGG
<220> FEATURE:
<221> NAME/KEY: misc_feature
<222> LOCATION: (61)..(63)
<223> OTHER INFORMATION: N61 to N63 are independently either TAT, TAC,
        TCA, TCT, TCC, TCG, AGT, AGC, GGA, GGT, GGC, GGG, CGA, CGT, CGC,
        CGG. AGA, or AGG
<220> FEATURE:
<221> NAME/KEY: misc_feature
<222> LOCATION: (64)..(66)
<223> OTHER INFORMATION: N64 to N66 are independently either TAT, TAC,
        TCA, TCT, TCC, TCG, AGT, AGC, GGA, GGT, GGC, GGG, CGA, CGT, CGC,
        CGG. AGA, or AGG

<400> SEQUENCE: 69
gtctattatt gtgctcgcnn nnnnnnnnnn nnnnnnnnnn nnnnnnnnnn nnnnnnnnnn      60
nnnnnngstw tkgactactg gggtcaagga                                       90

<210> SEQ ID NO 70
<211> LENGTH: 93
<212> TYPE: DNA
<213> ORGANISM: Artificial
<220> FEATURE:
<223> OTHER INFORMATION: synthetic H3-C17
<220> FEATURE:
<221> NAME/KEY: misc_feature
<222> LOCATION: (19)..(21)
<223> OTHER INFORMATION: N19 to N21 are independently either TAT, TAC,
        TCA, TCT, TCC, TCG, AGT, AGC, GGA, GGT, GGC, GGG, CGA, CGT, CGC,
        CGG. AGA, or AGG
<220> FEATURE:
<221> NAME/KEY: misc_feature
<222> LOCATION: (22)..(24)
<223> OTHER INFORMATION: N21 to N24 are independently either TAT, TAC,
        TCA, TCT, TCC, TCG, AGT, AGC, GGA, GGT, GGC, GGG, CGA, CGT, CGC,
        CGG. AGA, or AGG
<220> FEATURE:
<221> NAME/KEY: misc_feature
<222> LOCATION: (25)..(27)
<223> OTHER INFORMATION: N25 to N27 are independently either TAT, TAC,
        TCA, TCT, TCC, TCG, AGT, AGC, GGA, GGT, GGC, GGG, CGA, CGT, CGC,
        CGG. AGA, or AGG
<220> FEATURE:
<221> NAME/KEY: misc_feature
<222> LOCATION: (28)..(30)
<223> OTHER INFORMATION: N28 to N30 are independently either TAT, TAC,
        TCA, TCT, TCC, TCG, AGT, AGC, GGA, GGT, GGC, GGG, CGA, CGT, CGC,
        CGG. AGA, or AGG
<220> FEATURE:
<221> NAME/KEY: misc_feature
<222> LOCATION: (31)..(33)
<223> OTHER INFORMATION: N31 to N33 are independently either TAT, TAC,
        TCA, TCT, TCC, TCG, AGT, AGC, GGA, GGT, GGC, GGG, CGA, CGT, CGC,
        CGG. AGA, or AGG
<220> FEATURE:
<221> NAME/KEY: misc_feature
<222> LOCATION: (34)..(36)

```
<223> OTHER INFORMATION: N34 to N36 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (37)..(39)
<223> OTHER INFORMATION: N37 to N39 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (40)..(42)
<223> OTHER INFORMATION: N40 to N42 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (43)..(45)
<223> OTHER INFORMATION: N43 to N45 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (46)..(48)
<223> OTHER INFORMATION: N46 to N48 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (49)..(51)
<223> OTHER INFORMATION: N49 to N51 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (52)..(54)
<223> OTHER INFORMATION: N52 to N54 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (55)..(57)
<223> OTHER INFORMATION: N55 to N57 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (58)..(60)
<223> OTHER INFORMATION: N58 to N60 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (61)..(63)
<223> OTHER INFORMATION: N61 to N63 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (64)..(66)
<223> OTHER INFORMATION: N64 to N66 are independently either TAT, TAC,
      TCA, TCT, TCC, TCG, AGT, AGC, GGA, GGT, GGC, GGG, CGA, CGT, CGC,
      CGG. AGA, or AGG
<220> FEATURE:
<221> NAME/KEY: misc_feature
<222> LOCATION: (67)..(69)
<223> OTHER INFORMATION: N67 to N69 are independently either TAT, TAC,
      TCA, TCT, TCC, TCG, AGT, AGC, GGA, GGT, GGC, GGG, CGA, CGT, CGC,
      CGG. AGA, or AGG

<400> SEQUENCE: 70
gtctattatt gtgctcgcnn nnnnnnnnnn nnnnnnnnnn nnnnnnnnnn nnnnnnnnnn    60
nnnnnnnnng stwtkgacta ctgggggtcaa gga                                93

<210> SEQ ID NO 71
<211> LENGTH: 60
```

```
<212> TYPE: DNA
<213> ORGANISM: Artificial
<220> FEATURE:
<223> OTHER INFORMATION: synthetic H3-C6
<220> FEATURE:
<221> NAME/KEY: misc_feature
<222> LOCATION: (19)..(36)
<223> OTHER INFORMATION: N19 to N36 is any combination of A, T, C, or G,
      except TGT, TGC, TGA, TAA, TAG

<400> SEQUENCE: 71
gtctattatt gtgctcgcnn nnnnnnnnnn nnnnnngstw tkgactactg gggtcaagga      60

<210> SEQ ID NO 72
<211> LENGTH: 63
<212> TYPE: DNA
<213> ORGANISM: Artificial
<220> FEATURE:
<223> OTHER INFORMATION: synthetic H3-C7
<220> FEATURE:
<221> NAME/KEY: misc_feature
<222> LOCATION: (19)..(39)
<223> OTHER INFORMATION: N19 to N39 is any combination of A, T, C, or G,
      except TGT, TGC, TGA, TAA, TAG

<400> SEQUENCE: 72
gtctattatt gtgctcgcnn nnnnnnnnnn nnnnnnnnng stwtkgacta ctggggtcaa      60
gga                                                                   63

<210> SEQ ID NO 73
<211> LENGTH: 66
<212> TYPE: DNA
<213> ORGANISM: Artificial
<220> FEATURE:
<223> OTHER INFORMATION: synthetic H3-C8
<220> FEATURE:
<221> NAME/KEY: misc_feature
<222> LOCATION: (19)..(42)
<223> OTHER INFORMATION: N19 to N42 is any combination of A, T, C, or G,
      except TGT, TGC, TGA, TAA, TAG

<400> SEQUENCE: 73
gtctattatt gtgctcgcnn nnnnnnnnnn nnnnnnnnnn nngstwtkga ctactggggt      60
caagga                                                                66

<210> SEQ ID NO 74
<211> LENGTH: 69
<212> TYPE: DNA
<213> ORGANISM: Artificial
<220> FEATURE:
<223> OTHER INFORMATION: synthetic H3-C9
<220> FEATURE:
<221> NAME/KEY: misc_feature
<222> LOCATION: (19)..(45)
<223> OTHER INFORMATION: N19 to N45 is any combination of A, T, C, or G,
      except TGT, TGC, TGA, TAA, TAG

<400> SEQUENCE: 74
gtctattatt gtgctcgcnn nnnnnnnnnn nnnnnnnnnn nnnngstwt kgactactgg      60 ggtcaagga                                                             69

<210> SEQ ID NO 75
<211> LENGTH: 72
<212> TYPE: DNA
<213> ORGANISM: Artificial
<220> FEATURE:
<223> OTHER INFORMATION: synthetic H3-C10
<220> FEATURE:
```

```
<221> NAME/KEY: misc_feature
<222> LOCATION: (19)..(48)
<223> OTHER INFORMATION: N19 to N48 is any combination of A, T, C, or G,
      except TGT, TGC, TGA, TAA, TAG

<400> SEQUENCE: 75
gtctattatt gtgctcgcnn nnnnnnnnnn nnnnnnnnnn nnnnnnnngs twtkgactac    60
tggggtcaag ga                                                        72

<210> SEQ ID NO 76
<211> LENGTH: 75
<212> TYPE: DNA
<213> ORGANISM: Artificial
<220> FEATURE:
<223> OTHER INFORMATION: synthetic H3-C11
<220> FEATURE:
<221> NAME/KEY: misc_feature
<222> LOCATION: (19)..(51)
<223> OTHER INFORMATION: N19 to N51 is any combination of A, T, C, or G,
      except TGT, TGC, TGA, TAA, TAG

<400> SEQUENCE: 76
gtctattatt gtgctcgcnn nnnnnnnnnn nnnnnnnnnn nnnnnnnnnn ngstwtkgac    60
tactggggtc aagga                                                    75

<210> SEQ ID NO 77
<211> LENGTH: 78
<212> TYPE: DNA
<213> ORGANISM: Artificial
<220> FEATURE:
<223> OTHER INFORMATION: synthetic H3-C12
<220> FEATURE:
<221> NAME/KEY: misc_feature
<222> LOCATION: (19)..(54)
<223> OTHER INFORMATION: N19 to N54 is any combination of A, T, C, or G,
      except TGT, TGC, TGA, TAA, TAG

<400> SEQUENCE: 77
gtctattatt gtgctcgcnn nnnnnnnnnn nnnnnnnnnn nnnnnnnnnn nnnngstwtk    60
gactactggg gtcaagga                                                 78

<210> SEQ ID NO 78
<211> LENGTH: 81
<212> TYPE: DNA
<213> ORGANISM: Artificial
<220> FEATURE:
<223> OTHER INFORMATION: synthetic H3-C13
<220> FEATURE:
<221> NAME/KEY: misc_feature
<222> LOCATION: (19)..(57)
<223> OTHER INFORMATION: N19 to N57 is any combination of A, T, C, or G,
      except TGT, TGC, TGA, TAA, TAG

<400> SEQUENCE: 78
gtctattatt gtgctcgcnn nnnnnnnnnn nnnnnnnnnn nnnnnnnnnn nnnnnnngst    60
wtkgactact ggggtcaagg a                                             81

<210> SEQ ID NO 79
<211> LENGTH: 84
<212> TYPE: DNA
<213> ORGANISM: Artificial
<220> FEATURE:
<223> OTHER INFORMATION: synthetic H3-C14
<220> FEATURE:
<221> NAME/KEY: misc_feature
<222> LOCATION: (19)..(60)
<223> OTHER INFORMATION: N19 to N60 is any combination of A, T, C, or G,
``` except TGT, TGC, TGA, TAA, TAG

<400> SEQUENCE: 79
gtctattatt gtgctcgcnn nnnnnnnnnn nnnnnnnnnn nnnnnnnnnn nnnnnnnnnn    60
gstwtkgact actggggtca agga    84

<210> SEQ ID NO 80
<211> LENGTH: 87
<212> TYPE: DNA
<213> ORGANISM: Artificial
<220> FEATURE:
<223> OTHER INFORMATION: synthetic H3-C15
<220> FEATURE:
<221> NAME/KEY: misc_feature
<222> LOCATION: (19)..(63)
<223> OTHER INFORMATION: N19 to N63 is any combination of A, T, C, or G,
      except TGT, TGC, TGA, TAA, TAG

<400> SEQUENCE: 80
gtctattatt gtgctcgcnn nnnnnnnnnn nnnnnnnnnn nnnnnnnnnn nnnnnnnnnn    60
nnngstwtkg actactgggg tcaagga    87

<210> SEQ ID NO 81
<211> LENGTH: 90
<212> TYPE: DNA
<213> ORGANISM: Artificial
<220> FEATURE:
<223> OTHER INFORMATION: synthetic H3-C16
<220> FEATURE:
<221> NAME/KEY: misc_feature
<222> LOCATION: (19)..(66)
<223> OTHER INFORMATION: N19 to N66 is any combination of A, T, C, or G,
      except TGT, TGC, TGA, TAA, TAG

<400> SEQUENCE: 81
gtctattatt gtgctcgcnn nnnnnnnnnn nnnnnnnnnn nnnnnnnnnn nnnnnnnnnn    60
nnnnnngstw tkgactactg gggtcaagga    90

<210> SEQ ID NO 82
<211> LENGTH: 93
<212> TYPE: DNA
<213> ORGANISM: Artificial
<220> FEATURE:
<223> OTHER INFORMATION: synthetic H3-C17
<220> FEATURE:
<221> NAME/KEY: misc_feature
<222> LOCATION: (19)..(69)
<223> OTHER INFORMATION: N19 to N69 is any combination of A, T, C, or G,
      except TGT, TGC, TGA, TAA, TAG

<400> SEQUENCE: 82
gtctattatt gtgctcgcnn nnnnnnnnnn nnnnnnnnnn nnnnnnnnnn nnnnnnnnnn    60
nnnnnnnnng stwtkgacta ctggggtcaa gga    93

<210> SEQ ID NO 83
<211> LENGTH: 9
<212> TYPE: PRT
<213> ORGANISM: Artificial
<220> FEATURE:
<223> OTHER INFORMATION: synthetic HER2 binding clone 1 CDRL3

<400> SEQUENCE: 83

Gln Gln Ser Tyr Tyr Ser Pro Ser Thr
1               5

```
<210> SEQ ID NO 84
<211> LENGTH: 9
<212> TYPE: PRT
<213> ORGANISM: Artificial
<220> FEATURE:
<223> OTHER INFORMATION: synthetic HER2 binding clone 2 CDRL3

<400> SEQUENCE: 84

Gln Gln Ser Ser Tyr Tyr Pro Ser Thr
1               5

<210> SEQ ID NO 85
<211> LENGTH: 9
<212> TYPE: PRT
<213> ORGANISM: Artificial
<220> FEATURE:
<223> OTHER INFORMATION: synthetic HER2 binding clone 3 CDRL3

<400> SEQUENCE: 85

Gln Gln Ser Ser Tyr Tyr Pro Ser Thr
1               5

<210> SEQ ID NO 86
<211> LENGTH: 9
<212> TYPE: PRT
<213> ORGANISM: Artificial
<220> FEATURE:
<223> OTHER INFORMATION: synthetic HER2 binding clone 4 CDRL3

<400> SEQUENCE: 86

Gln Gln Ser Tyr Tyr Ser Pro Ser Thr
1               5

<210> SEQ ID NO 87
<211> LENGTH: 9
<212> TYPE: PRT
<213> ORGANISM: Artificial
<220> FEATURE:
<223> OTHER INFORMATION: synthetic HER2 binding clone 5 CDRL3

<400> SEQUENCE: 87

Gln Gln Ser Tyr Tyr Tyr Pro Ser Thr
1               5

<210> SEQ ID NO 88
<211> LENGTH: 9
<212> TYPE: PRT
<213> ORGANISM: Artificial
<220> FEATURE:
<223> OTHER INFORMATION: synthetic HER2 binding clone 6 CDRL3

<400> SEQUENCE: 88

Gln Gln Ser Tyr Tyr Ser Pro Ser Thr
1               5

<210> SEQ ID NO 89
<211> LENGTH: 9
<212> TYPE: PRT
<213> ORGANISM: Artificial
<220> FEATURE:
<223> OTHER INFORMATION: synthetic HER2 binding clone 7 CDRL3

<400> SEQUENCE: 89

Gln Gln Ser Tyr Tyr Tyr Pro Ser Thr
1               5

<210> SEQ ID NO 90
```

```
<211> LENGTH: 9
<212> TYPE: PRT
<213> ORGANISM: Artificial
<220> FEATURE:
<223> OTHER INFORMATION: synthetic HER2 binding clone 8 CDRL3

<400> SEQUENCE: 90

Gln Gln Tyr Tyr Tyr Tyr Pro Tyr Thr
1               5

<210> SEQ ID NO 91
<211> LENGTH: 9
<212> TYPE: PRT
<213> ORGANISM: Artificial
<220> FEATURE:
<223> OTHER INFORMATION: synthetic HER2 binding clone 9 CDRL3

<400> SEQUENCE: 91

Gln Gln Tyr Tyr Tyr Ser Pro Ser Thr
1               5

<210> SEQ ID NO 92
<211> LENGTH: 9
<212> TYPE: PRT
<213> ORGANISM: Artificial
<220> FEATURE:
<223> OTHER INFORMATION: synthetic HER2 binding clone 10 CDRL3

<400> SEQUENCE: 92

Gln Gln Ser Tyr Tyr Tyr Pro Tyr Thr
1               5

<210> SEQ ID NO 93
<211> LENGTH: 9
<212> TYPE: PRT
<213> ORGANISM: Artificial
<220> FEATURE:
<223> OTHER INFORMATION: synthetic HER2 binding clone 11 CDRL3

<400> SEQUENCE: 93

Gln Gln Ser Ser Tyr Ser Pro Tyr Thr
1               5

<210> SEQ ID NO 94
<211> LENGTH: 9
<212> TYPE: PRT
<213> ORGANISM: Artificial
<220> FEATURE:
<223> OTHER INFORMATION: synthetic HER2 binding clone 12 CDRL3

<400> SEQUENCE: 94

Gln Gln His Tyr Thr Thr Pro Pro Thr
1               5

<210> SEQ ID NO 95
<211> LENGTH: 9
<212> TYPE: PRT
<213> ORGANISM: Artificial
<220> FEATURE:
<223> OTHER INFORMATION: synthetic HER2 binding clone 13 CDRL3

<400> SEQUENCE: 95

Gln Gln Tyr Ser Tyr Tyr Pro Tyr Thr
1               5

<210> SEQ ID NO 96
<211> LENGTH: 9
```

```
<212> TYPE: PRT
<213> ORGANISM: Artificial
<220> FEATURE:
<223> OTHER INFORMATION: synthetic HER2 binding clone 14 CDRL3

<400> SEQUENCE: 96

Gln Gln Tyr Ser Tyr Tyr Pro Ser Thr
1               5

<210> SEQ ID NO 97
<211> LENGTH: 9
<212> TYPE: PRT
<213> ORGANISM: Artificial
<220> FEATURE:
<223> OTHER INFORMATION: synthetic HER2 binding clone 15 CDRL3

<400> SEQUENCE: 97

Gln Gln Tyr Ser Tyr Tyr Pro Tyr Thr
1               5

<210> SEQ ID NO 98
<211> LENGTH: 9
<212> TYPE: PRT
<213> ORGANISM: Artificial
<220> FEATURE:
<223> OTHER INFORMATION: synthetic HER2 binding clone 16 CDRL3

<400> SEQUENCE: 98

Gln Gln Ser Ser Tyr Ser Pro Ser Thr
1               5

<210> SEQ ID NO 99
<211> LENGTH: 9
<212> TYPE: PRT
<213> ORGANISM: Artificial
<220> FEATURE:
<223> OTHER INFORMATION: synthetic HER2 binding clone 17 CDRL3

<400> SEQUENCE: 99

Gln Gln Tyr Ser Tyr Tyr Pro Tyr Thr
1               5

<210> SEQ ID NO 100
<211> LENGTH: 9
<212> TYPE: PRT
<213> ORGANISM: Artificial
<220> FEATURE:
<223> OTHER INFORMATION: synthetic HER2 binding clone 18 CDRL3

<400> SEQUENCE: 100

Gln Gln Tyr Ser Tyr Tyr Pro Ser Thr
1               5

<210> SEQ ID NO 101
<211> LENGTH: 9
<212> TYPE: PRT
<213> ORGANISM: Artificial
<220> FEATURE:
<223> OTHER INFORMATION: synthetic HER2 binding clone 19 CDRL3

<400> SEQUENCE: 101

Gln Gln Tyr Ser Tyr Tyr Pro Tyr Thr
1               5

<210> SEQ ID NO 102
<211> LENGTH: 9
<212> TYPE: PRT
```

```
<213> ORGANISM: Artificial
<220> FEATURE:
<223> OTHER INFORMATION: synthetic HER2 binding clone 20 CDRL3

<400> SEQUENCE: 102

Gln Gln Tyr Ser Tyr Tyr Pro Tyr Thr
1               5

<210> SEQ ID NO 103
<211> LENGTH: 9
<212> TYPE: PRT
<213> ORGANISM: Artificial
<220> FEATURE:
<223> OTHER INFORMATION: synthetic HER2 binding clone 21 CDRL3

<400> SEQUENCE: 103

Gln Gln Tyr Ser Tyr Tyr Pro Tyr Thr
1               5

<210> SEQ ID NO 104
<211> LENGTH: 9
<212> TYPE: PRT
<213> ORGANISM: Artificial
<220> FEATURE:
<223> OTHER INFORMATION: synthetic HER2 binding clone 22 CDRL3

<400> SEQUENCE: 104

Gln Gln Tyr Ser Tyr Tyr Pro Tyr Thr
1               5

<210> SEQ ID NO 105
<211> LENGTH: 9
<212> TYPE: PRT
<213> ORGANISM: Artificial
<220> FEATURE:
<223> OTHER INFORMATION: synthetic HER2 binding clone 23 CDRL3

<400> SEQUENCE: 105

Gln Gln Tyr Ser Tyr Tyr Pro Tyr Thr
1               5

<210> SEQ ID NO 106
<211> LENGTH: 9
<212> TYPE: PRT
<213> ORGANISM: Artificial
<220> FEATURE:
<223> OTHER INFORMATION: synthetic HER2 binding clone 24 CDRL3

<400> SEQUENCE: 106

Gln Gln Tyr Ser Tyr Tyr Pro Tyr Thr
1               5

<210> SEQ ID NO 107
<211> LENGTH: 9
<212> TYPE: PRT
<213> ORGANISM: Artificial
<220> FEATURE:
<223> OTHER INFORMATION: synthetic HER2 binding clone 25 CDRL3

<400> SEQUENCE: 107

Gln Gln Tyr Ser Tyr Tyr Pro Ser Thr
1               5

<210> SEQ ID NO 108
<211> LENGTH: 9
<212> TYPE: PRT
<213> ORGANISM: Artificial
```

```
<220> FEATURE:
<223> OTHER INFORMATION: synthetic HER2 binding clone 26 CDRL3

<400> SEQUENCE: 108

Gln Gln Tyr Ser Tyr Tyr Pro Ser Thr
1               5

<210> SEQ ID NO 109
<211> LENGTH: 9
<212> TYPE: PRT
<213> ORGANISM: Artificial
<220> FEATURE:
<223> OTHER INFORMATION: synthetic HER2 binding clone 27 CDRL3

<400> SEQUENCE: 109

Gln Gln Tyr Ser Tyr Tyr Pro Tyr Thr
1               5

<210> SEQ ID NO 110
<211> LENGTH: 9
<212> TYPE: PRT
<213> ORGANISM: Artificial
<220> FEATURE:
<223> OTHER INFORMATION: synthetic HER2 binding clone 28 CDRL3

<400> SEQUENCE: 110

Gln Gln Tyr Ser Tyr Tyr Pro Tyr Thr
1               5

<210> SEQ ID NO 111
<211> LENGTH: 9
<212> TYPE: PRT
<213> ORGANISM: Artificial
<220> FEATURE:
<223> OTHER INFORMATION: synthetic HER2 binding clone 29 CDRL3

<400> SEQUENCE: 111

Gln Gln Ser Ser Tyr Ser Pro Ser Thr
1               5

<210> SEQ ID NO 112
<211> LENGTH: 9
<212> TYPE: PRT
<213> ORGANISM: Artificial
<220> FEATURE:
<223> OTHER INFORMATION: synthetic HER2 binding clone 30 CDRL3

<400> SEQUENCE: 112

Gln Gln Ser Ser Tyr Tyr Pro Tyr Thr
1               5

<210> SEQ ID NO 113
<211> LENGTH: 9
<212> TYPE: PRT
<213> ORGANISM: Artificial
<220> FEATURE:
<223> OTHER INFORMATION: synthetic HER2 binding clone 31 CDRL3

<400> SEQUENCE: 113

Gln Gln Ser Tyr Tyr Tyr Pro Ser Thr
1               5

<210> SEQ ID NO 114
<211> LENGTH: 9
<212> TYPE: PRT
<213> ORGANISM: Artificial
<220> FEATURE:
```

<223> OTHER INFORMATION: synthetic HER2 binding clone 32 CDRL3

<400> SEQUENCE: 114

Gln Gln Ser Ser Tyr Tyr Pro Tyr Thr
1               5

<210> SEQ ID NO 115
<211> LENGTH: 9
<212> TYPE: PRT
<213> ORGANISM: Artificial
<220> FEATURE:
<223> OTHER INFORMATION: synthetic HER2 binding clone 33 CDRL3

<400> SEQUENCE: 115

Gln Gln Ser Phe Ser Ser Pro Tyr Thr
1               5

<210> SEQ ID NO 116
<211> LENGTH: 9
<212> TYPE: PRT
<213> ORGANISM: Artificial
<220> FEATURE:
<223> OTHER INFORMATION: synthetic HER2 binding clone 34 CDRL3

<400> SEQUENCE: 116

Gln Gln Ser Tyr Ser Ser Pro Tyr Thr
1               5

<210> SEQ ID NO 117
<211> LENGTH: 9
<212> TYPE: PRT
<213> ORGANISM: Artificial
<220> FEATURE:
<223> OTHER INFORMATION: synthetic HER2 binding clone 35 CDRL3

<400> SEQUENCE: 117

Gln Gln Ser Tyr Ser Tyr Pro Ser Thr
1               5

<210> SEQ ID NO 118
<211> LENGTH: 9
<212> TYPE: PRT
<213> ORGANISM: Artificial
<220> FEATURE:
<223> OTHER INFORMATION: synthetic HER2 binding clone 36 CDRL3

<400> SEQUENCE: 118

Gln Gln Ser Phe Ser Tyr Pro Tyr Thr
1               5

<210> SEQ ID NO 119
<211> LENGTH: 9
<212> TYPE: PRT
<213> ORGANISM: Artificial
<220> FEATURE:
<223> OTHER INFORMATION: synthetic HER2 binding clone 37 CDRL3

<400> SEQUENCE: 119

Gln Gln Ser Tyr Ser Ser Pro Tyr Thr
1               5

<210> SEQ ID NO 120
<211> LENGTH: 9
<212> TYPE: PRT
<213> ORGANISM: Artificial
<220> FEATURE:
<223> OTHER INFORMATION: synthetic HER2 binding clone 38 CDRL3

```
<400> SEQUENCE: 120

Gln Gln Ser Tyr Ser Ser Pro Ser Thr
1               5

<210> SEQ ID NO 121
<211> LENGTH: 9
<212> TYPE: PRT
<213> ORGANISM: Artificial
<220> FEATURE:
<223> OTHER INFORMATION: synthetic HER2 binding clone 39 CDRL3

<400> SEQUENCE: 121

Gln Gln Ser Tyr Ser Tyr Pro Ser Thr
1               5

<210> SEQ ID NO 122
<211> LENGTH: 9
<212> TYPE: PRT
<213> ORGANISM: Artificial
<220> FEATURE:
<223> OTHER INFORMATION: synthetic HER2 binding clone 40 CDRL3

<400> SEQUENCE: 122

Gln Gln Ser Tyr Ser Ser Pro Tyr Thr
1               5

<210> SEQ ID NO 123
<211> LENGTH: 9
<212> TYPE: PRT
<213> ORGANISM: Artificial
<220> FEATURE:
<223> OTHER INFORMATION: synthetic HER2 binding clone 41 CDRL3

<400> SEQUENCE: 123

Gln Gln Ser Tyr Ser Ser Pro Ser Thr
1               5

<210> SEQ ID NO 124
<211> LENGTH: 9
<212> TYPE: PRT
<213> ORGANISM: Artificial
<220> FEATURE:
<223> OTHER INFORMATION: synthetic HER2 binding clone 42 CDRL3

<400> SEQUENCE: 124

Gln Gln Ser Tyr Ser Ser Pro Ser Thr
1               5

<210> SEQ ID NO 125
<211> LENGTH: 9
<212> TYPE: PRT
<213> ORGANISM: Artificial
<220> FEATURE:
<223> OTHER INFORMATION: synthetic HER2 binding clone 43 CDRL3

<400> SEQUENCE: 125

Gln Gln Ser Phe Ser Ser Pro Ser Thr
1               5

<210> SEQ ID NO 126
<211> LENGTH: 9
<212> TYPE: PRT
<213> ORGANISM: Artificial
<220> FEATURE:
<223> OTHER INFORMATION: synthetic HER2 binding clone 44 CDRL3
```

```
<400> SEQUENCE: 126

Gln Gln Ser Ser Ser Ser Pro Tyr Thr
1               5

<210> SEQ ID NO 127
<211> LENGTH: 9
<212> TYPE: PRT
<213> ORGANISM: Artificial
<220> FEATURE:
<223> OTHER INFORMATION: synthetic HER2 binding clone 45 CDRL3

<400> SEQUENCE: 127

Gln Gln Ser Tyr Ser Ser Pro Tyr Thr
1               5

<210> SEQ ID NO 128
<211> LENGTH: 9
<212> TYPE: PRT
<213> ORGANISM: Artificial
<220> FEATURE:
<223> OTHER INFORMATION: synthetic HER2 binding clone 46 CDRL3

<400> SEQUENCE: 128

Gln Gln Ser Ser Ser Ser Pro Tyr Thr
1               5

<210> SEQ ID NO 129
<211> LENGTH: 9
<212> TYPE: PRT
<213> ORGANISM: Artificial
<220> FEATURE:
<223> OTHER INFORMATION: synthetic HER2 binding clone 47 CDRL3

<400> SEQUENCE: 129

Gln Gln Ser Tyr Ser Ser Pro Ser Thr
1               5

<210> SEQ ID NO 130
<211> LENGTH: 9
<212> TYPE: PRT
<213> ORGANISM: Artificial
<220> FEATURE:
<223> OTHER INFORMATION: synthetic HER2 binding clone 48 CDRL3

<400> SEQUENCE: 130

Gln Gln Ser Ser Ser Tyr Pro Tyr Thr
1               5

<210> SEQ ID NO 131
<211> LENGTH: 9
<212> TYPE: PRT
<213> ORGANISM: Artificial
<220> FEATURE:
<223> OTHER INFORMATION: synthetic HER2 binding clone 49 CDRL3

<400> SEQUENCE: 131

Gln Ser Ser Tyr Ser Tyr Pro Ser Thr
1               5

<210> SEQ ID NO 132
<211> LENGTH: 9
<212> TYPE: PRT
<213> ORGANISM: Artificial
<220> FEATURE:
<223> OTHER INFORMATION: synthetic HER2 binding clone 50 CDRL3

<400> SEQUENCE: 132
```

```
Gln Gln Ser Ser Ser Pro Tyr Thr
1               5
```

<210> SEQ ID NO 133
<211> LENGTH: 9
<212> TYPE: PRT
<213> ORGANISM: Artificial
<220> FEATURE:
<223> OTHER INFORMATION: synthetic HER2 binding clone 51 CDRL3

<400> SEQUENCE: 133

```
Gln Gln Ser Ser Ser Tyr Pro Tyr Thr
1               5
```

<210> SEQ ID NO 134
<211> LENGTH: 9
<212> TYPE: PRT
<213> ORGANISM: Artificial
<220> FEATURE:
<223> OTHER INFORMATION: synthetic HER2 binding clone 52 CDRL3

<400> SEQUENCE: 134

```
Gln Gln Ser Ser Ser Tyr Pro Ser Thr
1               5
```

<210> SEQ ID NO 135
<211> LENGTH: 9
<212> TYPE: PRT
<213> ORGANISM: Artificial
<220> FEATURE:
<223> OTHER INFORMATION: synthetic HER2 binding clone 53 CDRL3

<400> SEQUENCE: 135

```
Gln Gln Ser Tyr Ser Ser Pro Ser Thr
1               5
```

<210> SEQ ID NO 136
<211> LENGTH: 9
<212> TYPE: PRT
<213> ORGANISM: Artificial
<220> FEATURE:
<223> OTHER INFORMATION: synthetic HER2 binding clone 54 CDRL3

<400> SEQUENCE: 136

```
Gln Gln Ser Ser Ser Ser Pro Tyr Thr
1               5
```

<210> SEQ ID NO 137
<211> LENGTH: 9
<212> TYPE: PRT
<213> ORGANISM: Artificial
<220> FEATURE:
<223> OTHER INFORMATION: synthetic HER2 binding clone 55 CDRL3

<400> SEQUENCE: 137

```
Gln Gln Ser Ser Ser Tyr Pro Ser Thr
1               5
```

<210> SEQ ID NO 138
<211> LENGTH: 9
<212> TYPE: PRT
<213> ORGANISM: Artificial
<220> FEATURE:
<223> OTHER INFORMATION: synthetic HER2 binding clone 56 CDRL3

<400> SEQUENCE: 138

Gln Gln Ser Ser Tyr Tyr Pro Ser Thr
1               5

<210> SEQ ID NO 139
<211> LENGTH: 9
<212> TYPE: PRT
<213> ORGANISM: Artificial
<220> FEATURE:
<223> OTHER INFORMATION: synthetic HER2 binding clone 57 CDRL3

<400> SEQUENCE: 139

Gln Gln Ser Ser Phe Ser Pro Tyr Thr
1               5

<210> SEQ ID NO 140
<211> LENGTH: 9
<212> TYPE: PRT
<213> ORGANISM: Artificial
<220> FEATURE:
<223> OTHER INFORMATION: synthetic HER2 binding clone 58 CDRL3

<400> SEQUENCE: 140

Gln Gln Ser Ser Ser Tyr Pro Tyr Thr
1               5

<210> SEQ ID NO 141
<211> LENGTH: 9
<212> TYPE: PRT
<213> ORGANISM: Artificial
<220> FEATURE:
<223> OTHER INFORMATION: synthetic HER2 binding clone 59 CDRL3

<400> SEQUENCE: 141

Gln Gln Ser Ser Ser Tyr Pro Ser Thr
1               5

<210> SEQ ID NO 142
<211> LENGTH: 9
<212> TYPE: PRT
<213> ORGANISM: Artificial
<220> FEATURE:
<223> OTHER INFORMATION: synthetic HER2 binding clone 60 CDRL3

<400> SEQUENCE: 142

Gln Gln Ser Ser Ser Ser Pro Tyr Thr
1               5

<210> SEQ ID NO 143
<211> LENGTH: 9
<212> TYPE: PRT
<213> ORGANISM: Artificial
<220> FEATURE:
<223> OTHER INFORMATION: synthetic HER2 binding clone 61 CDRL3

<400> SEQUENCE: 143

Gln Gln Ser Tyr Ser Ser Pro Tyr Thr
1               5

<210> SEQ ID NO 144
<211> LENGTH: 9
<212> TYPE: PRT
<213> ORGANISM: Artificial
<220> FEATURE:
<223> OTHER INFORMATION: synthetic HER2 binding clone 62 CDRL3

<400> SEQUENCE: 144

Gln Gln Ser Tyr Ser Ser Pro Ser Thr

```
1               5

<210> SEQ ID NO 145
<211> LENGTH: 9
<212> TYPE: PRT
<213> ORGANISM: Artificial
<220> FEATURE:
<223> OTHER INFORMATION: synthetic HER2 binding clone 63 CDRL3

<400> SEQUENCE: 145

Gln Gln Ser Tyr Ser Ser Pro Ser Thr
1               5

<210> SEQ ID NO 146
<211> LENGTH: 9
<212> TYPE: PRT
<213> ORGANISM: Artificial
<220> FEATURE:
<223> OTHER INFORMATION: synthetic HER2 binding clone 64 CDRL3

<400> SEQUENCE: 146

Gln Gln Ser Ser Ser Tyr Pro Tyr Thr
1               5

<210> SEQ ID NO 147
<211> LENGTH: 9
<212> TYPE: PRT
<213> ORGANISM: Artificial
<220> FEATURE:
<223> OTHER INFORMATION: synthetic HER2 binding clone 65 CDRL3

<400> SEQUENCE: 147

Gln Gln Ser Phe Ser Ser Pro Tyr Thr
1               5

<210> SEQ ID NO 148
<211> LENGTH: 9
<212> TYPE: PRT
<213> ORGANISM: Artificial
<220> FEATURE:
<223> OTHER INFORMATION: synthetic HER2 binding clone 66 CDRL3

<400> SEQUENCE: 148

Gln Gln Ser Tyr Ser Tyr Pro Ser Thr
1               5

<210> SEQ ID NO 149
<211> LENGTH: 9
<212> TYPE: PRT
<213> ORGANISM: Artificial
<220> FEATURE:
<223> OTHER INFORMATION: synthetic HER2 binding clone 67 CDRL3

<400> SEQUENCE: 149

Gln Gln Ser Tyr Ser Ser Pro Tyr Thr
1               5

<210> SEQ ID NO 150
<211> LENGTH: 9
<212> TYPE: PRT
<213> ORGANISM: Artificial
<220> FEATURE:
<223> OTHER INFORMATION: synthetic HER2 binding clone 68 CDRL3

<400> SEQUENCE: 150

Gln Gln Tyr Tyr Ser Ser Pro Tyr Thr
1               5
```

<210> SEQ ID NO 151
<211> LENGTH: 9
<212> TYPE: PRT
<213> ORGANISM: Artificial
<220> FEATURE:
<223> OTHER INFORMATION: synthetic HER2 binding clone 69 CDRL3

<400> SEQUENCE: 151

Gln Gln Ser Ser Tyr Pro Ser Thr
1               5

<210> SEQ ID NO 152
<211> LENGTH: 9
<212> TYPE: PRT
<213> ORGANISM: Artificial
<220> FEATURE:
<223> OTHER INFORMATION: synthetic HER2 binding clone 70 CDRL3

<400> SEQUENCE: 152

Gln Gln Tyr Tyr Ser Ser Pro Ser Thr
1               5

<210> SEQ ID NO 153
<211> LENGTH: 9
<212> TYPE: PRT
<213> ORGANISM: Artificial
<220> FEATURE:
<223> OTHER INFORMATION: synthetic HER2 binding clone 71 CDRL3

<400> SEQUENCE: 153

Gln Gln Ser Ser Tyr Tyr Pro Ser Thr
1               5

<210> SEQ ID NO 154
<211> LENGTH: 9
<212> TYPE: PRT
<213> ORGANISM: Artificial
<220> FEATURE:
<223> OTHER INFORMATION: synthetic HER2 binding clone 72 CDRL3

<400> SEQUENCE: 154

Gln Gln Ser Ser Phe Tyr Pro Ser Thr
1               5

<210> SEQ ID NO 155
<211> LENGTH: 9
<212> TYPE: PRT
<213> ORGANISM: Artificial
<220> FEATURE:
<223> OTHER INFORMATION: synthetic HER2 binding clone 73 CDRL3

<400> SEQUENCE: 155

Gln Gln Ser Ser Tyr Ser Pro Tyr Thr
1               5

<210> SEQ ID NO 156
<211> LENGTH: 9
<212> TYPE: PRT
<213> ORGANISM: Artificial
<220> FEATURE:
<223> OTHER INFORMATION: synthetic HER2 binding clone 74 CDRL3

<400> SEQUENCE: 156

Gln Gln Ser Ser Ser Tyr Pro Ser Thr
1               5

<210> SEQ ID NO 157
<211> LENGTH: 9
<212> TYPE: PRT
<213> ORGANISM: Artificial
<220> FEATURE:
<223> OTHER INFORMATION: synthetic HER2 binding clone 75 CDRL3

<400> SEQUENCE: 157

Gln Gln Ser Ser Ser Ser Pro Ser Thr
1               5

<210> SEQ ID NO 158
<211> LENGTH: 9
<212> TYPE: PRT
<213> ORGANISM: Artificial
<220> FEATURE:
<223> OTHER INFORMATION: synthetic HER2 binding clone 76 CDRL3

<400> SEQUENCE: 158

Gln Gln Tyr Tyr Tyr Tyr Pro Tyr Thr
1               5

<210> SEQ ID NO 159
<211> LENGTH: 9
<212> TYPE: PRT
<213> ORGANISM: Artificial
<220> FEATURE:
<223> OTHER INFORMATION: synthetic HER2 binding clone 77 CDRL3

<400> SEQUENCE: 159

Gln Gln Ser Ser Tyr Ser Pro Tyr Thr
1               5

<210> SEQ ID NO 160
<211> LENGTH: 9
<212> TYPE: PRT
<213> ORGANISM: Artificial
<220> FEATURE:
<223> OTHER INFORMATION: synthetic HER2 binding clone 78 CDRL3

<400> SEQUENCE: 160

Gln Gln Ser Ser Tyr Ser Pro Tyr Thr
1               5

<210> SEQ ID NO 161
<211> LENGTH: 9
<212> TYPE: PRT
<213> ORGANISM: Artificial
<220> FEATURE:
<223> OTHER INFORMATION: synthetic HER2 binding clone 79 CDRL3

<400> SEQUENCE: 161

Gln Gln Ser Ser Tyr Ser Pro Tyr Thr
1               5

<210> SEQ ID NO 162
<211> LENGTH: 9
<212> TYPE: PRT
<213> ORGANISM: Artificial
<220> FEATURE:
<223> OTHER INFORMATION: synthetic HER2 binding clone 80 CDRL3

<400> SEQUENCE: 162

Gln Gln Tyr Tyr Ser Ser Pro Tyr Thr
1               5

```
<210> SEQ ID NO 163
<211> LENGTH: 9
<212> TYPE: PRT
<213> ORGANISM: Artificial
<220> FEATURE:
<223> OTHER INFORMATION: synthetic HER2 binding clone 81 CDRL3

<400> SEQUENCE: 163

Gln Gln Ser Tyr Ser Tyr Pro Ser Thr
1               5

<210> SEQ ID NO 164
<211> LENGTH: 9
<212> TYPE: PRT
<213> ORGANISM: Artificial
<220> FEATURE:
<223> OTHER INFORMATION: synthetic HER2 binding clone 82 CDRL3

<400> SEQUENCE: 164

Gln Gln Tyr Ser Tyr Tyr Pro Ser Thr
1               5

<210> SEQ ID NO 165
<211> LENGTH: 9
<212> TYPE: PRT
<213> ORGANISM: Artificial
<220> FEATURE:
<223> OTHER INFORMATION: synthetic HER2 binding clone 83 CDRL3

<400> SEQUENCE: 165

Gln Gln Ser Ser Tyr Ser Pro Tyr Thr
1               5

<210> SEQ ID NO 166
<211> LENGTH: 9
<212> TYPE: PRT
<213> ORGANISM: Artificial
<220> FEATURE:
<223> OTHER INFORMATION: synthetic HER2 binding clone 84 CDRL3

<400> SEQUENCE: 166

Gln Gln Ser Ser Tyr Ser Pro Tyr Thr
1               5

<210> SEQ ID NO 167
<211> LENGTH: 9
<212> TYPE: PRT
<213> ORGANISM: Artificial
<220> FEATURE:
<223> OTHER INFORMATION: synthetic HER2 binding clone 85 CDRL3

<400> SEQUENCE: 167

Gln Gln Ser Ser Tyr Ser Pro Tyr Thr
1               5

<210> SEQ ID NO 168
<211> LENGTH: 9
<212> TYPE: PRT
<213> ORGANISM: Artificial
<220> FEATURE:
<223> OTHER INFORMATION: synthetic HER2 binding clone 86 CDRL3

<400> SEQUENCE: 168

Gln Gln Ser Ser Tyr Ser Pro Tyr Thr
1               5

<210> SEQ ID NO 169
```

```
<211> LENGTH: 9
<212> TYPE: PRT
<213> ORGANISM: Artificial
<220> FEATURE:
<223> OTHER INFORMATION: synthetic HER2 binding clone 87 CDRL3

<400> SEQUENCE: 169

Gln Gln Tyr Ser Tyr Tyr Pro Ser Thr
1               5

<210> SEQ ID NO 170
<211> LENGTH: 9
<212> TYPE: PRT
<213> ORGANISM: Artificial
<220> FEATURE:
<223> OTHER INFORMATION: synthetic HER2 binding clone 88 CDRL3

<400> SEQUENCE: 170

Gln Gln Ser Ser Ser Ser Pro Tyr Thr
1               5

<210> SEQ ID NO 171
<211> LENGTH: 9
<212> TYPE: PRT
<213> ORGANISM: Artificial
<220> FEATURE:
<223> OTHER INFORMATION: synthetic HER2 binding clone 89 CDRL3

<400> SEQUENCE: 171

Gln Gln Ser Ser Tyr Ser Pro Tyr Thr
1               5

<210> SEQ ID NO 172
<211> LENGTH: 9
<212> TYPE: PRT
<213> ORGANISM: Artificial
<220> FEATURE:
<223> OTHER INFORMATION: synthetic HER2 binding clone 90 CDRL3

<400> SEQUENCE: 172

Gln Gln Ser Ser Tyr Ser Pro Tyr Thr
1               5

<210> SEQ ID NO 173
<211> LENGTH: 9
<212> TYPE: PRT
<213> ORGANISM: Artificial
<220> FEATURE:
<223> OTHER INFORMATION: synthetic HER2 binding clone 91 CDRL3

<400> SEQUENCE: 173

Gln Gln Ser Ser Ser Ser Pro Tyr Thr
1               5

<210> SEQ ID NO 174
<211> LENGTH: 9
<212> TYPE: PRT
<213> ORGANISM: Artificial
<220> FEATURE:
<223> OTHER INFORMATION: synthetic HER2 binding clone 92 CDRL3

<400> SEQUENCE: 174

Gln Gln Tyr Tyr Ser Ser Pro Tyr Thr
1               5

<210> SEQ ID NO 175
<211> LENGTH: 9
```

```
<212> TYPE: PRT
<213> ORGANISM: Artificial
<220> FEATURE:
<223> OTHER INFORMATION: synthetic HER2 binding clone 93 CDRL3

<400> SEQUENCE: 175

Gln Gln Ser Ser Ser Ser Pro Tyr Thr
1               5

<210> SEQ ID NO 176
<211> LENGTH: 9
<212> TYPE: PRT
<213> ORGANISM: Artificial
<220> FEATURE:
<223> OTHER INFORMATION: synthetic HER2 binding clone 94 CDRL3

<400> SEQUENCE: 176

Gln Gln Ser Ser Tyr Tyr Pro Tyr Thr
1               5

<210> SEQ ID NO 177
<211> LENGTH: 9
<212> TYPE: PRT
<213> ORGANISM: Artificial
<220> FEATURE:
<223> OTHER INFORMATION: synthetic HER2 binding clone 95 CDRL3

<400> SEQUENCE: 177

Gln Gln Ser Tyr Tyr Tyr Pro Tyr Thr
1               5

<210> SEQ ID NO 178
<211> LENGTH: 9
<212> TYPE: PRT
<213> ORGANISM: Artificial
<220> FEATURE:
<223> OTHER INFORMATION: synthetic HER2 binding clone 96 CDRL3

<400> SEQUENCE: 178

Gln Gln Tyr Tyr Tyr Ser Pro Ser Thr
1               5

<210> SEQ ID NO 179
<211> LENGTH: 9
<212> TYPE: PRT
<213> ORGANISM: Artificial
<220> FEATURE:
<223> OTHER INFORMATION: synthetic HER2 binding clone 97 CDRL3

<400> SEQUENCE: 179

Gln Gln Tyr Ser Tyr Tyr Pro Tyr Thr
1               5

<210> SEQ ID NO 180
<211> LENGTH: 9
<212> TYPE: PRT
<213> ORGANISM: Artificial
<220> FEATURE:
<223> OTHER INFORMATION: synthetic HER2 binding clone 98 CDRL3

<400> SEQUENCE: 180

Gln Gln Tyr Ser Tyr Tyr Pro Tyr Thr
1               5

<210> SEQ ID NO 181
<211> LENGTH: 9
<212> TYPE: PRT
```

```
<213> ORGANISM: Artificial
<220> FEATURE:
<223> OTHER INFORMATION: synthetic HER2 binding clone 99 CDRL3

<400> SEQUENCE: 181

Gln Gln Tyr Ser Tyr Tyr Pro Tyr Thr
1               5

<210> SEQ ID NO 182
<211> LENGTH: 9
<212> TYPE: PRT
<213> ORGANISM: Artificial
<220> FEATURE:
<223> OTHER INFORMATION: synthetic HER2 binding clone 100 CDRL3

<400> SEQUENCE: 182

Gln Gln Ser Ser Tyr Tyr Pro Tyr Thr
1               5

<210> SEQ ID NO 183
<211> LENGTH: 9
<212> TYPE: PRT
<213> ORGANISM: Artificial
<220> FEATURE:
<223> OTHER INFORMATION: synthetic HER2 binding clone 101 CDRL3

<400> SEQUENCE: 183

Gln Gln Tyr Ser Tyr Tyr Pro Tyr Thr
1               5

<210> SEQ ID NO 184
<211> LENGTH: 9
<212> TYPE: PRT
<213> ORGANISM: Artificial
<220> FEATURE:
<223> OTHER INFORMATION: synthetic HER2 binding clone 102 CDRL3

<400> SEQUENCE: 184

Gln Gln Tyr Ser Tyr Tyr Pro Tyr Thr
1               5

<210> SEQ ID NO 185
<211> LENGTH: 9
<212> TYPE: PRT
<213> ORGANISM: Artificial
<220> FEATURE:
<223> OTHER INFORMATION: synthetic HER2 binding clone 103 CDRL3

<400> SEQUENCE: 185

Gln Gln Tyr Ser Tyr Tyr Pro Ser Thr
1               5

<210> SEQ ID NO 186
<211> LENGTH: 9
<212> TYPE: PRT
<213> ORGANISM: Artificial
<220> FEATURE:
<223> OTHER INFORMATION: synthetic HER2 binding clone 104 CDRL3

<400> SEQUENCE: 186

Gln Gln Tyr Ser Ser Ser Pro Ser Thr
1               5

<210> SEQ ID NO 187
<211> LENGTH: 9
<212> TYPE: PRT
<213> ORGANISM: Artificial
```

```
<220> FEATURE:
<223> OTHER INFORMATION: synthetic HER2 binding clone 105 CDRL3

<400> SEQUENCE: 187

Gln Gln Tyr Ser Ser Ser Pro Tyr Thr
1               5

<210> SEQ ID NO 188
<211> LENGTH: 9
<212> TYPE: PRT
<213> ORGANISM: Artificial
<220> FEATURE:
<223> OTHER INFORMATION: synthetic HER2 binding clone 106 CDRL3

<400> SEQUENCE: 188

Gln Gln Ser Tyr Ser Ser Pro Ser Thr
1               5

<210> SEQ ID NO 189
<211> LENGTH: 10
<212> TYPE: PRT
<213> ORGANISM: Artificial
<220> FEATURE:
<223> OTHER INFORMATION: synthetic HER2 binding clone 1 CDRH1

<400> SEQUENCE: 189

Gly Phe Ser Ile Ser Ser Ser Tyr Ile His
1               5                   10

<210> SEQ ID NO 190
<211> LENGTH: 10
<212> TYPE: PRT
<213> ORGANISM: Artificial
<220> FEATURE:
<223> OTHER INFORMATION: synthetic HER2 binding clone 2 CDRH1

<400> SEQUENCE: 190

Gly Phe Ser Ile Tyr Ser Ser Tyr Ile His
1               5                   10

<210> SEQ ID NO 191
<211> LENGTH: 10
<212> TYPE: PRT
<213> ORGANISM: Artificial
<220> FEATURE:
<223> OTHER INFORMATION: synthetic HER2 binding clone 3 CDRH1

<400> SEQUENCE: 191

Gly Phe Ser Ile Ser Ser Ser Tyr Ile His
1               5                   10

<210> SEQ ID NO 192
<211> LENGTH: 10
<212> TYPE: PRT
<213> ORGANISM: Artificial
<220> FEATURE:
<223> OTHER INFORMATION: synthetic HER2 binding clone 4 CDRH1

<400> SEQUENCE: 192

Gly Phe Tyr Ile Ser Tyr Ser Tyr Ile His
1               5                   10

<210> SEQ ID NO 193
<211> LENGTH: 10
<212> TYPE: PRT
<213> ORGANISM: Artificial
<220> FEATURE:
```

<223> OTHER INFORMATION: synthetic HER2 binding clone 5 CDRH1

<400> SEQUENCE: 193

Gly Phe Tyr Ile Ser Ser Ser Tyr Ile His
1               5                   10

<210> SEQ ID NO 194
<211> LENGTH: 10
<212> TYPE: PRT
<213> ORGANISM: Artificial
<220> FEATURE:
<223> OTHER INFORMATION: synthetic HER2 binding clone 6 CDRH1

<400> SEQUENCE: 194

Gly Phe Ser Ile Ser Tyr Ser Tyr Ile His
1               5                   10

<210> SEQ ID NO 195
<211> LENGTH: 10
<212> TYPE: PRT
<213> ORGANISM: Artificial
<220> FEATURE:
<223> OTHER INFORMATION: synthetic HER2 binding clone 7 CDRH1

<400> SEQUENCE: 195

Gly Phe Ser Ile Tyr Tyr Ser Tyr Ile His
1               5                   10

<210> SEQ ID NO 196
<211> LENGTH: 10
<212> TYPE: PRT
<213> ORGANISM: Artificial
<220> FEATURE:
<223> OTHER INFORMATION: synthetic HER2 binding clone 8 CDRH1

<400> SEQUENCE: 196

Gly Phe Ser Ile Tyr Ser Ser Tyr Ile His
1               5                   10

<210> SEQ ID NO 197
<211> LENGTH: 10
<212> TYPE: PRT
<213> ORGANISM: Artificial
<220> FEATURE:
<223> OTHER INFORMATION: synthetic HER2 binding clone 9 CDRH1

<400> SEQUENCE: 197

Gly Phe Ser Ile Ser Tyr Ser Tyr Ile His
1               5                   10

<210> SEQ ID NO 198
<211> LENGTH: 10
<212> TYPE: PRT
<213> ORGANISM: Artificial
<220> FEATURE:
<223> OTHER INFORMATION: synthetic HER2 binding clone 10 CDRH1

<400> SEQUENCE: 198

Gly Phe Ser Ile Tyr Ser Ser Tyr Ile His
1               5                   10

<210> SEQ ID NO 199
<211> LENGTH: 10
<212> TYPE: PRT
<213> ORGANISM: Artificial
<220> FEATURE:
<223> OTHER INFORMATION: synthetic HER2 binding clone 11 CDRH1

```
<400> SEQUENCE: 199

Gly Phe Ser Ile Tyr Ser Ser Ser Ile His
1               5                   10

<210> SEQ ID NO 200
<211> LENGTH: 10
<212> TYPE: PRT
<213> ORGANISM: Artificial
<220> FEATURE:
<223> OTHER INFORMATION: synthetic HER2 binding clone 12 CDRH1

<400> SEQUENCE: 200

Gly Phe Ser Ile Ser Ser Tyr Ser Ile His
1               5                   10

<210> SEQ ID NO 201
<211> LENGTH: 10
<212> TYPE: PRT
<213> ORGANISM: Artificial
<220> FEATURE:
<223> OTHER INFORMATION: synthetic HER2 binding clone 13 CDRH1

<400> SEQUENCE: 201

Gly Phe Ser Ile Ser Ser Ser Ser Ile His
1               5                   10

<210> SEQ ID NO 202
<211> LENGTH: 10
<212> TYPE: PRT
<213> ORGANISM: Artificial
<220> FEATURE:
<223> OTHER INFORMATION: synthetic HER2 binding clone 14 CDRH1

<400> SEQUENCE: 202

Gly Phe Tyr Ile Ser Ser Ser Ser Ile His
1               5                   10

<210> SEQ ID NO 203
<211> LENGTH: 10
<212> TYPE: PRT
<213> ORGANISM: Artificial
<220> FEATURE:
<223> OTHER INFORMATION: synthetic HER2 binding clone 15 CDRH1

<400> SEQUENCE: 203

Gly Phe Ser Ile Ser Ser Ser Ser Ile His
1               5                   10

<210> SEQ ID NO 204
<211> LENGTH: 10
<212> TYPE: PRT
<213> ORGANISM: Artificial
<220> FEATURE:
<223> OTHER INFORMATION: synthetic HER2 binding clone 16 CDRH1

<400> SEQUENCE: 204

Gly Phe Tyr Ile Ser Ser Tyr Ser Ile His
1               5                   10

<210> SEQ ID NO 205
<211> LENGTH: 10
<212> TYPE: PRT
<213> ORGANISM: Artificial
<220> FEATURE:
<223> OTHER INFORMATION: synthetic HER2 binding clone 17 CDRH1
```

```
<400> SEQUENCE: 205

Gly Phe Tyr Ile Ser Tyr Ser Ser Ile His
1               5                   10

<210> SEQ ID NO 206
<211> LENGTH: 10
<212> TYPE: PRT
<213> ORGANISM: Artificial
<220> FEATURE:
<223> OTHER INFORMATION: synthetic HER2 binding clone 18 CDRH1

<400> SEQUENCE: 206

Gly Phe Ser Ile Ser Tyr Ser Ser Ile His
1               5                   10

<210> SEQ ID NO 207
<211> LENGTH: 10
<212> TYPE: PRT
<213> ORGANISM: Artificial
<220> FEATURE:
<223> OTHER INFORMATION: synthetic HER2 binding clone 19 CDRH1

<400> SEQUENCE: 207

Gly Phe Tyr Ile Ser Ser Tyr Ser Ile His
1               5                   10

<210> SEQ ID NO 208
<211> LENGTH: 10
<212> TYPE: PRT
<213> ORGANISM: Artificial
<220> FEATURE:
<223> OTHER INFORMATION: synthetic HER2 binding clone 20 CDRH1

<400> SEQUENCE: 208

Gly Phe Ser Ile Ser Tyr Ser Ser Ile His
1               5                   10

<210> SEQ ID NO 209
<211> LENGTH: 10
<212> TYPE: PRT
<213> ORGANISM: Artificial
<220> FEATURE:
<223> OTHER INFORMATION: synthetic HER2 binding clone 21 CDRH1

<400> SEQUENCE: 209

Gly Phe Tyr Ile Ser Tyr Ser Ser Ile His
1               5                   10

<210> SEQ ID NO 210
<211> LENGTH: 10
<212> TYPE: PRT
<213> ORGANISM: Artificial
<220> FEATURE:
<223> OTHER INFORMATION: synthetic HER2 binding clone 22 CDRH1

<400> SEQUENCE: 210

Gly Phe Ser Ile Ser Tyr Ser Ser Ile His
1               5                   10

<210> SEQ ID NO 211
<211> LENGTH: 10
<212> TYPE: PRT
<213> ORGANISM: Artificial
<220> FEATURE:
<223> OTHER INFORMATION: synthetic HER2 binding clone 23 CDRH1

<400> SEQUENCE: 211
```

Gly Phe Ser Ile Ser Tyr Ser Ser Ile His
1               5                   10

<210> SEQ ID NO 212
<211> LENGTH: 10
<212> TYPE: PRT
<213> ORGANISM: Artificial
<220> FEATURE:
<223> OTHER INFORMATION: synthetic HER2 binding clone 24 CDRH1

<400> SEQUENCE: 212

Gly Phe Ser Ile Ser Tyr Ser Ser Ile His
1               5                   10

<210> SEQ ID NO 213
<211> LENGTH: 10
<212> TYPE: PRT
<213> ORGANISM: Artificial
<220> FEATURE:
<223> OTHER INFORMATION: synthetic HER2 binding clone 25 CDRH1

<400> SEQUENCE: 213

Gly Phe Ser Ile Ser Tyr Ser Ser Ile His
1               5                   10

<210> SEQ ID NO 214
<211> LENGTH: 10
<212> TYPE: PRT
<213> ORGANISM: Artificial
<220> FEATURE:
<223> OTHER INFORMATION: synthetic HER2 binding clone 26 CDRH1

<400> SEQUENCE: 214

Gly Phe Tyr Ile Ser Tyr Ser Ser Ile His
1               5                   10

<210> SEQ ID NO 215
<211> LENGTH: 10
<212> TYPE: PRT
<213> ORGANISM: Artificial
<220> FEATURE:
<223> OTHER INFORMATION: synthetic HER2 binding clone 27 CDRH1

<400> SEQUENCE: 215

Gly Phe Ser Ile Ser Tyr Ser Ser Ile His
1               5                   10

<210> SEQ ID NO 216
<211> LENGTH: 10
<212> TYPE: PRT
<213> ORGANISM: Artificial
<220> FEATURE:
<223> OTHER INFORMATION: synthetic HER2 binding clone 28 CDRH1

<400> SEQUENCE: 216

Gly Phe Ser Ile Ser Tyr Ser Ser Ile His
1               5                   10

<210> SEQ ID NO 217
<211> LENGTH: 10
<212> TYPE: PRT
<213> ORGANISM: Artificial
<220> FEATURE:
<223> OTHER INFORMATION: synthetic HER2 binding clone 29 CDRH1

<400> SEQUENCE: 217

Gly Phe Ser Ile Tyr Ser Ser Ser Ile His
1               5                   10

<210> SEQ ID NO 218
<211> LENGTH: 10
<212> TYPE: PRT
<213> ORGANISM: Artificial
<220> FEATURE:
<223> OTHER INFORMATION: synthetic HER2 binding clone 30 CDRH1

<400> SEQUENCE: 218

Gly Phe Ser Ile Ser Tyr Ser Ser Ile His
1               5                   10

<210> SEQ ID NO 219
<211> LENGTH: 10
<212> TYPE: PRT
<213> ORGANISM: Artificial
<220> FEATURE:
<223> OTHER INFORMATION: synthetic HER2 binding clone 31 CDRH1

<400> SEQUENCE: 219

Gly Phe Ser Ile Ser Tyr Ser Ser Ile His
1               5                   10

<210> SEQ ID NO 220
<211> LENGTH: 10
<212> TYPE: PRT
<213> ORGANISM: Artificial
<220> FEATURE:
<223> OTHER INFORMATION: synthetic HER2 binding clone 32 CDRH1

<400> SEQUENCE: 220

Gly Phe Ser Ile Ser Ser Ser Ser Ile His
1               5                   10

<210> SEQ ID NO 221
<211> LENGTH: 10
<212> TYPE: PRT
<213> ORGANISM: Artificial
<220> FEATURE:
<223> OTHER INFORMATION: synthetic HER2 binding clone 33 CDRH1

<400> SEQUENCE: 221

Gly Phe Ser Ile Ser Ser Tyr Tyr Ile His
1               5                   10

<210> SEQ ID NO 222
<211> LENGTH: 10
<212> TYPE: PRT
<213> ORGANISM: Artificial
<220> FEATURE:
<223> OTHER INFORMATION: synthetic HER2 binding clone 34 CDRH1

<400> SEQUENCE: 222

Gly Phe Tyr Ile Ser Ser Ser Ser Ile His
1               5                   10

<210> SEQ ID NO 223
<211> LENGTH: 10
<212> TYPE: PRT
<213> ORGANISM: Artificial
<220> FEATURE:
<223> OTHER INFORMATION: synthetic HER2 binding clone 35 CDRH1

<400> SEQUENCE: 223

Gly Phe Tyr Ile Ser Ser Ser Ser Ile His

```
<210> SEQ ID NO 224
<211> LENGTH: 10
<212> TYPE: PRT
<213> ORGANISM: Artificial
<220> FEATURE:
<223> OTHER INFORMATION: synthetic HER2 binding clone 36 CDRH1

<400> SEQUENCE: 224

Gly Phe Ser Ile Ser Ser Ser Ser Ile His
1               5                   10

<210> SEQ ID NO 225
<211> LENGTH: 10
<212> TYPE: PRT
<213> ORGANISM: Artificial
<220> FEATURE:
<223> OTHER INFORMATION: synthetic HER2 binding clone 37 CDRH1

<400> SEQUENCE: 225

Gly Phe Tyr Ile Ser Ser Tyr Ser Ile His
1               5                   10

<210> SEQ ID NO 226
<211> LENGTH: 10
<212> TYPE: PRT
<213> ORGANISM: Artificial
<220> FEATURE:
<223> OTHER INFORMATION: synthetic HER2 binding clone 38 CDRH1

<400> SEQUENCE: 226

Gly Phe Tyr Ile Ser Ser Ser Ser Ile His
1               5                   10

<210> SEQ ID NO 227
<211> LENGTH: 10
<212> TYPE: PRT
<213> ORGANISM: Artificial
<220> FEATURE:
<223> OTHER INFORMATION: synthetic HER2 binding clone 39 CDRH1

<400> SEQUENCE: 227

Gly Phe Ser Ile Ser Ser Ser Ser Ile His
1               5                   10

<210> SEQ ID NO 228
<211> LENGTH: 10
<212> TYPE: PRT
<213> ORGANISM: Artificial
<220> FEATURE:
<223> OTHER INFORMATION: synthetic HER2 binding clone 40 CDRH1

<400> SEQUENCE: 228

Gly Phe Tyr Ile Ser Ser Ser Ser Ile His
1               5                   10

<210> SEQ ID NO 229
<211> LENGTH: 10
<212> TYPE: PRT
<213> ORGANISM: Artificial
<220> FEATURE:
<223> OTHER INFORMATION: synthetic HER2 binding clone 41 CDRH1

<400> SEQUENCE: 229

Gly Phe Ser Ile Ser Ser Ser Ser Ile His
1               5                   10
```

<210> SEQ ID NO 230
<211> LENGTH: 10
<212> TYPE: PRT
<213> ORGANISM: Artificial
<220> FEATURE:
<223> OTHER INFORMATION: synthetic HER2 binding clone 42 CDRH1

<400> SEQUENCE: 230

Gly Phe Tyr Ile Ser Ser Ser Ser Ile His
1               5                   10

<210> SEQ ID NO 231
<211> LENGTH: 10
<212> TYPE: PRT
<213> ORGANISM: Artificial
<220> FEATURE:
<223> OTHER INFORMATION: synthetic HER2 binding clone 43 CDRH1

<400> SEQUENCE: 231

Gly Phe Ser Ile Ser Ser Ser Ser Ile His
1               5                   10

<210> SEQ ID NO 232
<211> LENGTH: 10
<212> TYPE: PRT
<213> ORGANISM: Artificial
<220> FEATURE:
<223> OTHER INFORMATION: synthetic HER2 binding clone 44 CDRH1

<400> SEQUENCE: 232

Gly Phe Ser Ile Ser Ser Ser Ser Ile His
1               5                   10

<210> SEQ ID NO 233
<211> LENGTH: 10
<212> TYPE: PRT
<213> ORGANISM: Artificial
<220> FEATURE:
<223> OTHER INFORMATION: synthetic HER2 binding clone 45 CDRH1

<400> SEQUENCE: 233

Gly Phe Tyr Ile Ser Ser Ser Ser Ile His
1               5                   10

<210> SEQ ID NO 234
<211> LENGTH: 10
<212> TYPE: PRT
<213> ORGANISM: Artificial
<220> FEATURE:
<223> OTHER INFORMATION: synthetic HER2 binding clone 46 CDRH1

<400> SEQUENCE: 234

Gly Phe Tyr Ile Ser Ser Tyr Ser Ile His
1               5                   10

<210> SEQ ID NO 235
<211> LENGTH: 10
<212> TYPE: PRT
<213> ORGANISM: Artificial
<220> FEATURE:
<223> OTHER INFORMATION: synthetic HER2 binding clone 47 CDRH1

<400> SEQUENCE: 235

Gly Phe Ser Ile Ser Ser Tyr Ser Ile His
1               5                   10

<210> SEQ ID NO 236
<211> LENGTH: 10
<212> TYPE: PRT
<213> ORGANISM: Artificial
<220> FEATURE:
<223> OTHER INFORMATION: synthetic HER2 binding clone 48 CDRH1

<400> SEQUENCE: 236

Gly Phe Tyr Ile Ser Ser Tyr Tyr Ile His
1               5                   10

<210> SEQ ID NO 237
<211> LENGTH: 10
<212> TYPE: PRT
<213> ORGANISM: Artificial
<220> FEATURE:
<223> OTHER INFORMATION: synthetic HER2 binding clone 49 CDRH1

<400> SEQUENCE: 237

Gly Phe Ser Ile Ser Ser Tyr Ser Ile His
1               5                   10

<210> SEQ ID NO 238
<211> LENGTH: 10
<212> TYPE: PRT
<213> ORGANISM: Artificial
<220> FEATURE:
<223> OTHER INFORMATION: synthetic HER2 binding clone 50 CDRH1

<400> SEQUENCE: 238

Gly Phe Tyr Ile Ser Ser Ser Ser Ile His
1               5                   10

<210> SEQ ID NO 239
<211> LENGTH: 10
<212> TYPE: PRT
<213> ORGANISM: Artificial
<220> FEATURE:
<223> OTHER INFORMATION: synthetic HER2 binding clone 51 CDRH1

<400> SEQUENCE: 239

Gly Phe Ser Ile Ser Ser Ser Ile His
1               5                   10

<210> SEQ ID NO 240
<211> LENGTH: 10
<212> TYPE: PRT
<213> ORGANISM: Artificial
<220> FEATURE:
<223> OTHER INFORMATION: synthetic HER2 binding clone 52 CDRH1

<400> SEQUENCE: 240

Gly Phe Tyr Ile Ser Ser Ser Ser Ile His
1               5                   10

<210> SEQ ID NO 241
<211> LENGTH: 10
<212> TYPE: PRT
<213> ORGANISM: Artificial
<220> FEATURE:
<223> OTHER INFORMATION: synthetic HER2 binding clone 53 CDRH1

<400> SEQUENCE: 241

Gly Phe Tyr Ile Ser Ser Ser Ser Ile His
1               5                   10

<210> SEQ ID NO 242
<211> LENGTH: 10
<212> TYPE: PRT
<213> ORGANISM: Artificial
<220> FEATURE:
<223> OTHER INFORMATION: synthetic HER2 binding clone 54 CDRH1

<400> SEQUENCE: 242

Gly Phe Tyr Ile Ser Ser Ser Ser Ile His
1               5                   10

<210> SEQ ID NO 243
<211> LENGTH: 10
<212> TYPE: PRT
<213> ORGANISM: Artificial
<220> FEATURE:
<223> OTHER INFORMATION: synthetic HER2 binding clone 55 CDRH1

<400> SEQUENCE: 243

Gly Phe Ser Ile Ser Ser Ser Ser Ile His
1               5                   10

<210> SEQ ID NO 244
<211> LENGTH: 10
<212> TYPE: PRT
<213> ORGANISM: Artificial
<220> FEATURE:
<223> OTHER INFORMATION: synthetic HER2 binding clone 56 CDRH1

<400> SEQUENCE: 244

Gly Phe Ser Ile Ser Ser Ser Ser Ile His
1               5                   10

<210> SEQ ID NO 245
<211> LENGTH: 10
<212> TYPE: PRT
<213> ORGANISM: Artificial
<220> FEATURE:
<223> OTHER INFORMATION: synthetic HER2 binding clone 57 CDRH1

<400> SEQUENCE: 245

Gly Phe Tyr Ile Ser Ser Ser Ser Ile His
1               5                   10

<210> SEQ ID NO 246
<211> LENGTH: 10
<212> TYPE: PRT
<213> ORGANISM: Artificial
<220> FEATURE:
<223> OTHER INFORMATION: synthetic HER2 binding clone 58 CDRH1

<400> SEQUENCE: 246

Gly Phe Tyr Ile Ser Ser Ser Ser Ile His
1               5                   10

<210> SEQ ID NO 247
<211> LENGTH: 10
<212> TYPE: PRT
<213> ORGANISM: Artificial
<220> FEATURE:
<223> OTHER INFORMATION: synthetic HER2 binding clone 59 CDRH1

<400> SEQUENCE: 247

Gly Phe Tyr Ile Ser Ser Tyr Ser Ile His
1               5                   10

<210> SEQ ID NO 248

```
<211> LENGTH: 10
<212> TYPE: PRT
<213> ORGANISM: Artificial
<220> FEATURE:
<223> OTHER INFORMATION: synthetic HER2 binding clone 60 CDRH1

<400> SEQUENCE: 248

Gly Phe Tyr Ile Ser Ser Ser Ser Ile His
1               5                   10

<210> SEQ ID NO 249
<211> LENGTH: 10
<212> TYPE: PRT
<213> ORGANISM: Artificial
<220> FEATURE:
<223> OTHER INFORMATION: synthetic HER2 binding clone 61 CDRH1

<400> SEQUENCE: 249

Gly Phe Tyr Ile Ser Ser Ser Ser Ile His
1               5                   10

<210> SEQ ID NO 250
<211> LENGTH: 10
<212> TYPE: PRT
<213> ORGANISM: Artificial
<220> FEATURE:
<223> OTHER INFORMATION: synthetic HER2 binding clone 62 CDRH1

<400> SEQUENCE: 250

Gly Phe Tyr Ile Ser Ser Ser Ser Ile His
1               5                   10

<210> SEQ ID NO 251
<211> LENGTH: 10
<212> TYPE: PRT
<213> ORGANISM: Artificial
<220> FEATURE:
<223> OTHER INFORMATION: synthetic HER2 binding clone 63 CDRH1

<400> SEQUENCE: 251

Gly Phe Tyr Ile Ser Ser Ser Ser Ile His
1               5                   10

<210> SEQ ID NO 252
<211> LENGTH: 10
<212> TYPE: PRT
<213> ORGANISM: Artificial
<220> FEATURE:
<223> OTHER INFORMATION: synthetic HER2 binding clone 64 CDRH1

<400> SEQUENCE: 252

Gly Phe Tyr Ile Ser Ser Tyr Ser Ile His
1               5                   10

<210> SEQ ID NO 253
<211> LENGTH: 10
<212> TYPE: PRT
<213> ORGANISM: Artificial
<220> FEATURE:
<223> OTHER INFORMATION: synthetic HER2 binding clone 65 CDRH1

<400> SEQUENCE: 253

Gly Phe Tyr Ile Ser Ser Tyr Ser Ile His
1               5                   10

<210> SEQ ID NO 254
<211> LENGTH: 10
```

<212> TYPE: PRT
<213> ORGANISM: Artificial
<220> FEATURE:
<223> OTHER INFORMATION: synthetic HER2 binding clone 66 CDRH1

<400> SEQUENCE: 254

Gly Phe Tyr Ile Ser Ser Ser Ser Ile His
1               5                   10

<210> SEQ ID NO 255
<211> LENGTH: 10
<212> TYPE: PRT
<213> ORGANISM: Artificial
<220> FEATURE:
<223> OTHER INFORMATION: synthetic HER2 binding clone 67 CDRH1

<400> SEQUENCE: 255

Gly Phe Tyr Ile Ser Ser Tyr Ser Ile His
1               5                   10

<210> SEQ ID NO 256
<211> LENGTH: 10
<212> TYPE: PRT
<213> ORGANISM: Artificial
<220> FEATURE:
<223> OTHER INFORMATION: synthetic HER2 binding clone 68 CDRH1

<400> SEQUENCE: 256

Gly Phe Ser Ile Tyr Tyr Ser Ser Ile His
1               5                   10

<210> SEQ ID NO 257
<211> LENGTH: 10
<212> TYPE: PRT
<213> ORGANISM: Artificial
<220> FEATURE:
<223> OTHER INFORMATION: synthetic HER2 binding clone 69 CDRH1

<400> SEQUENCE: 257

Gly Phe Tyr Ile Ser Ser Ser Ser Ile His
1               5                   10

<210> SEQ ID NO 258
<211> LENGTH: 10
<212> TYPE: PRT
<213> ORGANISM: Artificial
<220> FEATURE:
<223> OTHER INFORMATION: synthetic HER2 binding clone 70 CDRH1

<400> SEQUENCE: 258

Gly Phe Tyr Ile Ser Ser Ser Ser Ile His
1               5                   10

<210> SEQ ID NO 259
<211> LENGTH: 10
<212> TYPE: PRT
<213> ORGANISM: Artificial
<220> FEATURE:
<223> OTHER INFORMATION: synthetic HER2 binding clone 71 CDRH1

<400> SEQUENCE: 259

Gly Phe Tyr Ile Ser Ser Tyr Ser Ile His
1               5                   10

<210> SEQ ID NO 260
<211> LENGTH: 10
<212> TYPE: PRT

-continued

<213> ORGANISM: Artificial
<220> FEATURE:
<223> OTHER INFORMATION: synthetic HER2 binding clone 72 CDRH1

<400> SEQUENCE: 260

Gly Phe Tyr Ile Ser Tyr Tyr Ser Ile His
1               5                   10

<210> SEQ ID NO 261
<211> LENGTH: 10
<212> TYPE: PRT
<213> ORGANISM: Artificial
<220> FEATURE:
<223> OTHER INFORMATION: synthetic HER2 binding clone 73 CDRH1

<400> SEQUENCE: 261

Gly Phe Tyr Ile Ser Tyr Tyr Ser Ile His
1               5                   10

<210> SEQ ID NO 262
<211> LENGTH: 10
<212> TYPE: PRT
<213> ORGANISM: Artificial
<220> FEATURE:
<223> OTHER INFORMATION: synthetic HER2 binding clone 74 CDRH1

<400> SEQUENCE: 262

Gly Phe Tyr Ile Ser Ser Ser Ser Ile His
1               5                   10

<210> SEQ ID NO 263
<211> LENGTH: 10
<212> TYPE: PRT
<213> ORGANISM: Artificial
<220> FEATURE:
<223> OTHER INFORMATION: synthetic HER2 binding clone 75 CDRH1

<400> SEQUENCE: 263

Gly Phe Tyr Ile Ser Ser Ser Ser Ile His
1               5                   10

<210> SEQ ID NO 264
<211> LENGTH: 10
<212> TYPE: PRT
<213> ORGANISM: Artificial
<220> FEATURE:
<223> OTHER INFORMATION: synthetic HER2 binding clone 76 CDRH1

<400> SEQUENCE: 264

Gly Phe Tyr Ile Ser Ser Ser Ser Ile His
1               5                   10

<210> SEQ ID NO 265
<211> LENGTH: 10
<212> TYPE: PRT
<213> ORGANISM: Artificial
<220> FEATURE:
<223> OTHER INFORMATION: synthetic HER2 binding clone 77 CDRH1

<400> SEQUENCE: 265

Gly Phe Tyr Ile Ser Ser Ser Ser Ile His
1               5                   10

<210> SEQ ID NO 266
<211> LENGTH: 10
<212> TYPE: PRT
<213> ORGANISM: Artificial

```
<220> FEATURE:
<223> OTHER INFORMATION: synthetic HER2 binding clone 78 CDRH1

<400> SEQUENCE: 266

Gly Phe Tyr Ile Ser Ser Ser Ile His
1               5                   10

<210> SEQ ID NO 267
<211> LENGTH: 10
<212> TYPE: PRT
<213> ORGANISM: Artificial
<220> FEATURE:
<223> OTHER INFORMATION: synthetic HER2 binding clone 79 CDRH1

<400> SEQUENCE: 267

Gly Phe Ser Ile Ser Ser Ser Ile His
1               5                   10

<210> SEQ ID NO 268
<211> LENGTH: 10
<212> TYPE: PRT
<213> ORGANISM: Artificial
<220> FEATURE:
<223> OTHER INFORMATION: synthetic HER2 binding clone 80 CDRH1

<400> SEQUENCE: 268

Gly Phe Ser Ile Tyr Tyr Ser Ser Ile His
1               5                   10

<210> SEQ ID NO 269
<211> LENGTH: 10
<212> TYPE: PRT
<213> ORGANISM: Artificial
<220> FEATURE:
<223> OTHER INFORMATION: synthetic HER2 binding clone 81 CDRH1

<400> SEQUENCE: 269

Gly Phe Tyr Ile Ser Ser Ser Tyr Ile His
1               5                   10

<210> SEQ ID NO 270
<211> LENGTH: 10
<212> TYPE: PRT
<213> ORGANISM: Artificial
<220> FEATURE:
<223> OTHER INFORMATION: synthetic HER2 binding clone 82 CDRH1

<400> SEQUENCE: 270

Gly Phe Tyr Ile Ser Ser Ser Ser Ile His
1               5                   10

<210> SEQ ID NO 271
<211> LENGTH: 10
<212> TYPE: PRT
<213> ORGANISM: Artificial
<220> FEATURE:
<223> OTHER INFORMATION: synthetic HER2 binding clone 83 CDRH1

<400> SEQUENCE: 271

Gly Phe Tyr Ile Ser Ser Ser Ser Ile His
1               5                   10

<210> SEQ ID NO 272
<211> LENGTH: 10
<212> TYPE: PRT
<213> ORGANISM: Artificial
<220> FEATURE:
```

<223> OTHER INFORMATION: synthetic HER2 binding clone 84 CDRH1

<400> SEQUENCE: 272

Gly Phe Ser Ile Ser Ser Ser Ser Ile His
1               5                   10

<210> SEQ ID NO 273
<211> LENGTH: 10
<212> TYPE: PRT
<213> ORGANISM: Artificial
<220> FEATURE:
<223> OTHER INFORMATION: synthetic HER2 binding clone 85 CDRH1

<400> SEQUENCE: 273

Gly Phe Ser Ile Ser Ser Ser Ser Ile His
1               5                   10

<210> SEQ ID NO 274
<211> LENGTH: 10
<212> TYPE: PRT
<213> ORGANISM: Artificial
<220> FEATURE:
<223> OTHER INFORMATION: synthetic HER2 binding clone 86 CDRH1

<400> SEQUENCE: 274

Gly Phe Ser Ile Ser Tyr Ser Ser Ile His
1               5                   10

<210> SEQ ID NO 275
<211> LENGTH: 10
<212> TYPE: PRT
<213> ORGANISM: Artificial
<220> FEATURE:
<223> OTHER INFORMATION: synthetic HER2 binding clone 87 CDRH1

<400> SEQUENCE: 275

Gly Phe Tyr Ile Ser Tyr Ser Ser Ile His
1               5                   10

<210> SEQ ID NO 276
<211> LENGTH: 10
<212> TYPE: PRT
<213> ORGANISM: Artificial
<220> FEATURE:
<223> OTHER INFORMATION: synthetic HER2 binding clone 88 CDRH1

<400> SEQUENCE: 276

Gly Phe Tyr Ile Ser Ser Ser Ser Ile His
1               5                   10

<210> SEQ ID NO 277
<211> LENGTH: 10
<212> TYPE: PRT
<213> ORGANISM: Artificial
<220> FEATURE:
<223> OTHER INFORMATION: synthetic HER2 binding clone 89 CDRH1

<400> SEQUENCE: 277

Gly Phe Ser Ile Ser Ser Ser Ser Ile His
1               5                   10

<210> SEQ ID NO 278
<211> LENGTH: 10
<212> TYPE: PRT
<213> ORGANISM: Artificial
<220> FEATURE:
<223> OTHER INFORMATION: synthetic HER2 binding clone 90 CDRH1

```
<400> SEQUENCE: 278

Gly Phe Tyr Ile Ser Ser Ser Ser Ile His
1               5                   10

<210> SEQ ID NO 279
<211> LENGTH: 10
<212> TYPE: PRT
<213> ORGANISM: Artificial
<220> FEATURE:
<223> OTHER INFORMATION: synthetic HER2 binding clone 91 CDRH1

<400> SEQUENCE: 279

Gly Phe Ser Ile Ser Ser Ser Ser Ile His
1               5                   10

<210> SEQ ID NO 280
<211> LENGTH: 10
<212> TYPE: PRT
<213> ORGANISM: Artificial
<220> FEATURE:
<223> OTHER INFORMATION: synthetic HER2 binding clone 92 CDRH1

<400> SEQUENCE: 280

Gly Phe Tyr Ile Ser Ser Ser Ser Ile His
1               5                   10

<210> SEQ ID NO 281
<211> LENGTH: 10
<212> TYPE: PRT
<213> ORGANISM: Artificial
<220> FEATURE:
<223> OTHER INFORMATION: synthetic HER2 binding clone 93 CDRH1

<400> SEQUENCE: 281

Gly Phe Tyr Ile Ser Ser Ser Ser Ile His
1               5                   10

<210> SEQ ID NO 282
<211> LENGTH: 10
<212> TYPE: PRT
<213> ORGANISM: Artificial
<220> FEATURE:
<223> OTHER INFORMATION: synthetic HER2 binding clone 94 CDRH1

<400> SEQUENCE: 282

Gly Phe Ser Ile Ser Ser Ser Tyr Ile His
1               5                   10

<210> SEQ ID NO 283
<211> LENGTH: 10
<212> TYPE: PRT
<213> ORGANISM: Artificial
<220> FEATURE:
<223> OTHER INFORMATION: synthetic HER2 binding clone 95 CDRH1

<400> SEQUENCE: 283

Gly Phe Phe Ile Ser Tyr Tyr Tyr Ile His
1               5                   10

<210> SEQ ID NO 284
<211> LENGTH: 10
<212> TYPE: PRT
<213> ORGANISM: Artificial
<220> FEATURE:
<223> OTHER INFORMATION: synthetic HER2 binding clone 96 CDRH1
```

```
<400> SEQUENCE: 284

Gly Phe Ser Ile Tyr Ser Ser Tyr Ile His
1               5                   10

<210> SEQ ID NO 285
<211> LENGTH: 10
<212> TYPE: PRT
<213> ORGANISM: Artificial
<220> FEATURE:
<223> OTHER INFORMATION: synthetic HER2 binding clone 97 CDRH1

<400> SEQUENCE: 285

Gly Phe Tyr Ile Ser Tyr Ser Ser Ile His
1               5                   10

<210> SEQ ID NO 286
<211> LENGTH: 10
<212> TYPE: PRT
<213> ORGANISM: Artificial
<220> FEATURE:
<223> OTHER INFORMATION: synthetic HER2 binding clone 98 CDRH1

<400> SEQUENCE: 286

Gly Phe Tyr Ile Tyr Ser Tyr Ser Ile His
1               5                   10

<210> SEQ ID NO 287
<211> LENGTH: 10
<212> TYPE: PRT
<213> ORGANISM: Artificial
<220> FEATURE:
<223> OTHER INFORMATION: synthetic HER2 binding clone 99 CDRH1

<400> SEQUENCE: 287

Gly Phe Tyr Ile Ser Tyr Ser Ser Ile His
1               5                   10

<210> SEQ ID NO 288
<211> LENGTH: 10
<212> TYPE: PRT
<213> ORGANISM: Artificial
<220> FEATURE:
<223> OTHER INFORMATION: synthetic HER2 binding clone 100 CDRH1

<400> SEQUENCE: 288

Gly Phe Ser Ile Ser Tyr Ser Ser Ile His
1               5                   10

<210> SEQ ID NO 289
<211> LENGTH: 10
<212> TYPE: PRT
<213> ORGANISM: Artificial
<220> FEATURE:
<223> OTHER INFORMATION: synthetic HER2 binding clone 101 CDRH1

<400> SEQUENCE: 289

Gly Phe Ser Ile Ser Tyr Ser Ser Ile His
1               5                   10

<210> SEQ ID NO 290
<211> LENGTH: 10
<212> TYPE: PRT
<213> ORGANISM: Artificial
<220> FEATURE:
<223> OTHER INFORMATION: synthetic HER2 binding clone 102 CDRH1

<400> SEQUENCE: 290
```

Gly Phe Tyr Ile Ser Tyr Ser Ser Ile His
1               5                   10

<210> SEQ ID NO 291
<211> LENGTH: 10
<212> TYPE: PRT
<213> ORGANISM: Artificial
<220> FEATURE:
<223> OTHER INFORMATION: synthetic HER2 binding clone 103 CDRH1

<400> SEQUENCE: 291

Gly Phe Ser Ile Ser Tyr Ser Ser Ile His
1               5                   10

<210> SEQ ID NO 292
<211> LENGTH: 10
<212> TYPE: PRT
<213> ORGANISM: Artificial
<220> FEATURE:
<223> OTHER INFORMATION: synthetic HER2 binding clone 104 CDRH1

<400> SEQUENCE: 292

Gly Phe Ser Ile Ser Tyr Ser Tyr Ile His
1               5                   10

<210> SEQ ID NO 293
<211> LENGTH: 10
<212> TYPE: PRT
<213> ORGANISM: Artificial
<220> FEATURE:
<223> OTHER INFORMATION: synthetic HER2 binding clone 105 CDRH1

<400> SEQUENCE: 293

Gly Phe Ser Ile Ser Tyr Ser Tyr Ile His
1               5                   10

<210> SEQ ID NO 294
<211> LENGTH: 10
<212> TYPE: PRT
<213> ORGANISM: Artificial
<220> FEATURE:
<223> OTHER INFORMATION: synthetic HER2 binding clone 106 CDRH1

<400> SEQUENCE: 294

Gly Phe Tyr Ile Ser Tyr Ser Tyr Ile His
1               5                   10

<210> SEQ ID NO 295
<211> LENGTH: 17
<212> TYPE: PRT
<213> ORGANISM: Artificial
<220> FEATURE:
<223> OTHER INFORMATION: synthetic HER2 binding clone 1 CDRH2

<400> SEQUENCE: 295

Ser Ile Tyr Pro Tyr Ser Gly Tyr Thr Ser Tyr Ala Asp Ser Val Lys
1               5                   10                  15

Gly

<210> SEQ ID NO 296
<211> LENGTH: 17
<212> TYPE: PRT
<213> ORGANISM: Artificial
<220> FEATURE:
<223> OTHER INFORMATION: synthetic HER2 binding clone 2 CDRH2

```
<400> SEQUENCE: 296

Ser Ile Tyr Pro Tyr Ser Gly Tyr Thr Ser Tyr Ala Asp Ser Val Lys
1               5                   10                  15

Gly

<210> SEQ ID NO 297
<211> LENGTH: 17
<212> TYPE: PRT
<213> ORGANISM: Artificial
<220> FEATURE:
<223> OTHER INFORMATION: synthetic HER2 binding clone 3 CDRH2

<400> SEQUENCE: 297

Ser Ile Tyr Pro Tyr Ser Gly Tyr Thr Ser Tyr Ala Asp Ser Val Lys
1               5                   10                  15

Gly

<210> SEQ ID NO 298
<211> LENGTH: 17
<212> TYPE: PRT
<213> ORGANISM: Artificial
<220> FEATURE:
<223> OTHER INFORMATION: synthetic HER2 binding clone 4 CDRH2

<400> SEQUENCE: 298

Ser Ile Tyr Pro Tyr Ser Gly Tyr Thr Ser Tyr Ala Asp Ser Val Lys
1               5                   10                  15

Gly

<210> SEQ ID NO 299
<211> LENGTH: 17
<212> TYPE: PRT
<213> ORGANISM: Artificial
<220> FEATURE:
<223> OTHER INFORMATION: synthetic HER2 binding clone 5 CDRH2

<400> SEQUENCE: 299

Ser Ile Tyr Pro Tyr Ser Gly Tyr Thr Ser Tyr Ala Asp Ser Val Lys
1               5                   10                  15

Gly

<210> SEQ ID NO 300
<211> LENGTH: 17
<212> TYPE: PRT
<213> ORGANISM: Artificial
<220> FEATURE:
<223> OTHER INFORMATION: synthetic HER2 binding clone 6 CDRH2

<400> SEQUENCE: 300

Ser Ile Tyr Pro Ser Ser Gly Tyr Thr Ser Tyr Ala Asp Ser Val Lys
1               5                   10                  15

Gly

<210> SEQ ID NO 301
<211> LENGTH: 17
<212> TYPE: PRT
<213> ORGANISM: Artificial
<220> FEATURE:
<223> OTHER INFORMATION: synthetic HER2 binding clone 7 CDRH2

<400> SEQUENCE: 301

Ser Ile Tyr Pro Ser Ser Gly Tyr Thr Ser Tyr Ala Asp Ser Val Lys
1               5                   10                  15
```

Gly

<210> SEQ ID NO 302
<211> LENGTH: 17
<212> TYPE: PRT
<213> ORGANISM: Artificial
<220> FEATURE:
<223> OTHER INFORMATION: synthetic HER2 binding clone 8 CDRH2

<400> SEQUENCE: 302

Ser Ile Tyr Pro Ser Ser Gly Tyr Thr Ser Tyr Ala Asp Ser Val Lys
1               5                   10                  15

Gly

<210> SEQ ID NO 303
<211> LENGTH: 17
<212> TYPE: PRT
<213> ORGANISM: Artificial
<220> FEATURE:
<223> OTHER INFORMATION: synthetic HER2 binding clone 9 CDRH2

<400> SEQUENCE: 303

Ser Ile Tyr Pro Tyr Ser Gly Tyr Thr Ser Tyr Ala Asp Ser Val Lys
1               5                   10                  15

Gly

<210> SEQ ID NO 304
<211> LENGTH: 17
<212> TYPE: PRT
<213> ORGANISM: Artificial
<220> FEATURE:
<223> OTHER INFORMATION: synthetic HER2 binding clone 10 CDRH2

<400> SEQUENCE: 304

Ser Ile Tyr Pro Tyr Ser Gly Tyr Thr Ser Tyr Ala Asp Ser Val Lys
1               5                   10                  15

Gly

<210> SEQ ID NO 305
<211> LENGTH: 17
<212> TYPE: PRT
<213> ORGANISM: Artificial
<220> FEATURE:
<223> OTHER INFORMATION: synthetic HER2 binding clone 11 CDRH2

<400> SEQUENCE: 305

Ser Ile Tyr Pro Ser Ser Gly Ser Thr Tyr Tyr Ala Asp Ser Val Lys
1               5                   10                  15

Gly

<210> SEQ ID NO 306
<211> LENGTH: 17
<212> TYPE: PRT
<213> ORGANISM: Artificial
<220> FEATURE:
<223> OTHER INFORMATION: synthetic HER2 binding clone 12 CDRH2

<400> SEQUENCE: 306

Ser Ile Tyr Pro Tyr Ser Gly Ser Thr Ser Tyr Ala Asp Ser Val Lys
1               5                   10                  15

Gly

-continued

```
<210> SEQ ID NO 307
<211> LENGTH: 17
<212> TYPE: PRT
<213> ORGANISM: Artificial
<220> FEATURE:
<223> OTHER INFORMATION: synthetic HER2 binding clone 13 CDRH2

<400> SEQUENCE: 307

Ser Ile Tyr Pro Tyr Tyr Gly Tyr Thr Ser Tyr Ala Asp Ser Val Lys
1               5                   10                  15
Gly

<210> SEQ ID NO 308
<211> LENGTH: 17
<212> TYPE: PRT
<213> ORGANISM: Artificial
<220> FEATURE:
<223> OTHER INFORMATION: synthetic HER2 binding clone 14 CDRH2

<400> SEQUENCE: 308

Ser Ile Tyr Pro Tyr Tyr Gly Ser Thr Tyr Tyr Ala Asp Ser Val Lys
1               5                   10                  15
Gly

<210> SEQ ID NO 309
<211> LENGTH: 17
<212> TYPE: PRT
<213> ORGANISM: Artificial
<220> FEATURE:
<223> OTHER INFORMATION: synthetic HER2 binding clone 15 CDRH2

<400> SEQUENCE: 309

Ser Ile Tyr Pro Tyr Tyr Gly Tyr Thr Ser Tyr Ala Asp Ser Val Lys
1               5                   10                  15
Gly

<210> SEQ ID NO 310
<211> LENGTH: 17
<212> TYPE: PRT
<213> ORGANISM: Artificial
<220> FEATURE:
<223> OTHER INFORMATION: synthetic HER2 binding clone 16 CDRH2

<400> SEQUENCE: 310

Ser Ile Tyr Pro Ser Tyr Gly Tyr Thr Ser Tyr Ala Asp Ser Val Lys
1               5                   10                  15
Gly

<210> SEQ ID NO 311
<211> LENGTH: 17
<212> TYPE: PRT
<213> ORGANISM: Artificial
<220> FEATURE:
<223> OTHER INFORMATION: synthetic HER2 binding clone 17 CDRH2

<400> SEQUENCE: 311

Ser Ile Tyr Pro Tyr Tyr Gly Ser Thr Tyr Tyr Ala Asp Ser Val Lys
1               5                   10                  15
Gly

<210> SEQ ID NO 312
<211> LENGTH: 17
<212> TYPE: PRT
<213> ORGANISM: Artificial
```

```
<220> FEATURE:
<223> OTHER INFORMATION: synthetic HER2 binding clone 18 CDRH2

<400> SEQUENCE: 312

Ser Ile Tyr Pro Tyr Tyr Gly Ser Thr Tyr Tyr Ala Asp Ser Val Lys
1               5                   10                  15
Gly

<210> SEQ ID NO 313
<211> LENGTH: 17
<212> TYPE: PRT
<213> ORGANISM: Artificial
<220> FEATURE:
<223> OTHER INFORMATION: synthetic HER2 binding clone 19 CDRH2

<400> SEQUENCE: 313

Ser Ile Tyr Pro Tyr Tyr Gly Ser Thr Tyr Tyr Ala Asp Ser Val Lys
1               5                   10                  15
Gly

<210> SEQ ID NO 314
<211> LENGTH: 17
<212> TYPE: PRT
<213> ORGANISM: Artificial
<220> FEATURE:
<223> OTHER INFORMATION: synthetic HER2 binding clone 20 CDRH2

<400> SEQUENCE: 314

Ser Ile Tyr Pro Tyr Tyr Gly Tyr Thr Ser Tyr Ala Asp Ser Val Lys
1               5                   10                  15
Gly

<210> SEQ ID NO 315
<211> LENGTH: 17
<212> TYPE: PRT
<213> ORGANISM: Artificial
<220> FEATURE:
<223> OTHER INFORMATION: synthetic HER2 binding clone 21 CDRH2

<400> SEQUENCE: 315

Ser Ile Tyr Pro Tyr Tyr Gly Tyr Thr Ser Tyr Ala Asp Ser Val Lys
1               5                   10                  15
Gly

<210> SEQ ID NO 316
<211> LENGTH: 17
<212> TYPE: PRT
<213> ORGANISM: Artificial
<220> FEATURE:
<223> OTHER INFORMATION: synthetic HER2 binding clone 22 CDRH2

<400> SEQUENCE: 316

Ser Ile Tyr Pro Tyr Tyr Gly Tyr Thr Ser Tyr Ala Asp Ser Val Lys
1               5                   10                  15
Gly

<210> SEQ ID NO 317
<211> LENGTH: 17
<212> TYPE: PRT
<213> ORGANISM: Artificial
<220> FEATURE:
<223> OTHER INFORMATION: synthetic HER2 binding clone 23 CDRH2

<400> SEQUENCE: 317
```

Ser Ile Tyr Pro Ser Tyr Gly Tyr Thr Ser Tyr Ala Asp Ser Val Lys
1               5                   10                  15

Gly

<210> SEQ ID NO 318
<211> LENGTH: 17
<212> TYPE: PRT
<213> ORGANISM: Artificial
<220> FEATURE:
<223> OTHER INFORMATION: synthetic HER2 binding clone 24 CDRH2

<400> SEQUENCE: 318

Ser Ile Tyr Pro Tyr Tyr Gly Tyr Thr Ser Tyr Ala Asp Ser Val Lys
1               5                   10                  15

Gly

<210> SEQ ID NO 319
<211> LENGTH: 17
<212> TYPE: PRT
<213> ORGANISM: Artificial
<220> FEATURE:
<223> OTHER INFORMATION: synthetic HER2 binding clone 25 CDRH2

<400> SEQUENCE: 319

Ser Ile Tyr Pro Tyr Tyr Gly Tyr Thr Ser Tyr Ala Asp Ser Val Lys
1               5                   10                  15

Gly

<210> SEQ ID NO 320
<211> LENGTH: 17
<212> TYPE: PRT
<213> ORGANISM: Artificial
<220> FEATURE:
<223> OTHER INFORMATION: synthetic HER2 binding clone 26 CDRH2

<400> SEQUENCE: 320

Ser Ile Tyr Pro Tyr Tyr Gly Ser Thr Tyr Tyr Ala Asp Ser Val Lys
1               5                   10                  15

Gly

<210> SEQ ID NO 321
<211> LENGTH: 17
<212> TYPE: PRT
<213> ORGANISM: Artificial
<220> FEATURE:
<223> OTHER INFORMATION: synthetic HER2 binding clone 27 CDRH2

<400> SEQUENCE: 321

Ser Ile Tyr Pro Tyr Tyr Gly Tyr Thr Ser Tyr Ala Asp Ser Val Lys
1               5                   10                  15

Gly

<210> SEQ ID NO 322
<211> LENGTH: 17
<212> TYPE: PRT
<213> ORGANISM: Artificial
<220> FEATURE:
<223> OTHER INFORMATION: synthetic HER2 binding clone 28 CDRH2

<400> SEQUENCE: 322

Ser Ile Tyr Pro Ser Tyr Gly Ser Tyr Tyr Ala Asp Ser Val Lys
1               5                   10                  15

Gly

<210> SEQ ID NO 323
<211> LENGTH: 17
<212> TYPE: PRT
<213> ORGANISM: Artificial
<220> FEATURE:
<223> OTHER INFORMATION: synthetic HER2 binding clone 29 CDRH2

<400> SEQUENCE: 323

Tyr Ile Tyr Pro Ser Ser Gly Ser Thr Tyr Tyr Ala Asp Ser Val Lys
1               5                   10                  15

Gly

<210> SEQ ID NO 324
<211> LENGTH: 17
<212> TYPE: PRT
<213> ORGANISM: Artificial
<220> FEATURE:
<223> OTHER INFORMATION: synthetic HER2 binding clone 30 CDRH2

<400> SEQUENCE: 324

Ser Ile Ser Pro Tyr Tyr Gly Ser Thr Tyr Tyr Ala Asp Ser Val Lys
1               5                   10                  15

Gly

<210> SEQ ID NO 325
<211> LENGTH: 17
<212> TYPE: PRT
<213> ORGANISM: Artificial
<220> FEATURE:
<223> OTHER INFORMATION: synthetic HER2 binding clone 31 CDRH2

<400> SEQUENCE: 325

Ser Ile Ser Pro Tyr Ser Gly Ser Thr Ser Tyr Ala Asp Ser Val Lys
1               5                   10                  15

Gly

<210> SEQ ID NO 326
<211> LENGTH: 17
<212> TYPE: PRT
<213> ORGANISM: Artificial
<220> FEATURE:
<223> OTHER INFORMATION: synthetic HER2 binding clone 32 CDRH2

<400> SEQUENCE: 326

Ser Ile Ser Pro Tyr Ser Gly Tyr Thr Ser Tyr Ala Asp Ser Val Lys
1               5                   10                  15

Gly

<210> SEQ ID NO 327
<211> LENGTH: 17
<212> TYPE: PRT
<213> ORGANISM: Artificial
<220> FEATURE:
<223> OTHER INFORMATION: synthetic HER2 binding clone 33 CDRH2

<400> SEQUENCE: 327

Tyr Ile Ser Pro Ser Ser Gly Tyr Thr Tyr Tyr Ala Asp Ser Val Lys
1               5                   10                  15

Gly

<210> SEQ ID NO 328

```
<211> LENGTH: 17
<212> TYPE: PRT
<213> ORGANISM: Artificial
<220> FEATURE:
<223> OTHER INFORMATION: synthetic HER2 binding clone 34 CDRH2

<400> SEQUENCE: 328

Ser Ile Tyr Pro Ser Ser Gly Tyr Thr Ser Tyr Ala Asp Ser Val Lys
1               5                   10                  15

Gly

<210> SEQ ID NO 329
<211> LENGTH: 17
<212> TYPE: PRT
<213> ORGANISM: Artificial
<220> FEATURE:
<223> OTHER INFORMATION: synthetic HER2 binding clone 35 CDRH2

<400> SEQUENCE: 329

Ser Ile Tyr Pro Ser Ser Gly Tyr Thr Ser Tyr Ala Asp Ser Val Lys
1               5                   10                  15

Gly

<210> SEQ ID NO 330
<211> LENGTH: 17
<212> TYPE: PRT
<213> ORGANISM: Artificial
<220> FEATURE:
<223> OTHER INFORMATION: synthetic HER2 binding clone 36 CDRH2

<400> SEQUENCE: 330

Ser Ile Ser Pro Ser Ser Gly Tyr Thr Ser Tyr Ala Asp Ser Val Lys
1               5                   10                  15

Gly

<210> SEQ ID NO 331
<211> LENGTH: 17
<212> TYPE: PRT
<213> ORGANISM: Artificial
<220> FEATURE:
<223> OTHER INFORMATION: synthetic HER2 binding clone 37 CDRH2

<400> SEQUENCE: 331

Ser Ile Tyr Pro Ser Ser Gly Tyr Thr Tyr Tyr Ala Asp Ser Val Lys
1               5                   10                  15

Gly

<210> SEQ ID NO 332
<211> LENGTH: 17
<212> TYPE: PRT
<213> ORGANISM: Artificial
<220> FEATURE:
<223> OTHER INFORMATION: synthetic HER2 binding clone 38 CDRH2

<400> SEQUENCE: 332

Ser Ile Tyr Pro Ser Ser Gly Tyr Thr Ser Tyr Ala Asp Ser Val Lys
1               5                   10                  15

Gly

<210> SEQ ID NO 333
<211> LENGTH: 17
<212> TYPE: PRT
<213> ORGANISM: Artificial
<220> FEATURE:
```

<223> OTHER INFORMATION: synthetic HER2 binding clone 39 CDRH2

<400> SEQUENCE: 333

Ser Ile Tyr Pro Ser Ser Gly Tyr Thr Ser Tyr Ala Asp Ser Val Lys
1               5                   10                  15
Gly

<210> SEQ ID NO 334
<211> LENGTH: 17
<212> TYPE: PRT
<213> ORGANISM: Artificial
<220> FEATURE:
<223> OTHER INFORMATION: synthetic HER2 binding clone 40 CDRH2

<400> SEQUENCE: 334

Tyr Ile Tyr Pro Ser Ser Gly Tyr Thr Ser Tyr Ala Asp Ser Val Lys
1               5                   10                  15
Gly

<210> SEQ ID NO 335
<211> LENGTH: 17
<212> TYPE: PRT
<213> ORGANISM: Artificial
<220> FEATURE:
<223> OTHER INFORMATION: synthetic HER2 binding clone 41 CDRH2

<400> SEQUENCE: 335

Ser Ile Tyr Pro Ser Ser Gly Tyr Thr Ser Tyr Ala Asp Ser Val Lys
1               5                   10                  15
Gly

<210> SEQ ID NO 336
<211> LENGTH: 17
<212> TYPE: PRT
<213> ORGANISM: Artificial
<220> FEATURE:
<223> OTHER INFORMATION: synthetic HER2 binding clone 42 CDRH2

<400> SEQUENCE: 336

Tyr Ile Tyr Pro Ser Ser Gly Tyr Thr Ser Tyr Ala Asp Ser Val Lys
1               5                   10                  15
Gly

<210> SEQ ID NO 337
<211> LENGTH: 17
<212> TYPE: PRT
<213> ORGANISM: Artificial
<220> FEATURE:
<223> OTHER INFORMATION: synthetic HER2 binding clone 43 CDRH2

<400> SEQUENCE: 337

Tyr Ile Ser Pro Tyr Ser Gly Tyr Thr Ser Tyr Ala Asp Ser Val Lys
1               5                   10                  15
Gly

<210> SEQ ID NO 338
<211> LENGTH: 17
<212> TYPE: PRT
<213> ORGANISM: Artificial
<220> FEATURE:
<223> OTHER INFORMATION: synthetic HER2 binding clone 44 CDRH2

<400> SEQUENCE: 338

Ser Ile Tyr Pro Ser Ser Gly Tyr Thr Ser Tyr Ala Asp Ser Val Lys
1               5                   10                  15

Gly

<210> SEQ ID NO 339
<211> LENGTH: 17
<212> TYPE: PRT
<213> ORGANISM: Artificial
<220> FEATURE:
<223> OTHER INFORMATION: synthetic HER2 binding clone 45 CDRH2

<400> SEQUENCE: 339

Ser Ile Tyr Pro Ser Ser Gly Ser Thr Ser Tyr Ala Asp Ser Val Lys
1               5                   10                  15

Gly

<210> SEQ ID NO 340
<211> LENGTH: 17
<212> TYPE: PRT
<213> ORGANISM: Artificial
<220> FEATURE:
<223> OTHER INFORMATION: synthetic HER2 binding clone 46 CDRH2

<400> SEQUENCE: 340

Tyr Ile Ser Pro Ser Ser Gly Tyr Thr Ser Tyr Ala Asp Ser Val Lys
1               5                   10                  15

Gly

<210> SEQ ID NO 341
<211> LENGTH: 17
<212> TYPE: PRT
<213> ORGANISM: Artificial
<220> FEATURE:
<223> OTHER INFORMATION: synthetic HER2 binding clone 47 CDRH2

<400> SEQUENCE: 341

Ser Ile Tyr Pro Ser Ser Gly Tyr Thr Ser Tyr Ala Asp Ser Val Lys
1               5                   10                  15

Gly

<210> SEQ ID NO 342
<211> LENGTH: 17
<212> TYPE: PRT
<213> ORGANISM: Artificial
<220> FEATURE:
<223> OTHER INFORMATION: synthetic HER2 binding clone 48 CDRH2

<400> SEQUENCE: 342

Ser Ile Ser Pro Ser Ser Gly Tyr Thr Ser Tyr Ala Asp Ser Val Lys
1               5                   10                  15

Gly

<210> SEQ ID NO 343
<211> LENGTH: 17
<212> TYPE: PRT
<213> ORGANISM: Artificial
<220> FEATURE:
<223> OTHER INFORMATION: synthetic HER2 binding clone 49 CDRH2

<400> SEQUENCE: 343

Ser Ile Tyr Pro Ser Ser Gly Tyr Thr Ser Tyr Ala Asp Ser Val Lys
1               5                   10                  15

Gly

```
<210> SEQ ID NO 344
<211> LENGTH: 17
<212> TYPE: PRT
<213> ORGANISM: Artificial
<220> FEATURE:
<223> OTHER INFORMATION: synthetic HER2 binding clone 50 CDRH2

<400> SEQUENCE: 344

Ser Ile Tyr Pro Ser Ser Gly Tyr Thr Tyr Tyr Ala Asp Ser Val Lys
1               5                   10                  15

Gly

<210> SEQ ID NO 345
<211> LENGTH: 17
<212> TYPE: PRT
<213> ORGANISM: Artificial
<220> FEATURE:
<223> OTHER INFORMATION: synthetic HER2 binding clone 51 CDRH2

<400> SEQUENCE: 345

Tyr Ile Tyr Pro Ser Ser Gly Tyr Thr Ser Tyr Ala Asp Ser Val Lys
1               5                   10                  15

Gly

<210> SEQ ID NO 346
<211> LENGTH: 17
<212> TYPE: PRT
<213> ORGANISM: Artificial
<220> FEATURE:
<223> OTHER INFORMATION: synthetic HER2 binding clone 52 CDRH2

<400> SEQUENCE: 346

Ser Ile Tyr Pro Ser Tyr Gly Tyr Thr Ser Tyr Ala Asp Ser Val Lys
1               5                   10                  15

Gly

<210> SEQ ID NO 347
<211> LENGTH: 17
<212> TYPE: PRT
<213> ORGANISM: Artificial
<220> FEATURE:
<223> OTHER INFORMATION: synthetic HER2 binding clone 53 CDRH2

<400> SEQUENCE: 347

Tyr Ile Tyr Pro Ser Ser Gly Ser Thr Ser Tyr Ala Asp Ser Val Lys
1               5                   10                  15

Gly

<210> SEQ ID NO 348
<211> LENGTH: 17
<212> TYPE: PRT
<213> ORGANISM: Artificial
<220> FEATURE:
<223> OTHER INFORMATION: synthetic HER2 binding clone 54 CDRH2

<400> SEQUENCE: 348

Ser Ile Tyr Pro Ser Ser Gly Tyr Thr Tyr Tyr Ala Asp Ser Val Lys
1               5                   10                  15

Gly

<210> SEQ ID NO 349
<211> LENGTH: 17
```

<210> SEQ ID NO 349
<211> LENGTH: 17
<212> TYPE: PRT
<213> ORGANISM: Artificial
<220> FEATURE:
<223> OTHER INFORMATION: synthetic HER2 binding clone 55 CDRH2

<400> SEQUENCE: 349

Ser Ile Tyr Pro Ser Ser Gly Tyr Thr Ser Tyr Ala Asp Ser Val Lys
1               5                   10                  15
Gly

<210> SEQ ID NO 350
<211> LENGTH: 17
<212> TYPE: PRT
<213> ORGANISM: Artificial
<220> FEATURE:
<223> OTHER INFORMATION: synthetic HER2 binding clone 56 CDRH2

<400> SEQUENCE: 350

Ser Ile Tyr Pro Ser Ser Gly Ser Thr Ser Tyr Ala Asp Ser Val Lys
1               5                   10                  15
Gly

<210> SEQ ID NO 351
<211> LENGTH: 17
<212> TYPE: PRT
<213> ORGANISM: Artificial
<220> FEATURE:
<223> OTHER INFORMATION: synthetic HER2 binding clone 57 CDRH2

<400> SEQUENCE: 351

Ser Ile Ser Pro Ser Ser Gly Tyr Thr Ser Tyr Ala Asp Ser Val Lys
1               5                   10                  15
Gly

<210> SEQ ID NO 352
<211> LENGTH: 17
<212> TYPE: PRT
<213> ORGANISM: Artificial
<220> FEATURE:
<223> OTHER INFORMATION: synthetic HER2 binding clone 58 CDRH2

<400> SEQUENCE: 352

Tyr Ile Tyr Pro Ser Ser Gly Tyr Thr Ser Tyr Ala Asp Ser Val Lys
1               5                   10                  15
Gly

<210> SEQ ID NO 353
<211> LENGTH: 17
<212> TYPE: PRT
<213> ORGANISM: Artificial
<220> FEATURE:
<223> OTHER INFORMATION: synthetic HER2 binding clone 59 CDRH2

<400> SEQUENCE: 353

Ser Tyr Tyr Pro Ser Ser Gly Tyr Thr Ser Tyr Ala Asp Ser Val Lys
1               5                   10                  15
Gly

<210> SEQ ID NO 354
<211> LENGTH: 17
<212> TYPE: PRT
<213> ORGANISM: Artificial
<220> FEATURE:
<223> OTHER INFORMATION: synthetic HER2 binding clone 60 CDRH2

```
<400> SEQUENCE: 354

Tyr Ile Ser Pro Ser Ser Gly Tyr Thr Ser Tyr Ala Asp Ser Val Lys
1               5                   10                  15

Gly

<210> SEQ ID NO 355
<211> LENGTH: 17
<212> TYPE: PRT
<213> ORGANISM: Artificial
<220> FEATURE:
<223> OTHER INFORMATION: synthetic HER2 binding clone 61 CDRH2

<400> SEQUENCE: 355

Ser Ile Tyr Pro Ser Ser Gly Tyr Thr Ser Tyr Ala Asp Ser Val Lys
1               5                   10                  15

Gly

<210> SEQ ID NO 356
<211> LENGTH: 17
<212> TYPE: PRT
<213> ORGANISM: Artificial
<220> FEATURE:
<223> OTHER INFORMATION: synthetic HER2 binding clone 62 CDRH2

<400> SEQUENCE: 356

Tyr Ile Tyr Pro Ser Ser Gly Tyr Thr Ser Tyr Ala Asp Ser Val Lys
1               5                   10                  15

Gly

<210> SEQ ID NO 357
<211> LENGTH: 17
<212> TYPE: PRT
<213> ORGANISM: Artificial
<220> FEATURE:
<223> OTHER INFORMATION: synthetic HER2 binding clone 63 CDRH2

<400> SEQUENCE: 357

Tyr Ile Tyr Pro Ser Ser Gly Tyr Thr Tyr Tyr Ala Asp Ser Val Lys
1               5                   10                  15

Gly

<210> SEQ ID NO 358
<211> LENGTH: 17
<212> TYPE: PRT
<213> ORGANISM: Artificial
<220> FEATURE:
<223> OTHER INFORMATION: synthetic HER2 binding clone 64 CDRH2

<400> SEQUENCE: 358

Ser Ile Tyr Pro Ser Ser Gly Ser Thr Ser Tyr Ala Asp Ser Val Lys
1               5                   10                  15

Gly

<210> SEQ ID NO 359
<211> LENGTH: 17
<212> TYPE: PRT
<213> ORGANISM: Artificial
<220> FEATURE:
<223> OTHER INFORMATION: synthetic HER2 binding clone 65 CDRH2

<400> SEQUENCE: 359

Ser Ile Ser Pro Ser Ser Gly Tyr Thr Ser Tyr Ala Asp Ser Val Lys
```

```
1               5                   10                  15
Gly

<210> SEQ ID NO 360
<211> LENGTH: 17
<212> TYPE: PRT
<213> ORGANISM: Artificial
<220> FEATURE:
<223> OTHER INFORMATION: synthetic HER2 binding clone 66 CDRH2

<400> SEQUENCE: 360

Ser Ile Tyr Pro Ser Ser Gly Tyr Thr Ser Tyr Ala Asp Ser Val Lys
1               5                   10                  15
Gly

<210> SEQ ID NO 361
<211> LENGTH: 17
<212> TYPE: PRT
<213> ORGANISM: Artificial
<220> FEATURE:
<223> OTHER INFORMATION: synthetic HER2 binding clone 67 CDRH2

<400> SEQUENCE: 361

Tyr Ile Ser Pro Ser Ser Gly Tyr Thr Ser Tyr Ala Asp Ser Val Lys
1               5                   10                  15
Gly

<210> SEQ ID NO 362
<211> LENGTH: 17
<212> TYPE: PRT
<213> ORGANISM: Artificial
<220> FEATURE:
<223> OTHER INFORMATION: synthetic HER2 binding clone 68 CDRH2

<400> SEQUENCE: 362

Ser Ile Ser Pro Tyr Ser Gly Ser Thr Ser Tyr Ala Asp Ser Val Lys
1               5                   10                  15
Gly

<210> SEQ ID NO 363
<211> LENGTH: 17
<212> TYPE: PRT
<213> ORGANISM: Artificial
<220> FEATURE:
<223> OTHER INFORMATION: synthetic HER2 binding clone 69 CDRH2

<400> SEQUENCE: 363

Tyr Ile Tyr Pro Ser Ser Gly Tyr Thr Ser Tyr Ala Asp Ser Val Lys
1               5                   10                  15
Gly

<210> SEQ ID NO 364
<211> LENGTH: 17
<212> TYPE: PRT
<213> ORGANISM: Artificial
<220> FEATURE:
<223> OTHER INFORMATION: synthetic HER2 binding clone 70 CDRH2

<400> SEQUENCE: 364

Ser Ile Tyr Pro Tyr Ser Gly Ser Thr Ser Tyr Ala Asp Ser Val Lys
1               5                   10                  15
Gly
```

```
<210> SEQ ID NO 365
<211> LENGTH: 17
<212> TYPE: PRT
<213> ORGANISM: Artificial
<220> FEATURE:
<223> OTHER INFORMATION: synthetic HER2 binding clone 71 CDRH2

<400> SEQUENCE: 365

Ser Ile Ser Pro Tyr Ser Gly Tyr Thr Ser Tyr Ala Asp Ser Val Lys
1               5                   10                  15

Gly

<210> SEQ ID NO 366
<211> LENGTH: 17
<212> TYPE: PRT
<213> ORGANISM: Artificial
<220> FEATURE:
<223> OTHER INFORMATION: synthetic HER2 binding clone 72 CDRH2

<400> SEQUENCE: 366

Ser Ile Ser Pro Ser Ser Gly Tyr Thr Ser Tyr Ala Asp Ser Val Lys
1               5                   10                  15

Gly

<210> SEQ ID NO 367
<211> LENGTH: 17
<212> TYPE: PRT
<213> ORGANISM: Artificial
<220> FEATURE:
<223> OTHER INFORMATION: synthetic HER2 binding clone 73 CDRH2

<400> SEQUENCE: 367

Ser Ile Ser Pro Tyr Ser Gly Tyr Thr Ser Tyr Ala Asp Ser Val Lys
1               5                   10                  15

Gly

<210> SEQ ID NO 368
<211> LENGTH: 17
<212> TYPE: PRT
<213> ORGANISM: Artificial
<220> FEATURE:
<223> OTHER INFORMATION: synthetic HER2 binding clone 74 CDRH2

<400> SEQUENCE: 368

Ser Ile Tyr Pro Ser Ser Gly Tyr Thr Ser Tyr Ala Asp Ser Val Lys
1               5                   10                  15

Gly

<210> SEQ ID NO 369
<211> LENGTH: 17
<212> TYPE: PRT
<213> ORGANISM: Artificial
<220> FEATURE:
<223> OTHER INFORMATION: synthetic HER2 binding clone 75 CDRH2

<400> SEQUENCE: 369

Ser Ile Tyr Pro Tyr Tyr Gly Ser Thr Ser Tyr Ala Asp Ser Val Lys
1               5                   10                  15

Gly

<210> SEQ ID NO 370
<211> LENGTH: 17
<212> TYPE: PRT
```

```
<213> ORGANISM: Artificial
<220> FEATURE:
<223> OTHER INFORMATION: synthetic HER2 binding clone 76 CDRH2

<400> SEQUENCE: 370

Tyr Ile Tyr Pro Ser Ser Gly Ser Thr Ser Tyr Ala Asp Ser Val Lys
1               5                   10                  15

Gly

<210> SEQ ID NO 371
<211> LENGTH: 17
<212> TYPE: PRT
<213> ORGANISM: Artificial
<220> FEATURE:
<223> OTHER INFORMATION: synthetic HER2 binding clone 77 CDRH2

<400> SEQUENCE: 371

Tyr Ile Ser Pro Ser Ser Gly Tyr Thr Tyr Tyr Ala Asp Ser Val Lys
1               5                   10                  15

Gly

<210> SEQ ID NO 372
<211> LENGTH: 17
<212> TYPE: PRT
<213> ORGANISM: Artificial
<220> FEATURE:
<223> OTHER INFORMATION: synthetic HER2 binding clone 78 CDRH2

<400> SEQUENCE: 372

Ser Ile Ser Pro Ser Ser Gly Ser Thr Ser Tyr Ala Asp Ser Val Lys
1               5                   10                  15

Gly

<210> SEQ ID NO 373
<211> LENGTH: 17
<212> TYPE: PRT
<213> ORGANISM: Artificial
<220> FEATURE:
<223> OTHER INFORMATION: synthetic HER2 binding clone 79 CDRH2

<400> SEQUENCE: 373

Ser Ile Ser Pro Ser Ser Gly Tyr Thr Ser Tyr Ala Asp Ser Val Lys
1               5                   10                  15

Gly

<210> SEQ ID NO 374
<211> LENGTH: 17
<212> TYPE: PRT
<213> ORGANISM: Artificial
<220> FEATURE:
<223> OTHER INFORMATION: synthetic HER2 binding clone 80 CDRH2

<400> SEQUENCE: 374

Ser Ile Tyr Pro Tyr Ser Gly Ser Thr Ser Tyr Ala Asp Ser Val Lys
1               5                   10                  15

Gly

<210> SEQ ID NO 375
<211> LENGTH: 17
<212> TYPE: PRT
<213> ORGANISM: Artificial
<220> FEATURE:
<223> OTHER INFORMATION: synthetic HER2 binding clone 81 CDRH2
```

<400> SEQUENCE: 375

Tyr Ile Ser Pro Ser Ser Gly Tyr Thr Ser Tyr Ala Asp Ser Val Lys
1               5                   10                  15
Gly

<210> SEQ ID NO 376
<211> LENGTH: 17
<212> TYPE: PRT
<213> ORGANISM: Artificial
<220> FEATURE:
<223> OTHER INFORMATION: synthetic HER2 binding clone 82 CDRH2

<400> SEQUENCE: 376

Tyr Ile Ser Pro Ser Ser Gly Tyr Thr Ser Tyr Ala Asp Ser Val Lys
1               5                   10                  15
Gly

<210> SEQ ID NO 377
<211> LENGTH: 17
<212> TYPE: PRT
<213> ORGANISM: Artificial
<220> FEATURE:
<223> OTHER INFORMATION: synthetic HER2 binding clone 83 CDRH2

<400> SEQUENCE: 377

Ser Ile Ser Pro Ser Ser Gly Tyr Thr Ser Tyr Ala Asp Ser Val Lys
1               5                   10                  15
Gly

<210> SEQ ID NO 378
<211> LENGTH: 17
<212> TYPE: PRT
<213> ORGANISM: Artificial
<220> FEATURE:
<223> OTHER INFORMATION: synthetic HER2 binding clone 84 CDRH2

<400> SEQUENCE: 378

Tyr Ile Ser Pro Tyr Ser Gly Tyr Thr Tyr Tyr Ala Asp Ser Val Lys
1               5                   10                  15
Gly

<210> SEQ ID NO 379
<211> LENGTH: 17
<212> TYPE: PRT
<213> ORGANISM: Artificial
<220> FEATURE:
<223> OTHER INFORMATION: synthetic HER2 binding clone 85 CDRH2

<400> SEQUENCE: 379

Tyr Ile Ser Pro Tyr Ser Gly Tyr Thr Tyr Tyr Ala Asp Ser Val Lys
1               5                   10                  15
Gly

<210> SEQ ID NO 380
<211> LENGTH: 17
<212> TYPE: PRT
<213> ORGANISM: Artificial
<220> FEATURE:
<223> OTHER INFORMATION: synthetic HER2 binding clone 86 CDRH2

<400> SEQUENCE: 380

Tyr Ile Tyr Pro Tyr Ser Gly Ser Thr Ser Tyr Ala Asp Ser Val Lys
1               5                   10                  15

Gly

<210> SEQ ID NO 381
<211> LENGTH: 17
<212> TYPE: PRT
<213> ORGANISM: Artificial
<220> FEATURE:
<223> OTHER INFORMATION: synthetic HER2 binding clone 87 CDRH2

<400> SEQUENCE: 381

Ser Ile Ser Pro Ser Tyr Gly Tyr Thr Ser Tyr Ala Asp Ser Val Lys
1               5                   10                  15

Gly

<210> SEQ ID NO 382
<211> LENGTH: 17
<212> TYPE: PRT
<213> ORGANISM: Artificial
<220> FEATURE:
<223> OTHER INFORMATION: synthetic HER2 binding clone 88 CDRH2

<400> SEQUENCE: 382

Ser Ile Ser Pro Ser Tyr Gly Tyr Thr Ser Tyr Ala Asp Ser Val Lys
1               5                   10                  15

Gly

<210> SEQ ID NO 383
<211> LENGTH: 17
<212> TYPE: PRT
<213> ORGANISM: Artificial
<220> FEATURE:
<223> OTHER INFORMATION: synthetic HER2 binding clone 89 CDRH2

<400> SEQUENCE: 383

Ser Ile Tyr Pro Tyr Ser Gly Tyr Thr Ser Tyr Ala Asp Ser Val Lys
1               5                   10                  15

Gly

<210> SEQ ID NO 384
<211> LENGTH: 17
<212> TYPE: PRT
<213> ORGANISM: Artificial
<220> FEATURE:
<223> OTHER INFORMATION: synthetic HER2 binding clone 90 CDRH2

<400> SEQUENCE: 384

Ser Ile Ser Pro Tyr Ser Gly Tyr Thr Ser Tyr Ala Asp Ser Val Lys
1               5                   10                  15

Gly

<210> SEQ ID NO 385
<211> LENGTH: 17
<212> TYPE: PRT
<213> ORGANISM: Artificial
<220> FEATURE:
<223> OTHER INFORMATION: synthetic HER2 binding clone 91 CDRH2

<400> SEQUENCE: 385

Tyr Ile Tyr Pro Tyr Ser Gly Tyr Thr Tyr Tyr Ala Asp Ser Val Lys
1               5                   10                  15

Gly

<210> SEQ ID NO 386
<211> LENGTH: 17
<212> TYPE: PRT
<213> ORGANISM: Artificial
<220> FEATURE:
<223> OTHER INFORMATION: synthetic HER2 binding clone 92 CDRH2

<400> SEQUENCE: 386

Tyr Ile Ser Pro Ser Ser Gly Tyr Thr Ser Tyr Ala Asp Ser Val Lys
1               5                   10                  15
Gly

<210> SEQ ID NO 387
<211> LENGTH: 17
<212> TYPE: PRT
<213> ORGANISM: Artificial
<220> FEATURE:
<223> OTHER INFORMATION: synthetic HER2 binding clone 93 CDRH2

<400> SEQUENCE: 387

Tyr Ile Ser Pro Ser Ser Gly Tyr Thr Ser Tyr Ala Asp Ser Val Lys
1               5                   10                  15
Gly

<210> SEQ ID NO 388
<211> LENGTH: 17
<212> TYPE: PRT
<213> ORGANISM: Artificial
<220> FEATURE:
<223> OTHER INFORMATION: synthetic HER2 binding clone 94 CDRH2

<400> SEQUENCE: 388

Tyr Ile Ser Pro Ser Tyr Gly Ser Thr Tyr Tyr Ala Asp Ser Val Lys
1               5                   10                  15
Gly

<210> SEQ ID NO 389
<211> LENGTH: 17
<212> TYPE: PRT
<213> ORGANISM: Artificial
<220> FEATURE:
<223> OTHER INFORMATION: synthetic HER2 binding clone 95 CDRH2

<400> SEQUENCE: 389

Ser Ile Ser Pro Ser Ser Gly Tyr Thr Ser Tyr Ala Asp Ser Val Lys
1               5                   10                  15
Gly

<210> SEQ ID NO 390
<211> LENGTH: 17
<212> TYPE: PRT
<213> ORGANISM: Artificial
<220> FEATURE:
<223> OTHER INFORMATION: synthetic HER2 binding clone 96 CDRH2

<400> SEQUENCE: 390

Ser Ile Tyr Pro Tyr Ser Gly Tyr Thr Ser Tyr Ala Asp Ser Val Lys
1               5                   10                  15
Gly

<210> SEQ ID NO 391
<211> LENGTH: 17
<212> TYPE: PRT
<213> ORGANISM: Artificial

```
<220> FEATURE:
<223> OTHER INFORMATION: synthetic HER2 binding clone 97 CDRH2

<400> SEQUENCE: 391

Ser Ile Tyr Pro Tyr Tyr Gly Ser Thr Tyr Tyr Ala Asp Ser Val Lys
1               5                   10                  15

Gly

<210> SEQ ID NO 392
<211> LENGTH: 17
<212> TYPE: PRT
<213> ORGANISM: Artificial
<220> FEATURE:
<223> OTHER INFORMATION: synthetic HER2 binding clone 98 CDRH2

<400> SEQUENCE: 392

Ser Ile Tyr Pro Tyr Tyr Gly Tyr Thr Ser Tyr Ala Asp Ser Val Lys
1               5                   10                  15

Gly

<210> SEQ ID NO 393
<211> LENGTH: 17
<212> TYPE: PRT
<213> ORGANISM: Artificial
<220> FEATURE:
<223> OTHER INFORMATION: synthetic HER2 binding clone 99 CDRH2

<400> SEQUENCE: 393

Ser Ile Tyr Pro Tyr Tyr Gly Ser Thr Tyr Tyr Ala Asp Ser Val Lys
1               5                   10                  15

Gly

<210> SEQ ID NO 394
<211> LENGTH: 17
<212> TYPE: PRT
<213> ORGANISM: Artificial
<220> FEATURE:
<223> OTHER INFORMATION: synthetic HER2 binding clone 100 CDRH2

<400> SEQUENCE: 394

Ser Ile Tyr Pro Tyr Tyr Gly Ser Thr Tyr Tyr Ala Asp Ser Val Lys
1               5                   10                  15

Gly

<210> SEQ ID NO 395
<211> LENGTH: 17
<212> TYPE: PRT
<213> ORGANISM: Artificial
<220> FEATURE:
<223> OTHER INFORMATION: synthetic HER2 binding clone 101 CDRH2

<400> SEQUENCE: 395

Ser Ile Tyr Pro Ser Tyr Gly Tyr Thr Ser Tyr Ala Asp Ser Val Lys
1               5                   10                  15

Gly

<210> SEQ ID NO 396
<211> LENGTH: 17
<212> TYPE: PRT
<213> ORGANISM: Artificial
<220> FEATURE:
<223> OTHER INFORMATION: synthetic HER2 binding clone 102 CDRH2

<400> SEQUENCE: 396
```

Ser Ile Tyr Pro Tyr Tyr Gly Tyr Thr Ser Tyr Ala Asp Ser Val Lys
1               5                   10                  15

Gly

<210> SEQ ID NO 397
<211> LENGTH: 17
<212> TYPE: PRT
<213> ORGANISM: Artificial
<220> FEATURE:
<223> OTHER INFORMATION: synthetic HER2 binding clone 103 CDRH2

<400> SEQUENCE: 397

Ser Ile Tyr Pro Tyr Tyr Gly Ser Thr Tyr Tyr Ala Asp Ser Val Lys
1               5                   10                  15

Gly

<210> SEQ ID NO 398
<211> LENGTH: 17
<212> TYPE: PRT
<213> ORGANISM: Artificial
<220> FEATURE:
<223> OTHER INFORMATION: synthetic HER2 binding clone 104 CDRH2

<400> SEQUENCE: 398

Ser Ile Tyr Pro Ser Ser Gly Tyr Thr Ser Tyr Ala Asp Ser Val Lys
1               5                   10                  15

Gly

<210> SEQ ID NO 399
<211> LENGTH: 17
<212> TYPE: PRT
<213> ORGANISM: Artificial
<220> FEATURE:
<223> OTHER INFORMATION: synthetic HER2 binding clone 105 CDRH2

<400> SEQUENCE: 399

Ser Ile Tyr Pro Ser Ser Gly Tyr Thr Ser Tyr Ala Asp Ser Val Lys
1               5                   10                  15

Gly

<210> SEQ ID NO 400
<211> LENGTH: 17
<212> TYPE: PRT
<213> ORGANISM: Artificial
<220> FEATURE:
<223> OTHER INFORMATION: synthetic HER2 binding clone 106 CDRH2

<400> SEQUENCE: 400

Ser Ile Tyr Pro Ser Ser Gly Tyr Thr Ser Tyr Ala Asp Ser Val Lys
1               5                   10                  15

Gly

<210> SEQ ID NO 401
<211> LENGTH: 8
<212> TYPE: PRT
<213> ORGANISM: Artificial
<220> FEATURE:
<223> OTHER INFORMATION: synthetic HER2 binding clone 106 CDRH2

<400> SEQUENCE: 401

Tyr Tyr Ser Ser Gly Phe Asp Tyr
1               5

<210> SEQ ID NO 402
<211> LENGTH: 8
<212> TYPE: PRT
<213> ORGANISM: Artificial
<220> FEATURE:
<223> OTHER INFORMATION: synthetic HER2 binding clone 2 CDRH3

<400> SEQUENCE: 402

Tyr Tyr Gly Tyr Gly Met Asp Tyr
1               5

<210> SEQ ID NO 403
<211> LENGTH: 8
<212> TYPE: PRT
<213> ORGANISM: Artificial
<220> FEATURE:
<223> OTHER INFORMATION: synthetic HER2 binding clone 3 CDRH3

<400> SEQUENCE: 403

Tyr Tyr Gly Tyr Gly Leu Asp Tyr
1               5

<210> SEQ ID NO 404
<211> LENGTH: 8
<212> TYPE: PRT
<213> ORGANISM: Artificial
<220> FEATURE:
<223> OTHER INFORMATION: synthetic HER2 binding clone 4 CDRH3

<400> SEQUENCE: 404

Tyr Tyr Gly Tyr Gly Phe Asp Tyr
1               5

<210> SEQ ID NO 405
<211> LENGTH: 8
<212> TYPE: PRT
<213> ORGANISM: Artificial
<220> FEATURE:
<223> OTHER INFORMATION: synthetic HER2 binding clone 5 CDRH3

<400> SEQUENCE: 405

Tyr Tyr Gly Ser Gly Phe Asp Tyr
1               5

<210> SEQ ID NO 406
<211> LENGTH: 8
<212> TYPE: PRT
<213> ORGANISM: Artificial
<220> FEATURE:
<223> OTHER INFORMATION: synthetic HER2 binding clone 6 CDRH3

<400> SEQUENCE: 406

Tyr Tyr Gly Gly Ala Phe Asp Tyr
1               5

<210> SEQ ID NO 407
<211> LENGTH: 9
<212> TYPE: PRT
<213> ORGANISM: Artificial
<220> FEATURE:
<223> OTHER INFORMATION: synthetic HER2 binding clone 7 CDRH3

<400> SEQUENCE: 407

Tyr Tyr Gly Arg Gly Ala Met Asp Tyr
1               5

```
<210> SEQ ID NO 408
<211> LENGTH: 9
<212> TYPE: PRT
<213> ORGANISM: Artificial
<220> FEATURE:
<223> OTHER INFORMATION: synthetic HER2 binding clone 8 CDRH3

<400> SEQUENCE: 408

Tyr Ser Tyr Ser Gly Ala Leu Asp Tyr
1               5

<210> SEQ ID NO 409
<211> LENGTH: 9
<212> TYPE: PRT
<213> ORGANISM: Artificial
<220> FEATURE:
<223> OTHER INFORMATION: synthetic HER2 binding clone 9 CDRH3

<400> SEQUENCE: 409

Tyr Arg Tyr Tyr Gly Ala Leu Asp Tyr
1               5

<210> SEQ ID NO 410
<211> LENGTH: 9
<212> TYPE: PRT
<213> ORGANISM: Artificial
<220> FEATURE:
<223> OTHER INFORMATION: synthetic HER2 binding clone 10 CDRH3

<400> SEQUENCE: 410

Tyr Arg Tyr Gly Gly Ala Met Asp Tyr
1               5

<210> SEQ ID NO 411
<211> LENGTH: 10
<212> TYPE: PRT
<213> ORGANISM: Artificial
<220> FEATURE:
<223> OTHER INFORMATION: synthetic HER2 binding clone 11 CDRH3

<400> SEQUENCE: 411

Tyr Tyr Gly Gly Tyr Tyr Gly Met Asp Tyr
1               5                   10

<210> SEQ ID NO 412
<211> LENGTH: 10
<212> TYPE: PRT
<213> ORGANISM: Artificial
<220> FEATURE:
<223> OTHER INFORMATION: synthetic HER2 binding clone 12 CDRH3

<400> SEQUENCE: 412

Tyr Ser Tyr Tyr Tyr Tyr Ala Leu Asp Tyr
1               5                   10

<210> SEQ ID NO 413
<211> LENGTH: 10
<212> TYPE: PRT
<213> ORGANISM: Artificial
<220> FEATURE:
<223> OTHER INFORMATION: synthetic HER2 binding clone 13 CDRH3

<400> SEQUENCE: 413

Ser Ser Tyr Tyr Tyr Tyr Gly Met Asp Tyr
1               5                   10

<210> SEQ ID NO 414
```

```
<211> LENGTH: 10
<212> TYPE: PRT
<213> ORGANISM: Artificial
<220> FEATURE:
<223> OTHER INFORMATION: synthetic HER2 binding clone 14 CDRH3

<400> SEQUENCE: 414

Ser Ser Tyr Tyr Tyr Tyr Gly Phe Asp Tyr
1               5                   10

<210> SEQ ID NO 415
<211> LENGTH: 10
<212> TYPE: PRT
<213> ORGANISM: Artificial
<220> FEATURE:
<223> OTHER INFORMATION: synthetic HER2 binding clone 15 CDRH3

<400> SEQUENCE: 415

Ser Ser Tyr Tyr Tyr Tyr Gly Leu Asp Tyr
1               5                   10

<210> SEQ ID NO 416
<211> LENGTH: 10
<212> TYPE: PRT
<213> ORGANISM: Artificial
<220> FEATURE:
<223> OTHER INFORMATION: synthetic HER2 binding clone 16 CDRH3

<400> SEQUENCE: 416

Ser Gly Gly Tyr Ser Arg Gly Ile Asp Tyr
1               5                   10

<210> SEQ ID NO 417
<211> LENGTH: 10
<212> TYPE: PRT
<213> ORGANISM: Artificial
<220> FEATURE:
<223> OTHER INFORMATION: synthetic HER2 binding clone 17 CDRH3

<400> SEQUENCE: 417

Gly Tyr Ser Tyr Ser Arg Gly Ile Asp Tyr
1               5                   10

<210> SEQ ID NO 418
<211> LENGTH: 10
<212> TYPE: PRT
<213> ORGANISM: Artificial
<220> FEATURE:
<223> OTHER INFORMATION: synthetic HER2 binding clone 18 CDRH3

<400> SEQUENCE: 418

Gly Tyr Ser Tyr Ser Arg Gly Met Asp Tyr
1               5                   10

<210> SEQ ID NO 419
<211> LENGTH: 10
<212> TYPE: PRT
<213> ORGANISM: Artificial
<220> FEATURE:
<223> OTHER INFORMATION: synthetic HER2 binding clone 19 CDRH3

<400> SEQUENCE: 419

Gly Ser Ser Tyr Ser Tyr Gly Met Asp Tyr
1               5                   10

<210> SEQ ID NO 420
<211> LENGTH: 10
```

```
<212> TYPE: PRT
<213> ORGANISM: Artificial
<220> FEATURE:
<223> OTHER INFORMATION: synthetic HER2 binding clone 20 CDRH3

<400> SEQUENCE: 420

Gly Ser Gly Tyr Gly Tyr Gly Met Asp Tyr
1               5                   10

<210> SEQ ID NO 421
<211> LENGTH: 10
<212> TYPE: PRT
<213> ORGANISM: Artificial
<220> FEATURE:
<223> OTHER INFORMATION: synthetic HER2 binding clone 21 CDRH3

<400> SEQUENCE: 421

Gly Ser Gly Tyr Gly Tyr Gly Ile Asp Tyr
1               5                   10

<210> SEQ ID NO 422
<211> LENGTH: 10
<212> TYPE: PRT
<213> ORGANISM: Artificial
<220> FEATURE:
<223> OTHER INFORMATION: synthetic HER2 binding clone 22 CDRH3

<400> SEQUENCE: 422

Gly Arg Arg Tyr Ser Arg Gly Ile Asp Tyr
1               5                   10

<210> SEQ ID NO 423
<211> LENGTH: 10
<212> TYPE: PRT
<213> ORGANISM: Artificial
<220> FEATURE:
<223> OTHER INFORMATION: synthetic HER2 binding clone 23 CDRH3

<400> SEQUENCE: 423

Gly Gly Ser Tyr Gly Tyr Gly Met Asp Tyr
1               5                   10

<210> SEQ ID NO 424
<211> LENGTH: 10
<212> TYPE: PRT
<213> ORGANISM: Artificial
<220> FEATURE:
<223> OTHER INFORMATION: synthetic HER2 binding clone 24 CDRH3

<400> SEQUENCE: 424

Gly Gly Ser Tyr Gly Tyr Gly Met Asp Tyr
1               5                   10

<210> SEQ ID NO 425
<211> LENGTH: 10
<212> TYPE: PRT
<213> ORGANISM: Artificial
<220> FEATURE:
<223> OTHER INFORMATION: synthetic HER2 binding clone 25 CDRH3

<400> SEQUENCE: 425

Gly Gly Arg Tyr Gly Tyr Gly Leu Asp Tyr
1               5                   10

<210> SEQ ID NO 426
<211> LENGTH: 10
<212> TYPE: PRT
```

```
<213> ORGANISM: Artificial
<220> FEATURE:
<223> OTHER INFORMATION: synthetic HER2 binding clone 26 CDRH3

<400> SEQUENCE: 426

Gly Gly Arg Tyr Gly Arg Gly Ile Asp Tyr
1               5                   10

<210> SEQ ID NO 427
<211> LENGTH: 10
<212> TYPE: PRT
<213> ORGANISM: Artificial
<220> FEATURE:
<223> OTHER INFORMATION: synthetic HER2 binding clone 27 CDRH3

<400> SEQUENCE: 427

Gly Gly Gly Tyr Gly Tyr Gly Ile Asp Tyr
1               5                   10

<210> SEQ ID NO 428
<211> LENGTH: 10
<212> TYPE: PRT
<213> ORGANISM: Artificial
<220> FEATURE:
<223> OTHER INFORMATION: synthetic HER2 binding clone 28 CDRH3

<400> SEQUENCE: 428

Gly Gly Gly Tyr Gly Tyr Gly Ile Asp Tyr
1               5                   10

<210> SEQ ID NO 429
<211> LENGTH: 12
<212> TYPE: PRT
<213> ORGANISM: Artificial
<220> FEATURE:
<223> OTHER INFORMATION: synthetic HER2 binding clone 29 CDRH3

<400> SEQUENCE: 429

Tyr Tyr Tyr Ser Gly Gly Ser Tyr Gly Met Asp Tyr
1               5                   10

<210> SEQ ID NO 430
<211> LENGTH: 12
<212> TYPE: PRT
<213> ORGANISM: Artificial
<220> FEATURE:
<223> OTHER INFORMATION: synthetic HER2 binding clone 30 CDRH3

<400> SEQUENCE: 430

Ser Tyr Ser Ser Tyr Tyr Ser Ser Gly Met Asp Tyr
1               5                   10

<210> SEQ ID NO 431
<211> LENGTH: 12
<212> TYPE: PRT
<213> ORGANISM: Artificial
<220> FEATURE:
<223> OTHER INFORMATION: synthetic HER2 binding clone 31 CDRH3

<400> SEQUENCE: 431

Arg Tyr Tyr Tyr Tyr Tyr Tyr Ser Ala Phe Asp Tyr
1               5                   10

<210> SEQ ID NO 432
<211> LENGTH: 14
<212> TYPE: PRT
<213> ORGANISM: Artificial
```

```
<220> FEATURE:
<223> OTHER INFORMATION: synthetic HER2 binding clone 32 CDRH3

<400> SEQUENCE: 432

Tyr Tyr Tyr Tyr Ser Tyr Tyr Ser Gly Gly Ala Ile Asp Tyr
1               5                   10

<210> SEQ ID NO 433
<211> LENGTH: 14
<212> TYPE: PRT
<213> ORGANISM: Artificial
<220> FEATURE:
<223> OTHER INFORMATION: synthetic HER2 binding clone 33 CDRH3

<400> SEQUENCE: 433

Ser Tyr Tyr Tyr Ser Tyr Tyr Ser Gly Tyr Gly Met Asp Tyr
1               5                   10

<210> SEQ ID NO 434
<211> LENGTH: 14
<212> TYPE: PRT
<213> ORGANISM: Artificial
<220> FEATURE:
<223> OTHER INFORMATION: synthetic HER2 binding clone 34 CDRH3

<400> SEQUENCE: 434

Ser Tyr Tyr Tyr Ser Tyr Tyr Ser Gly Tyr Gly Leu Asp Tyr
1               5                   10

<210> SEQ ID NO 435
<211> LENGTH: 14
<212> TYPE: PRT
<213> ORGANISM: Artificial
<220> FEATURE:
<223> OTHER INFORMATION: synthetic HER2 binding clone 35 CDRH3

<400> SEQUENCE: 435

Ser Tyr Tyr Tyr Ser Tyr Tyr Gly Tyr Gly Met Asp Tyr
1               5                   10

<210> SEQ ID NO 436
<211> LENGTH: 14
<212> TYPE: PRT
<213> ORGANISM: Artificial
<220> FEATURE:
<223> OTHER INFORMATION: synthetic HER2 binding clone 36 CDRH3

<400> SEQUENCE: 436

Ser Tyr Tyr Gly Ser Tyr Tyr Gly Tyr Gly Phe Asp Tyr
1               5                   10

<210> SEQ ID NO 437
<211> LENGTH: 14
<212> TYPE: PRT
<213> ORGANISM: Artificial
<220> FEATURE:
<223> OTHER INFORMATION: synthetic HER2 binding clone 37 CDRH3

<400> SEQUENCE: 437

Ser Ser Tyr Tyr Gly Tyr Tyr Ser Gly Tyr Gly Ile Asp Tyr
1               5                   10

<210> SEQ ID NO 438
<211> LENGTH: 14
<212> TYPE: PRT
<213> ORGANISM: Artificial
<220> FEATURE:
```

<223> OTHER INFORMATION: synthetic HER2 binding clone 38 CDRH3

<400> SEQUENCE: 438

Ser Ser Tyr Tyr Ser Tyr Ser Gly Tyr Gly Leu Asp Tyr
1               5                   10

<210> SEQ ID NO 439
<211> LENGTH: 14
<212> TYPE: PRT
<213> ORGANISM: Artificial
<220> FEATURE:
<223> OTHER INFORMATION: synthetic HER2 binding clone 39 CDRH3

<400> SEQUENCE: 439

Gly Tyr Tyr Tyr Ser Tyr Tyr Gly Tyr Gly Met Asp Tyr
1               5                   10

<210> SEQ ID NO 440
<211> LENGTH: 14
<212> TYPE: PRT
<213> ORGANISM: Artificial
<220> FEATURE:
<223> OTHER INFORMATION: synthetic HER2 binding clone 40 CDRH3

<400> SEQUENCE: 440

Gly Tyr Tyr Tyr Ser Tyr Tyr Gly Ser Ala Met Asp Tyr
1               5                   10

<210> SEQ ID NO 441
<211> LENGTH: 14
<212> TYPE: PRT
<213> ORGANISM: Artificial
<220> FEATURE:
<223> OTHER INFORMATION: synthetic HER2 binding clone 41 CDRH3

<400> SEQUENCE: 441

Gly Tyr Tyr Tyr Ser Tyr Ser Gly Tyr Gly Met Asp Tyr
1               5                   10

<210> SEQ ID NO 442
<211> LENGTH: 14
<212> TYPE: PRT
<213> ORGANISM: Artificial
<220> FEATURE:
<223> OTHER INFORMATION: synthetic HER2 binding clone 42 CDRH3

<400> SEQUENCE: 442

Gly Tyr Tyr Tyr Ser Tyr Tyr Gly Tyr Ala Leu Asp Tyr
1               5                   10

<210> SEQ ID NO 443
<211> LENGTH: 14
<212> TYPE: PRT
<213> ORGANISM: Artificial
<220> FEATURE:
<223> OTHER INFORMATION: synthetic HER2 binding clone 43 CDRH3

<400> SEQUENCE: 443

Gly Tyr Tyr Tyr Ser Tyr Tyr Gly Tyr Ala Ile Asp Tyr
1               5                   10

<210> SEQ ID NO 444
<211> LENGTH: 14
<212> TYPE: PRT
<213> ORGANISM: Artificial
<220> FEATURE:
<223> OTHER INFORMATION: synthetic HER2 binding clone 44 CDRH3

<400> SEQUENCE: 444

Gly Tyr Tyr Tyr Ser Tyr Tyr Ser Gly Tyr Ala Met Asp Tyr
1               5                   10

<210> SEQ ID NO 445
<211> LENGTH: 14
<212> TYPE: PRT
<213> ORGANISM: Artificial
<220> FEATURE:
<223> OTHER INFORMATION: synthetic HER2 binding clone 45 CDRH3

<400> SEQUENCE: 445

Gly Tyr Tyr Tyr Ser Tyr Tyr Ser Gly Tyr Gly Ile Asp Tyr
1               5                   10

<210> SEQ ID NO 446
<211> LENGTH: 14
<212> TYPE: PRT
<213> ORGANISM: Artificial
<220> FEATURE:
<223> OTHER INFORMATION: synthetic HER2 binding clone 46 CDRH3

<400> SEQUENCE: 446

Gly Tyr Tyr Tyr Ser Tyr Tyr Ser Gly Tyr Gly Leu Asp Tyr
1               5                   10

<210> SEQ ID NO 447
<211> LENGTH: 14
<212> TYPE: PRT
<213> ORGANISM: Artificial
<220> FEATURE:
<223> OTHER INFORMATION: synthetic HER2 binding clone 47 CDRH3

<400> SEQUENCE: 447

Gly Tyr Tyr Tyr Ser Tyr Tyr Ser Gly Tyr Gly Met Asp Tyr
1               5                   10

<210> SEQ ID NO 448
<211> LENGTH: 14
<212> TYPE: PRT
<213> ORGANISM: Artificial
<220> FEATURE:
<223> OTHER INFORMATION: synthetic HER2 binding clone 48 CDRH3

<400> SEQUENCE: 448

Gly Tyr Tyr Tyr Ser Tyr Tyr Ser Gly Ser Gly Leu Asp Tyr
1               5                   10

<210> SEQ ID NO 449
<211> LENGTH: 14
<212> TYPE: PRT
<213> ORGANISM: Artificial
<220> FEATURE:
<223> OTHER INFORMATION: synthetic HER2 binding clone 49 CDRH3

<400> SEQUENCE: 449

Gly Tyr Tyr Tyr Ser Tyr Tyr Gly Gly Tyr Gly Met Asp Tyr
1               5                   10

<210> SEQ ID NO 450
<211> LENGTH: 14
<212> TYPE: PRT
<213> ORGANISM: Artificial
<220> FEATURE:
<223> OTHER INFORMATION: synthetic HER2 binding clone 50 CDRH3

```
<400> SEQUENCE: 450

Gly Tyr Tyr Tyr Ser Tyr Tyr Gly Gly Tyr Gly Ile Asp Tyr
1               5                   10

<210> SEQ ID NO 451
<211> LENGTH: 14
<212> TYPE: PRT
<213> ORGANISM: Artificial
<220> FEATURE:
<223> OTHER INFORMATION: synthetic HER2 binding clone 51 CDRH3

<400> SEQUENCE: 451

Gly Tyr Tyr Tyr Ser Tyr Tyr Gly Gly Tyr Gly Met Asp Tyr
1               5                   10

<210> SEQ ID NO 452
<211> LENGTH: 14
<212> TYPE: PRT
<213> ORGANISM: Artificial
<220> FEATURE:
<223> OTHER INFORMATION: synthetic HER2 binding clone 52 CDRH3

<400> SEQUENCE: 452

Gly Tyr Tyr Tyr Ser Tyr Tyr Gly Gly Tyr Gly Met Asp Tyr
1               5                   10

<210> SEQ ID NO 453
<211> LENGTH: 14
<212> TYPE: PRT
<213> ORGANISM: Artificial
<220> FEATURE:
<223> OTHER INFORMATION: synthetic HER2 binding clone 53 CDRH3

<400> SEQUENCE: 453

Gly Tyr Tyr Tyr Ser Tyr Tyr Gly Gly Tyr Gly Met Asp Tyr
1               5                   10

<210> SEQ ID NO 454
<211> LENGTH: 14
<212> TYPE: PRT
<213> ORGANISM: Artificial
<220> FEATURE:
<223> OTHER INFORMATION: synthetic HER2 binding clone 54 CDRH3

<400> SEQUENCE: 454

Gly Tyr Tyr Tyr Ser Tyr Tyr Gly Gly Tyr Gly Leu Asp Tyr
1               5                   10

<210> SEQ ID NO 455
<211> LENGTH: 14
<212> TYPE: PRT
<213> ORGANISM: Artificial
<220> FEATURE:
<223> OTHER INFORMATION: synthetic HER2 binding clone 55 CDRH3

<400> SEQUENCE: 455

Gly Tyr Tyr Tyr Ser Tyr Tyr Gly Gly Tyr Gly Met Asp Tyr
1               5                   10

<210> SEQ ID NO 456
<211> LENGTH: 14
<212> TYPE: PRT
<213> ORGANISM: Artificial
<220> FEATURE:
<223> OTHER INFORMATION: synthetic HER2 binding clone 56 CDRH3

<400> SEQUENCE: 456
```

Gly Tyr Tyr Tyr Ser Tyr Tyr Gly Gly Tyr Gly Met Asp Tyr
1               5                   10

<210> SEQ ID NO 457
<211> LENGTH: 14
<212> TYPE: PRT
<213> ORGANISM: Artificial
<220> FEATURE:
<223> OTHER INFORMATION: synthetic HER2 binding clone 57 CDRH3

<400> SEQUENCE: 457

Gly Tyr Tyr Tyr Gly Tyr Tyr Ser Gly Tyr Gly Ile Asp Tyr
1               5                   10

<210> SEQ ID NO 458
<211> LENGTH: 14
<212> TYPE: PRT
<213> ORGANISM: Artificial
<220> FEATURE:
<223> OTHER INFORMATION: synthetic HER2 binding clone 58 CDRH3

<400> SEQUENCE: 458

Gly Ser Tyr Tyr Ser Tyr Tyr Ser Gly Tyr Gly Met Asp Tyr
1               5                   10

<210> SEQ ID NO 459
<211> LENGTH: 14
<212> TYPE: PRT
<213> ORGANISM: Artificial
<220> FEATURE:
<223> OTHER INFORMATION: synthetic HER2 binding clone 59 CDRH3

<400> SEQUENCE: 459

Gly Ser Tyr Tyr Ser Tyr Tyr Ser Gly Tyr Ala Ile Asp Tyr
1               5                   10

<210> SEQ ID NO 460
<211> LENGTH: 14
<212> TYPE: PRT
<213> ORGANISM: Artificial
<220> FEATURE:
<223> OTHER INFORMATION: synthetic HER2 binding clone 60 CDRH3

<400> SEQUENCE: 460

Gly Ser Tyr Tyr Ser Tyr Tyr Ser Gly Tyr Ala Phe Asp Tyr
1               5                   10

<210> SEQ ID NO 461
<211> LENGTH: 14
<212> TYPE: PRT
<213> ORGANISM: Artificial
<220> FEATURE:
<223> OTHER INFORMATION: synthetic HER2 binding clone 61 CDRH3

<400> SEQUENCE: 461

Gly Ser Tyr Tyr Ser Tyr Tyr Ser Gly Ser Gly Ile Asp Tyr
1               5                   10

<210> SEQ ID NO 462
<211> LENGTH: 14
<212> TYPE: PRT
<213> ORGANISM: Artificial
<220> FEATURE:
<223> OTHER INFORMATION: synthetic HER2 binding clone 62 CDRH3

<400> SEQUENCE: 462

```
Gly Ser Tyr Tyr Gly Tyr Tyr Gly Ser Ala Ile Asp Tyr
1               5                   10
```

<210> SEQ ID NO 463
<211> LENGTH: 14
<212> TYPE: PRT
<213> ORGANISM: Artificial
<220> FEATURE:
<223> OTHER INFORMATION: synthetic HER2 binding clone 63 CDRH3

<400> SEQUENCE: 463

```
Gly Ser Tyr Tyr Gly Tyr Tyr Gly Ser Gly Met Asp Tyr
1               5                   10
```

<210> SEQ ID NO 464
<211> LENGTH: 14
<212> TYPE: PRT
<213> ORGANISM: Artificial
<220> FEATURE:
<223> OTHER INFORMATION: synthetic HER2 binding clone 64 CDRH3

<400> SEQUENCE: 464

```
Gly Ser Tyr Tyr Gly Tyr Tyr Ser Gly Ser Gly Met Asp Tyr
1               5                   10
```

<210> SEQ ID NO 465
<211> LENGTH: 14
<212> TYPE: PRT
<213> ORGANISM: Artificial
<220> FEATURE:
<223> OTHER INFORMATION: synthetic HER2 binding clone 65 CDRH3

<400> SEQUENCE: 465

```
Gly Ser Gly Tyr Ser Tyr Tyr Gly Gly Tyr Gly Leu Asp Tyr
1               5                   10
```

<210> SEQ ID NO 466
<211> LENGTH: 14
<212> TYPE: PRT
<213> ORGANISM: Artificial
<220> FEATURE:
<223> OTHER INFORMATION: synthetic HER2 binding clone 66 CDRH3

<400> SEQUENCE: 466

```
Gly Ser Tyr Ser Gly Tyr Tyr Tyr Gly Tyr Gly Leu Asp Tyr
1               5                   10
```

<210> SEQ ID NO 467
<211> LENGTH: 14
<212> TYPE: PRT
<213> ORGANISM: Artificial
<220> FEATURE:
<223> OTHER INFORMATION: synthetic HER2 binding clone 67 CDRH3

<400> SEQUENCE: 467

```
Gly Arg Tyr Ser Gly Tyr Tyr Gly Gly Tyr Gly Met Asp Tyr
1               5                   10
```

<210> SEQ ID NO 468
<211> LENGTH: 15
<212> TYPE: PRT
<213> ORGANISM: Artificial
<220> FEATURE:
<223> OTHER INFORMATION: synthetic HER2 binding clone 68 CDRH3

<400> SEQUENCE: 468

```
Tyr Tyr Tyr Ser Ser Gly Tyr Tyr Tyr Tyr Ala Phe Asp Tyr
```

```
<210> SEQ ID NO 469
<211> LENGTH: 15
<212> TYPE: PRT
<213> ORGANISM: Artificial
<220> FEATURE:
<223> OTHER INFORMATION: synthetic HER2 binding clone 69 CDRH3

<400> SEQUENCE: 469

Tyr Ser Tyr Ser Tyr Tyr Gly Tyr Tyr Gly Ser Gly Met Asp Tyr
1               5                   10                  15

<210> SEQ ID NO 470
<211> LENGTH: 15
<212> TYPE: PRT
<213> ORGANISM: Artificial
<220> FEATURE:
<223> OTHER INFORMATION: synthetic HER2 binding clone 70 CDRH3

<400> SEQUENCE: 470

Tyr Arg Ser Tyr Tyr Ser Tyr Arg Tyr Gly Tyr Gly Met Asp Tyr
1               5                   10                  15

<210> SEQ ID NO 471
<211> LENGTH: 15
<212> TYPE: PRT
<213> ORGANISM: Artificial
<220> FEATURE:
<223> OTHER INFORMATION: synthetic HER2 binding clone 71 CDRH3

<400> SEQUENCE: 471

Tyr Gly Tyr Tyr Tyr Ser Tyr Tyr Gly Gly Ser Gly Leu Asp Tyr
1               5                   10                  15

<210> SEQ ID NO 472
<211> LENGTH: 15
<212> TYPE: PRT
<213> ORGANISM: Artificial
<220> FEATURE:
<223> OTHER INFORMATION: synthetic HER2 binding clone 72 CDRH3

<400> SEQUENCE: 472

Tyr Gly Tyr Tyr Tyr Ser Tyr Tyr Gly Gly Ser Gly Leu Asp Tyr
1               5                   10                  15

<210> SEQ ID NO 473
<211> LENGTH: 15
<212> TYPE: PRT
<213> ORGANISM: Artificial
<220> FEATURE:
<223> OTHER INFORMATION: synthetic HER2 binding clone 73 CDRH3

<400> SEQUENCE: 473

Tyr Gly Tyr Ser Tyr Ser Tyr Ser Ser Gly Ser Ala Leu Asp Tyr
1               5                   10                  15

<210> SEQ ID NO 474
<211> LENGTH: 15
<212> TYPE: PRT
<213> ORGANISM: Artificial
<220> FEATURE:
<223> OTHER INFORMATION: synthetic HER2 binding clone 74 CDRH3

<400> SEQUENCE: 474

Ser Tyr Tyr Tyr Gly Gly Tyr Tyr Ser Gly Tyr Gly Met Asp Tyr
1               5                   10                  15
```

```
<210> SEQ ID NO 475
<211> LENGTH: 15
<212> TYPE: PRT
<213> ORGANISM: Artificial
<220> FEATURE:
<223> OTHER INFORMATION: synthetic HER2 binding clone 75 CDRH3

<400> SEQUENCE: 475

Arg Arg Ser Tyr Tyr Ser Tyr Arg Tyr Ser Tyr Gly Leu Asp Tyr
1               5                   10                  15

<210> SEQ ID NO 476
<211> LENGTH: 15
<212> TYPE: PRT
<213> ORGANISM: Artificial
<220> FEATURE:
<223> OTHER INFORMATION: synthetic HER2 binding clone 76 CDRH3

<400> SEQUENCE: 476

Arg Arg Ser Tyr Tyr Ser Tyr Ser Arg Ser Tyr Ala Met Asp Tyr
1               5                   10                  15

<210> SEQ ID NO 477
<211> LENGTH: 16
<212> TYPE: PRT
<213> ORGANISM: Artificial
<220> FEATURE:
<223> OTHER INFORMATION: synthetic HER2 binding clone 77 CDRH3

<400> SEQUENCE: 477

Tyr Tyr Tyr Gly Tyr Tyr Ser Tyr Tyr Ser Gly Tyr Gly Leu Asp Tyr
1               5                   10                  15

<210> SEQ ID NO 478
<211> LENGTH: 16
<212> TYPE: PRT
<213> ORGANISM: Artificial
<220> FEATURE:
<223> OTHER INFORMATION: synthetic HER2 binding clone 78 CDRH3

<400> SEQUENCE: 478

Tyr Tyr Tyr Gly Tyr Tyr Ser Tyr Tyr Gly Gly Ser Gly Leu Asp Tyr
1               5                   10                  15

<210> SEQ ID NO 479
<211> LENGTH: 16
<212> TYPE: PRT
<213> ORGANISM: Artificial
<220> FEATURE:
<223> OTHER INFORMATION: synthetic HER2 binding clone 79 CDRH3

<400> SEQUENCE: 479

Tyr Tyr Tyr Gly Tyr Tyr Ser Tyr Tyr Gly Gly Ser Ala Met Asp Tyr
1               5                   10                  15

<210> SEQ ID NO 480
<211> LENGTH: 16
<212> TYPE: PRT
<213> ORGANISM: Artificial
<220> FEATURE:
<223> OTHER INFORMATION: synthetic HER2 binding clone 80 CDRH3

<400> SEQUENCE: 480

Tyr Tyr Tyr Ser Gly Gly Ser Tyr Tyr Tyr Tyr Ala Phe Asp Tyr
1               5                   10                  15
```

<210> SEQ ID NO 481
<211> LENGTH: 16
<212> TYPE: PRT
<213> ORGANISM: Artificial
<220> FEATURE:
<223> OTHER INFORMATION: synthetic HER2 binding clone 81 CDRH3

<400> SEQUENCE: 481

Tyr Tyr Tyr Ser Tyr Tyr Ser Tyr Tyr Ser Tyr Gly Gly Ile Asp Tyr
1               5                   10                  15

<210> SEQ ID NO 482
<211> LENGTH: 16
<212> TYPE: PRT
<213> ORGANISM: Artificial
<220> FEATURE:
<223> OTHER INFORMATION: synthetic HER2 binding clone 82 CDRH3

<400> SEQUENCE: 482

Tyr Tyr Ser Ser Tyr Tyr Ser Tyr Tyr Tyr Tyr Gly Gly Met Asp Tyr
1               5                   10                  15

<210> SEQ ID NO 483
<211> LENGTH: 16
<212> TYPE: PRT
<213> ORGANISM: Artificial
<220> FEATURE:
<223> OTHER INFORMATION: synthetic HER2 binding clone 83 CDRH3

<400> SEQUENCE: 483

Tyr Ser Tyr Tyr Tyr Tyr Ser Tyr Tyr Tyr Gly Ser Ala Met Asp Tyr
1               5                   10                  15

<210> SEQ ID NO 484
<211> LENGTH: 16
<212> TYPE: PRT
<213> ORGANISM: Artificial
<220> FEATURE:
<223> OTHER INFORMATION: synthetic HER2 binding clone 84 CDRH3

<400> SEQUENCE: 484

Tyr Ser Tyr Tyr Tyr Tyr Ser Tyr Ser Gly Tyr Gly Phe Asp Tyr
1               5                   10                  15

<210> SEQ ID NO 485
<211> LENGTH: 16
<212> TYPE: PRT
<213> ORGANISM: Artificial
<220> FEATURE:
<223> OTHER INFORMATION: synthetic HER2 binding clone 85 CDRH3

<400> SEQUENCE: 485

Tyr Ser Tyr Tyr Tyr Tyr Ser Tyr Ser Gly Tyr Gly Phe Asp Tyr
1               5                   10                  15

<210> SEQ ID NO 486
<211> LENGTH: 16
<212> TYPE: PRT
<213> ORGANISM: Artificial
<220> FEATURE:
<223> OTHER INFORMATION: synthetic HER2 binding clone 86 CDRH3

<400> SEQUENCE: 486

Tyr Ser Tyr Tyr Tyr Tyr Ser Tyr Tyr Gly Gly Ser Ala Phe Asp Tyr
1               5                   10                  15

```
<210> SEQ ID NO 487
<211> LENGTH: 16
<212> TYPE: PRT
<213> ORGANISM: Artificial
<220> FEATURE:
<223> OTHER INFORMATION: synthetic HER2 binding clone 87 CDRH3

<400> SEQUENCE: 487

Tyr Ser Tyr Tyr Tyr Tyr Ser Tyr Tyr Gly Gly Ser Gly Met Asp Tyr
1               5                   10                  15

<210> SEQ ID NO 488
<211> LENGTH: 16
<212> TYPE: PRT
<213> ORGANISM: Artificial
<220> FEATURE:
<223> OTHER INFORMATION: synthetic HER2 binding clone 88 CDRH3

<400> SEQUENCE: 488

Tyr Ser Tyr Tyr Tyr Tyr Ser Tyr Tyr Gly Gly Ser Gly Leu Asp Tyr
1               5                   10                  15

<210> SEQ ID NO 489
<211> LENGTH: 16
<212> TYPE: PRT
<213> ORGANISM: Artificial
<220> FEATURE:
<223> OTHER INFORMATION: synthetic HER2 binding clone 89 CDRH3

<400> SEQUENCE: 489

Tyr Ser Tyr Ser Tyr Tyr Gly Tyr Tyr Gly Ser Gly Leu Asp Tyr
1               5                   10                  15

<210> SEQ ID NO 490
<211> LENGTH: 16
<212> TYPE: PRT
<213> ORGANISM: Artificial
<220> FEATURE:
<223> OTHER INFORMATION: synthetic HER2 binding clone 90 CDRH3

<400> SEQUENCE: 490

Tyr Ser Ser Tyr Tyr Tyr Ser Tyr Tyr Ser Gly Ser Gly Leu Asp Tyr
1               5                   10                  15

<210> SEQ ID NO 491
<211> LENGTH: 16
<212> TYPE: PRT
<213> ORGANISM: Artificial
<220> FEATURE:
<223> OTHER INFORMATION: synthetic HER2 binding clone 91 CDRH3

<400> SEQUENCE: 491

Ser Ser Tyr Tyr Tyr Tyr Ser Tyr Tyr Gly Gly Ser Gly Ile Asp Tyr
1               5                   10                  15

<210> SEQ ID NO 492
<211> LENGTH: 16
<212> TYPE: PRT
<213> ORGANISM: Artificial
<220> FEATURE:
<223> OTHER INFORMATION: synthetic HER2 binding clone 92 CDRH3

<400> SEQUENCE: 492

Arg Ser Tyr Tyr Tyr Tyr Ser Tyr Tyr Tyr Ser Arg Ala Met Asp Tyr
1               5                   10                  15

<210> SEQ ID NO 493
```

```
<211> LENGTH: 17
<212> TYPE: PRT
<213> ORGANISM: Artificial
<220> FEATURE:
<223> OTHER INFORMATION: synthetic HER2 binding clone 93 CDRH3

<400> SEQUENCE: 493

Ser Tyr Ser Ser Tyr Tyr Ser Tyr Tyr Ser Ser Tyr Gly Gly Met Asp
1               5                   10                  15

Tyr

<210> SEQ ID NO 494
<211> LENGTH: 21
<212> TYPE: PRT
<213> ORGANISM: Artificial
<220> FEATURE:
<223> OTHER INFORMATION: synthetic HER2 binding clone 94 CDRH3

<400> SEQUENCE: 494

Tyr Arg Tyr Tyr Tyr Ser Arg Tyr Gly Tyr Arg Tyr Tyr Tyr Tyr
1               5                   10                  15

Arg Ala Leu Asp Tyr
            20

<210> SEQ ID NO 495
<211> LENGTH: 8
<212> TYPE: PRT
<213> ORGANISM: Artificial
<220> FEATURE:
<223> OTHER INFORMATION: synthetic HER2 binding clone 95 CDRH3

<400> SEQUENCE: 495

Arg Tyr Ser Ser Gly Met Asp Tyr
1               5

<210> SEQ ID NO 496
<211> LENGTH: 9
<212> TYPE: PRT
<213> ORGANISM: Artificial
<220> FEATURE:
<223> OTHER INFORMATION: synthetic HER2 binding clone 96 CDRH3

<400> SEQUENCE: 496

Tyr Ser His Ser Gly Ala Phe Asp Tyr
1               5

<210> SEQ ID NO 497
<211> LENGTH: 10
<212> TYPE: PRT
<213> ORGANISM: Artificial
<220> FEATURE:
<223> OTHER INFORMATION: synthetic HER2 binding clone 97 CDRH3

<400> SEQUENCE: 497

Gly Tyr Ser Tyr Gly His Gly Ile Asp Tyr
1               5                   10

<210> SEQ ID NO 498
<211> LENGTH: 10
<212> TYPE: PRT
<213> ORGANISM: Artificial
<220> FEATURE:
<223> OTHER INFORMATION: synthetic HER2 binding clone 98 CDRH3

<400> SEQUENCE: 498

Gly Ser Ser Phe Gly Arg Gly Phe Asp Tyr
```

```
1               5                   10

<210> SEQ ID NO 499
<211> LENGTH: 10
<212> TYPE: PRT
<213> ORGANISM: Artificial
<220> FEATURE:
<223> OTHER INFORMATION: synthetic HER2 binding clone 99 CDRH3

<400> SEQUENCE: 499

Gly Ser Ser Tyr Ser Trp Gly Leu Asp Tyr
1               5                   10

<210> SEQ ID NO 500
<211> LENGTH: 10
<212> TYPE: PRT
<213> ORGANISM: Artificial
<220> FEATURE:
<223> OTHER INFORMATION: synthetic HER2 binding clone 100 CDRH3

<400> SEQUENCE: 500

Gly Ser Arg Tyr Ser His Gly Met Asp Tyr
1               5                   10

<210> SEQ ID NO 501
<211> LENGTH: 10
<212> TYPE: PRT
<213> ORGANISM: Artificial
<220> FEATURE:
<223> OTHER INFORMATION: synthetic HER2 binding clone 101 CDRH3

<400> SEQUENCE: 501

Gly Ala Ser Tyr Gly Tyr Gly Met Asp Tyr
1               5                   10

<210> SEQ ID NO 502
<211> LENGTH: 10
<212> TYPE: PRT
<213> ORGANISM: Artificial
<220> FEATURE:
<223> OTHER INFORMATION: synthetic HER2 binding clone 102 CDRH3

<400> SEQUENCE: 502

Gly Met Ser Tyr Gly Tyr Gly Met Asp Tyr
1               5                   10

<210> SEQ ID NO 503
<211> LENGTH: 10
<212> TYPE: PRT
<213> ORGANISM: Artificial
<220> FEATURE:
<223> OTHER INFORMATION: synthetic HER2 binding clone 103 CDRH3

<400> SEQUENCE: 503

Gly Gly Arg Tyr Asn His Gly Leu Asp Tyr
1               5                   10

<210> SEQ ID NO 504
<211> LENGTH: 17
<212> TYPE: PRT
<213> ORGANISM: Artificial
<220> FEATURE:
<223> OTHER INFORMATION: synthetic HER2 binding clone 104 CDRH3

<400> SEQUENCE: 504

Glu Tyr Tyr Gln Gly Tyr Gly Pro Tyr Arg Ser Thr Tyr Gly Leu Asp
1               5                   10                  15
```

Tyr

<210> SEQ ID NO 505
<211> LENGTH: 19
<212> TYPE: PRT
<213> ORGANISM: Artificial
<220> FEATURE:
<223> OTHER INFORMATION: synthetic HER2 binding clone 105 CDRH3

<400> SEQUENCE: 505

Ser Ser Trp Ser Ser Arg Gly Val Ser Tyr Ser Arg Thr Ala Gly Gly
1               5                   10                  15

Met Asp Tyr

<210> SEQ ID NO 506
<211> LENGTH: 20
<212> TYPE: PRT
<213> ORGANISM: Artificial
<220> FEATURE:
<223> OTHER INFORMATION: synthetic HER2 binding clone 106 CDRH3

<400> SEQUENCE: 506

Glu Gly Tyr Tyr Ser Val Ser Gly Ser Tyr Ser Tyr Ser Thr Arg Gly
1               5                   10                  15

Gly Pro Asp Tyr
            20

<210> SEQ ID NO 507
<211> LENGTH: 9
<212> TYPE: PRT
<213> ORGANISM: Artificial
<220> FEATURE:
<223> OTHER INFORMATION: synthetic DR5 binding clone 1 CDRL3

<400> SEQUENCE: 507

Gln Gln Tyr Ser Ser Tyr Pro Ser Thr
1               5

<210> SEQ ID NO 508
<211> LENGTH: 9
<212> TYPE: PRT
<213> ORGANISM: Artificial
<220> FEATURE:
<223> OTHER INFORMATION: synthetic DR5 binding clone 2 CDRL3

<400> SEQUENCE: 508

Gln Gln Tyr Ser Ser Tyr Pro Ser Thr
1               5

<210> SEQ ID NO 509
<211> LENGTH: 9
<212> TYPE: PRT
<213> ORGANISM: Artificial
<220> FEATURE:
<223> OTHER INFORMATION: synthetic DR5 binding clone 3 CDRL3

<400> SEQUENCE: 509

Gln Gln Tyr Tyr Tyr Tyr Pro Ser Thr
1               5

<210> SEQ ID NO 510
<211> LENGTH: 9
<212> TYPE: PRT
<213> ORGANISM: Artificial
<220> FEATURE:

<223> OTHER INFORMATION: synthetic DR5 binding clone 4 CDRL3

<400> SEQUENCE: 510

Gln Gln Tyr Ser Ser Tyr Pro Ser Thr
1               5

<210> SEQ ID NO 511
<211> LENGTH: 9
<212> TYPE: PRT
<213> ORGANISM: Artificial
<220> FEATURE:
<223> OTHER INFORMATION: synthetic DR5 binding clone 5 CDRL3

<400> SEQUENCE: 511

Gln Gln His Tyr Thr Thr Pro Pro Thr
1               5

<210> SEQ ID NO 512
<211> LENGTH: 9
<212> TYPE: PRT
<213> ORGANISM: Artificial
<220> FEATURE:
<223> OTHER INFORMATION: synthetic DR5 binding clone 6 CDRL3

<400> SEQUENCE: 512

Gln Gln Tyr Tyr Ser Ser Pro Ser Thr
1               5

<210> SEQ ID NO 513
<211> LENGTH: 9
<212> TYPE: PRT
<213> ORGANISM: Artificial
<220> FEATURE:
<223> OTHER INFORMATION: synthetic DR5 binding clone 7 CDRL3

<400> SEQUENCE: 513

Gln Gln Tyr Ser Tyr Ser Pro Ser Thr
1               5

<210> SEQ ID NO 514
<211> LENGTH: 9
<212> TYPE: PRT
<213> ORGANISM: Artificial
<220> FEATURE:
<223> OTHER INFORMATION: synthetic DR5 binding clone 8 CDRL3

<400> SEQUENCE: 514

Gln Gln Tyr Tyr Tyr Ser Pro Ser Thr
1               5

<210> SEQ ID NO 515
<211> LENGTH: 9
<212> TYPE: PRT
<213> ORGANISM: Artificial
<220> FEATURE:
<223> OTHER INFORMATION: synthetic DR5 binding clone 9 CDRL3

<400> SEQUENCE: 515

Gln Gln Tyr Ser Ser Ser Pro Ser Thr
1               5

<210> SEQ ID NO 516
<211> LENGTH: 9
<212> TYPE: PRT
<213> ORGANISM: Artificial
<220> FEATURE:
<223> OTHER INFORMATION: synthetic DR5 binding clone 10 CDRL3

```
<400> SEQUENCE: 516

Gln Gln His Tyr Thr Thr Pro Pro Thr
1               5

<210> SEQ ID NO 517
<211> LENGTH: 9
<212> TYPE: PRT
<213> ORGANISM: Artificial
<220> FEATURE:
<223> OTHER INFORMATION: synthetic DR5 binding clone 11 CDRL3

<400> SEQUENCE: 517

Gln Gln Tyr Tyr Ser Ser Pro Ser Thr
1               5

<210> SEQ ID NO 518
<211> LENGTH: 9
<212> TYPE: PRT
<213> ORGANISM: Artificial
<220> FEATURE:
<223> OTHER INFORMATION: synthetic DR5 binding clone 12 CDRL3

<400> SEQUENCE: 518

Gln Gln Tyr Tyr Ser Ser Pro Tyr Thr
1               5

<210> SEQ ID NO 519
<211> LENGTH: 9
<212> TYPE: PRT
<213> ORGANISM: Artificial
<220> FEATURE:
<223> OTHER INFORMATION: synthetic DR5 binding clone 13 CDRL3

<400> SEQUENCE: 519

Gln Gln Tyr Tyr Ser Ser Pro Ser Thr
1               5

<210> SEQ ID NO 520
<211> LENGTH: 9
<212> TYPE: PRT
<213> ORGANISM: Artificial
<220> FEATURE:
<223> OTHER INFORMATION: synthetic DR5 binding clone 14 CDRL3

<400> SEQUENCE: 520

Gln Gln Tyr Ser Ser Ser Pro Ser Thr
1               5

<210> SEQ ID NO 521
<211> LENGTH: 9
<212> TYPE: PRT
<213> ORGANISM: Artificial
<220> FEATURE:
<223> OTHER INFORMATION: synthetic DR5 binding clone 15 CDRL3

<400> SEQUENCE: 521

Gln Gln Ser Ser Tyr Ser Pro Ser Thr
1               5

<210> SEQ ID NO 522
<211> LENGTH: 9
<212> TYPE: PRT
<213> ORGANISM: Artificial
<220> FEATURE:
<223> OTHER INFORMATION: synthetic DR5 binding clone 16 CDRL3
```

```
<400> SEQUENCE: 522

Gln Gln Tyr Tyr Ser Ser Pro Ser Thr
1               5

<210> SEQ ID NO 523
<211> LENGTH: 9
<212> TYPE: PRT
<213> ORGANISM: Artificial
<220> FEATURE:
<223> OTHER INFORMATION: synthetic DR5 binding clone 17 CDRL3

<400> SEQUENCE: 523

Gln Gln Tyr Tyr Ser Ser Pro Ser Thr
1               5

<210> SEQ ID NO 524
<211> LENGTH: 10
<212> TYPE: PRT
<213> ORGANISM: Artificial
<220> FEATURE:
<223> OTHER INFORMATION: synthetic DR5 binding clone 1 CDRH1

<400> SEQUENCE: 524

Gly Phe Ser Ile Tyr Ser Tyr Ser Ile His
1               5                   10

<210> SEQ ID NO 525
<211> LENGTH: 10
<212> TYPE: PRT
<213> ORGANISM: Artificial
<220> FEATURE:
<223> OTHER INFORMATION: synthetic DR5 binding clone 2 CDRH1

<400> SEQUENCE: 525

Gly Phe Ser Ile Tyr Ser Ser Ser Ile His
1               5                   10

<210> SEQ ID NO 526
<211> LENGTH: 10
<212> TYPE: PRT
<213> ORGANISM: Artificial
<220> FEATURE:
<223> OTHER INFORMATION: synthetic DR5 binding clone 3 CDRH1

<400> SEQUENCE: 526

Gly Phe Tyr Ile Tyr Ser Tyr Ser Ile His
1               5                   10

<210> SEQ ID NO 527
<211> LENGTH: 10
<212> TYPE: PRT
<213> ORGANISM: Artificial
<220> FEATURE:
<223> OTHER INFORMATION: synthetic DR5 binding clone 4 CDRH1

<400> SEQUENCE: 527

Gly Phe Ser Ile Tyr Ser Ser Ser Ile His
1               5                   10

<210> SEQ ID NO 528
<211> LENGTH: 10
<212> TYPE: PRT
<213> ORGANISM: Artificial
<220> FEATURE:
<223> OTHER INFORMATION: synthetic DR5 binding clone 5 CDRH1

<400> SEQUENCE: 528
```

Gly Phe Ser Ile Tyr Ser Ser Ser Ile His
1               5                   10

<210> SEQ ID NO 529
<211> LENGTH: 10
<212> TYPE: PRT
<213> ORGANISM: Artificial
<220> FEATURE:
<223> OTHER INFORMATION: synthetic DR5 binding clone 6 CDRH1

<400> SEQUENCE: 529

Gly Phe Tyr Ile Ser Tyr Ser Ser Ile His
1               5                   10

<210> SEQ ID NO 530
<211> LENGTH: 10
<212> TYPE: PRT
<213> ORGANISM: Artificial
<220> FEATURE:
<223> OTHER INFORMATION: synthetic DR5 binding clone 7 CDRH1

<400> SEQUENCE: 530

Gly Phe Ser Ile Ser Ser Ser Ser Ile His
1               5                   10

<210> SEQ ID NO 531
<211> LENGTH: 10
<212> TYPE: PRT
<213> ORGANISM: Artificial
<220> FEATURE:
<223> OTHER INFORMATION: synthetic DR5 binding clone 8 CDRH1

<400> SEQUENCE: 531

Gly Phe Tyr Ile Ser Ser Ser Ser Ile His
1               5                   10

<210> SEQ ID NO 532
<211> LENGTH: 10
<212> TYPE: PRT
<213> ORGANISM: Artificial
<220> FEATURE:
<223> OTHER INFORMATION: synthetic DR5 binding clone 9 CDRH1

<400> SEQUENCE: 532

Gly Phe Ser Ile Ser Ser Ser Ser Ile His
1               5                   10

<210> SEQ ID NO 533
<211> LENGTH: 10
<212> TYPE: PRT
<213> ORGANISM: Artificial
<220> FEATURE:
<223> OTHER INFORMATION: synthetic DR5 binding clone 10 CDRH1

<400> SEQUENCE: 533

Gly Phe Tyr Ile Tyr Ser Ser Ser Ile His
1               5                   10

<210> SEQ ID NO 534
<211> LENGTH: 10
<212> TYPE: PRT
<213> ORGANISM: Artificial
<220> FEATURE:
<223> OTHER INFORMATION: synthetic DR5 binding clone 11 CDRH1

<400> SEQUENCE: 534

```
Gly Phe Ser Ile Ser Ser Ser Ser Ile His
1               5                   10
```

<210> SEQ ID NO 535
<211> LENGTH: 10
<212> TYPE: PRT
<213> ORGANISM: Artificial
<220> FEATURE:
<223> OTHER INFORMATION: synthetic DR5 binding clone 12 CDRH1

<400> SEQUENCE: 535

```
Gly Phe Ser Ile Ser Ser Ser Ser Ile His
1               5                   10
```

<210> SEQ ID NO 536
<211> LENGTH: 10
<212> TYPE: PRT
<213> ORGANISM: Artificial
<220> FEATURE:
<223> OTHER INFORMATION: synthetic DR5 binding clone 13 CDRH1

<400> SEQUENCE: 536

```
Gly Phe Ser Ile Ser Ser Ser Ser Ile His
1               5                   10
```

<210> SEQ ID NO 537
<211> LENGTH: 10
<212> TYPE: PRT
<213> ORGANISM: Artificial
<220> FEATURE:
<223> OTHER INFORMATION: synthetic DR5 binding clone 14 CDRH1

<400> SEQUENCE: 537

```
Gly Phe Tyr Ile Ser Ser Ser Tyr Ile His
1               5                   10
```

<210> SEQ ID NO 538
<211> LENGTH: 10
<212> TYPE: PRT
<213> ORGANISM: Artificial
<220> FEATURE:
<223> OTHER INFORMATION: synthetic DR5 binding clone 15 CDRH1

<400> SEQUENCE: 538

```
Gly Phe Tyr Ile Tyr Ser Ser Ser Ile His
1               5                   10
```

<210> SEQ ID NO 539
<211> LENGTH: 10
<212> TYPE: PRT
<213> ORGANISM: Artificial
<220> FEATURE:
<223> OTHER INFORMATION: synthetic DR5 binding clone 16 CDRH1

<400> SEQUENCE: 539

```
Gly Phe Tyr Ile Tyr Ser Ser Ser Ile His
1               5                   10
```

<210> SEQ ID NO 540
<211> LENGTH: 10
<212> TYPE: PRT
<213> ORGANISM: Artificial
<220> FEATURE:
<223> OTHER INFORMATION: synthetic DR5 binding clone 17 CDRH1

<400> SEQUENCE: 540

```
Gly Phe Tyr Ile Ser Ser Ser Ser Ile His
```

1               5                   10

<210> SEQ ID NO 541
<211> LENGTH: 17
<212> TYPE: PRT
<213> ORGANISM: Artificial
<220> FEATURE:
<223> OTHER INFORMATION: synthetic DR5 binding clone 1 CDRH2

<400> SEQUENCE: 541

Ser Ile Ser Pro Tyr Tyr Gly Tyr Thr Ser Tyr Ala Asp Ser Val Lys
1               5                   10                  15

Gly

<210> SEQ ID NO 542
<211> LENGTH: 17
<212> TYPE: PRT
<213> ORGANISM: Artificial
<220> FEATURE:
<223> OTHER INFORMATION: synthetic DR5 binding clone 2 CDRH2

<400> SEQUENCE: 542

Ser Ile Tyr Pro Tyr Ser Gly Ser Thr Ser Tyr Ala Asp Ser Val Lys
1               5                   10                  15

Gly

<210> SEQ ID NO 543
<211> LENGTH: 17
<212> TYPE: PRT
<213> ORGANISM: Artificial
<220> FEATURE:
<223> OTHER INFORMATION: synthetic DR5 binding clone 3 CDRH2

<400> SEQUENCE: 543

Ser Ile Ser Pro Tyr Tyr Gly Ser Thr Ser Tyr Ala Asp Ser Val Lys
1               5                   10                  15

Gly

<210> SEQ ID NO 544
<211> LENGTH: 17
<212> TYPE: PRT
<213> ORGANISM: Artificial
<220> FEATURE:
<223> OTHER INFORMATION: synthetic DR5 binding clone 4 CDRH2

<400> SEQUENCE: 544

Tyr Ile Ser Pro Ser Tyr Gly Tyr Thr Tyr Tyr Ala Asp Ser Val Lys
1               5                   10                  15

Gly

<210> SEQ ID NO 545
<211> LENGTH: 17
<212> TYPE: PRT
<213> ORGANISM: Artificial
<220> FEATURE:
<223> OTHER INFORMATION: synthetic DR5 binding clone 5 CDRH2

<400> SEQUENCE: 545

Ser Ile Ser Pro Tyr Ser Gly Tyr Thr Tyr Tyr Ala Asp Ser Val Lys
1               5                   10                  15

Gly

<210> SEQ ID NO 546

```
<211> LENGTH: 17
<212> TYPE: PRT
<213> ORGANISM: Artificial
<220> FEATURE:
<223> OTHER INFORMATION: synthetic DR5 binding clone 6 CDRH2

<400> SEQUENCE: 546

Tyr Ile Ser Pro Tyr Ser Gly Tyr Thr Tyr Tyr Ala Asp Ser Val Lys
1               5                   10                  15

Gly

<210> SEQ ID NO 547
<211> LENGTH: 17
<212> TYPE: PRT
<213> ORGANISM: Artificial
<220> FEATURE:
<223> OTHER INFORMATION: synthetic DR5 binding clone 7 CDRH2

<400> SEQUENCE: 547

Ser Ile Ser Pro Ser Tyr Gly Tyr Thr Ser Tyr Ala Asp Ser Val Lys
1               5                   10                  15

Gly

<210> SEQ ID NO 548
<211> LENGTH: 17
<212> TYPE: PRT
<213> ORGANISM: Artificial
<220> FEATURE:
<223> OTHER INFORMATION: synthetic DR5 binding clone 8 CDRH2

<400> SEQUENCE: 548

Ser Ile Ser Pro Ser Ser Gly Ser Thr Tyr Tyr Ala Asp Ser Val Lys
1               5                   10                  15

Gly

<210> SEQ ID NO 549
<211> LENGTH: 17
<212> TYPE: PRT
<213> ORGANISM: Artificial
<220> FEATURE:
<223> OTHER INFORMATION: synthetic DR5 binding clone 9 CDRH2

<400> SEQUENCE: 549

Ser Ile Ser Pro Tyr Tyr Gly Tyr Thr Tyr Tyr Ala Asp Ser Val Lys
1               5                   10                  15

Gly

<210> SEQ ID NO 550
<211> LENGTH: 17
<212> TYPE: PRT
<213> ORGANISM: Artificial
<220> FEATURE:
<223> OTHER INFORMATION: synthetic DR5 binding clone 10 CDRH2

<400> SEQUENCE: 550

Ser Ile Ser Pro Ser Ser Gly Ser Thr Tyr Tyr Ala Asp Ser Val Lys
1               5                   10                  15

Gly

<210> SEQ ID NO 551
<211> LENGTH: 17
<212> TYPE: PRT
<213> ORGANISM: Artificial
<220> FEATURE:
```

<223> OTHER INFORMATION: synthetic DR5 binding clone 11 CDRH2

<400> SEQUENCE: 551

Tyr Ile Ser Pro Tyr Ser Gly Tyr Thr Ser Tyr Ala Asp Ser Val Lys
1               5                   10                  15
Gly

<210> SEQ ID NO 552
<211> LENGTH: 17
<212> TYPE: PRT
<213> ORGANISM: Artificial
<220> FEATURE:
<223> OTHER INFORMATION: synthetic DR5 binding clone 12 CDRH2

<400> SEQUENCE: 552

Tyr Ile Tyr Pro Tyr Ser Gly Tyr Thr Ser Tyr Ala Asp Ser Val Lys
1               5                   10                  15
Gly

<210> SEQ ID NO 553
<211> LENGTH: 17
<212> TYPE: PRT
<213> ORGANISM: Artificial
<220> FEATURE:
<223> OTHER INFORMATION: synthetic DR5 binding clone 13 CDRH2

<400> SEQUENCE: 553

Ser Ile Ser Pro Ser Ser Gly Tyr Thr Ser Tyr Ala Asp Ser Val Lys
1               5                   10                  15
Gly

<210> SEQ ID NO 554
<211> LENGTH: 17
<212> TYPE: PRT
<213> ORGANISM: Artificial
<220> FEATURE:
<223> OTHER INFORMATION: synthetic DR5 binding clone 14 CDRH2

<400> SEQUENCE: 554

Ser Ile Ser Pro Ser Tyr Gly Tyr Thr Tyr Tyr Ala Asp Ser Val Lys
1               5                   10                  15
Gly

<210> SEQ ID NO 555
<211> LENGTH: 17
<212> TYPE: PRT
<213> ORGANISM: Artificial
<220> FEATURE:
<223> OTHER INFORMATION: synthetic DR5 binding clone 15 CDRH2

<400> SEQUENCE: 555

Ser Ile Ser Pro Ser Ser Gly Tyr Thr Ser Tyr Ala Asp Ser Val Lys
1               5                   10                  15
Gly

<210> SEQ ID NO 556
<211> LENGTH: 17
<212> TYPE: PRT
<213> ORGANISM: Artificial
<220> FEATURE:
<223> OTHER INFORMATION: synthetic DR5 binding clone 16 CDRH2

<400> SEQUENCE: 556

```
Tyr Ile Ser Pro Tyr Tyr Gly Ser Thr Ser Tyr Ala Asp Ser Val Lys
1               5                   10                  15

Gly

<210> SEQ ID NO 557
<211> LENGTH: 17
<212> TYPE: PRT
<213> ORGANISM: Artificial
<220> FEATURE:
<223> OTHER INFORMATION: synthetic DR5 binding clone 17 CDRH2

<400> SEQUENCE: 557

Tyr Ile Ser Pro Ser Tyr Gly Ser Thr Tyr Tyr Ala Asp Ser Val Lys
1               5                   10                  15

Gly

<210> SEQ ID NO 558
<211> LENGTH: 16
<212> TYPE: PRT
<213> ORGANISM: Artificial
<220> FEATURE:
<223> OTHER INFORMATION: synthetic DR5 binding clone 1 CDRH3

<400> SEQUENCE: 558

Arg Tyr Tyr Ser Tyr Arg Ser Tyr Ser Tyr Tyr Ser Gly Leu Asp Tyr
1               5                   10                  15

<210> SEQ ID NO 559
<211> LENGTH: 16
<212> TYPE: PRT
<213> ORGANISM: Artificial
<220> FEATURE:
<223> OTHER INFORMATION: synthetic DR5 binding clone 2 CDRH3

<400> SEQUENCE: 559

Arg Tyr Tyr Ser Ser Ser Tyr Arg Ser Ser Tyr Gly Met Asp Tyr
1               5                   10                  15

<210> SEQ ID NO 560
<211> LENGTH: 16
<212> TYPE: PRT
<213> ORGANISM: Artificial
<220> FEATURE:
<223> OTHER INFORMATION: synthetic DR5 binding clone 3 CDRH3

<400> SEQUENCE: 560

Tyr Tyr Tyr Ser Tyr Tyr Tyr Gly Ser Tyr Tyr Gly Leu Asp Tyr
1               5                   10                  15

<210> SEQ ID NO 561
<211> LENGTH: 18
<212> TYPE: PRT
<213> ORGANISM: Artificial
<220> FEATURE:
<223> OTHER INFORMATION: synthetic DR5 binding clone 4 CDRH3

<400> SEQUENCE: 561

Arg Arg Tyr Ser Arg Tyr Tyr Arg Tyr Ser Ser Arg Tyr Arg Gly Phe
1               5                   10                  15

Asp Tyr

<210> SEQ ID NO 562
<211> LENGTH: 17
<212> TYPE: PRT
<213> ORGANISM: Artificial
```

```
<220> FEATURE:
<223> OTHER INFORMATION: synthetic DR5 binding clone 5 CDRH3

<400> SEQUENCE: 562

Tyr Arg Ser Tyr Arg Tyr Gly Tyr Tyr Arg Gly Gly Tyr Gly Phe Asp
1               5                   10                  15

Tyr

<210> SEQ ID NO 563
<211> LENGTH: 17
<212> TYPE: PRT
<213> ORGANISM: Artificial
<220> FEATURE:
<223> OTHER INFORMATION: synthetic DR5 binding clone 6 CDRH3

<400> SEQUENCE: 563

Tyr Arg Ser Tyr Arg Tyr Gly Tyr Tyr Arg Gly Ser Tyr Ala Leu Asp
1               5                   10                  15

Tyr

<210> SEQ ID NO 564
<211> LENGTH: 17
<212> TYPE: PRT
<213> ORGANISM: Artificial
<220> FEATURE:
<223> OTHER INFORMATION: synthetic DR5 binding clone 7 CDRH3

<400> SEQUENCE: 564

Tyr Arg Ser Tyr Arg Tyr Gly Ser Tyr Arg Gly Ser Tyr Gly Phe Asp
1               5                   10                  15

Tyr

<210> SEQ ID NO 565
<211> LENGTH: 17
<212> TYPE: PRT
<213> ORGANISM: Artificial
<220> FEATURE:
<223> OTHER INFORMATION: synthetic DR5 binding clone 8 CDRH3

<400> SEQUENCE: 565

Tyr Arg Ser Tyr Arg Tyr Gly Ser Tyr Tyr Gly Ser Tyr Gly Phe Asp
1               5                   10                  15

Tyr

<210> SEQ ID NO 566
<211> LENGTH: 17
<212> TYPE: PRT
<213> ORGANISM: Artificial
<220> FEATURE:
<223> OTHER INFORMATION: synthetic DR5 binding clone 9 CDRH3

<400> SEQUENCE: 566

Tyr Arg Arg Tyr Tyr Tyr Gly Tyr Tyr Tyr Gly Gly Tyr Gly Phe Asp
1               5                   10                  15

Tyr

<210> SEQ ID NO 567
<211> LENGTH: 17
<212> TYPE: PRT
<213> ORGANISM: Artificial
<220> FEATURE:
<223> OTHER INFORMATION: synthetic DR5 binding clone 10 CDRH3

<400> SEQUENCE: 567
```

```
Tyr Arg Arg Tyr Arg Tyr Gly Tyr Tyr Ser Gly Gly Tyr Gly Phe Asp
1               5                   10                  15

Tyr

<210> SEQ ID NO 568
<211> LENGTH: 17
<212> TYPE: PRT
<213> ORGANISM: Artificial
<220> FEATURE:
<223> OTHER INFORMATION: synthetic DR5 binding clone 11 CDRH3

<400> SEQUENCE: 568

Tyr Arg Arg Tyr Arg Tyr Gly Ser Tyr Tyr Ser Gly Tyr Ala Phe Asp
1               5                   10                  15

Tyr

<210> SEQ ID NO 569
<211> LENGTH: 17
<212> TYPE: PRT
<213> ORGANISM: Artificial
<220> FEATURE:
<223> OTHER INFORMATION: synthetic DR5 binding clone 12 CDRH3

<400> SEQUENCE: 569

Tyr Arg Arg Tyr Arg Tyr Gly Tyr Ser Tyr Gly Ser Tyr Gly Phe Asp
1               5                   10                  15

Tyr

<210> SEQ ID NO 570
<211> LENGTH: 17
<212> TYPE: PRT
<213> ORGANISM: Artificial
<220> FEATURE:
<223> OTHER INFORMATION: synthetic DR5 binding clone 13 CDRH3

<400> SEQUENCE: 570

Tyr Arg Gly Tyr Arg Tyr Gly Tyr Tyr Arg Gly Gly Tyr Ala Phe Asp
1               5                   10                  15

Tyr

<210> SEQ ID NO 571
<211> LENGTH: 17
<212> TYPE: PRT
<213> ORGANISM: Artificial
<220> FEATURE:
<223> OTHER INFORMATION: synthetic DR5 binding clone 14 CDRH3

<400> SEQUENCE: 571

Arg Arg Tyr Tyr Arg Tyr Gly Tyr Ser Arg Gly Ser Tyr Gly Leu Asp
1               5                   10                  15

Tyr

<210> SEQ ID NO 572
<211> LENGTH: 17
<212> TYPE: PRT
<213> ORGANISM: Artificial
<220> FEATURE:
<223> OTHER INFORMATION: synthetic DR5 binding clone 15 CDRH3

<400> SEQUENCE: 572

Arg Arg Ser Tyr Arg Tyr Gly Ser Tyr Arg Gly Ser Tyr Ala Phe Asp
1               5                   10                  15
```

Tyr

<210> SEQ ID NO 573
<211> LENGTH: 17
<212> TYPE: PRT
<213> ORGANISM: Artificial
<220> FEATURE:
<223> OTHER INFORMATION: synthetic DR5 binding clone 16 CDRH3

<400> SEQUENCE: 573

Arg Arg Pro Tyr Arg Tyr Gly Arg Ser Arg Gly Tyr Tyr Ala Phe Asp
1               5                   10                  15

Tyr

<210> SEQ ID NO 574
<211> LENGTH: 17
<212> TYPE: PRT
<213> ORGANISM: Artificial
<220> FEATURE:
<223> OTHER INFORMATION: synthetic DR5 binding clone 17 CDRH3

<400> SEQUENCE: 574

Met Arg Arg Tyr His Tyr Gly Arg Tyr Ser Gly Ala Tyr Gly Leu Asp
1               5                   10                  15

Tyr

<210> SEQ ID NO 575
<211> LENGTH: 17
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either R or Y
<220> FEATURE:
<221> NAME/KEY: MISC_FEATURE
<222> LOCATION: (10)..(10)
<223> OTHER INFORMATION: X is either Y or R
<220> FEATURE:
<221> NAME/KEY: MISC_FEATURE
<222> LOCATION: (14)..(14)
<223> OTHER INFORMATION: X is either R or Y

<400> SEQUENCE: 575

Xaa Arg Ser Tyr Arg Tyr Gly Ser Tyr Xaa Gly Ser Tyr Xaa Phe Asp
1               5                   10                  15

Tyr

<210> SEQ ID NO 576
<211> LENGTH: 10
<212> TYPE: PRT
<213> ORGANISM: Artificial
<220> FEATURE:
<223> OTHER INFORMATION: synthetic CDRH1

<400> SEQUENCE: 576

Gly Phe Tyr Ile Ser Ser Ser Ser Ile His
1               5                   10

<210> SEQ ID NO 577
<211> LENGTH: 17
<212> TYPE: PRT
<213> ORGANISM: Artificial
<220> FEATURE:
<223> OTHER INFORMATION: synthetic CDRH2

<400> SEQUENCE: 577

Ser Ile Ser Pro Ser Ser Gly Ser Thr Tyr Tyr Ala Asp Ser Val Lys
1               5                   10                  15

Gly

<210> SEQ ID NO 578
<211> LENGTH: 17
<212> TYPE: PRT
<213> ORGANISM: Artificial
<220> FEATURE:
<223> OTHER INFORMATION: synthetic CDRH3

<400> SEQUENCE: 578

Tyr Arg Ser Tyr Arg Tyr Gly Ser Tyr Tyr Gly Ser Tyr Gly Phe Asp
1               5                   10                  15

Tyr

<210> SEQ ID NO 579
<211> LENGTH: 10
<212> TYPE: PRT
<213> ORGANISM: Artificial
<220> FEATURE:
<223> OTHER INFORMATION: synthetic CDRH1

<400> SEQUENCE: 579

Gly Phe Tyr Ile Tyr Ser Ser Ser Ile His
1               5                   10

<210> SEQ ID NO 580
<211> LENGTH: 17
<212> TYPE: PRT
<213> ORGANISM: Artificial
<220> FEATURE:
<223> OTHER INFORMATION: synthetic CDRH2

<400> SEQUENCE: 580

Ser Ile Ser Pro Ser Ser Gly Tyr Thr Ser Tyr Ala Asp Ser Val Lys
1               5                   10                  15

Gly

<210> SEQ ID NO 581
<211> LENGTH: 17
<212> TYPE: PRT
<213> ORGANISM: Artificial
<220> FEATURE:
<223> OTHER INFORMATION: synthetic CDRH3

<400> SEQUENCE: 581

Arg Arg Ser Tyr Arg Tyr Gly Ser Tyr Arg Gly Ser Tyr Ala Phe Asp
1               5                   10                  15

Tyr

<210> SEQ ID NO 582
<211> LENGTH: 9
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either R or Y
<220> FEATURE:
<221> NAME/KEY: MISC_FEATURE

```
<222> LOCATION: (2)..(2)
<223> OTHER INFORMATION: X is either R, S, or Y
<220> FEATURE:
<221> NAME/KEY: MISC_FEATURE
<222> LOCATION: (3)..(3)
<223> OTHER INFORMATION: X is either S, G, Y, or H
<220> FEATURE:
<221> NAME/KEY: MISC_FEATURE
<222> LOCATION: (4)..(4)
<223> OTHER INFORMATION: X is either S, G, Y, or R
<220> FEATURE:
<221> NAME/KEY: MISC_FEATURE
<222> LOCATION: (5)..(5)
<223> OTHER INFORMATION: X is either G or A
<220> FEATURE:
<221> NAME/KEY: MISC_FEATURE
<222> LOCATION: (6)..(6)
<223> OTHER INFORMATION: X is either F, M, L, or A
<220> FEATURE:
<221> NAME/KEY: MISC_FEATURE
<222> LOCATION: (7)..(7)
<223> OTHER INFORMATION: X is either F, M, L, or no amino acid

<400> SEQUENCE: 582

Xaa Xaa Xaa Xaa Xaa Xaa Xaa Asp Tyr
1               5

<210> SEQ ID NO 583
<211> LENGTH: 10
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either G, S, or Y
<220> FEATURE:
<221> NAME/KEY: MISC_FEATURE
<222> LOCATION: (2)..(2)
<223> OTHER INFORMATION: X is either Y, S, G, R, A, or M
<220> FEATURE:
<221> NAME/KEY: MISC_FEATURE
<222> LOCATION: (3)..(3)
<223> OTHER INFORMATION: X is either G, R, S, or Y
<220> FEATURE:
<221> NAME/KEY: MISC_FEATURE
<222> LOCATION: (4)..(4)
<223> OTHER INFORMATION: X is either F, G, or Y
<220> FEATURE:
<221> NAME/KEY: MISC_FEATURE
<222> LOCATION: (5)..(5)
<223> OTHER INFORMATION: X is either G, N, S, or Y
<220> FEATURE:
<221> NAME/KEY: MISC_FEATURE
<222> LOCATION: (6)..(6)
<223> OTHER INFORMATION: X is either H, R, W, or Y
<220> FEATURE:
<221> NAME/KEY: MISC_FEATURE
<222> LOCATION: (7)..(7)
<223> OTHER INFORMATION: X is either A or G
<220> FEATURE:
<221> NAME/KEY: MISC_FEATURE
<222> LOCATION: (8)..(8)
<223> OTHER INFORMATION: X is either F, I, L, or M

<400> SEQUENCE: 583

Xaa Xaa Xaa Xaa Xaa Xaa Xaa Xaa Asp Tyr
1               5                   10

<210> SEQ ID NO 584
<211> LENGTH: 21
<212> TYPE: PRT
<213> ORGANISM: Artificial
<220> FEATURE:
```

```
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either Y, S, R, G, or E
<220> FEATURE:
<221> NAME/KEY: MISC_FEATURE
<222> LOCATION: (2)..(2)
<223> OTHER INFORMATION: X is either Y, S, R, or G
<220> FEATURE:
<221> NAME/KEY: MISC_FEATURE
<222> LOCATION: (3)..(3)
<223> OTHER INFORMATION: X is either S, Y, G, or W
<220> FEATURE:
<221> NAME/KEY: MISC_FEATURE
<222> LOCATION: (4)..(4)
<223> OTHER INFORMATION: X is either S, Y, G, or W
<220> FEATURE:
<221> NAME/KEY: MISC_FEATURE
<222> LOCATION: (5)..(5)
<223> OTHER INFORMATION: X is either G, Y, or S
<220> FEATURE:
<221> NAME/KEY: MISC_FEATURE
<222> LOCATION: (6)..(6)
<223> OTHER INFORMATION: X is either G, Y, S, R, or V
<220> FEATURE:
<221> NAME/KEY: MISC_FEATURE
<222> LOCATION: (7)..(7)
<223> OTHER INFORMATION: X is either S, Y, G, or R
<220> FEATURE:
<221> NAME/KEY: MISC_FEATURE
<222> LOCATION: (8)..(8)
<223> OTHER INFORMATION: X is either Y, S, G, R, P, or V
<220> FEATURE:
<221> NAME/KEY: MISC_FEATURE
<222> LOCATION: (9)..(9)
<223> OTHER INFORMATION: X is either G, A, R, S, or Y
<220> FEATURE:
<221> NAME/KEY: MISC_FEATURE
<222> LOCATION: (10)..(10)
<223> OTHER INFORMATION: X is either M, F, G, Y, S, or R
<220> FEATURE:
<221> NAME/KEY: MISC_FEATURE
<222> LOCATION: (11)..(11)
<223> OTHER INFORMATION: X is either A, G, R, S, Y, or no amino acid
<220> FEATURE:
<221> NAME/KEY: MISC_FEATURE
<222> LOCATION: (12)..(12)
<223> OTHER INFORMATION: X is either A, F, G, I, L, M, R, S, T, Y, or no
     amino acid
<220> FEATURE:
<221> NAME/KEY: MISC_FEATURE
<222> LOCATION: (13)..(13)
<223> OTHER INFORMATION: X is either A, F, G, L, M, S, T, Y, or no amino
     acid
<220> FEATURE:
<221> NAME/KEY: MISC_FEATURE
<222> LOCATION: (14)..(14)
<223> OTHER INFORMATION: X is either L, M, F, I, G, Y, A, T, or no amino
     acid
<220> FEATURE:
<221> NAME/KEY: MISC_FEATURE
<222> LOCATION: (15)..(15)
<223> OTHER INFORMATION: X is either M, L, Y, G, R, or no amino acid
<220> FEATURE:
<221> NAME/KEY: MISC_FEATURE
<222> LOCATION: (16)..(16)
<223> OTHER INFORMATION: X is either G, Y, or no amino acid
<220> FEATURE:
<221> NAME/KEY: MISC_FEATURE
<222> LOCATION: (17)..(17)
<223> OTHER INFORMATION: X is either G, R, M, or no amino acid
<220> FEATURE:
<221> NAME/KEY: MISC_FEATURE
<222> LOCATION: (18)..(18)
<223> OTHER INFORMATION: X is either A, P, or no amino acid
<220> FEATURE:
<221> NAME/KEY: MISC_FEATURE
<222> LOCATION: (19)..(19)
```

<223> OTHER INFORMATION: X is either L or no amino acid

<400> SEQUENCE: 584

Xaa Xaa Xaa Xaa Xaa Xaa Xaa Xaa Xaa Xaa Xaa Xaa Xaa Xaa Xaa
1               5                   10                  15

Xaa Xaa Xaa Asp Tyr
            20

<210> SEQ ID NO 585
<211> LENGTH: 6
<212> TYPE: DNA
<213> ORGANISM: Artificial
<220> FEATURE:
<223> OTHER INFORMATION: synthetic sequence upstream of transcription
      initiation
<220> FEATURE:
<221> NAME/KEY: misc_feature
<222> LOCATION: (2)..(2)
<223> OTHER INFORMATION: N can be any nucleotide

<400> SEQUENCE: 585 cncaat                                                                    6

<210> SEQ ID NO 586
<211> LENGTH: 6
<212> TYPE: DNA
<213> ORGANISM: Artificial
<220> FEATURE:
<223> OTHER INFORMATION: synthetic signal

<400> SEQUENCE: 586 aataaa                                                                    6

<210> SEQ ID NO 587
<211> LENGTH: 9
<212> TYPE: PRT
<213> ORGANISM: Artificial
<220> FEATURE:
<223> OTHER INFORMATION: synthetic CDRL3
<220> FEATURE:
<221> NAME/KEY: MISC_FEATURE
<222> LOCATION: (6)..(6)
<223> OTHER INFORMATION: X is either Y or S

<400> SEQUENCE: 587

Gln Gln Ser Tyr Tyr Xaa Pro Ser Thr
1               5

<210> SEQ ID NO 588
<211> LENGTH: 10
<212> TYPE: PRT
<213> ORGANISM: Artificial
<220> FEATURE:
<223> OTHER INFORMATION: synthetic CDRH1
<220> FEATURE:
<221> NAME/KEY: MISC_FEATURE
<222> LOCATION: (5)..(5)
<223> OTHER INFORMATION: X is independently either Y or S
<220> FEATURE:
<221> NAME/KEY: MISC_FEATURE
<222> LOCATION: (6)..(6)
<223> OTHER INFORMATION: X is independently either Y or S

<400> SEQUENCE: 588

Gly Phe Ser Ile Xaa Xaa Ser Tyr Ile His
1               5                   10

<210> SEQ ID NO 589

```
<211> LENGTH: 17
<212> TYPE: PRT
<213> ORGANISM: Artificial
<220> FEATURE:
<223> OTHER INFORMATION: synthetic CDRH2
<220> FEATURE:
<221> NAME/KEY: MISC_FEATURE
<222> LOCATION: (5)..(5)
<223> OTHER INFORMATION: X is independently either Y or S

<400> SEQUENCE: 589

Ser Ile Tyr Pro Xaa Ser Gly Tyr Thr Ser Tyr Ala Asp Ser Lys Val
1               5                   10                  15
Gly

<210> SEQ ID NO 590
<211> LENGTH: 10
<212> TYPE: PRT
<213> ORGANISM: Artificial
<220> FEATURE:
<223> OTHER INFORMATION: synthetic CDRH1
<220> FEATURE:
<221> NAME/KEY: MISC_FEATURE
<222> LOCATION: (3)..(3)
<223> OTHER INFORMATION: X is either Y or S

<400> SEQUENCE: 590

Gly Phe Xaa Ile Ser Tyr Ser Ser Ile His
1               5                   10

<210> SEQ ID NO 591
<211> LENGTH: 17
<212> TYPE: PRT
<213> ORGANISM: Artificial
<220> FEATURE:
<223> OTHER INFORMATION: synthetic CDRH2
<220> FEATURE:
<221> NAME/KEY: MISC_FEATURE
<222> LOCATION: (5)..(5)
<223> OTHER INFORMATION: X is independently either Y or S
<220> FEATURE:
<221> NAME/KEY: MISC_FEATURE
<222> LOCATION: (8)..(8)
<223> OTHER INFORMATION: X is independently either Y or S
<220> FEATURE:
<221> NAME/KEY: MISC_FEATURE
<222> LOCATION: (10)..(10)
<223> OTHER INFORMATION: X is independently either Y or S

<400> SEQUENCE: 591

Ser Ile Tyr Pro Xaa Tyr Gly Xaa Thr Xaa Tyr Ala Asp Ser Lys Val
1               5                   10                  15
Gly

<210> SEQ ID NO 592
<211> LENGTH: 16
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either Y, S, or R
<220> FEATURE:
<221> NAME/KEY: MISC_FEATURE
<222> LOCATION: (2)..(2)
<223> OTHER INFORMATION: X is either Y or S
<220> FEATURE:
<221> NAME/KEY: MISC_FEATURE
<222> LOCATION: (3)..(3)
```

```
<223> OTHER INFORMATION: X is either G, Y, or S
<220> FEATURE:
<221> NAME/KEY: MISC_FEATURE
<222> LOCATION: (4)..(4)
<223> OTHER INFORMATION: X is either Y, S, R, or G
<220> FEATURE:
<221> NAME/KEY: MISC_FEATURE
<222> LOCATION: (10)..(10)
<223> OTHER INFORMATION: X is either Y, S, or G
<220> FEATURE:
<221> NAME/KEY: MISC_FEATURE
<222> LOCATION: (12)..(12)
<223> OTHER INFORMATION: X is either Y, S, G, or R
<220> FEATURE:
<221> NAME/KEY: MISC_FEATURE
<222> LOCATION: (13)..(13)
<223> OTHER INFORMATION: X is either G or A
<220> FEATURE:
<221> NAME/KEY: MISC_FEATURE
<222> LOCATION: (14)..(14)
<223> OTHER INFORMATION: X is either M, I, F, or L

<400> SEQUENCE: 592

Xaa Xaa Xaa Xaa Tyr Tyr Ser Tyr Tyr Xaa Gly Xaa Xaa Xaa Asp Tyr
1               5                   10                  15

<210> SEQ ID NO 593
<211> LENGTH: 10
<212> TYPE: PRT
<213> ORGANISM: Artificial
<220> FEATURE:
<223> OTHER INFORMATION: synthetic CDRH2
<220> FEATURE:
<221> NAME/KEY: MISC_FEATURE
<222> LOCATION: (3)..(3)
<223> OTHER INFORMATION: X is either Y or S

<400> SEQUENCE: 593

Gly Phe Xaa Ile Ser Ser Ser Ser Ile His
1               5                   10

<210> SEQ ID NO 594
<211> LENGTH: 17
<212> TYPE: PRT
<213> ORGANISM: Artificial
<220> FEATURE:
<223> OTHER INFORMATION: synthetic CDRH2
<220> FEATURE:
<221> NAME/KEY: MISC_FEATURE
<222> LOCATION: (1)..(1)
<223> OTHER INFORMATION: X is independently Y or S
<220> FEATURE:
<221> NAME/KEY: MISC_FEATURE
<222> LOCATION: (3)..(3)
<223> OTHER INFORMATION: X is independently Y or S
<220> FEATURE:
<221> NAME/KEY: MISC_FEATURE
<222> LOCATION: (10)..(10)
<223> OTHER INFORMATION: X is independently Y or S

<400> SEQUENCE: 594

Xaa Ile Xaa Pro Ser Ser Gly Tyr Thr Xaa Tyr Ala Asp Ser Lys Val
1               5                   10                  15

Gly

<210> SEQ ID NO 595
<211> LENGTH: 184
<212> TYPE: PRT
<213> ORGANISM: homo sapiens

<400> SEQUENCE: 595
```

```
Met Ser Ala Leu Leu Ile Leu Ala Leu Val Gly Ala Ala Val Ala Asp
1               5                   10                  15

Tyr Lys Asp Asp Asp Lys Leu Ser Ala Leu Ile Thr Gln Gln Asp
            20                  25                  30

Leu Ala Pro Gln Gln Arg Val Ala Pro Gln Gln Lys Arg Ser Ser Pro
                35                  40                  45

Ser Glu Gly Leu Cys Pro Pro Gly His His Ile Ser Glu Asp Gly Arg
        50                  55                  60

Asp Cys Ile Ser Cys Lys Tyr Gly Gln Asp Tyr Ser Thr His Trp Asn
65                  70                  75                  80

Asp Leu Leu Phe Cys Leu Arg Cys Thr Arg Cys Asp Ser Gly Glu Val
                85                  90                  95

Glu Leu Ser Pro Cys Thr Thr Thr Arg Asn Thr Val Cys Gln Cys Glu
                100                 105                 110

Glu Gly Thr Phe Arg Glu Glu Asp Ser Pro Glu Met Cys Arg Lys Cys
            115                 120                 125

Arg Thr Gly Cys Pro Arg Gly Met Val Lys Val Gly Asp Cys Thr Pro
        130                 135                 140

Trp Ser Asp Ile Glu Cys Val His Lys Glu Ser Gly Thr Lys His Ser
145                 150                 155                 160

Gly Glu Ala Pro Ala Val Glu Thr Val Thr Ser Ser Pro Gly Thr
                165                 170                 175

Pro Ala Ser Pro Cys Ser Leu Ser
            180

<210> SEQ ID NO 596
<211> LENGTH: 17
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (3)..(3)
<223> OTHER INFORMATION: X is either Y, S, R, P, or G
<220> FEATURE:
<221> NAME/KEY: MISC_FEATURE
<222> LOCATION: (8)..(8)
<223> OTHER INFORMATION: X is either R, Y, or S
<220> FEATURE:
<221> NAME/KEY: MISC_FEATURE
<222> LOCATION: (9)..(9)
<223> OTHER INFORMATION: X is either G, Y, or S
<220> FEATURE:
<221> NAME/KEY: MISC_FEATURE
<222> LOCATION: (10)..(10)
<223> OTHER INFORMATION: X is either S, Y, or R
<220> FEATURE:
<221> NAME/KEY: MISC_FEATURE
<222> LOCATION: (14)..(14)
<223> OTHER INFORMATION: X is either G or A
<220> FEATURE:
<221> NAME/KEY: MISC_FEATURE
<222> LOCATION: (15)..(15)
<223> OTHER INFORMATION: X is either L or F

<400> SEQUENCE: 596

Tyr Arg Xaa Tyr Arg Tyr Gly Xaa Xaa Xaa Gly Ser Tyr Xaa Xaa Asp
1               5                   10                  15

Tyr

<210> SEQ ID NO 597
<211> LENGTH: 9
<212> TYPE: PRT
```

```
<213> ORGANISM: Artificial
<220> FEATURE:
<223> OTHER INFORMATION: synthetic CDRL3
<220> FEATURE:
<221> NAME/KEY: MISC_FEATURE
<222> LOCATION: (3)..(3)
<223> OTHER INFORMATION: X is independently Y or S
<220> FEATURE:
<221> NAME/KEY: MISC_FEATURE
<222> LOCATION: (4)..(4)
<223> OTHER INFORMATION: X is independently Y or S
<220> FEATURE:
<221> NAME/KEY: MISC_FEATURE
<222> LOCATION: (5)..(5)
<223> OTHER INFORMATION: X is independently Y or S

<400> SEQUENCE: 597

Gln Gln Xaa Xaa Xaa Ser Pro Ser Thr
1               5

<210> SEQ ID NO 598
<211> LENGTH: 10
<212> TYPE: PRT
<213> ORGANISM: Artificial
<220> FEATURE:
<223> OTHER INFORMATION: synthetic CDRH1
<220> FEATURE:
<221> NAME/KEY: MISC_FEATURE
<222> LOCATION: (3)..(3)
<223> OTHER INFORMATION: X is independently either Y or S
<220> FEATURE:
<221> NAME/KEY: MISC_FEATURE
<222> LOCATION: (5)..(5)
<223> OTHER INFORMATION: X is independently either Y or S

<400> SEQUENCE: 598

Gly Phe Xaa Ile Xaa Ser Ser Ser Ile His
1               5                   10

<210> SEQ ID NO 599
<211> LENGTH: 17
<212> TYPE: PRT
<213> ORGANISM: Artificial
<220> FEATURE:
<223> OTHER INFORMATION: synthetic CDRH2
<220> FEATURE:
<221> NAME/KEY: MISC_FEATURE
<222> LOCATION: (1)..(1)
<223> OTHER INFORMATION: X is independently either Y or S
<220> FEATURE:
<221> NAME/KEY: MISC_FEATURE
<222> LOCATION: (5)..(5)
<223> OTHER INFORMATION: X is independently either Y or S
<220> FEATURE:
<221> NAME/KEY: MISC_FEATURE
<222> LOCATION: (6)..(6)
<223> OTHER INFORMATION: X is independently either Y or S
<220> FEATURE:
<221> NAME/KEY: MISC_FEATURE
<222> LOCATION: (10)..(10)
<223> OTHER INFORMATION: X is independently either Y or S

<400> SEQUENCE: 599

Xaa Ile Ser Pro Xaa Xaa Gly Tyr Thr Xaa Tyr Ala Asp Ser Lys Val
1               5                   10                  15
Gly

<210> SEQ ID NO 600
<211> LENGTH: 7
<212> TYPE: PRT
<213> ORGANISM: Artificial
<220> FEATURE:
```

<223> OTHER INFORMATION: synthetic BDF1 CDRH1

<400> SEQUENCE: 600

Ile Gly Lys Ser Gly Ile His
1               5

<210> SEQ ID NO 601
<211> LENGTH: 14
<212> TYPE: PRT
<213> ORGANISM: Artificial
<220> FEATURE:
<223> OTHER INFORMATION: synthetic BDF1 CDRH2

<400> SEQUENCE: 601

Val Ala Val Ile Tyr Pro His Asp Gly Asn Thr Ala Tyr Ala
1               5                   10

<210> SEQ ID NO 602
<211> LENGTH: 10
<212> TYPE: PRT
<213> ORGANISM: Artificial
<220> FEATURE:
<223> OTHER INFORMATION: synthetic BDF1 CDRH3

<400> SEQUENCE: 602

Arg Leu Ala Leu Val Arg Met Trp Met Asp
1               5                   10

<210> SEQ ID NO 603
<211> LENGTH: 16
<212> TYPE: PRT
<213> ORGANISM: Artificial
<220> FEATURE:
<223> OTHER INFORMATION: synthetic CDRH3

<400> SEQUENCE: 603

Tyr Ser Ser Tyr Tyr Ser Tyr Tyr Ser Ser Ser Ser Tyr Ser Tyr
1               5                   10                  15

<210> SEQ ID NO 604
<211> LENGTH: 411
<212> TYPE: PRT
<213> ORGANISM: Homo sapiens

<400> SEQUENCE: 604

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Leu
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe

```
              130                 135                 140
Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Ile Ile Ile Gly Val Thr Val Ala
                    180                 185                 190

Ala Val Val Leu Ile Val Ala Val Phe Val Cys Lys Ser Leu Leu Trp
            195                 200                 205

Lys Lys Val Leu Pro Tyr Leu Lys Gly Ile Cys Ser Gly Gly Gly Gly
        210                 215                 220

Asp Pro Glu Arg Val Asp Arg Ser Ser Gln Arg Pro Gly Ala Glu Asp
225                 230                 235                 240

Asn Val Leu Asn Glu Ile Val Ser Ile Leu Gln Pro Thr Gln Val Pro
                245                 250                 255

Glu Gln Glu Met Glu Val Gln Glu Pro Ala Glu Pro Thr Gly Val Asn
                260                 265                 270

Met Leu Ser Pro Gly Glu Ser Glu His Leu Leu Glu Pro Ala Glu Ala
            275                 280                 285

Glu Arg Ser Gln Arg Arg Arg Leu Leu Val Pro Ala Asn Glu Gly Asp
        290                 295                 300

Pro Thr Glu Thr Leu Arg Gln Cys Phe Asp Asp Phe Ala Asp Leu Val
305                 310                 315                 320

Pro Phe Asp Ser Trp Glu Pro Leu Met Arg Lys Leu Gly Leu Met Asp
                325                 330                 335

Asn Glu Ile Lys Val Ala Lys Ala Glu Ala Ala Gly His Arg Asp Thr
                340                 345                 350

Leu Tyr Thr Met Leu Ile Lys Trp Val Asn Lys Thr Gly Arg Asp Ala
            355                 360                 365

Ser Val His Thr Leu Leu Asp Ala Leu Glu Thr Leu Gly Glu Arg Leu
        370                 375                 380

Ala Lys Gln Lys Ile Glu Asp His Leu Leu Ser Ser Gly Lys Phe Met
385                 390                 395                 400

Tyr Leu Glu Gly Asn Ala Asp Ser Ala Leu Ser
                405                 410

<210> SEQ ID NO 605
<211> LENGTH: 120
<212> TYPE: PRT
<213> ORGANISM: Mus musculus

<400> SEQUENCE: 605

Gly Leu Gln Arg Pro Glu Glu Ser Pro Ser Arg Gly Pro Cys Leu Ala
1               5                   10                  15

Gly Gln Tyr Leu Ser Glu Gly Asn Cys Lys Pro Cys Arg Glu Gly Ile
                20                  25                  30

Asp Tyr Thr Ser His Ser Asn His Ser Leu Asp Ser Cys Ile Leu Cys
            35                  40                  45

Thr Val Cys Lys Glu Asp Lys Val Val Glu Thr Arg Cys Asn Ile Thr
        50                  55                  60

Thr Asn Thr Val Cys Arg Cys Lys Pro Gly Thr Phe Glu Asp Lys Asp
65                  70                  75                  80

Ser Pro Glu Ile Cys Gln Ser Cys Ser Asn Cys Thr Asp Gly Glu Glu
                85                  90                  95
```

```
Glu Leu Thr Ser Cys Thr Pro Arg Glu Asn Arg Lys Cys Val Ser Lys
                100                 105                 110

Thr Ala Trp Ala Ser Trp His Lys
        115                 120

<210> SEQ ID NO 606
<211> LENGTH: 281
<212> TYPE: PRT
<213> ORGANISM: Homo sapiens

<400> SEQUENCE: 606

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 607
<211> LENGTH: 168
<212> TYPE: PRT
<213> ORGANISM: Artificial
<220> FEATURE:
<223> OTHER INFORMATION: synthetic Apo-2L

<400> SEQUENCE: 607

Val Arg Glu Arg Gly Pro Gln Arg Val Ala Ala His Ile Thr Gly Thr
```

```
            1               5                  10                 15
Arg Gly Arg Ser Asn Thr Leu Ser Ser Pro Asn Ser Lys Asn Glu Lys
            20                 25                 30

Ala Leu Gly Arg Lys Ile Asn Ser Trp Glu Ser Ser Arg Ser Gly His
            35                 40                 45

Ser Phe Leu Ser Asn Leu His Leu Arg Asn Gly Glu Leu Val Ile His
            50                 55                 60

Glu Lys Gly Phe Tyr Tyr Ile Tyr Ser Gln Thr Tyr Phe Arg Phe Gln
65                  70                 75                 80

Glu Glu Ile Lys Glu Asn Thr Lys Asn Asp Lys Gln Met Val Gln Tyr
            85                 90                 95

Ile Tyr Lys Tyr Thr Ser Tyr Pro Asp Pro Ile Leu Leu Met Lys Ser
            100                105                110

Ala Arg Asn Ser Cys Trp Ser Lys Asp Ala Glu Tyr Gly Leu Tyr Ser
            115                120                125

Ile Tyr Gln Gly Gly Ile Phe Glu Leu Lys Glu Asn Asp Arg Ile Phe
            130                135                140

Val Ser Val Thr Asn Glu His Leu Ile Asp Met Asp His Glu Ala Ser
145                 150                155                160

Phe Phe Gly Ala Phe Leu Val Gly
                  165

<210> SEQ ID NO 608
<211> LENGTH: 6
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(3)
<223> OTHER INFORMATION: X are any amino acid, except cysteine
<220> FEATURE:
<221> NAME/KEY: MISC_FEATURE
<222> LOCATION: (4)..(4)
<223> OTHER INFORMATION: X is any amino acid, except cysteine and can
      vary in length
<220> FEATURE:
<221> NAME/KEY: MISC_FEATURE
<222> LOCATION: (5)..(6)
<223> OTHER INFORMATION: X are any amino acids, except cysteine

<400> SEQUENCE: 608

Xaa Xaa Xaa Xaa Xaa Xaa
1               5

<210> SEQ ID NO 609
<211> LENGTH: 9
<212> TYPE: PRT
<213> ORGANISM: Artificial
<220> FEATURE:
<223> OTHER INFORMATION: synthetic CDRL3
<220> FEATURE:
<221> NAME/KEY: MISC_FEATURE
<222> LOCATION: (3)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid

<400> SEQUENCE: 609

Gln Gln Xaa Xaa Xaa Xaa Pro Xaa Thr
1               5
```

```
<210> SEQ ID NO 610
<211> LENGTH: 9
<212> TYPE: PRT
<213> ORGANISM: Artificial
<220> FEATURE:
<223> OTHER INFORMATION: synthetic CDRL3
<220> FEATURE:
<221> NAME/KEY: MISC_FEATURE
<222> LOCATION: (3)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid

<400> SEQUENCE: 610

Gln Gln Xaa Xaa Xaa Xaa Pro Xaa Thr
1               5

<210> SEQ ID NO 611
<211> LENGTH: 19
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(17)
<223> OTHER INFORMATION: X is S and one of A, C, F, G, I, L, W, P, R, T,
      W, or Y, or are not present
<220> FEATURE:
<221> NAME/KEY: MISC_FEATURE
<222> LOCATION: (18)..(18)
<223> OTHER INFORMATION: X is G or A, or is not present
<220> FEATURE:
<221> NAME/KEY: MISC_FEATURE
<222> LOCATION: (19)..(19)
<223> OTHER INFORMATION: X is F, L, I, or M, or is not present

<400> SEQUENCE: 611

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 612
<211> LENGTH: 10
<212> TYPE: PRT
<213> ORGANISM: Artificial
<220> FEATURE:
<223> OTHER INFORMATION: synthetic CDRH1
<220> FEATURE:
<221> NAME/KEY: MISC_FEATURE
<222> LOCATION: (3)..(3)
<223> OTHER INFORMATION: X is S and one of Y, W, R, or F
<220> FEATURE:
<221> NAME/KEY: MISC_FEATURE
<222> LOCATION: (5)..(8)
<223> OTHER INFORMATION: X is S and one of Y, W, R, or F

<400> SEQUENCE: 612

Gly Phe Xaa Ile Xaa Xaa Xaa Xaa Ile His
1               5                   10

<210> SEQ ID NO 613
<211> LENGTH: 17
<212> TYPE: PRT
<213> ORGANISM: Artificial
<220> FEATURE:
<223> OTHER INFORMATION: synthetic CDRH2
<220> FEATURE:
<221> NAME/KEY: MISC_FEATURE
```

```
<222> LOCATION: (1)..(1)
<223> OTHER INFORMATION: X is S and one of Y, W, R, or F
<220> FEATURE:
<221> NAME/KEY: MISC_FEATURE
<222> LOCATION: (3)..(3)
<223> OTHER INFORMATION: X is S and one of Y, W, R, or F
<220> FEATURE:
<221> NAME/KEY: MISC_FEATURE
<222> LOCATION: (5)..(6)
<223> OTHER INFORMATION: X is S and one of Y, W, R, or F
<220> FEATURE:
<221> NAME/KEY: MISC_FEATURE
<222> LOCATION: (8)..(8)
<223> OTHER INFORMATION: X is S and one of Y, W, R, or F
<220> FEATURE:
<221> NAME/KEY: MISC_FEATURE
<222> LOCATION: (10)..(10)
<223> OTHER INFORMATION: X is S and one of Y, W, R, or F

<400> SEQUENCE: 613

Xaa Ile Xaa Pro Xaa Xaa Gly Xaa Thr Xaa Tyr Ala Asp Ser Val Lys
1               5                   10                  15
Gly

<210> SEQ ID NO 614
<211> LENGTH: 10
<212> TYPE: PRT
<213> ORGANISM: Artificial
<220> FEATURE:
<223> OTHER INFORMATION: synthetic CDRH1
<220> FEATURE:
<221> NAME/KEY: MISC_FEATURE
<222> LOCATION: (3)..(3)
<223> OTHER INFORMATION: X is any naturally occurring amino acid, except
      cysteine
<220> FEATURE:
<221> NAME/KEY: MISC_FEATURE
<222> LOCATION: (5)..(8)
<223> OTHER INFORMATION: X is any naturally occurring amino acid, except
      cysteine

<400> SEQUENCE: 614

Gly Phe Xaa Ile Xaa Xaa Xaa Xaa Ile His
1               5                   10

<210> SEQ ID NO 615
<211> LENGTH: 17
<212> TYPE: PRT
<213> ORGANISM: Artificial
<220> FEATURE:
<223> OTHER INFORMATION: synthetic CDRH2
<220> FEATURE:
<221> NAME/KEY: MISC_FEATURE
<222> LOCATION: (1)..(1)
<223> OTHER INFORMATION: X is any amino acid, except cysteine
<220> FEATURE:
<221> NAME/KEY: MISC_FEATURE
<222> LOCATION: (3)..(3)
<223> OTHER INFORMATION: X is any amino acid, except cysteine
<220> FEATURE:
<221> NAME/KEY: MISC_FEATURE
<222> LOCATION: (5)..(6)
<223> OTHER INFORMATION: X is any amino acid, except cysteine
<220> FEATURE:
<221> NAME/KEY: MISC_FEATURE
<222> LOCATION: (8)..(8)
<223> OTHER INFORMATION: X is any amino acid, except cysteine
<220> FEATURE:
<221> NAME/KEY: MISC_FEATURE
<222> LOCATION: (10)..(10)
<223> OTHER INFORMATION: X is any amino acid, except cysteine

<400> SEQUENCE: 615
```

```
Xaa Ile Xaa Pro Xaa Xaa Gly Xaa Thr Xaa Tyr Ala Asp Ser Val Lys
1               5                   10                  15

Gly

<210> SEQ ID NO 616
<211> LENGTH: 10
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(5)
<223> OTHER INFORMATION: X is any amino acid, except cystine
<220> FEATURE:
<221> NAME/KEY: MISC_FEATURE
<222> LOCATION: (6)..(6)
<223> OTHER INFORMATION: X is any amino acid, except cysteine, and can
      vary in length
<220> FEATURE:
<221> NAME/KEY: MISC_FEATURE
<222> LOCATION: (7)..(8)
<223> OTHER INFORMATION: X is any amino acid, except cysteine

<400> SEQUENCE: 616

Xaa Xaa Xaa Xaa Xaa Xaa Xaa Xaa Asp Tyr
1               5                   10

<210> SEQ ID NO 617
<211> LENGTH: 21
<212> TYPE: PRT
<213> ORGANISM: Artificial
<220> FEATURE:
<223> OTHER INFORMATION: synthetic CDRH3
<220> FEATURE:
<221> NAME/KEY: MISC_FEATURE
<222> LOCATION: (1)..(1)
<223> OTHER INFORMATION: X is either Y, S, G, R, or E
<220> FEATURE:
<221> NAME/KEY: MISC_FEATURE
<222> LOCATION: (2)..(2)
<223> OTHER INFORMATION: X is either Y, S, G, R, M, or A
<220> FEATURE:
<221> NAME/KEY: MISC_FEATURE
<222> LOCATION: (3)..(3)
<223> OTHER INFORMATION: X is either Y, S, G, R, W, or H
<220> FEATURE:
<221> NAME/KEY: MISC_FEATURE
<222> LOCATION: (4)..(4)
<223> OTHER INFORMATION: X is either Y, S, G, R, F, or Q
<220> FEATURE:
<221> NAME/KEY: MISC_FEATURE
<222> LOCATION: (5)..(5)
<223> OTHER INFORMATION: X is either G, Y, N, A, or S
<220> FEATURE:
<221> NAME/KEY: MISC_FEATURE
<222> LOCATION: (6)..(6)
<223> OTHER INFORMATION: X is either F, M, L, A, R, G, H, W, V, Y, or S
<220> FEATURE:
<221> NAME/KEY: MISC_FEATURE
<222> LOCATION: (7)..(7)
<223> OTHER INFORMATION: X is either M, L, G, A, R, F, Y, or S, or is
      not present
<220> FEATURE:
<221> NAME/KEY: MISC_FEATURE
<222> LOCATION: (8)..(8)
<223> OTHER INFORMATION: X is either M, L, F, I, R, G, P, V, Y, or S, or
      is not present
<220> FEATURE:
<221> NAME/KEY: MISC_FEATURE
<222> LOCATION: (9)..(9)
<223> OTHER INFORMATION: X is either G, Y, R, or S, or is not present
<220> FEATURE:
<221> NAME/KEY: MISC_FEATURE
<222> LOCATION: (10)..(10)
```

```
<223> OTHER INFORMATION: X is either M, F, G, Y, R, or S, or is not
      present
<220> FEATURE:
<221> NAME/KEY: MISC_FEATURE
<222> LOCATION: (11)..(11)
<223> OTHER INFORMATION: X is either A, G, Y, R, or S, or is not present
<220> FEATURE:
<221> NAME/KEY: MISC_FEATURE
<222> LOCATION: (12)..(12)
<223> OTHER INFORMATION: X is either I, M, F, A, G, R, T, Y, or S, or is
      not present
<220> FEATURE:
<221> NAME/KEY: MISC_FEATURE
<222> LOCATION: (13)..(13)
<223> OTHER INFORMATION: X is either F, M, L, G, A, T, Y, or S, or is
      not present
<220> FEATURE:
<221> NAME/KEY: MISC_FEATURE
<222> LOCATION: (14)..(14)
<223> OTHER INFORMATION: X is either L, F, M, I, G, A, T, or Y, or is
      not present
<220> FEATURE:
<221> NAME/KEY: MISC_FEATURE
<222> LOCATION: (15)..(15)
<223> OTHER INFORMATION: X is either M, Y, G, L, or R, or is not present
<220> FEATURE:
<221> NAME/KEY: MISC_FEATURE
<222> LOCATION: (16)..(16)
<223> OTHER INFORMATION: X is either Y or G, or is not present
<220> FEATURE:
<221> NAME/KEY: MISC_FEATURE
<222> LOCATION: (17)..(17)
<223> OTHER INFORMATION: X is either R, M, or G, or is not present
<220> FEATURE:
<221> NAME/KEY: MISC_FEATURE
<222> LOCATION: (18)..(18)
<223> OTHER INFORMATION: X is either G or A
<220> FEATURE:
<221> NAME/KEY: MISC_FEATURE
<222> LOCATION: (19)..(19)
<223> OTHER INFORMATION: X is either F, M, L, or I

<400> SEQUENCE: 617

Xaa Xaa Xaa Xaa Xaa Xaa Xaa Xaa Xaa Xaa Xaa Xaa Xaa Xaa Xaa Xaa
1               5                   10                  15

Xaa Xaa Xaa Asp Tyr
            20

<210> SEQ ID NO 618
<211> LENGTH: 48
<212> TYPE: DNA
<213> ORGANISM: Artificial
<220> FEATURE:
<223> OTHER INFORMATION: synthetic oligonucleotides

<400> SEQUENCE: 618
gcagcttctg gcttctmtat ttmttmttmt tmtatacact gggtgcgt            48

<210> SEQ ID NO 619
<211> LENGTH: 60
<212> TYPE: DNA
<213> ORGANISM: Artificial
<220> FEATURE:
<223> OTHER INFORMATION: synthetic oligonucleotides

<400> SEQUENCE: 619
ctggaatggg ttgcatmtat ttmtccatmt tmtggtttmta cttmttatgc cgatagcgtc   60

<210> SEQ ID NO 620
<211> LENGTH: 54
<212> TYPE: DNA
<213> ORGANISM: Artificial
```

```
<220> FEATURE:
<223> OTHER INFORMATION: synthetic oligonucleotides

<400> SEQUENCE: 620
acttattact gtcagcaatm ttmttmttmt ccatmtacgt tcggacaggg tacc          54

<210> SEQ ID NO 621
<211> LENGTH: 54
<212> TYPE: DNA
<213> ORGANISM: Artificial
<220> FEATURE:
<223> OTHER INFORMATION: synthetic oligonucleotides

<400> SEQUENCE: 621
gtctattatt gtgctcgckc tkctkctkct gstwtkgact actggggtca agga          54

<210> SEQ ID NO 622
<211> LENGTH: 57
<212> TYPE: DNA
<213> ORGANISM: Artificial
<220> FEATURE:
<223> OTHER INFORMATION: synthetic oligonucleotides

<400> SEQUENCE: 622
gtctattatt gtgctcgckc tkctkctkct kctgstwtkg actactgggg tcaagga       57

<210> SEQ ID NO 623
<211> LENGTH: 60
<212> TYPE: DNA
<213> ORGANISM: Artificial
<220> FEATURE:
<223> OTHER INFORMATION: synthetic oligonucleotides

<400> SEQUENCE: 623
gtctattatt gtgctcgckc tkctkctkct kctkctgstw tkgactactg ggtcaagga    60

<210> SEQ ID NO 624
<211> LENGTH: 63
<212> TYPE: DNA
<213> ORGANISM: Artificial
<220> FEATURE:
<223> OTHER INFORMATION: synthetic oligonucleotides

<400> SEQUENCE: 624
gtctattatt gtgctcgckc tkctkctkct kctkctkctg stwtkgacta ctggggtcaa   60
gga                                                                 63

<210> SEQ ID NO 625
<211> LENGTH: 66
<212> TYPE: DNA
<213> ORGANISM: Artificial
<220> FEATURE:
<223> OTHER INFORMATION: synthetic oligonucleotides

<400> SEQUENCE: 625
gtctattatt gtgctcgckc tkctkctkct kctkctkctk ctgstwtkga ctactggggt   60
caagga                                                              66

<210> SEQ ID NO 626
<211> LENGTH: 69
<212> TYPE: DNA
<213> ORGANISM: Artificial
<220> FEATURE:
<223> OTHER INFORMATION: synthetic oligonucleotides
```

```
<400> SEQUENCE: 626
gtctattatt gtgctcgckc tkctkctkct kctkctkctk ctkctgstwt kgactactgg    60
ggtcaagga                                                           69

<210> SEQ ID NO 627
<211> LENGTH: 72
<212> TYPE: DNA
<213> ORGANISM: Artificial
<220> FEATURE:
<223> OTHER INFORMATION: synthetic oligonucleotides

<400> SEQUENCE: 627
gtctattatt gtgctcgckc tkctkctkct kctkctkctk ctkctkctgs twtkgactac    60
tggggtcaag ga                                                       72

<210> SEQ ID NO 628
<211> LENGTH: 75
<212> TYPE: DNA
<213> ORGANISM: Artificial
<220> FEATURE:
<223> OTHER INFORMATION: synthetic oligonucleotides

<400> SEQUENCE: 628
gtctattatt gtgctcgckc tkctkctkct kctkctkctk ctkctkctkc tgstwtkgac    60
tactggggtc aagga                                                    75

<210> SEQ ID NO 629
<211> LENGTH: 78
<212> TYPE: DNA
<213> ORGANISM: Artificial
<220> FEATURE:
<223> OTHER INFORMATION: synthetic oligonucleotides

<400> SEQUENCE: 629
gtctattatt gtgctcgckc tkctkctkct kctkctkctk ctkctkctkc tkctgstwtk    60
gactactggg gtcaagga                                                 78

<210> SEQ ID NO 630
<211> LENGTH: 81
<212> TYPE: DNA
<213> ORGANISM: Artificial
<220> FEATURE:
<223> OTHER INFORMATION: synthetic oligonucleotides

<400> SEQUENCE: 630
gtctattatt gtgctcgckc tkctkctkct kctkctkctk ctkctkctkc tkctkctgst    60
wtkgactact ggggtcaagg a                                             81

<210> SEQ ID NO 631
<211> LENGTH: 84
<212> TYPE: DNA
<213> ORGANISM: Artificial
<220> FEATURE:
<223> OTHER INFORMATION: synthetic oligonucleotides

<400> SEQUENCE: 631
gtctattatt gtgctcgckc tkctkctkct kctkctkctk ctkctkctkc tkctkctkct    60
gstwtkgact actggggtca agga                                          84

<210> SEQ ID NO 632
<211> LENGTH: 87
```

```
<212> TYPE: DNA
<213> ORGANISM: Artificial
<220> FEATURE:
<223> OTHER INFORMATION: synthetic oligonucleotides

<400> SEQUENCE: 632
gtctattatt gtgctcgckc tkctkctkct kctkctkctk ctkctkctkc tkctkctkct      60
kctgstwtkg actactgggg tcaagga                                          87

<210> SEQ ID NO 633
<211> LENGTH: 90
<212> TYPE: DNA
<213> ORGANISM: Artificial
<220> FEATURE:
<223> OTHER INFORMATION: synthetic oligonucleotides

<400> SEQUENCE: 633
gtctattatt gtgctcgckc tkctkctkct kctkctkctk ctkctkctkc tkctkctkct      60
kctkctgstw tkgactactg gggtcaagga                                       90

<210> SEQ ID NO 634
<211> LENGTH: 93
<212> TYPE: DNA
<213> ORGANISM: Artificial
<220> FEATURE:
<223> OTHER INFORMATION: synthetic oligonucleotides

<400> SEQUENCE: 634
gtctattatt gtgctcgckc tkctkctkct kctkctkctk ctkctkctkc tkctkctkct      60
kctkctkctg stwtkgacta ctggggtcaa gga                                   93

<210> SEQ ID NO 635
<211> LENGTH: 54
<212> TYPE: DNA
<213> ORGANISM: Artificial
<220> FEATURE:
<223> OTHER INFORMATION: synthetic oligonucleotides

<400> SEQUENCE: 635
gtctattatt gtgctcgcts ctsctsctsc gstwtkgact actggggtca agga            54

<210> SEQ ID NO 636
<211> LENGTH: 57
<212> TYPE: DNA
<213> ORGANISM: Artificial
<220> FEATURE:
<223> OTHER INFORMATION: synthetic oligonucleotides

<400> SEQUENCE: 636
gtctattatt gtgctcgcts ctsctsctsc tscgstwtkg actactgggg tcaagga         57

<210> SEQ ID NO 637
<211> LENGTH: 60
<212> TYPE: DNA
<213> ORGANISM: Artificial
<220> FEATURE:
<223> OTHER INFORMATION: synthetic oligonucleotides

<400> SEQUENCE: 637
gtctattatt gtgctcgcts ctsctsctsc tsctscgstw tkgactactg ggtcaagga       60

<210> SEQ ID NO 638
<211> LENGTH: 63
<212> TYPE: DNA
```

```
<213> ORGANISM: Artificial
<220> FEATURE:
<223> OTHER INFORMATION: synthetic oligonucleotides

<400> SEQUENCE: 638
gtctattatt gtgctcgcts ctsctsctsc tsctsctscg stwtkgacta ctggggtcaa      60
gga                                                                  63

<210> SEQ ID NO 639
<211> LENGTH: 66
<212> TYPE: DNA
<213> ORGANISM: Artificial
<220> FEATURE:
<223> OTHER INFORMATION: synthetic oligonucleotides

<400> SEQUENCE: 639
gtctattatt gtgctcgcts ctsctsctsc tsctsctsct scgstwtkga ctactggggt      60
caagga                                                               66

<210> SEQ ID NO 640
<211> LENGTH: 69
<212> TYPE: DNA
<213> ORGANISM: Artificial
<220> FEATURE:
<223> OTHER INFORMATION: synthetic oligonucleotides

<400> SEQUENCE: 640
gtctattatt gtgctcgcts ctsctsctsc tsctsctsct sctscgstwt kgactactgg      60
ggtcaagga                                                            69

<210> SEQ ID NO 641
<211> LENGTH: 72
<212> TYPE: DNA
<213> ORGANISM: Artificial
<220> FEATURE:
<223> OTHER INFORMATION: synthetic oligonucleotides

<400> SEQUENCE: 641
gtctattatt gtgctcgcts ctsctsctsc tsctsctsct sctsctscgs twtkgactac      60
tggggtcaag ga                                                        72

<210> SEQ ID NO 642
<211> LENGTH: 75
<212> TYPE: DNA
<213> ORGANISM: Artificial
<220> FEATURE:
<223> OTHER INFORMATION: synthetic oligonucleotides

<400> SEQUENCE: 642
gtctattatt gtgctcgcts ctsctsctsc tsctsctsct sctsctscts cgstwtkgac      60
tactggggtc aagga                                                     75

<210> SEQ ID NO 643
<211> LENGTH: 78
<212> TYPE: DNA
<213> ORGANISM: Artificial
<220> FEATURE:
<223> OTHER INFORMATION: synthetic oligonucleotides

<400> SEQUENCE: 643
gtctattatt gtgctcgcts ctsctsctsc tsctsctsct sctsctscts ctscgstwtk      60
gactactggg gtcaagga                                                  78
```

<210> SEQ ID NO 644
<211> LENGTH: 81
<212> TYPE: DNA
<213> ORGANISM: Artificial
<220> FEATURE:
<223> OTHER INFORMATION: synthetic oligonucleotides

<400> SEQUENCE: 644
gtctattatt gtgctcgcts ctsctsctsc tsctsctsct sctsctscts ctsctscgst    60
wtkgactact ggggtcaagg a                                              81

<210> SEQ ID NO 645
<211> LENGTH: 84
<212> TYPE: DNA
<213> ORGANISM: Artificial
<220> FEATURE:
<223> OTHER INFORMATION: synthetic oligonucleotides

<400> SEQUENCE: 645
gtctattatt gtgctcgcts ctsctsctsc tsctsctsct sctsctscts ctsctsctsc    60
gstwtkgact actggggtca agga                                           84

<210> SEQ ID NO 646
<211> LENGTH: 87
<212> TYPE: DNA
<213> ORGANISM: Artificial
<220> FEATURE:
<223> OTHER INFORMATION: synthetic oligonucleotides

<400> SEQUENCE: 646
gtctattatt gtgctcgcts ctsctsctsc tsctsctsct sctsctscts ctsctsctsc    60
tscgstwtkg actactgggg tcaagga                                        87

<210> SEQ ID NO 647
<211> LENGTH: 90
<212> TYPE: DNA
<213> ORGANISM: Artificial
<220> FEATURE:
<223> OTHER INFORMATION: synthetic oligonucleotides

<400> SEQUENCE: 647
gtctattatt gtgctcgcts ctsctsctsc tsctsctsct sctsctscts ctsctsctsc    60
tsctscgstw tkgactactg gggtcaagga                                     90

<210> SEQ ID NO 648
<211> LENGTH: 93
<212> TYPE: DNA
<213> ORGANISM: Artificial
<220> FEATURE:
<223> OTHER INFORMATION: synthetic oligonucleotides

<400> SEQUENCE: 648
gtctattatt gtgctcgcts ctsctsctsc tsctsctsct sctsctscts ctsctsctsc    60
tsctsctscg stwtkgacta ctggggtcaa gga                                 93

<210> SEQ ID NO 649
<211> LENGTH: 54
<212> TYPE: DNA
<213> ORGANISM: Artificial
<220> FEATURE:
<223> OTHER INFORMATION: synthetic oligonucleotides

<400> SEQUENCE: 649
gtctattatt gtgctcgcty ctyctyctyc gstwtkgact actggggtca agga            54

<210> SEQ ID NO 650
<211> LENGTH: 57
<212> TYPE: DNA
<213> ORGANISM: Artificial
<220> FEATURE:
<223> OTHER INFORMATION: synthetic oligonucleotides

<400> SEQUENCE: 650
gtctattatt gtgctcgcty ctyctyctyc tycgstwtkg actactgggg tcaagga         57

<210> SEQ ID NO 651
<211> LENGTH: 60
<212> TYPE: DNA
<213> ORGANISM: Artificial
<220> FEATURE:
<223> OTHER INFORMATION: synthetic oligonucleotides

<400> SEQUENCE: 651
gtctattatt gtgctcgcty ctyctyctyc tyctycgstw tkgactactg ggtcaagga      60

<210> SEQ ID NO 652
<211> LENGTH: 63
<212> TYPE: DNA
<213> ORGANISM: Artificial
<220> FEATURE:
<223> OTHER INFORMATION: synthetic oligonucleotides

<400> SEQUENCE: 652
gtctattatt gtgctcgcty ctyctyctyc tyctyctycg stwtkgacta ctggggtcaa     60
gga                                                                    63

<210> SEQ ID NO 653
<211> LENGTH: 66
<212> TYPE: DNA
<213> ORGANISM: Artificial
<220> FEATURE:
<223> OTHER INFORMATION: synthetic oligonucleotides

<400> SEQUENCE: 653
gtctattatt gtgctcgcty ctyctyctyc tyctyctyct ycgstwtkga ctactggggt     60
caagga                                                                 66

<210> SEQ ID NO 654
<211> LENGTH: 69
<212> TYPE: DNA
<213> ORGANISM: Artificial
<220> FEATURE:
<223> OTHER INFORMATION: synthetic oligonucleotides

<400> SEQUENCE: 654
gtctattatt gtgctcgcty ctyctyctyc tyctyctyct yctycgstwt kgactactgg     60
ggtcaagga                                                              69

<210> SEQ ID NO 655
<211> LENGTH: 72
<212> TYPE: DNA
<213> ORGANISM: Artificial
<220> FEATURE:
<223> OTHER INFORMATION: synthetic oligonucleotides

<400> SEQUENCE: 655

```
gtctattatt gtgctcgcty ctyctyctyc tyctyctyct yctyctycgs twtkgactac    60
tggggtcaag ga                                                       72

<210> SEQ ID NO 656
<211> LENGTH: 75
<212> TYPE: DNA
<213> ORGANISM: Artificial
<220> FEATURE:
<223> OTHER INFORMATION: synthetic oligonucleotides

<400> SEQUENCE: 656
gtctattatt gtgctcgcty ctyctyctyc tyctyctyct yctyctycty cgstwtkgac    60
tactggggtc aagga                                                    75

<210> SEQ ID NO 657
<211> LENGTH: 78
<212> TYPE: DNA
<213> ORGANISM: Artificial
<220> FEATURE:
<223> OTHER INFORMATION: synthetic oligonucleotides

<400> SEQUENCE: 657
gtctattatt gtgctcgcty ctyctyctyc tyctyctyct yctyctycty ctycgstwtk    60
gactactggg gtcaagga                                                 78

<210> SEQ ID NO 658
<211> LENGTH: 81
<212> TYPE: DNA
<213> ORGANISM: Artificial
<220> FEATURE:
<223> OTHER INFORMATION: synthetic oligonucleotides

<400> SEQUENCE: 658
gtctattatt gtgctcgcty ctyctyctyc tyctyctyct yctyctycty ctyctycgst    60
wtkgactact ggggtcaagg a                                             81

<210> SEQ ID NO 659
<211> LENGTH: 84
<212> TYPE: DNA
<213> ORGANISM: Artificial
<220> FEATURE:
<223> OTHER INFORMATION: synthetic oligonucleotides

<400> SEQUENCE: 659
gtctattatt gtgctcgcty ctyctyctyc tyctyctyct yctyctycty ctyctyctyc    60
gstwtkgact actggggtca agga                                          84

<210> SEQ ID NO 660
<211> LENGTH: 87
<212> TYPE: DNA
<213> ORGANISM: Artificial
<220> FEATURE:
<223> OTHER INFORMATION: synthetic oligonucleotides

<400> SEQUENCE: 660
gtctattatt gtgctcgcty ctyctyctyc tyctyctyct yctyctycty ctyctyctyc    60
tycgstwtkg actactgggg tcaagga                                       87

<210> SEQ ID NO 661
<211> LENGTH: 90
<212> TYPE: DNA
```

```
<213> ORGANISM: Artificial
<220> FEATURE:
<223> OTHER INFORMATION: synthetic oligonucleotides

<400> SEQUENCE: 661
gtctattatt gtgctcgcty ctyctyctyc tyctyctyct yctyctycty ctyctyctyc    60
tyctycgstw tkgactactg gggtcaagga                                     90

<210> SEQ ID NO 662
<211> LENGTH: 93
<212> TYPE: DNA
<213> ORGANISM: Artificial
<220> FEATURE:
<223> OTHER INFORMATION: synthetic oligonucleotides

<400> SEQUENCE: 662
gtctattatt gtgctcgcty ctyctyctyc tyctyctyct yctyctycty ctyctyctyc    60
tyctyctycg stwtkgacta ctggggtcaa gga                                 93

<210> SEQ ID NO 663
<211> LENGTH: 54
<212> TYPE: DNA
<213> ORGANISM: Artificial
<220> FEATURE:
<223> OTHER INFORMATION: synthetic oligonucleotides

<400> SEQUENCE: 663
gtctattatt gtgctcgcrg crgcrgcrgc gstwtkgact actggggtca agga           54

<210> SEQ ID NO 664
<211> LENGTH: 57
<212> TYPE: DNA
<213> ORGANISM: Artificial
<220> FEATURE:
<223> OTHER INFORMATION: synthetic oligonucleotides

<400> SEQUENCE: 664
gtctattatt gtgctcgcrg crgcrgcrgc rgcgstwtkg actactgggg tcaagga        57

<210> SEQ ID NO 665
<211> LENGTH: 60
<212> TYPE: DNA
<213> ORGANISM: Artificial
<220> FEATURE:
<223> OTHER INFORMATION: synthetic oligonucleotides

<400> SEQUENCE: 665
gtctattatt gtgctcgcrg crgcrgcrgc rgcrgcgstw tkgactactg gggtcaagga    60

<210> SEQ ID NO 666
<211> LENGTH: 63
<212> TYPE: DNA
<213> ORGANISM: Artificial
<220> FEATURE:
<223> OTHER INFORMATION: synthetic oligonucleotides

<400> SEQUENCE: 666
gtctattatt gtgctcgcrg crgcrgcrgc rgcrgcrgcg stwtkgacta ctggggtcaa    60
gga                                                                  63

<210> SEQ ID NO 667
<211> LENGTH: 66
<212> TYPE: DNA
<213> ORGANISM: Artificial
```

```
<220> FEATURE:
<223> OTHER INFORMATION: synthetic oligonucleotides

<400> SEQUENCE: 667
gtctattatt gtgctcgcrg crgcrgcrgc rgcrgcrgcr gcgstwtkga ctactggggt    60
caagga                                                              66

<210> SEQ ID NO 668
<211> LENGTH: 69
<212> TYPE: DNA
<213> ORGANISM: Artificial
<220> FEATURE:
<223> OTHER INFORMATION: synthetic oligonucleotides

<400> SEQUENCE: 668
gtctattatt gtgctcgcrg crgcrgcrgc rgcrgcrgcr gcrgcgstwt kgactactgg    60
ggtcaagga                                                           69

<210> SEQ ID NO 669
<211> LENGTH: 72
<212> TYPE: DNA
<213> ORGANISM: Artificial
<220> FEATURE:
<223> OTHER INFORMATION: synthetic oligonucleotides

<400> SEQUENCE: 669
gtctattatt gtgctcgcrg crgcrgcrgc rgcrgcrgcr gcrgcrgcgs twtkgactac    60
tggggtcaag ga                                                       72

<210> SEQ ID NO 670
<211> LENGTH: 75
<212> TYPE: DNA
<213> ORGANISM: Artificial
<220> FEATURE:
<223> OTHER INFORMATION: synthetic oligonucleotides

<400> SEQUENCE: 670
gtctattatt gtgctcgcrg crgcrgcrgc rgcrgcrgcr gcrgcrgcrg cgstwtkgac    60
tactggggtc aagga                                                    75

<210> SEQ ID NO 671
<211> LENGTH: 78
<212> TYPE: DNA
<213> ORGANISM: Artificial
<220> FEATURE:
<223> OTHER INFORMATION: synthetic oligonucleotides

<400> SEQUENCE: 671
gtctattatt gtgctcgcrg crgcrgcrgc rgcrgcrgcr gcrgcrgcrg crgcgstwtk    60
gactactggg gtcaagga                                                 78

<210> SEQ ID NO 672
<211> LENGTH: 81
<212> TYPE: DNA
<213> ORGANISM: Artificial
<220> FEATURE:
<223> OTHER INFORMATION: synthetic oligonucleotides

<400> SEQUENCE: 672
gtctattatt gtgctcgcrg crgcrgcrgc rgcrgcrgcr gcrgcrgcrg crgcrgcgst    60
wtkgactact ggggtcaagg a                                             81
```

<210> SEQ ID NO 673
<211> LENGTH: 84
<212> TYPE: DNA
<213> ORGANISM: Artificial
<220> FEATURE:
<223> OTHER INFORMATION: synthetic oligonucleotides

<400> SEQUENCE: 673
gtctattatt gtgctcgcrg crgcrgcrgc rgcrgcrgcr gcrgcrgcrg crgcrgcrgc     60
gstwtkgact actggggtca agga     84

<210> SEQ ID NO 674
<211> LENGTH: 87
<212> TYPE: DNA
<213> ORGANISM: Artificial
<220> FEATURE:
<223> OTHER INFORMATION: synthetic oligonucleotides

<400> SEQUENCE: 674
gtctattatt gtgctcgcrg crgcrgcrgc rgcrgcrgcr gcrgcrgcrg crgcrgcrgc     60
rgcgstwtkg actactgggg tcaagga     87

<210> SEQ ID NO 675
<211> LENGTH: 90
<212> TYPE: DNA
<213> ORGANISM: Artificial
<220> FEATURE:
<223> OTHER INFORMATION: synthetic oligonucleotides

<400> SEQUENCE: 675
gtctattatt gtgctcgcrg crgcrgcrgc rgcrgcrgcr gcrgcrgcrg crgcrgcrgc     60
rgcrgcgstw tkgactactg ggtcaagga     90

<210> SEQ ID NO 676
<211> LENGTH: 93
<212> TYPE: DNA
<213> ORGANISM: Artificial
<220> FEATURE:
<223> OTHER INFORMATION: synthetic oligonucleotides

<400> SEQUENCE: 676
gtctattatt gtgctcgcrg crgcrgcrgc rgcrgcrgcr gcrgcrgcrg crgcrgcrgc     60
rgcrgcrgcg stwtkgacta ctggggtcaa gga     93

<210> SEQ ID NO 677
<211> LENGTH: 54
<212> TYPE: DNA
<213> ORGANISM: Artificial
<220> FEATURE:
<223> OTHER INFORMATION: synthetic oligonucleotides

<400> SEQUENCE: 677
gtctattatt gtgctcgcak cakcakcakc gstwtkgact actggggtca agga     54

<210> SEQ ID NO 678
<211> LENGTH: 57
<212> TYPE: DNA
<213> ORGANISM: Artificial
<220> FEATURE:
<223> OTHER INFORMATION: synthetic oligonucleotides

<400> SEQUENCE: 678
gtctattatt gtgctcgcak cakcakcakc akcgstwtkg actactgggg tcaagga     57

<210> SEQ ID NO 679
<211> LENGTH: 60
<212> TYPE: DNA
<213> ORGANISM: Artificial
<220> FEATURE:
<223> OTHER INFORMATION: synthetic oligonucleotides

<400> SEQUENCE: 679
gtctattatt gtgctcgcak cakcakcakc akcakcgstw tkgactactg gggtcaagga    60

<210> SEQ ID NO 680
<211> LENGTH: 63
<212> TYPE: DNA
<213> ORGANISM: Artificial
<220> FEATURE:
<223> OTHER INFORMATION: synthetic oligonucleotides

<400> SEQUENCE: 680
gtctattatt gtgctcgcak cakcakcakc akcakcakcg stwtkgacta ctggggtcaa    60
gga    63

<210> SEQ ID NO 681
<211> LENGTH: 66
<212> TYPE: DNA
<213> ORGANISM: Artificial
<220> FEATURE:
<223> OTHER INFORMATION: synthetic oligonucleotides

<400> SEQUENCE: 681
gtctattatt gtgctcgcak cakcakcakc akcakcakca kcgstwtkga ctactggggt    60
caagga    66

<210> SEQ ID NO 682
<211> LENGTH: 69
<212> TYPE: DNA
<213> ORGANISM: Artificial
<220> FEATURE:
<223> OTHER INFORMATION: synthetic oligonucleotides

<400> SEQUENCE: 682
gtctattatt gtgctcgcak cakcakcakc akcakcakca kcakcgstwt kgactactgg    60
ggtcaagga    69

<210> SEQ ID NO 683
<211> LENGTH: 72
<212> TYPE: DNA
<213> ORGANISM: Artificial
<220> FEATURE:
<223> OTHER INFORMATION: synthetic oligonucleotides

<400> SEQUENCE: 683
gtctattatt gtgctcgcak cakcakcakc akcakcakca kcakcakcgs twtkgactac    60
tggggtcaag ga    72

<210> SEQ ID NO 684
<211> LENGTH: 75
<212> TYPE: DNA
<213> ORGANISM: Artificial
<220> FEATURE:
<223> OTHER INFORMATION: synthetic oligonucleotides

<400> SEQUENCE: 684

```
gtctattatt gtgctcgcak cakcakcakc akcakcakca kcakcakcak cgstwtkgac        60
tactggggtc aagga                                                        75

<210> SEQ ID NO 685
<211> LENGTH: 78
<212> TYPE: DNA
<213> ORGANISM: Artificial
<220> FEATURE:
<223> OTHER INFORMATION: synthetic oligonucleotides

<400> SEQUENCE: 685
gtctattatt gtgctcgcak cakcakcakc akcakcakca kcakcakcak cakcgstwtk        60
gactactggg gtcaagga                                                     78

<210> SEQ ID NO 686
<211> LENGTH: 81
<212> TYPE: DNA
<213> ORGANISM: Artificial
<220> FEATURE:
<223> OTHER INFORMATION: synthetic oligonucleotides

<400> SEQUENCE: 686
gtctattatt gtgctcgcak cakcakcakc akcakcakca kcakcakcak cakcakcgst        60
wtkgactact ggggtcaagg a                                                 81

<210> SEQ ID NO 687
<211> LENGTH: 84
<212> TYPE: DNA
<213> ORGANISM: Artificial
<220> FEATURE:
<223> OTHER INFORMATION: synthetic oligonucleotides

<400> SEQUENCE: 687
gtctattatt gtgctcgcak cakcakcakc akcakcakca kcakcakcak cakcakcakc        60
gstwtkgact actggggtca agga                                              84

<210> SEQ ID NO 688
<211> LENGTH: 87
<212> TYPE: DNA
<213> ORGANISM: Artificial
<220> FEATURE:
<223> OTHER INFORMATION: synthetic oligonucleotides

<400> SEQUENCE: 688
gtctattatt gtgctcgcak cakcakcakc akcakcakca kcakcakcak cakcakcakc        60
akcgstwtkg actactgggg tcaagga                                           87

<210> SEQ ID NO 689
<211> LENGTH: 90
<212> TYPE: DNA
<213> ORGANISM: Artificial
<220> FEATURE:
<223> OTHER INFORMATION: synthetic oligonucleotides

<400> SEQUENCE: 689
gtctattatt gtgctcgcak cakcakcakc akcakcakca kcakcakcak cakcakcakc        60
akcakcgstw tkgactactg gggtcaagga                                        90

<210> SEQ ID NO 690
<211> LENGTH: 93
<212> TYPE: DNA
<213> ORGANISM: Artificial
```

```
<220> FEATURE:
<223> OTHER INFORMATION: synthetic oligonucleotides

<400> SEQUENCE: 690
gtctattatt gtgctcgcak cakcakcakc akcakcakca kcakcakcak cakcakcakc    60
akcakcakcg stwtkgacta ctggggtcaa gga                                 93

<210> SEQ ID NO 691
<211> LENGTH: 54
<212> TYPE: DNA
<213> ORGANISM: Artificial
<220> FEATURE:
<223> OTHER INFORMATION: synthetic oligonucleotides

<400> SEQUENCE: 691
gtctattatt gtgctcgcty atyatyatya gstwtkgact actggggtca agga          54

<210> SEQ ID NO 692
<211> LENGTH: 57
<212> TYPE: DNA
<213> ORGANISM: Artificial
<220> FEATURE:
<223> OTHER INFORMATION: synthetic oligonucleotides

<400> SEQUENCE: 692
gtctattatt gtgctcgcty atyatyatya tyagstwtkg actactgggg tcaagga       57

<210> SEQ ID NO 693
<211> LENGTH: 60
<212> TYPE: DNA
<213> ORGANISM: Artificial
<220> FEATURE:
<223> OTHER INFORMATION: synthetic oligonucleotides

<400> SEQUENCE: 693
gtctattatt gtgctcgcty atyatyatya tyatyagstw tkgactactg ggtcaagga    60

<210> SEQ ID NO 694
<211> LENGTH: 63
<212> TYPE: DNA
<213> ORGANISM: Artificial
<220> FEATURE:
<223> OTHER INFORMATION: synthetic oligonucleotides

<400> SEQUENCE: 694
gtctattatt gtgctcgcty atyatyatya tyatyatyag stwtkgacta ctggggtcaa   60
gga                                                                  63

<210> SEQ ID NO 695
<211> LENGTH: 66
<212> TYPE: DNA
<213> ORGANISM: Artificial
<220> FEATURE:
<223> OTHER INFORMATION: synthetic oligonucleotides

<400> SEQUENCE: 695
gtctattatt gtgctcgcty atyatyatya tyatyatyat yagstwtkga ctactggggt   60
caagga                                                               66

<210> SEQ ID NO 696
<211> LENGTH: 69
<212> TYPE: DNA
<213> ORGANISM: Artificial
<220> FEATURE:
```

<223> OTHER INFORMATION: synthetic oligonucleotides

<400> SEQUENCE: 696
gtctattatt gtgctcgcty atyatyatya tyatyatyat yatyagstwt kgactactgg    60
ggtcaagga    69

<210> SEQ ID NO 697
<211> LENGTH: 72
<212> TYPE: DNA
<213> ORGANISM: Artificial
<220> FEATURE:
<223> OTHER INFORMATION: synthetic oligonucleotides

<400> SEQUENCE: 697
gtctattatt gtgctcgcty atyatyatya tyatyatyat yatyatyags twtkgactac    60
tggggtcaag ga    72

<210> SEQ ID NO 698
<211> LENGTH: 75
<212> TYPE: DNA
<213> ORGANISM: Artificial
<220> FEATURE:
<223> OTHER INFORMATION: synthetic oligonucleotides

<400> SEQUENCE: 698
gtctattatt gtgctcgcty atyatyatya tyatyatyat yatyatyaty agstwtkgac    60
tactggggtc aagga    75

<210> SEQ ID NO 699
<211> LENGTH: 78
<212> TYPE: DNA
<213> ORGANISM: Artificial
<220> FEATURE:
<223> OTHER INFORMATION: synthetic oligonucleotides

<400> SEQUENCE: 699
gtctattatt gtgctcgcty atyatyatya tyatyatyat yatyatyaty atyagstwtk    60
gactactggg gtcaagga    78

<210> SEQ ID NO 700
<211> LENGTH: 81
<212> TYPE: DNA
<213> ORGANISM: Artificial
<220> FEATURE:
<223> OTHER INFORMATION: synthetic oligonucleotides

<400> SEQUENCE: 700
gtctattatt gtgctcgcty atyatyatya tyatyatyat yatyatyaty atyatyagst    60
wtkgactact ggggtcaagg a    81

<210> SEQ ID NO 701
<211> LENGTH: 84
<212> TYPE: DNA
<213> ORGANISM: Artificial
<220> FEATURE:
<223> OTHER INFORMATION: synthetic oligonucleotides

<400> SEQUENCE: 701
gtctattatt gtgctcgcty atyatyatya tyatyatyat yatyatyaty atyatyatya    60
gstwtkgact actggggtca agga    84

```
<210> SEQ ID NO 702
<211> LENGTH: 87
<212> TYPE: DNA
<213> ORGANISM: Artificial
<220> FEATURE:
<223> OTHER INFORMATION: synthetic oligonucleotides

<400> SEQUENCE: 702
gtctattatt gtgctcgcty atyatyatya tyatyatyat yatyatyaty atyatyatya        60
tyagstwtkg actactgggg tcaagga                                            87

<210> SEQ ID NO 703
<211> LENGTH: 90
<212> TYPE: DNA
<213> ORGANISM: Artificial
<220> FEATURE:
<223> OTHER INFORMATION: synthetic oligonucleotides

<400> SEQUENCE: 703
gtctattatt gtgctcgcty atyatyatya tyatyatyat yatyatyaty atyatyatya        60
tyatyagstw tkgactactg gggtcaagga                                         90

<210> SEQ ID NO 704
<211> LENGTH: 93
<212> TYPE: DNA
<213> ORGANISM: Artificial
<220> FEATURE:
<223> OTHER INFORMATION: synthetic oligonucleotides

<400> SEQUENCE: 704
gtctattatt gtgctcgcty atyatyatya tyatyatyat yatyatyaty atyatyatya        60
tyatyatyag stwtkgacta ctggggtcaa gga                                     93

<210> SEQ ID NO 705
<211> LENGTH: 54
<212> TYPE: DNA
<213> ORGANISM: Artificial
<220> FEATURE:
<223> OTHER INFORMATION: synthetic oligonucleotides

<400> SEQUENCE: 705
gtctattatt gtgctcgcar carcarcarc gstwtkgact actggggtca agga              54

<210> SEQ ID NO 706
<211> LENGTH: 57
<212> TYPE: DNA
<213> ORGANISM: Artificial
<220> FEATURE:
<223> OTHER INFORMATION: synthetic oligonucleotides

<400> SEQUENCE: 706
gtctattatt gtgctcgcar carcarcarc arcgstwtkg actactgggg tcaagga           57

<210> SEQ ID NO 707
<211> LENGTH: 60
<212> TYPE: DNA
<213> ORGANISM: Artificial
<220> FEATURE:
<223> OTHER INFORMATION: synthetic oligonucleotides

<400> SEQUENCE: 707
gtctattatt gtgctcgcar carcarcarc arcarcgstw tkgactactg gggtcaagga        60

<210> SEQ ID NO 708
```

```
<211> LENGTH: 63
<212> TYPE: DNA
<213> ORGANISM: Artificial
<220> FEATURE:
<223> OTHER INFORMATION: synthetic oligonucleotides

<400> SEQUENCE: 708
gtctattatt gtgctcgcar carcarcarc arcarcarcg stwtkgacta ctggggtcaa    60
gga                                                                 63

<210> SEQ ID NO 709
<211> LENGTH: 66
<212> TYPE: DNA
<213> ORGANISM: Artificial
<220> FEATURE:
<223> OTHER INFORMATION: synthetic oligonucleotides

<400> SEQUENCE: 709
gtctattatt gtgctcgcar carcarcarc arcarcarca rcgstwtkga ctactggggt    60
caagga                                                              66

<210> SEQ ID NO 710
<211> LENGTH: 69
<212> TYPE: DNA
<213> ORGANISM: Artificial
<220> FEATURE:
<223> OTHER INFORMATION: synthetic oligonucleotides

<400> SEQUENCE: 710
gtctattatt gtgctcgcar carcarcarc arcarcarca rcarcgstwt kgactactgg    60
ggtcaagga                                                           69

<210> SEQ ID NO 711
<211> LENGTH: 72
<212> TYPE: DNA
<213> ORGANISM: Artificial
<220> FEATURE:
<223> OTHER INFORMATION: synthetic oligonucleotides

<400> SEQUENCE: 711
gtctattatt gtgctcgcar carcarcarc arcarcarca rcarcarcgs twtkgactac    60
tggggtcaag ga                                                       72

<210> SEQ ID NO 712
<211> LENGTH: 75
<212> TYPE: DNA
<213> ORGANISM: Artificial
<220> FEATURE:
<223> OTHER INFORMATION: synthetic oligonucleotides

<400> SEQUENCE: 712
gtctattatt gtgctcgcar carcarcarc arcarcarca rcarcarcar cgstwtkgac    60
tactggggtc aagga                                                    75

<210> SEQ ID NO 713
<211> LENGTH: 78
<212> TYPE: DNA
<213> ORGANISM: Artificial
<220> FEATURE:
<223> OTHER INFORMATION: synthetic oligonucleotides

<400> SEQUENCE: 713
gtctattatt gtgctcgcar carcarcarc arcarcarca rcarcarcar carcgstwtk    60
```

```
gactactggg gtcaagga                                              78

<210> SEQ ID NO 714
<211> LENGTH: 81
<212> TYPE: DNA
<213> ORGANISM: Artificial
<220> FEATURE:
<223> OTHER INFORMATION: synthetic oligonucleotides

<400> SEQUENCE: 714
gtctattatt gtgctcgcar carcarcarc arcarcarca rcarcarcar carcarcgst      60
wtkgactact ggggtcaagg a                                               81

<210> SEQ ID NO 715
<211> LENGTH: 84
<212> TYPE: DNA
<213> ORGANISM: Artificial
<220> FEATURE:
<223> OTHER INFORMATION: synthetic oligonucleotides

<400> SEQUENCE: 715
gtctattatt gtgctcgcar carcarcarc arcarcarca rcarcarcar carcarcarc      60
gstwtkgact actggggtca agga                                            84

<210> SEQ ID NO 716
<211> LENGTH: 87
<212> TYPE: DNA
<213> ORGANISM: Artificial
<220> FEATURE:
<223> OTHER INFORMATION: synthetic oligonucleotides

<400> SEQUENCE: 716
gtctattatt gtgctcgcar carcarcarc arcarcarca rcarcarcar carcarcarc      60
arcgstwtkg actactgggg tcaagga                                         87

<210> SEQ ID NO 717
<211> LENGTH: 90
<212> TYPE: DNA
<213> ORGANISM: Artificial
<220> FEATURE:
<223> OTHER INFORMATION: synthetic oligonucleotides

<400> SEQUENCE: 717
gtctattatt gtgctcgcar carcarcarc arcarcarca rcarcarcar carcarcarc      60
arcarcgstw tkgactactg gggtcaagga                                      90

<210> SEQ ID NO 718
<211> LENGTH: 93
<212> TYPE: DNA
<213> ORGANISM: Artificial
<220> FEATURE:
<223> OTHER INFORMATION: synthetic oligonucleotides

<400> SEQUENCE: 718
gtctattatt gtgctcgcar carcarcarc arcarcarca rcarcarcar carcarcarc      60
arcarcarcg stwtkgacta ctggggtcaa gga                                  93

<210> SEQ ID NO 719
<211> LENGTH: 54
<212> TYPE: DNA
<213> ORGANISM: Artificial
<220> FEATURE:
```

<223> OTHER INFORMATION: synthetic oligonucleotides

<400> SEQUENCE: 719
gtctattatt gtgctcgcyc tyctyctyct gstwtkgact actggggtca agga      54

<210> SEQ ID NO 720
<211> LENGTH: 57
<212> TYPE: DNA
<213> ORGANISM: Artificial
<220> FEATURE:
<223> OTHER INFORMATION: synthetic oligonucleotides

<400> SEQUENCE: 720
gtctattatt gtgctcgcyc tyctyctyct yctgstwtkg actactgggg tcaagga      57

<210> SEQ ID NO 721
<211> LENGTH: 60
<212> TYPE: DNA
<213> ORGANISM: Artificial
<220> FEATURE:
<223> OTHER INFORMATION: synthetic oligonucleotides

<400> SEQUENCE: 721
gtctattatt gtgctcgcyc tyctyctyct yctyctgstw tkgactactg ggtcaagga      60

<210> SEQ ID NO 722
<211> LENGTH: 63
<212> TYPE: DNA
<213> ORGANISM: Artificial
<220> FEATURE:
<223> OTHER INFORMATION: synthetic oligonucleotides

<400> SEQUENCE: 722
gtctattatt gtgctcgcyc tyctyctyct yctyctyctg stwtkgacta ctggggtcaa      60
gga      63

<210> SEQ ID NO 723
<211> LENGTH: 66
<212> TYPE: DNA
<213> ORGANISM: Artificial
<220> FEATURE:
<223> OTHER INFORMATION: synthetic oligonucleotides

<400> SEQUENCE: 723
gtctattatt gtgctcgcyc tyctyctyct yctyctycty ctgstwtkga ctactggggt      60
caagga      66

<210> SEQ ID NO 724
<211> LENGTH: 69
<212> TYPE: DNA
<213> ORGANISM: Artificial
<220> FEATURE:
<223> OTHER INFORMATION: synthetic oligonucleotides

<400> SEQUENCE: 724
gtctattatt gtgctcgcyc tyctyctyct yctyctycty ctyctgstwt kgactactgg      60
ggtcaagga      69

<210> SEQ ID NO 725
<211> LENGTH: 72
<212> TYPE: DNA
<213> ORGANISM: Artificial
<220> FEATURE:
<223> OTHER INFORMATION: synthetic oligonucleotides

<400> SEQUENCE: 725
gtctattatt gtgctcgcyc tyctyctyct yctyctycty ctyctyctgs twtkgactac    60
tggggtcaag ga    72

<210> SEQ ID NO 726
<211> LENGTH: 75
<212> TYPE: DNA
<213> ORGANISM: Artificial
<220> FEATURE:
<223> OTHER INFORMATION: synthetic oligonucleotides

<400> SEQUENCE: 726
gtctattatt gtgctcgcyc tyctyctyct yctyctycty ctyctyctyc tgstwtkgac    60
tactggggtc aagga    75

<210> SEQ ID NO 727
<211> LENGTH: 78
<212> TYPE: DNA
<213> ORGANISM: Artificial
<220> FEATURE:
<223> OTHER INFORMATION: synthetic oligonucleotides

<400> SEQUENCE: 727
gtctattatt gtgctcgcyc tyctyctyct yctyctycty ctyctyctyc tyctgstwtk    60
gactactggg gtcaagga    78

<210> SEQ ID NO 728
<211> LENGTH: 81
<212> TYPE: DNA
<213> ORGANISM: Artificial
<220> FEATURE:
<223> OTHER INFORMATION: synthetic oligonucleotides

<400> SEQUENCE: 728
gtctattatt gtgctcgcyc tyctyctyct yctyctycty ctyctyctyc tyctyctgst    60
wtkgactact ggggtcaagg a    81

<210> SEQ ID NO 729
<211> LENGTH: 84
<212> TYPE: DNA
<213> ORGANISM: Artificial
<220> FEATURE:
<223> OTHER INFORMATION: synthetic oligonucleotides

<400> SEQUENCE: 729
gtctattatt gtgctcgcyc tyctyctyct yctyctycty ctyctyctyc tyctyctyct    60
gstwtkgact actggggtca agga    84

<210> SEQ ID NO 730
<211> LENGTH: 87
<212> TYPE: DNA
<213> ORGANISM: Artificial
<220> FEATURE:
<223> OTHER INFORMATION: synthetic oligonucleotides

<400> SEQUENCE: 730
gtctattatt gtgctcgcyc tyctyctyct yctyctycty ctyctyctyc tyctyctyct    60
yctgstwtkg actactgggg tcaagga    87

<210> SEQ ID NO 731

```
<211> LENGTH: 90
<212> TYPE: DNA
<213> ORGANISM: Artificial
<220> FEATURE:
<223> OTHER INFORMATION: synthetic oligonucleotides

<400> SEQUENCE: 731
gtctattatt gtgctcgcyc tyctyctyct yctyctycty ctyctyctyc tyctyctyct      60
yctyctgstw tkgactactg gggtcaagga                                       90

<210> SEQ ID NO 732
<211> LENGTH: 93
<212> TYPE: DNA
<213> ORGANISM: Artificial
<220> FEATURE:
<223> OTHER INFORMATION: synthetic oligonucleotides

<400> SEQUENCE: 732
gtctattatt gtgctcgcyc tyctyctyct yctyctycty ctyctyctyc tyctyctyct      60
yctyctyctg stwtkgacta ctggggtcaa gga                                   93

<210> SEQ ID NO 733
<211> LENGTH: 54
<212> TYPE: DNA
<213> ORGANISM: Artificial
<220> FEATURE:
<223> OTHER INFORMATION: synthetic oligonucleotides

<400> SEQUENCE: 733
gtctattatt gtgctcgcmg cmgcmgcmgc gstwtkgact actggggtca agga            54

<210> SEQ ID NO 734
<211> LENGTH: 57
<212> TYPE: DNA
<213> ORGANISM: Artificial
<220> FEATURE:
<223> OTHER INFORMATION: synthetic oligonucleotides

<400> SEQUENCE: 734
gtctattatt gtgctcgcmg cmgcmgcmgc mgcgstwtkg actactgggg tcaagga         57

<210> SEQ ID NO 735
<211> LENGTH: 60
<212> TYPE: DNA
<213> ORGANISM: Artificial
<220> FEATURE:
<223> OTHER INFORMATION: synthetic oligonucleotides

<400> SEQUENCE: 735
gtctattatt gtgctcgcmg cmgcmgcmgc mgcmgcgstw tkgactactg ggtcaagga       60

<210> SEQ ID NO 736
<211> LENGTH: 63
<212> TYPE: DNA
<213> ORGANISM: Artificial
<220> FEATURE:
<223> OTHER INFORMATION: synthetic oligonucleotides

<400> SEQUENCE: 736
gtctattatt gtgctcgcmg cmgcmgcmgc mgcmgcmgcg stwtkgacta ctggggtcaa      60
gga                                                                    63

<210> SEQ ID NO 737
<211> LENGTH: 66
```

```
<212> TYPE: DNA
<213> ORGANISM: Artificial
<220> FEATURE:
<223> OTHER INFORMATION: synthetic oligonucleotides

<400> SEQUENCE: 737
gtctattatt gtgctcgcmg cmgcmgcmgc mgcmgcmgcm gcgstwtkga ctactggggt      60
caagga                                                                66

<210> SEQ ID NO 738
<211> LENGTH: 69
<212> TYPE: DNA
<213> ORGANISM: Artificial
<220> FEATURE:
<223> OTHER INFORMATION: synthetic oligonucleotides

<400> SEQUENCE: 738
gtctattatt gtgctcgcmg cmgcmgcmgc mgcmgcmgcm gcmgcgstwt kgactactgg      60
ggtcaagga                                                             69

<210> SEQ ID NO 739
<211> LENGTH: 72
<212> TYPE: DNA
<213> ORGANISM: Artificial
<220> FEATURE:
<223> OTHER INFORMATION: synthetic oligonucleotides

<400> SEQUENCE: 739
gtctattatt gtgctcgcmg cmgcmgcmgc mgcmgcmgcm gcmgcmgcgs twtkgactac      60
tggggtcaag ga                                                         72

<210> SEQ ID NO 740
<211> LENGTH: 75
<212> TYPE: DNA
<213> ORGANISM: Artificial
<220> FEATURE:
<223> OTHER INFORMATION: synthetic oligonucleotides

<400> SEQUENCE: 740
gtctattatt gtgctcgcmg cmgcmgcmgc mgcmgcmgcm gcmgcmgcmg cgstwtkgac      60
tactggggtc aagga                                                      75

<210> SEQ ID NO 741
<211> LENGTH: 78
<212> TYPE: DNA
<213> ORGANISM: Artificial
<220> FEATURE:
<223> OTHER INFORMATION: synthetic oligonucleotides

<400> SEQUENCE: 741
gtctattatt gtgctcgcmg cmgcmgcmgc mgcmgcmgcm gcmgcmgcmg cmgcgstwtk      60
gactactggg gtcaagga                                                   78

<210> SEQ ID NO 742
<211> LENGTH: 81
<212> TYPE: DNA
<213> ORGANISM: Artificial
<220> FEATURE:
<223> OTHER INFORMATION: synthetic oligonucleotides

<400> SEQUENCE: 742
gtctattatt gtgctcgcmg cmgcmgcmgc mgcmgcmgcm gcmgcmgcmg cmgcmgcgst      60
```

```
wtkgactact ggggtcaagg a                                              81

<210> SEQ ID NO 743
<211> LENGTH: 84
<212> TYPE: DNA
<213> ORGANISM: Artificial
<220> FEATURE:
<223> OTHER INFORMATION: synthetic oligonucleotides

<400> SEQUENCE: 743
gtctattatt gtgctcgcmg cmgcmgcmgc mgcmgcmgcm gcmgcmgcmg cmgcmgcmgc    60
gstwtkgact actggggtca agga                                           84

<210> SEQ ID NO 744
<211> LENGTH: 87
<212> TYPE: DNA
<213> ORGANISM: Artificial
<220> FEATURE:
<223> OTHER INFORMATION: synthetic oligonucleotides

<400> SEQUENCE: 744
gtctattatt gtgctcgcmg cmgcmgcmgc mgcmgcmgcm gcmgcmgcmg cmgcmgcmgc    60
mgcgstwtkg actactgggg tcaagga                                        87

<210> SEQ ID NO 745
<211> LENGTH: 90
<212> TYPE: DNA
<213> ORGANISM: Artificial
<220> FEATURE:
<223> OTHER INFORMATION: synthetic oligonucleotides

<400> SEQUENCE: 745
gtctattatt gtgctcgcmg cmgcmgcmgc mgcmgcmgcm gcmgcmgcmg cmgcmgcmgc    60
mgcmgcgstw tkgactactg gggtcaagga                                     90

<210> SEQ ID NO 746
<211> LENGTH: 93
<212> TYPE: DNA
<213> ORGANISM: Artificial
<220> FEATURE:
<223> OTHER INFORMATION: synthetic oligonucleotides

<400> SEQUENCE: 746
gtctattatt gtgctcgcmg cmgcmgcmgc mgcmgcmgcm gcmgcmgcmg cmgcmgcmgc    60
mgcmgcmgcg stwtkgacta ctggggtcaa gga                                 93

<210> SEQ ID NO 747
<211> LENGTH: 54
<212> TYPE: DNA
<213> ORGANISM: Artificial
<220> FEATURE:
<223> OTHER INFORMATION: synthetic oligonucleotides

<400> SEQUENCE: 747
gtctattatt gtgctcgcas cascascasc gstwtkgact actggggtca agga           54

<210> SEQ ID NO 748
<211> LENGTH: 57
<212> TYPE: DNA
<213> ORGANISM: Artificial
<220> FEATURE:
<223> OTHER INFORMATION: synthetic oligonucleotides

<400> SEQUENCE: 748
```

```
gtctattatt gtgctcgcas cascascasc ascgstwtkg actactgggg tcaagga        57
```

<210> SEQ ID NO 749
<211> LENGTH: 60
<212> TYPE: DNA
<213> ORGANISM: Artificial
<220> FEATURE:
<223> OTHER INFORMATION: synthetic oligonucleotides

<400> SEQUENCE: 749

```
gtctattatt gtgctcgcas cascascasc ascascgstw tkgactactg gggtcaagga      60
```

<210> SEQ ID NO 750
<211> LENGTH: 63
<212> TYPE: DNA
<213> ORGANISM: Artificial
<220> FEATURE:
<223> OTHER INFORMATION: synthetic oligonucleotides

<400> SEQUENCE: 750

```
gtctattatt gtgctcgcas cascascasc ascascascg stwtkgacta ctggggtcaa      60
gga                                                                    63
```

<210> SEQ ID NO 751
<211> LENGTH: 66
<212> TYPE: DNA
<213> ORGANISM: Artificial
<220> FEATURE:
<223> OTHER INFORMATION: synthetic oligonucleotides

<400> SEQUENCE: 751

```
gtctattatt gtgctcgcas cascascasc ascascasca scgstwtkga ctactggggt      60
caagga                                                                 66
```

<210> SEQ ID NO 752
<211> LENGTH: 69
<212> TYPE: DNA
<213> ORGANISM: Artificial
<220> FEATURE:
<223> OTHER INFORMATION: synthetic oligonucleotides

<400> SEQUENCE: 752

```
gtctattatt gtgctcgcas cascascasc ascascasca scascgstwt kgactactgg      60
ggtcaagga                                                              69
```

<210> SEQ ID NO 753
<211> LENGTH: 72
<212> TYPE: DNA
<213> ORGANISM: Artificial
<220> FEATURE:
<223> OTHER INFORMATION: synthetic oligonucleotides

<400> SEQUENCE: 753

```
gtctattatt gtgctcgcas cascascasc ascascasca scascascgs twtkgactac      60
tggggtcaag ga                                                          72
```

<210> SEQ ID NO 754
<211> LENGTH: 75
<212> TYPE: DNA
<213> ORGANISM: Artificial
<220> FEATURE:
<223> OTHER INFORMATION: synthetic oligonucleotides

```
<400> SEQUENCE: 754
gtctattatt gtgctcgcas cascascasc ascascasca scascascas cgstwtkgac      60
tactggggtc aagga                                                       75

<210> SEQ ID NO 755
<211> LENGTH: 78
<212> TYPE: DNA
<213> ORGANISM: Artificial
<220> FEATURE:
<223> OTHER INFORMATION: synthetic oligonucleotides

<400> SEQUENCE: 755
gtctattatt gtgctcgcas cascascasc ascascasca scascascas cascgstwtk      60
gactactggg gtcaagga                                                    78

<210> SEQ ID NO 756
<211> LENGTH: 81
<212> TYPE: DNA
<213> ORGANISM: Artificial
<220> FEATURE:
<223> OTHER INFORMATION: synthetic oligonucleotides

<400> SEQUENCE: 756
gtctattatt gtgctcgcas cascascasc ascascasca scascascas cascascgst      60
wtkgactact ggggtcaagg a                                                81

<210> SEQ ID NO 757
<211> LENGTH: 84
<212> TYPE: DNA
<213> ORGANISM: Artificial
<220> FEATURE:
<223> OTHER INFORMATION: synthetic oligonucleotides

<400> SEQUENCE: 757
gtctattatt gtgctcgcas cascascasc ascascasca scascascas cascascasc      60
gstwtkgact actggggtca agga                                             84

<210> SEQ ID NO 758
<211> LENGTH: 87
<212> TYPE: DNA
<213> ORGANISM: Artificial
<220> FEATURE:
<223> OTHER INFORMATION: synthetic oligonucleotides

<400> SEQUENCE: 758
gtctattatt gtgctcgcas cascascasc ascascasca scascascas cascascasc      60
ascgstwtkg actactgggg tcaagga                                          87

<210> SEQ ID NO 759
<211> LENGTH: 90
<212> TYPE: DNA
<213> ORGANISM: Artificial
<220> FEATURE:
<223> OTHER INFORMATION: synthetic oligonucleotides

<400> SEQUENCE: 759
gtctattatt gtgctcgcas cascascasc ascascasca scascascas cascascasc      60
ascascgstw tkgactactg gggtcaagga                                       90

<210> SEQ ID NO 760
<211> LENGTH: 93
```

```
<212> TYPE: DNA
<213> ORGANISM: Artificial
<220> FEATURE:
<223> OTHER INFORMATION: synthetic oligonucleotides

<400> SEQUENCE: 760
gtctattatt gtgctcgcas cascascasc ascascasca scascascas cascascasc    60
ascascascg stwtkgacta ctggggtcaa gga                                 93

<210> SEQ ID NO 761
<211> LENGTH: 54
<212> TYPE: DNA
<213> ORGANISM: Artificial
<220> FEATURE:
<223> OTHER INFORMATION: synthetic oligonucleotides

<400> SEQUENCE: 761
gtctattatt gtgctcgcts gtsgtsgtsg gstwtkgact actgggtca agga            54

<210> SEQ ID NO 762
<211> LENGTH: 57
<212> TYPE: DNA
<213> ORGANISM: Artificial
<220> FEATURE:
<223> OTHER INFORMATION: synthetic oligonucleotides

<400> SEQUENCE: 762
gtctattatt gtgctcgcts gtsgtsgtsg tsggstwtkg actactgggg tcaagga        57

<210> SEQ ID NO 763
<211> LENGTH: 60
<212> TYPE: DNA
<213> ORGANISM: Artificial
<220> FEATURE:
<223> OTHER INFORMATION: synthetic oligonucleotides

<400> SEQUENCE: 763
gtctattatt gtgctcgcts gtsgtsgtsg tsgtsggstw tkgactactg gggtcaagga    60

<210> SEQ ID NO 764
<211> LENGTH: 63
<212> TYPE: DNA
<213> ORGANISM: Artificial
<220> FEATURE:
<223> OTHER INFORMATION: synthetic oligonucleotides

<400> SEQUENCE: 764
gtctattatt gtgctcgcts gtsgtsgtsg tsgtsgtsgg stwtkgacta ctggggtcaa    60
gga                                                                  63

<210> SEQ ID NO 765
<211> LENGTH: 66
<212> TYPE: DNA
<213> ORGANISM: Artificial
<220> FEATURE:
<223> OTHER INFORMATION: synthetic oligonucleotides

<400> SEQUENCE: 765
gtctattatt gtgctcgcts gtsgtsgtsg tsgtsgtsgt sggstwtkga ctactggggt    60
caagga                                                               66

<210> SEQ ID NO 766
<211> LENGTH: 69
<212> TYPE: DNA
```

<213> ORGANISM: Artificial
<220> FEATURE:
<223> OTHER INFORMATION: synthetic oligonucleotides

<400> SEQUENCE: 766
gtctattatt gtgctcgcts gtsgtsgtsg tsgtsgtsgt sgtsggstwt kgactactgg    60
ggtcaagga                                                           69

<210> SEQ ID NO 767
<211> LENGTH: 72
<212> TYPE: DNA
<213> ORGANISM: Artificial
<220> FEATURE:
<223> OTHER INFORMATION: synthetic oligonucleotides

<400> SEQUENCE: 767
gtctattatt gtgctcgcts gtsgtsgtsg tsgtsgtsgt sgtsgtsggs twtkgactac    60
tggggtcaag ga                                                       72

<210> SEQ ID NO 768
<211> LENGTH: 75
<212> TYPE: DNA
<213> ORGANISM: Artificial
<220> FEATURE:
<223> OTHER INFORMATION: synthetic oligonucleotides

<400> SEQUENCE: 768
gtctattatt gtgctcgcts gtsgtsgtsg tsgtsgtsgt sgtsgtsgts ggstwtkgac    60
tactggggtc aagga                                                    75

<210> SEQ ID NO 769
<211> LENGTH: 78
<212> TYPE: DNA
<213> ORGANISM: Artificial
<220> FEATURE:
<223> OTHER INFORMATION: synthetic oligonucleotides

<400> SEQUENCE: 769
gtctattatt gtgctcgcts gtsgtsgtsg tsgtsgtsgt sgtsgtsgts gtsggstwtk    60
gactactggg gtcaagga                                                 78

<210> SEQ ID NO 770
<211> LENGTH: 81
<212> TYPE: DNA
<213> ORGANISM: Artificial
<220> FEATURE:
<223> OTHER INFORMATION: synthetic oligonucleotides

<400> SEQUENCE: 770
gtctattatt gtgctcgcts gtsgtsgtsg tsgtsgtsgt sgtsgtsgts gtsgtsggst    60
wtkgactact ggggtcaagg a                                             81

<210> SEQ ID NO 771
<211> LENGTH: 84
<212> TYPE: DNA
<213> ORGANISM: Artificial
<220> FEATURE:
<223> OTHER INFORMATION: synthetic oligonucleotides

<400> SEQUENCE: 771
gtctattatt gtgctcgcts gtsgtsgtsg tsgtsgtsgt sgtsgtsgts gtsgtsgtsg    60
gstwtkgact actggggtca agga                                          84

```
<210> SEQ ID NO 772
<211> LENGTH: 87
<212> TYPE: DNA
<213> ORGANISM: Artificial
<220> FEATURE:
<223> OTHER INFORMATION: synthetic oligonucleotides

<400> SEQUENCE: 772
gtctattatt gtgctcgcts gtsgtsgtsg tsgtsgtsgt sgtsgtsgts gtsgtsgtsg      60
tsggstwtkg actactgggg tcaagga                                         87

<210> SEQ ID NO 773
<211> LENGTH: 90
<212> TYPE: DNA
<213> ORGANISM: Artificial
<220> FEATURE:
<223> OTHER INFORMATION: synthetic oligonucleotides

<400> SEQUENCE: 773
gtctattatt gtgctcgcts gtsgtsgtsg tsgtsgtsgt sgtsgtsgts gtsgtsgtsg      60
tsgtsggstw tkgactactg gggtcaagga                                      90

<210> SEQ ID NO 774
<211> LENGTH: 93
<212> TYPE: DNA
<213> ORGANISM: Artificial
<220> FEATURE:
<223> OTHER INFORMATION: synthetic oligonucleotides

<400> SEQUENCE: 774
gtctattatt gtgctcgcts gtsgtsgtsg tsgtsgtsgt sgtsgtsgts gtsgtsgtsg      60
tsgtsgtsgg stwtkgacta ctggggtcaa gga                                  93

<210> SEQ ID NO 775
<211> LENGTH: 54
<212> TYPE: DNA
<213> ORGANISM: Artificial
<220> FEATURE:
<223> OTHER INFORMATION: synthetic oligonucleotides

<400> SEQUENCE: 775
gtctattatt gtgctcgctm ttmttmttmt gstwtkgact actggggtca agga            54

<210> SEQ ID NO 776
<211> LENGTH: 57
<212> TYPE: DNA
<213> ORGANISM: Artificial
<220> FEATURE:
<223> OTHER INFORMATION: synthetic oligonucleotides

<400> SEQUENCE: 776
gtctattatt gtgctcgctm ttmttmttmt tmtgstwtkg actactgggg tcaagga         57

<210> SEQ ID NO 777
<211> LENGTH: 60
<212> TYPE: DNA
<213> ORGANISM: Artificial
<220> FEATURE:
<223> OTHER INFORMATION: synthetic oligonucleotides

<400> SEQUENCE: 777
gtctattatt gtgctcgctm ttmttmttmt tmttmtgstw tkgactactg ggtcaagga       60
```

<210> SEQ ID NO 778
<211> LENGTH: 63
<212> TYPE: DNA
<213> ORGANISM: Artificial
<220> FEATURE:
<223> OTHER INFORMATION: synthetic oligonucleotides

<400> SEQUENCE: 778
gtctattatt gtgctcgctm ttmttmttmt tmttmttmtg stwtkgacta ctggggtcaa   60
gga                                                                 63

<210> SEQ ID NO 779
<211> LENGTH: 66
<212> TYPE: DNA
<213> ORGANISM: Artificial
<220> FEATURE:
<223> OTHER INFORMATION: synthetic oligonucleotides

<400> SEQUENCE: 779
gtctattatt gtgctcgctm ttmttmttmt tmttmttmtt mtgstwtkga ctactgggt    60 caagga                                                              66

<210> SEQ ID NO 780
<211> LENGTH: 69
<212> TYPE: DNA
<213> ORGANISM: Artificial
<220> FEATURE:
<223> OTHER INFORMATION: synthetic oligonucleotides

<400> SEQUENCE: 780
gtctattatt gtgctcgctm ttmttmttmt tmttmttmtt mttmtgstwt kgactactgg   60
ggtcaagga                                                           69

<210> SEQ ID NO 781
<211> LENGTH: 72
<212> TYPE: DNA
<213> ORGANISM: Artificial
<220> FEATURE:
<223> OTHER INFORMATION: synthetic oligonucleotides

<400> SEQUENCE: 781
gtctattatt gtgctcgctm ttmttmttmt tmttmttmtt mttmttmtgs twtkgactac   60
tggggtcaag ga                                                       72

<210> SEQ ID NO 782
<211> LENGTH: 75
<212> TYPE: DNA
<213> ORGANISM: Artificial
<220> FEATURE:
<223> OTHER INFORMATION: synthetic oligonucleotides

<400> SEQUENCE: 782
gtctattatt gtgctcgctm ttmttmttmt tmttmttmtt mttmttmttm tgstwtkgac   60
tactggggtc aagga                                                    75

<210> SEQ ID NO 783
<211> LENGTH: 78
<212> TYPE: DNA
<213> ORGANISM: Artificial
<220> FEATURE:
<223> OTHER INFORMATION: synthetic oligonucleotides

<400> SEQUENCE: 783

```
gtctattatt gtgctcgctm ttmttmttmt tmttmttmtt mttmttmttm ttmtgstwtk    60
gactactggg gtcaagga                                                  78
```

<210> SEQ ID NO 784
<211> LENGTH: 81
<212> TYPE: DNA
<213> ORGANISM: Artificial
<220> FEATURE:
<223> OTHER INFORMATION: synthetic oligonucleotides

<400> SEQUENCE: 784

```
gtctattatt gtgctcgctm ttmttmttmt tmttmttmtt mttmttmttm ttmttmtgst    60
wtkgactact ggggtcaagg a                                              81
```

<210> SEQ ID NO 785
<211> LENGTH: 84
<212> TYPE: DNA
<213> ORGANISM: Artificial
<220> FEATURE:
<223> OTHER INFORMATION: synthetic oligonucleotides

<400> SEQUENCE: 785

```
gtctattatt gtgctcgctm ttmttmttmt tmttmttmtt mttmttmttm ttmttmttmt    60
gstwtkgact actggggtca agga                                           84
```

<210> SEQ ID NO 786
<211> LENGTH: 87
<212> TYPE: DNA
<213> ORGANISM: Artificial
<220> FEATURE:
<223> OTHER INFORMATION: synthetic oligonucleotides

<400> SEQUENCE: 786

```
gtctattatt gtgctcgctm ttmttmttmt tmttmttmtt mttmttmttm ttmttmttmt    60
tmtgstwtkg actactgggg tcaagga                                        87
```

<210> SEQ ID NO 787
<211> LENGTH: 90
<212> TYPE: DNA
<213> ORGANISM: Artificial
<220> FEATURE:
<223> OTHER INFORMATION: synthetic oligonucleotides

<400> SEQUENCE: 787

```
gtctattatt gtgctcgctm ttmttmttmt tmttmttmtt mttmttmttm ttmttmttmt    60
tmttmtgstw tkgactactg gggtcaagga                                     90
```

<210> SEQ ID NO 788
<211> LENGTH: 93
<212> TYPE: DNA
<213> ORGANISM: Artificial
<220> FEATURE:
<223> OTHER INFORMATION: synthetic oligonucleotides

<400> SEQUENCE: 788

```
gtctattatt gtgctcgctm ttmttmttmt tmttmttmtt mttmttmttm ttmttmttmt    60
tmttmttmtg stwtkgacta ctggggtcaa gga                                 93
```

<210> SEQ ID NO 789
<211> LENGTH: 9
<212> TYPE: PRT

<213> ORGANISM: Artificial
<220> FEATURE:
<223> OTHER INFORMATION: synthetic CDRL3

<400> SEQUENCE: 789

Gln Gln Ser Tyr Tyr Ser Pro Ser Thr
1               5

<210> SEQ ID NO 790
<211> LENGTH: 9
<212> TYPE: PRT
<213> ORGANISM: Artificial
<220> FEATURE:
<223> OTHER INFORMATION: synthetic CDRL3

<400> SEQUENCE: 790

Gln Gln Ser Tyr Tyr Ser Pro Ser Thr
1               5

<210> SEQ ID NO 791
<211> LENGTH: 9
<212> TYPE: PRT
<213> ORGANISM: Artificial
<220> FEATURE:
<223> OTHER INFORMATION: synthetic CDRL3

<400> SEQUENCE: 791

Gln Gln Ser Tyr Tyr Tyr Pro Ser Thr
1               5

<210> SEQ ID NO 792
<211> LENGTH: 9
<212> TYPE: PRT
<213> ORGANISM: Artificial
<220> FEATURE:
<223> OTHER INFORMATION: synthetic CDRL3

<400> SEQUENCE: 792

Gln Gln Ser Tyr Tyr Ser Pro Ser Thr
1               5

<210> SEQ ID NO 793
<211> LENGTH: 9
<212> TYPE: PRT
<213> ORGANISM: Artificial
<220> FEATURE:
<223> OTHER INFORMATION: synthetic CDRL3

<400> SEQUENCE: 793

Gln Gln Ser Tyr Tyr Ser Pro Ser Thr
1               5

<210> SEQ ID NO 794
<211> LENGTH: 9
<212> TYPE: PRT
<213> ORGANISM: Artificial
<220> FEATURE:
<223> OTHER INFORMATION: synthetic CDRL3

<400> SEQUENCE: 794

Gln Gln Tyr Tyr Tyr Ser Pro Ser Thr
1               5

<210> SEQ ID NO 795
<211> LENGTH: 9
<212> TYPE: PRT
<213> ORGANISM: Artificial

```
<220> FEATURE:
<223> OTHER INFORMATION: synthetic CDRL3

<400> SEQUENCE: 795

Gln Gln Ser Tyr Tyr Tyr Pro Ser Thr
1               5

<210> SEQ ID NO 796
<211> LENGTH: 9
<212> TYPE: PRT
<213> ORGANISM: Artificial
<220> FEATURE:
<223> OTHER INFORMATION: synthetic CDRL3

<400> SEQUENCE: 796

Gln Gln Ser Tyr Tyr Tyr Pro Ser Thr
1               5

<210> SEQ ID NO 797
<211> LENGTH: 9
<212> TYPE: PRT
<213> ORGANISM: Artificial
<220> FEATURE:
<223> OTHER INFORMATION: synthetic CDRL3

<400> SEQUENCE: 797

Gln Gln Ser Tyr Tyr Ser Pro Ser Thr
1               5

<210> SEQ ID NO 798
<211> LENGTH: 9
<212> TYPE: PRT
<213> ORGANISM: Artificial
<220> FEATURE:
<223> OTHER INFORMATION: synthetic CDRL3

<400> SEQUENCE: 798

Gln Gln Ser Tyr Tyr Ser Pro Ser Thr
1               5

<210> SEQ ID NO 799
<211> LENGTH: 9
<212> TYPE: PRT
<213> ORGANISM: Artificial
<220> FEATURE:
<223> OTHER INFORMATION: synthetic CDRL3

<400> SEQUENCE: 799

Gln Gln Ser Tyr Tyr Tyr Pro Ser Thr
1               5

<210> SEQ ID NO 800
<211> LENGTH: 9
<212> TYPE: PRT
<213> ORGANISM: Artificial
<220> FEATURE:
<223> OTHER INFORMATION: synthetic CDRL3

<400> SEQUENCE: 800

Gln Gln Tyr Tyr Tyr Ser Pro Ser Thr
1               5

<210> SEQ ID NO 801
<211> LENGTH: 9
<212> TYPE: PRT
<213> ORGANISM: Artificial
<220> FEATURE:
```

<223> OTHER INFORMATION: synthetic CDRL3

<400> SEQUENCE: 801

Gln Gln Ser Tyr Tyr Tyr Pro Ser Thr
1               5

<210> SEQ ID NO 802
<211> LENGTH: 9
<212> TYPE: PRT
<213> ORGANISM: Artificial
<220> FEATURE:
<223> OTHER INFORMATION: synthetic CDRL3

<400> SEQUENCE: 802

Gln Gln Tyr Tyr Tyr Tyr Pro Tyr Thr
1               5

<210> SEQ ID NO 803
<211> LENGTH: 9
<212> TYPE: PRT
<213> ORGANISM: Artificial
<220> FEATURE:
<223> OTHER INFORMATION: synthetic CDRL3

<400> SEQUENCE: 803

Gln Gln Ser Tyr Tyr Ser Pro Ser Thr
1               5

<210> SEQ ID NO 804
<211> LENGTH: 9
<212> TYPE: PRT
<213> ORGANISM: Artificial
<220> FEATURE:
<223> OTHER INFORMATION: synthetic CDRL3

<400> SEQUENCE: 804

Gln Gln Tyr Tyr Tyr Tyr Pro Ser Thr
1               5

<210> SEQ ID NO 805
<211> LENGTH: 9
<212> TYPE: PRT
<213> ORGANISM: Artificial
<220> FEATURE:
<223> OTHER INFORMATION: synthetic CDRL3

<400> SEQUENCE: 805

Gln Gln Ser Tyr Tyr Tyr Pro Ser Thr
1               5

<210> SEQ ID NO 806
<211> LENGTH: 9
<212> TYPE: PRT
<213> ORGANISM: Artificial
<220> FEATURE:
<223> OTHER INFORMATION: synthetic CDRL3

<400> SEQUENCE: 806

Gln Gln Tyr Tyr Tyr Ser Pro Ser Thr
1               5

<210> SEQ ID NO 807
<211> LENGTH: 9
<212> TYPE: PRT
<213> ORGANISM: Artificial
<220> FEATURE:
<223> OTHER INFORMATION: synthetic CDRL3

<400> SEQUENCE: 807

Gln Gln Ser Tyr Tyr Ser Pro Ser Thr
1               5

<210> SEQ ID NO 808
<211> LENGTH: 9
<212> TYPE: PRT
<213> ORGANISM: Artificial
<220> FEATURE:
<223> OTHER INFORMATION: synthetic CDRL3

<400> SEQUENCE: 808

Gln Gln Tyr Tyr Tyr Ser Pro Ser Thr
1               5

<210> SEQ ID NO 809
<211> LENGTH: 9
<212> TYPE: PRT
<213> ORGANISM: Artificial
<220> FEATURE:
<223> OTHER INFORMATION: synthetic CDRL3

<400> SEQUENCE: 809

Gln Gln Ser Tyr Tyr Tyr Pro Ser Thr
1               5

<210> SEQ ID NO 810
<211> LENGTH: 9
<212> TYPE: PRT
<213> ORGANISM: Artificial
<220> FEATURE:
<223> OTHER INFORMATION: synthetic CDRL3

<400> SEQUENCE: 810

Gln Gln Ser Tyr Tyr Ser Pro Ser Thr
1               5

<210> SEQ ID NO 811
<211> LENGTH: 9
<212> TYPE: PRT
<213> ORGANISM: Artificial
<220> FEATURE:
<223> OTHER INFORMATION: synthetic CDRL3

<400> SEQUENCE: 811

Gln Gln Ser Tyr Tyr Ser Pro Ser Thr
1               5

<210> SEQ ID NO 812
<211> LENGTH: 9
<212> TYPE: PRT
<213> ORGANISM: Artificial
<220> FEATURE:
<223> OTHER INFORMATION: synthetic CDRL3

<400> SEQUENCE: 812

Gln Gln Tyr Ser Tyr Tyr Pro Tyr Thr
1               5

<210> SEQ ID NO 813
<211> LENGTH: 9
<212> TYPE: PRT
<213> ORGANISM: Artificial
<220> FEATURE:
<223> OTHER INFORMATION: synthetic CDRL3

```
<400> SEQUENCE: 813

Gln Gln Tyr Ser Ser Tyr Pro Tyr Thr
1               5

<210> SEQ ID NO 814
<211> LENGTH: 9
<212> TYPE: PRT
<213> ORGANISM: Artificial
<220> FEATURE:
<223> OTHER INFORMATION: synthetic CDRL3

<400> SEQUENCE: 814

Gln Gln Tyr Ser Tyr Tyr Pro Tyr Thr
1               5

<210> SEQ ID NO 815
<211> LENGTH: 9
<212> TYPE: PRT
<213> ORGANISM: Artificial
<220> FEATURE:
<223> OTHER INFORMATION: synthetic CDRL3

<400> SEQUENCE: 815

Gln Gln Ser Tyr Ser Ser Pro Tyr Thr
1               5

<210> SEQ ID NO 816
<211> LENGTH: 10
<212> TYPE: PRT
<213> ORGANISM: Artificial
<220> FEATURE:
<223> OTHER INFORMATION: synthetic CDRH1

<400> SEQUENCE: 816

Gly Phe Tyr Ile Ser Ser Ser Tyr Ile His
1               5                   10

<210> SEQ ID NO 817
<211> LENGTH: 10
<212> TYPE: PRT
<213> ORGANISM: Artificial
<220> FEATURE:
<223> OTHER INFORMATION: synthetic CDRH1

<400> SEQUENCE: 817

Gly Phe Tyr Ile Ser Ser Ser Tyr Ile His
1               5                   10

<210> SEQ ID NO 818
<211> LENGTH: 10
<212> TYPE: PRT
<213> ORGANISM: Artificial
<220> FEATURE:
<223> OTHER INFORMATION: synthetic CDRH1

<400> SEQUENCE: 818

Gly Phe Ser Ile Ser Ser Ser Tyr Ile His
1               5                   10

<210> SEQ ID NO 819
<211> LENGTH: 10
<212> TYPE: PRT
<213> ORGANISM: Artificial
<220> FEATURE:
<223> OTHER INFORMATION: synthetic CDRH1

<400> SEQUENCE: 819
```

```
Gly Phe Ser Ile Ser Tyr Ser Tyr Ile His
1               5                   10

<210> SEQ ID NO 820
<211> LENGTH: 10
<212> TYPE: PRT
<213> ORGANISM: Artificial
<220> FEATURE:
<223> OTHER INFORMATION: synthetic CDRH1

<400> SEQUENCE: 820

Gly Phe Ser Ile Ser Ser Ser Tyr Ile His
1               5                   10

<210> SEQ ID NO 821
<211> LENGTH: 10
<212> TYPE: PRT
<213> ORGANISM: Artificial
<220> FEATURE:
<223> OTHER INFORMATION: synthetic CDRH1

<400> SEQUENCE: 821

Gly Phe Ser Ile Tyr Ser Ser Tyr Ile His
1               5                   10

<210> SEQ ID NO 822
<211> LENGTH: 10
<212> TYPE: PRT
<213> ORGANISM: Artificial
<220> FEATURE:
<223> OTHER INFORMATION: synthetic CDRH1

<400> SEQUENCE: 822

Gly Phe Ser Ile Ser Tyr Ser Tyr Ile His
1               5                   10

<210> SEQ ID NO 823
<211> LENGTH: 10
<212> TYPE: PRT
<213> ORGANISM: Artificial
<220> FEATURE:
<223> OTHER INFORMATION: synthetic CDRH1

<400> SEQUENCE: 823

Gly Phe Ser Ile Ser Ser Ser Tyr Ile His
1               5                   10

<210> SEQ ID NO 824
<211> LENGTH: 10
<212> TYPE: PRT
<213> ORGANISM: Artificial
<220> FEATURE:
<223> OTHER INFORMATION: synthetic CDRH1

<400> SEQUENCE: 824

Gly Phe Ser Ile Tyr Tyr Ser Tyr Ile His
1               5                   10

<210> SEQ ID NO 825
<211> LENGTH: 10
<212> TYPE: PRT
<213> ORGANISM: Artificial
<220> FEATURE:
<223> OTHER INFORMATION: synthetic CDRH1

<400> SEQUENCE: 825
```

Gly Phe Ser Ile Tyr Tyr Ser Tyr Ile His
1               5                   10

<210> SEQ ID NO 826
<211> LENGTH: 10
<212> TYPE: PRT
<213> ORGANISM: Artificial
<220> FEATURE:
<223> OTHER INFORMATION: synthetic CDRH1

<400> SEQUENCE: 826

Gly Phe Ser Ile Tyr Ser Ser Tyr Ile His
1               5                   10

<210> SEQ ID NO 827
<211> LENGTH: 10
<212> TYPE: PRT
<213> ORGANISM: Artificial
<220> FEATURE:
<223> OTHER INFORMATION: synthetic CDRH1

<400> SEQUENCE: 827

Gly Phe Ser Ile Ser Tyr Ser Tyr Ile His
1               5                   10

<210> SEQ ID NO 828
<211> LENGTH: 10
<212> TYPE: PRT
<213> ORGANISM: Artificial
<220> FEATURE:
<223> OTHER INFORMATION: synthetic CDRH1

<400> SEQUENCE: 828

Gly Phe Ser Ile Tyr Tyr Ser Tyr Ile His
1               5                   10

<210> SEQ ID NO 829
<211> LENGTH: 10
<212> TYPE: PRT
<213> ORGANISM: Artificial
<220> FEATURE:
<223> OTHER INFORMATION: synthetic CDRH1

<400> SEQUENCE: 829

Gly Phe Ser Ile Tyr Tyr Ser Tyr Ile His
1               5                   10

<210> SEQ ID NO 830
<211> LENGTH: 10
<212> TYPE: PRT
<213> ORGANISM: Artificial
<220> FEATURE:
<223> OTHER INFORMATION: synthetic CDRH1

<400> SEQUENCE: 830

Gly Phe Ser Ile Ser Ser Ser Tyr Ile His
1               5                   10

<210> SEQ ID NO 831
<211> LENGTH: 10
<212> TYPE: PRT
<213> ORGANISM: Artificial
<220> FEATURE:
<223> OTHER INFORMATION: synthetic CDRH1

<400> SEQUENCE: 831

Gly Phe Ser Ile Ser Tyr Ser Tyr Ile His

<210> SEQ ID NO 832
<211> LENGTH: 10
<212> TYPE: PRT
<213> ORGANISM: Artificial
<220> FEATURE:
<223> OTHER INFORMATION: synthetic CDRH1

<400> SEQUENCE: 832

Gly Phe Tyr Ile Tyr Ser Ser Tyr Ile His
1               5                   10

<210> SEQ ID NO 833
<211> LENGTH: 10
<212> TYPE: PRT
<213> ORGANISM: Artificial
<220> FEATURE:
<223> OTHER INFORMATION: synthetic CDRH1

<400> SEQUENCE: 833

Gly Phe Ser Ile Ser Ser Ser Tyr Ile His
1               5                   10

<210> SEQ ID NO 834
<211> LENGTH: 10
<212> TYPE: PRT
<213> ORGANISM: Artificial
<220> FEATURE:
<223> OTHER INFORMATION: synthetic CDRH1

<400> SEQUENCE: 834

Gly Phe Ser Ile Ser Ser Ser Tyr Ile His
1               5                   10

<210> SEQ ID NO 835
<211> LENGTH: 10
<212> TYPE: PRT
<213> ORGANISM: Artificial
<220> FEATURE:
<223> OTHER INFORMATION: synthetic CDRH1

<400> SEQUENCE: 835

Gly Phe Ser Ile Tyr Ser Ser Tyr Ile His
1               5                   10

<210> SEQ ID NO 836
<211> LENGTH: 10
<212> TYPE: PRT
<213> ORGANISM: Artificial
<220> FEATURE:
<223> OTHER INFORMATION: synthetic CDRH1

<400> SEQUENCE: 836

Gly Phe Ser Ile Ser Ser Ser Tyr Ile His
1               5                   10

<210> SEQ ID NO 837
<211> LENGTH: 10
<212> TYPE: PRT
<213> ORGANISM: Artificial
<220> FEATURE:
<223> OTHER INFORMATION: synthetic CDRH1

<400> SEQUENCE: 837

Gly Phe Tyr Ile Ser Tyr Ser Tyr Ile His
1               5                   10

<210> SEQ ID NO 838
<211> LENGTH: 10
<212> TYPE: PRT
<213> ORGANISM: Artificial
<220> FEATURE:
<223> OTHER INFORMATION: synthetic CDRH1

<400> SEQUENCE: 838

Gly Phe Ser Ile Ser Tyr Ser Tyr Ile His
1               5                   10

<210> SEQ ID NO 839
<211> LENGTH: 10
<212> TYPE: PRT
<213> ORGANISM: Artificial
<220> FEATURE:
<223> OTHER INFORMATION: synthetic CDRH1

<400> SEQUENCE: 839

Gly Phe Ser Ile Ser Tyr Ser Ser Ile His
1               5                   10

<210> SEQ ID NO 840
<211> LENGTH: 10
<212> TYPE: PRT
<213> ORGANISM: Artificial
<220> FEATURE:
<223> OTHER INFORMATION: synthetic CDRH1

<400> SEQUENCE: 840

Gly Phe Ser Ile Ser Tyr Ser Ser Ile His
1               5                   10

<210> SEQ ID NO 841
<211> LENGTH: 10
<212> TYPE: PRT
<213> ORGANISM: Artificial
<220> FEATURE:
<223> OTHER INFORMATION: synthetic CDRH1

<400> SEQUENCE: 841

Gly Phe Ser Ile Ser Tyr Ser Ser Ile His
1               5                   10

<210> SEQ ID NO 842
<211> LENGTH: 10
<212> TYPE: PRT
<213> ORGANISM: Artificial
<220> FEATURE:
<223> OTHER INFORMATION: synthetic CDRH1

<400> SEQUENCE: 842

Gly Phe Ser Ile Ser Ser Ser Ser Ile His
1               5                   10

<210> SEQ ID NO 843
<211> LENGTH: 17
<212> TYPE: PRT
<213> ORGANISM: Artificial
<220> FEATURE:
<223> OTHER INFORMATION: synthetic CDRH2

<400> SEQUENCE: 843

Ser Ile Tyr Pro Tyr Ser Gly Tyr Thr Ser Tyr Ala Asp Ser Val Lys
1               5                   10                  15

```
<210> SEQ ID NO 844
<211> LENGTH: 17
<212> TYPE: PRT
<213> ORGANISM: Artificial
<220> FEATURE:
<223> OTHER INFORMATION: synthetic CDRH2

<400> SEQUENCE: 844

Ser Ile Tyr Pro Tyr Ser Gly Tyr Thr Ser Tyr Ala Asp Ser Val Lys
1               5                   10                  15
Gly

<210> SEQ ID NO 845
<211> LENGTH: 17
<212> TYPE: PRT
<213> ORGANISM: Artificial
<220> FEATURE:
<223> OTHER INFORMATION: synthetic CDRH2

<400> SEQUENCE: 845

Ser Ile Tyr Pro Tyr Ser Gly Tyr Thr Ser Tyr Ala Asp Ser Val Lys
1               5                   10                  15
Gly

<210> SEQ ID NO 846
<211> LENGTH: 17
<212> TYPE: PRT
<213> ORGANISM: Artificial
<220> FEATURE:
<223> OTHER INFORMATION: synthetic CDRH2

<400> SEQUENCE: 846

Ser Ile Tyr Pro Tyr Ser Gly Tyr Thr Ser Tyr Ala Asp Ser Val Lys
1               5                   10                  15
Gly

<210> SEQ ID NO 847
<211> LENGTH: 17
<212> TYPE: PRT
<213> ORGANISM: Artificial
<220> FEATURE:
<223> OTHER INFORMATION: synthetic CDRH2

<400> SEQUENCE: 847

Ser Ile Tyr Pro Tyr Ser Gly Tyr Thr Ser Tyr Ala Asp Ser Val Lys
1               5                   10                  15
Gly

<210> SEQ ID NO 848
<211> LENGTH: 17
<212> TYPE: PRT
<213> ORGANISM: Artificial
<220> FEATURE:
<223> OTHER INFORMATION: synthetic CDRH2

<400> SEQUENCE: 848

Ser Ile Tyr Pro Tyr Ser Gly Tyr Thr Ser Tyr Ala Asp Ser Val Lys
1               5                   10                  15
Gly

<210> SEQ ID NO 849
```

-continued

```
<211> LENGTH: 17
<212> TYPE: PRT
<213> ORGANISM: Artificial
<220> FEATURE:
<223> OTHER INFORMATION: synthetic CDRH2

<400> SEQUENCE: 849

Ser Ile Tyr Pro Ser Ser Gly Tyr Thr Ser Tyr Ala Asp Ser Val Lys
1               5                   10                  15

Gly

<210> SEQ ID NO 850
<211> LENGTH: 17
<212> TYPE: PRT
<213> ORGANISM: Artificial
<220> FEATURE:
<223> OTHER INFORMATION: synthetic CDRH2

<400> SEQUENCE: 850

Ser Ile Tyr Pro Tyr Ser Gly Tyr Thr Ser Tyr Ala Asp Ser Val Lys
1               5                   10                  15

Gly

<210> SEQ ID NO 851
<211> LENGTH: 17
<212> TYPE: PRT
<213> ORGANISM: Artificial
<220> FEATURE:
<223> OTHER INFORMATION: synthetic CDRH2

<400> SEQUENCE: 851

Ser Ile Tyr Pro Ser Ser Gly Tyr Thr Ser Tyr Ala Asp Ser Val Lys
1               5                   10                  15

Gly

<210> SEQ ID NO 852
<211> LENGTH: 17
<212> TYPE: PRT
<213> ORGANISM: Artificial
<220> FEATURE:
<223> OTHER INFORMATION: synthetic CDRH2

<400> SEQUENCE: 852

Ser Ile Tyr Pro Ser Ser Gly Tyr Thr Ser Tyr Ala Asp Ser Val Lys
1               5                   10                  15

Gly

<210> SEQ ID NO 853
<211> LENGTH: 17
<212> TYPE: PRT
<213> ORGANISM: Artificial
<220> FEATURE:
<223> OTHER INFORMATION: synthetic CDRH2

<400> SEQUENCE: 853

Ser Ile Tyr Pro Tyr Ser Gly Tyr Thr Ser Tyr Ala Asp Ser Val Lys
1               5                   10                  15

Gly

<210> SEQ ID NO 854
<211> LENGTH: 17
<212> TYPE: PRT
<213> ORGANISM: Artificial
<220> FEATURE:
```

<223> OTHER INFORMATION: synthetic CDRH2

<400> SEQUENCE: 854

Ser Ile Tyr Pro Tyr Ser Gly Tyr Thr Ser Tyr Ala Asp Ser Val Lys
1               5                   10                  15

Gly

<210> SEQ ID NO 855
<211> LENGTH: 17
<212> TYPE: PRT
<213> ORGANISM: Artificial
<220> FEATURE:
<223> OTHER INFORMATION: synthetic CDRH2

<400> SEQUENCE: 855

Ser Ile Tyr Pro Ser Ser Gly Tyr Thr Ser Tyr Ala Asp Ser Val Lys
1               5                   10                  15

Gly

<210> SEQ ID NO 856
<211> LENGTH: 17
<212> TYPE: PRT
<213> ORGANISM: Artificial
<220> FEATURE:
<223> OTHER INFORMATION: synthetic CDRH2

<400> SEQUENCE: 856

Ser Ile Tyr Pro Ser Ser Gly Tyr Thr Ser Tyr Ala Asp Ser Val Lys
1               5                   10                  15

Gly

<210> SEQ ID NO 857
<211> LENGTH: 17
<212> TYPE: PRT
<213> ORGANISM: Artificial
<220> FEATURE:
<223> OTHER INFORMATION: synthetic CDRH2

<400> SEQUENCE: 857

Ser Ile Tyr Pro Tyr Ser Gly Tyr Thr Ser Tyr Ala Asp Ser Val Lys
1               5                   10                  15

Gly

<210> SEQ ID NO 858
<211> LENGTH: 17
<212> TYPE: PRT
<213> ORGANISM: Artificial
<220> FEATURE:
<223> OTHER INFORMATION: synthetic CDRH2

<400> SEQUENCE: 858

Ser Ile Tyr Pro Tyr Ser Gly Tyr Thr Ser Tyr Ala Asp Ser Val Lys
1               5                   10                  15

Gly

<210> SEQ ID NO 859
<211> LENGTH: 17
<212> TYPE: PRT
<213> ORGANISM: Artificial
<220> FEATURE:
<223> OTHER INFORMATION: synthetic CDRH2

<400> SEQUENCE: 859

Ser Ile Tyr Pro Tyr Ser Gly Tyr Thr Ser Tyr Ala Asp Ser Val Lys
1               5                   10                  15

Gly

<210> SEQ ID NO 860
<211> LENGTH: 17
<212> TYPE: PRT
<213> ORGANISM: Artificial
<220> FEATURE:
<223> OTHER INFORMATION: synthetic CDRH2

<400> SEQUENCE: 860

Ser Ile Tyr Pro Tyr Ser Gly Tyr Thr Ser Tyr Ala Asp Ser Val Lys
1               5                   10                  15

Gly

<210> SEQ ID NO 861
<211> LENGTH: 17
<212> TYPE: PRT
<213> ORGANISM: Artificial
<220> FEATURE:
<223> OTHER INFORMATION: synthetic CDRH2

<400> SEQUENCE: 861

Ser Ile Tyr Pro Tyr Ser Gly Tyr Thr Ser Tyr Ala Asp Ser Val Lys
1               5                   10                  15

Gly

<210> SEQ ID NO 862
<211> LENGTH: 17
<212> TYPE: PRT
<213> ORGANISM: Artificial
<220> FEATURE:
<223> OTHER INFORMATION: synthetic CDRH2

<400> SEQUENCE: 862

Ser Ile Tyr Pro Tyr Ser Gly Tyr Thr Ser Tyr Ala Asp Ser Val Lys
1               5                   10                  15

Gly

<210> SEQ ID NO 863
<211> LENGTH: 17
<212> TYPE: PRT
<213> ORGANISM: Artificial
<220> FEATURE:
<223> OTHER INFORMATION: synthetic CDRH2

<400> SEQUENCE: 863

Ser Ile Tyr Pro Tyr Ser Gly Tyr Thr Ser Tyr Ala Asp Ser Val Lys
1               5                   10                  15

Gly

<210> SEQ ID NO 864
<211> LENGTH: 17
<212> TYPE: PRT
<213> ORGANISM: Artificial
<220> FEATURE:
<223> OTHER INFORMATION: synthetic CDRH2

<400> SEQUENCE: 864

Ser Ile Tyr Pro Tyr Ser Gly Tyr Thr Ser Tyr Ala Asp Ser Val Lys
1               5                   10                  15

Gly

<210> SEQ ID NO 865
<211> LENGTH: 17
<212> TYPE: PRT
<213> ORGANISM: Artificial
<220> FEATURE:
<223> OTHER INFORMATION: synthetic CDRH2

<400> SEQUENCE: 865

Ser Ile Tyr Pro Tyr Ser Gly Tyr Thr Ser Tyr Ala Asp Ser Val Lys
1               5                   10                  15

Gly

<210> SEQ ID NO 866
<211> LENGTH: 17
<212> TYPE: PRT
<213> ORGANISM: Artificial
<220> FEATURE:
<223> OTHER INFORMATION: synthetic CDRH2

<400> SEQUENCE: 866

Ser Ile Tyr Pro Tyr Tyr Gly Tyr Thr Tyr Tyr Ala Asp Ser Val Lys
1               5                   10                  15

Gly

<210> SEQ ID NO 867
<211> LENGTH: 17
<212> TYPE: PRT
<213> ORGANISM: Artificial
<220> FEATURE:
<223> OTHER INFORMATION: synthetic CDRH2

<400> SEQUENCE: 867

Ser Ile Tyr Pro Tyr Tyr Gly Tyr Thr Tyr Tyr Ala Asp Ser Val Lys
1               5                   10                  15

Gly

<210> SEQ ID NO 868
<211> LENGTH: 17
<212> TYPE: PRT
<213> ORGANISM: Artificial
<220> FEATURE:
<223> OTHER INFORMATION: synthetic CDRH2

<400> SEQUENCE: 868

Ser Ile Tyr Pro Tyr Tyr Gly Tyr Thr Ser Tyr Ala Asp Ser Val Lys
1               5                   10                  15

Gly

<210> SEQ ID NO 869
<211> LENGTH: 17
<212> TYPE: PRT
<213> ORGANISM: Artificial
<220> FEATURE:
<223> OTHER INFORMATION: synthetic CDRH2

<400> SEQUENCE: 869

Tyr Ile Ser Pro Ser Ser Gly Tyr Thr Ser Tyr Ala Asp Ser Val Lys
1               5                   10                  15

Gly

<210> SEQ ID NO 870
<211> LENGTH: 8

```
<212> TYPE: PRT
<213> ORGANISM: Artificial
<220> FEATURE:
<223> OTHER INFORMATION: synthetic CDRH3

<400> SEQUENCE: 870

Tyr Tyr Ser Tyr Ala Phe Asp Tyr
1               5

<210> SEQ ID NO 871
<211> LENGTH: 8
<212> TYPE: PRT
<213> ORGANISM: Artificial
<220> FEATURE:
<223> OTHER INFORMATION: synthetic CDRH3

<400> SEQUENCE: 871

Tyr Tyr Ser Ser Gly Phe Asp Tyr
1               5

<210> SEQ ID NO 872
<211> LENGTH: 8
<212> TYPE: PRT
<213> ORGANISM: Artificial
<220> FEATURE:
<223> OTHER INFORMATION: synthetic CDRH3

<400> SEQUENCE: 872

Tyr Tyr Ser Ser Gly Phe Asp Tyr
1               5

<210> SEQ ID NO 873
<211> LENGTH: 8
<212> TYPE: PRT
<213> ORGANISM: Artificial
<220> FEATURE:
<223> OTHER INFORMATION: synthetic CDRH3

<400> SEQUENCE: 873

Tyr Tyr Ser Ser Gly Phe Asp Tyr
1               5

<210> SEQ ID NO 874
<211> LENGTH: 8
<212> TYPE: PRT
<213> ORGANISM: Artificial
<220> FEATURE:
<223> OTHER INFORMATION: synthetic CDRH3

<400> SEQUENCE: 874

Tyr Tyr Ser Tyr Ala Leu Asp Tyr
1               5

<210> SEQ ID NO 875
<211> LENGTH: 8
<212> TYPE: PRT
<213> ORGANISM: Artificial
<220> FEATURE:
<223> OTHER INFORMATION: synthetic CDRH3

<400> SEQUENCE: 875

Trp Trp Ser Ser Ala Phe Asp Tyr
1               5

<210> SEQ ID NO 876
<211> LENGTH: 8
<212> TYPE: PRT
```

<213> ORGANISM: Artificial
<220> FEATURE:
<223> OTHER INFORMATION: synthetic CDRH3

<400> SEQUENCE: 876

Trp Trp Ser Ser Ala Met Asp Tyr
1               5

<210> SEQ ID NO 877
<211> LENGTH: 8
<212> TYPE: PRT
<213> ORGANISM: Artificial
<220> FEATURE:
<223> OTHER INFORMATION: synthetic CDRH3

<400> SEQUENCE: 877

Trp Trp Ser Trp Gly Phe Asp Tyr
1               5

<210> SEQ ID NO 878
<211> LENGTH: 8
<212> TYPE: PRT
<213> ORGANISM: Artificial
<220> FEATURE:
<223> OTHER INFORMATION: synthetic CDRH3

<400> SEQUENCE: 878

Trp Trp Ser Ser Ala Phe Asp Tyr
1               5

<210> SEQ ID NO 879
<211> LENGTH: 8
<212> TYPE: PRT
<213> ORGANISM: Artificial
<220> FEATURE:
<223> OTHER INFORMATION: synthetic CDRH3

<400> SEQUENCE: 879

Trp Trp Ser Ser Gly Phe Asp Tyr
1               5

<210> SEQ ID NO 880
<211> LENGTH: 8
<212> TYPE: PRT
<213> ORGANISM: Artificial
<220> FEATURE:
<223> OTHER INFORMATION: synthetic CDRH3

<400> SEQUENCE: 880

Trp Trp Ser Ser Ala Phe Asp Tyr
1               5

<210> SEQ ID NO 881
<211> LENGTH: 8
<212> TYPE: PRT
<213> ORGANISM: Artificial
<220> FEATURE:
<223> OTHER INFORMATION: synthetic CDRH3

<400> SEQUENCE: 881

Trp Trp Ser Trp Ala Phe Asp Tyr
1               5

<210> SEQ ID NO 882
<211> LENGTH: 8
<212> TYPE: PRT
<213> ORGANISM: Artificial

```
<220> FEATURE:
<223> OTHER INFORMATION: synthetic CDRH3

<400> SEQUENCE: 882

Trp Trp Ser Ser Ala Phe Asp Tyr
1               5

<210> SEQ ID NO 883
<211> LENGTH: 8
<212> TYPE: PRT
<213> ORGANISM: Artificial
<220> FEATURE:
<223> OTHER INFORMATION: synthetic CDRH3

<400> SEQUENCE: 883

Trp Trp Ser Ser Ala Phe Asp Tyr
1               5

<210> SEQ ID NO 884
<211> LENGTH: 8
<212> TYPE: PRT
<213> ORGANISM: Artificial
<220> FEATURE:
<223> OTHER INFORMATION: synthetic CDRH3

<400> SEQUENCE: 884

Trp Trp Ser Ser Ala Leu Asp Tyr
1               5

<210> SEQ ID NO 885
<211> LENGTH: 8
<212> TYPE: PRT
<213> ORGANISM: Artificial
<220> FEATURE:
<223> OTHER INFORMATION: synthetic CDRH3

<400> SEQUENCE: 885

Trp Trp Ser Ser Ala Phe Asp Tyr
1               5

<210> SEQ ID NO 886
<211> LENGTH: 8
<212> TYPE: PRT
<213> ORGANISM: Artificial
<220> FEATURE:
<223> OTHER INFORMATION: synthetic CDRH3

<400> SEQUENCE: 886

Trp Trp Ser Ser Gly Phe Asp Tyr
1               5

<210> SEQ ID NO 887
<211> LENGTH: 8
<212> TYPE: PRT
<213> ORGANISM: Artificial
<220> FEATURE:
<223> OTHER INFORMATION: synthetic CDRH3

<400> SEQUENCE: 887

Trp Trp Ser Ser Ala Phe Asp Tyr
1               5

<210> SEQ ID NO 888
<211> LENGTH: 8
<212> TYPE: PRT
<213> ORGANISM: Artificial
<220> FEATURE:
```

<223> OTHER INFORMATION: synthetic CDRH3

<400> SEQUENCE: 888

Trp Trp Ser Ser Ala Leu Asp Tyr
1               5

<210> SEQ ID NO 889
<211> LENGTH: 8
<212> TYPE: PRT
<213> ORGANISM: Artificial
<220> FEATURE:
<223> OTHER INFORMATION: synthetic CDRH3

<400> SEQUENCE: 889

Trp Ser Ser Ser Gly Phe Asp Tyr
1               5

<210> SEQ ID NO 890
<211> LENGTH: 8
<212> TYPE: PRT
<213> ORGANISM: Artificial
<220> FEATURE:
<223> OTHER INFORMATION: synthetic CDRH3

<400> SEQUENCE: 890

Trp Trp Ser Ser Ala Met Asp Tyr
1               5

<210> SEQ ID NO 891
<211> LENGTH: 8
<212> TYPE: PRT
<213> ORGANISM: Artificial
<220> FEATURE:
<223> OTHER INFORMATION: synthetic CDRH3

<400> SEQUENCE: 891

Trp Trp Ser Ser Ala Leu Asp Tyr
1               5

<210> SEQ ID NO 892
<211> LENGTH: 8
<212> TYPE: PRT
<213> ORGANISM: Artificial
<220> FEATURE:
<223> OTHER INFORMATION: synthetic CDRH3

<400> SEQUENCE: 892

Trp Trp Ser Ser Ala Leu Asp Tyr
1               5

<210> SEQ ID NO 893
<211> LENGTH: 12
<212> TYPE: PRT
<213> ORGANISM: Artificial
<220> FEATURE:
<223> OTHER INFORMATION: synthetic CDRH3

<400> SEQUENCE: 893

Phe Ser Phe Ser Ser Ser Ser Phe Ala Met Asp Tyr
1               5                   10

<210> SEQ ID NO 894
<211> LENGTH: 12
<212> TYPE: PRT
<213> ORGANISM: Artificial
<220> FEATURE:
<223> OTHER INFORMATION: synthetic CDRH3

```
<400> SEQUENCE: 894

Phe Ser Phe Ser Ser Ser Ser Phe Ala Ile Asp Tyr
1               5                   10

<210> SEQ ID NO 895
<211> LENGTH: 13
<212> TYPE: PRT
<213> ORGANISM: Artificial
<220> FEATURE:
<223> OTHER INFORMATION: synthetic CDRH3

<400> SEQUENCE: 895

Phe Phe Phe Phe Ser Ser Ser Phe Phe Gly Phe Asp Tyr
1               5                   10

<210> SEQ ID NO 896
<211> LENGTH: 15
<212> TYPE: PRT
<213> ORGANISM: Artificial
<220> FEATURE:
<223> OTHER INFORMATION: synthetic CDRH3

<400> SEQUENCE: 896

Tyr Tyr Ser Ser Tyr Tyr Ser Tyr Tyr Ser Phe Gly Leu Asp Tyr
1               5                   10                  15

<210> SEQ ID NO 897
<211> LENGTH: 9
<212> TYPE: PRT
<213> ORGANISM: Artificial
<220> FEATURE:
<223> OTHER INFORMATION: synthetic CDRL3

<400> SEQUENCE: 897

Gln Gln Ser Trp Trp Trp Pro Trp Thr
1               5

<210> SEQ ID NO 898
<211> LENGTH: 9
<212> TYPE: PRT
<213> ORGANISM: Artificial
<220> FEATURE:
<223> OTHER INFORMATION: synthetic CDRL3

<400> SEQUENCE: 898

Gln Gln Ser Trp Trp Trp Pro Ser Thr
1               5

<210> SEQ ID NO 899
<211> LENGTH: 9
<212> TYPE: PRT
<213> ORGANISM: Artificial
<220> FEATURE:
<223> OTHER INFORMATION: synthetic CDRL3

<400> SEQUENCE: 899

Gln Gln Ser Trp Trp Ser Pro Ser Thr
1               5

<210> SEQ ID NO 900
<211> LENGTH: 9
<212> TYPE: PRT
<213> ORGANISM: Artificial
<220> FEATURE:
<223> OTHER INFORMATION: synthetic CDRL3
```

```
<400> SEQUENCE: 900

Gln Gln Trp Trp Trp Trp Pro Trp Thr
1               5

<210> SEQ ID NO 901
<211> LENGTH: 9
<212> TYPE: PRT
<213> ORGANISM: Artificial
<220> FEATURE:
<223> OTHER INFORMATION: synthetic CDRL3

<400> SEQUENCE: 901

Gln Gln Trp Trp Trp Trp Pro Ser Thr
1               5

<210> SEQ ID NO 902
<211> LENGTH: 9
<212> TYPE: PRT
<213> ORGANISM: Artificial
<220> FEATURE:
<223> OTHER INFORMATION: synthetic CDRL3

<400> SEQUENCE: 902

Gln Gln Ser Trp Trp Trp Pro Ser Thr
1               5

<210> SEQ ID NO 903
<211> LENGTH: 9
<212> TYPE: PRT
<213> ORGANISM: Artificial
<220> FEATURE:
<223> OTHER INFORMATION: synthetic CDRL3

<400> SEQUENCE: 903

Gln Gln Trp Trp Trp Trp Pro Ser Thr
1               5

<210> SEQ ID NO 904
<211> LENGTH: 9
<212> TYPE: PRT
<213> ORGANISM: Artificial
<220> FEATURE:
<223> OTHER INFORMATION: synthetic CDRL3

<400> SEQUENCE: 904

Gln Gln Trp Trp Trp Trp Pro Ser Thr
1               5

<210> SEQ ID NO 905
<211> LENGTH: 9
<212> TYPE: PRT
<213> ORGANISM: Artificial
<220> FEATURE:
<223> OTHER INFORMATION: synthetic CDRL3

<400> SEQUENCE: 905

Gln Gln Trp Trp Trp Trp Pro Ser Thr
1               5

<210> SEQ ID NO 906
<211> LENGTH: 9
<212> TYPE: PRT
<213> ORGANISM: Artificial
<220> FEATURE:
<223> OTHER INFORMATION: synthetic CDRL3

<400> SEQUENCE: 906
```

Gln Gln Trp Ser Trp Trp Pro Ser Thr
1               5

<210> SEQ ID NO 907
<211> LENGTH: 9
<212> TYPE: PRT
<213> ORGANISM: Artificial
<220> FEATURE:
<223> OTHER INFORMATION: synthetic CDRL3

<400> SEQUENCE: 907

Gln Gln Trp Ser Ser Trp Pro Ser Thr
1               5

<210> SEQ ID NO 908
<211> LENGTH: 9
<212> TYPE: PRT
<213> ORGANISM: Artificial
<220> FEATURE:
<223> OTHER INFORMATION: synthetic CDRL3

<400> SEQUENCE: 908

Gln Gln Trp Ser Ser Trp Pro Ser Thr
1               5

<210> SEQ ID NO 909
<211> LENGTH: 9
<212> TYPE: PRT
<213> ORGANISM: Artificial
<220> FEATURE:
<223> OTHER INFORMATION: synthetic CDRL3

<400> SEQUENCE: 909

Gln Gln Ser Ser Ser Ser Pro Ser Thr
1               5

<210> SEQ ID NO 910
<211> LENGTH: 9
<212> TYPE: PRT
<213> ORGANISM: Artificial
<220> FEATURE:
<223> OTHER INFORMATION: synthetic CDRL3

<400> SEQUENCE: 910

Gln Gln Trp Ser Trp Ser Pro Ser Thr
1               5

<210> SEQ ID NO 911
<211> LENGTH: 9
<212> TYPE: PRT
<213> ORGANISM: Artificial
<220> FEATURE:
<223> OTHER INFORMATION: synthetic CDRL3

<400> SEQUENCE: 911

Gln Gln Trp Ser Ser Trp Pro Ser Thr
1               5

<210> SEQ ID NO 912
<211> LENGTH: 9
<212> TYPE: PRT
<213> ORGANISM: Artificial
<220> FEATURE:
<223> OTHER INFORMATION: synthetic CDRL3

<400> SEQUENCE: 912

Gln Gln Trp Ser Ser Trp Pro Ser Thr
1               5

<210> SEQ ID NO 913
<211> LENGTH: 9
<212> TYPE: PRT
<213> ORGANISM: Artificial
<220> FEATURE:
<223> OTHER INFORMATION: synthetic CDRL3

<400> SEQUENCE: 913

Gln Gln Ser Tyr Tyr Ser Pro Ser Thr
1               5

<210> SEQ ID NO 914
<211> LENGTH: 9
<212> TYPE: PRT
<213> ORGANISM: Artificial
<220> FEATURE:
<223> OTHER INFORMATION: synthetic CDRL3

<400> SEQUENCE: 914

Gln Gln Tyr Tyr Tyr Ser Pro Ser Thr
1               5

<210> SEQ ID NO 915
<211> LENGTH: 9
<212> TYPE: PRT
<213> ORGANISM: Artificial
<220> FEATURE:
<223> OTHER INFORMATION: synthetic CDRL3

<400> SEQUENCE: 915

Gln Gln Ser Tyr Tyr Tyr Pro Ser Thr
1               5

<210> SEQ ID NO 916
<211> LENGTH: 9
<212> TYPE: PRT
<213> ORGANISM: Artificial
<220> FEATURE:
<223> OTHER INFORMATION: synthetic CDRL3

<400> SEQUENCE: 916

Gln Gln Ser Tyr Tyr Tyr Pro Ser Thr
1               5

<210> SEQ ID NO 917
<211> LENGTH: 9
<212> TYPE: PRT
<213> ORGANISM: Artificial
<220> FEATURE:
<223> OTHER INFORMATION: synthetic CDRL3

<400> SEQUENCE: 917

Gln Gln Ser Tyr Tyr Tyr Pro Ser Thr
1               5

<210> SEQ ID NO 918
<211> LENGTH: 9
<212> TYPE: PRT
<213> ORGANISM: Artificial
<220> FEATURE:
<223> OTHER INFORMATION: synthetic CDRL3

<400> SEQUENCE: 918

Gln Gln Ser Tyr Tyr Tyr Pro Ser Thr

```
1               5

<210> SEQ ID NO 919
<211> LENGTH: 9
<212> TYPE: PRT
<213> ORGANISM: Artificial
<220> FEATURE:
<223> OTHER INFORMATION: synthetic CDRL3

<400> SEQUENCE: 919

Gln Gln Ser Tyr Tyr Ser Pro Ser Thr
1               5

<210> SEQ ID NO 920
<211> LENGTH: 9
<212> TYPE: PRT
<213> ORGANISM: Artificial
<220> FEATURE:
<223> OTHER INFORMATION: synthetic CDRL3

<400> SEQUENCE: 920

Gln Gln Ser Ser Ser Ser Pro Ser Thr
1               5

<210> SEQ ID NO 921
<211> LENGTH: 9
<212> TYPE: PRT
<213> ORGANISM: Artificial
<220> FEATURE:
<223> OTHER INFORMATION: synthetic CDRL3

<400> SEQUENCE: 921

Gln Gln Ser Tyr Ser Tyr Pro Tyr Thr
1               5

<210> SEQ ID NO 922
<211> LENGTH: 9
<212> TYPE: PRT
<213> ORGANISM: Artificial
<220> FEATURE:
<223> OTHER INFORMATION: synthetic CDRL3

<400> SEQUENCE: 922

Gln Gln Tyr Tyr Ser Ser Pro Tyr Thr
1               5

<210> SEQ ID NO 923
<211> LENGTH: 9
<212> TYPE: PRT
<213> ORGANISM: Artificial
<220> FEATURE:
<223> OTHER INFORMATION: synthetic CDRL3

<400> SEQUENCE: 923

Gln Gln Tyr Tyr Ser Ser Pro Tyr Thr
1               5

<210> SEQ ID NO 924
<211> LENGTH: 10
<212> TYPE: PRT
<213> ORGANISM: Artificial
<220> FEATURE:
<223> OTHER INFORMATION: synthetic CDRH1

<400> SEQUENCE: 924

Gly Phe Ser Ile Trp Trp Ser Trp Ile His
1               5                   10
```

```
<210> SEQ ID NO 925
<211> LENGTH: 10
<212> TYPE: PRT
<213> ORGANISM: Artificial
<220> FEATURE:
<223> OTHER INFORMATION: synthetic CDRH1

<400> SEQUENCE: 925

Gly Phe Ser Ile Trp Trp Ser Trp Ile His
1               5                   10

<210> SEQ ID NO 926
<211> LENGTH: 10
<212> TYPE: PRT
<213> ORGANISM: Artificial
<220> FEATURE:
<223> OTHER INFORMATION: synthetic CDRH1

<400> SEQUENCE: 926

Gly Phe Ser Ile Trp Trp Ser Trp Ile His
1               5                   10

<210> SEQ ID NO 927
<211> LENGTH: 10
<212> TYPE: PRT
<213> ORGANISM: Artificial
<220> FEATURE:
<223> OTHER INFORMATION: synthetic CDRH1

<400> SEQUENCE: 927

Gly Phe Ser Ile Trp Trp Ser Trp Ile His
1               5                   10

<210> SEQ ID NO 928
<211> LENGTH: 10
<212> TYPE: PRT
<213> ORGANISM: Artificial
<220> FEATURE:
<223> OTHER INFORMATION: synthetic CDRH1

<400> SEQUENCE: 928

Gly Phe Ser Ile Trp Ser Ser Trp Ile His
1               5                   10

<210> SEQ ID NO 929
<211> LENGTH: 10
<212> TYPE: PRT
<213> ORGANISM: Artificial
<220> FEATURE:
<223> OTHER INFORMATION: synthetic CDRH1

<400> SEQUENCE: 929

Gly Phe Ser Ile Trp Trp Ser Trp Ile His
1               5                   10

<210> SEQ ID NO 930
<211> LENGTH: 10
<212> TYPE: PRT
<213> ORGANISM: Artificial
<220> FEATURE:
<223> OTHER INFORMATION: synthetic CDRH1

<400> SEQUENCE: 930

Gly Phe Ser Ile Ser Trp Ser Trp Ile His
1               5                   10
```

<210> SEQ ID NO 931
<211> LENGTH: 10
<212> TYPE: PRT
<213> ORGANISM: Artificial
<220> FEATURE:
<223> OTHER INFORMATION: synthetic CDRH1

<400> SEQUENCE: 931

Gly Phe Ser Ile Trp Trp Ser Trp Ile His
1               5                   10

<210> SEQ ID NO 932
<211> LENGTH: 10
<212> TYPE: PRT
<213> ORGANISM: Artificial
<220> FEATURE:
<223> OTHER INFORMATION: synthetic CDRH1

<400> SEQUENCE: 932

Gly Phe Ser Ile Trp Trp Ser Trp Ile His
1               5                   10

<210> SEQ ID NO 933
<211> LENGTH: 10
<212> TYPE: PRT
<213> ORGANISM: Artificial
<220> FEATURE:
<223> OTHER INFORMATION: synthetic CDRH1

<400> SEQUENCE: 933

Gly Phe Ser Ile Trp Trp Ser Trp Ile His
1               5                   10

<210> SEQ ID NO 934
<211> LENGTH: 10
<212> TYPE: PRT
<213> ORGANISM: Artificial
<220> FEATURE:
<223> OTHER INFORMATION: synthetic CDRH1

<400> SEQUENCE: 934

Gly Phe Trp Ile Trp Ser Ser Ser Ile His
1               5                   10

<210> SEQ ID NO 935
<211> LENGTH: 10
<212> TYPE: PRT
<213> ORGANISM: Artificial
<220> FEATURE:
<223> OTHER INFORMATION: synthetic CDRH1

<400> SEQUENCE: 935

Gly Phe Trp Ile Trp Ser Ser Ser Ile His
1               5                   10

<210> SEQ ID NO 936
<211> LENGTH: 10
<212> TYPE: PRT
<213> ORGANISM: Artificial
<220> FEATURE:
<223> OTHER INFORMATION: synthetic CDRH1

<400> SEQUENCE: 936

Gly Phe Ser Ile Ser Ser Ser Trp Ile His
1               5                   10

<210> SEQ ID NO 937
<211> LENGTH: 10
<212> TYPE: PRT
<213> ORGANISM: Artificial
<220> FEATURE:
<223> OTHER INFORMATION: synthetic CDRH1

<400> SEQUENCE: 937

Gly Phe Ser Ile Ser Ser Ser Ser Ile His
1               5                   10

<210> SEQ ID NO 938
<211> LENGTH: 10
<212> TYPE: PRT
<213> ORGANISM: Artificial
<220> FEATURE:
<223> OTHER INFORMATION: synthetic CDRH1

<400> SEQUENCE: 938

Gly Phe Trp Ile Trp Ser Ser Ser Ile His
1               5                   10

<210> SEQ ID NO 939
<211> LENGTH: 10
<212> TYPE: PRT
<213> ORGANISM: Artificial
<220> FEATURE:
<223> OTHER INFORMATION: synthetic CDRH1

<400> SEQUENCE: 939

Gly Phe Ser Ile Trp Ser Ser Ser Ile His
1               5                   10

<210> SEQ ID NO 940
<211> LENGTH: 10
<212> TYPE: PRT
<213> ORGANISM: Artificial
<220> FEATURE:
<223> OTHER INFORMATION: synthetic CDRH1

<400> SEQUENCE: 940

Gly Phe Ser Ile Tyr Ser Tyr Tyr Ile His
1               5                   10

<210> SEQ ID NO 941
<211> LENGTH: 10
<212> TYPE: PRT
<213> ORGANISM: Artificial
<220> FEATURE:
<223> OTHER INFORMATION: synthetic CDRH1

<400> SEQUENCE: 941

Gly Phe Tyr Ile Ser Tyr Ser Tyr Ile His
1               5                   10

<210> SEQ ID NO 942
<211> LENGTH: 10
<212> TYPE: PRT
<213> ORGANISM: Artificial
<220> FEATURE:
<223> OTHER INFORMATION: synthetic CDRH1

<400> SEQUENCE: 942

Gly Phe Tyr Ile Ser Ser Ser Tyr Ile His
1               5                   10

<210> SEQ ID NO 943

```
<211> LENGTH: 10
<212> TYPE: PRT
<213> ORGANISM: Artificial
<220> FEATURE:
<223> OTHER INFORMATION: synthetic CDRH1

<400> SEQUENCE: 943

Gly Phe Ser Ile Ser Ser Ser Tyr Ile His
1               5                   10

<210> SEQ ID NO 944
<211> LENGTH: 10
<212> TYPE: PRT
<213> ORGANISM: Artificial
<220> FEATURE:
<223> OTHER INFORMATION: synthetic CDRH1

<400> SEQUENCE: 944

Gly Phe Ser Ile Ser Ser Ser Tyr Ile His
1               5                   10

<210> SEQ ID NO 945
<211> LENGTH: 10
<212> TYPE: PRT
<213> ORGANISM: Artificial
<220> FEATURE:
<223> OTHER INFORMATION: synthetic CDRH1

<400> SEQUENCE: 945

Gly Phe Ser Ile Tyr Ser Ser Tyr Ile His
1               5                   10

<210> SEQ ID NO 946
<211> LENGTH: 10
<212> TYPE: PRT
<213> ORGANISM: Artificial
<220> FEATURE:
<223> OTHER INFORMATION: synthetic CDRH1

<400> SEQUENCE: 946

Gly Phe Tyr Ile Ser Ser Ser Tyr Ile His
1               5                   10

<210> SEQ ID NO 947
<211> LENGTH: 10
<212> TYPE: PRT
<213> ORGANISM: Artificial
<220> FEATURE:
<223> OTHER INFORMATION: synthetic CDRH1

<400> SEQUENCE: 947

Gly Phe Tyr Ile Ser Tyr Ser Ser Ile His
1               5                   10

<210> SEQ ID NO 948
<211> LENGTH: 10
<212> TYPE: PRT
<213> ORGANISM: Artificial
<220> FEATURE:
<223> OTHER INFORMATION: synthetic CDRH1

<400> SEQUENCE: 948

Gly Phe Tyr Ile Ser Ser Ser Ser Ile His
1               5                   10

<210> SEQ ID NO 949
<211> LENGTH: 10
```

```
<212> TYPE: PRT
<213> ORGANISM: Artificial
<220> FEATURE:
<223> OTHER INFORMATION: synthetic CDRH1

<400> SEQUENCE: 949

Gly Phe Ser Ile Tyr Tyr Ser Ser Ile His
1               5                   10

<210> SEQ ID NO 950
<211> LENGTH: 10
<212> TYPE: PRT
<213> ORGANISM: Artificial
<220> FEATURE:
<223> OTHER INFORMATION: synthetic CDRH1

<400> SEQUENCE: 950

Gly Phe Ser Ile Tyr Tyr Ser Ser Ile His
1               5                   10

<210> SEQ ID NO 951
<211> LENGTH: 17
<212> TYPE: PRT
<213> ORGANISM: Artificial
<220> FEATURE:
<223> OTHER INFORMATION: synthetic CDRH2

<400> SEQUENCE: 951

Ser Ile Ser Pro Ser Ser Gly Trp Thr Ser Tyr Ala Asp Ser Val Lys
1               5                   10                  15

Gly

<210> SEQ ID NO 952
<211> LENGTH: 17
<212> TYPE: PRT
<213> ORGANISM: Artificial
<220> FEATURE:
<223> OTHER INFORMATION: synthetic CDRH2

<400> SEQUENCE: 952

Ser Ile Ser Pro Ser Ser Gly Trp Thr Ser Tyr Ala Asp Ser Val Lys
1               5                   10                  15

Gly

<210> SEQ ID NO 953
<211> LENGTH: 17
<212> TYPE: PRT
<213> ORGANISM: Artificial
<220> FEATURE:
<223> OTHER INFORMATION: synthetic CDRH2

<400> SEQUENCE: 953

Ser Ile Tyr Pro Ser Ser Gly Tyr Thr Ser Tyr Ala Asp Ser Val Lys
1               5                   10                  15

Gly

<210> SEQ ID NO 954
<211> LENGTH: 17
<212> TYPE: PRT
<213> ORGANISM: Artificial
<220> FEATURE:
<223> OTHER INFORMATION: synthetic CDRH2

<400> SEQUENCE: 954

Ser Ile Ser Pro Ser Ser Gly Trp Thr Ser Tyr Ala Asp Ser Val Lys
```

```
1               5                   10                  15

Gly

<210> SEQ ID NO 955
<211> LENGTH: 17
<212> TYPE: PRT
<213> ORGANISM: Artificial
<220> FEATURE:
<223> OTHER INFORMATION: synthetic CDRH2

<400> SEQUENCE: 955

Ser Ile Ser Pro Ser Ser Gly Trp Thr Ser Tyr Ala Asp Ser Val Lys
1               5                   10                  15

Gly

<210> SEQ ID NO 956
<211> LENGTH: 17
<212> TYPE: PRT
<213> ORGANISM: Artificial
<220> FEATURE:
<223> OTHER INFORMATION: synthetic CDRH2

<400> SEQUENCE: 956

Ser Ile Ser Pro Ser Ser Gly Trp Thr Ser Tyr Ala Asp Ser Val Lys
1               5                   10                  15

Gly

<210> SEQ ID NO 957
<211> LENGTH: 17
<212> TYPE: PRT
<213> ORGANISM: Artificial
<220> FEATURE:
<223> OTHER INFORMATION: synthetic CDRH2

<400> SEQUENCE: 957

Ser Ile Trp Pro Ser Ser Gly Trp Thr Ser Tyr Ala Asp Ser Val Lys
1               5                   10                  15

Gly

<210> SEQ ID NO 958
<211> LENGTH: 17
<212> TYPE: PRT
<213> ORGANISM: Artificial
<220> FEATURE:
<223> OTHER INFORMATION: synthetic CDRH2

<400> SEQUENCE: 958

Ser Ile Ser Pro Ser Ser Gly Trp Thr Ser Tyr Ala Asp Ser Val Lys
1               5                   10                  15

Gly

<210> SEQ ID NO 959
<211> LENGTH: 17
<212> TYPE: PRT
<213> ORGANISM: Artificial
<220> FEATURE:
<223> OTHER INFORMATION: synthetic CDRH2

<400> SEQUENCE: 959

Ser Ile Ser Pro Ser Ser Gly Trp Thr Ser Tyr Ala Asp Ser Val Lys
1               5                   10                  15

Gly
```

<210> SEQ ID NO 960
<211> LENGTH: 17
<212> TYPE: PRT
<213> ORGANISM: Artificial
<220> FEATURE:
<223> OTHER INFORMATION: synthetic CDRH2

<400> SEQUENCE: 960

Ser Ile Ser Pro Ser Ser Gly Trp Thr Ser Tyr Ala Asp Ser Val Lys
1               5                   10                  15
Gly

<210> SEQ ID NO 961
<211> LENGTH: 17
<212> TYPE: PRT
<213> ORGANISM: Artificial
<220> FEATURE:
<223> OTHER INFORMATION: synthetic CDRH2

<400> SEQUENCE: 961

Trp Ile Ser Pro Ser Ser Gly Ser Thr Trp Tyr Ala Asp Ser Val Lys
1               5                   10                  15
Gly

<210> SEQ ID NO 962
<211> LENGTH: 17
<212> TYPE: PRT
<213> ORGANISM: Artificial
<220> FEATURE:
<223> OTHER INFORMATION: synthetic CDRH2

<400> SEQUENCE: 962

Trp Ile Ser Pro Ser Ser Gly Ser Thr Trp Tyr Ala Asp Ser Val Lys
1               5                   10                  15
Gly

<210> SEQ ID NO 963
<211> LENGTH: 17
<212> TYPE: PRT
<213> ORGANISM: Artificial
<220> FEATURE:
<223> OTHER INFORMATION: synthetic CDRH2

<400> SEQUENCE: 963

Trp Ile Trp Pro Ser Ser Gly Trp Thr Ser Tyr Ala Asp Ser Val Lys
1               5                   10                  15
Gly

<210> SEQ ID NO 964
<211> LENGTH: 17
<212> TYPE: PRT
<213> ORGANISM: Artificial
<220> FEATURE:
<223> OTHER INFORMATION: synthetic CDRH2

<400> SEQUENCE: 964

Trp Ile Ser Pro Ser Trp Gly Ser Thr Trp Tyr Ala Asp Ser Val Lys
1               5                   10                  15
Gly

<210> SEQ ID NO 965
<211> LENGTH: 17
<212> TYPE: PRT

```
<213> ORGANISM: Artificial
<220> FEATURE:
<223> OTHER INFORMATION: synthetic CDRH2

<400> SEQUENCE: 965

Trp Ile Ser Pro Ser Ser Gly Ser Thr Trp Tyr Ala Asp Ser Val Lys
1               5                   10                  15

Gly

<210> SEQ ID NO 966
<211> LENGTH: 17
<212> TYPE: PRT
<213> ORGANISM: Artificial
<220> FEATURE:
<223> OTHER INFORMATION: synthetic CDRH2

<400> SEQUENCE: 966

Trp Ile Ser Pro Ser Ser Gly Ser Thr Trp Tyr Ala Asp Ser Val Lys
1               5                   10                  15

Gly

<210> SEQ ID NO 967
<211> LENGTH: 17
<212> TYPE: PRT
<213> ORGANISM: Artificial
<220> FEATURE:
<223> OTHER INFORMATION: synthetic CDRH2

<400> SEQUENCE: 967

Ser Ile Tyr Pro Ser Ser Gly Tyr Thr Ser Tyr Ala Asp Ser Val Lys
1               5                   10                  15

Gly

<210> SEQ ID NO 968
<211> LENGTH: 17
<212> TYPE: PRT
<213> ORGANISM: Artificial
<220> FEATURE:
<223> OTHER INFORMATION: synthetic CDRH2

<400> SEQUENCE: 968

Ser Ile Tyr Pro Tyr Ser Gly Tyr Thr Ser Tyr Ala Asp Ser Val Lys
1               5                   10                  15

Gly

<210> SEQ ID NO 969
<211> LENGTH: 17
<212> TYPE: PRT
<213> ORGANISM: Artificial
<220> FEATURE:
<223> OTHER INFORMATION: synthetic CDRH2

<400> SEQUENCE: 969

Ser Ile Tyr Pro Ser Gly Tyr Thr Ser Tyr Ala Asp Ser Val Lys
1               5                   10                  15

Gly

<210> SEQ ID NO 970
<211> LENGTH: 17
<212> TYPE: PRT
<213> ORGANISM: Artificial
<220> FEATURE:
<223> OTHER INFORMATION: synthetic CDRH2
```

```
<400> SEQUENCE: 970

Ser Ile Tyr Pro Tyr Ser Gly Tyr Thr Ser Tyr Ala Asp Ser Val Lys
1               5                   10                  15

Gly

<210> SEQ ID NO 971
<211> LENGTH: 17
<212> TYPE: PRT
<213> ORGANISM: Artificial
<220> FEATURE:
<223> OTHER INFORMATION: synthetic CDRH2

<400> SEQUENCE: 971

Ser Ile Tyr Pro Tyr Ser Gly Tyr Thr Ser Tyr Ala Asp Ser Val Lys
1               5                   10                  15

Gly

<210> SEQ ID NO 972
<211> LENGTH: 17
<212> TYPE: PRT
<213> ORGANISM: Artificial
<220> FEATURE:
<223> OTHER INFORMATION: synthetic CDRH2

<400> SEQUENCE: 972

Ser Ile Tyr Pro Tyr Ser Gly Tyr Thr Ser Tyr Ala Asp Ser Val Lys
1               5                   10                  15

Gly

<210> SEQ ID NO 973
<211> LENGTH: 17
<212> TYPE: PRT
<213> ORGANISM: Artificial
<220> FEATURE:
<223> OTHER INFORMATION: synthetic CDRH2

<400> SEQUENCE: 973

Ser Ile Tyr Pro Tyr Ser Gly Tyr Thr Ser Tyr Ala Asp Ser Val Lys
1               5                   10                  15

Gly

<210> SEQ ID NO 974
<211> LENGTH: 17
<212> TYPE: PRT
<213> ORGANISM: Artificial
<220> FEATURE:
<223> OTHER INFORMATION: synthetic CDRH2

<400> SEQUENCE: 974

Ser Ile Ser Pro Tyr Ser Gly Tyr Thr Tyr Tyr Ala Asp Ser Val Lys
1               5                   10                  15

Gly

<210> SEQ ID NO 975
<211> LENGTH: 17
<212> TYPE: PRT
<213> ORGANISM: Artificial
<220> FEATURE:
<223> OTHER INFORMATION: synthetic CDRH2

<400> SEQUENCE: 975

Tyr Ile Ser Pro Ser Ser Gly Tyr Thr Tyr Tyr Ala Asp Ser Val Lys
1               5                   10                  15
```

Gly

<210> SEQ ID NO 976
<211> LENGTH: 17
<212> TYPE: PRT
<213> ORGANISM: Artificial
<220> FEATURE:
<223> OTHER INFORMATION: synthetic CDRH2

<400> SEQUENCE: 976

Ser Ile Tyr Pro Tyr Ser Gly Ser Thr Tyr Tyr Ala Asp Ser Val Lys
1               5                   10                  15
Gly

<210> SEQ ID NO 977
<211> LENGTH: 17
<212> TYPE: PRT
<213> ORGANISM: Artificial
<220> FEATURE:
<223> OTHER INFORMATION: synthetic CDRH2

<400> SEQUENCE: 977

Ser Ile Tyr Pro Ser Ser Gly Ser Thr Tyr Tyr Ala Asp Ser Val Lys
1               5                   10                  15
Gly

<210> SEQ ID NO 978
<211> LENGTH: 8
<212> TYPE: PRT
<213> ORGANISM: Artificial
<220> FEATURE:
<223> OTHER INFORMATION: synthetic CDRH3

<400> SEQUENCE: 978

Trp Trp Ser Ser Ala Ile Asp Tyr
1               5

<210> SEQ ID NO 979
<211> LENGTH: 8
<212> TYPE: PRT
<213> ORGANISM: Artificial
<220> FEATURE:
<223> OTHER INFORMATION: synthetic CDRH3

<400> SEQUENCE: 979

Trp Trp Ser Ser Ala Leu Asp Tyr
1               5

<210> SEQ ID NO 980
<211> LENGTH: 8
<212> TYPE: PRT
<213> ORGANISM: Artificial
<220> FEATURE:
<223> OTHER INFORMATION: synthetic CDRH3

<400> SEQUENCE: 980

Trp Trp Ser Ser Ala Leu Asp Tyr
1               5

<210> SEQ ID NO 981
<211> LENGTH: 8
<212> TYPE: PRT
<213> ORGANISM: Artificial
<220> FEATURE:
<223> OTHER INFORMATION: synthetic CDRH3

<400> SEQUENCE: 981

Trp Trp Ser Ser Gly Met Asp Tyr
1               5

<210> SEQ ID NO 982
<211> LENGTH: 8
<212> TYPE: PRT
<213> ORGANISM: Artificial
<220> FEATURE:
<223> OTHER INFORMATION: synthetic CDRH3

<400> SEQUENCE: 982

Trp Trp Ser Ser Ala Leu Asp Tyr
1               5

<210> SEQ ID NO 983
<211> LENGTH: 8
<212> TYPE: PRT
<213> ORGANISM: Artificial
<220> FEATURE:
<223> OTHER INFORMATION: synthetic CDRH3

<400> SEQUENCE: 983

Trp Trp Ser Ser Ala Phe Asp Tyr
1               5

<210> SEQ ID NO 984
<211> LENGTH: 8
<212> TYPE: PRT
<213> ORGANISM: Artificial
<220> FEATURE:
<223> OTHER INFORMATION: synthetic CDRH3

<400> SEQUENCE: 984

Trp Trp Ser Ser Ala Leu Asp Tyr
1               5

<210> SEQ ID NO 985
<211> LENGTH: 8
<212> TYPE: PRT
<213> ORGANISM: Artificial
<220> FEATURE:
<223> OTHER INFORMATION: synthetic CDRH3

<400> SEQUENCE: 985

Trp Ser Ser Ser Ala Phe Asp Tyr
1               5

<210> SEQ ID NO 986
<211> LENGTH: 8
<212> TYPE: PRT
<213> ORGANISM: Artificial
<220> FEATURE:
<223> OTHER INFORMATION: synthetic CDRH3

<400> SEQUENCE: 986

Trp Trp Ser Ser Ala Met Asp Tyr
1               5

<210> SEQ ID NO 987
<211> LENGTH: 8
<212> TYPE: PRT
<213> ORGANISM: Artificial
<220> FEATURE:
<223> OTHER INFORMATION: synthetic CDRH3

```
<400> SEQUENCE: 987

Trp Ser Ser Trp Gly Leu Asp Tyr
1               5

<210> SEQ ID NO 988
<211> LENGTH: 12
<212> TYPE: PRT
<213> ORGANISM: Artificial
<220> FEATURE:
<223> OTHER INFORMATION: synthetic CDRH3

<400> SEQUENCE: 988

Ser Ser Trp Ser Ser Trp Ser Ser Ala Leu Asp Tyr
1               5                   10

<210> SEQ ID NO 989
<211> LENGTH: 12
<212> TYPE: PRT
<213> ORGANISM: Artificial
<220> FEATURE:
<223> OTHER INFORMATION: synthetic CDRH3

<400> SEQUENCE: 989

Ser Ser Trp Ser Ser Trp Ser Ser Ala Leu Asp Tyr
1               5                   10

<210> SEQ ID NO 990
<211> LENGTH: 12
<212> TYPE: PRT
<213> ORGANISM: Artificial
<220> FEATURE:
<223> OTHER INFORMATION: synthetic CDRH3

<400> SEQUENCE: 990

Ser Ser Ser Ser Ser Trp Trp Ser Ala Ile Asp Tyr
1               5                   10

<210> SEQ ID NO 991
<211> LENGTH: 12
<212> TYPE: PRT
<213> ORGANISM: Artificial
<220> FEATURE:
<223> OTHER INFORMATION: synthetic CDRH3

<400> SEQUENCE: 991

Ser Ser Trp Ser Ser Trp Ser Trp Ala Leu Asp Tyr
1               5                   10

<210> SEQ ID NO 992
<211> LENGTH: 12
<212> TYPE: PRT
<213> ORGANISM: Artificial
<220> FEATURE:
<223> OTHER INFORMATION: synthetic CDRH3

<400> SEQUENCE: 992

Ser Ser Trp Ser Ser Trp Ser Ser Ala Met Asp Tyr
1               5                   10

<210> SEQ ID NO 993
<211> LENGTH: 12
<212> TYPE: PRT
<213> ORGANISM: Artificial
<220> FEATURE:
<223> OTHER INFORMATION: synthetic CDRH3

<400> SEQUENCE: 993
```

Ser Ser Trp Ser Ser Trp Ser Ala Met Asp Tyr
1               5                   10

<210> SEQ ID NO 994
<211> LENGTH: 8
<212> TYPE: PRT
<213> ORGANISM: Artificial
<220> FEATURE:
<223> OTHER INFORMATION: synthetic CDRH3

<400> SEQUENCE: 994

Tyr Tyr Ser Tyr Ala Leu Asp Tyr
1               5

<210> SEQ ID NO 995
<211> LENGTH: 8
<212> TYPE: PRT
<213> ORGANISM: Artificial
<220> FEATURE:
<223> OTHER INFORMATION: synthetic CDRH3

<400> SEQUENCE: 995

Tyr Tyr Ser Tyr Ala Phe Asp Tyr
1               5

<210> SEQ ID NO 996
<211> LENGTH: 8
<212> TYPE: PRT
<213> ORGANISM: Artificial
<220> FEATURE:
<223> OTHER INFORMATION: synthetic CDRH3

<400> SEQUENCE: 996

Tyr Tyr Ser Tyr Ala Phe Asp Tyr
1               5

<210> SEQ ID NO 997
<211> LENGTH: 8
<212> TYPE: PRT
<213> ORGANISM: Artificial
<220> FEATURE:
<223> OTHER INFORMATION: synthetic CDRH3

<400> SEQUENCE: 997

Tyr Tyr Ser Ser Ala Phe Asp Tyr
1               5

<210> SEQ ID NO 998
<211> LENGTH: 8
<212> TYPE: PRT
<213> ORGANISM: Artificial
<220> FEATURE:
<223> OTHER INFORMATION: synthetic CDRH3

<400> SEQUENCE: 998

Tyr Tyr Ser Tyr Ala Leu Asp Tyr
1               5

<210> SEQ ID NO 999
<211> LENGTH: 8
<212> TYPE: PRT
<213> ORGANISM: Artificial
<220> FEATURE:
<223> OTHER INFORMATION: synthetic CDRH3

<400> SEQUENCE: 999

Tyr Tyr Ser Tyr Ala Phe Asp Tyr
1               5

<210> SEQ ID NO 1000
<211> LENGTH: 8
<212> TYPE: PRT
<213> ORGANISM: Artificial
<220> FEATURE:
<223> OTHER INFORMATION: synthetic CDRH3

<400> SEQUENCE: 1000

Tyr Tyr Ser Tyr Ala Leu Asp Tyr
1               5

<210> SEQ ID NO 1001
<211> LENGTH: 14
<212> TYPE: PRT
<213> ORGANISM: Artificial
<220> FEATURE:
<223> OTHER INFORMATION: synthetic CDRH3

<400> SEQUENCE: 1001

Ser Ser Tyr Ser Tyr Tyr Tyr Ser Tyr Ala Leu Asp Tyr
1               5                   10

<210> SEQ ID NO 1002
<211> LENGTH: 15
<212> TYPE: PRT
<213> ORGANISM: Artificial
<220> FEATURE:
<223> OTHER INFORMATION: synthetic CDRH3

<400> SEQUENCE: 1002

Tyr Tyr Ser Ser Tyr Tyr Ser Tyr Tyr Ser Tyr Ala Leu Asp Tyr
1               5                   10                  15

<210> SEQ ID NO 1003
<211> LENGTH: 18
<212> TYPE: PRT
<213> ORGANISM: Artificial
<220> FEATURE:
<223> OTHER INFORMATION: synthetic CDRH3

<400> SEQUENCE: 1003

Tyr Tyr Ser Ser Tyr Ser Ser Ser Ser Ser Tyr Tyr Tyr Ala Phe
1               5                   10                  15

Asp Tyr

<210> SEQ ID NO 1004
<211> LENGTH: 19
<212> TYPE: PRT
<213> ORGANISM: Artificial
<220> FEATURE:
<223> OTHER INFORMATION: synthetic CDRH3

<400> SEQUENCE: 1004

Tyr Tyr Ser Ser Ser Ser Ser Tyr Ser Ser Tyr Tyr Tyr Ala
1               5                   10

Phe Asp Tyr

<210> SEQ ID NO 1005
<211> LENGTH: 48
<212> TYPE: DNA
<213> ORGANISM: Artificial
<220> FEATURE:
<223> OTHER INFORMATION: synthetic oligonucleotides

```
<400> SEQUENCE: 1005
gcagcttctg gcttctycat ttyctyctyc tycatacact gggtgcgt                48

<210> SEQ ID NO 1006
<211> LENGTH: 60
<212> TYPE: DNA
<213> ORGANISM: Artificial
<220> FEATURE:
<223> OTHER INFORMATION: synthetic oligonucleotides

<400> SEQUENCE: 1006
ctggaatggg ttgcatycat ttycccatyc tycggttyca cttyctatgc cgatagcgtc   60

<210> SEQ ID NO 1007
<211> LENGTH: 54
<212> TYPE: DNA
<213> ORGANISM: Artificial
<220> FEATURE:
<223> OTHER INFORMATION: synthetic oligonucleotides

<400> SEQUENCE: 1007
acttattact gtcagcaaty ctyctyctyc ccatycacgt tcggacaggg tacc          54

<210> SEQ ID NO 1008
<211> LENGTH: 48
<212> TYPE: DNA
<213> ORGANISM: Artificial
<220> FEATURE:
<223> OTHER INFORMATION: synthetic oligonucleotides

<400> SEQUENCE: 1008
gcagcttctg gcttcmgcat tmgcmgcmgc mgcatacact gggtgcgt                48

<210> SEQ ID NO 1009
<211> LENGTH: 60
<212> TYPE: DNA
<213> ORGANISM: Artificial
<220> FEATURE:
<223> OTHER INFORMATION: synthetic oligonucleotides

<400> SEQUENCE: 1009
ctggaatggg ttgcamgcat tmgcccamgc mgcggtmgca ctmgctatgc cgatagcgtc   60

<210> SEQ ID NO 1010
<211> LENGTH: 54
<212> TYPE: DNA
<213> ORGANISM: Artificial
<220> FEATURE:
<223> OTHER INFORMATION: synthetic oligonucleotides

<400> SEQUENCE: 1010
acttattact gtcagcaamg cmgcmgcmgc ccamgcacgt tcggacaggg tacc          54

<210> SEQ ID NO 1011
<211> LENGTH: 48
<212> TYPE: DNA
<213> ORGANISM: Artificial
<220> FEATURE:
<223> OTHER INFORMATION: synthetic oligonucleotides

<400> SEQUENCE: 1011
gcagcttctg gcttctsgat ttsgtsgtsg tsgatacact gggtgcgt                48

<210> SEQ ID NO 1012
```

```
<211> LENGTH: 60
<212> TYPE: DNA
<213> ORGANISM: Artificial
<220> FEATURE:
<223> OTHER INFORMATION: synthetic oligonucleotides

<400> SEQUENCE: 1012
ctggaatggg ttgcatsgat ttsgccatsg tsgggttsga cttsgtatgc cgatagcgtc        60

<210> SEQ ID NO 1013
<211> LENGTH: 54
<212> TYPE: DNA
<213> ORGANISM: Artificial
<220> FEATURE:
<223> OTHER INFORMATION: synthetic oligonucleotides

<400> SEQUENCE: 1013
acttattact gtcagcaats gtsgtsgtsg ccatsgacgt tcggacaggg tacc              54
```

BINDING POLYPEPTIDES AND USES THEREOF

CROSS REFERENCE TO RELATED APPLICATIONS

This application is a nonprovisional application which claims priority to U.S. Ser. No. 60/742,185 filed Dec. 2, 2005 and U.S. Ser. No. 60/805,553 filed Jun. 22, 2006, all of which applications are incorporated by reference herein.

FIELD OF THE INVENTION

The invention generally relates to variant CDRs diversified using highly limited amino acid repertoires, and libraries comprising a plurality of such sequences. The invention also relates to fusion polypeptides comprising these variant CDRs. The invention also relates to methods and compositions useful for identifying novel binding polypeptides that can be used therapeutically or as reagents.

BACKGROUND

Phage display technology has provided a powerful tool for generating and selecting novel proteins that bind to a ligand, such as an antigen. Using the techniques of phage display allows the generation of large libraries of protein variants that can be rapidly sorted for those sequences that bind to a target antigen with high affinity. Nucleic acids encoding variant polypeptides are fused to a nucleic acid sequence encoding a viral coat protein, such as the gene III protein or the gene VIII protein. Monovalent phage display systems where the nucleic acid sequence encoding the protein or polypeptide is fused to a nucleic acid sequence encoding a portion of the gene III protein have been developed. (Bass, S., *Proteins*, 8:309 (1990); Lowman and Wells, *Methods: A Companion to Methods in Enzymology*, 3:205 (1991)). In a monovalent phage display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

The demonstration of expression of peptides on the surface of filamentous phage and the expression of functional antibody fragments in the periplasm of *E. coli* was important in the development of antibody phage display libraries. (Smith et al., *Science* (1985), 228:1315; Skerra and Pluckthun, *Science* (1988), 240:1038). Libraries of antibodies or antigen binding polypeptides have been prepared in a number of ways including by altering a single gene by inserting random DNA sequences or by cloning a family of related genes. Methods for displaying antibodies or antigen binding fragments using phage display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with desired characteristics.

Phage display technology has several advantages over conventional hybridoma and recombinant methods for preparing antibodies with the desired characteristics. This technology allows the development of large libraries of antibodies with diverse sequences in less time and without the use of animals. Preparation of hybridomas or preparation of humanized antibodies can easily require several months of preparation. In addition, since no immunization is required, phage antibody libraries can be generated for antigens which are toxic or have low antigenicity (Hogenboom, *Immunotechniques* (1988), 4:1-20). Phage antibody libraries can also be used to generate and identify novel human antibodies.

Antibodies have become very useful as therapeutic agents for a wide variety of conditions. For example, humanized antibodies to HER-2, a tumor antigen, are useful in the diagnosis and treatment of cancer. Other antibodies, such as anti-INF-γ antibody, are useful in treating inflammatory conditions such as Crohn's disease. Phage display libraries have been used to generate human antibodies from immunized and non-immunized humans, germ line sequences, or naïve B cell Ig repertoires (Barbas & Burton, *Trends Biotech* (1996), 14:230; Griffiths et al., *EMBO J.* (1994), 13:3245; Vaughan et al., *Nat. Biotech.* (1996), 14:309; Winter EP 0368 684 B1). Naïve, or nonimmune, antigen binding libraries have been generated using a variety of lymphoidal tissues. Some of these libraries are commercially available, such as those developed by Cambridge Antibody Technology and Morphosys (Vaughan et al., *Nature Biotech* 14:309 (1996); Knappik et al., *J. Mol. Biol.* 296:57 (1999)). However, many of these libraries have limited diversity.

The ability to identify and isolate high affinity antibodies from a phage display library is important in isolating novel human antibodies for therapeutic use. Isolation of high affinity antibodies from a library is traditionally thought to be dependent, at least in part, on the size of the library, the efficiency of production in bacterial cells and the diversity of the library. See, e.g., Knappik et al., *J. Mol. Biol.* (1999), 296:57. The size of the library is decreased by inefficiency of production due to improper folding of the antibody or antigen binding protein and the presence of stop codons. Expression in bacterial cells can be inhibited if the antibody or antigen binding domain is not properly folded. Expression can be improved by mutating residues in turns at the surface of the variable/constant interface, or at selected CDR residues. (Deng et al., *J. Biol. Chem.* (1994), 269:9533, Ulrich et al., *PNAS* (1995), 92:11907-11911; Forsberg et al., *J. Biol. Chem.* (1997), 272:12430). The sequence of the framework region is a factor in providing for proper folding when antibody phage libraries are produced in bacterial cells.

Generating a diverse library of antibodies or antigen binding proteins is also important to isolation of high affinity antibodies. Libraries with diversification in limited CDRs have been generated using a variety of approaches. See, e.g., Tomlinson, *Nature Biotech.* (2000), 18:989-994. CDR3 regions are of interest in part because they often are found to participate in antigen binding. CDR3 regions on the heavy chain vary greatly in size, sequence and structural conformation.

Others have also generated diversity by randomizing CDR regions of the variable heavy and light chains using all 20 amino acids at each position. It was thought that using all 20 amino acids would result in a large diversity of sequences of variant antibodies and increase the chance of identifying novel antibodies. (Barbas, *PNAS* 91:3809 (1994); Yelton, D E, *J. Immunology*, 155:1994 (1995); Jackson, J. R., *J. Immunology*, 154:3310 (1995) and Hawkins, R E, *J. Mol. Biology*, 226:889 (1992)).

There have also been attempts to create diversity by restricting the group of amino acid substitutions in some CDRs to reflect the amino acid distribution in naturally occurring antibodies. See, Garrard & Henner, *Gene* (1993), 128:103; Knappik et al., *J. Mol. Biol.* (1999), 296:57. However, these attempts have had varying success and have not been applied in a systematic and quantitative manner. Creating diversity in the CDR regions while minimizing the number of amino acid changes has been a challenge. Furthermore, in some instances, once a first library has been generated according to one set of criteria, it may be desirable to further enhance the diversity of the first library. However, this requires that the first library has sufficient diversity and yet remain sufficiently small in size such that further diversity can be introduced without substantially exceeding practical limitations such as yield, etc.

Some groups have reported theoretical and experimental analyses of the minimum number of amino acid repertoire that is needed for generating proteins. However, these analyses have generally been limited in scope and nature, and substantial skepticism and questions remain regarding the feasibility of generating polypeptides having complex functions using a restricted set of amino acid types. See, e.g., Riddle et al., *Nat. Struct. Biol.* (1997), 4(10):805-809; Shang et al., *Proc. Natl. Acad. Sci. USA* (1994), 91:8373-8377; Heinz et al., *Proc. Natl. Acad. Sci. USA* (1992), 89:3751-3755; Regan & Degrado, *Science* (1988), 241:976-978; Kamteker et al., *Science* (1993), 262:1680-1685; Wang & Wang, *Nat. Struct. Biol.* (1999), 6(11):1033-1038; Xiong et al., *Proc. Natl. Acad. Sci. USA* (1995), 92:6349-6353; Heinz et al., *Proc. Natl. Acad. Sci. USA* (1992), 89:3751-3755; Cannata et al., *Bioinformatics* (2002), 18(8):1102-1108; Davidson et al., *Nat. Struct. Biol.* (1995), 2(10):856-863; Murphy et al., *Prot. Eng.* (2000), 13(3):149-152; Brown & Sauer, *Proc. Natl. Acad. Sci. USA* (1999), 96:1983-1988; Akanuma et al., *Proc. Natl. Acad. Sci.* (2002), 99(21):13549-13553; Chan, *Nat. Struct. Biol.* (1999), 6(11):994-996.

Thus, there remains a need to improve methods of generating libraries that comprise functional polypeptides having a sufficient degree of sequence diversity, yet are sufficiently amenable for further manipulations directed at further diversification, high yield expression, etc. The invention described herein meets this need and provides other benefits.

DISCLOSURE OF THE INVENTION

The present invention provides simplified and flexible methods of generating polypeptides comprising variant CDRs that comprise sequences with restricted diversity yet retain target antigen binding capability. Unlike conventional methods that are based on the proposition that adequate diversity of target binders can be generated only if a particular CDR(s), or all CDRs are diversified, and unlike conventional notions that adequate diversity is dependent upon the broadest range of amino acid substitutions (generally by substitution using all or most of the 20 amino acids), the invention provides methods capable of generating high quality target binders that are not necessarily dependent upon diversifying a particular CDR(s) or a particular number of CDRs of a reference polypeptide or source antibody. The invention is based, at least in part, on the surprising and unexpected finding that highly diverse libraries of high quality comprising functional polypeptides capable of binding target antigens can be generated by diversifying a minimal number of amino acid positions with a highly restricted number of amino acid residues. Methods of the invention are rapid, convenient and flexible, based on using restricted codon sets that encode a low number of amino acids. The restricted sequence diversity, and thus generally smaller size of the populations (e.g., libraries) of polypeptides generated by methods of the invention allows for further diversification of these populations, where necessary or desired. This is an advantage generally not provided by conventional methods. Candidate binder polypeptides generated by the invention possess high-quality target binding characteristics and have structural characteristics that provide for high yield of production in cell culture. The invention provides methods for generating these binder polypeptides, methods for using these polypeptides, and compositions comprising the same.

In one aspect, the invention provides fusion polypeptides comprising diversified CDR(s) and a heterologous polypeptide sequence (in certain embodiments, that of at least a portion of a viral polypeptide), as single polypeptides and as a member of a plurality of unique individual polypeptides that are candidate binders to targets of interest. Compositions (such as libraries) comprising such polypeptides find use in a variety of applications, for example, as pools of candidate immunoglobulin polypeptides (for example, antibodies and antibody fragments) that bind to targets of interest. Such polypeptides may also be generated using non-immunoglobulin scaffolds (for example, proteins, such as human growth hormone, etc.). The invention encompasses various aspects, including polynucleotides and polypeptides generated according to methods of the invention, and systems, kits and articles of manufacture for practicing methods of the invention, and/or using polypeptides/polynucleotides and/or compositions of the invention.

In one aspect, the invention provides a method of generating a polypeptide comprising at least one, two, three, four, five or all variant CDRs selected from the group consisting of H1, H2, H3, L1, L2 and L3, wherein said polypeptide is capable of binding a target antigen of interest, said method comprising identifying at least one (or any number up to all) solvent accessible and highly diverse amino acid position in a reference CDR corresponding to the variant CDR; and (ii) varying the amino acid at the solvent accessible and high diverse position by generating variant copies of the CDR using a restricted codon set (the definition of "restricted codon set" as provided below).

Various aspects and embodiments of methods of the invention are useful for generating and/or using a pool comprising a plurality of polypeptides of the invention, in particular for selecting and identifying candidate binders to target antigens of interest. For example, the invention provides a method of generating a composition comprising a plurality of polypeptides, each polypeptide comprising at least one, two, three, four, five or all variant CDRs selected from the group consisting of H1, H2, H3, L1, L2 and L3, wherein said polypeptide is capable of binding a target antigen of interest, said method comprising identifying at least one (or any number up to all) solvent accessible and highly diverse amino acid position in a reference CDR corresponding to the variant CDR; and (ii) varying the amino acid at the solvent accessible and high diverse position by generating variant copies of the CDR using a restricted codon set; wherein a plurality of polypeptides are generated by amplifying a template polynucleotide with a set of oligonucleotides comprising highly restricted degeneracy in the sequence encoding a variant amino acid, wherein said restricted degeneracy reflects the limited number of codon sequences of the restricted codon set.

In another example, the invention provides a method comprising: constructing an expression vector comprising a polynucleotide sequence which encodes a light chain, a heavy chain, or both the light chain and the heavy chain variable domains of a source antibody comprising at least one, two, three, four, five or all CDRs selected from the group consisting of CDR L1, L2, L3, H1, H2, and H3; and mutating at least one, two, three, four, five or all CDRs of the source antibody at least one (or any number up to all) solvent accessible and highly diverse amino acid position using a restricted codon set.

In another example, the invention provides a method comprising: constructing a library of phage or phagemid particles displaying a plurality of polypeptides of the invention; contacting the library of particles with a target antigen under conditions suitable for binding of the particles to the target antigen; and separating the particles that bind from those that do not bind to the target antigen.

In any of the methods of the invention described herein, a solvent accessible and/or highly diverse amino acid position can be any that meet the criteria as described herein, in particular any combination of the positions as described herein, for example any combination of the positions described for the polypeptides of the invention (as described in greater detail herein). Suitable variant amino acids can be any that meet the criteria as described herein, for example variant amino acids in polypeptides of the invention as described in greater detail below.

Designing diversity in CDRs may involve designing diversity in the length and/or in sequence of the CDR. For example, CDRH3 may be diversified in length to be, e.g., 7 to 21 amino acids in length, and/or in its sequence, for example by varying highly diverse and/or solvent accessible positions with amino acids encoded by a restricted codon set. In some embodiments, a portion of CDRH3 has a length ranging from 5 to 21, 7 to 20, 9 to 15, or 11 to 13 amino acids, and has a variant amino acid at one or more positions encoded by a restricted codon set that encodes a limited number of amino acids such as codon sets encoding no more than 19, 15, 10, 8, 6, 4 or 2 amino acids. In some embodiments, the C terminal end has an amino acid sequence AM, AMDY, or DY.

In some embodiments, polypeptides of the invention can be in a variety of forms as long as the target binding function of the polypeptides is retained. In some embodiments, a polypeptide of the invention is a fusion polypeptide (i.e. a fusion of two or more sequences from heterologous polypeptides). Polypeptides with diversified CDRs according to the invention can be prepared as fusion polypeptides to at least a portion of a viral coat protein, for example, for use in phage display. Viral coat proteins that can be used for display of the polypeptides of the invention comprise protein p III, major coat protein pVIII, Soc (T4 phage), Hoc (T4 phage), gpD (lambda phage), pVI, or variants or fragments thereof. In some embodiments, the fusion polypeptide is fused to at least a portion of a viral coat protein, such as a viral coat protein selected from the group consisting of pIII, pvIII, Soc, Hoc, gpD, pVI, and variants or fragments thereof.

In some embodiments, in which the polypeptide with diversified CDRs is one or more antibody variable domains, the antibody variable domains can be displayed on the surface of the virus in a variety of formats including ScFv, Fab, ScFv$_2$, F(ab')$_2$ and F(ab)$_2$. For display of the polypeptides in bivalent manner, the fusion protein in certain embodiments includes a dimerization domain. The dimerization domain can comprise a dimerization sequence and/or a sequence comprising one or more cysteine residues. The dimerization domain can be linked, directly or indirectly, to the C-terminal end of a heavy chain variable or constant domain (e.g., CH1). The structure of the dimerization domain can be varied depending on whether the antibody variable domain is produced as a fusion protein component with the viral coat protein component (e.g., without an amber stop codon after dimerization domain) or whether the antibody variable domain is produced predominantly without the viral coat protein component (e.g., with an amber stop codon after dimerization domain). When the antibody variable domain is produced predominantly as a fusion protein with the viral coat protein component, one or more disulfide bonds and/or a single dimerization sequence provides for bivalent display. For antibody variable domains predominantly produced without being fused to a viral coat protein component (e.g. with an amber stop codon), the dimerization domain can comprise both a cysteine residue and a dimerization sequence.

In addition, optionally, a fusion polypeptide can comprise a tag that may be useful in purification, detection and/or screening such as FLAG, poly-his, gD tag, c-myc, fluorescence protein or B-galactosidase. In one embodiment, a fusion polypeptide comprises a light chain variable or constant domain fused to a polypeptide tag.

In another aspect of the invention, a polypeptide such as an antibody variable domain is obtained from a single source or template molecule. The source or template molecule can be selected or designed for characteristics such as good yield and stability when produced in prokaryotic or eukaryotic cell culture, and/or to accommodate CDRH3 regions of varying lengths. The sequence of the template molecule can be altered to improve folding and/or display of the variable domain when presented as a fusion protein with a phage coat protein component. For example, a source antibody may comprise the amino acid sequence of the variable domains of humanized antibody 4D5 (light chain variable domain (FIG. 1; SEQ ID NO: 1)); (heavy chain variable domain (FIG. 1; SEQ ID NO: 2)). For example, in an antibody variable domain of a heavy or light chain, framework region residues can be modified or altered from the source or template molecule to improve folding, yield, display or affinity of the antibody variable domain. In some embodiments, framework residues are selected to be modified from the source or template molecule when the amino acid in the framework position of the source molecule is different from the amino acid or amino acids commonly found at that position in naturally occurring antibodies or in a subgroup consensus sequence. The amino acids at those positions can be changed to the amino acids most commonly found in the naturally occurring antibodies or in a subgroup consensus sequence at that position. In one embodiment, framework residue 71 of the heavy chain may be R, V or A. In another example, framework residue 93 of the heavy chain may be S or A. In yet another example, framework residue 94 may be R, K or T or encoded by MRT. In another example, framework residue 93 is A and framework residue 94 is R. In yet another example, framework residue 49 in the heavy chain may be alanine or glycine. Framework residues in the light chain may also be changed. For example, the amino acid at position 66 may be arginine or glycine. Framework regions for the wild-type humanized antibody 4D5-8 light chain and heavy chain sequences are shown in FIG. 6 (SEQ ID NOs:6-9 and 10-13, respectively). Framework regions for variant versions of the humanized antibody 4D5-8 light chain and heavy chain sequences wherein the light chain is modified at position 66 and the heavy chain is modified at positions 71, 73, and 78 are shown in FIG. 7 (SEQ ID NOs:14-17 and 18-21, respectively).

Methods of the invention are capable of generating a large variety of polypeptides comprising a diverse set of CDR sequences. In an embodiment, a one or more libraries are formed using the methods of the invention as described herein. The libraries are screened for binding to target antigens, e.g. human DR5 and HER-2.

Immunoglobulin heavy chain variable domains randomized to provide diversity are provided. In one embodiment, a polypeptide comprises an immunoglobulin heavy chain variable domain, wherein:

(i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from S and Y; wherein X2 is selected from Y and S; wherein X3 is selected from Y and S; wherein X4 is selected from Y and S; and wherein X5 is selected from Y and S;

(ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-D-Y (SEQ ID NO:31), wherein X1 is position 95 according to the Kabat numbering system, and wherein X1 is selected from R, Y and M; X2 is selected from Y and R; X3 is selected from Y, S, R, P and G, X4 is selected from Y and S; X5 is selected from Y, S, R and H; X6 is selected from R, Y and S; X7 is selected from G, Y and S; X8 is selected from R, Y and S; X9 is selected from G, Y and S; X10 is selected from R, Y and S; X11 is selected from G, Y and S; X12 is selected from S, Y, R, G and A; X13 is selected from G and Y; X14 is selected from L, M, R, G, and A; and X15 is selected from G, F and L or is not present; and X16 is F or is not present.

In another embodiment, a polypeptide comprises an immunoglobulin heavy chain variable domain, wherein:

(i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;

(ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:24), wherein X1 is position 95 according to the Kabat numbering system, and wherein the amino acids at each of positions X1-X6 are selected from a pool of amino acids in a molar ratio of 50% Y, 25% S, and 25% G; wherein the amino acids at each of positions X7-X17 are selected from a pool of amino acids in a molar ratio of 50% Y, 25% S, and 25% G, or are not present; wherein X18 is selected from G and A; and wherein X19 is selected from I, M, L, and F.

In another embodiment, a polypeptide comprises an immunoglobulin heavy chain variable domain, wherein:

(i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;

(ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:26), wherein X1 is position 95 according to the Kabat numbering system, and wherein the amino acids at each of positions X1-X6 are selected from a pool of amino acids in a molar ratio of 25% Y, 50% S, and 25% R; wherein the amino acids at each of positions X7-X17 are selected from a pool of amino acids in a molar ratio of 25% Y, 50% S, and 25% R, or are not present; wherein X18 is selected from G and A; and wherein X19 is selected from I, M, L, and F.

In another embodiment, a polypeptide comprises an immunoglobulin heavy chain variable domain, wherein:

(i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;

(ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:27), wherein X1 is position 95 according to the Kabat numbering system, and wherein the amino acids at each of positions X1-X6 are selected from a pool of amino acids in a molar ratio of 38% Y, 25% S, 25% G, and 12% R; wherein the amino acids at each of positions X7-X17 are selected from a pool of amino acids in a molar ratio of 38% Y, 25% S, 25% G, and 12% R, or are not present; wherein X18 is selected from G and A; and wherein X19 is selected from I, M, L, and F.

In another embodiment, a polypeptide comprises an immunoglobulin heavy chain variable domain, wherein:

(i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;

(ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:28), wherein X1 is position 95 according to the Kabat numbering system, and wherein the amino acids at each of positions X1-X6 are selected from a pool of amino acids in a molar ratio of 20% Y, 26% S, 26% G, 13% R, 1% A, 1% D, 1% E, 1% F, 1% H, 1% I, 1% K, 1% L, 1% M, 1% N, 1% P, 1% Q, 1% T, 1% V, and 1% W; wherein the amino acids at each of positions X7-X17 are selected from a pool of amino acids in a molar ratio of 20% Y, 26% S, 26% G, 13% R, 1% A, 1% D, 1% E, 1% F, 1% H, 1% I, 1% K, 1%, 1% M, 1% N, 1% P, 1% Q, 1% T, 1% V, and 1% W, or are not present; wherein X18 is selected from and A; and wherein X19 is selected from I, M, L, and F.

In one aspect, CDRH1 comprises at least one amino acid sequence selected from any one of SEQ ID NOs:524-540 and 189-294 or at least one CDRH1 amino acid sequence selected from any of the sequences in FIG. 11A or FIG. 15. CDRH2 comprises at least one amino acid sequence selected from SEQ ID NOs:541-557 and 295-400 or at least one CDHR2 amino acid sequence selected from any of the sequences in FIG. 11A or FIG. 15. CDRH3 comprises at least one amino acid sequence selected from SEQ ID NOs:558-574 and 401-506 or at least one CDHR3 amino acid sequence selected from any of the sequences in FIG. 1A or FIG. 15.

In another aspect, CDRH3 comprises X1 selected from R and Y; X3 is S; X8 is S; X9 is Y; and X10 is Y or R. In another embodiment, CDRH3 comprises an amino acid sequence X1-R-S-Y-R-Y-G-S-Y-X10-G-S-Y-X14-F-D-Y (SEQ ID NO:575).

In another aspect, the polypeptide binds to human DR5 or binds to human DR5 and murine DR5. In some embodiments, the polypeptide is an antibody.

In an embodiment, the antibody comprises a heavy chain variable domain comprising: i) a CDRH1 comprising an amino acid sequence GFYISSSSIH (SEQ ID NO:576); ii) a CDRH2 comprising an amino acid sequence SISPSSG-STYYADSVKG (SEQ ID NO:577); and iii) a CDRH3 comprising an amino acid sequence YRSYRYGSYYGSYGFDY (SEQ ID NO:578). In an embodiment, the antibody comprises a heavy chain variable domain comprising: i) a CDRH1 comprising an amino acid sequence GFYIYSSSIH (SEQ ID NO:579); ii) a CDRH2 comprising an amino acid sequence SISPSSGYTSYADSVKG (SEQ ID NO:580); and iii) a CDRH3 comprising and amino acid sequence RRSYRYG-SYRGSYAFDY (SEQ ID NO:581).

In another aspect, the polypeptide further comprises a light chain variable domain wherein
(i) CDRL3 comprises an amino acid sequence Q-Q-X1-X2-X3-X4-P-X5-T (SEQ ID NO:25); wherein X1 is at position 91 and is selected from Y, H and S; X2 is selected from Y and S; X3 is selected from Y, S and T; X4 is selected from Y, S and T; and X5 is selected from S, P and Y. In an embodiment, a CDRL1 comprises an amino acid sequence RASQDVN-TAVA (SEQ ID NO:29). In an embodiment, a CDRL2 comprises an amino acid sequence SASSLYS (SEQ ID NO:30).

In another embodiment, a polypeptide comprises an immunoglobulin heavy chain variable domain, wherein (i) CDRH1 comprises amino acid sequence G-F-X1-I-X2-X3-X4-X5-I-H (SEQ ID NO:22); wherein X1 is at position 28 according to Kabat numbering and is selected from S and Y; X2 is selected from S and Y; X3 is selected from S and Y; X4 is selected from S and Y; and X5 is selected from S and Y; (ii) CDR142 comprises an amino acid sequence of X1-I-X2-P-X3-X4-G-X5-T-X6-Y-A-D-S-V-K-G (SEQ ID NO:23); wherein X1 is at amino acid position 50 according to Kabat numbering and is selected from S and Y; X2 is selected from S and Y; X3 is selected from S and Y; X4 is selected from S and Y; X5 is selected from S and Y; and X6 is selected from S and Y; and (iii) CDRH3 comprises an amino acid sequence X1-X2-X3-X4-X5-X6-X7-D-Y (SEQ ID NO:582), wherein X1 is at amino acid position 95 according to Kabat numbering and is selected from Y and R; X2 is selected from Y, S and R; X3 is selected from S, G, Y and H; X4 is selected from S, G, Y and R; X5 is selected from G and A; X6 is selected from F, M, L, and A; and X7 is selected from F, M, and L or is missing.

In one aspect, CDRH1 comprises at least one amino acid sequence selected from any one of SEQ ID NOs:189-198. CDRH2 comprises at least one amino acid sequence selected from SEQ ID NOs:295-304. CDRH3 comprises at least one amino acid sequence selected from SEQ ID NOs:401-410.

In another embodiment, a polypeptide comprises an immunoglobulin heavy chain variable domain, wherein (i) CDRH1 comprises amino acid sequence G-F-X1-I-X2-X3-X4-X5-I-H (SEQ ID NO:22); wherein X1 is at position 28 according to Kabat numbering and is selected from S and Y; X2 is selected from S and Y; X3 is selected from S and Y; X4 is selected from S and Y; and X5 is selected from S and Y; (ii) CDRH2 comprises an amino acid sequence of X1-I-X2-P-X3-X4-G-X5-T-X6-Y-A-D-S-V-K-G (SEQ ID NO:22); wherein X1 is at amino acid position 50 according to Kabat numbering and is selected from S and Y; X2 is selected from S and Y; X3 is selected from S and Y; X4 is selected from S and Y; and X5 is selected from S and Y; and (iii) CDRH3 comprises an amino acid sequence X1-X2-X3-X4-X5-X6-X7-X8-D-Y (SEQ ID NO:583), wherein X1 is at amino acid position 95 according to Kabat numbering and is selected from Y, S and G; X2 is selected from Y, S, G, R, A, and M; X3 is selected from G, Y, S and R; X4 is selected from G, Y and F; X5 is selected from Y, S, N, and G; X6 is selected from Y, R, H and W; X7 is selected from G and A; and X8 is selected from F, M, L and I.

In one aspect, CDRH1 comprises at least one amino acid sequence selected from any one of SEQ ID NOs:199-216. CDRH2 comprises at least one amino acid sequence selected from SEQ ID NOs:305-322. CDRH3 comprises at least one amino acid sequence selected from SEQ ID NOs:411-428.

In another embodiment, a polypeptide comprises an immunoglobulin heavy chain variable domain, wherein
(i) CDRH1 comprises amino acid sequence G-F-X1-I-X2-X3-X4-X5-I-H (SEQ ID NO:22); wherein X1 is at position 28 according to Kabat numbering and is selected from S and Y; X2 is selected from S and Y; X3 is selected from S and Y; X4 is selected from S and Y; and X5 is selected from S and Y;
(ii) CDRH2 comprises an amino acid sequence of X1-I-X2-P-X3-X4-G-X5-T-X6-Y-A-D-S-V-K-G (SEQ ID NO:23); wherein X1 is at amino acid position 50 according to Kabat numbering and is selected from S and Y; X2 is selected from S and Y; X3 is selected from S and Y; X4 is selected from S and Y; and X5 is selected from S and Y; and
(iii) CDRH3 comprises an amino acid sequence of X1-X2-X3-X4-X5-X6-X7-X8-X9-X10-X11-X12-X13-X14-X15-X16-X17-X18-X19-D-Y (SEQ ID NO:584), wherein X1 is at amino acid position 95 and is selected from Y, S, R, G and E; X2 is selected from Y, S, R and G; X3 is selected from S, Y, G and W; X4 is selected from S, Y, G and Q; X5 is selected from G, Y and S; X6 is selected from G, Y, S, R and V; X7 is selected from S, Y, G and R; X8 is selected from Y, S, G, R, P and V; X9 is selected from G, A, Y, S and R; X10 is selected from M, F, G, Y, S and R; X11 is selected from A, Y, S, G and R or is not present; X12 is selected from I, M, F, L, A, G, S, Y, R, and T or is not present; X13 is selected from F, M, L, G, A, Y, T, and S or is not present; X14 is selected from L, M, F, I, G, Y, A, and T or is not present; X15 is selected from M, L, Y, G and R or is not present; X16 is selected from Y and G or is not present; X17 is selected from R, M, and G or is not present; X18 is selected from P and A or is not present; and X18 is L or is not present.

In another embodiment, a polypeptide comprises an immunoglobulin heavy chain variable domain, wherein:
(i) CDRH1 comprises an amino acid sequence G-F-X1-I-X2-X3-X4-X5-I-H, wherein G is position 26 and X1 is position 28 according to the Kabat numbering system; and wherein X1-X5 are naturally occurring amino acids other than cysteine;

(ii) CDRH2 comprises an amino acid sequence: X6-I-X7-P-X8-X9-G-X10-T-X11-Y-A-D-S-V-K-G, wherein X6 is position 50 according to the Kabat numbering system, and wherein X6-X11 are naturally occurring amino acids other than cysteine; and (iii) CDRH3 comprises an amino acid sequence: X12-X13-X14-X15-X16-(X17)$_n$-X18-X19-D-Y, wherein X12 is position 95 according to the Kabat numbering system, and wherein n is a suitable number that would retain the functional activity of the heavy chain variable domain, and wherein X12-X19 are naturally occurring amino acids other than cysteine.

In one aspect, n is 1 to 12. In one aspect, X1 is selected from Y and S; X2 is selected from Y and S; X3 is selected from Y and S; X4 is selected from Y and S; X5 is selected from Y and S, and X6 is selected from Y and S. In one aspect, X6 is selected from Y and S; X7 is selected from Y and S; X8 is selected from Y and S; X9 is selected from Y and S; X10 is selected from Y and S; and X11 is selected from Y and S. In one aspect, the amino acids at each of positions X12-X17 are selected from a pool of amino acids in a molar ratio of 50% Y, 25% S, and 25% G, X18 is selected from G and A, and X19 is selected from I, M, L, and F. In an alternative aspect, the amino acids at each of positions X12-X17 are selected from a pool of amino acids in a molar ratio of 25% Y, 50% S, and 25% R, X18 is selected from G and A, and X19 is selected from I, M, L, and F. In another alternative aspect, the amino acids at each of positions X12-X17 are selected from a pool of amino acids in a molar ratio of 38% Y, 25% S, 25% G, and 12% R, X18 is selected from G and A, and X19 is selected from I, M, L, and F. In another alternative aspect, the amino acids at each of positions X12-X17 are selected from a pool of amino acids in a molar ratio of 20% Y, 26% S, 26% G, 13% R, 1% A, 1% D, 1% E, 1% F, 1% H, 1% I, 1% K, 1% L, 1% M, 1% N, 1% P, 1% Q, 1% T, 1% V, and 1% W, X18 is selected from G and A, and X19 is selected from I, M, L, and F. In one aspect, CDRH1 comprises an amino acid sequence selected from SEQ ID NOS: 217-294 or any of the CDRH1 sequences in FIG. 11. In one aspect, CDRH2 comprises an amino acid sequence selected from SEQ ID NOS: 323-400 or any of the CDRH2 sequences in FIG. 11. In one aspect, CDRH3 comprises an amino acid sequence selected from SEQ ID NOS: 429-506 or any of the CDRH3 sequences in FIG. 11.

In another embodiment, a polypeptide comprising an immunoglobulin heavy chain variable domain is provided, wherein:
(i) CDRH1 comprises an amino acid sequence G-F-X1-I-X2-X3-X4-X5-I-H (e.g. SEQ ID NO:22), wherein G is position 26 and X1 is position 28 according to the Kabat numbering system; and wherein X1-X5 are naturally occurring amino acids other than cysteine;
(ii) CDRH2 comprises an amino acid sequence: X6-I-X7-P-X8-X9-S-X10-T-X11-Y-A-D-S-V-K-G (e.g. SEQ ID NO:23), wherein X6 is position 50 according to the Kabat numbering system, and wherein X6-X11 are naturally occurring amino acids other than cysteine; and
(iii) CDRH3 comprises an amino acid sequence: X12-X13-X14-(X15)$_n$-X16-X17 (e.g. SEQ ID NO:24), wherein X14 is position 95 according to the Kabat numbering system, and wherein n is a suitable number that would retain the functional activity of the heavy chain variable domain, and wherein X12-X17 are naturally occurring amino acids other than cysteine.

In one aspect, n is 1 to 14. In another aspect, X1 is selected from Y and S; X2 is selected from Y and S; X3 is selected from Y and S; X4 is selected from Y and S; and X5 is selected from Y and S. In another aspect, X1 is selected from W and S; X2 is selected from W and S; X3 is selected from W and S; X4 is selected from W and S; and X5 is selected from W and S. In another aspect, X1 is selected from R and S; X2 is selected from R and S; X3 is selected from R and S; X4 is selected from R and S; and X5 is selected from R and S. In another aspect, X1 is selected from F and S; X2 is selected from F and S; X3 is selected from F and S; X4 is selected from F and S; and X5 is selected from F and S. In another aspect, X6 is selected from Y and S; X7 is selected from Y and S; X8 is selected from Y and S; X9 is selected from Y and S; X10 is selected from Y and S; and X11 is selected from Y and S. In another aspect, X6 is selected from W and S; X7 is selected from W and S; X8 is selected from W and S; X9 is selected from W and S; X10 is selected from W and S; and X11 is selected from W and S. In another aspect, X6 is selected from R and S; X7 is selected from R and S; X8 is selected from R and S; X9 is selected from R and S; X10 is selected from R and S; and X11 is selected from R and S. In another aspect, X6 is selected from F and S; X7 is selected from F and S; X8 is selected from F and S; X9 is selected from F and S; X10 is selected from F and S; and X11 is selected from F and S. In another aspect, X12 is selected from Y and S; X13 is selected from Y and S; X14 is selected from Y and S; X15 is selected from Y and S; X16 is selected from G and A; and X17 is selected from F, L, I, and M. In another aspect, X12 is selected from W and S; X13 is selected from W and S; X14 is selected from W and S; X15 is selected from W and S; X16 is selected from G and A; and X7 is selected from F, L, I, and M. In another aspect, X12 is selected from R and S; X13 is selected from R and S; X14 is selected from R and S; X15 is selected from R and S; X16 is selected from G and A; and X17 is selected from F, L, I, and M. In another aspect, X12 is selected from F and S; wherein X13 is selected from F and S; X14 is selected from F and S; X15 is selected from F and S; X16 is selected from G and A; and X17 is selected from F, L, I, and M.

In another aspect, the amino acids at each of positions X12-X15 are selected from S and one of A, C, F, G, I, L, N, P, R, T, W, and Y; X16 is selected from G and A; and X17 is selected from F, L, I, and M.

In another embodiment, a polypeptide comprises an immunoglobulin heavy chain variable domain, wherein:
(i) CDRH1 comprises an amino acid sequence G-F-X1-I-X2-X3-X4-X5-I-1H, wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;
(ii) CDRH2 comprises an amino acid sequence: X1-I-X2-P-X3-X4-G-X5-T-X6-Y-A-D-S-V-K-G, wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and
(iii) CDRH3 comprises an amino acid sequence: X1-X2-X3-X4-X5-X6-X7-X8-X9-X10-X11-X12-X13-X14-X15-X16-X17-X18-X19, wherein X1 is position 95 according to the Kabat numbering system, and wherein the amino acids at each of positions X1-X17 are selected from S and one of A, C, F, G, I, L, N, P, R, T, W, or Y, or are not present; wherein X18 is selected from G and A; and wherein X19 is selected from F, L, I, and M.

In one aspect, CDRH1 comprises at least one amino acid sequence selected from any one of SEQ ID NOs:816-842 or at least one CDRH1 amino acid sequence selected from any of the sequences in FIG. 21A. CDRH2 comprises at least one amino acid sequence selected from SEQ ID NOs:843-869 or at least one CDRH2 amino acid sequence selected from any of the sequences in FIG. 21A. CDRH3 comprises at least one amino acid sequence selected from SEQ ID NOs:870-896 or at least one CDRH3 amino acid sequence selected from any of the sequences in FIG. 21A.

In another embodiment, a polypeptide comprises an immunoglobulin heavy chain variable domain, wherein:
(i) CDRH1 comprises an amino acid sequence G-F-X1-I-X2-X3-X4-X5-I-H, wherein G is position 26 and X1 is position 28 according to the Kabat numbering system; wherein the amino acid at each of positions X1-X5 is selected from S and one of Y, W, R, or F;
(ii) CDRH2 comprises an amino acid sequence: X1-I-X2-P-X3-X4-G-X5-T-X6-Y-A-D-S-V-K-G, wherein X1 is position 50 according to the Kabat numbering system; wherein the amino acid at each of positions X1-X6 is selected from S and one of Y, W, R, or F; and
(iii) CDRH3 comprises an amino acid sequence: X1-X2-X3-X4-X5-X6-X7-X8-X9-X10-X11-X12-X13-X14-X15-X16-X17-X18-X19, wherein X1 is position 95 according to the Kabat numbering system, and wherein the amino acids at each of positions X1-X19 are selected from S and one of Y, W, R, or F, or are not present; wherein X18 is selected from G and A; and wherein X19 is selected from F, L, I, and M.

In one aspect, CDRH1 comprises at least one amino acid sequence selected from any one of SEQ ID NOs:924-950 or at least one CDRH1 amino acid sequence selected from any of the sequences in FIG. 24A. CDRH2 comprises at least one amino acid sequence selected from SEQ ID NOs:951-977 or at least one CDRH2 amino acid sequence selected from any of the sequences in FIG. 24A. CDRH3 comprises at least one amino acid sequence selected from SEQ ID NOs:978-1004 or at least one CDRH3 amino acid sequence selected from any of the sequences in FIG. 24A.

In one aspect, the polypeptide binds human HER-2. In some embodiments, the polypeptide comprises an antibody. In an embodiment, the antibody comprises a heavy chain variable domain comprising
i) a CDRH1 comprising an amino acid sequence GFSIYSSYIH (SEQ ID NO:821);
ii) a CDRH2 comprising an amino acid sequence SIYPYS-GYTSYADSVKG (SEQ ID NO:848); and
iii) a CDRH3 comprising an amino acid sequence WWS-SAFDY (SEQ ID NO: 875). In another embodiment, the antibody comprises heavy chain variable domain comprises:
i) a CDRH1 comprising an amino acid sequence GFSIW-WSWIH (SEQ ID NO:932);
ii) a CDRH2 comprising an amino acid sequence SISPSS-GWTSYADSVKG (SEQ ID NO:959); and
iii) a CDRH3 comprising an amino acid sequence WWS-SAMDY (SEQ ID NO:986). In another embodiment, the antibody comprises a heavy chain variable domain comprising:
i) a CDRH1 comprising an amino acid sequence GFSISSSYIH (SEQ ID NO:944);
ii) a CDRH2 comprising an amino acid sequence SIYPYS-GYTSYADSVKG (SEQ ID NO:971); and
iii) a CDRH3 comprising an amino acid sequence YYSY-ALDY (SEQ ID NO:998). In another embodiment, the antibody comprises a heavy chain variable domain comprising
i) a CDRH1 comprising an amino acid sequence GFYISSSSIH (SEQ ID NO:230);

ii) a CDRH2 comprising an amino acid sequence YIYPSS-GYTSYADSVKG (SEQ ID NO:336); and
iii) a CDRH3 comprising an amino acid sequence GYYYSYYSGYALDY (SEQ ID NO:442).

In another aspect, the antibody, further comprises a light chain variable domain comprising a CDRL3 sequence, wherein CDRL3 comprises an amino acid sequence of Q-Q-X1-X2-X3-X4-P-X5-T (SEQ ID NO:25), wherein X1 is at position 91 according to Kabat numbering and is selected from S and Y; X2 is selected from S, Y and F; X3 is selected from Y, S and F; X4 is selected from Y and S; X5 is selected from S and Y.

In another embodiment, a polypeptide comprising an immunoglobulin light chain variable domain is provided, wherein CDRL3 comprises an amino acid sequence: Q-Q-X1-X2-X3-X4-P-X5-T (SEQ ID NO:25), wherein X1 is position 91 according to the Kabat numbering system, wherein X1 is selected from Y and S, wherein X2 is selected from Y and S; wherein X3 is selected from Y and S; wherein X4 is selected from Y and S; and wherein X5 is selected from Y and S. In another embodiment, a polypeptide comprises an immunoglobulin light chain variable domain, wherein CDRL3 comprises an amino acid sequence: Q-Q-X1-X2-X3-X4-P-X5-T, wherein X1 is position 91 according to the Kabat numbering system, and wherein the amino acids at each of positions X1-X5 are selected from S and one of Y, W, R, or F. In one aspect, CDRL3 comprises an amino acid sequence selected from SEQ ID NOS: 83-188, 507-523, 789-815 and 897-923 or any of the CDRL3 sequences in FIG. 11, 15, 21, or 24.

In another embodiment, a polypeptide comprising an immunoglobulin light chain variable domain is provided, wherein:
(i) CDRL1 comprises a first consensus hypervariable sequence or variant thereof comprising substitution at one or more positions compared to a corresponding consensus hypervariable sequence;
(ii) CDRL2 comprises a second consensus hypervariable sequence or variant thereof comprising substitution at one or more positions compared to a corresponding consensus hypervariable sequence; and
(iii) CDRL3 comprises an amino acid sequence: Q-Q-X1-X2-X3-(X4)$_n$-X5-X6-T (e.g. SEQ ID NO:25), wherein X1-X6 are any naturally occurring amino acids other than cysteine, and wherein X1 is position 91 according to the Kabat numbering system.

In one aspect, X1 is position 91 according to the Kabat numbering system, X1 is selected from Y and S; X2 is selected from Y and S; X3 is selected from Y and S; X4 is selected from Y and S; X5 is selected from P and L; and X6 is selected from F, L, I, and V. In one aspect, n is 1 to 3. In one aspect, CDRL3 comprises an amino acid sequence selected from SEQ ID NOS: 83-188, 507-523, 789-815 and 897-923 or any of the CDRL3 sequences in FIG. 11, 15, 21, or 24. In one aspect, the first consensus hypervariable sequence is R-A-S-Q-D-V-N-T-A-V-A (SEQ ID NO: 29). In one aspect, the second consensus hypervariable sequence is S-A-S-S-L-Y-S (SEQ ID NO: 30).

In another embodiment, a polypeptide comprising an immunoglobulin light chain variable domain is provided, wherein:
(i) CDRL1 comprises a first consensus hypervariable sequence or variant thereof comprising substitution at one or more positions compared to a corresponding consensus hypervariable sequence;
(ii) CDRL2 comprises a second consensus hypervariable sequence or variant thereof comprising substitution at one or more positions compared to a corresponding consensus hypervariable sequence; and
(iii) CDRL3 comprises an amino acid sequence: Q-Q-X1-X2-X3-X4-P-X5-T (e.g. SEQ ID NO:25), wherein X1-X5 are any naturally occurring amino acids other than cysteine, and X1 is position 91 according to the Kabat numbering system.

In one aspect, X1 is position 91 according to the Kabat numbering system, X1 is selected from Y and S, X2 is selected from Y and S; X3 is selected from Y and S; X4 is selected from Y and S; and X5 is selected from Y and S. In another aspect, X1 is position 91 according to the Kabat numbering system, and the amino acids at each of positions X1-X5 are selected from S and one of Y, W, R, and F. In one aspect, CDRL3 comprises an amino acid sequence selected from SEQ ID NOS: 83-188, 507-523, 789-815 and 897-923 or any of the CDRL3 sequences in FIG. 11, 15, 21, or 24. In another aspect, the first consensus hypervariable sequence is R-A-S-Q-D-V-N-T-A-V-A (SEQ ID NO: 29). In another aspect, the second consensus hypervariable sequence is S-A-S-S-L-Y-S (SEQ ID NO: 30).

In certain embodiments, a polypeptide comprises at least two antibody variable domains comprising: (a) a heavy chain antibody variable domain comprising any of the above-recited heavy chain polypeptides, and (b) a light chain antibody variable domain comprising any of the above-recited light chain polypeptides is provided.

In certain embodiments, an antibody comprising a polypeptide comprising an immunoglobulin heavy chain variable domain according to any of the above-recited heavy chain polypeptides, and a polypeptide comprising an immunoglobulin light chain variable domain according to any of the above-recited light chain polypeptides is provided.

In certain aspects, the above-recited polypeptides and antibodies further comprise a dimerization domain linked to the C-terminal region of a heavy chain antibody variable domain. In certain such aspects, the dimerization domain comprises a leucine zipper domain or a sequence comprising at least one cysteine residue. In certain such aspects, the dimerization domain comprises a hinge region from an antibody and a leucine zipper. In certain other aspects, the dimerization domain is a single cysteine.

In one embodiment, a fusion polypeptide comprising any of the above-recited polypeptides is provided, wherein an antibody variable domain comprising the above-recited polypeptide is fused to at least a portion of a viral coat protein. In one aspect, the viral coat protein is selected from the group consisting of protein pIII, major coat protein pVIII, Soc, Hoc, gpD, pv1, and variants thereof. In one aspect, the fusion polypeptide further comprises a dimerization domain between the variable domain and the viral coat protein. In one such aspect, the variable domain is a heavy chain variable domain. In another aspect, the fusion polypeptide further comprises a variable domain fused to a peptide tag. In one such aspect, the variable domain is a light chain variable domain. In another such aspect, the peptide tag is selected from the group consisting of gD, c-myc, poly-his, a fluorescence protein, and β-galactosidase.

In one embodiment, one or more of the above-described polypeptides further comprise framework regions FR1, FR2, FR3, and/or FR4 for an antibody variable domain corresponding to the variant CDRH1, CDRH2, CDRH3, and/or CDRL3, wherein the framework regions are obtained from a single antibody template. In certain such embodiments, each of the framework regions comprises an amino acid sequence corresponding to the framework region amino acid sequences of antibody 4D5 (SEQ ID NOS: 6-9 and 10-13) or a variant of antibody 4D5 (SEQ ID NOS: 14-17 and 18-21).

In one embodiment, a library is provided that comprises a plurality of one or more of the above-described polypeptides, wherein the library has at least $1 \times 10^4$ distinct antibody variable domain sequences.

In another embodiment, a method of generating a composition comprising a plurality of polypeptides is provided, comprising:
(a) generating a plurality of polypeptides comprising:
(i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;
(ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and
(iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:24), wherein X1 is position 95 according to the Kabat numbering system, and wherein the amino acids at each of positions X1-X6 are selected from a pool of amino acids in a molar ratio of 50% Y, 25% S, and 25% G; wherein the amino acids at each of positions X7-X17 are selected from a pool of amino acids in a molar ratio of 50% Y, 25% S, and 25% G, or are not present; wherein X18 is selected from G and A; and wherein X19 is selected from I, M, L, and F.

In one aspect, the method further comprises:
(b) generating a plurality of polypeptides comprising:
(i) CDRL1 comprising a first consensus hypervariable sequence or variant thereof comprising substitution at one or more positions compared to a corresponding consensus hypervariable sequence;
(ii) CDRL2 comprising a second consensus hypervariable sequence or variant thereof comprising substitution at one or more positions compared to a corresponding consensus hypervariable sequence; and
(iii) CDRL3 comprising an amino acid sequence: Q-Q-X1-X2-X3-X4-P-X5-T (SEQ ID NO:25), wherein X1 is position 91 according to the Kabat numbering system, and wherein X1 is selected from Y and S, wherein X2 is selected from Y and S; wherein X3 is selected from Y and S; wherein X4 is selected from Y and S; and wherein X5 is selected from Y and S.

In one aspect, the plurality of polypeptides are encoded by a plurality of polynucleotides.

In another embodiment, a method of generating a composition comprising a plurality of polypeptides is provided, comprising:
(a) generating a plurality of polypeptides comprising:
(i) CDRH1 comprising an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;

(ii) CDRH2 comprising an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprising an amino acid sequence: X1-X2-X3-X4-X5-X6-X7-X8-X9-X10-X11-X12-X13-X14-X15-X16-X17-X18-X19-D-Y (SEQ ID NO:26), wherein X1 is position 95 according to the Kabat numbering system, and wherein the amino acids at each of positions X1-X6 are selected from a pool of amino acids in a molar ratio of 25% Y, 50% S, and 25% R; wherein the amino acids at each of positions X7-X17 are selected from a pool of amino acids in a molar ratio of 25% Y, 50% S, and 25% R; wherein X18 is selected from G and A; and wherein X19 is selected from I, M, L, and F.

In one aspect, the method further comprises:
(b) generating a plurality of polypeptides comprising:
(i) CDRL1 comprising a first consensus hypervariable sequence or variant thereof comprising substitution at one or more positions compared to a corresponding consensus hypervariable sequence;
(ii) CDRL2 comprising a second consensus hypervariable sequence or variant thereof comprising substitution at one or more positions compared to a corresponding consensus hypervariable sequence; and
(iii) CDRL3 comprising an amino acid sequence: Q-Q-X1-X2-X3-X4-P-X5-T (SEQ ID NO:25), wherein X1 is position 91 according to the Kabat numbering system, and wherein X1 is selected from Y and S, wherein X2 is selected from Y and S; wherein X3 is selected from Y and S; wherein X4 is selected from Y and S; and wherein X5 is selected from Y and S.

In one aspect, the plurality of polypeptides are encoded by a plurality of polynucleotides.

In another embodiment, a method of generating a composition comprising a plurality of polypeptides is provided, comprising:
(a) generating a plurality of polypeptides comprising:
(i) CDRH1 comprising an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;
(ii) CDRH2 comprising an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and
(iii) CDRH3 comprising an amino acid sequence: X1-X2-X3-X4-X5-X6-X7-X8-X9-X10-X11-X12-X13-X14-X15-X16-X17-X18-X19-D-Y (SEQ ID NO:27), wherein X1 is position 95 according to the Kabat numbering system, and wherein the amino acids at each of positions X1-X6 are selected from a pool of amino acids in a molar ratio of 38% Y, 25% S, 25% G, and 12% R; wherein the amino acids at each of positions X7-X17 are selected from a pool of amino acids in a molar ratio of 38% Y, 25% S, 25% G, and 12% R, or are not present; wherein X18 is selected from G and A; and wherein X19 is selected from I, M, L, and F.

In one aspect, the method further comprises:
(b) generating a plurality of polypeptides comprising:
(i) CDRL1 comprising a first consensus hypervariable sequence or variant thereof comprising substitution at one or more positions compared to a corresponding consensus hypervariable sequence;
(ii) CDRL2 comprising a second consensus hypervariable sequence or variant thereof comprising substitution at one or more positions compared to a corresponding consensus hypervariable sequence; and
(iii) CDRL3 comprising an amino acid sequence: Q-Q-X1-X2-X3-X4-P-X5-T (SEQ ID NO:25), wherein X1 is position 91 according to the Kabat numbering system, and wherein X1 is selected from Y and S, wherein X2 is selected from Y and S; wherein X3 is selected from Y and S; wherein X4 is selected from Y and S; and wherein X5 is selected from Y and S.

In one aspect, the plurality of polypeptides are encoded by a plurality of polynucleotides.

In another embodiment, a method of generating a composition comprising a plurality of polypeptides is provided, comprising:
(a) generating a plurality of polypeptides comprising:
(i) CDRH1 comprising an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;
(ii) CDRH2 comprising an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and
(iii) CDRH3 comprising an amino acid sequence: X1-X2-X3-X4-X5-X6-X7-X8-X9-X10-X11-X12-X13-X14-X15-X16-X17-X18-X19-D-Y (SEQ ID NO:28), wherein X1 is position 95 according to the Kabat numbering system, and wherein the amino acids at each of positions X1-X6 are selected from a pool of amino acids in a molar ratio of 20% Y, 26% S, 26% G, 13% R, 1% A, 1% D, 1% E, 1% F, 1% H, 1% I, 1% K, 1% L, 1% M, 1% N, 1% P, 1% Q, 1% T, 1% V, and 1% W; wherein the amino acids at each of positions X7-X17 are selected from a pool of amino acids in a molar ratio of 20% Y, 26% S, 26% G, 13% R, 1% A, 1% D, 1% E, 1% F, 1% H, 1% I, 1% K, 1% L, 1% M, 1% N, 1% P, 1% Q, 1% T, 1% V, and 1% W, or are not present; wherein X18 is selected from G and A; and wherein X19 is selected from I, M, L, and F.

In one aspect, the method further comprises:
(b) generating a plurality of polypeptides comprising:
(i) CDRL1 comprising a first consensus hypervariable sequence or variant thereof comprising substitution at one or more positions compared to a corresponding consensus hypervariable sequence;
(ii) CDRL2 comprising a second consensus hypervariable sequence or variant thereof comprising substitution at one or more positions compared to a corresponding consensus hypervariable sequence; and (iii) CDRL3 comprising an amino acid sequence: Q-Q-X1-X2-X3-X4-P-X5-T (SEQ ID NO:25), wherein X1 is position 91 according to the Kabat numbering system, and wherein X1 is selected from Y and S, wherein X2 is selected from Y and S; wherein X3 is selected from Y and S; wherein X4 is selected from Y and S; and wherein X5 is selected from Y and S.

In one aspect, the first consensus hypervariable sequence comprises a Kabat consensus CDRL1 sequence. In one such aspect, the first consensus hypervariable sequence is R-A-S-Q-D-V-N-T-A-V-A (SEQ ID NO: 29). In one aspect, the second consensus hypervariable sequence comprises a Kabat consensus CDRL2 sequence. In one such aspect, the second consensus hypervariable sequence is S-A-S-S-L-Y-S (SEQ ID NO: 30). In one aspect, the plurality of polypeptides are encoded by a plurality of polynucleotides.

In an embodiment, a method of generating a composition comprising a plurality of polypeptides is provided, comprising:
(a) generating a plurality of polypeptides comprising:
  (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;
  (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and
  (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:24), wherein X1 is position 95 according to the Kabat numbering system, and wherein X1 is selected from Y, S, G, R and E; X2 is selected from Y, S, G, R, M and A; X3 is selected from G, Y, S, R, W, and H, X4 is selected from Y, S, G, R, F and Q; X5 is selected from G, Y, N, A, and S; X6 is selected from F, M, L, A, R, G, H, W, V, Y and S; X7 is selected from M, L, G, A, R, F, Y and S or is not present; X8 is selected from M, L, F, I, R, G, P, V, Y and S or is not present; X9 is selected from G, Y, R, and S or is not present; X10 is selected from M, F, G, Y, R, and S or is not present; X11 is selected from A, G, Y, R, and S or is not present; X12 is selected from I, M, L, F, A, G, R, T, Y and S or is not present; X13 is selected from F, M, L, G, A, T, Y and S or is not present; X14 is selected from L, F, M, I, G, A, T, and Y or is not present; X15 is selected from M, Y G, L, and R or is not present; X16 is selected from Y and G or is not present; X17 is selected from R, M, and G or is not present; X18 is selected from P and A or is not present; and X19 is L or not present.

In one aspect, CDRH1 comprises an amino acid sequence selected from SEQ ID NOs: 189-294. In one aspect, CDRH2 comprises an amino acid sequence selected from SEQ ID NOs: 295-400. In one aspect, CDRH3 comprises an amino acid sequence selected from SEQ ID NOs: 401-506.

In one aspect, the method further comprises:
(b) generating a plurality of polypeptides comprising:
  (i) CDRL1 comprising a first consensus hypervariable sequence or variant thereof comprising substitution at one or more positions compared to a corresponding consensus hypervariable sequence;
  (ii) CDRL2 comprising a second consensus hypervariable sequence or variant thereof comprising substitution at one or more positions compared to a corresponding consensus hypervariable sequence; and
  (iii) CDRL3 comprising an amino acid sequence: Q-Q-X1-X2-X3-X4-P-X5-T (SEQ ID NO:25), wherein X1 is position 91 according to the Kabat numbering system, and wherein X1 is selected from Y and S, wherein X2 is selected from Y and S; wherein X3 is selected from Y and S; wherein X4 is selected from Y and S; and wherein X5 is selected from Y and S.

In one aspect, the plurality of polypeptides are encoded by a plurality of polynucleotides.

In one embodiment, a method of generating a composition comprising a plurality of polypeptides is provided, comprising:
(a) generating a plurality of polypeptides comprising:
  (i) CDRH1 comprising an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S;
  (ii) CDRH2 comprising an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and
  (iii) CDRH3 comprising an amino acid sequence: X1-X2-X3-X4-X5-X6-X7-X8-X9-X10-X11-X12-X13-X14-X15-X16-X17-X18-X19 (e.g. SEQ ID NO:24), wherein X1 is position 95 according to the Kabat numbering system, and wherein the amino acids at each of positions X1-X17 are selected from S and one of A, C, F, G, I, L, N, P, R, T, W, or Y, or are not present; wherein X18 is selected from G and A; and wherein X19 is selected from F, L, I, and M.

In one aspect, the method further comprises:
(b) generating a plurality of polypeptides comprising:
  (i) CDRL1 comprising a first consensus hypervariable sequence or variant thereof comprising substitution at one or more positions compared to a corresponding consensus hypervariable sequence;
  (ii) CDRL2 comprising a second consensus hypervariable sequence or variant thereof comprising substitution at one or more positions compared to a corresponding consensus hypervariable sequence; and
  (iii) CDRL3 comprising an amino acid sequence: Q-Q-X1-X2-X3-X4-P-X5-T (SEQ ID NO:25), wherein X1 is position 91 according to the Kabat numbering system; wherein X1 is selected from Y and S; wherein X2 is selected from Y and S; wherein X3 is selected from Y and S; wherein X4 is selected from Y and S; and wherein X5 is selected from Y and S.

In one embodiment, a method of generating a composition comprising a plurality of polypeptides is provided, comprising:
(a) generating a plurality of polypeptides comprising:
  (i) CDRH1 comprises an amino acid sequence G-F-X1-I-X2-X3-X4-X5-I-H (e.g. SEQ ID NO:22), wherein G is position 26 and X1 is position 28 according to the Kabat numbering system; wherein the amino acid at each of positions X1-X5 is selected from S and one of Y, W, R, or F;

(ii) CDRH2 comprises an amino acid sequence: X1-I-X2-P-X3-X4-G-X5-T-X6-Y-A-D-S-V-K-G (e.g. SEQ ID NO:23), wherein X1 is position 50 according to the Kabat numbering system; wherein the amino acid at each of positions X1-X6 is selected from S and one of Y, W, R, or F; and (iii) CDRH3 comprises an amino acid sequence: X1-X2-X3-X4-X5-X6-X7-X8-X9-X10-X11-X12-X13-X14-X15-X16-X17-X18-X19 (e.g. SEQ ID NO:26), wherein X1 is position 95 according to the Kabat numbering system, and wherein the amino acids at each of positions X1-X17 are selected from S and one of Y, W, R, or F, or are not present; wherein X18 is selected from G and A; and wherein X19 is selected from F, L, I, and M.

In another aspect, the method further comprises:

(b) generating a plurality of polypeptides comprising:

(i) CDRL1 comprising a first consensus hypervariable sequence or variant thereof comprising substitution at one or more positions compared to a corresponding consensus hypervariable sequence;

(ii) CDRL2 comprising a second consensus hypervariable sequence or variant thereof comprising substitution at one or more positions compared to a corresponding consensus hypervariable sequence; and (iii) CDRL3 comprising an amino acid sequence: Q-Q-X1-X2-X3-X4-P-X5-T (e.g. SEQ ID NO:25), wherein X1 is position 91 according to the Kabat numbering system; and wherein the amino acids at each of positions X1-X5 are selected from S and one of Y, W, R, and F.

In one embodiment, a method of generating one or more of the above-described CDRH1, CDRH2, CDRH3, CDRL1, CDRL2, and CDRL3 sequences is provided, comprising:

(a) constructing an expression vector comprising a polynucleotide sequence which encodes a light chain variable domain, a heavy chain variable domain, or both of a source antibody comprising at least one, two, three, four, five or all CDRs of the source antibody selected from the group consisting of CDRL1, CDRL2, CDRL3, CDRH1, CDRH2, and CDRH3; and (b) mutating at least one, two three, four, five or all CDRs of the source antibody to generate one or more of the above-described hypervariable regions.

In one embodiment, a method of selecting for a polypeptide that binds to a target antigen is provided, comprising:

(a) generating a composition with a plurality of one or more of the above-described polypeptides;

(b) selecting one or more polypeptides from the composition that binds to a target antigen;

(c) isolating the one or more polypeptides that bind to the target antigen from polypeptides that do not bind to the target antigen; and (d) identifying the one or more polypeptides that bind to the target antigen that have a desired affinity for the target antigen.

In one embodiment, a method of selecting for an antigen binding variable domain that binds to a target antigen from a library of antibody variable domains is provided, comprising:

(a) contacting one or more of the above-described libraries with a target antigen;

(b) separating one or more polypeptides that specifically bind to the target antigen from polypeptides that do not specifically bind to the target antigen, recovering the one or more polypeptides that specifically bind to the target antigen, and incubating the one or more polypeptides that specifically bind to the target antigen in a series of solutions comprising decreasing amounts of the target antigen in a concentration from about 0.1 nM to about 1000 nM; and (c) selecting the one or more polypeptides that specifically bind to the target antigen and that can bind to the lowest concentration of the target antigen or that have an affinity of about 0.1 nM to about 200 nM.

In one aspect, the target antigen is HER2 or DR5. In one aspect, the concentration of the target antigen is about 100 to about 250 nM. In one aspect, the concentration of target antigen is about 25 to about 100 nM. In some embodiments, one or more of the libraries, clones or polypeptides are screened against a panel of antigens including the target antigen. In some embodiments, those clones or polypeptides that specifically bind to the target antigen and do not substantially crossreact with any of the other antigen on the panel are selected. The panel of antigens can include at least three and up to 100 different antigens. In some cases, the panel of antigens includes 3 to 100, 3 to 50, 3 to 25, or 3 to 10 different antigens.

In one embodiment, a method of selecting for a polypeptide that binds to a target antigen from a library of polypeptides is provided, comprising:

(a) isolating one or more polypeptides that specifically bind to the target antigen by contacting a library comprising a plurality of any of the above-described polypeptides with an immobilized target antigen under conditions suitable for binding;

(b) separating the one or more polypeptides that specifically bind to the target antigen from polypeptides that do not specifically bind to the target antigen, and recovering the one or more polypeptides that specifically bind to the target antigen to obtain a subpopulation enriched for the one or more polypeptides that specifically bind to the target antigen; and (c) optionally, repeating steps (a)-(b) at least twice, each repetition using the subpopulation enriched for the one or more polypeptides that specifically bind to the target antigen obtained from the previous round of selection.

In one aspect, the method further comprises:

(d) incubating the subpopulation with a concentration of labeled target antigen in the range of about 0.1 nM to about 1000 nM to form a mixture, under conditions suitable for binding;

(e) contacting the mixture with an immobilized agent that binds to the label on the target antigen;

(f) detecting the one or more polypeptides that specifically bind to the labeled target antigen, and recovering the one or more polypeptides that specifically bind to the labeled target antigen from the labeled target antigen; and (g) optionally, repeating steps (d) to (f) at least twice, each repetition using the subpopulation enriched for the one or more polypeptides that specifically bind to the labeled target antigen obtained from the previous round of selection, and using a lower concentration of labeled target antigen than the previous round of selection.

In one aspect, the method further comprises adding an excess of unlabeled target antigen to the mixture and incubating the mixture for a period of time sufficient to recover one or more polypeptides that specifically bind to the target antigen with low affinity. In some embodiments, in any of the methods described herein, one or more of the libraries, clones or polypeptides are screened against a panel of antigens including the target antigen. In some embodiments, those clones or polypeptides that specifically bind to the target antigen and do not substantially crossreact with any of the other antigen on the panel are selected. The panel of antigens can include at least three and up to 100 different antigens. In some cases, the panel of antigens includes 3 to 100, 3 to 50, 3 to 25, or 3 to 10 different antigens.

In one embodiment, a method of isolating one or more polypeptides that specifically bind to a target antigen with high affinity is provided, comprising:
(a) contacting a library comprising a plurality of any of the above-described polypeptides with a target antigen at a concentration of at least about 0.1 nM to about 1000 nM to isolate one or more polypeptides that specifically bind to the target antigen;
(b) recovering the one or more polypeptides that specifically bind to the target antigen from the target antigen to obtain a subpopulation enriched for the one or more polypeptides that specifically bind to the target antigen; and
(c) optionally repeating steps (a) and (b) at least twice, each repetition using the subpopulation obtained from the previous round of selection and using a decreased concentration of target antigen from that used in the previous round to isolate one or more polypeptides that bind specifically to the target antigen at the lowest concentration of target antigen.

In one embodiment, an assay for selecting one or more polypeptides that bind to a target antigen from a library comprising a plurality of any of the above-described polypeptides is provided, comprising:
(a) contacting the library with a concentration of labeled target antigen at a concentration range of about 0.1 nM to about 1000 nM, under conditions suitable for formation of one or more complexes between the labeled target antigen and one or more polypeptides that specifically bind the target antigen;
(b) isolating the one or more complexes and separating the one or more polypeptides that specifically bind the target antigen from the labeled target antigen to obtain a subpopulation enriched for the one or more polypeptides that specifically bind the target antigen; and
(c) optionally, repeating steps (a) and (b) at least twice, each time using the subpopulation obtained from the previous round of selection and using a lower concentration of target antigen than was used in the previous round.

In one aspect, the assay further comprises adding an excess of unlabeled target antigen to the one or more complexes. In one aspect, steps (a) and (b) are repeated twice, wherein the concentration of target antigen in the first round of selection is about 100 nM to about 250 nM, wherein the concentration of target antigen in the second round of selection is about 25 nM to about 100 nM, and wherein the concentration of target antigen in the third round of selection is about 0.1 nM to about 25 nM.

In one embodiment, a method of screening a library comprising a plurality of any of the above-described polypeptides is provided, comprising:
(a) incubating a first sample of the library with a target antigen under conditions suitable for binding of the polypeptides to the target antigen;
(b) incubating a second sample of the library in the absence of a target antigen;
(c) contacting each of the first sample and the second sample with immobilized target antigen under conditions suitable for binding of the polypeptide to the immobilized target antigen;
(d) detecting the polypeptide bound to immobilized target antigen for each sample; and
(e) determining the affinity of the polypeptide for the target antigen by calculating the ratio of the amounts of bound polypeptide from the first sample over the amount of bound polypeptide from the second sample.

In one aspect, the target antigen is DR5 or HER-2. In one aspect, the concentration of the target antigen is about 100 to about 250 nM. In one aspect, the concentration of target antigen is about 25 to about 100 nM. In some embodiments, one or more of the libraries, clones or polypeptides are screened against a panel of antigens including the target antigen. In some embodiments, those clones or polypeptides that specifically bind to the target antigen and do not substantially crossreact with any of the other antigen on the panel are selected. The panel of antigens can include at least three and up to 100 different antigens. In some cases, the panel of antigens includes 3 to 100, 3 to 50, 3 to 25, or 3 to 10 different antigens.

In one embodiment, one or more of the above-described polypeptides specifically binds human DR5. In one aspect, the polypeptide is an antibody that specifically binds human DR5. In one such aspect, the antibody comprises the framework regions of the 4D5 antibody. In one such aspect, the antibody comprises the framework regions of a variant 4D5 antibody. In one such aspect, the antibody is a monoclonal antibody. In one such aspect, the antibody is a bispecific antibody. In one such aspect, the antibody is a synthetic antibody.

In one embodiment, an anti-DR5 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from S and Y; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-D-Y (SEQ ID NO:31), wherein X1 is position 95 according to the Kabat numbering system, and wherein X1 is selected from R, Y and M; X2 is selected from Y and R; X3 is selected from Y, S, R, P and G, X4 is selected from Y and S; X5 is selected from Y, S, R and H; X6 is selected from R, Y and S; X7 is selected from G, Y and S; X8 is selected from R, Y and S; X9 is selected from G, Y and S; X10 is selected from R, Y and S; X11 is selected from G, Y and S; X12 is selected from S, Y, R, G and A; X13 is selected from G and Y; X14 is selected from L, M, R, G, and A; and X15 is selected from G, F and L, or is not present; and X16 is F or is not present.

In another embodiment, an anti-DR5 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:24), wherein X1 is position 95 according to the Kabat numbering system, and wherein the amino acids at each of positions X1-X6 are selected from a pool of amino acids in a molar ratio of 50% Y, 25% S, and 25% G; wherein the amino acids at each of positions X7-X17 are selected from a pool of amino acids in a molar ratio of 50% Y, 25% S, and 25% G, or are not present; wherein X18 is selected from G and A; and wherein X19 is selected from I, M, L, and F.

In another embodiment, an anti-DR5 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:26), wherein X1 is position 95 according to the Kabat numbering system, and wherein the amino acids at each of positions X1-X6 are selected from a pool of amino acids in a molar ratio of 25% Y, 50% S, and 25% R; wherein the amino acids at each of positions X7-X17 are selected from a pool of amino acids in a molar ratio of 25% Y, 50% S, and 25% R, or are not present; wherein X18 is selected from G and A; and wherein X19 is selected from I, M, L, and F.

In another embodiment, an anti-DR5 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:27), wherein X1 is position 95 according to the Kabat numbering system, and wherein the amino acids at each of positions X1-X6 are selected from a pool of amino acids in a molar ratio of 38% Y, 25% S, 25% G, and 12% R; wherein the amino acids at each of positions X7-X17 are selected from a pool of amino acids in a molar ratio of 38% Y, 25% S, 25% G, and 12% R, or are not present; wherein X18 is selected from G and A; and wherein X19 is selected from I, M, L, and F.

In another embodiment, an anti-DR5 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:28), wherein X1 is position 95 according to the Kabat numbering system, and wherein the amino acids at each of positions X1-X6 are selected from a pool of amino acids in a molar ratio of 20% Y, 26% S, 26% G, 13% R, 1% A, 1% D, 1% E, 1% F, 1% H, 1% I, 1% K, 1% L, 1% M, 1% N, 1% P, 1% Q, 1% T, 1% V, and 1% W; wherein the amino acids at each of positions X7-X17 are selected from a pool of amino acids in a molar ratio of 20% Y, 26% S, 26% G, 13% R, 1% A, 1% D, 1% E, 1% F, 1% H, 1% I, 1% K, 1% L, 1% M, 1% N, 1% P, 1% Q, 1% T, 1% V, and 1% W, or are not present; wherein X18 is selected from G and A; and wherein X19 is selected from I, M, L, and F.

In some embodiments, the anti-DR5 antibody comprises a CDRH1 comprising an amino acid sequence selected from any one of SEQ ID NOs:524 to 540 as shown in FIG. 15. The anti-DR5 antibody may also comprise a CDRH2 comprising an amino acid sequence selected from SEQ ID NOs:541 to 557 as shown in FIG. 15. The anti-DR5 antibody may also comprise a CDRH3 comprising an amino acid sequence selected from SEQ ID NOs:558 to 574 as shown in FIG. 15. In one aspect, an antibody that specifically binds human DR5 comprises CDRH1, CDRH2, CDRH3, and CDRL3 sequences corresponding to the CDRH1, CDRH2, CDRH3, and CDRL3 sequences set forth in FIG. 15 for any one of Fabs 1-17.

In some embodiments, the anti-DR5 antibody comprises a CDRH3 wherein the amino acid position of X1 is position 95 and is selected from R and Y; X3 is at position 97 and is S; X8 is amino acid position 100b and is S; X9 is amino acid position 100c and is Y; and X10 is at amino acid position 100d and is Y or R. In an embodiment, the CDRH3 comprises an amino acid sequence X1-R-S-Y-R-Y-G-S-Y-X10-G-S-Y-X14-F-D-Y (SEQ ID NO:575). In a specific embodiment, an anti-DR5 antibody comprises a heavy chain variable domain comprising: i) a CDRH1 comprising an amino acid sequence GFYISSSSIH (SEQ ID NO:576); ii) a CDRH2 comprising an amino acid sequence SISPSSGSTYYADSVKG (SEQ ID NO:577); and iii) a CDRH3 comprising and amino acid sequence YRSYRYGSYYGSYGFDY (SEQ ID NO:578). In another specific embodiment, anti-DR5 antibody comprises a heavy chain variable domain comprising: i) a CDRH1 comprising an amino acid sequence GFYIYSSSIH (SEQ ID NO:579); ii) a CDRH2 comprising an amino acid sequence SISPSSGYTSYADSVKG (SEQ ID NO:580); and iii) a CDRH3 comprising and amino acid sequence RRSYRYGSYRGSYAFDY (SEQ ID NO:581).

In some embodiments, an anti-DR5 antibody comprises a CDRH1 comprising an amino acid sequence GFX1IX2SSSIH (SEQ ID NO:598) when X1 and X2 are Y or S. In other embodiments, an anti-DR5 antibody comprises a CDRH2 comprising an amino acid sequence X1ISPX3X4GYTX6YADSKVG (SEQ ID NO:599) and wherein X1, X3, X4 and X6 are Y or S. In another embodiment, an anti-DR5 antibody comprises a CDRH3 comprising an amino acid sequence YRX3YRYGX8X9X10GSYX14X15DY (SEQ ID NO:596), wherein X3 is selected from Y, S, R, P and G; X8 is selected from R, Y and S; X9 is selected from G, Y and S; X10 is selected from S, Y and R; X14 is selected from G and A; and X15 is selected from L and F.

In some embodiments, the anti-DR5 antibody bind to humans DR5 with an $IC_{50}$ of 1 to 20 nM. In other embodiments, the anti-DR5 antibody binds to human and murine DR5.

The anti-DR5 antibodies may optionally further comprise a light chain variable domain wherein (i) CDRL3 comprises an amino acid sequence Q-Q-X1-X2-X3-X4-P-X5-T (SEQ ID NO:25); wherein X1 is at position 91 and is selected from Y, H and S; X2 is selected from Y and S; X3 is selected from Y, S and T; X4 is selected from Y, S and T; and X5 is selected from S, P and Y. The anti-DR5 antibodies may also optionally comprise a light chain variable domain wherein CDRL3 comprises and amino acid sequence QQXIX2X3SPST (SEQ ID NO:597), wherein X1, X2 and X3 are Y or S. The light chain variable domain may further comprise a CDRL3 that comprises an amino acid sequence selected from the group consisting of SEQ ID NOs:507 to 523 as shown in FIG. 15. The antibody may also further comprise a CDRL1 that comprises an amino acid sequence RASQDVNTAVA (SEQ ID NO:29). The antibody may also further comprise a CDRL2 that comprises an amino acid sequence SASSLYS (SEQ ID NO:30).

In one aspect, the antibodies specific for DR5 are screened for agonist or antagonist activity. Such antibodies can be screened in a DR5 receptor signaling assay, such as an apoptosis assay as described herein. Agonist antibodies increase apoptosis as compared to control and antagonist antibodies decrease apoptosis.

In one embodiment, an isolated polynucleotide encoding any of the above-described antibodies that specifically binds human DR5 is provided. In one embodiment, a vector comprising an isolated polynucleotide encoding any of the above-described antibodies that specifically binds human DR5 is provided. In one embodiment, a host cell transformed with a vector comprising an isolated polynucleotide encoding any of the above-described antibodies that specifically bind human DR5 is provided. In one embodiment, a process of producing an antibody is provided, comprising culturing a host cell transformed with a vector comprising an isolated polynucleotide encoding any of the above-described antibodies that specifically bind human DR5 such that the polynucleotide is expressed. In one aspect, the process further comprises recovering the antibody from the host cell culture. In one aspect, the process further comprises recovering the antibody from the host cell culture medium.

In one embodiment, a method of using one or more of the above-described antibodies that specifically bind human DR5 for treating a disorder associated with abnormal angiogenesis in a mammal in need of treatment thereof is provided, comprising the step of administering the one or more antibodies to the mammal. In some embodiments, antibodies to DR5 that inhibit apoptosis may be useful in conditions where inhibition of cell death is desired (e.g. macular degeneration). In one aspect, the disorder is cancer. In some embodiments, the anti-DR5 antibody increases apoptosis. In one such aspect, the cancer is selected from breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, and multiple myeloma. In another aspect, the treatment further comprises the step of administering a second therapeutic agent simultaneously or sequentially with the antibody. In one such aspect, the second therapeutic agent is selected from an anti-angiogenic agent, an anti-neoplastic agent, a chemotherapeutic agent, and a cytotoxic agent.

In one embodiment, a method of treating a mammal suffering from or at risk of developing an inflammatory or immune disorder is provided, comprising the step of treating the mammal with one or more Fabs of one or more of the above-described antibodies that specifically bind human DR5. In one aspect, the inflammatory or immune disorder is rheumatoid arthritis. In some embodiments, the anti-DR5 antibody increases apoptosis.

The methods described herein also provide for isolation of an anti-HER-2 antibodies. In one embodiment, an anti-HER-2 antibody comprises an immunoglobulin heavy chain variable domain, wherein (i) CDRH1 comprises amino acid sequence G-F-X1-I-X2-X3-X4-X5-I-H (SEQ ID NO:22); wherein X1 is at position 28 according to Kabat numbering and is selected from S and Y; X2 is selected from S and Y; X3 is selected from S and Y; X4 is selected from S and Y; and X5 is selected from S and Y; (ii) CDRH2 comprises an amino acid sequence of X1-I-X2-P-X3-X4-G-X5-T-X6-Y-A-D-S-V-K-G (SEQ ID NO:23); wherein X1 is at amino acid position 50 according to Kabat numbering and is selected from S and Y; X2 is selected from S and Y; X3 is selected from S and Y; X4 is selected from S and Y; X5 is selected from S and Y; and X6 is selected from S and Y; and (iii) CDRH3 comprises an amino acid sequence X1-X2-X3-X4-X5-X6-X7-D-Y (SEQ ID NO:582), wherein X1 is at amino acid position 95 according to Kabat numbering and is selected from Y and R; X2 is selected from Y, S and R; X3 is selected from S, G, Y and H; X4 is selected from S, G, Y and R; X5 is selected from G and A; X6 is selected from F, M, L, and A; and X7 is selected from F, M, and L or is missing.

In another embodiment, an anti-HER-2 antibody comprises an immunoglobulin heavy chain variable domain, wherein (i) CDRH1 comprises amino acid sequence G-F-X1-I-X2-X3-X4-X5-I-H (SEQ ID NO:22); wherein X1 is at position 28 according to Kabat numbering and is selected from S and Y; X2 is selected from S and Y; X3 is selected from S and Y; X4 is selected from S and Y; and X5 is selected from S and Y; (ii) CDRH2 comprises an amino acid sequence of X1-I-X2-P-X3-X4-G-X5-T-X6-Y-A-D-S-V-K-G (SEQ ID NO:23); wherein X1 is at amino acid position 50 according to Kabat numbering and is selected from S and Y; X2 is selected from S and Y; X3 is selected from S and Y; X4 is selected from S and Y; and X5 is selected from S and Y; and (iii) CDRH3 comprises an amino acid sequence X1-X2-X3-X4-X5-X6-X7-X8-D-Y (SEQ ID NO:583), wherein X1 is at amino acid position 95 according to Kabat numbering and is selected from Y, S and G; X2 is selected from Y, S, G, R, A, and M; X3 is selected from G, Y, S and R; X4 is selected from G, Y and F; X5 is selected from Y, S, N, and G; X6 is selected from Y, R, H and W; X7 is selected from G and A; and X8 is selected from F, M, L and I.

In another embodiment, an anti-HER-2 antibody comprises an immunoglobulin heavy chain variable domain, wherein (i) CDRH1 comprises amino acid sequence G-F-X1-I-X2-X3-X4-X5-I-H (SEQ ID NO:22); wherein X1 is at position 28 according to Kabat numbering and is selected from S and Y; X2 is selected from S and Y; X3 is selected from S and Y; X4 is selected from S and Y; and X5 is selected from S and Y; (ii) CDRH2 comprises an amino acid sequence of X1-I-

X2-P-X3-X4-G-X5-T-X6-Y-A-D-S-V-K-G (SEQ ID NO:23); wherein X1 is at amino acid position 50 according to Kabat numbering and is selected from S and Y; X2 is selected from S and Y; X3 is selected from S and Y; X4 is selected from S and Y; and X5 is selected from S and Y; and (iii) CDRH3 comprises an amino acid sequence of X1-X2-X3-X4-X5-X6-X7-X8-X9-X10-X11-X12-X13-X14-X15-X16-X17-X18-X19-D-Y (SEQ ID NO:584), wherein X1 is at amino acid position 95 and is selected from Y, S, R, G and E; X2 is selected from Y, S, R and G; X3 is selected from S, Y, G and W; X4 is selected from S, Y, G and Q; X5 is selected from G, Y and S; X6 is selected from G, Y, S, R and V; X7 is selected from S, Y, G and R; X8 is selected from Y, S, G, R, P and V; X9 is selected from G, A, Y, S and R; X10 is selected from M, F, G, Y, S and R; X11 is selected from A, Y, S, G and R or is not present; X12 is selected from I, M, F, L, A, G, S, Y, R, and T or is not present; X13 is selected from F, M, L, G, A, Y, T, and S or is not present; X14 is selected from L, M, F, I, G, Y, A, and T or is not present; X15 is selected from M, L, Y, G and R or is not present; X16 is selected from Y and G or is not present; X17 is selected from R, M, and G or is not present; X18 is selected from P and A or is not present; and X18 is L or is not present.

In yet another embodiment, an anti-HER-2 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:24), wherein X1 is position 95 according to the Kabat numbering system, and wherein the amino acids at each of positions X1-X6 are selected from a pool of amino acids in a molar ratio of 50% Y, 25% S, and 25% G; wherein the amino acids at each of positions X7-X17 are selected from a pool of amino acids in a molar ratio of 50% Y, 25% S, and 25% G, or are not present; wherein X18 is selected from G and A; and wherein X19 is selected from I, M, L, and F.

In yet another embodiment, an anti-HER-2 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:26), wherein X1 is position 95 according to the Kabat numbering system, and wherein the amino acids at each of positions X1-X6 are selected from a pool of amino acids in a molar ratio of 25% Y, 50% S, and 25% R; wherein the amino acids at each of positions X7-X17 are selected from a pool of amino acids in a molar ratio of 25% Y, 50% S, and 25% R, or are not present; wherein X18 is selected from G and A; and wherein X19 is selected from I, M, L, and F.

In yet another embodiment, an anti-HER-2 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:27), wherein X1 is position 95 according to the Kabat numbering system, and wherein the amino acids at each of positions X1-X6 are selected from a pool of amino acids in a molar ratio of 38% Y, 25% S, 25% G, and 12% R; wherein the amino acids at each of positions X7-X17 are selected from a pool of amino acids in a molar ratio of 38% Y, 25% S, 25% G, and 12% R, or are not present; wherein X18 is selected from G and A; and wherein X19 is selected from I, M, L, and F.

In another embodiment, an anti-HER-2 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19-D-Y (SEQ ID NO:28), wherein X1 is position 95 according to the Kabat numbering system, and wherein the amino acids at each of positions X1-X6 are selected from a pool of amino acids in a molar ratio of 20% Y, 26% S, 26% G, 13% R, 1% A, 1% D, 1% E, 1% F, 1% H, 1% I, 1% K, 1% L, 1% M, 1% N, 1% P, 1% Q, 1% T, 1% V, and 1% W; wherein the amino acids at each of positions X7-X17 are selected from a pool of amino acids in a molar ratio of 20% Y, 26% S, 26% G, 13% R, 1% A, 1% D, 1% E, 1% F, 1% H, 1% I, 1% K, 1% L, 1% M, 1% N, 1% P, 1% Q, 1% T, 1% V, and 1% W, or are not present; wherein X18 is selected from G and A; and wherein X19 is selected from I, M, L, and F.

In another embodiment, an anti-HER-2 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprising an amino acid sequence: X1-X2-X3-X4-X5-X6-X7-X8-X9-X10-X11-X12-X13-X14-X15-X16-X17-X18-X19 (e.g. SEQ ID NO:26), wherein X1 is position 95 according to the Kabat numbering system, and wherein the amino acids at each of positions X1-X19 are selected from S and one of A, C, F, G, I, L, N, P, R, T, W, or Y, or are not present; wherein X18 is selected from G and A or is not present; and wherein X19 is selected from F, L, I, and M or is not present.

In another embodiment, an anti-HER-2 antibody comprises an immunoglobulin heavy chain variable domain, wherein: (i) CDRH1 comprises an amino acid sequence G-F-X1-I-X2-X3-X4-X5-I-H (SEQ ID NO:22), wherein G is position 26 and X1 is position 28 according to the Kabat numbering system; wherein X1 is selected from Y and S; wherein X2 is selected from Y and S; wherein X3 is selected from Y and S; wherein X4 is selected from Y and S; and wherein X5 is selected from Y and S; (ii) CDRH2 comprises an amino acid sequence: X1-I-X2-P-X3-X4-G-X5-T-X6-Y-A-D-S-V-K-G (SEQ ID NO:23), wherein X1 is position 50 according to the Kabat numbering system; wherein X1 is selected from Y and S; wherein X2 is selected from Y and S; wherein X3 is selected from Y and S; wherein X4 is selected from Y and S; wherein X5 is selected from Y and S; and wherein X6 is selected from Y and S; and (iii) CDRH3 comprises an amino acid sequence: X1-X2-X3-X4-X5-X6-X7-X8-X9-X10-X11-X12-X13-X14-X15-X16-X17-X18-X19 (e.g. SEQ ID NO:26), wherein X1 is position 95 according to the Kabat numbering system, and wherein the amino acids at each of positions X1-X19 are selected from S and one of Y, W, R, or F, or are not present; wherein X18 is selected from G and A; and wherein X19 is selected from F, L, I, and M.

In some embodiments, the anti-HER-2 antibody may comprise a CDRH1 comprising an amino acid sequence selected from the group consisting of SEQ ID NOS:189 to 294 as shown in FIG. 11. The anti-HER-2 antibody may also comprise a CDRH2 comprising an amino acid sequence selected from the group consisting of SEQ ID NOS:295 to 400 as shown in FIG. 11. The anti-HER-2 antibody may also comprise a CDRH3 comprising an amino acid sequence selected from the group consisting of SEQ ID NOS:401-506 as shown in FIG. 11. In some embodiments, the anti-HER-2 antibody may comprise a CDRH1 comprising an amino acid sequence selected from the group consisting of SEQ ID NOS:816-842 as shown in FIG. 21A. The anti-HER-2 antibody may also comprise a CDRH2 comprising an amino acid sequence selected from the group consisting of SEQ ID NOS:843-869 as shown in FIG. 21A. The anti-HER-2 antibody may also comprise a CDRH3 comprising an amino acid sequence selected from the group consisting of SEQ ID NOS:870-896 as shown in FIG. 21A. In some embodiments, the anti-HER-2 antibody may comprise a CDRH1 comprising an amino acid sequence selected from the group consisting of SEQ ID NOS:924-950 as shown in FIG. 24A. The anti-HER-2 antibody may also comprise a CDRH2 comprising an amino acid sequence selected from the group consisting of SEQ ID NOS:951-977 as shown in FIG. 24A. The anti-HER-2 antibody may also comprise a CDRH3 comprising an amino acid sequence selected from the group consisting of SEQ ID NOS:978-1004 as shown in FIG. 24A.

In one aspect, an antibody that specifically binds human HER2 comprises CDRH1, CDRH2, CDRH3, and CDRL3 sequences corresponding to the CDRH1, CDRH2, CDRH3, and CDRL3 sequences set forth in FIG. 11 for any one of Fabs 1-106. In one aspect, an antibody that specifically binds human HER2 comprises CDRH1, CDRH2, CDRH3, and CDRL3 sequences corresponding to the CDRH1, CDRH2, CDRH3, and CDRL3 sequences set forth in FIG. 21A for any one of clones B1-B28. In another aspect, an antibody that specifically binds human HER2 comprises CDRH1, CDRH2, CDRH3, and CDRL3 sequences corresponding to the CDRH1, CDRH2, CDRH3, and CDRL3 sequences set forth in FIG. 24A for any one of clones G29-G61.

In some embodiments, an anti-HER-2 antibody comprises a CDRH1 comprising an amino acid sequence GFSIX2X3SYIH (SEQ ID NO:588), wherein X2 and X3 are Y or S. An anti-HER-2 antibody may also comprise a CDRH2 that comprises an amino acid sequence SIYPX3SGYTSYADSKVG (SEQ ID NO:589), wherein X3 is Y or S. An anti-HER-2 antibody may further comprise a variable light chain domain that comprises a CDRL-3 that comprises an amino acid sequence QQSYYX4PST (SEQ ID NO:587), wherein X4 is Y or S.

In some embodiments, an anti-HER-2 antibody comprises an amino acid sequence GFX1ISYSSIH (SEQ ID NO:590), wherein X1 is Y or S. An anti-HER-2 antibody may further comprise a CDRH2 that comprises an amino acid sequence SIYPX3YGX5TX6YADSKVG (SEQ ID NO:591), wherein X3, X5 and X6 are Y or S.

In another embodiment, an anti-HER-2 antibody comprises a CDRH1 that has an amino acid sequence GFXI-ISSSSIH (SEQ ID NO:593), wherein X1 is y or S. An anti-HER-2 antibody may further comprise a CDRH2 that has an amino acid sequence X1IX2PSSGYTX6YADSKVG (SEQ ID NO:594), wherein X1, X2 and X6 are Y or S. An anti-HER-2 antibody may further comprise a CDRH3 that has an amino acid sequence XIX2X3X4YYSYYX10GX12X13x14DY (SEQ ID NO:592), wherein X1 is selected from Y, S and R; X2 is selected from Y and S; X3 is selected from G, Y and S; X4 is selected from G, Y and S; X4 is selected from Y, S, R and G; X10 is selected from Y, S and G; X12 is selected from Y, S, G and R; X13 is selected from G and A and X14 is selected from I, F, M and L.

In some embodiments, the anti-HER-2 antibody may optionally further comprise a light chain variable domain comprising a CDRL3 sequence, wherein CDRL3 comprises an amino acid sequence of Q-Q-X1-X2-X3-X4-P-X5-T (SEQ ID NO:25), wherein X1 is at position 91 according to Kabat numbering and is selected from S and Y; X2 is selected from S, Y and F; X3 is selected from Y, S and F; X4 is selected from Y and S; X5 is selected from S and Y. The light chain variable domain may further comprise a CDRL3 that comprises an amino acid sequence selected from the group consisting of SEQ ID NOs:83 to 188 as shown in FIG. 11, SEQ ID NOs:789-815 in FIG. 21A, and SEQ ID NOs:897-923 in FIG. 24A. The antibody may also, further comprise a CDRL1 that comprises an amino acid sequence RASQDVNTAVA (SEQ ID NO:29). The antibody may also further comprise a CDRL2 that comprises an amino acid sequence SASSLYS (SEQ ID NO:30).

In one aspect, the polypeptide is an antibody that specifically binds HER2. In one such aspect, the antibody comprises the framework regions of the 4D5 antibody. In one such aspect, the antibody comprises the framework regions of a variant 4D5 antibody. In one such aspect, the antibody is a monoclonal antibody. In one such aspect, the antibody is a bispecific antibody.

In one embodiment, an isolated polynucleotide encoding any of the above-described antibodies that specifically binds HER2 is provided. In one embodiment, a vector comprising an isolated polynucleotide encoding any of the above-described antibodies that specifically binds HER2 is provided. In one embodiment, a host cell transformed with a vector comprising an isolated polynucleotide encoding any of the above-described antibodies that specifically bind HER2 is provided. In one embodiment, a process of producing an antibody is provided, comprising culturing a host cell transformed with a vector comprising an isolated polynucleotide encoding any of the above-described antibodies that specifically bind HER2 such that the polynucleotide is expressed. In one aspect, the process further comprises recovering the antibody from the host cell culture. In one aspect, the process further comprises recovering the antibody from the host cell culture medium.

In one embodiment, a method of using one or more of the above-described antibodies that specifically bind HER2 or treating a HER2-related disorder, comprising the step of administering the one or more antibodies to the mammal. In another aspect, the treatment further comprises the step of administering a second therapeutic agent simultaneously or sequentially with the antibody. In one such aspect, the second therapeutic agent is selected from an anti-angiogenic agent, an anti-neoplastic agent, a chemotherapeutic agent, and a cytotoxic agent.

In one embodiment, a method of treating a mammal suffering from or at risk of developing a HER2-related disorder, comprising the step of treating the mammal with one or more Fabs of one or more of the above-described antibodies that specifically bind HER2. In one embodiment, one or more of the above-described polypeptides specifically binds HER2.

In one aspect, a polypeptide of the invention comprises at least one, or both, of heavy chain and light chain antibody variable domains, wherein the antibody variable domain comprises one, two or three variant CDRs as described herein (e.g., as described in the foregoing).

In some embodiments, a polypeptide of the invention (in particular those comprising an antibody variable domain) further comprises an antibody framework sequence, e.g., FR1, FR2, FR3 and/or FR4 for an antibody variable domain corresponding to the variant CDR, the FR sequences obtained from a single antibody template. In one embodiment, the FR sequences are obtained from a human antibody. In one embodiment, the FR sequences are obtained from a human consensus sequence (e.g., subgroup III consensus sequence). In one embodiment, the framework sequences comprise a modified consensus sequence as described herein (e.g., comprising modifications at position 49, 71, 93 and/or 94 in the heavy chain, and/or position 66 in the light chain). In one embodiment, framework regions have the sequences of the framework regions from wild-type humanized antibody 4D5-8 light chain and heavy chain (shown in FIG. 16 (SEQ ID NOS: 6-9 and 10-13, respectively)). In one embodiment, framework regions have the sequences of the framework regions from a variant version of the humanized antibody 4D5-8 light chain and heavy chain, wherein the light chain is modified at position 66 and the heavy chain is modified at positions 71, 73, and 78 (shown in FIG. 17 (SEQ ID NOS: 14-17 and 18-21)).

In some embodiments, a polypeptide of the invention comprises a light chain and a heavy chain antibody variable domain, wherein the light chain variable domain comprises at least 1, 2 or 3 variant CDRs selected from the group consisting of CDR L1, L2 and L3, and the heavy chain variable domain comprises at least 1, 2 or 3 variant CDRs selected from the group consisting of CDR H1, H2 and H3.

In some embodiments, a polypeptide of the invention is an ScFv. In some embodiments, it is a Fab fragment. In some embodiments, it is a F(ab)$_2$ or F(ab')$_2$. Accordingly, in some embodiments, a polypeptide of the invention further comprises a dimerization domain. In some embodiments, the dimerization domain is located between an antibody heavy chain or light chain variable domain and at least a portion of a viral coat protein. The dimerization domain can comprise a dimerization sequence, and/or sequence comprising one or more cysteine residues. The dimerization domain can be linked, directly or indirectly, to the C-terminal end of a heavy chain variable or constant domain. The structure of the dimerization domain can be varied depending on whether the antibody variable domain is produced as a fusion protein component with the viral coat protein component (without an amber stop codon after dimerization domain) or whether the antibody variable domain is produced predominantly without viral coat protein component (e.g., with an amber stop codon after dimerization domain). When the antibody variable domain is produced predominantly as a fusion protein with viral coat protein component, one or more disulfide bond and/or a single dimerization sequence provides for bivalent display. For antibody variable domains predominantly produced without being fused to a viral coat protein component (e.g. with amber stop), it is preferable, though not required, to have a dimerization domain comprising both a cysteine residue and a dimerization sequence. In some embodiments, heavy chains of the F(ab)$_2$ dimerize at a dimerization domain not including a hinge region. The dimerization domain may comprise a leucine zipper sequence (for example, a GCN4 sequence such as GRMKQLEDKVEELLSKNYHLENE-VARLKKLVGERG (SEQ ID NO: 3)).

In some embodiments, a polypeptide of the invention further comprises a light chain constant domain fused to a light chain variable domain, which in some embodiments comprises at least one, two or three variant CDRs. In some embodiments of polypeptides of the invention, the polypeptide comprises a heavy chain constant domain fused to a heavy chain variable domain, which in some embodiments comprises at least one, two or three variant CDRs.

In some instances, it may be preferable to mutate a framework residue such that it is variant with respect to a reference polypeptide or source antibody. For example, framework residue 71 of the heavy chain may be amino acid R, V or A. In another example, framework residue 93 of the heavy chain may be amino acid S or A. In yet another example, framework residue 94 of the heavy chain may be amino acid R, K or T or encoded by MRT. In yet another example, framework residue 49 of the heavy chain may be amino acid A or G. Framework residues in the light chain may also be mutated. For example, framework residue 66 in the light chain may be amino acid R or G.

As described herein, a variant CDR refers to a CDR with a sequence variance as compared to the corresponding CDR of a single reference polypeptide/source antibody. Accordingly, the CDRs of a single polypeptide of the invention can in certain embodiments correspond to the set of CDRs of a single reference polypeptide or source antibody. Polypeptides of the invention may comprise any one or combinations of variant CDRs. For example, a polypeptide of the invention may comprise a variant CDRH1 and variant CDRH2. A polypeptide of the invention may comprise a variant CDRH1, variant CDRH2 and a variant CDRH3. In another example, a polypeptide of the invention may comprise a variant CDRH1, variant CDRH2, variant CDRH3 and variant CDRL3. In another example, a polypeptide of the invention comprises a variant CDRL1, variant CDRL2 and variant CDRL3. Any polypeptide of the invention may further comprise a variant CDRL3. Any polypeptide of the invention may further comprise a variant CDRH3.

In one embodiment, a polypeptide of the invention comprises one or more variant CDR sequences as depicted in FIGS. 7, 19 and 22. In one embodiment, a polypeptide of the invention comprises one or more variant CDR sequences as depicted in FIG. 11A. In one embodiment, a polypeptide of the invention comprises one or more variant CDR sequences as depicted in FIG. 15. In another embodiment, a polypeptide of the invention comprises one or more variant CDR sequences as depicted in FIGS. 21A-21B. In another embodiment, a polypeptide of the invention comprises one or more variant CDR sequences as depicted in FIG. 24A.

Polypeptides of the invention may be in a complex with one another. For example, the invention provides a polypeptide complex comprising two polypeptides, wherein each polypeptide is a polypeptide of the invention, and wherein one of said polypeptides comprises at least one, two or all of variant CDRs H1, H2 and H3, and the other polypeptide comprises a variant light chain CDR (e.g., CDR L3). A polypeptide complex may comprise a first and a second polypeptide (wherein the first and second polypeptides are polypeptides of the invention), wherein the first polypeptide comprises at least one, two or three variant light chain CDRs, and the second polypeptide comprises at least one, two or three variant heavy chain CDRs. The invention also provides complexes of polypeptides that comprise the same variant CDR sequences. Complexing can be mediated by any suitable technique, including by dimerization/multimerization at a dimerization/multimerization domain such as those described herein or covalent interactions (such as through a disulfide linkage) (which in some contexts is part of a dimerization domain, for example a dimerization domain may contain a leucine zipper sequence and a cysteine).

In another aspect, the invention provides compositions comprising polypeptides and/or polynucleotides of the invention. For example, the invention provides a composition comprising a plurality of any of the polypeptides of the invention described herein. Said plurality may comprise polypeptides encoded by a plurality of polynucleotides generated using a set of oligonucleotides comprising degeneracy in the sequence encoding a variant amino acid, wherein said degeneracy is that of the multiple codon sequences of the restricted codon set encoding the variant amino acid. A composition comprising a polynucleotide or polypeptide or library of the invention may be in the form of a kit or an article of manufacture (optionally packaged with instructions, buffers, etc.).

In one aspect, the invention provides a polynucleotide encoding a polypeptide of the invention as described herein. In another aspect, the invention provides a vector comprising a sequence encoding a polypeptide of the invention. The vector can be, for example, a replicable expression vector (for example, the replicable expression vector can be M13, f1, fd, Pf3 phage or a derivative thereof, or a lambdoid phage, such as lambda, 21, phi80, phi81, 82, 424, 434, etc., or a derivative thereof). The vector can comprise a promoter region linked to the sequence encoding a polypeptide of the invention. The promoter can be any suitable for expression of the polypeptide, for example, the lac Z promoter system, the alkaline phosphatase pho A promoter (Ap), the bacteriophage $1_{PL}$ promoter (a temperature sensitive promoter), the tac promoter, the tryptophan promoter, and the bacteriophage T7 promoter. Thus, the invention also provides a vector comprising a promoter selected from the group consisting of the foregoing promoter systems.

Polypeptides of the invention can be displayed in any suitable form in accordance with the need and desire of the practitioner. For example, a polypeptide of the invention can be displayed on a viral surface, for example, a phage or phagemid viral particle. Accordingly, the invention provides viral particles comprising a polypeptide of the invention and/or polynucleotide encoding a polypeptide of the invention.

In one aspect, the invention provides a population comprising a plurality of polypeptide or polynucleotide of the invention, wherein each type of polypeptide or polynucleotide is a polypeptide or polynucleotide of the invention as described herein.

In some embodiments, polypeptides and/or polynucleotides are provided as a library, for example, a library comprising a plurality of at least about $1\times10^4$, $1\times10^5$, $1\times10^6$, $1\times10^7$, $1\times10^8$ distinct polypeptide and/or polynucleotide sequences of the invention. In another aspect, the invention also provides a library comprising a plurality of the viruses or viral particles of the invention, each virus or virus particle displaying a polypeptide of the invention. A library of the invention may comprise viruses or viral particles displaying any number of distinct polypeptides (sequences), for example, at least about $1\times10^4$, $1\times10^5$, $1\times10^6$, $1\times10^7$, $1\times10^8$ distinct polypeptides.

In another aspect, the invention provides host cells comprising a polynucleotide or vector comprising a sequence encoding a polypeptide of the invention.

In another aspect, the invention provides methods for selecting for high affinity binders to specific target antigens. In certain such embodiments, the specific target antigen includes, but is not limited to, HER2 or DR5.

The methods of the invention provide populations of polypeptides (for example, libraries of polypeptides (e.g., antibody variable domains)) with one or more diversified CDR regions. These libraries are sorted (selected) and/or screened to identify high affinity binders to a target antigen. In one aspect, polypeptide binders from the library are selected for binding to target antigens, and for affinity. The polypeptide binders selected using one or more of these selection strategies, may then be screened for affinity and/or for specificity (binding only to target antigen and not to non-target antigens).

In one aspect, a method of the invention comprises generating a plurality of polypeptides with one or more diversified CDR regions, sorting the plurality of polypeptides for binders to a target antigen by contacting the plurality of polypeptides with a target antigen under conditions suitable for binding; separating the binders to the target antigen from those that do not bind; isolating the binders; and identifying the high affinity binders (or any binders having a desired binding affinity). The affinity of the binders that bind to the target antigen can be determined using a variety of techniques known in the art, for example, competition ELISA such as described herein. Optionally, the polypeptides can be fused to a polypeptide tag, such as gD, poly his or FLAG, which can be used to sort binders in combination with sorting for the target antigen.

Another embodiment provides a method of isolating or selecting for an antibody variable domain that binds to a target antigen from a library of antibody variable domains, said method comprising: a) contacting a population comprising a plurality of polypeptides of the invention with an immobilized target antigen under conditions suitable for binding to isolate target antigen polypeptide binders; b) separating the polypeptide binders from nonbinders, and eluting the binders from the target antigen; c) optionally, repeating steps a-b at least once (in some embodiments, at least twice).

In some embodiments, a method may further comprise: d) incubating the polypeptide binders with a concentration of labeled target antigen in the range of 0.1 nM to 1000 nM under conditions suitable for binding to form a mixture; e) contacting the mixture with an immobilized agent that binds to the label on the target antigen; f) eluting the polypeptide binders from the labeled target antigen; g) optionally, repeating steps d) to f) at least once (in some embodiments, at least twice), using a successively lower concentration of labeled target antigen each time. Optionally, the method may comprise adding an excess of unlabelled target antigen to the mixture and incubating for a period of time sufficient to elute low affinity binders from the labeled target antigen.

Another aspect of the invention provides a method of isolating or selecting for high affinity binders (or binders having a desired binding affinity) to a target antigen. In one embodiment, said method comprises: a) contacting a population comprising a plurality of polypeptides of the invention with a target antigen, wherein the antigen is provided at a concentration in the range of about 0.1 nM to 1000 nM to isolate polypeptide binders to the target antigen; b) separating the polypeptide binders from the target antigen; c) optionally, repeating steps a-b at least once (in some embodiments, at least twice), each time with a successively lower concentration of target antigen to isolate polypeptide binders that bind to lowest concentration of target antigen; d) selecting the polypeptide binder that binds to the lowest concentration of the target antigen for high affinity (or any desired affinity) by incubating the polypeptide binders with several different dilutions of the target antigen and determining the IC50 of the polypeptide binder; and e) identifying a polypeptide binder that has a desired affinity for the target antigen. Said affinity can be, for example, about 0.1 nM to 200 nM, 0.5 nM to 150 nM, 1 nM to 100 nM, and/or 25 nM to 75 nM.

Another embodiment provides an assay for isolating or selecting polypeptide binders comprising (a) contacting a population comprising a plurality of polypeptides of the invention with a labeled target antigen, wherein the labeled target antigen is provided at a concentration in a range of 0.1 nM to 1000 nM, under conditions suitable for binding to form a complex of a polypeptide binder and the labeled target antigen; b) isolating the complexes and separating the polypeptide binder from the labeled target antigen; c) optionally, repeating steps a-b at least once, each time using a lower concentration of target antigen. Optionally, the method may further comprise contacting the complex of polypeptide binder and target antigen with an excess of unlabelled target antigen. In one embodiment, the steps of the method are repeated twice and the concentration of target in a first round of selection is in the range of about 100 nM to 250 nM, and, in a second round of selection (if performed) is in the range of about 25 nM to 100 nM, and in the third round of selection (if performed) is in the range of about 0.1 nM to 25 nM.

The invention also includes a method of screening a population comprising a plurality of polypeptides of the invention, said method comprising: a) incubating a first sample of the population of polypeptides with a target antigen under conditions suitable for binding of the polypeptides to the target antigen; b) subjecting a second sample of the population of polypeptides to a similar incubation but in the absence of the target antigen; (c) contacting each of the first and second sample with immobilized target antigen under conditions suitable for binding of the polypeptides to the immobilized target antigen; d) detecting amount of polypeptides bound to immobilized target antigen for each sample; e) determining affinity of a particular polypeptide for the target antigen by calculating the ratio of the amount of the particular polypeptide that is bound in the first sample over the amount of the particular polypeptide that is bound in the second sample.

The libraries generated as described herein may also be screened for binding to a specific target and for lack of binding to nontarget antigens. In one aspect, the invention provides a method of screening for a polypeptide, such as an antibody variable domain of the invention, that binds to a specific target antigen from a library of antibody variable domains, said method comprising: a) generating a population comprising a plurality of polypeptides of the invention; b) contacting the population of polypeptides with a target antigen under conditions suitable for binding; c) separating a binder polypeptide in the library from nonbinder polypeptides; d) identifying a target antigen-specific binder polypeptide by determining whether the binder polypeptide binds to a non-target antigen; and e) isolating a target antigen-specific binder polypeptide. In some embodiments, step (e) comprises eluting the binder polypeptide from the target antigen, and amplifying a replicable expression vector encoding said binder polypeptide. In some embodiments, one or more of the libraries, clones or polypeptides are screened against a panel of antigens including the target antigen. In some embodiments, those clones or polypeptides that specifically bind to the target antigen and do not substantially crossreact with any of the other antigen on the panel are selected. The panel of antigens can include at least three and up to 100 different antigens. In some cases, the panel of antigens includes 3 to 100, 3 to 50, 3 to 25, or 3 to 10 different antigens.

Combinations of any of the sorting/selection methods described above may be combined with the screening methods. For example, in one embodiment, polypeptide binders are first selected for binding to an immobilized target antigen. Polypeptide binders that bind to the immobilized target antigen can then be screened for binding to the target antigen and for lack of binding to nontarget antigens. Polypeptide binders that bind specifically to the target antigen can be amplified as necessary. These polypeptide binders can be selected for higher affinity by contact with a concentration of a labeled target antigen to form a complex, wherein the concentration range of labeled target antigen is from about 0.1 nM to about 1000 nM, and the complexes are isolated by contact with an agent that binds to the label on the target antigen. A polypeptide binder can then be eluted from the labeled target antigen and optionally, the rounds of selection are repeated, and each time a lower concentration of labeled target antigen is used. The binder polypeptides that can be isolated using this selection method can then be screened for high affinity using for example, the solution phase ELISA assay as described, e.g., in Examples 2 and 4 or other conventional methods known in the art. Populations of polypeptides of the invention used in methods of the invention can be provided in any form suitable for the selection/screening steps. For example, the polypeptides can be in free soluble form, attached to a matrix, or present at the surface of a viral particle such as phage or phagemid particle. In some embodiments of methods of the invention, the plurality of polypeptides are encoded by a plurality of replicable vectors provided in the form of a library. In selection/screening methods described herein, vectors encoding a binder polypeptide may be further amplified to provide sufficient quantities of the polypeptide for use in repetitions of the selection/screening steps (which, as indicated above, are optional in methods of the invention).

In one embodiment, the invention provides a method of selecting for a polypeptide that binds to a target antigen comprising:
  a) generating a composition comprising a plurality of polypeptides of the invention as described herein;
  b) selecting a polypeptide binder that binds to a target antigen from the composition;
  c) isolating the polypeptide binder from the nonbinders;
  d) identifying binders of the desired affinity from the isolated polypeptide binders.

In another embodiment, the invention provides a method of selecting for an antigen binding variable domain that binds to a target antigen from a library of antibody variable domains comprising:
  a) contacting the library of antibody variable domains of the invention (as described herein) with a target antigen;
  b) separating binders from nonbinders, and eluting the binders from the target antigen and incubating the binders in a solution with decreasing amounts of the target antigen in a concentration from about 0.1 nM to 1000 nM;
  c) selecting the binders that can bind to the lowest concentration of the target antigen and that have an affinity of about 0.1 nM to 200 nM.

In some embodiments, the concentration of target antigen is about 100 to 250 nM, or about 25 to 100 nM.

In one embodiment, the invention provides a method of selecting for a polypeptide that binds to a target antigen from a library of polypeptides comprising:
  a) isolating polypeptide binders to a target antigen by contacting a library comprising a plurality of polypeptides of the invention (as described herein) with an immobilized target antigen under conditions suitable for binding;
  b) separating the polypeptide binders in the library from nonbinders and eluting the binders from the target antigen to obtain a subpopulation enriched for the binders; and
  c) optionally, repeating steps a-b at least once (in some embodiments at least twice), each repetition using the subpopulation of binders obtained from the previous round of selection.

In some embodiments, methods of the invention further comprise the steps of:
  d) incubating the subpopulation of polypeptide binders with a concentration of labeled target antigen in the range of 0.1 nM to 1000 nM under conditions suitable for binding to form a mixture;
  e) contacting the mixture with an immobilized agent that binds to the label on the target antigen;
  f) detecting the polypeptide binders bound to labeled target antigens and eluting the polypeptide binders from the labeled target antigen;
  g) optionally, repeating steps d) to f) at least once (in some embodiments, at least twice), each repetition using the subpopulation of binders obtained from the previous round of selection and using a lower concentration of labeled target antigen than the previous round.

In some embodiments, these methods further comprise adding an excess of unlabelled target antigen to the mixture and incubating for a period of time sufficient to elute low affinity binders from the labeled target antigen.

In another embodiment, the invention provides a method of isolating high affinity binders to a target antigen comprising:
  a) contacting a library comprising a plurality of polypeptides of the invention (as described herein) with a target antigen in a concentration of at least about 0.1 nM to 1000 nM to isolate polypeptide binders to the target antigen;
  b) separating the polypeptide binders from the target antigen to obtain a subpopulation enriched for the polypeptide binders; and
  c) optionally, repeating steps a) and b) at least once (in some embodiments, at least twice), each repetition using the subpopulation of binders obtained from the previous round of selection and using a decreased concentration of target antigen than the previous round to isolate polypeptide binders that bind to the lowest concentration of target antigen.

In one aspect, the invention provides an assay for selecting polypeptide binders from a library comprising a plurality of polypeptides of the invention (as described herein) comprising:
  a) contacting the library with a concentration of labeled target antigen in a concentration range of 0.1 nM to 1000 nM, under conditions suitable for binding to form a complex of a polypeptide binder and the labeled target antigen;
  b) isolating the complexes and separating the polypeptide binders from the labeled target antigen to obtain a subpopulation enriched for the binders;
  c) optionally, repeating steps a-b at least once (in some embodiments, at least twice), each time using the subpopulation of binders obtained from the previous round of selection and using a lower concentration of target antigen than the previous round.

In some embodiments, the method further comprises adding an excess of unlabelled target antigen to the complex of the polypeptide binder and target antigen. In some embodiments, the steps set forth above are repeated at least once (in some embodiments, at least twice) and the concentration of target in the first round of selection is about 100 nM to 250 nM, and in the second round of selection is about 25 nM to 100 nM, and in the third round of selection is about 0.1 nM to 25 nM.

In another aspect, the invention provides a method of screening a library comprising a plurality of polypeptides of the invention, said method comprising:
  a) incubating a first sample of the library with a concentration of a target antigen under conditions suitable for binding of the polypeptides to the target antigen;
  b) incubating a second sample of the library without a target antigen;
  c) contacting each of the first and second sample with immobilized target antigen under conditions suitable for binding of the polypeptide to the immobilized target antigen;
  d) detecting the polypeptide bound to immobilized target antigen for each sample;
  e) determining affinity of the polypeptide for the target antigen by calculating the ratio of the amounts of bound polypeptide from the first sample over the amount of bound polypeptide from the second sample.

Diagnostic and therapeutic uses for binder polypeptides of the invention are contemplated. In one diagnostic application, the invention provides a method for determining the presence of a protein of interest comprising exposing a sample suspected of containing the protein to a binder polypeptide of the invention and determining binding of the binder polypeptide to the sample. For this use, the invention provides a kit comprising the binder polypeptide and instructions for using the binder polypeptide to detect the protein.

The invention further provides: isolated nucleic acid encoding the binder polypeptide; a vector comprising the nucleic acid, optionally, operably linked to control sequences recognized by a host cell transformed with the vector; a host cell transformed with the vector; a process for producing the binder polypeptide comprising culturing this host cell so that the nucleic acid is expressed and, optionally, recovering the binder polypeptide from the host cell culture (e.g. from the host cell culture medium).

The invention also provides a composition comprising a binder polypeptide of the invention and a carrier (e.g., a pharmaceutically acceptable carrier) or diluent. This composition for therapeutic use is sterile and may be lyophilized. Also contemplated is the use of a binder polypeptide of this invention in the manufacture of a medicament for treating an indication described herein. The composition can further comprise a second therapeutic agent such as a chemotherapeutic agent, a cytotoxic agent or an anti-angiogenic agent.

The invention further provides a method for treating a mammal, comprising administering an effective amount of a binder polypeptide of the invention to the mammal. The mammal to be treated in the method may be a nonhuman mammal, e.g. a primate suitable for gathering preclinical data or a rodent (e.g., mouse or rat or rabbit). The nonhuman mammal may be healthy (e.g. in toxicology studies) or may be suffering from a disorder to be treated with the binder polypeptide of interest. In one embodiment, the mammal is suffering from a DR5-related disorder. In another embodiment, the mammal is suffering from a HER2-related disorder.

In one embodiment, the mammal is suffering from or is at risk of developing abnormal angiogenesis (e.g., pathological angiogenesis). In one specific embodiment, the disorder is a cancer selected from the group consisting of colorectal cancer, renal cell carcinoma, ovarian cancer, lung cancer, non-small-cell lung cancer (NSCLC), bronchoalveolar carcinoma and pancreatic cancer. In another embodiment, the disorder is a disease caused by ocular neovascularisation, e.g., diabetic blindness, retinopathies, primarily diabetic retinopathy, age-induced macular degeneration and rubeosis. In another embodiment, the mammal to be treated is suffering from or is at risk of developing an edema (e.g., an edema associated with brain tumors, an edema associated with stroke, or a cerebral edema). In another embodiment, the mammal is suffering from or at risk of developing a disorder or illness selected from the group consisting of rheumatoid arthritis, inflammatory bowel disease, refractory ascites, psoriasis, sarcoidosis, arterial arteriosclerosis, sepsis, burns and pancreatitis. According to another embodiment, the mammal is suffering from or is at risk of developing a genitourinary illness selected from the group consisting of polycystic ovarian disease (POD), endometriosis and uterine fibroids. In one embodiment, the disorder is a disease caused by dysregulation of cell survival (e.g., abnormal amount of cell death), including but not limited to cancer, disorders of the immune system, disorders of the nervous system and disorders of the vascular system. The amount of binder polypeptide of the invention that is administered will be a therapeutically effective amount to treat the disorder. In dose escalation studies, a variety of doses of the binder polypeptide may be administered to the mammal. In another embodiment, a therapeutically effective amount of the binder polypeptide is administered to a human patient to treat a disorder in that patient.

In one embodiment, binder polypeptides of this invention useful for treating tumors, malignancies, and other disorders related to abnormal angiogenesis, including inflammatory or immunologic disorders and/or diabetes or other insulin-related disorders described herein are Fab or scFv antibodies. Accordingly, such binder polypeptides can be used in the manufacture of a medicament for treating an inflammatory or immune disease. A mammal that is suffering from or is at risk for developing a disorder or illness described herein can be treated by administering, a second therapeutic agent, simultaneously, sequentially or in combination with, a polypeptide (e.g., an antibody) of this invention. It should be understood that other therapeutic agents, in addition to the second therapeutic agent, can be administered to the mammal or used in the manufacture of a medicament for the desired indications.

These polypeptides can be used to understand the role of host stromal cell collaboration in the growth of implanted non-host tumors, such as in mouse models wherein human tumors have been implanted. These polypeptides can be used in methods of identifying human tumors that can escape therapeutic treatment by observing or monitoring the growth of the tumor implanted into a rodent or rabbit after treatment with a polypeptide of this invention. The polypeptides of this invention can also be used to study and evaluate combination therapies with a polypeptide of this invention and other therapeutic agents. The polypeptides of this invention can be used to study the role of a target molecule of interest in other diseases by administering the polypeptides to an animal suffering from the disease or a similar disease and determining whether one or more symptoms of the disease are alleviated.

For the sake of clarity, in the description herein, unless specifically or contextually indicated otherwise, all amino acid numberings are according to Kabat et al. (see further elaboration in "Definitions" below).

BRIEF DESCRIPTION OF THE FIGURES

FIG. 1 depicts the sequences of a 4D5 light chain and heavy chain variable domain (SEQ ID NOs:1 & 2, respectively).

FIG. 3 shows the frequency of amino acids (identified by single letter code) in human antibody light chain CDR sequences from the Kabat database. The frequency of each amino acid at a particular amino acid position is shown starting with the most frequent amino acid at that position at the left and continuing on to the right to the least frequent amino acid. The number below the amino acid represents the number of naturally occurring sequences in the Kabat database that have that amino acid in that position.

FIG. 4 shows the frequency of amino acids (identified by single letter code) in human antibody heavy chain CDR sequences from the Kabat database. The frequency of each amino acid at a particular amino acid position is shown starting with the most frequent amino acid at that position at the left and continuing on to the right to the least frequent amino acid. The number below the amino acid represents the number of naturally occurring sequences in the Kabat database that have that amino acid in that position. Framework amino acid positions 71, 93 and 94 are also shown.

FIG. 6 depicts framework region sequences of huMAb4D5-8 light and heavy chains. Numbers in superscript/bold indicate amino acid positions according to Kabat.

FIG. 7 depicts modified/variant framework region sequences of huMAb4D5-8 light and heavy chains. Numbers in superscript/bold indicate amino acid positions according to Kabat.

FIG. 8 illustrates the randomization scheme for each diversified CDR position in the YSGR-A, YSGR-B, YSGR-C, and YSGR-D libraries, as described in Example 1.

FIGS. 9A-9D show mutagenic oligonucleotides used in the construction of the YSGR-A, YSGR-B, YSGR-C, and YSGR-D libraries, as described in Example 3. Equimolar DNA degeneracies are represented in the codon sets (W=A/T, K=G/T, M=A/C, N=A/C/G/T, R=A/G, S=G/C, Y=T/C). Codon sets are represented in the IUB code. The notation "XXX" in the H3-A6-H3-A17 oligonucleotides represents Tyr/Ser/Gly-encoding codons at a molar ratio of 50/25/25, respectively. The notation "XXX" in the H3-B6-H3-B17 oligonucleotides represents Tyr/Ser/Arg-encoding codons at a molar ratio of 25/50/25, respectively. The notation "XXX" in the H3-C6-H3-C17 oligonucleotides represents Tyr/Ser/Gly/Arg-encoding codons at a molar ratio of 38/25/25/12, respectively. The notation "XXX" in the H3-D6 to H3-D17 oligonucleotides represents Tyr/Ser/Gly/Arg/Ala Asp/Glu/Phe/His/Ile/Lys/Leu/Met/Asn/Pro/Gln/Thr/Val/Trp-encoding codons at a molar ratio of 20/26/26/13/1/1/1/1/1/1/1/1/1/1/1/1/1/1/1, respectively.

FIG. 10 shows enrichment ratios for library YSGR-A-D following 5 rounds of selection against human DR5 or human HER-2, as described in Example 2. Numbers are shown as X/Y, with X representing the number of unique clones and Y representing the number of clones specifically binding to human DR5 or human HER-2. Specific clones are identified as those exhibiting binding to human DR5 or to human HER-2 that was at least ten times greater (based on ELISA signal read at 450 nm) than binding to bovine serum albumin (BSA).

FIG. 11A shows the sequences of CDRH1, CDRH2, CDRH3 and CDRL3 for 106 clones that bind to human HER-2. FIG. 11B shows the results of ELISA assays for each of the clones set forth in FIG. 11A. Numbers in bold indicates strong binding (signal of 2 to 10).

FIG. 12 shows the amino acid sequences for CDRL3, CDRH1, CDRH2, and CDRH3 from specific binders to human HER-2 with short (e.g. 6-7 residue) CDRH3 regions isolated from the YSGR-A-D library, as described in Example 2. Consensus sequences are shown for CDRL3, CDRH1, and CDRH2. (Clone numbers correspond to those shown in FIG. 11.)

FIG. 13 shows the amino acid sequences for CDRH1, CDRH2, and CDRH3 from specific binders to human HER-2 with a CDRH3 having 8 amino acids isolated from the YSGR-A-D library as described in Example 2. Consensus sequences are shown for CDRH1, CDRH2 and CDRH3. (Clone numbers 1-19 correspond to clone numbers in FIG. 11 as follows: 17, 97, 18, 19, 98, 99, 100, 20, 21, 22, 23, 24, 101, 102, 25, 103, 26, 27 and 28, respectively.)

FIG. 14 shows the amino acid sequences for CDRH1, CDRH2, and CDRH3 from the specific binders to human HER-2 with medium length CDRH3 regions (e.g. about 12-14 amino acids) isolated from the YSGR-A-D library, as described in Example 2. Consensus sequences are shown for CDRH1, CDRH2, and CDRH3. The consensus sequence was determined for CDRH3 by shifting some of the CDRH3 sequences over two amino acids so that the CDRH3 sequence starts at position 97 rather than position 95.

FIG. 15 shows the CDRL3, CDRH1, CDRH2, and CDRH3 sequences of binders to human DR5, and the $IC_{50}$ for some of the binders for human DR5.

FIGS. 19A and 19B illustrate the randomization scheme for each diversified CDR position in the Binary H3 libraries (SAH3, SCH3, SFH3, SGH3, SIH3, SLH3, SNH3, SPH3, SRH3, STH3, SWH3, and SYH3), as described in Example 4. The indicated amino acid positions are numbered according to Kabat.

FIGS. 20A-20L show mutagenic oligonucleotides used in the construction of the Binary H3 libraries (SAH3 (FIG. 20A), SCH3 (FIG. 20B), SFH3 (FIG. 20C), SGH3 (FIG. 20D), SIH3 (FIG. 20E), SLH3 (FIG. 20F), SNH3 (FIG. 20G), SPH3 (FIG. 20H), SRH3 (FIG. 20I), STH3 (FIG. 20J), SWH3 (FIG. 20K), and SYH3 (FIG. 20L)), as described in Example 4 (SEQ ID NOS:618-788). Equimolar DNA degeneracies are represented in the codon sets (W=A/T, K=G/T, M=A/C, N=A/C/G/T, R=A/G, S=G/C, Y=T/C). Codon sets are represented in the IUB code.

FIG. 21A shows amino acid sequences for CDRL3, CDRH1, CDRH2, and CDRH3 from the specific binders to HER2 isolated from the pooled Binary H3 libraries (SXH3), as described in Example 5 (SEQ ID NOS:789-896). FIG. 21B shows the results of ELISA assays for each of the clones set forth in FIG. 21A. Dark shading indicates strong binding (signal of 2 to 10).

FIG. 22 illustrates the randomization scheme for each diversified CDR position in the Binary Surface libraries (SY, SW, SR, and SF), as described in Example 6. The indicated amino acid positions are numbered according to Kabat.

FIG. 23 shows mutagenic oligonucleotides used in the construction of certain of the Binary Surface libraries (SW, SR, and SF), as described in Example 6 (SEQ ID NOS:1005-1013). Equimolar DNA degeneracies are represented in the codon sets (W=A/T, K=G/T, M=A/C, N=A/C/G/T, R=A/G, S=G/C, Y=T/C). Codon sets are represented in the IUB code.

FIG. 24A shows amino acid sequences for CDRL3, CDRH1, CDRH2, and CDRH3 from the specific binders to HER2 isolated from the pooled Surface Binary libraries (SX-surface), as described in Example 8 (SEQ ID NOS:897-1004). FIG. 24B shows the results of ELISA assays for each of the clones set forth in FIG. 24A. Dark shading indicates strong binding (signal of 2 to 10), and light shading indicates weak binding (signal of 0.25 to 2).

Trp, Ser:Arg, or Ser:Phe) obtained herein from the binary SXH3 library or the binary SX-surface library.

Figure 26B:
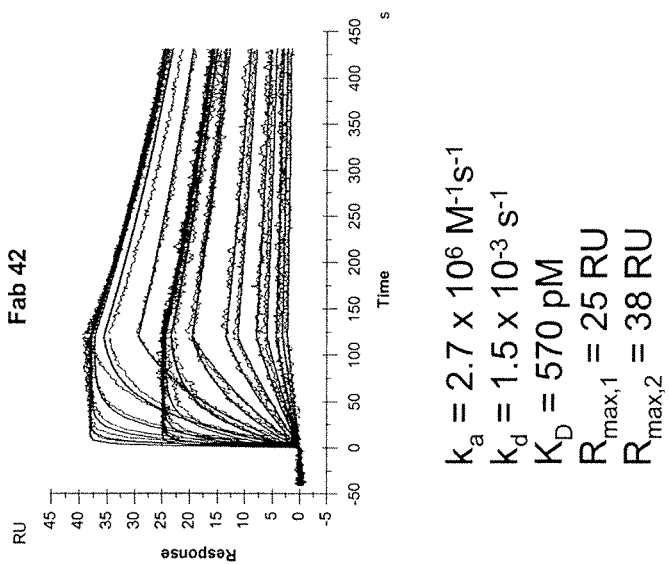

FIGS. 26A and B depicts surface plasmon resonance binding analyses of soluble Fab proteins from three HER2-binding clones (clone B11, clone G54, and clone YSGR-A-42) to immobilized HER2. Clone B11 had a $k_a$ of $1.9 \times 10^6$ $M^{-1}s^{-1}$, a $k_d$ of $1.7 \times 10^{-3}$ $s^{-1}$, and a $K_D$ of 890 pM. Clone G54 had a $k_a$ of $2.0 \times 10^5$ $M^{-1}s^{-1}$, a $k_d$ of $2.2 \times 10^{-3}$ $s^{-1}$, and a $K_D$ of 11 nM. Clone YSGR-A-42 had a $k_a$ of $2.7 \times 10^6$ $M^{-1}s^{-1}$, a $k_d$ of $1.5 \times 10^{-3}$ $s^{-1}$, and a $K_D$ of 570 pM.

FIG. 27 shows the results of flow cytometric analyses of binding of anti-HER2 fabs isolated from each of the YSGR (clone A-42), SX-surface (clones G37 and G54), and SXH3 libraries (clone B11) to NR6 or H2NR6-4D5 cells, as described in Example 7.

Figure 28:
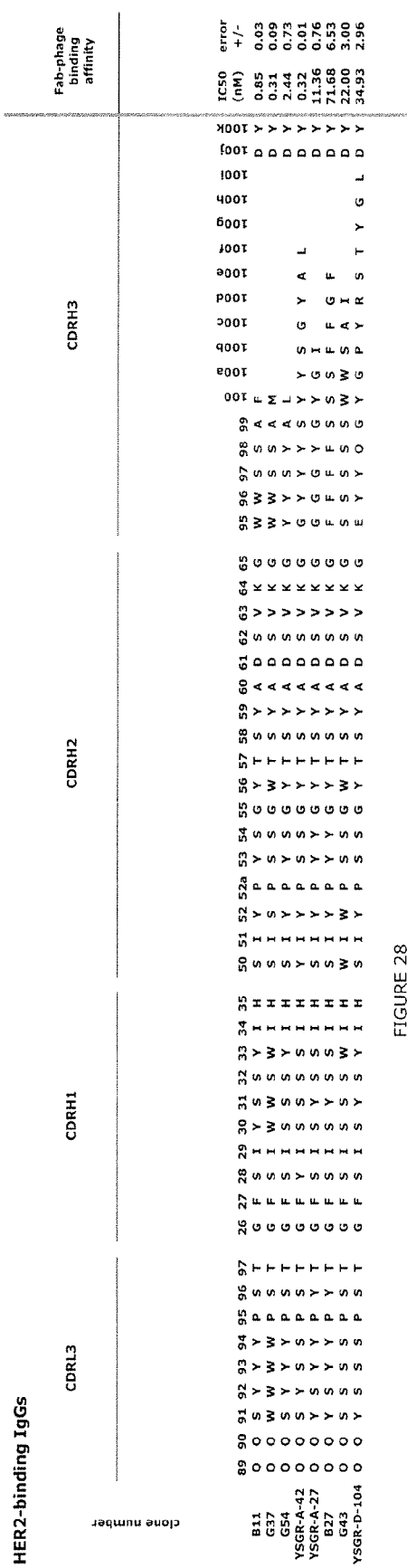

FIG. 28 shows the sequences for CDRH1, CDRH2, CDRH3, and CDRL3 for each of HER2-binding IgGs B11, G37, G54, YSGR-A-42, YSGR-A-27, B27, G43, and YSGR-D-104. FIG. 28 also shows the IC50 values for the Fab version of each clone.

FIG. 29 shows the results of competitive binding assays described in Example 7 to determine the ability of each of the indicated HER2-specific IgGs to compete for binding to HER2 with Omnitarg, Herceptin, and each of the other IgGs.

MODES FOR CARRYING OUT THE INVENTION

The invention provides novel, unconventional, greatly simplified and flexible methods for diversifying CDR sequences (including antibody variable domain sequences), and libraries comprising a multiplicity, generally a great multiplicity of diversified CDRs (including antibody variable domain sequences). Such libraries provide combinatorial libraries useful for, for example, selecting and/or screening for synthetic antibody clones with desirable activities such as binding affinities and avidities. These libraries are useful for identifying immunoglobulin polypeptide sequences that are capable of interacting with any of a wide variety of target antigens. For example, libraries comprising diversified immunoglobulin polypeptides of the invention expressed as phage displays are particularly useful for, and provide a high throughput, efficient and automatable systems of, selecting and/or screening for antigen binding molecules of interest. The methods of the invention are designed to provide high affinity binders to target antigens with minimal changes to a source or template molecule and provide for good production yields when the antibody or antigens binding fragments are produced in cell culture.

Methods and compositions of the invention provide numerous additional advantages. For example, relatively simple variant CDR sequences can be generated, using codon sets encoding a restricted number of amino acids (as opposed to the conventional approach of using codon sets encoding the maximal number of amino acids), while retaining sufficient diversity of unique target binding sequences. The simplified nature (and generally relatively smaller size) of sequence populations generated according to the invention permits further diversification once a population, or sub-population thereof, has been identified to possess the desired characteristics.

The simplified nature of sequences of target antigen binders obtained by methods of the invention leaves significantly greater room for individualized further sequence modifications to achieve the desired results. For example, such sequence modifications are routinely performed in affinity maturation, humanization, etc. By basing diversification on restricted codon sets that encode only a limited number of amino acids, it would be possible to target different epitopes using different restricted codon sets, thus providing the practitioner greater control of the diversification approach as compared with randomization based on a maximal number of amino acids. An added advantage of using restricted codon sets is that undesirable amino acids can be eliminated from the process, for example, methionine or stop codons, thus improving the overall quality and productivity of a library. Furthermore, in some instances, it may be desirable to limit the conformational diversity of potential binders. Methods and compositions of the invention provide the flexibility for achieving this objective. For example, the presence of certain amino acids, such as tyrosine, in a sequence results in fewer rotational conformations.

DEFINITIONS

Amino acids are represented herein as either a single letter code or as the three letter code or both.

The term "affinity purification" means the purification of a molecule based on a specific attraction or binding of the molecule to a chemical or binding partner to form a combination or complex which allows the molecule to be separated from impurities while remaining bound or attracted to the partner moiety.

The term "antibody" is used in the broadest sense and specifically covers single monoclonal antibodies (including agonist and antagonist antibodies), antibody compositions with polyepitopic specificity, affinity matured antibodies, humanized antibodies, chimeric antibodies, as well as antigen binding fragments (e.g., Fab, F(ab')$_2$, scFv and Fv), so long as they exhibit the desired biological activity. In one embodiment, the term "antibody" also includes human antibodies. As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). $V_H$ refers to the variable domain of the heavy chain. $V_L$ refers to the variable domain of the light chain. According to the compositions and methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). In some instances, a complementarity determining region can include amino acids from both a CDR region defined according to Kabat and a hypervariable loop. For example, the CDRH1 of the heavy chain of antibody 4D5 includes amino acids 26 to 35. The consensus sequence for CDRL I (according to the Kabat definition) in the 4D5 antibody is R-A-S-Q-D-V-N-T-A-V-A (SEQ ID NO:29). The consensus sequence for CDRL2 (according to the Kabat definition) in the 4D5 antibody is S-A-S-S-L-Y-S (SEQ ID NO:30).

"Framework regions" (hereinafter "FR") are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 3549 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues can be adjusted accordingly. For example, when CDRH1 includes amino acids H26-H35, the heavy chain FR1 residues are at positions 1-25 and the FR2 residues are at positions 36-49.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, e.g. NNK, NNS, XYZ, DVK and the like. Synthesis of oligonucleotides with selected nucleotide "degeneracy" at certain positions is well known in that art, for example the TRIM approach (Knappek et al.; J. Mol. Biol. (1999), 296: 57-86); Garrard & Henner, Gene (1993), 128:103). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

The term "restricted codon set", and variations thereof, as used herein refers to a codon set that encodes a much more limited number of amino acids than the codon sets typically utilized in art methods of generating sequence diversity. In one aspect of the invention, restricted codon sets used for sequence diversification encode from 2 to 10, from 2 to 8, from 2 to 6, from 2 to 4, or only 2 amino acids. In some embodiments, a restricted codon set used for sequence diversification encodes at least 2 but 10 or fewer, 8 or fewer, 6 or fewer, 4 or fewer amino acids. In a typical example, a tetranomial codon set is used. Examples of tetranomial codon sets include RMC, RMG, RRC, RSA, MKC, YMT, RST, KMT, SRC, MRT and WMT, as known in the art. In another typical example, a binomial codon set is used. Examples of binomial codon sets include TMT, KAT, YAC, WAC, TWC, TYT, YTC, WTC, KTT, YCT, MCG, SCG, MGC, SGT, GRT, GKT and GYT. Determination of suitable restricted codons, and the identification of specific amino acids encoded by a particular restricted codon, is well known and would be evident to one skilled in the art, Determination of suitable amino acid sets to be used for diversification of a CDR sequence can be empirical and/or guided by criteria known in the art (e.g., inclusion of a combination of hydrophobic and hydrophilic amino acid types, etc.)

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. $F(ab')_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in *The Pharmacology of Monoclonal Antibodies*, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The expression "linear antibodies" refers to the antibodies described in Zapata et al., *Protein Eng.*, 8(10):1057-1062 (1995). Briefly, these antibodies comprise a pair of tandem Fd segments ($V_H$-$C_H1$-$V_H$-$C_H1$) which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1 \times 10^{-7}$ M, for example no more than about $1 \times 10^{-8}$ M and as a further example no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, for example at least 80%, for example at least 85%, for example at least 90%, and for example at least 95%. Identity or similarity with respect to this sequence is defined herein as the percentage of amino acid residues in the candidate sequence that are identical (i.e. same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method, e.g., to more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "antagonist" is used in the broadest sense, and includes any molecule that partially or fully blocks, inhibits, or neutralizes one or more biological activities of target molecules described herein (e.g. DR5 or HER-2) in vitro, in situ, or in vivo. Examples of such biological activities of DR5 include binding of Apo2L/TRAIL to DR5, induction of apoptosis as well as those further reported in the literature. Examples of such biological activities of HER-2 include binding of ligands such as heregulins, tyrosine phosphorylation of HER-2, induction of proliferation as well as apoptosis, and as well as those further reported in the literature. An antagonist may function in a direct or indirect manner. For instance, the antagonist may function to partially or fully block, inhibit or neutralize one or more biological activities of a ligand of target molecule, in vitro, in situ, or in vivo as a result of its direct binding to the target molecule. The antagonist may also function indirectly to partially or fully block, inhibit or neutralize one or more biological activities of target molecule, in vitro, in situ, or in vivo as a result of, e.g., blocking or inhibiting another effector molecule. The antagonist molecule may comprise a "dual" antagonist activity wherein the molecule is capable of partially or fully blocking, inhibiting or neutralizing a biological activity of target molecule.

The term "agonist" is used in the broadest sense, and includes any molecule that partially or fully enhances, stimulates or activates one or more biological activities of target molecule described herein (e.g. DR5 or HER-2), in vitro, in situ, or in vivo. Examples of such biological activities of DR5, include binding of Apo-2L and apoptosis as well as those further reported in the literature. Examples of such biological activities of HER-2 include binding of ligands such as heregulins, tyrosine phosphorylation of the receptor, induction of proliferation as well as apoptosis, and as well as those further reported in the literature. An agonist may function in a direct or indirect manner. For instance, the agonist may function to partially or fully enhance, stimulate or activate one or more biological activities of the target molecule, in vitro, in situ, or in vivo as a result of its direct binding to the target molecule, which causes receptor activation or signal transduction. The agonist may also function indirectly to partially or fully enhance, stimulate or activate one or more biological activities of the target molecule, in vitro, in situ, or in vivo as a result of, e.g., stimulating another effector molecule which then causes target molecule activation or signal transduction. It is contemplated that an agonist may act as an enhancer molecule which functions indirectly to enhance or increase target molecule activation or activity. For instance, an agonist may enhance activity of endogenous Apo-2L in a mammal. This could be accomplished, for example, by pre-complexing DR5 or by stabilizing complexes of the respective ligand with the DR5 receptor.

"Cell", "cell line", and "cell culture" are used interchangeably herein and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell. The coat protein may be the major coat protein or may be a minor coat protein. A "major" coat protein is generally a coat protein which is present in the viral coat at least about 5, at least about 7, at least about 10 copies of the protein or more. A major coat protein may be present in tens, hundreds or even thousands of copies per virion. An example of a major coat protein is the p8 protein of filamentous phage.

The "detection limit" for a chemical entity in a particular assay is the minimum concentration of that entity which can be detected above the background level for that assay. For example, in the phage ELISA, the "detection limit" for a particular phage displaying a particular antigen binding fragment is the phage concentration at which the particular phage produces an ELISA signal above that produced by a control phage not displaying the antigen binding fragment.

"DR5 receptor" or "DR5" when used herein encompasses native sequence receptor and receptor variants. These terms encompass DR5 receptor expressed in a variety of mammals, including humans. DR5 receptor may be endogenously expressed as occurs naturally in a variety of human tissue lineages, or may be expressed by recombinant or synthetic methods. A "native sequence DR5 receptor" comprises a polypeptide having the same amino acid sequence as an DR5 receptor derived from nature. Thus, a native sequence DR5 receptor can have the amino acid sequence of naturally-occurring DR5 receptor from any mammal. Such native sequence DR5 receptor can be isolated from nature or can be produced by recombinant or synthetic means. The term "native sequence DR5 receptor" specifically encompasses naturally-occurring truncated or secreted forms of the receptor (e.g., a soluble form containing, for instance, an extracellular domain sequence), naturally-occurring variant forms (e.g., alternatively spliced forms) and naturally-occurring allelic variants. Receptor variants may include fragments or deletion mutants of the native sequence DR5 receptor. The 411 amino acid sequence of human DR5 is shown in Table 1 and is the sequence of FIG. 3A as published in WO 98/51793 on Nov. 19, 1998. A transcriptional splice variant of human DR5 is known in the art. This DR5 splice variant encodes the 440 amino acid sequence of human DR5 shown in FIGS. 3B and 3C as published in WO 98/35986 on Aug. 20, 1998. Polypeptide sequences of murine DR5 and an extracellular domain of DR5 are also shown in Table 1 below.

Biological activities of DR5 include (a) having the ability to induce or stimulate or signal apoptosis in at least one type of mammalian cancer cell or virally-infected cell in vivo or ex vivo, (b) capable of binding a naturally-occurring Apo2L/TRAIL polypeptide. Assays for determining biological activity such as apoptosis can be conducted using methods known in the art, such as DNA fragmentation (see, e.g., Marsters et al., Curr. Biology, 6: 1669 (1996)), caspase inactivation, DR5 binding (see, e.g., WO 98/51793, published Nov. 19, 1998. The terms "apoptosis" and "apoptotic activity" are used in a broad sense and refer to the orderly or controlled form of cell death in mammals that is typically accompanied by one or more characteristic cell events, including condensation of cytoplasm, loss of plasma membrane microvilli, segmentation of the nucleus, degradation of chromosomal DNA or loss of mitochondrial function. This activity can be determined and measured, for instance, by cell viability assays (such as Alamar blue assays or MTT assays), FACS analysis, caspase activation, DNA fragmentation (see, for example, Nicoletti et al., J. Immunol. Methods, -139:271-279 (1991), and poly-ADP ribose polymerase, "PARP", cleavage assays known in the art.

"DR5 receptor antibody", "DR5 antibody", or "anti-DR5 antibody" is used in a broad sense to refer to antibodies that bind to at least one form of a DR5 receptor. Optionally the DR5 antibody is fused or linked to a heterologous sequence or molecule. Preferably the heterologous sequence allows or assists the antibody to form higher order or oligomeric complexes. Optionally, the DR5 antibody binds to DR5 receptor but does not bind or cross-react with any additional Apo-2L receptor (e.g. DR4, DcR1, or DcR2). Optionally, the antibody is an agonist of DR5 signalling activity. Optionally, the DR5 antibody of the invention binds to a DR5 receptor at a concentration range of about 0.1 nM to about 20 mM as measured in a BIAcore binding assay (as described herein) Optionally, some embodiments, antibodies of the invention exhibit an IC 50 value of about 1 nM to about 20 nM as measured in a binding assay (such as competition phage ELISA as described in the examples below).

The terms "Apo2L/TRAIL", "Apo-2L", and "TRAIL" are used herein to refer to a polypeptide sequence which includes amino acid residues 114-281, inclusive, 95-281, inclusive, residues 92-281, inclusive, residues 91-281, inclusive, residues 41-281, inclusive, residues 15-281, inclusive, or residues 1-281, inclusive, of the amino acid sequence shown in Table 1, as well as biologically active fragments, deletional, insertional, or substitutional variants of the above sequences. The Apo-2L polypeptides may be encoded by the native nucleotide sequence as described and shown in FIG. 1 of WO2005100399.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. In certain embodiments, the two portions of the polypeptide are obtained from heterologous or different polypeptides.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from a mammal or plant. The DNA may, optionally, include marker or selection genes, for example, antibiotic resistance genes, temperature resistance genes, etc.

As used herein, "highly diverse position" refers to a position of an amino acid located in the variable regions of the light and heavy chains that have a number of different amino acids represented at the position when the amino acid sequences of known and/or naturally occurring antibodies or antigen binding fragments are compared. The highly diverse positions are typically in the CDR regions. In one aspect, the ability to determine highly diverse positions in known and/or naturally occurring antibodies is facilitated by the data provided by Kabat, Sequences of Proteins of Immunological Interest (National Institutes of Health, Bethesda, Md., 1987 and 1991). An internet-based database located at http://www.bioinforg.uk.abs.structures.html provides an extensive collection and alignment of light (http/www.bioinf.org.uk.abs.lc.align and heavy chain (http/www.bioinf.org.uk.abs.hc.align sequences and facilitates determination of highly diverse positions in these sequences. According to the invention, an amino acid position is highly diverse if it has from about 2 to about 11, from about 4 to about 9, and/or from about 5 to about 7 different possible amino acid residue variations at that position. In some embodiments, an amino acid position is highly diverse if it has at least about 2, at least about 4, at least about 6, and/or at least about 8 different possible amino acid residue variations at that position.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or 14 DNA polymerase in the presence of the four deoxyribonucleotide triphosphates. The DNA is then purified by phenol-chloroform extraction and ethanol precipitation or by silica purification. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step. Other ligation methods are well known in the art.

A "mutation" is a deletion, insertion, or substitution of a nucleotide(s) relative to a reference nucleotide sequence, such as a wild type sequence.

As used herein, "natural" or "naturally occurring" antibodies, refers to antibodies identified from a nonsynthetic source, for example, from a differentiated antigen-specific B cell obtained ex vivo, or its corresponding hybridoma cell line, or from antibodies obtained from the serum of an animal. These antibodies can include antibodies generated in any type of immune response, either natural or otherwise induced. Natural antibodies include the amino acid sequences, and the nucleotide sequences that constitute or encode these antibodies, for example, as identified in the Kabat database. As used herein, natural antibodies are different than "synthetic antibodies", synthetic antibodies referring to antibody sequences that have been changed from a source or template sequence, for example, by the replacement, deletion, or addition, of an amino acid, or more than one amino acid, at a certain position with a different amino acid, the different amino acid providing an antibody sequence different from the source antibody sequence.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contingent and in reading frame. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.*, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology,* 3:205-0216 (1991).

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. In certain embodiments, the phage is a filamentous bacteriophage, such as an M13, fl, fd, Pf3 phage or a derivative thereof, or a lambdoid phage, such as lambda, 21, phi80, phi81, 82, 424, 434, etc., or a derivative thereof.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published 4 May 1988, or via deoxynucleoside H-phosphonate intermediates as described by Froeshler et al., *Nucl. Acids, Res.,* 14:5399-5407 (1986)). Further methods include the polymerase chain reaction defined below and other autoprimer methods and oligonucleotide syntheses on solid supports. All of these methods are described in Engels et al., *Agnew. Chem. Int. Ed. Engl.,* 28:716-734 (1989). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation.

DNA is "purified" when the DNA is separated from non-nucleic acid impurities. The impurities may be polar, non-polar, ionic, etc.

A "source antibody", as used herein, refers to an antibody or antigen binding fragment whose antigen binding sequence serves as the template sequence upon which diversification according to the criteria described herein is performed. In certain embodiments, an antigen binding sequence generally includes an antibody variable region, and at least one CDR including framework regions.

As used herein, "solvent accessible position" refers to a position of an amino acid residue in the variable regions of the heavy and light chains of a source antibody or antigen binding fragment that is determined, based on structure, ensemble of structures and/or modeled structure of the antibody or antigen binding fragment, as potentially available for solvent access and/or contact with a molecule, such as an antibody-specific antigen. These positions are typically found in the CDRs and on the exterior of the protein. The solvent accessible positions of an antibody or antigen binding fragment, as defined herein, can be determined using any of a number of algorithms known in the art. In certain embodiments, solvent accessible positions are determined using coordinates from a 3-dimensional model of an antibody (or portion thereof, e.g., an antibody variable domain, or CDR segment(s)), using a computer program such as the Insight II program (Accelrys, San Diego, Calif.). Solvent accessible positions can also be determined using algorithms known in the art (e.g., Lee and Richards, J. Mol. Biol. 55, 379 (1971) and Connolly, J. Appl. Cryst. 16, 548 (1983)). Determination of solvent accessible positions can be performed using software suitable for protein modeling and 3-dimensional structural information obtained from an antibody (or portion thereof). Software that can be utilized for these purposes includes SYBYL. Biopolymer Module software (Tripos Associates). Generally, in certain embodiments, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios ((1994) "ARVOMOL/CONTOUR: molecular surface areas and volumes on Personal Computers." *Comput. Chem.* 18(4): 377-386; and (1995). "Variations of Surface Areas and Volumes in Distinct Molecular Surfaces of Biomolecules." *J. Mol. Model.* 1: 46-53.)

A "transcription regulatory element" will contain one or more of the following components: an enhancer element, a promoter, an operator sequence, a repressor gene, and a transcription termination sequence. These components are well known in the art. U.S. Pat. No. 5,667,780.

A "transformant" is a cell which has taken up and maintained DNA as evidenced by the expression of a phenotype associated with the DNA (e.g., antibiotic resistance conferred by a protein encoded by the DNA).

"Transformation" means a process whereby a cell takes up DNA and becomes a "transformant". The DNA uptake may be permanent or transient.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). In certain embodiments, affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al., *J. Mol. Biol.* 226:889-896 (1992).

The "Kd" or "Kd value" is the dissociation constant for the interaction of one molecule with another. In one embodiment, the Kd value is measured by a radiolabeled protein binding assay (RIA). In one embodiment, an RIA for DR5 or HER-2 can be performed with the Fab version of an anti-DR5 or HER-2 antibody and a DR5 or HER-2 molecule respectively as described by the following assay that measures solution binding affinity of Fabs for DR5 or HER-2 by equilibrating a Fab with a minimal concentration of ($^{125}$I)-labeled DR5 or HER-2 in the presence of a titration series of unlabeled DR5 or HER-2 molecule respectively, then capturing bound DR5 or HER-2 molecule respectively with an anti-Fab antibody-coated plate (Chen, et al., (1999) *J. Mol. Biol* 293:865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-absorbent plate (Nunc #269620), 100 pM or 26 pM [$^{125}$I] DR5 or HER-2 are mixed with serial dilutions of a Fab of interest, e.g., Fab-12 (Presta et al., (1997) *Cancer Res.* 57:4593-4599). The Fab of interest is then incubated overnight; however, the incubation may continue for 65 hours to insure that equilibrium is reached. Thereafter, the mixtures are transferred to the capture plate for incubation at room temperature for one hour. The solution is then removed and the plate washed eight times with 0.1% Tween-20 in PBS. When the plates had dried, 150 μl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays According to another embodiment the Kd or Kd value can be measured by using surface plasmon resonance assays using a BIAcore™-2000 or a BIAcore™-3000 instrument (BIAcore, Inc., Piscataway, N.J.). In one embodiment, the Kd value of anti-DR5 or HER-2 molecule antibodies for DR5 or HER-2 molecule respectively is determined using BIAcore™ analysis according to the following protocol. Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Human DR5 or HER-2 molecule is diluted with 10 mM sodium acetate, pH 4.8, to 5 μg/ml (~0.2 μM) before injection at a flow rate of 5 μl/minute to achieve approximately 10 response units (RU) of coupled protein. Following the injection of human DR5 or HER-2, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgram. The equilibrium dissociation constant (Kd) was calculated as the ratio $k_{off}/k_{on}$. See, e.g., Chen, Y., et al., (1999) *J. Mol. Biol* 293:865-881.

A "disorder" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic related disorders.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

The term "immune related disease" means a disease in which a component of the immune system of a mammal causes, mediates or otherwise contributes to morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimotols thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barc syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis: Crohns disease), gluten-sensitive enteropathy, and Whipples disease, autoimmune or immune-mediated skin diseases including bullous skin diseases, erythema multiform and contact dermatitis, psoriasis, allergic diseases such as asthma, allergic rhinitis, atopic dermatitis, food hypersensitivity and urticaria, and immunologic diseases of the lung such as eosinophilic pneumonias.

"Autoimmune disease" is used herein in a broad, general sense to refer to disorders or conditions in mammals in which destruction of normal or healthy tissue arises from humoral or cellular immune responses of the individual mammal to his or her own tissue constituents. Examples include, but are not limited to, systemic lupus erythematosus, thyroiditis, rheumatoid arthritis, psoriasis, multiple sclerosis, autoimmune diabetes, and inflammatory bowel disease (IBD).

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

"Mammal" for purposes of treatment refers to any animal classified as a mammal, including humans, domestic and farm animals, nonhuman primates, and zoo, sports, or pet animals, such as dogs, horses, cats, cows, etc.

The term "anti-neoplastic composition" refers to a composition useful in treating cancer comprising at least one active therapeutic agent, e.g., "anti-cancer agent." Examples of therapeutic agents (anti-cancer agents) include, but are not limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "epitope tagged" when used herein refers to an antibody mutant fused to an "epitope tag". The epitope tag polypeptide has enough residues to provide an epitope against which an antibody thereagainst can be made, yet is short enough such that it does not interfere with activity of the antibody mutant. The epitope tag preferably also is fairly unique so that the antibody thereagainst does not substantially cross-react with other epitopes. Suitable tag polypeptides generally have at least 6 amino acid residues and usually between about 8-50 amino acid residues (in certain embodiments between about 9-30 residues). Examples include, but are not limited to, the flu HA tag polypeptide and its antibody 12CA5 (Field et al. *Mol. Cell. Biol.* 8:2159-2165 (1988)); the c-myc tag and the 8F9, 3C7, 6E10, G4, B7 and 9E10 antibodies thereagainst (Evan et al., *Mol. Cell. Biol.* 5(12):3610-3616 (1985)); and the Herpes Simplex virus glycoprotein D (gD) tag and its antibody (Paborsky et al., *Protein Engineering* 3(6):547-553 (1990)). In certain embodiments, the epitope tag is a "salvage receptor binding epitope".

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin I and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1I and calicheamicin omegaI1 (see, e.g., Agnew, *Chem. Intl. Ed. Engl.,* 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® (doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chlorambucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase I inhibitor; ABARELIX® mmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell whose growth is dependent upon activity of a target molecule of interest either in vitro or in vivo. Thus, the growth inhibitory agent may be one which significantly reduces the percentage of target molecule-dependent cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anti-cancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,1-trihydroxy-8-(hydroxyacetyl)-1-methoxy-5,12-naphthacenedione.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society*

Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

For the treatment of rheumatoid arthritis ("RA"), the patient can be treated with an antibody of the invention in conjunction with any one or more of the following drugs: DMARDS (disease-modifying anti-rheumatic drugs (e.g., methotrexate), NSAI or NSAID (non-steroidal anti-inflammatory drugs), HUMIRA™ (adalimumab; Abbott Laboratories), ARAVA® (leflunomide), REMICADE® (infliximab; Centocor Inc., of Malvern, Pa.), ENBREL™ (etanercept; Immunex, Wash.), and COX-2 inhibitors. DMARDs commonly used in RA are hydroxycloroquine, sulfasalazine, methotrexate, leflunomide, etanercept, infliximab, azathioprine, D-penicillamine, Gold (oral), Gold (intramuscular), minocycline, cyclosporine, and Staphylococcal protein A immunoadsorption. Adalimumab is a human monoclonal antibody that binds to TNF. Infliximab is a chimeric monoclonal antibody that binds to TNF. Etanercept is an "immunoadhesin" fusion protein consisting of the extracellular ligand binding portion of the human 75 kD (p75) tumor necrosis factor receptor (TNFR) linked to the Fc portion of a human IgG1. For conventional treatment of RA, see, e.g., "Guidelines for the management of rheumatoid arthritis" *Arthritis & Rheumatism* 46(2): 328-346 (February, 2002). In a specific embodiment, the RA patient is treated with a CD20 antibody of the invention in conjunction with methotrexate (MTX). An exemplary dosage of MTX is about 7.5-25 mg/kg/wk. MTX can be administered orally and subcutaneously.

For the treatment of ankylosing spondylitis, psoriatic arthritis and Crohn's disease, the patient can be treated with an antibody of the invention in conjunction with, for example, Remicade® (infliximab; from Centocor Inc., of Malvern, Pa.), and/or ENBREL (etanercept; Immunex, Wash.).

For treatments for SLE, the patient can be treated with an antibody of the invention in conjunction with, for example, a high-dose corticosteroids and/or cyclophosphamide (HDCC).

For the treatment of psoriasis, patients can be administered an antibody of this invention in conjunction with topical treatments, such as topical steroids, anthralin, calcipotriene, clobetasol, and tazarotene, or with methotrexate, retinoids, cyclosporine, PUVA and UVB therapies. In one embodiment, the psoriasis patient is treated with the antibody sequentially or concurrently with cyclosporine.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A "variant" or "mutant" of a starting or reference polypeptide (e.g., a source antibody or its variable domain(s)/CDR(s)), such as a fusion protein (polypeptide) or a heterologous polypeptide (heterologous to a phage), is a polypeptide that 1) has an amino acid sequence different from that of the starting or reference polypeptide and 2) was derived from the starting or reference polypeptide through either natural or artificial (manmade) mutagenesis. Such variants include, for example, deletions from, and/or insertions into and/or substitutions of, residues within the amino acid sequence of the polypeptide of interest. For example, a fusion polypeptide of the invention generated using an oligonucleotide comprising a restricted codon set that encodes a sequence with a variant amino acid (with respect to the amino acid found at the corresponding position in a source antibody/antigen binding fragment) would be a variant polypeptide with respect to a source antibody and/or antigen binding fragment and/or CDR. Thus, a variant CDR refers to a CDR comprising a variant sequence with respect to a starting or reference polypeptide sequence (such as that of a source antibody and/or antigen binding fragment and/or CDR). A variant amino acid, in this context, refers to an amino acid different from the amino acid at the corresponding position in a starting or reference polypeptide sequence (such as that of a source antibody and/or antigen binding fragment and/or CDR). Any combination of deletion, insertion, and substitution may be made to arrive at the final variant or mutant construct, provided that the final construct possesses the desired functional characteristics. In some of the examples described herein, binder sequences contain point mutations such as deletions or additions. The amino acid changes also may alter post-translational processes of the polypeptide, such as changing the number or position of glycosylation sites. Methods for generating amino acid sequence variants of polypeptides are described in U.S. Pat. No. 5,534,615, expressly incorporated herein by reference.

A "wild type" or "reference" sequence or the sequence of a "wild type" or "reference" protein/polypeptide, such as a coat protein, or a CDR or variable domain of a source antibody, may be the reference sequence from which variant polypeptides are derived through the introduction of mutations. In general, the "wild type" sequence for a given protein is the sequence that is most common in nature. Similarly, a "wild type" gene sequence is the sequence for that gene which is most commonly found in nature. Mutations may be introduced into a "wild type" gene (and thus the protein it encodes) either through natural processes or through man induced means. The products of such processes are "variant" or "mutant" forms of the original "wild type" protein or gene.

A "plurality" of a substance, such as a polypeptide or polynucleotide of the invention, as used herein, generally refers to a collection of two or more types or kinds of the substance. There are two or more types or kinds of a substance if two or more of the substances differ from each other with respect to a particular characteristic, such as the variant amino acid found at a particular amino acid position. For example, there is a plurality of polypeptides of the invention if there are two or more polypeptides of the invention that are substantially the same, or are identical in sequence except for the sequence of a variant CDR or except for the variant amino acid at a particular solvent accessible and highly diverse amino acid position. In another example, there is a plurality of polynucleotides of the invention if there are two or more polynucleotides of the invention that are substantially the same or identical in sequence except for the sequence that encodes a variant CDR or except for the sequence that encodes a variant amino acid for a particular solvent accessible and highly diverse amino acid position.

The invention provides methods for generating and isolating novel target antigen binding polypeptides, such as antibodies or antigen binding fragments, that can have a high affinity for a selected antigen. A plurality of different binder polypeptides are prepared by mutating (diversifying) one or more selected amino acid positions in a source antibody light chain variable domain and/or heavy chain variable domain with restricted codon sets to generate a library of binder polypeptides with variant amino acids in at least one CDR sequence, wherein the number of types of variant amino acids is kept to a minimum (i.e., 19 or fewer, 15 or fewer, 10 or fewer, 8 or fewer, 6 or fewer, 4 or fewer, or only 2, but generally at least 2). The amino acid positions include those that are solvent accessible, for example as determined by analyzing the structure of a source antibody, and/or that are highly diverse among known and/or natural occurring immunoglobulin polypeptides. A further advantage afforded by the limited nature of diversification of the invention is that additional amino acid positions other than those that are highly diverse and/or solvent accessible can also be diversified in accordance with the need or desire of the practitioner; examples of these embodiments are described herein.

The amino acid positions that are solvent accessible and highly diverse are in certain embodiments those in the CDR regions of the antibody variable domains selected from the group consisting of CDRL1, CDRL2, CDRL3, CDRH1, CDRH2, CDRH3, and mixtures thereof. Amino acid positions are each mutated using a restricted codon set encoding a limited number of amino acids, the choice of amino acids generally being independent of the commonly occurring amino acids at each position. In some embodiments, when a solvent accessible and highly diverse position in a CDR region is to be mutated, a codon set is selected that encodes from 2 to 10, from 2 to 8, from 2 to 6, from 2 to 4, and/or only 2 amino acids. In some embodiments, when a solvent accessible and highly diverse position in a CDR region is to be mutated, a codon set is selected that encodes from 2 to 19, 2 to 15, 2 to 10, from 3 to 9, from 4 to 8, and/or from 5 to 7 amino acids. In some embodiments, a codon set encodes at least 2, but 19 or fewer, 15 or fewer, 10 or fewer, 8 or fewer, 6 or fewer, 4 or fewer amino acids. CDR sequences can also be diversified by varying the length. For example, for CDRH3, variant CDRH3 regions can be generated that have different lengths and/or are randomized at selected positions using restricted codon sets.

The diversity of the library of the polypeptides comprising variant CDRs is designed using codon sets that encode only a limited number of amino acids, such that a minimum but sufficient amount of sequence diversity is introduced into a CDR. The number of positions mutated in the CDR is minimized and the variant amino acids at each position are designed to include a limited number of amino acids, independent of the amino acids that deemed to be commonly occurring at that position in known and/or naturally occurring CDRs. In certain embodiments, a single antibody, including at least one CDR, is used as the source antibody. It is surprising that a library of antibody variable domains having diversity in sequences and size can be generated using a single source antibody as a template and targeting diversity to particular positions using an unconventionally limited number of amino acid substitutions.

Design of Diversity of Antibody Variable Domains

In one aspect of the invention, high quality libraries of antibody variable domains are generated. The libraries have restricted diversity of different sequences of CDR sequences, for example, diversity of the antibody variable domains. The libraries include high affinity binding antibody variable domains for one or more antigens, including, for example, DR5 and human HER-2. The diversity in the library is designed by selecting amino acid positions that are solvent accessible and highly diverse in a single source antibody and mutating those positions in at least one CDR using restricted codon sets. The restricted codon set can in certain embodiments encode fewer than 19, 15, 10, 8, 6, or 4 amino acids, or encodes only 2 amino acids.

One source antibody is humanized antibody 4D5, but the methods for diversification can be applied to other source antibodies whose sequence is known. A source antibody can be a naturally occurring antibody, synthetic antibody, recombinant antibody, humanized antibody, germ line derived antibody, chimeric antibody, affinity matured antibody, or antigen binding fragment thereof. The antibodies can be obtained from a variety of mammalian species including humans, mice and rats. In some embodiments, a source antibody is an antibody that is obtained after one or more initial affinity screening rounds, but prior to an affinity maturation step(s). A source antibody may be selected or modified to provide for high yield and stability when produced in cell culture.

Antibody 4D5 is a humanized antibody specific for a cancer-associated antigen known as HER-2 (erbB2). The antibody includes variable domains having consensus framework regions; a few positions were reverted to mouse sequence during the process of increasing affinity of the humanized antibody. The sequence and crystal structure of humanized antibody 4D5 have been described in U.S. Pat. No. 6,054,297, Carter et al., PNAS 89:4285 (1992), the crystal structure is shown in J. Mol. Biol. 229:969 (1993) and online at http://www.ncbi.nlm.nih.gov/Structure/mmdb/mmdbsrv.cgi?form=6&db=t&Dopt=s&uid=990, http://www.ncbi.nlm.nih.gov/Structure/mmdb/mmdbsrv.cgi?form=6&db=t&Dopt=s&uid=991, and http://www.ncbi.nlm.nih.gov/Structure/mmdb/mmdbsrv.cgi?form=6&db=t&Dopt=s&uid=992.

A criterion for generating diversity in antibody variable domains is to mutate residues at positions that are solvent accessible (as defined above). These positions are typically found in the CDRs, and are typically on the exterior of the protein. In certain embodiments, solvent accessible positions are determined using coordinates from a 3-dimensional model of an antibody, using a computer program such as the InsightII program (Accelrys, San Diego, Calif.). Solvent accessible positions can also be determined using algorithms known in the art (e.g., Lee and Richards, J. Mol. Biol. 55, 379 (1971) and Connolly, J. Appl. Cryst. 16, 548 (1983)). Determination of solvent accessible positions can be performed using software suitable for protein modeling and 3-dimensional structural information obtained from an antibody. Software that can be utilized for these purposes includes SYBYL Biopolymer Module software (Tripos Associates). Generally in certain embodiments, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios ((1994) "ARVO-MOL/CONTOUR: molecular surface areas and volumes on Personal Computers", *Comput. Chem.* 18(4): 377-386; and "Variations of Surface Areas and Volumes in Distinct Molecular Surfaces of Biomolecules." *J. Mol. Model.* (1995), 1: 46-53).

Figure 2:
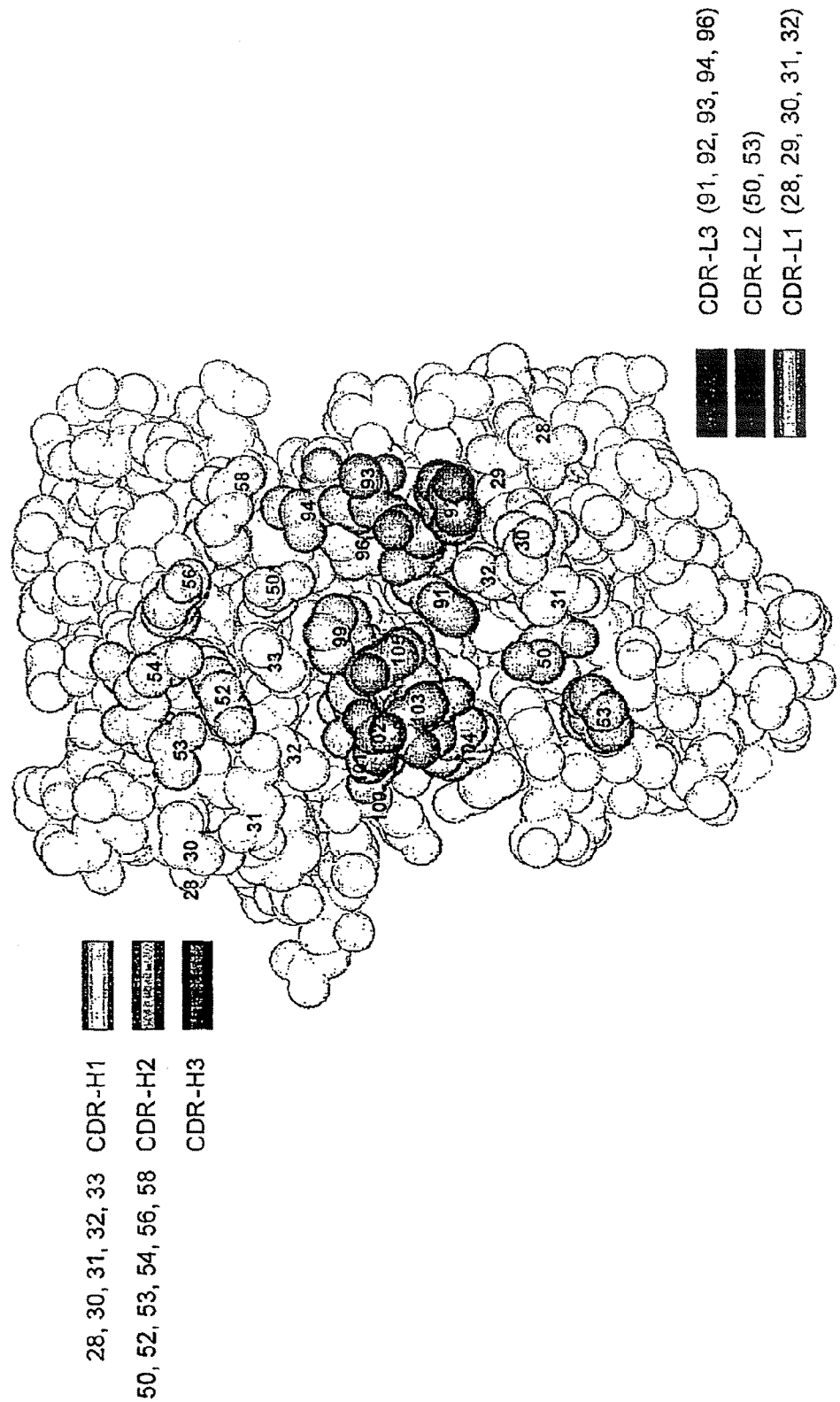
FIG. 2 shows a 3-D modeled structure of humanized 4D5 showing CDR residues that form contiguous patches. Contiguous patches are formed by amino acid residues 28, 29, 30, 31 and 32 in CDRL1; amino acids residues 50 and 53 of CDRL2; amino acid residues 91, 92, 93, 94 and 96 of CDRL3; amino acid residues 28, 30, 31, 32, 33 in CDRH1; and amino acid residues 50, 52, 53, 54, 56, and 58 in CDRH2.

In some instances, selection of solvent accessible residues is further refined by choosing solvent accessible residues that collectively form a minimum contiguous patch, for example when the reference polypeptide or source antibody is in its 3-D folded structure. For example, as shown in FIG. 2, a compact (minimum) contiguous patch is formed by residues selected for CDRH1/H2/H3/L1/L2/L3 of humanized 4D5. A compact (minimum) contiguous patch may comprise only a subset (for example, 2-5 CDRs) of the full range of CDRs, for example, CDRH1/H2/H3/L3. Solvent accessible residues that do not contribute to formation of such a patch may optionally be excluded from diversification. Refinement of selection by this criterion permits the practitioner to minimize, as desired, the number of residues to be diversified. For example, residue 28 in H1 can optionally be excluded in diversification since it is on the edge of the patch. However, this selection criterion can also be used, where desired, to choose residues to be diversified that may not necessarily be deemed solvent accessible. For example, a residue that is not deemed solvent accessible, but forms a contiguous patch in the 3-D folded structure with other residues that are deemed solvent accessible may be selected for diversification. An example of this is CDRL1-29. Selection of such residues would be evident to one skilled in the art, and its appropriateness can also be determined empirically and according to the needs and desires of the skilled practitioner.

The solvent accessible positions identified from the crystal structure of humanized antibody 4D5 for each CDR are as follows (residue position according to Kabat):

CDRL1: 28, 30, 31, 32
CDRL2: 50, 53
CDRL3: 91, 92, 93, 94, 96
CDRH1: 28, 30, 31, 32, 33
CDRH2: 50, 52, 52A, 53, 54, 55, 56, 57, 58.

In addition, in some embodiments, residue 29 of CDRL1 may also be selected based on its inclusion in a contiguous patch comprising other solvent accessible residues. All or a subset of the solvent accessible positions as set forth above may be diversified in methods and compositions of the invention. For example, in some embodiments, only positions 50, 52, 52a, 53-56, and 58 are randomized in CDRH2.

Another criterion for selecting positions to be mutated is those positions which show variability in amino acid sequence when the sequences of known and/or natural antibodies are compared. A highly diverse position refers to a position of an amino acid located in the variable regions of the light or heavy chains that have a number of different amino acids represented at the position when the amino acid sequences of known and/or natural antibodies/antigen binding fragments are compared. The highly diverse positions can be in the CDR regions. The positions of CDRH3 are all considered highly diverse. In certain embodiments, amino acid residues are highly diverse if they have from about 2 to about 19 (although the numbers can range as described herein) different possible amino acid residue variations at that position.

Figure 4:
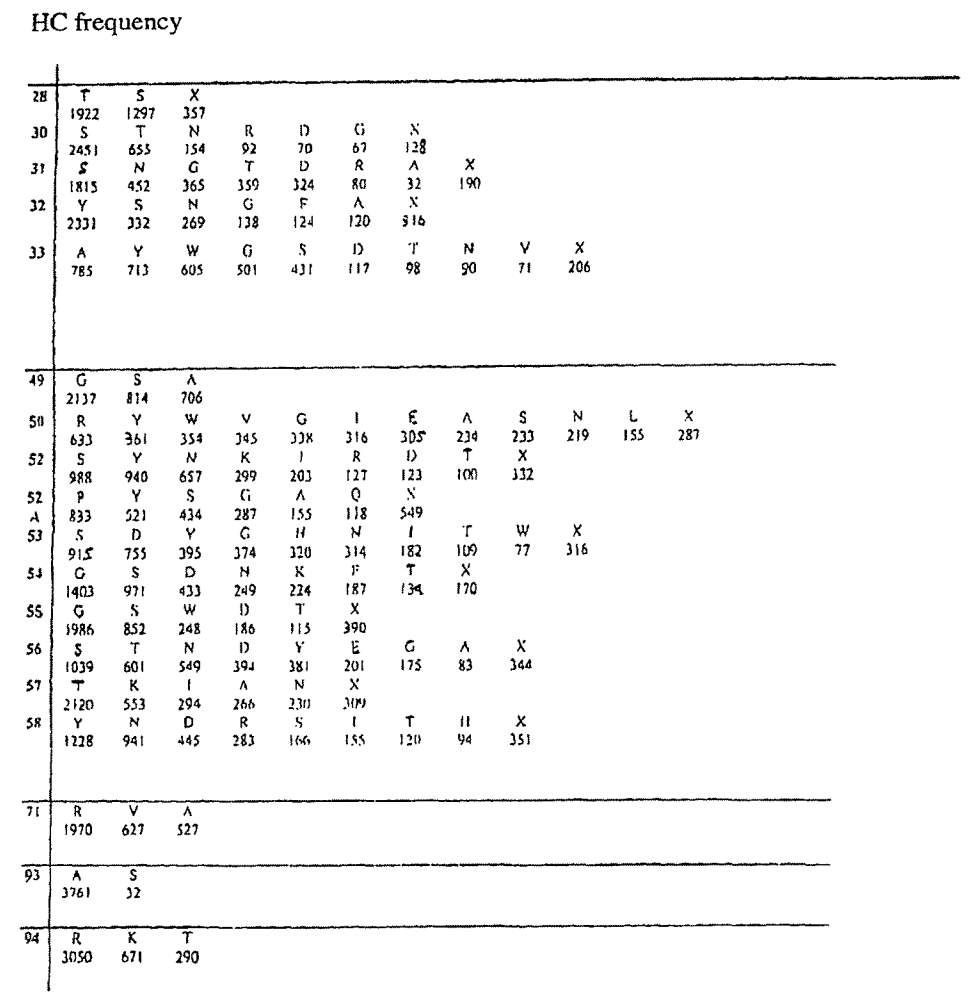

In one aspect, identification of highly diverse positions in known and/or naturally occurring antibodies is facilitated by the data provided by Kabat, Sequences of Proteins of Immunological interest (National Institutes of Health, Bethesda, Md., 1987 and 1991). An internet-based database located at http://www.bioinf.org.uk/abs/structures.html provides an extensive collection and alignment of light (http://www.bioinf.org.uk/abs/lc.align and heavy chain (http://www.bioinf.org.uk/abs/hc.align sequences and facilitates determination of highly diverse positions in these sequences. The diversity at the solvent accessible positions of humanized antibody 4D5 in known and/or naturally occurring light and heavy chains is shown in FIGS. 3 and 4.

In one aspect of the invention, the highly diverse and solvent accessible residues in at least one, two, three, four, five or all CDRs selected from the group consisting of CDRL1, CDRL2, CDRL3, CDRH1, CDRH2, CDRH3, and mixtures thereof are mutated (i.e., randomized using restricted codon sets as described herein). For example, a population of polypeptides may be generated by diversifying at least one solvent accessible and/or highly diverse residue in CDRL3 and CDRH3 using restricted codons. Accordingly, the invention provides for a large number of novel antibody sequences formed by replacing at least one solvent accessible and highly diverse position of at least one CDR of the source antibody variable domain with variant amino acids encoded by a restricted codon. For example, a variant CDR or antibody variable domain can comprise a variant amino acid in one or more of amino acid positions 28, 30, 31, 32, 33, and/or 34 of CDRH1; and/or in one or more of amino acid positions 50, 52, 52a, 53, 54, 55, 56 and/or 58 of CDRH2; and/or in one or more of amino acid positions 95-100, 100a, 100b, and 100c of CDRH3; and/or in one or more of amino acid positions 28, 29, 30 and/or 31 of CDRL1; and/or in one or more of amino acid positions 50 and/or 53 in CDRL2; and/or in one or more of amino acid positions 91, 92, 93, 94, 95 and/or 96 in CDRL3. In another example, a variant CDR or antibody variable domain can comprise a variant amino acid in one or more of amino acid positions 28, 30, 31, 32, and/or 33 of CDRH1; and/or in one or more of amino acid positions 50, 52, 53, 54, 56 and/or 58 of CDRH2; and/or in one or more of amino acid positions 95-100, 100a, 100b, and 100c of CDRH3; and/or in one or more of amino acid positions 28, 29, 30 and/or 31 of CDRH1; and/or in one or more of amino acid positions 50 and/or 53 in CDRL2; and/or in one or more of amino acid positions 91, 92, 93, 94, and/or 96 in CDRL3. The variant amino acids at these positions are encoded by restricted codon sets, as described herein.

As discussed above, the variant amino acids are encoded by restricted codon sets. A codon set is a set of different nucleotide triplet sequences which can be used to form a set of oligonucleotides used to encode the desired group of amino acids. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one aspect, the restricted repertoire of amino acids intended to occupy one or more of the solvent accessible and highly diverse positions in CDRs of humanized antibody 4D5 are determined (based on the desire of the practitioner, which can be based on any of a number of criteria, including specific amino acids desired for particular positions, specific amino acid(s) desired to be absent from a particular position, size of library desired, characteristic of antigen binders sought, etc.).

Heavy chain CDR3s (CDRH3s) in known antibodies have diverse sequences, structural conformations, and lengths. CDRH3s are often found in the middle of the antigen binding pocket and often participate in antigen contact. The design of CDRH3 may thus be developed separately from that of the other CDRs because it can be difficult to predict the structural conformation of CDRH3 and the amino acid diversity in this region is especially diverse in known antibodies. In accordance with the present invention, CDRH3 is designed to generate diversity at specific positions within CDRH3, for example, positions 95, 96, 97, 98, 99, 100, 100a, 100b, and 100c (e.g., according to Kabat numbering in antibody 4D5). In some embodiments, diversity is also generated by varying CDRH3 length using restricted codon sets. Length diversity can be of any range determined empirically to be suitable for generating a population of polypeptides containing substantial proportions of antigen binding proteins. For example, polypeptides comprising variant CDRH3 can be generated having the sequence X1-X2-X3-X4-X5-(X6)$_n$-X7-X8-X9-D-Y (SEQ ID NO:4), wherein X1-X9 are amino acids encoded by restricted codon sets, and n is of various lengths, for example, n=1-11, 5-11, or 7-11. Other examples of possible n values are 1, 2, 3, 4, 5, 6, 7, 8, 9, 10, and 11. Illustrative embodiments of oligonucleotides that can be utilized to provide for variety in CDRH3 sequence length include those shown in FIG. 9A-9D, FIG. 20A-L and FIG. 23.

It is contemplated that the sequence diversity of libraries created by introduction of variant amino acids in a particular CDR, for example, CDRH3, can be increased by combining the variant CDR with other CDRs comprising variations in other regions of the antibody, specifically in other CDRs of either the light or heavy chain variable sequences. It is contemplated that the nucleic acid sequences that encode members of this set can be further diversified by introduction of other variant amino acids in the CDRs of either the light or heavy chain sequences, via codon sets. Thus, for example, in one embodiment, CDRH3 sequences from fusion polypeptides that bind a target antigen can be combined with diversified CDRL3, CDRH1, or CDRH2 sequences, or any combination of diversified CDRs.

It should be noted that in some instances framework residues may be varied relative to the sequence of a source antibody or antigen binding fragment, for example, to reflect a consensus sequence or to improve stability or display. For example, framework residues 49, 93, 94 or 71 in the heavy chain may be varied. Heavy chain framework residue 93 may be serine or alanine (which is the human consensus sequence amino acid at that position.) Heavy chain framework residue 94 may be changed to reflect framework consensus sequence from threonine to arginine or lysine. Another example of a framework residue that may be altered is heavy chain framework residue 71, which is R in about 1970 polypeptides, V in about 627 polypeptides and A in about 527 polypeptides, as found in the Kabat database. Heavy chain framework residue 49 may be alanine or glycine. In addition, optionally, the 3 N-terminal amino acids of the heavy chain variable domain can be removed. In the light chain, optionally, the arginine at amino acid position 66 can be changed to glycine. In one embodiment, heavy chain framework residue 93 is alanine and heavy chain framework residue 94 is arginine.

In one aspect, the invention provides vector constructs for generating fusion polypeptides that bind with significant affinity to potential ligands. These constructs comprise a dimerizable domain that when present in a fusion polypeptide provides for increased tendency for heavy chains to dimerize to form dimers of Fab or Fab' antibody fragments/portions. These dimerization domains may include, e.g., a heavy chain hinge sequence (for example, a sequence comprising TCPPCPAPELLG (SEQ ID NO: 5) that may be present in the fusion polypeptide). Dimerization domains in fusion phage polypeptides bring two sets of fusion polypeptides (LC/HC-phage protein/fragment (such as pIII)) together, thus allowing formation of suitable linkages (such as interheavy chain disulfide bridges) between the two sets of fusion polypeptides. Vector constructs containing such dimerization domains can be used to achieve divalent display of antibody variable domains, for example the diversified fusion proteins described herein, on phage. In certain embodiments, the intrinsic affinity of each monomeric antibody fragment (fusion polypeptide) is not significantly altered by fusion to the dimerization domain. In certain embodiments, dimerization results in divalent phage display which provides increased avidity of phage binding, with significant decrease in off-rate, which can be determined by methods known in the art and as described herein. Dimerization domain-containing vectors of the invention may or may not also include an amber stop codon after the dimerization domain.

Dimerization can be varied to achieve different display characteristics. Dimerization domains can comprise a sequence comprising a cysteine residue, a hinge region from a full-length antibody, a dimerization sequence such as leucine zipper sequence or GCN4 zipper sequence or mixtures thereof. Dimerization sequences are known in the art, and include, for example, the GCN4 zipper sequence (GRMKQLEDKVEELLSKNYHLENE-VARLKKLVGERG) (SEQ ID NO: 3). The dimerization domain is in certain embodiments located at the C-terminal end of the heavy chain variable or constant domain sequence and/or between the heavy chain variable or constant domain sequence and any viral coat protein component sequence. An amber stop codon may also be present at or after the C-terminal end of the dimerization domain. In one embodiment, wherein an amber stop codon is present, the dimerization domain encodes at least one cysteine and a dimerizing sequence such as leucine zipper. In another embodiment, wherein no amber stop codon is present, the dimerization domain may comprise a single cysteine residue.

The polypeptides of the invention can also be fused to other types of polypeptides in order to provide for display of the variant polypeptides or to provide for purification, screening or sorting, and detection of the polypeptide. For embodiment involving phage display, the polypeptides of the invention are fused to all or a portion of a viral coat protein. Examples of viral coat protein include protein PIII, major coat protein, pVIII, Soc, Hoc, gpD, pVI and variants thereof. In addition, the variant polypeptides generated according to the methods of the invention can optionally be fused to a polypeptide marker or tag such as FLAG, polyhistidine, gD, c-myc, B-galactosidase and the like.

Methods of Generating Libraries of Randomized Variable Domains

Methods of substituting an amino acid of choice into a template nucleic acid are well established in the art, some of which are described herein. For example, libraries can be created by targeting solvent accessible and/or highly diverse positions in at least one CDR region for amino acid substitution with variant amino acids using the Kunkel method. See, for example, Kunkel et al., Methods Enzymol. (1987), 154: 367-382. Generation of randomized sequences is also described below in the Examples.

The sequence of oligonucleotides includes one or more of the designed restricted codon sets for different lengths of CDRH3 or for the solvent accessible and highly diverse positions in a CDR. A codon set is a set of different nucleotide triplet sequences used to encode desired variant amino acids. Codon sets can be represented using symbols to designate particular nucleotides or equimolar mixtures of nucleotides as shown below according to the IUB code. Typically, a codon set is represented by three capital letters, e.g., KAT, TMT and the like.

IUB CODES
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T)
N (A or C or G or T)

For example, in the codon set TMT, T is the nucleotide thymine; and M can be A or C. This codon set can present multiple codons and can encode only a limited number of amino acids, namely tyrosine and serine.

Oligonucleotide or primer sets can be synthesized using standard methods. A set of oligonucleotides can be synthesized, for example, by solid phase synthesis, containing sequences that represent all possible combinations of nucleotide triplets provided by the restricted codon set and that will encode the desired restricted group of amino acids. Synthesis of oligonucleotides with selected nucleotide "degeneracy" at certain positions is well known in that art. Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a CDR (for example, as contained within a variable domain) nucleic acid template and also can include restriction enzyme sites for cloning purposes.

In one method, nucleic acid sequences encoding variant amino acids can be created by oligonucleotide-mediated mutagenesis of a nucleic acid sequence encoding a source or template polypeptide such as the antibody variable domain of 4D5. This technique is well known in the art as described by Zoller et al. Nucleic Acids Res. 10:6487-6504 (1987). Briefly, nucleic acid sequences encoding variant amino acids are created by hybridizing an oligonucleotide set encoding the desired restricted codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the restricted codon sets as provided by the oligonucleotide set. Nucleic acids encoding other source or template molecules are known or can be readily determined.

Generally, oligonucleotides of at least 25 nucleotides in length are used. An optimal oligonucleotide will have at least 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *Proc. Natl. Acad. Sci. USA,* 75:5765 (1978).

The DNA template is generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.,* 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. ((1987) Meth. Enzymol., 153:3). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat protein components and dimerization domains, using established molecular biology techniques.

The sequence of the PCR primers includes one or more of the designed codon sets for the solvent accessible and highly diverse positions in a CDR region. As described above, a codon set is a set of different nucleotide triplet sequences used to encode desired variant amino acids.

Oligonucleotide sets can be used in a polymerase chain reaction using a variable region nucleic acid template sequence as the template to create nucleic acid cassettes. The variable region nucleic acid template sequence can be any portion of the light or heavy immunoglobulin chains containing the target nucleic acid sequences (i.e., nucleic acid sequences encoding amino acids targeted for substitution). The variable region nucleic acid template sequence is a portion of a double stranded DNA molecule having a first nucleic acid strand and complementary second nucleic acid strand. The variable region nucleic acid template sequence contains at least a portion of a variable domain and has at least one CDR. In some cases, the variable region nucleic acid template sequence contains more than one CDR. An upstream portion and a downstream portion of the variable region nucleic acid template sequence can be targeted for hybridization with members of an upstream oligonucleotide set and a downstream oligonucleotide set.

A first oligonucleotide of the upstream primer set can hybridize to the first nucleic acid strand and a second oligonucleotide of the downstream primer set can hybridize to the second nucleic acid strand. The oligonucleotide primers can include one or more codon sets and be designed to hybridize to a portion of the variable region nucleic acid template sequence. Use of these oligonucleotides can introduce two or more codon sets into the PCR product (i.e., the nucleic acid cassette) following PCR. The oligonucleotide primer that hybridizes to regions of the nucleic acid sequence encoding the antibody variable domain includes portions that encode CDR residues that are targeted for amino acid substitution.

The upstream and downstream oligonucleotide sets can also be synthesized to include restriction sites within the oligonucleotide sequence. These restriction sites can facilitate the insertion of the nucleic acid cassettes [i.e., PCR reaction products] into an expression vector having additional antibody sequences. In certain embodiments, the restriction sites are designed to facilitate the cloning of the nucleic acid cassettes without introducing extraneous nucleic acid sequences or removing original CDR or framework nucleic acid sequences.

Nucleic acid cassettes can be cloned into any suitable vector for expression of a portion or the entire light or heavy chain sequence containing the targeted amino acid substitutions generated. According to methods detailed in the invention, the nucleic acid cassette is cloned into a vector allowing production of a portion or the entire light or heavy chain sequence fused to all or a portion of a viral coat protein (i.e., creating a fusion protein) and displayed on the surface of a particle or cell. While several types of vectors are available and may be used to practice this invention, phagemid vectors are convenient, as they may be constructed with relative ease, and can be readily amplified. Phagemid vectors generally contain a variety of components including promoters, signal sequences, phenotypic selection genes, origin of replication sites, and other necessary components as are known to those of ordinary skill in the art.

In another embodiment, wherein a particular variant amino acid combination is to be expressed, the nucleic acid cassette contains a sequence that is able to encode all or a portion of the heavy or light chain variable domain, and is able to encode the variant amino acid combinations. For production of antibodies containing these variant amino acids or combinations of variant amino acids, as in a library, the nucleic acid cassettes can be inserted into an expression vector containing additional antibody sequence, for example all or portions of the variable or constant domains of the light and heavy chain variable regions. These additional antibody sequences can also be fused to other nucleic acid sequences, such as sequences which encode viral coat protein components and therefore allow production of a fusion protein.

Vectors

One aspect of the invention includes a replicable expression vector comprising a nucleic acid sequence encoding a gene fusion, wherein the gene fusion encodes a fusion protein comprising a CDR-containing polypeptide (such as an antibody variable domain), or an antibody variable domain and a constant domain, fused to all or a portion of a viral coat protein. Also included is a library of diverse replicable expression vectors comprising a plurality of gene fusions encoding a plurality of different fusion proteins including a plurality of the fusion polypeptides generated with diverse sequences as described above. The vectors can include a variety of components and may be constructed to allow for movement of antibody variable domain between different vectors and/or to provide for display of the fusion proteins in different formats.

Examples of vectors include phage vectors and phagemid vectors (which is illustrated herein, and described in greater detail above). A phage vector generally has a phage origin of replication allowing phage replication and phage particle formation. The phage is generally a filamentous bacteriophage, such as an M13, f1, fd, Pf3 phage or a derivative thereof, or a lambdoid phage, such as lambda, 21, phi80, phi81, 82, 424, 434, etc., or a derivative thereof.

Examples of viral coat proteins include infectivity protein PIII (sometimes also designated p3), major coat protein PVIII, Soc (T4), Hoc (T4), gpD (of bacteriophage lambda), minor bacteriophage coat protein 6 (pVI) (filamentous phage; *J Immunol Methods*. 1999 Dec. 10; 231 (1-2):39-51), variants of the M13 bacteriophage major coat protein (P8) (*Protein Sci* 2000 April; 9(4):647-54). The fusion protein can be displayed on the surface of a phage and suitable phage systems include M13KO7 helper phage, M13R408, M13-VCS, and Phi X 174, pJuFo phage system (J. Virol. 2001 August; 75(15): 7107-13.v), hyperphage (*Nat. Biotechnol.* 2001 January; 19(1):75-8). In certain embodiments, the helper phage is M13KO7, and the coat protein is the M13 Phage gene III coat protein. In certain embodiments, the host is *E. coli*, and protease deficient strains of *E. coli*. Vectors, such as the fth 1 vector (*Nucleic Acids Res.* 2001 May 15; 29(10):E50-0) can be useful for the expression of the fusion protein.

The expression vector also can have a secretory signal sequence fused to the DNA encoding a CDR-containing fusion polypeptide (e.g., each subunit of an antibody, or fragment thereof). This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., *Gene,* 68:1931 (1983), MalE, PhoA and other genes. In one embodiment, a prokaryotic signal sequence for practicing this invention is the *E. coli* heat-stable enterotoxin II (STII) signal sequence as described by Chang et al., *Gene* 55:189 (1987), and/or malE.

As indicated above, a vector also typically includes a promoter to drive expression of the fusion polypeptide. Promoters most commonly used in prokaryotic vectors include the lac Z promoter system, the alkaline phosphatase pho A promoter (Ap), the bacteriophage $1_{PL}$ promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable promoters may be used as well.

The vector can also include other nucleic acid sequences, for example, sequences encoding gD tags, c-Myc epitopes, poly-histidine tags, fluorescence proteins (e.g., GFP), or beta-galactosidase protein which can be useful for detection or purification of the fusion protein expressed on the surface of the phage or cell. Nucleic acid sequences encoding, for example, a gD tag, also provide for positive or negative selection of cells or virus expressing the fusion protein. In some embodiments, the gD tag is fused to an antibody variable domain which is not fused to the viral coat protein component. Nucleic acid sequences encoding, for example, a poly-histidine tag, are useful for identifying fusion proteins including antibody variable domains that bind to a specific antigen using immunohistochemistry. Tags useful for detection of antigen binding can be fused to either an antibody variable domain not fused to a viral coat protein component or an antibody variable domain fused to a viral coat protein component.

Another useful component of the vectors used to practice this invention is phenotypic selection genes. Typical phenotypic selection genes are those encoding proteins that confer antibiotic resistance upon the host cell. By way of illustration, the ampicillin resistance gene (amp), and the tetracycline resistance gene (tetr) are readily employed for this purpose.

The vector can also include nucleic acid sequences containing unique restriction sites and suppressible stop codons. The unique restriction sites are useful for moving antibody variable domains between different vectors and expression systems, especially useful for production of full-length antibodies or antigen binding fragments in cell cultures. The suppressible stop codons are useful to control the level of expression of the fusion protein and to facilitate purification of soluble antibody fragments. For example, an amber stop codon can be read as Gln in a supE host to enable phage display, while in a non-supE host it is read as a stop codon to produce soluble antibody fragments without fusion to phage coat proteins. These synthetic sequences can be fused to one or more antibody variable domains in the vector.

It is sometimes beneficial to use vector systems that allow the nucleic acid encoding an antibody sequence of interest, for example a CDR having variant amino acids, to be easily removed from the vector system and placed into another vector system. For example, appropriate restriction sites can be engineered in a vector system to facilitate the removal of the nucleic acid sequence encoding an antibody or antibody variable domain having variant amino acids. The restriction sequences are usually chosen to be unique in the vectors to facilitate efficient excision and ligation into new vectors. Antibodies or antibody variable domains can then be expressed from vectors without extraneous fusion sequences, such as viral coat proteins or other sequence tags.

Between nucleic acid encoding antibody variable or constant domain (gene 1) and the viral coat protein component (gene 2), DNA encoding a termination or stop codon may be inserted, such termination codons including UAG (amber), UAA (ocher) and UGA (opel). (*Microbiology,* Davis et al., Harper & Row, New York, 1980, pp. 237, 245-47 and 374). The termination or stop codon expressed in a wild type host cell results in the synthesis of the gene 1 protein product without the gene 2 protein attached. However, growth in a suppressor host cell results in the synthesis of detectable quantities of fused protein. Such suppressor host cells are well known and described, such as *E. coli* suppressor strain (Bullock et al., *BioTechniques* 5:376-379 (1987)). Any acceptable method may be used to place such a termination codon into the mRNA encoding the fusion polypeptide.

The suppressible codon may be inserted between the first gene encoding an antibody variable or constant domain, and a second gene encoding at least a portion of a phage coat protein. Alternatively, the suppressible termination codon may be inserted adjacent to the fusion site by replacing the last amino acid triplet in the antibody variable domain or the first amino acid in the phage coat protein. The suppressible termination codon may be located at or after the C-terminal end of a dimerization domain. When the plasmid containing the suppressible codon is grown in a suppressor host cell, it results in the detectable production of a fusion polypeptide containing the polypeptide and the coat protein. When the plasmid is grown in a non-suppressor host cell, the antibody variable domain is synthesized substantially without fusion to the phage coat protein due to termination at the inserted suppressible triplet UAG, UAA, or UGA. In the non-suppressor cell the antibody variable domain is synthesized and secreted from the host cell due to the absence of the fused phage coat protein which otherwise anchored it to the host membrane.

In some embodiments, the CDR being diversified (randomized) may have a stop codon engineered in the template sequence (referred to herein as a "stop template"). This feature provides for detection and selection of successfully diversified sequences based on successful repair of the stop codon(s) in the template sequence due to incorporation of the oligonucleotide(s) comprising the sequence(s) for the variant amino acids of interest. This feature is further illustrated in the Examples below.

The light and/or heavy chain antibody variable or constant domains can also be fused to an additional peptide sequence, the additional peptide sequence providing for the interaction of one or more fusion polypeptides on the surface of the viral particle or cell. These peptide sequences are herein referred to as "dimerization domains". Dimerization domains may comprise at least one or more of a dimerization sequence, or at least one sequence comprising a cysteine residue or both. Suitable dimerization sequences include those of proteins having amphipathic alpha helices in which hydrophobic residues are regularly spaced and allow the formation of a dimer by interaction of the hydrophobic residues of each protein; such proteins and portions of proteins include, for example, leucine zipper regions. Dimerization domains can also comprise one or more cysteine residues (e.g. as provided by inclusion of an antibody hinge sequence within the dimerization domain). The cysteine residues can provide for dimerization by formation of one or more disulfide bonds. In one embodiment, wherein a stop codon is present after the dimerization domain, the dimerization domain comprises at least one cysteine residue. In some embodiments, the dimerization domains are located between the antibody variable or constant domain and the viral coat protein component.

In some cases the vector encodes a single antibody-phage polypeptide in a single chain form containing, for example, both the heavy and light chain variable regions fused to a coat protein. In these cases the vector is considered to be "monocistronic", expressing one transcript under the control of a certain promoter. For example, a vector may utilize a promoter (such as the alkaline phosphatase (AP) or Tac promoter) to drive expression of a monocistronic sequence encoding VL and VH domains, with a linker peptide between the VL and VH domains. This cistronic sequence may be connected at the 5' end to a signal sequence (such as an *E. coli* malE or heat-stable enterotoxin II (STII) signal sequence) and at its 3' end to all or a portion of a viral coat protein (such as the bacteriophage pIII protein). The fusion polypeptide encoded by a vector of this embodiment is referred to herein as "ScFv-pIII". In some embodiments, a vector may further comprise a sequence encoding a dimerization domain (such as a leucine zipper) at its 3' end, between the second variable domain sequence (e.g., VH) and the viral coat protein sequence. Fusion polypeptides comprising the dimerization domain are capable of dimerizing to form a complex of two scFv polypeptides (referred to herein as "(ScFv)$_2$-pIII)").

In other cases, the variable regions of the heavy and light chains can be expressed as separate polypeptides, the vector thus being "bicistronic", allowing the expression of separate transcripts. In these vectors, a suitable promoter, such as the Ptac or PhoA promoter, is used to drive expression of a bicistronic message. A first cistron encoding, for example, a light chain variable and constant domain, may be connected at the 5' end to a signal sequence, such as *E. coli* malE or heat-stable enterotoxin II (STII) signal sequence, and at the 3' end to a nucleic acid sequence encoding a tag sequence, such as gD tag. A second cistron, encoding, for example, a heavy chain variable domain and constant domain CH1, is connected at its 5' end to a signal sequence, such as *E. coli* malE or heat-stable enterotoxin II (STII) signal sequence, and at the 3' end to all or a portion of a viral coat protein.

In one embodiment of a vector which provides a bicistronic message and for display of F(ab')$_2$-pIII, a suitable promoter, such as Ptac or PhoA (AP) promoter, drives expression of a first cistron encoding a light chain variable and constant domain operably linked at 5' end to a signal sequence such as the *E. coli* malE or heat stable enterotoxin II (STII) signal sequence, and at the 3' end to a nucleic acid sequence encoding a tag sequence such as gD tag. The second cistron encodes, for example, a heavy chain variable and constant domain operatively linked at 5' end to a signal sequence such as *E. coli* malE or heat stable enterotoxin II (STII) signal sequence, and at 3' end has a dimerization domain comprising IgG hinge sequence and a leucine zipper sequence followed by at least a portion of viral coat protein.

Display of Fusion Polypeptides

Fusion polypeptides of a CDR-containing polypeptide (for example, an antibody variable domain) can be displayed on the surface of a cell, virus, or phagemid particle in a variety of formats. These formats include single chain Fv fragment (scFv), F(ab) fragment and multivalent forms of these fragments. For example, multivalent forms include a dimer of ScFv, Fab, or F(ab'), herein referred to as (ScFv)$_2$, F(ab)$_2$ and F(ab')$_2$, respectively. The multivalent forms of display are advantageous in some contexts in part because they have more than one antigen binding site which generally results in the identification of lower affinity clones and also allows for more efficient sorting of rare clones during the selection process.

Methods for displaying fusion polypeptides comprising antibody fragments, on the surface of bacteriophage, are well known in the art, for example as described in patent publication number WO 92/01047 and herein. Other patent publications WO 92/20791; WO 93/06213; WO 93/11236 and WO 93/19172, describe related methods and are all herein incorporated by reference. Other publications have shown the identification of antibodies with artificially rearranged V gene repertoires against a variety of antigens displayed on the surface of phage (for example, H. R. Hoogenboom & G. Winter, J. Mol. Biol. 227 381-388 (1992); and as disclosed in WO 93/06213 and WO 93/11236).

When a vector is constructed for display in a scFv format, it includes nucleic acid sequences encoding an antibody variable light chain domain and an antibody variable heavy chain variable domain. Typically, the nucleic acid sequence encoding an antibody variable heavy chain domain is fused to a viral coat protein component. One or both of the antibody variable domains can have variant amino acids in at least one CDR region. The nucleic acid sequence encoding the antibody variable light chain is connected to the antibody variable heavy chain domain by a nucleic acid sequence encoding a peptide linker. The peptide linker typically contains about 5 to 15 amino acids. Optionally, other sequences encoding, for example, tags useful for purification or detection can be fused at the 3' end of either the nucleic acid sequence encoding the antibody variable light chain or antibody variable heavy chain domain or both.

When a vector is constructed for F(ab) display, it includes nucleic acid sequences encoding antibody variable domains and antibody constant domains. A nucleic acid encoding a variable light chain domain is fused to a nucleic acid sequence encoding a light chain constant domain. A nucleic acid sequence encoding an antibody heavy chain variable domain is fused to a nucleic acid sequence encoding a heavy chain constant CH1 domain. Typically, the nucleic acid sequence encoding the heavy chain variable and constant domains are fused to a nucleic acid sequence encoding all or part of a viral coat protein. One or both of the antibody variable light or heavy chain domains can have variant amino acids in at least one CDR. In some embodiments, the heavy chain variable and constant domains are expressed as a fusion with at least a portion of a viral coat protein, and the light chain variable and constant domains are expressed separately from the heavy chain viral coat fusion protein. The heavy and light chains associate with one another, which may be by covalent or non-covalent bonds. Optionally, other sequences encoding, for example, polypeptide tags useful for purification or detection, can be fused at the 3' end of either the nucleic acid sequence encoding the antibody light chain constant domain or antibody heavy chain constant domain or both.

In some embodiments, a bivalent moiety, for example, a F(ab)₂ dimer or F(ab')₂ dimer, is used for displaying antibody fragments with the variant amino acid substitutions on the surface of a particle. It has been found that F(ab')₂ dimers generally have the same affinity as F(ab) dimers in a solution phase antigen binding assay but the off rate for F(ab')₂ are reduced because of a higher avidity. Therefore, the bivalent format (for example, F(ab')₂) is a particularly useful format since it can allow for the identification of lower affinity clones and also allows more efficient sorting of rare clones during the selection process.

Introduction of Vectors into Host Cells

Vectors constructed as described in accordance with the invention are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle.

Replicable expression vectors are introduced into host cells using a variety of methods. In one embodiment, vectors can be introduced into cells using electroporation as described in WO/00106717. Cells are grown in culture in standard culture broth, optionally for about 6-48 hours (or to $OD_{600}$=0.6–0.8) at about 37° C., and then the broth is centrifuged and the supernatant removed (e.g. decanted). In some embodiments, initial purification includes resuspending the cell pellet in a buffer solution (e.g. 1.0 mM HEPES pH 7.4) followed by recentrifugation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration.

In certain embodiments, the recipient cell is the electroporation competent E. coli strain of the present invention, which is E. coli strain SS320 (Sidhu et al., Methods Enzymol. (2000), 328:333-363). Strain SS320 was prepared by mating MC1061 cells with XL1-BLUE cells under conditions sufficient to transfer the fertility episome (F' plasmid) or XL1-BLUE into the MC1061 cells. Strain SS320 has been deposited with the American Type Culture Collection (ATCC), 10801 University Boulevard, Manassas, Va. USA, on Jun. 18, 1998 and assigned Deposit Accession No. 98795. Any F' episome which enables phage replication in the strain may be used in the invention. Suitable episomes are available from strains deposited with ATCC or are commercially available (CJ236, CSH18, DHF', JM101, JM103, JM105, JM107, JM109, JM110), KS1000, XL1-BLUE, 71-18 and others).

The use of higher DNA concentrations during electroporation (about 10×) increases the transformation efficiency and increases the amount of DNA transformed into the host cells. The use of high cell concentrations also increases the efficiency (about 10×). The larger amount of transferred DNA produces larger libraries having greater diversity and representing a greater number of unique members of a combinatorial library. Transformed cells are generally selected by growth on antibiotic containing medium.

Selection (Sorting) and Screening for Binders to Targets of Choice

Use of phage display for identifying target antigen binders, with its various permutations and variations in methodology, are well established in the art. One approach involves constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, followed by a process that entails selection or sorting by contacting the recombinant phage particles with a target antigen so that at least a portion of the population of particles bind to the target with the objective to increase and enrich the subsets of the particles which bind from particles relative to particles that do not bind in the process of selection. The selected pool can be amplified by infecting host cells, such as fresh XL1-Blue cells, for another round of sorting on the same target with different or same stringency. The resulting pool of variants are then screened against the target antigens to identify novel high affinity binding proteins. These novel high affinity binding proteins can be useful as therapeutic agents as antagonists or agonists, and/or as diagnostic and research reagents.

Fusion polypeptides such as antibody variable domains comprising the variant amino acids can be expressed on the surface of a phage, phagemid particle or a cell and then selected and/or screened for the ability of members of the group of fusion polypeptides to bind a target antigen which is typically an antigen of interest. The processes of selection for binders to target can also be include sorting on a generic protein having affinity for antibody variable domains such as protein L or a tag specific antibody which binds to antibody or antibody fragments displayed on phage, which can be used to enrich for library members that display correctly folded antibody fragments (fusion polypeptides).

Target proteins, such as the DR5 receptor and HER-2, may be isolated from natural sources or prepared by recombinant methods by procedures known in the art. Sequences of human and murine DR5 are provided in Table 1. Sequence and preparation of HER-2 ECD has been described in Franklin M C. Carey K D. Vajdos F F. Leahy D J. de Vos A M. Sliwkowski M X., Insights into ErbB signaling from the structure of the ErbB2-pertuzumab complex, Cancer Cell. 5(4):317-28, 2004. The sequence of an extracellular domain amino acids 23-646 of HER-2 is provided at the Protein DataBank Record 1S78 (2004). Target antigens can include a number of molecules of therapeutic interest.

A variety of strategies of selection (sorting) for affinity can be used. One example is a solid-support method or plate sorting or immobilized target sorting. Another example is a solution-binding method.

For the solid support method, the target protein may be attached to a suitable solid or semi solid matrix. Such matrices are known in the art, such as agarose beads, acrylamide beads, glass beads, cellulose, various acrylic copolymers, hydroxyalkyl methacrylate gels, polyacrylic and polymethacrylic copolymers, nylon, neutral and ionic carriers, and the like. Attachment of the target protein to the matrix may be accomplished by methods described, e.g., in Methods in Enzymology, 44 (1976), or by other means known in the art.

After attachment of the target antigen to the matrix, the immobilized target is contacted with the library expressing the fusion polypeptides under conditions suitable for binding of at least a subset of the phage particle population with the immobilized target antigen. Normally, the conditions, including pH, ionic strength, temperature and the like will mimic physiological conditions. Bound particles ("binders") to the immobilized target are separated from those particles that do not bind to the target by washing. Wash conditions can be adjusted to result in removal of all but the high affinity binders. Binders may be dissociated from the immobilized target by a variety of methods. These methods include competitive dissociation using the wild-type ligand (e.g. excess target antigen), altering pH and/or ionic strength, and methods known in the art. Selection of binders typically involves elution from an affinity matrix with a suitable elution material such as acid like 0.1M HCl or ligand. Elution with increasing concentrations of ligand could elute displayed binding molecules of increasing affinity.

The binders can be isolated and then re-amplified in suitable host cells by infecting the cells with the viral particles that are binders (and helper phage if necessary, e.g., when the viral particle is a phagemid particle) and the host cells are cultured under conditions suitable for amplification of the particles that display the desired fusion polypeptide. The phage particles are then collected and the selection process is repeated one or more times until binders of the target antigen are enriched. Any number of rounds of selection or sorting can be utilized. One of the selection or sorting procedures can involve isolating binders that bind to a generic affinity protein such as protein L or an antibody to a polypeptide tag present in a displayed polypeptide such as antibody to the gD protein or polyhistidine tag. Counterselection may be included in one or more rounds of selection or sorting to isolate binders that also exhibit undesired binding to one or more non-target antigens.

One aspect of the invention involves selection against libraries of the invention using a novel selection method which is termed "solution-binding method". The invention allows solution phase sorting with much improved efficiency over conventional solution sorting methods. The solution binding method may be used for finding original binders from a random library or finding improved binders from a library that was designated to improve affinity of a particular binding clone or group of clones. The method comprises contacting a plurality of polypeptides, such as those displayed on phage or phagemid particles (library), with a target antigen labeled or fused with a tag molecule. The tag could be biotin or other moieties for which specific binders are available. The stringency of the solution phase can be varied by using decreasing concentrations of labeled target antigen in the first solution binding phase. To further increase the stringency, the first solution binding phase can be followed by a second solution phase having high concentration of unlabelled target antigen after the initial binding with the labeled target in the first solution phase. Usually, 100 to 1000 fold of unlabelled target over labeled target is used in the second phase (if included). The length of time of incubation of the first solution phase can vary from a few minutes to one to two hours or longer to reach equilibrium. Using a shorter time for binding in this first phase may bias or select for binders that have fast on-rate. The length of time and temperature of incubation in second phase can be varied to increase the stringency. This provides for a selection bias for binders that have slow rate of coming off the target (off-rate). After contacting the plurality of polypeptides (displayed on the phage/phagemid particles) with a target antigen, the phage or phagemid particles that are bound to labeled targets are separated from phage that do not bind. The particle-target mixture from solution phase of binding is isolated by contacting it with the labeled target moiety and allowing for its binding to, a molecule that binds the labeled target moiety for a short period of time (e.g., 2-5 minutes). The initial concentration of the labeled target antigen can range from about 0.1 nM to about 1000 nM. The bound particles are eluted and can be propagated for next round of sorting. In certain embodiments, multiple rounds of sorting are performed using a lower concentration of labeled target antigen with each round of sorting.

For example, an initial sort or selection using about 100 to 250 nM labeled target antigen should be sufficient to capture a wide range of affinities, although this factor can be determined empirically and/or to suit the desire of the practitioner. In the second round of selection, about 25 to 100 nM of labeled target antigen may be used. In the third round of selection, about 0.1 to 25 nM of labeled target antigen may be used. For example, to improve the affinity of a 100 nM binder, it may be desirable to start with 20 nM and then progress to 5 and 1 nM labeled target, then, followed by even lower concentrations such as about 0.1 nM labeled target antigen.

The conventional solution sorting involves use of beads like streptavidin-coated beads, which is very cumbersome to use and often results in very low efficiency of phage binder recovery. The conventional solution sorting with beads takes much longer than 2-5 minutes and is less feasible to adapt to high throughput automation than the invention described above.

As described herein, combinations of solid support and solution sorting methods can be advantageously used to isolate binders having desired characteristics. After selection/sorting on target antigen for a few rounds, screening of individual clones from the selected pool generally is performed to identify specific binders with the desired properties/characteristics. In some embodiments, the process of screening is carried out by automated systems to allow for high-throughput screening of library candidates.

Two major screening methods are described below. However, other methods known in the art may also be used in the methods of the invention. The first screening method comprises a phage ELISA assay with immobilized target antigen, which provides for identification of a specific binding clone from a non-binding clone. Specificity can be determined by simultaneous assay of the clone on target coated well and BSA or other non-target protein coated wells. This assay is automatable for high throughput screening.

One embodiment provides a method of selecting for an antibody variable domain that binds to a specific target antigen from a library of antibody variable domain by generating a library of replicable expression vectors comprising a plurality of polypeptides; contacting the library with a target antigen and at least one nontarget antigen under conditions suitable for binding; separating the polypeptide binders in the library from the nonbinders; identifying the binders that bind to the target antigen and do not bind to the nontarget antigen; eluting the binders from the target antigen; and amplifying the replicable expression vectors comprising the polypeptide binder that bind to a specific antigen.

The second screening assay is an affinity screening assay that provides for screening for clones that have high affinity from clones that have low affinity in a high throughput manner. In the assay, each clone is assayed with and without first incubating with target antigen of certain concentration for a period of time (e.g., 30-60 minutes) before application to target coated wells briefly (e.g., 5-15 minutes). Then bound phage is measured by usual phage ELISA method, e.g. using anti-M13 HRP conjugates. The ratio of binding signal of the two wells, one well having been preincubated with target and the other well not preincubated with target antigen is an indication of affinity. The selection of the concentration of target for first incubation depends on the affinity range of interest. For example, if binders with affinity higher than 10 nM are desired, 100 nM of target in the first incubation is often used. Once binders are found from a particular round of sorting (selection), these clones can be screened with an affinity screening assay to identify binders with higher affinity.

Combinations of any of the sorting/selection methods described above may be combined with the screening methods. For example, in one embodiment, polypeptide binders are first selected for binding to immobilized target antigen. Polypeptide binders that bind to the immobilized target antigen can then be amplified and screened for binding to the target antigen and for lack of binding to nontarget antigens. Polypeptide binders that bind specifically to the target antigen are amplified. These polypeptide binders can then selected for higher affinity by contact with a concentration of a labeled target antigen to form a complex, wherein the concentration ranges of labeled target antigen from about 0.1 nM to about 1000 nM, the complexes are isolated by contact with an agent that binds to the label on the target antigen. The polypeptide binders are then eluted from the labeled target antigen and optionally, the rounds of selection are repeated, each time a lower concentration of labeled target antigen is used. The high affinity polypeptide binders isolated using this selection method can then be screened for high affinity using a variety of methods known in the art, some of which are described herein.

These methods can provide for finding clones with high affinity without having to perform long and complex competition affinity assays on a large number of clones. The intensive aspect of doing complex assays of many clones often is a significant obstacle to finding best clones from a selection. This method is especially useful in affinity improvement efforts where multiple binders with similar affinity can be recovered from the selection process. Different clones may have very different efficiency of expression/display on phage or phagemid particles. Those clones more highly expressed have better chances being recovered. That is, the selection can be biased by the display or expression level of the variants. The solution-binding sorting method of the invention can improve the selection process for finding binders with high affinity. This method is an affinity screening assay that provides a significant advantage in screening for the best binders quickly and easily.

The antibodies or antigen binding fragments can be further selected for functional activity, for example, for example, antagonist or agonist activity. For example, anti-HER-2 antibodies can be selected for the ability to inhibit tyrosine phosphorylation of HER-2, proliferation of cancer cells or to induce apoptosis of cancer cells. Assays for identifying and measuring these activities are described for example in WO98/17797.

In addition, anti-DR5 antibodies can be selected for the ability to induce apoptosis of cancer cells and/or inhibit the function of inflammatory cells. In other embodiments, anti-DR5 antibodies are selected for the ability to compete with Apo-2L for binding to DR5. In yet other embodiments, anti-human DR5 antibodies are selected for binding to murine and/or cynomolgous DR5. Assays for determining biological activity can be conducted using methods known in the art, such as DNA fragmentation (see, e.g., Marsters et al., Curr. Biology, 6: 1669 (1996)), caspase inactivation, DR5 binding (see, e.g., WO 98/51793, published Nov. 19, 1998. Apoptosis can be measured by identifying condensation of cytoplasm, loss of plasma membrane microvilli, segmentation of the nucleus, degradation of chromosomal DNA or loss of mitochondrial function. This activity can be determined and measured, for instance, by cell viability assays (such as Alamar blue assays or MTT assays), FACS analysis, caspase activation, DNA fragmentation (see, for example, Nicoletti et al., J. Immunol. Methods, -139:271-279 (1991), and poly-ADP ribose polymerase, "PARP", cleavage assays known in the art.

In one embodiment, as assay for apoptosis involves making two fold serial dilutions of control standard and an anti-DR5 antibody in 96-well tissue culture plates. Apo-2 ligand (amino acids 114-281, described in PCT US00/17579) is tested for comparison. Colo-205 (20000 cells~well) human colon carcinoma cells (ATCC) are seeded into the 96-well plates. The plates are incubated at 37 for 24 hours. AlamazBlue (Trek Diagnostic Systems, Inc.) is added to the wells for the last 3 hours of the 24 hours incubation time. Fluorescence is read using a 96-well fluorometer with excitation at 530 nm and emission of 590 nm. The results are expressed in relative fluorescence units (RFU).

After binders are identified by binding to the target antigen, and/or functional assays the nucleic acid can be extracted. Extracted DNA can then be used directly to transform *E. coli* host cells or alternatively, the encoding sequences can be amplified, for example using PCR with suitable primers, and sequenced by any typical sequencing method. Variable domain DNA of the binders can be restriction enzyme digested and then inserted into a vector for protein expression.

Populations comprising polypeptides having CDR(s) with restricted sequence diversity generated according to methods of the invention can be used to isolate binders against a variety of targets, including those listed in FIGS. 11, 15, 21A, and 24A. These binders may comprise one or more variant CDRs comprising diverse sequences generated using restricted codons. In some embodiments, a variant CDR is CDRH3 comprising sequence diversity generated by amino acid substitution with restricted codon sets and/or amino acid insertions resulting from varying CDRH3 lengths. Illustrative oligonucleotides useful for generating fusion polypeptides of the invention include those listed in FIG. 9A-D, FIG. 20A-L, and FIG. 23. One or more variant CDRs may be combined. In some embodiments, only CDRH3 is diversified. In other embodiments, two or more heavy chain CDRs, including CDRH3, are variant. In other embodiments, one or more heavy chain CDRs, excluding CDRH3, are variant. In some embodiments, at least one heavy chain and at least one light chain CDR are variant. In some embodiments, at least one, two, three, four, five or all of CDRs H1, H2, H3, L1, L2 and L3 are variant.

In some cases, it can be beneficial to combine one or more diversified light chain CDRs with novel binders isolated from a population of polypeptides comprising one or more diversified heavy chain CDRs. This process may be referred to as a 2-step process. An example of a 2-step process comprises first determining binders (generally lower affinity binders) within one or more libraries generated by randomizing one or more CDRs, wherein the CDRs randomized in each library are different or, where the same CDR is randomized, it is randomized to generate different sequences. Binders from a heavy chain library can then be randomized with CDR diversity in a light chain CDRs by, for example, a mutagenesis technique such as that of Kunkel, or by cloning (cut-and-paste (e.g. by ligating different CDR sequences together)) the new light chain library into the existing heavy chain binders that has only a fixed light chain. The pool can then be further sorted against one or more targets to identify binders possessing increased affinity. For example, binders (for example, low affinity binders) obtained from sorting an H1/H2/H3 may be fused with library of an L1 L2/L3 diversity to replace its original fixed L1/L2/L3, wherein the new libraries are then further sorted against a target of interest to obtain another set of binders (for example, high affinity binders). Novel antibody sequences can be identified that display higher binding affinity to any of a variety of target antigens.

In some embodiments, libraries comprising polypeptides of the invention are subjected to a plurality of sorting rounds, wherein each sorting round comprises contacting the binders obtained from the previous round with a target antigen distinct from the target antigen(s) of the previous round(s). Preferably, but not necessarily, the target antigens are homologous in sequence, for example members of a family of related but distinct polypeptides, such as, but not limited to, cytokines (for example, alpha interferon subtypes).

Generation of Libraries Comprising Variant CDR-Containing Polypeptides

Libraries of variant CDR polypeptides can be generated by mutating the solvent accessible and/or highly diverse positions in at least one CDR of an antibody variable domain. Some or all of the CDRs can be mutated using the methods of the invention. In some embodiments, it may be preferable to generate diverse antibody libraries by mutating positions in CDRH1, CDRH2 and CDRH3 to form a single library or by mutating positions in CDRL3 and CDRH3 to form a single library or by mutating positions in CDRL3 and CDRH1, CDRH2 and CDRH3 to form a single library.

A library of antibody variable domains can be generated, for example, having mutations in the solvent accessible and/or highly diverse positions of CDRH1, CDRH2 and CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

In one embodiment, a library is created by substitution of original amino acids with a limited set of variant amino acids in the CDRH1, CDRH2, and/or CDRH3 region of the variable region of the heavy chain sequence and/or the CDRL3 region of the variable region of the light chain sequence. According to the invention, this library can contain a plurality of antibody sequences, wherein the sequence diversity is primarily in the CDRH3 region of the heavy chain sequence.

In one aspect, the library is created in the context of the humanized antibody 4D5 sequence, or the sequence of the framework amino acids of the humanized antibody 4D5 sequence. In certain embodiments, the library is created by substitution of at least residues 28 and 30-33 of CDRH1, residues 50, 52-54, 56, and 58 of CDRH2, residues 95, 96, 97, 98, 99, 100, 100a, 100b, and 100c of CDRH3, and residues 91-94 and 96 of CDRL3 with the amino acids set forth as shown in FIG. 8 for the "YSGR-A" library. In certain embodiments, the library is created by substitution of at least residues 28 and 30-33 of CDRH1, residues 50, 52-54, 56, and 58 of CDRH2, residues 95, 96, 97, 98, 99, 100, 100a, 100b, and 100c of CDRH3, and residues 91-94 and 96 of CDRL3 with the amino acids set forth as shown in FIG. 8 for the "YSGR-B" library. In certain embodiments, the library is created by substitution of at least residues 28 and 30-33 of CDRH1, residues 50, 52-54, 56, and 58 of CDRH2, residues 95, 96, 97, 98, 99, 100, 100a, 100b, and 100c of CDRH3, and residues 91-94 and 96 of CDRL3 with the amino acids set forth as shown in FIG. 8 for the "YSGR-C" library. In certain embodiments, the library is created by substitution of at least residues 28 and 30-33 of CDRH1, residues 50, 52-54, 56, and 58 of CDRH2, residues 95, 96, 97, 98, 99, 100, 100a, 100b, and 100c of CDRH3, and residues 91-94 and 96 of CDRL3 with the amino acids set forth as shown in FIG. 8 for the "YSGR-D" library. The amino acid positions of 100b and 100c may have a different alphabetical identifier depending on the length of the CDRH3, but these positions are the last two CDRH3 positions before position 101. Examples of suitable oligonucleotide sequences include, but are not limited to, those listed in FIGS. 9A-D and can be determined by one skilled in the art according to the criteria described herein.

In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19A for the "SAH3" library. In certain embodiments, the library is created by substitution of at least residues 28 and 30-33 of CDRL3, residues 50, 52, 53, 54, 56, and 58 of CDRH2, residues 95-100m of CDRH3, and residues 91-94 and 96 of CDRL3 with the amino acids set forth as shown in FIG. 19A for the "SCH3" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19A for the "SFH3" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19A for the "SGH3" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19A for the "SIH3" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19A for the "SLH3" library. As the length of CDRH3 varies, the last two positions before position 101 may have different alphabetical identifier depending on the length of the CDRH3, but these positions are the last two CDRH3 positions before position 101. Examples of suitable oligonucleotide sequences include, but are not limited to, those listed in FIGS. 20A-20L, and can be determined by one skilled in the art according to the criteria described herein.

In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19B for the "SNH3" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19B for the "SPH3" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19B for the "SRH3" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19B for the "STH3" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19B for the "SWH3" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 19B for the "SYH3" library. As the length of CDRH3 varies, the last two positions before position 101 may have different alphabetical identifier depending on the length of the CDRH3, but these positions are the last two CDRH3 positions before position 101. Examples of suitable oligonucleotide sequences include, but are not limited to, those listed in FIGS. 20A-20L, and can be determined by one skilled in the art according to the criteria described herein.

In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 22 for the "SY" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 22 for the "SW" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 22 for the "SR" library. In certain embodiments, the library is created by substitution of at least residues 28 and 30-33 of CDRH1, residues 50, 52, 53, 54, 56, and 58 of CDRH2, residues 95-100m of CDRH3, and residues 91-94 and 96 of CDRL3 with the amino acids set forth as shown in FIG. 22 for the "SF" library. As the length of CDRH3 varies, the last two positions before position 101 may have different alphabetical identifier depending on the length of the CDRH3, but these positions are the last two CDRH3 positions before position 101. Examples of suitable oligonucleotide sequences include, but are not limited to, those listed in FIG. 23, and can be determined by one skilled in the art according to the criteria described herein.

In certain embodiments, a library is created by pooling other libraries. In one embodiment, the "SXH3" library as used herein comprises the SAH3, SCH3, SFH3, SGH3, SIH3, SLH3, SNH3, SPH3, SRH3, STH3, SWH3, and SYH3 libraries. In another embodiment, the "SX-surface" library comprises the "SY", "SW", "SR", and "SF" libraries.

In another embodiment, different CDRH3 designs are utilized to isolate high affinity binders and to isolate binders for a variety of epitopes. For diversity in CDRH3, multiple libraries can be constructed separately with different lengths of H3 and then combined to select for binders to target antigens. The range of lengths of CDRH3 generated in this library can be 10-21, 11-21, 12-21, 13-21, 14-21, 15-21, 16-21, 17-21, 18-21, 19-21, 20-21, amino acids, although lengths different from this can also be generated. Diversity can also be generated in CDRH1 and CDRH2, as indicated above. In one embodiment of a library, diversity in H1 and H2 is generated utilizing the oligonucleotides illustrated in FIGS. 9A-D, 20A-L, and FIG. 23. Other oligonucleotides with varying sequences can also be used. Oligonucleotides can be used singly or pooled in any of a variety of combinations depending on practical needs and desires of the practitioner. In some embodiments, randomized positions in heavy chain CDRs include those listed in FIGS. 8, 9, 11, 15, 19, 21, 22, 23, and 24.

Multiple libraries can be pooled and sorted using solid support selection and solution sorting methods as described herein. Multiple sorting strategies may be employed. For example, one variation involves sorting on target bound to a solid, followed by sorting for a tag that may be present on the fusion polypeptide (e.g. anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

Of the binders isolated from the pooled libraries as described above, it has been discovered that in some instances affinity may be further improved by providing limited diversity in the light chain. Light chain diversity may be, but is not necessarily, generated by diversifying amino acid positions 91-96 in CDRL3 or a subset thereof. In one embodiment, the randomized positions are those listed in FIGS. 8, 9, 11, 15, 19, 21, 22, 23, and 24.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield. Any combination of codon sets and CDRs can be diversified according to methods of the invention.

Vectors, Host Cells and Recombinant Methods

For recombinant production of an antibody polypeptide of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of either prokaryotic or eukaryotic (generally mammalian) origin.

Generating Antibodies Using Prokaryotic Host Cells:
Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene,* 159:203 (1995).

The present invention provides an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

In certain embodiments, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marces-* cans, *Klebsiella, Proteus, Shigella, Rhizobia, Vitreoscilla,* or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nnpc-fepE) degP41 kan$^R$ (U.S. Pat. No. 5,639,635). Other strains and derivatives thereof, such as *E. coli* 294 (ATCC 31,446), *E. coli* B, *E. coli*$_\lambda$ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the temperature ranges from about 20° C. to about 39° C., from about 25° C. to about 37° C., and/or about 30° C. may be used. The pH of the medium may be any pH ranging from about 5 to about 9, depending mainly on the host organism. For *E. coli,* the pH can be about 6.8 to about 7.4, and can be about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. The phosphate-limiting medium can be C.R.A.P medium (see, e.g., Simmons et al., *J. Immunol. Methods* (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant can be filtered and concentrated for further purification of the produced proteins. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity; in certain embodiments, the large-scale fermentors have about 1,000 to 100,000 liters of capacity. These fermentors use agitator impellers to distribute oxygen and nutrients, especially glucose (a common carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction times may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41kD cell wall protein from *Staphylococcus aureas* which binds with a high affinity to the Fc region of antibodies. Lindmark et al (1983) *J. Immunol. Meth.* 62:1-13. In certain embodiments, the solid phase to which Protein A is immobilized is a column comprising a glass or silica surface. In certain embodiments, the solid phase to which Protein A is immobilized is a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

Generating Antibodies Using, Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. In certain embodiments, the heterologous signal sequence selected is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II (e.g., primate metallothionein genes), adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO:585) region where N may be any nucleotide. At the 3' end of most eukaryotic genes is an AATAAA (SEQ ID NO:586) sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601

(1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody polypeptide-encoding sequence. In certain embodiments, the enhancer is located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5. In certain embodiments, the low pH hydrophobic interaction chromatography is performed at low salt concentrations (e.g., from about 0-0.25M salt).

Activity Assays

The antibodies of the present invention can be characterized for their physical/chemical properties and biological functions by various assays known in the art.

The purified immunoglobulins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments, the immunoglobulins produced herein are analyzed for their biological activity. In some embodiments, the immunoglobulins of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays.

The antibodies or antigen binding fragments can be further selected for functional activity, for example, antagonist or agonist activity. For example, anti-HER-2 antibodies can be selected for the ability to inhibit tyrosine phosphorylation of HER-2, inhibit proliferation of cancer cells or to induce apoptosis of cancer cells. Assays for identifying and measuring these activities are described for example in WO98/17797.

In addition, anti-DR5 antibodies can be selected for the ability to induce apoptosis of cancer cells and/or inhibit the function of inflammatory cells. In other embodiments, anti-DR5 antibodies are selected for the ability to compete with Apo-2L for binding to DR5. In yet other embodiments, anti-human DR5 antibodies are selected for binding to murine and/or cynomolgous DR5. Assays for determining biological activity can be conducted using methods known in the art, such as DNA fragmentation (see, e.g., Marsters et al., Curr. Biology, 6: 1669 (1996)), caspase inactivation, DR5 binding (see, e.g., WO 98/51793, published Nov. 19, 1998. Apoptosis can be measured by identifying condensation of cytoplasm, loss of plasma membrane microvilli, segmentation of the nucleus, degradation of chromosomal DNA or loss of mitochondria 1 function. This activity can be determined and measured, for instance, by cell viability assays (such as Alamar blue assays or MTT assays), FACS analysis, caspase activation, DNA fragmentation (see, for example, Nicoletti et al., J. Immunol. Methods, -139:271-279 (1991), and poly-ADP ribose polymerase, "PARP", cleavage assays known in the art.

In one embodiment, as assay for apoptosis involves making two fold serial dilutions of control standard and an anti-DR5 antibody in 96-well tissue culture plates. 5 Apo-2 ligand (amino acids 114-281, described in PCT US00/17579) is tested for comparison. Colo-205 (20000 cells~well) human colon carcinoma cells (ATCC) are seeded into the 96-well plates. The plates are incubated at 37 for 24 hours. AlamazBlue (Trek Diagnostic Systems, Inc.) is added to the wells for the last 3 hours of the 24 hours incubation time. Fluorescence is read using a 96-well fluorometer with excitation at 530 nm and emission of 590 nm. The results are expressed in relative fluorescence units (RFU).

In one embodiment, the present invention contemplates an altered antibody that possesses some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, for example as described in Gazzano-Santoro et al., J Immunol. Methods 202:163 (1996), may be performed. FcRn binding and in vivo clearance/half life determinations can also be performed using methods known in the art, e.g., those described in the Examples section.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901). Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623).

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody Variants

In one aspect, the invention provides antibody fragments comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

To increase the half-life of the antibodies or polypeptide containing the amino acid sequences of this invention, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence of this invention so that the fusion protein expressed by the engineered nucleic acid molecule comprises the salvage receptor binding epitope and a polypeptide sequence of this invention. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule (e.g., Ghetie, V et al., (2000) Ann. Rev. Immunol. 18:739-766, Table 1). Antibodies with substitutions in an Fc region thereof and increased serum half-lives are also described in WO00/42072 (Presta, L.), WO 02/060919; Shields, R. L., et al., (2001) JBC 276(9):6591-6604; Hinton, P. R., (2004) JBC 279(8):6213-6216). In another embodiment, the serum half-life can also be increased, for example, by attaching other polypeptide sequences. For example, antibodies of this invention or other polypeptide containing the amino acid sequences of this invention can be attached to serum albumin or a portion of serum albumin that binds to the FcRn receptor or a serum albumin binding peptide so that serum albumin binds to the antibody or polypeptide, e.g., such polypeptide sequences are disclosed in WO01/45746. In one embodiment, the serum albumin peptide to be attached comprises an amino acid sequence of DICLPRWGCLW (SEQ ID NO:608). In another embodiment, the half-life of a Fab according to this invention is increased by these methods. See also, Dennis, M. S., et al., (2002) JBC 277(38):35035-35043 for serum albumin binding peptide sequences.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions" in the table below, or as further described below in reference to amino acid classes, may be introduced and the products screened.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |

-continued

| Original Residue | Exemplary Substitutions | Preferred Substitutions |
|---|---|---|
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (1), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody used in methods of the invention may comprise one or more alterations as compared to the wild type counterpart antibody, for example in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), for example, as described in WO99/51642. See also Duncan & Winter Nature 322:738-40 (1988); U.S. Pat. No. 5,648,260; U.S. Pat. No. 5,624,821; and WO94/29351 concerning other examples of Fc region variants.

Immunoconjugates

The invention also pertains to immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (eds.), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19): 1573-1581; Mandler et al (2000) Bioorganic & Med. Chem. Letters 10: 1025-1028; Mandler et al. (2002) Bioconjugate Chem. 13:786-791), maytansinoids (EP 1391213; Liu et al., (1996) Proc. Natl. Acad. Sci. USA 93:8618-8623), and calicheamicin (Lode et al. (1998) Cancer Res. 58:2928; Hinman et al. (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al. (2000) Eur. Jour. Nucl. Med. 27(7):766-77; Wiseman et al. (2002) Blood 99(12):4336-42; Witzig et al. (2002) J. Clin. Oncol. 20(10):2453-63; Witzig et al. (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al. (2003) Nature Biotechnology 21(7):778-784) and are under therapeutic development.

Chemotherapeutic agents useful in the generation of such immunoconjugates have been described above. Enzymatically active toxins and fragments thereof that can be used include without limitation diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SDPP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothecene, and CC1065, and the derivatives of these toxins that have toxin activity, are also contemplated herein.

Maytansine and Maytansinoids

In one embodiment, an antibody (full length or fragments) of the invention is conjugated to one or more maytansinoid molecules.

Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-Maytansinoid Conjugates (Immunoconjugates)

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. In certain embodiments, maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl) cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In certain embodiments, coupling agents include N-succinimidyl-3-(2-pyridyldithio)propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In one embodiment, the linkage is formed at the C-3 position of maytansinol or a maytansinol analogue.

Calicheamicin

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^1$, $\alpha_2^1$, $\alpha_3^1$, N-acetyl-$\gamma_1^1$, PSAG and $\theta_1^1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tC^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al. (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl) cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

$$Ab\text{-}(L\text{-}D)_p \qquad\qquad I$$

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody drug conjugates of the invention may also be produced by modification of the antibody to introduce electrophilic moieties, which can react with nucleophilic substitutents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, *Bioconjugate Techniques*). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Antibody Derivatives

The antibodies of the present invention can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Pharmaceutical Formulations

Therapeutic formulations comprising an antibody of the invention are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine;

monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated. In certain such embodiments, the compounds have complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished, e.g., by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used in, for example, in vitro, ex vivo and in vivo therapeutic methods. Antibodies of the invention can be used as an antagonist to partially or fully block the specific antigen activity in vitro, ex vivo and/or in vivo. Moreover, at least some of the antibodies of the invention can neutralize antigen activity from other species. Accordingly, the antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, the antibody of the invention can be used for inhibiting antigen activities by contacting the antibody with the antigen such that antigen activity is inhibited. In certain embodiments, the antigen is a human protein molecule.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. In certain embodiments, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the immunoglobulin cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

Blocking or antagonist antibodies of the invention that are therapeutically useful include, for example but are not limited to, anti-HER-2 antibodies. For example, the anti-HER-2 antibodies of the invention can be used to treat, inhibit, delay progression of, prevent/delay recurrence of, ameliorate, or prevent diseases, disorders or conditions associated with abnormal expression and/or activity of one or more antigen molecules, including but not limited to malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders In one aspect, a blocking antibody of the invention is specific to a ligand antigen, and inhibits the antigen activity by blocking or interfering with the ligand-receptor interaction involving the ligand antigen, thereby inhibiting the corresponding signal pathway and other molecular or cellular events. The invention also features receptor-specific antibodies which do not necessarily prevent ligand binding but interfere with receptor activation, thereby inhibiting any responses that would normally be initiated by the ligand binding. In certain embodiments, the invention also encompasses antibodies that either preferably or exclusively bind to ligand-receptor complexes. An antibody of the invention can also act as an agonist of a particular antigen receptor, thereby potentiating, enhancing or activating either all or partial activities of the ligand-mediated receptor activation.

HER-2 associated disorders or conditions and diagnostic assays are described in U.S. Pat. No. 6,387,371, which is hereby incorporated by reference. See also WO98/17797. Administration to a patient of a therapeutically effective amount of anti-HER-2 receptor antibodies inhibit tumor cell growth and are useful for treating cancer. Trastuzumab (Genentech, Inc.) is a recombinant humanized monoclonal antibody directed at the HER-2 extracellular domain for the treatment of HER-2 over-expressed/HER-2 gene amplified cancer, particularly metastatic breast cancer (MBC). Such antibodies are useful in the treatment of other cancers especially those which over express HER-2. The antibody can also be administered to patients in combination with other therapeutics, e.g., paclitaxel or Tarceva®.

In some embodiments, an anti-DR5 antibody induces apoptosis of cancer cells. In some embodiments, the anti-DR5 antibody is an agonist of DR5. In other embodiments, the antibody competes for binding to DR5 with Apo-2L.

As noted above, DR5 antibodies of the invention have various utilities. For example, DR5 agonistic antibodies may be employed in methods for treating pathological conditions in mammals such as cancer or immune-related diseases. Immune related conditions include rheumatoid arthritis, systemic lupus erythematosis, scleroderma, idiopathic inflammatory myopathies, sjogrens syndrome, systemic vasculitis, sarcoidosis, autoimmune hemolytic anemias, thyroiditis, immune related renal disease such as glomerulonephritis, demyelinating disease such as multiple sclerosis, autoimmune skin diseases such as psoriasis, inflammatory and filtration lung disease, and allergic disease such as asthma.

Diagnosis in mammals of the various pathological conditions described herein can be made by the skilled practitioner. Diagnostic techniques are available in the art which allow, e.g., for the diagnosis or detection of cancer or immune related disease in a mammal. For instance, cancers may be identified through techniques, including but not limited to, palpation, blood analysis, x-ray, NMR and the like. Immune related diseases can also be readily identified. For example, in systemic lupus erythematosus, the central mediator of disease is the production of auto-reactive antibodies to self proteins/tissues and the subsequent generation of immune-mediated inflammation. Multiple organs and systems are affected clinically including kidney, lung, musculoskeletal system, mucocutaneous, eye, central nervous system, cardiovascular system, gastrointestinal tract, bone marrow and blood. Medical practitioners are familiar with a number diseases in which intervention of the immune and/or inflammatory response have benefit.

In certain embodiments, an immunoconjugate comprising an antibody conjugated with a cytotoxic agent is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, chemotherapeutic agent(s) (including cocktails of chemotherapeutic agents), other cytotoxic agent(s), anti-angiogenic agent(s), cytokines, and/or growth inhibitory agent(s). Where an antibody of the invention inhibits tumor growth, it may be particularly desirable to combine it with one or more other therapeutic agent(s) which also inhibits tumor growth. For instance, an antibody of the invention may be combined with an anti-VEGF antibody (e.g., AVASTIN) and/or anti-ErbB antibodies (e.g. HERCEPTIN™ anti-HER-2 antibody) in a treatment scheme, e.g. in treating any of the diseases described herein, including colorectal cancer, metastatic breast cancer and kidney cancer. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody of the invention can occur prior to, and/or following, administration of the adjunct therapy or therapies.

The antibody of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, for example by injections, such as intravenous or subcutaneous injections, depending in part on whether the administration is brief or chronic.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody is an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein, wherein the composition comprises a further cytotoxic agent. The article of manufacture in this embodiment of the invention may further comprise a package insert indicating that the first and second antibody compositions can be used to treat a particular condition, for example cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Having generally described the invention, the same will be more readily understood by reference to the following examples, which are provided by way of illustration and are not intended as limiting.

EXAMPLE 1

Figure 5:
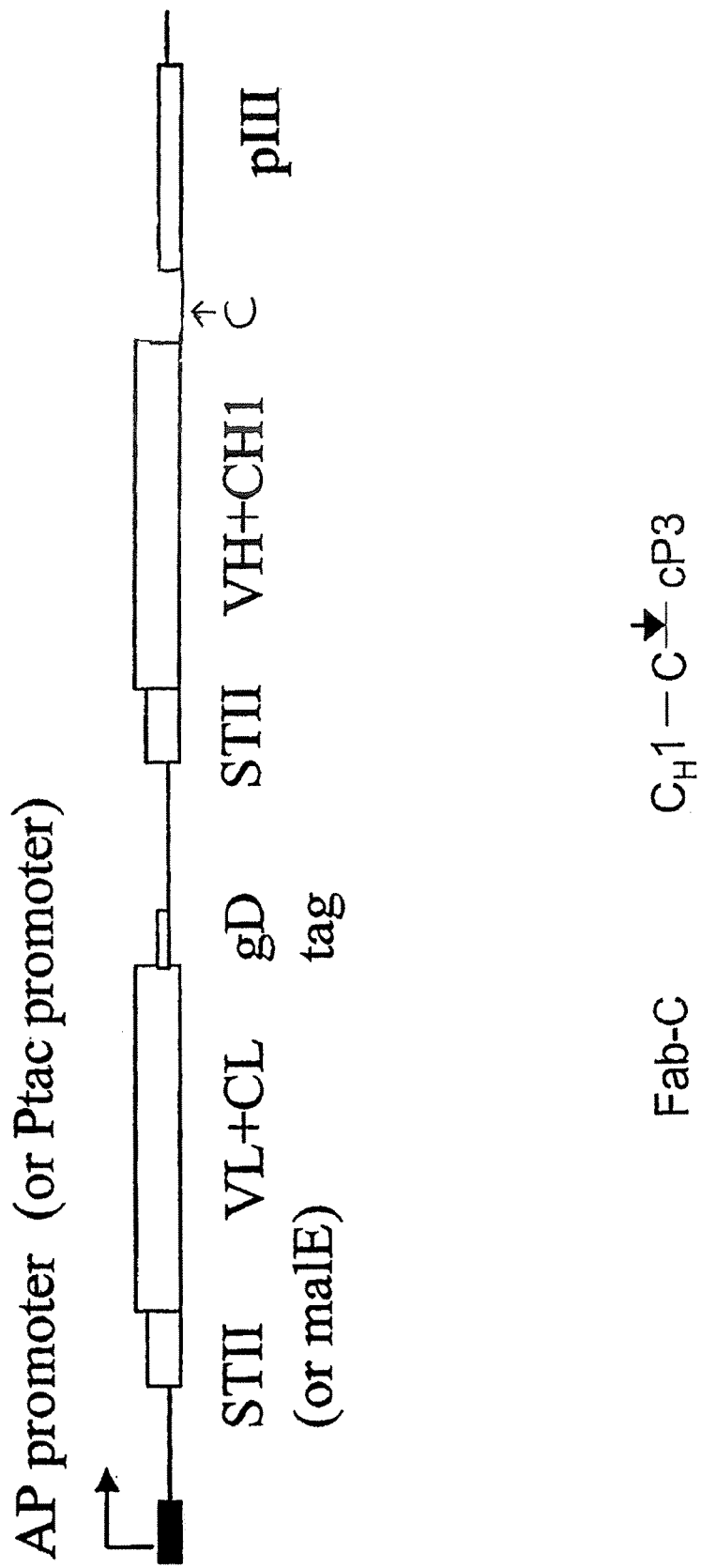
FIG. 5 schematically illustrates a bicistronic vector allowing expression of separate transcripts for display of F(ab)$_2$. A suitable promoter drives expression of the first and second cistron. The first cistron encodes a secretion signal sequence (malE or stII), a light chain variable and constant domain and a gD tag. The second cistron encodes a secretion signal, a sequence encoding heavy chain variable domain and constant domain 1 (CH1) and cysteine dimerization domain and at least a portion of the viral coat protein.

Construction of Phage-Displayed Fab Libraries with CDR Residues Enriched in Tyr, Ser, Gly, and Arg Phage-displayed Fab libraries were constructed using a phagemid vector, Fab-C, that resulted in the display of bivalent Fab moieties dimerized by a free cysteine inserted between the Fab heavy chain and the C-terminal domain of the gene-3 minor coat protein (P3C). This vector was constructed as described in U.S. Patent Application Publication No. US20050119455 and in Lee et al., J. Immunol. Meth. 284: 119-132 (2004). The vector (schematically illustrated in FIG. 5) comprises humanized antibody 4D5 variable domains under the control of the IPTG-inducible Ptac promoter. Humanized antibody 4D5 has mostly human consensus sequence framework regions in the heavy and light chains, and CDR regions from a mouse monoclonal antibody specific for HER-2. Methods of making the anti-HER-2 antibody and the identity of the variable domain sequences are provided in U.S. Pat. Nos. 5,821,337 and 6,054,297.

Four libraries were constructed: YSGR-A, YSGR-B, YSGR-C, and YSGR-D. The libraries were constructed with randomized residues in all three heavy chain CDRs and light chain CDR3. Each library was randomized at positions 91-94 and 96 of CDRL3, positions 28 and 30-33 of CDRH1, positions 50, 52-54, 56, and 58 of CDRH2, and positions 95-100, 100a, 100b, and 100c of CDRH3. The type and ratio of the amino acids allowed at each of the randomized positions is described in FIG. 8. In addition, the length of CDRH3 was varied by using oligonucleotides that replaced the seven wild-type codons from positions 95 to 100a with six to seventeen codons. Thus, in certain instances, the codon corresponding to position 100a of the heavy chain was not present (for example, when the mutagenesis was performed with mutagenic oligonucleotides H3-A6 (SEQ ID NO:35), H3-B6 (SEQ ID NO:47), H3-C6 (SEQ ID NO:59) or H3-D6 (SEQ ID NO:71), as described below. See FIG. 9A-D The type and ratio of the amino acids allowed at those positions were the same as the ones described in FIG. 8 for positions 95-100a of CDRH3.

Libraries were constructed using the method of Kunkel (Kunkel, T. A., Roberts, J. D. & Zakour, R. A., Methods Enzymol. (1987), 154, 367-382) with previously described methods (Sidhu, S. S., Lowman, H. B., Cunningham, B. C. & Wells, J. A., Methods Enzymol. (2000), 328, 333-363). A unique "stop template" version of the Fab display vector Fab-C was used to generate all four libraries, as described in Example 1.

Mutagenic oligonucleotides with degenerate codons at the positions to be diversified were used to simultaneously (a) introduce CDR diversity and (b) repair the stop codons. The sequences of those mutagenic oligonucleotides are shown in FIGS. 9A-9D. For all libraries, diversity was introduced into CDR-H1, CDR-H2, and CDR-H3 with oligonucleotides H1, H2 and L3, respectively (SEQ ID NOs:). For library YSGR-A, diversity was introduced into CDR-H3 with an equimolar mixture of oligonucleotides H3-A6, H3-A7, H3-A8, H3-A9, H3-A10, H3-A11, H3-A12, H3-A13, H3-A14, H3-A15, H3-A16, and H3-A17 (SEQ ID NOs:35-46). For library YSGR-B, diversity was introduced into CDR-H3 with an equimolar mixture of oligonucleotides H3-B6, H3-B7, H3-B8, H3-B9, H3-B10, H3-B11, H3-B12, H3-B13, H3-B14, H3-B15, H3-B16, and H3-B17 (SEQ ID NOs:47-58). For library YSGR-C, diversity was introduced into CDR-H3 with an equimolar mixture of oligonucleotides H3-C6, H3-C7, H3-C8, H3-C9, H3-C10, H3-C11, H3-C12, H3-C13, H3-C14, H3-C15, H3-C16, and H3-C17 (SEQ ID NOs:59-70). For library YSGR-D, diversity was introduced into CDR-H3 with an equimolar mixture of oligonucleotides H3-D6, H3-D7, H3-D8, H3-D9, H3-D10, H3-D11, H3-D12, H3-D13, H3-D14, H3-D15, H3-D16, and H3-D17 (SEQ ID NOs:71-82). Each of mutagenic oligonucleotides H3-A6 to H3-A17 (SEQ ID NOs:35-46), H3-B6 to H3-B17 (SEQ ID NOs:47-58), H3-C6 to H3-C17 (SEQ ID NOs:59-70) and H3-D6 to H3-D17 (SEQ ID NOs:71-82) encoded an alanine at position 93 of the heavy chain. The mutagenic oligonucleotides for all CDRs to be randomized were incorporated simultaneously in a single mutagenesis reaction, so that simultaneous incorporation of all the mutagenic oligonucleotides resulted in the introduction of the designed diversity at each position and simultaneously repaired all the TAA stop codons. Thus, an open reading frame was generated that encoded a Fab library member fused to a homodimerizing cysteine bridge and P3C. Following mutagenesis, the four libraries were combined to create a single library, called library YSGR-A-D.

The mutagenesis reactions were electroporated into E. coli SS320 (Sidhu et al., supra). The transformed cells were grown overnight in the presence of M13-KO7 helper phage (New England Biolabs, Beverly, Mass.) to produce phage particles that encapsulated the phagemid DNA and displayed Fab fragments on their surfaces. The combined library contained greater than $3\times10^{10}$ unique members.

EXAMPLE 2

Selection of Specific Antibodies from Naïve Library YSGR-A-D

Phage from library YSGR-A-D (described in Example 1, above) were cycled through rounds of binding selection to enrich for clones binding to human DR5 or HER-2. The binding selections were conducted using previously described methods (Sidhu et al., supra).

A human DR5 sequence is shown in Table 1. An extracellular domain of DR5 as shown in Table 1 was utilized in the binding selection. Likewise, an extracellular domain of a human HER-2 sequence is prepared as described in Franklin M C. Carey K D. Vajdos F F. Leahy D J. de Vos A M. Sliwkowski M X. Insights into ErbB signaling from the structure of the ErbB2-pertuzumab complex. Cancer Cell. 5(4): 317-28, 2004. A sequence for human HER-2 ECD (amino acids 23-646) is provided at the Protein DataBank Record 1S78 (2004).

NUNC 96-well Maxisorp immunoplates were coated overnight at 4° C. with 5 µg/mL target protein (human DR5 or human HER-2) and blocked for 2 hours with a solution of PBT (phosphate buffered saline additionally containing 0.2% BSA and 0.05% Tween 20 (Sigma)). After overnight growth at 37° C., phage were concentrated by precipitation with PEG/NaCl and resuspended in PBT, as described previously (Sidhu et al., supra). Phage solutions (about $10^{12}$ phage/mL) were added to the coated immunoplates. Following a two hour incubation to permit phage binding, the plates were washed ten times with PBT. Bound phage were eluted with 0.1 M HCl for ten minutes and the eluant was neutralized with 1.0 M Tris base. Eluted phage were amplified in E. coli XL1-blue and used for further rounds of selection.

The libraries were subjected to five rounds of selection against each target protein. Individual clones from each round of selection were grown in a 96-well format in 500 µL of 2YT broth supplemented with carbenicillin and M13-K07. The culture supernatants were used directly in phage ELISAs (Sidhu et al., supra) to detect phage-displayed Fabs that bound to plates coated with target protein but not to plates coated with BSA. Specific binders were defined as those phage clones that exhibited an ELISA signal at least 10-fold greater on target-coated plates in comparison with BSA-coated plates. Individual clones were screened after 4 and 5 rounds of selection for binding to human DR5 or human HER-2. The specific binders were subjected to sequence analysis. Specific binders were also analyzed using spot affinity ELISA, specificity ELISA, specificity ELISA, and affinity for HER2 using methods as described herein. (See FIG. 11B.) As shown in FIG. 10, the YSGR-A-D library produced specific binders against both target proteins.

Figure 11A:
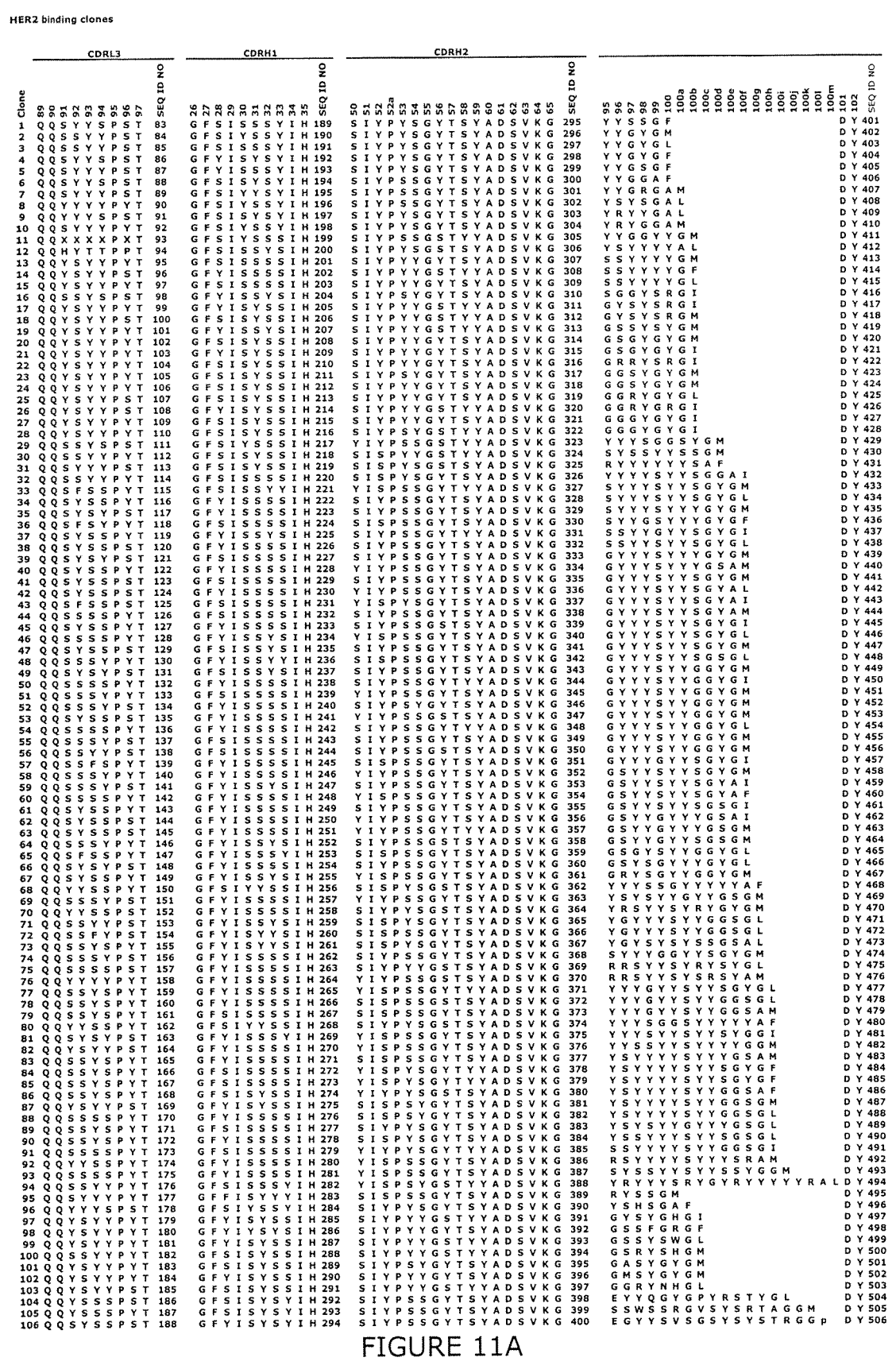

Of the 240 clones identified that specifically bound to human HER-2, 106 of them had unique CDR sequences (see FIG. 11). The unique sequences fell into 3 categories: 1) 6-7 residue CDRH3 sequences; 2) eight residue CDRH3 sequences; and 3) medium length CDR sequences with tyrosine, serine and glycine in the sequence.

The anti-HER-2 heavy chain variable domains show a preference for short CDRH3 (e.g. 6-7 amino acids in positions corresponding to 95 to 100a) sequences not included in the oligo library. (See FIG. 12). The CDRH3 shows a conserved tyrosine residue at the N terminal end in position 95. The other conserved position is found at position 99 which is predominantly a glycine. Consensus sequences are shown for CDRL3: QQSYYX4PST (SEQ ID NO:587); CDRH1: GFSIX2X3SYIH (SEQ ID NO:588); and CDRH2: SIYPX3SGYTSYADSKVG (SEQ ID NO:589), where X represents an amino acid position for which a consensus residue was not identified and wherein X positions in each CDR are Y or S.

The heavy chain variable domains having CDRH3 with eight amino acids have conserved glycines at the N and C terminal ends of CDRH3 (at positions 95 and 100a). Position 98 is also conserved with a tyrosine. Position 99 of an eight amino acid CDRH3 shows a preference for a small amino acid such as G, S, A, or T. This position is followed by a large amino acid at position 100, such as R, H, Y, and W. Consensus sequences are shown for CDRH1:GFX1ISYSSIH (SEQ ID NO:590); and CDRH2:SIYPX3YGX5TX6YADSKVG (SEQ ID NO:591), where X represents an amino acid position for which a consensus residue was not identified and is Y or S.

Analysis of the heavy chain variable domains with medium length (e.g. about 12 to 14 amino acids) CDRH3 regions provides a CDRH3 consensus sequence X1X2X3X4YYSYYX10GX12X13X14DY (SEQ ID NO:592), where X represents an amino acid position for which a consensus residue was not identified, wherein X1 is selected from Y, S and R; X2 is selected from Y and S; X3 is selected from G, Y and S; X4 is selected from Y, S, R and G; X10 is selected from Y, S and G; X12 is selected from Y, S, G and R; X13 is selected from G and A; and X14 is selected from I, F, F and L. (See FIG. 14). As the CDRH3 forms a loop, the consensus for CDRH3 was developed by shifting the sequence for some clones over two amino acids so that position 95 of the sequence would align with position 97 of the reference sequence which in this case was the sequence of clone 52. Consensus sequences are also shown for CDRH1: GFX1ISSSSIH(SEQ ID NO:593); and CDRH2: X1IX2PSSGYTX6YADSKVG (SEQ ID NO:594), where X represents an amino acid position for which a consensus residue was not identified and is Y or S.

As described in FIG. 11B, several of the clones bound to HER2 with between 0.1 to 10 nm $IC_{50}$. For the most part, these high affinity binders had little or no cross reactivity with other antigens, such as VEGF, DR5, insulin, neutravidin, human growth hormone, human or IGF-1

As shown in FIG. 10, 144 clones were identified that expressed Fabs that were specific binders for human DR5. Sequence analysis identified 18 unique amino acid sequences from those 144 clones, shown in FIG. 15.

The $IC_{50}$ of each of these binders were determined by competitive phage ELISA, as follows. NUNC 96-well Maxisorp immunoplates were coated overnight at 4° C. with hDR5-ECD (5 ug/ml) and blocked with BSA. Phage displaying Fabs were propagated in E. coli XL1-blue with the addition of M13-KO7 helper phage. After overnight growth at 37° C. in 2YT media, phage were concentrated by precipitation with PEG/NaCl and resuspended in phosphate-buffered saline (PBS), 0.5% (w/v) BSA, 0.1% (v/v) Tween 20 (PBT buffer). Phage were serially diluted in PBT buffer and binding was measured to determine a phage concentration giving ~50% of the signal at saturation. A fixed, subsaturating concentration of phage was preincubated for 2 h with serial dilutions of hDR5-ECD and then transferred to assay plates coated with hDR5-ECD. After 15 min incubation, the plates were washed with PBS, 0.05% Tween 20 and incubated 30 min with horseradish peroxidase/anti-M13 antibody conjugate (1:5000 dilution in PBT buffer). The plates were washed, developed with TMB substrate, quenched with 1.0 M $H_3PO_4$, and read spectrophotometrically at 450 nm. The binding affinities of the anti-hDR5 ligands were determined as $IC_{50}$ values defined as the concentration of hDR5-ECD that blocked 50% of the phage binding to the immobilized hDR5-ECD.

Figure 16:
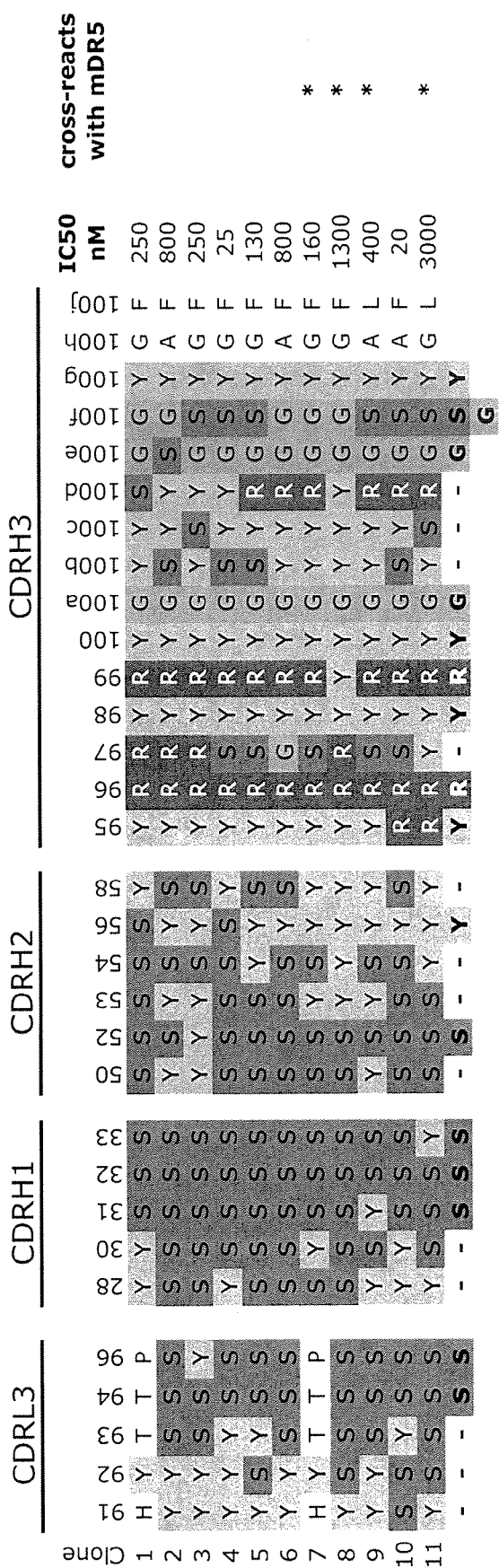
FIG. 16 shows the amino acid sequences for CDRL3, CDRH1, CDRH2, and CDRH3 from the specific binders to human DR5 isolated from the YSGR-A-D library, as described in Example 2. The $IC_{50}$ of the clones for binding to human DR5 are shown. Clones that crossreact with murine DR5 are also identified. Consensus sequences are shown for CDRL3, CDRH1, CDRH2, and CDRH3. (Clone numbers 1-11 correspond to clone numbers 10, 11, 12, 8, 7, 13, 5, 9, 6, 15 and 14 of FIG. 15.)

The clones were analyzed for binding to the extracellular domains of human DR5 (SEQ ID NO:595). The binders with the lowest $IC_{50}$ have predominantly serine in CDRH1 and arginine in CDRH3 at positions 96, and 99. Analysis of the heavy chain variable domains CDRH3 regions provides a CDRH3 consensus sequence YRX3YRYGX8X9X10GSYX14X15DY (SEQ ID NO:596), wherein X3 is selected from Y, S, R, P and G; X8 is selected from R, Y and S; X9 is selected from G and Y; X10 is selected from S, Y and R, X14 is selected from G and A; and X15 is selected from L and F, where X represents an amino acid position for which a consensus residue was not identified. (See FIG. 16). Consensus sequences are also shown for CDRL3:QQXIX2X3SPST (SEQ ID NO:597), wherein X1, X2 and X3 are Y or S; CDRH1:GFX1IX2SSSIH (SEQ ID NO:598); and CDRH2:X1ISPX3X4GYTX6YADSKVG (SEQ ID NO:599), where X represents an amino acid position for which a consensus residue was not identified and is Y or S. The consensus sequences may be utilized inter alia to form new libraries of antibody variable domains. In CDRH3, the amino acids in positions 97, 100b, 100c, 100h, and 100i may contribute to higher affinity.

Figure 17:
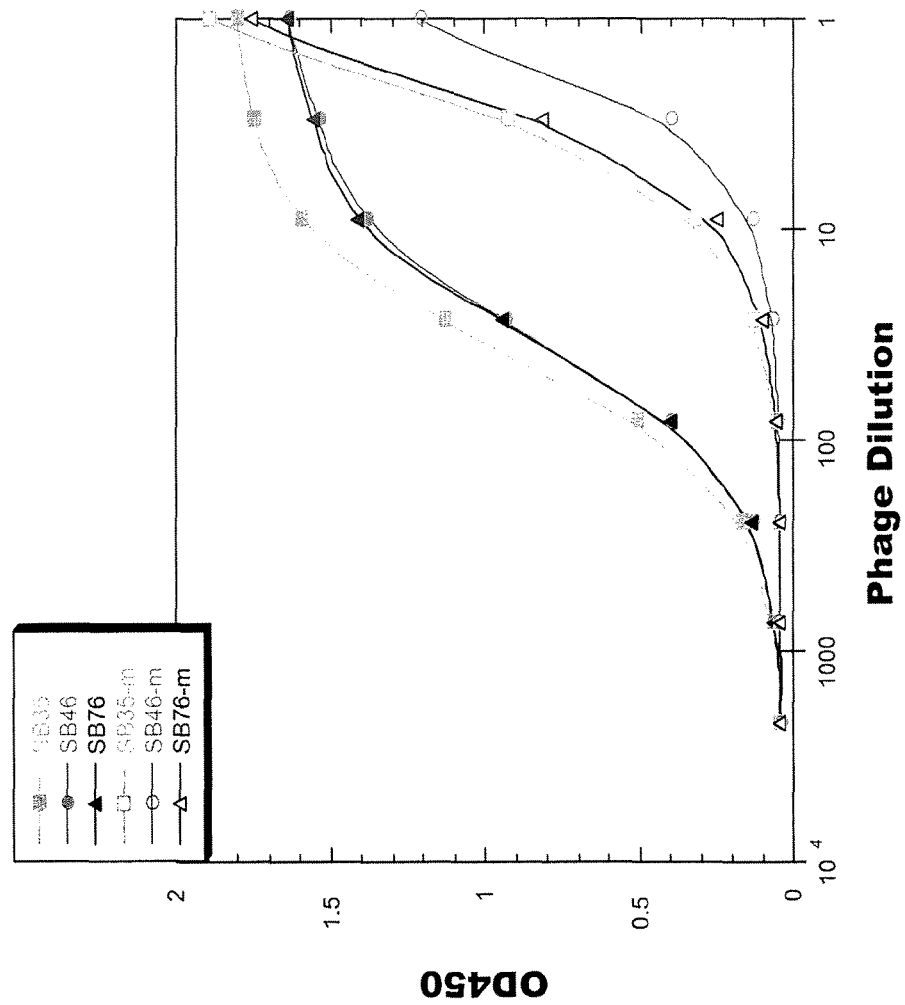
FIG. 17 shows the binding curves for specific binders for human DR5 isolated from the YSGR-A-D library. Some of the specific binders also bind to murine DR-5.

The clones were also analyzed for binding to murine DR5 using the competitive phage ELISA described above. Several clones were isolated from the YSGR A-D library that bound both human DR5 and murine DR5, although binding to murine DR5 was at much lower affinity. (See FIG. 17) This library provided for isolation of antibodies that can bind to both murine and human DR5 indicating that the binders identified were unique as compared to a total random CDRH3 (all twenty amino acids) and a YS CDRH3 library. Changing the diversity of amino acids allowed at each position may provide antibodies that bind to different epitopes and have unique biological functions. Anti-DR5 antibodies that bind to both murine and human CDRs may bind to different epitopes than those anti-DR5 antibodies from previously developed libraries.

EXAMPLE 3

Analysis of Binders to DR5

The binding site for the Apo 2L ligand to human DR5 has been previously mapped and the crystal structure for the binding site determined (See Hymowitz et al., Molecular Cell 4:564 (1999); WO01/19861). The crystal structure and models can be used to map the binding of anti-DR5 antibodies.

Figure 18:
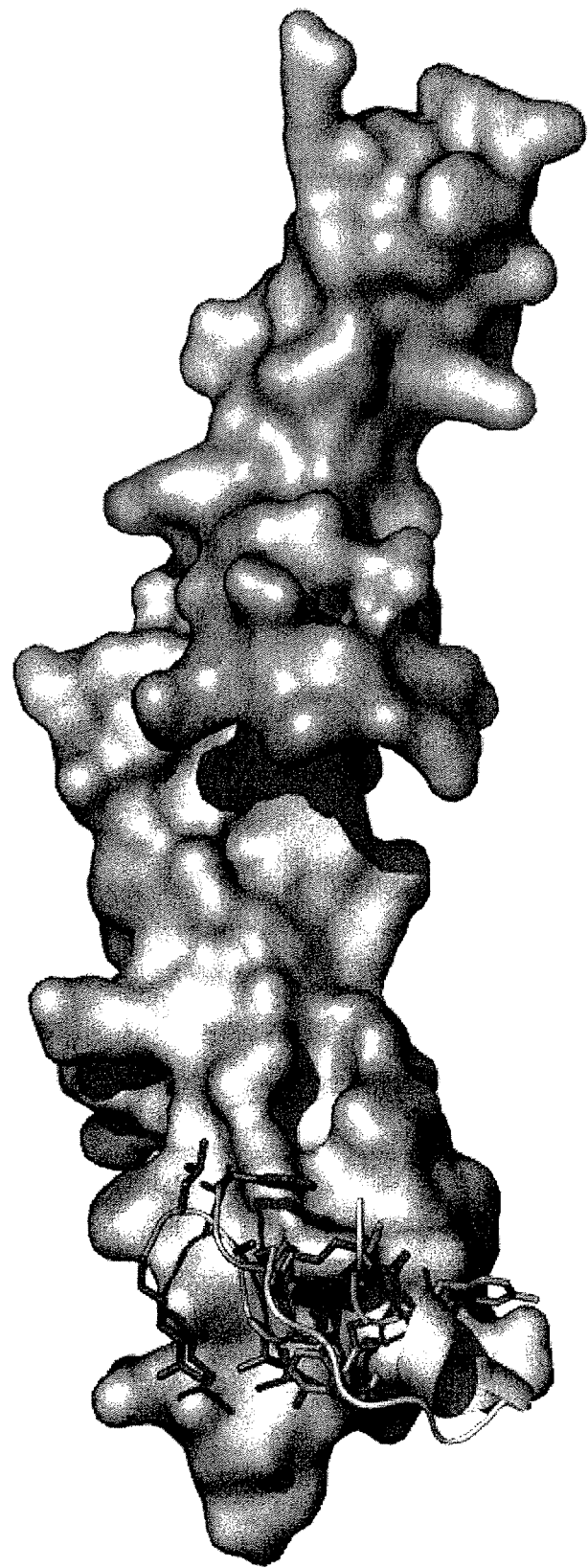
FIG. 18 shows a 3D model depicting where Apo-2L ligand, The YSD1 antibody, and BFD1 antibody bind to the DR5 receptor. The binding region of the antibodies overlap one another. The binding site of these antibodies is distinct from most of the residues of the binding site of the Apo-2L ligand.

Previous studies have identified antibodies that bind to human DR5. These antibodies are designated BDF1 and YSD1. The antibody BDF1 was isolated from a library in which CDRs were randomized with all 20 amino acids and has CDR sequences: 1) CDRH1 sequence of IGKSGIH (SEQ ID NO:600); 2) CDR2 a sequence of VAVIYPHDGNTAYA (SEQ ID NO:601); and 3) CDRH3 sequence of RLALVRM-WMD (SEQ ID NO:602). The YSD1 antibody was isolated from a library in which CDR positions were varied with tyrosine and serine and has a CDRH3 sequence of YSSYYSYYYSSSSYSY (SEQ ID NO:603). The binding site of these antibodies on human DR5 is located at the N terminus of the molecule and has little overlap with that of the Apo 2L, ligand, which is predominately found at the C terminus (amino acids of the 50s loop e.g. amino acids 50-65 and amino acids of 90s loop, e.g. amino acids 91 to 104 of DR5). A model showing the binding of the CDRH3 regions of each of these antibodies is shown in FIG. 18. The CDRH3 of BDF1 and YSD1 overlap and form a hot spot for binding to DR5. The binding of YSD1 CDRH3 is mediated by tyrosines and the binding of BFD1 is mediated by the LAL sequence. The binding of YSD 1 to DR5 involves DR5 leucine, glutamine, alanine, phenylalanine, and arginine residues.

EXAMPLE 4

Construction of Phage-Displayed Fab Libraries with CDRH1, H2, and L3 Residues Enriched in Tyr and Ser and CDRH3 residues enriched in Ser and Ala, Cys, Phe, Gly, Ile, Leu, Asn, Pro, Arg, Thr, Trp, or Tyr Phage-displayed Fab libraries were constructed using a phagemid vector, Fab-C, that resulted in the display of bivalent Fab moieties dimerized by a free cysteine inserted between the Fab heavy chain and the C-terminal domain of the gene-3 minor coat protein (P3C), as previously described in Example 1.

Twelve libraries were constructed: SAH3, SCH3, SFH3, SGH3, SLH3, SNH3, SPH3, SRH3, STH3, SWH3, and SYH3. The libraries were constructed with randomized residues in all three heavy chain CDRs and light chain CDR3. Each library was randomized at positions 91-94 and 96 of CDRL3, positions 28 and 30-33 of CDRH1, positions 50, 52-54, 56, and 58 of CDRH2, and positions 95-100, 100a to 100m of CDRH3. The type and ratio of the amino acids allowed at each of the randomized positions is described in FIGS. 19A-19B. In addition, the length of CDRH3 was varied by using oligonucleotides that replaced the six wild-type codons between positions 95 and 100 with 4 to 17 codons. The type and ratio of the amino acids allowed at those positions were the same as the ones described in FIGS. 19A-19B for positions 95-100 of CDRH3.

Libraries were constructed using the method of Kunkel (Kunkel et al., Methods Enzymol. (1987) 154: 367-382) with previously described methods (Sidhu et al., Methods Enzymol. (2000) 328: 333-363). A unique "stop template" version of the Fab display vector Fab-C was used to generate all four libraries, as described in Example 1.

Mutagenic oligonucleotides with degenerate codons at the positions to be diversified were used to simultaneously (a) introduce CDR diversity and (b) repair the stop codons. The sequences of those mutagenic oligonucleotides are shown in FIGS. 20A-20L. For all libraries, diversity was introduced into CDRH1, CDRH2, and CDRL3 with oligonucleotides H1, H2, and L3, respectively (SEQ ID NOs: ).

For library SAH3, diversity was introduced into CDRH3 with an equimolar mixture of oligonucleotides H3-SA4, H3-SA5, H3-SA6, H3-SA7, H3-SA8, 143-SA9, H3-SA10, H3-SA11, H3-SA12, H3-SA13, 143-SA14, H3-SA15, H3-SA16, and H3-SA17 (SEQ ID NOs: 621-634).

For library SCH3, diversity was introduced into CDRH3 with an equimolar mixture of oligonucleotides H3-SC4, H3-SC5, H3-SC6, H3-SC7, H3-SC8, H3-SC9, H3-SC10, H3-SC11, H3-SC12, H3-SC13, H3-SC14, H3-SC15, H3-SC16, and H3-SC17 (SEQ ID NOs: 635-648).

For library SFH3, diversity was introduced into CDR-H3 with an equimolar mixture of oligonucleotides H3-SF4, H3-SF5, H3-SF6, H3-SF7, H3-SF8, H3-SF9, H3-SF10, H3-SF11, H3-SF12, H3-SF13, H3-SF14, H3-SF15, H3-SF16, and H3-SF17 (SEQ ID NOs: 649-662).

For library SGH3, diversity was introduced into CDRH3 with an equimolar mixture of oligonucleotides H3-SG4, H3-SG5, H3-SG6, H3-SG7, H3-SG8, H3-SG9, H3-SG10, H3-SG11, H3-SG12, H3-SG13, H3-SG14, H3-SG15, H3-SG16, and H3-SG17 (SEQ ID NOs: 663-676).

For library SIH3, diversity was introduced into CDR-H3 with an equimolar mixture of oligonucleotides H3-SI4, L13-SI5, H3-SI6, H3-SI7, H3-SI8, H3-SI9, H3-SI10, H3-SI11, H3-S12, H3-SI13, H3-SI14, H3-SI15, H3-SI16, and H3-SI17 (SEQ ID NOs: 677-690).

For library SLH3, diversity was introduced into CDR-H3 with an equimolar mixture of oligonucleotides H3-SL4, H3-SL5, H3-SL6, H3-SL7, H3-SL8, H3-SL9, H3-SL10, H3-SL11, H3-SL12, H3-SL13, H3-SL14, H3-SL15, H3-SL16, and H3-SL17 (SEQ ID NOs: 691-704).

For library SNH3, diversity was introduced into CDR-H3 with an equimolar mixture of oligonucleotides H3-SN4, H3-SN5, H3-SN6, H3-SN7, H3-SN8, H3-SN9, H3-SN10, H3-SN11, H3-SN12, H3-SN13, H3-SN14, H3-SN15, H3-SN16, and H3-SN17 (SEQ ID NOs: 705-718).

For library SPH3, diversity was introduced into CDR-H3 with an equimolar mixture of oligonucleotides H3-SP4, H3-SP5, H3-SP6, H3-SP7, H3-SP8, H3-SP9, H3-SP10, H3-SP11, H3-SP12, H3-SP13, H3-SP14, H3-SP15, H3-SP16, and H3-SP17 (SEQ ID NOs: 719-732).

For library SRH3, diversity was introduced into CDR-H3 with an equimolar mixture of oligonucleotides H3-SR4, H3-SR5, H3-SR6, H3-SR7, H3-SR8, H3-SR9, H3-SR10, H3-SR11, H3-SR12, H3-SR13, H3-SR14, H3-SR15, H3-SR16, and H3-SR17 (SEQ ID NOs: 733-746).

For library STH3, diversity was introduced into CDR-H3 with an equimolar mixture of oligonucleotides H3-ST4, H3-ST5, H3-ST6, H3-ST7, H3-ST8, H3-ST9, H3-ST10, H3-ST11, H3-ST12, H3-ST13, H3-ST14, H3-ST15, H3-ST16, and H3-ST17 (SEQ ID NOs: 747-760).

For library SWH3, diversity was introduced into CDR-H3 with an equimolar mixture of oligonucleotides H3-SW4, H3-SW5, H3-SW6, H3-SW7, H3-SW8, H3-SW9, H3-SW10, H3-SW11, H3-SW12, H3-SW13, H3-SW14, H3-SW15, H3-SW16, and H3-SW17 (SEQ ID NOs: 761-774).

For library SYH3, diversity was introduced into CDR-H3 with an equimolar mixture of oligonucleotides H3-SY4, H3-SY5, H3-SY6, H3-SY7, H3-SY8, H3-SY9, H3-SY10, H3-SY11, H3-SY12, H3-SY13, H3-SY14, H3-SY15, H3-SY16, and H3-SY17 (SEQ ID NOs: 775-788).

The mutagenic oligonucleotides for all CDRs to be randomized were incorporated in a single mutagenesis reaction, so that simultaneous incorporation of all the mutagenic oligonucleotides resulted in the introduction of the designed diversity at each position and repair of all of the TAA stop codons. Thus, an open reading frame was generated that encoded a Fab library member fused to a homodimerizing cysteine bridge and P3C. Following mutagenesis, the twelve libraries were combined to create a single library, called library SXH3.

The mutagenesis reactions were electroporated into *E. coli* SS320 (Sidhu et al., supra). The transformed cells were grown overnight in the presence of M13-K07 helper phage (New England Biolabs, Beverly, Mass.) to produce phage particles that encapsulated the phagemid DNA and displayed Fab fragments on their surfaces. The combined library contained greater than $3 \times 10^{10}$ unique members.

EXAMPLE 5

Selection of Specific Antibodies from Naïve Library SXH3

Phage from library SXH3 (described in Example 4, above) were cycled through rounds of binding selection to enrich for clones binding to human HER2. The binding selections were conducted using previously described methods (Sidhu et al., supra).

NUNC 96-well Maxisorp immunoplates were coated overnight at 4° C. with 5 µg/mL target protein (HER2) and blocked for two hours with a solution of PBT (Sigma). After overnight growth at 37° C., phage were concentrated by precipitation with PEG/NaCl and resuspended in PBT, as described previously (Sidhu et al., supra). Phage solutions (about $10^{12}$ phage/mL) were added to the coated immunoplates. Following a two hour incubation to permit phage binding, the plates were washed ten times with PBT. Bound phage were eluted with 0.1M HCl for ten minutes and the eluant was neutralized with 1.0 M Tris base. Eluted phage were amplified in *E. coli* XL1-blue and used for further rounds of selection.

The libraries were subjected to six rounds of selection against the target protein. Individual clones from each round of selection were grown in a 96-well format in 500 µL of 2YT broth supplemented with carbenicillin and M13-K07. The culture supernatants were used directly in phage ELISAs (Sidhu et al., supra) to detect phage-displayed Fabs that bound to plates coated with target protein but not to plates coated with BSA. Specific binders were defined as those phage clones that exhibited an ELISA signal at least 10-fold greater on target-coated plates in comparison with BSA-coated plates. Individual clones were screened after 4, 5, and 6 rounds of selection for binding to human HER2. The specific binders were subjected to sequence analysis. As shown in FIG. 21, the SXH3 library produced specific binders to the target protein.

Figure 21A:
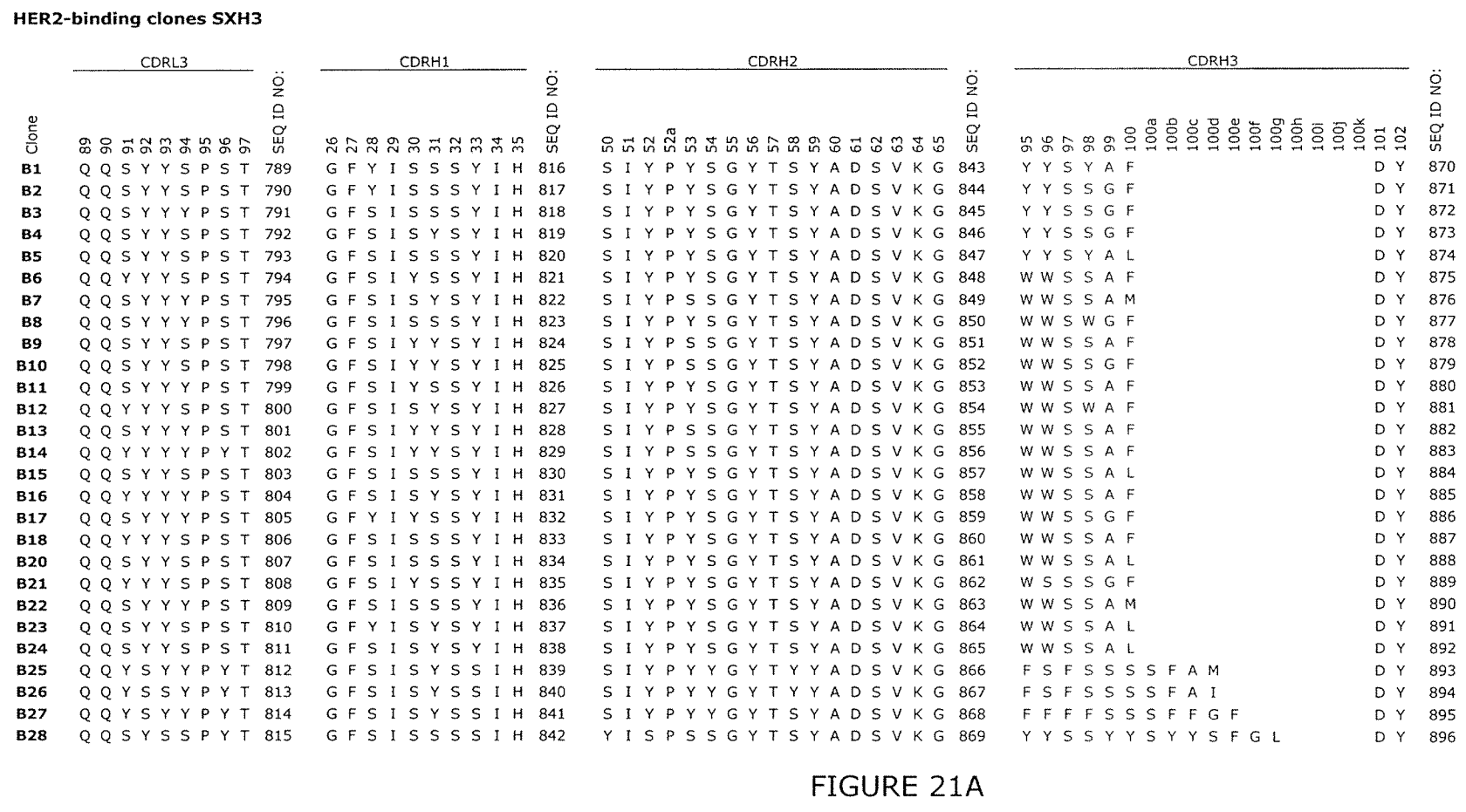

Of the 72 clones identified that specifically bound to HER2, 27 of them had unique CDR sequences (see FIG. 21A). The unique sequences fell into three categories: (I) CDR sequences with randomized positions limited to binary Tyr/Ser (clone nos. B1-5 and B28); (b) CDR sequences with randomized positions limited to binary Trp/Ser (clone nos. B6-24); (c) CDR sequences with randomized positions limited to binary Phe/Ser (clone nos. B25-27). These clones were also highly specific for HER2 and did not display cross-reactivity to five other control proteins, human VEGF, human DR5, human insulin, neutravidin, human IGF-1, or HGH (see FIG. 21B). The inhibitory concentration for each clone is shown in FIG. 21B.

Figure 25:
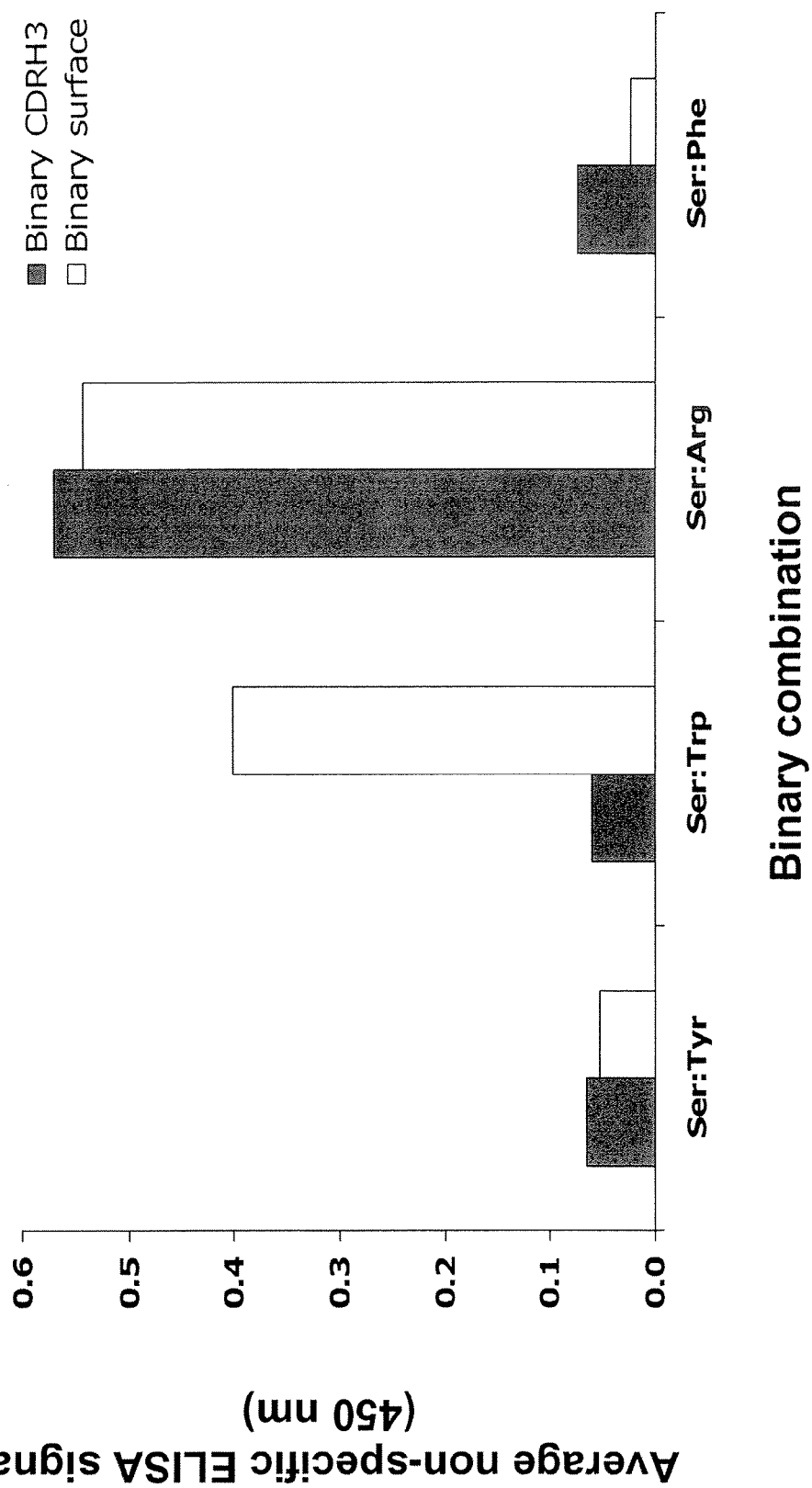
FIG. 25 graphically depicts the specificity of Fabs containing different binary amino acid combinations (Ser:Tyr, Ser.

A phage ELISA was used to test the ability of all clones to cross-react with a panel of six antigens other than the target antigen. Phage were produced in a 96-well format as described and phage supernatants were diluted 3-fold in PBT buffer. The diluted phage supernatant was transferred to plates coated with human VEGF, HER2, human DR5, human insulin, neutravidin, human IGF-1, HGH, or BSA and incubated for one hour with gentle shaking at room temperature. The plates were washed with PBS including 0.05% Tween 20 and were incubated for 30 minutes with horseradish peroxidase/anti-M13 antibody conjugate (diluted 1:5000 in PT buffer) (Pharmacia). The plates were washed, developed with tetramethylbenzidine (TMB) substrate (Kirkegaard and Perry Laboratories) and quenched with 1.0 M $H_3PO_4$. Absorbance was determined spectrophotometrically at 450 nm. Weak cross-reactivity was defined as a signal between 0.2-2.0 and strong cross-reactivity was defined as a signal about 2.0. The results for HER2 binding clones are shown in FIG. 21B. As shown in FIG. 25, of the SXH3 clones isolated, the S:R clones displayed the greatest average non-specific binding (0.5-0.6 OD at 450 nm by ELISA assay), while the S:W, S:Y, and S:F clones each displayed similar low levels of average non-specific binding (0-0.1 OD at 450 nm by ELISA assay).

A competitive phage ELISA was used to estimate the binding affinities of HER2-binding phage-displayed Fabs. Phage were produced in a 96-well format as described, and phage supernatants were serially diluted in PBT buffer, then incubated on plates coated with HER2 for 15 minutes. The plates were washed with PBS including 0.05% Tween 20 and were incubated for 30 minutes with horseradish peroxidase/anti-M13 antibody conjugate (diluted 1:5000 in PT buffer) (Pharmacia). The plates were washed, developed with tetramethylbenzidine (TMB) substrate (Kirkegaard and Perry Laboratories) and quenched with 1.0 M $H_3PO_4$. Absorbance was measured spectrophotometrically at 450 nm to determine the phage concentration giving about 50% of the signal at saturation. A fixed, sub-saturating concentration of phage was diluted two fold in PBT buffer or PBT buffer containing two-fold serial dilutions of HER2 protein from 250 nM HER2 to 0.12 nM HER2. The mixtures were incubated for one hour with gentle shaking at room temperature, transferred to plates coated with HER2 and the plates were incubated for 15 minutes. The plates were washed and treated exactly as above. The binding affinities were estimated as $IC_{50}$ values (defined as the concentration of antigen that blocked 50% of the phage binding to the immobilized antigen). The results are shown in FIG. 21B.

EXAMPLE 6

Construction of Phage-displayed Fab Libraries with CDR Residues Enriched in Ser and Phe, Arg, Trp, or Tyr Phage-displayed Fab libraries were constructed using a phagemid vector, Fab-C, that resulted in the display of bivalent Fab moieties dimerized by a free cysteine inserted between the Fab heavy chain and the C-terminal domain of the gene-3 minor coat protein (P3C), as previously described in Example 1.

Four libraries were constructed: SFH3, SRH3, SWH3, and SYH3. The libraries were constructed with randomized residues in all three heavy chain CDRs and light chain CDR3. Each library was randomized at positions 91-94 and 96 of CDRL3, positions 28 and 30-33 of CDRH1, positions 50, 52-54, 56, and 58 of CDRH2, and positions 95-100, 100a to 100m of CDRH3. The type and ratio of the amino acids allowed at each of the randomized positions is described in FIG. 22. In addition, the length of CDRH3 was varied by using oligonucleotides that replaced the six wild-type codons between positions 95 and 100 with 4 to 17 codons. The type and ratio of the amino acids allowed at those positions were the same as the ones described in FIG. 22 for positions 95-100 of CDRH3.

Libraries were constructed using the method of Kunkel (Kunkel, T. A., Roberts, J. D. & Zakour, R. A., Methods Enzymol. (1987), 154, 367-382) with previously described methods (Sidhu, S. S., Lowman, H. B., Cunningham, B. C. & Wells, J. A., Methods Enzymol. (2000), 328, 333-363). A unique "stop template" version of the Fab display vector Fab-C was used to generate all four libraries, as described in Example 1.

Mutagenic oligonucleotides with degenerate codons at the positions to be diversified were used to simultaneously (a) introduce CDR diversity and (b) repair the stop codons. The sequences of those mutagenic oligonucleotides are shown in FIGS. 20 and 23. For the library SF-surface, diversity was introduced into CDR-L3, CDR-H1 and CDR-H2 with the oligonucleotides L3-SF, H1-SF and H2-SF respectively (SEQ ID NOs: ) (FIG. 23) and diversity was introduced into CDR-H3 with an equimolar mixture of oligonucleotides H3-SF4, H3-SF5, H3-SF6, H3-SF7, H3-SF8, H3-SF9, H3-SF10, H3-SF11, H3-SF12, H3-SF13, H3-SF14, H3-SF15, H3-SF16, and H3-SF17 (SEQ ID NOs:649-662) (FIG. 20C).

For the library SR-surface, diversity was introduced into CDR-L3, CDR-H1 and CDR-H2 with the oligonucleotides L3-SR, H1-SR and H2-SR respectively (SEQ ID NOs: ) (FIG. 23) and diversity was introduced into CDR-H3 with an equimolar mixture of oligonucleotides H3-SR4, H3-SR5, H3-SR6, H3-SR7, H3-SR8, H3-SR9, H3-SR10, H3-SR11, H3-SR12, H3-SR13, H3-SR14, H3-SR15, H3-SR16, and H3-SR17 (SEQ ID NOs: 733-746) (FIG. 20I).

For the library SW-surface, diversity was introduced into CDR-L3, CDR-H1 and CDR-H2 with the oligonucleotides L3-SW, H1-SW and H2-SW respectively (SEQ ID NOs: 747-760) (FIG. 23) and diversity was introduced into CDR-H3 with an equimolar mixture of oligonucleotides H3-SW4, H3-SW5, H3-SW6, H3-SW7, H3-SW8, H3-SW9, H3-SW10, H3-SW11, H3-SW12, H3-SW13, H3-SW14, H3-SW15, H3-SW16, and H3-SW17 (SEQ ID NOs: 761-774) (FIG. 20K).

For the library SY-surface, diversity was introduced into CDR-L3, CDR-H1 and CDR-H2 with the oligonucleotides L3, H1 and H2 respectively (SEQ ID NOs: ) (FIG. 20A) and diversity was introduced into CDR-H3 with an equimolar mixture of oligonucleotides H3-SY4, H3-SY5, H3-SY6, H3-SY7, H3-SY8, H3-SY9, H3-SY10, H3-SY11, H3-SY12, H3-SY13, H3-SY14, H3-SY15, H3-SY16, and H3-SY17 (SEQ ID NOs: 775-788) (FIG. 20L).

The mutagenic oligonucleotides for all CDRs to be randomized were incorporated in a single mutagenesis reaction, so that simultaneous incorporation of all the mutagenic oligonucleotides resulted in the introduction of the designed diversity at each position and repaired all the TAA stop codons. Thus, an open reading frame was generated that encoded a Fab library member fused to a homodimerizing cysteine bridge and P3C. Following mutagenesis, the four libraries were combined to create a single library, called library SX-surface.

The mutagenesis reactions were electroporated into E. coli SS320 (Sidhu et al., supra). The transformed cells were grown overnight in the presence of M13-KO7 helper phage (New England Biolabs, Beverly, Mass.) to produce phage particles that encapsulated the phagemid DNA and displayed Fab fragments on their surfaces. The combined library contained greater than $3 \times 10^{10}$ unique members.

EXAMPLE 7

Selection of Specific Antibodies from Naïve Library SX Surface

Phage from library SX-surface (described in Example 6, above) were cycled through rounds of binding selection to enrich for clones binding to human HER2. The binding selections were conducted using previously described methods (Sidhu et al., supra).

NUNC 96-well Maxisorp immunoplates were coated overnight at 4° C. with 5 μg/mL target protein (human HER2) and blocked for 2 hours with a solution of PBT (Sigma). After overnight growth at 37° C., phage were concentrated by precipitation with PEG/NaCl and resuspended in PBT, as described previously (Sidhu et al., supra). Phage solutions (about $10^{12}$ phage/mL) were added to the coated immunoplates. Following a two hour incubation to permit phage binding, the plates were washed ten times with PBT. Bound phage were eluted with 0.1 M HCl for ten minutes and the eluant was neutralized with 1.0 M Tris base. Eluted phage were amplified in E. coli X1-blue and used for further rounds of selection.

The libraries were subjected to six rounds of selection against each target protein. Individual clones from each round of selection were grown in a 96-well format in 500 μl, of 2YT broth supplemented with carbenicillin and M13-K07. The culture supernatants were used directly in phage ELISAs (Sidhu et al., supra) to detect phage-displayed Fabs that bound to plates coated with target protein but not to plates coated with BSA. Specific binders were defined as those phage clones that exhibited an ELISA signal at least 10-fold greater on target-coated plates in comparison with BSA-coated plates. Individual clones were screened after 4, 5 and 6 rounds of selection for binding to human HER2. The specific binders were subjected to sequence analysis. As shown in FIG. 24, the SX-surface library produced specific binders against the target protein.

Figure 24A:
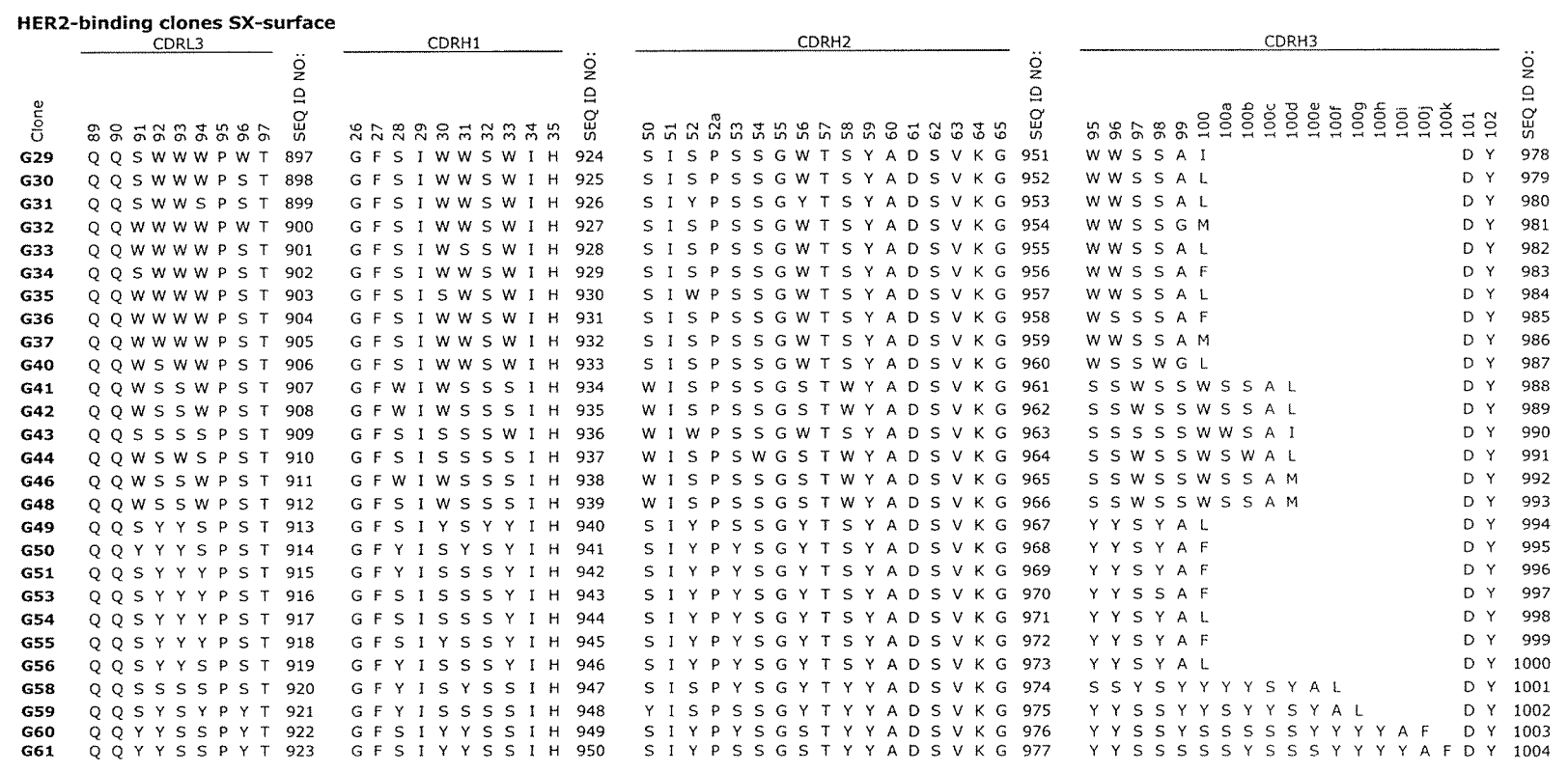

Of the 81 clones identified that specifically bound to HER2, 27 of them had unique CDR sequences (see FIG. 24A). The unique sequences fell into two categories: (a) CDR sequences with randomized positions limited to binary Tyr/Ser (clone nos. G49-61); (b) CDR sequences with randomized positions limited to binary Trp/Ser (clone nos. G29-48). The Tyr/Ser clones were highly specific for HER2 and did not display cross-reactivity to five other control proteins, human VEGF, human DR5, human insulin, neutravidin, human IGF-1 or HGH (see FIG. 24B). However, some of the Trp/Ser clones were cross-reactive (see FIG. 24B). The inhibitory concentration for each clone is shown in FIG. 24B.

A phage ELISA was used to test the ability of all clones to cross-react with a panel of six antigens other than the target antigen. Phage were produced in a 96-well format as described above and phage supernatants were diluted 3-fold in PBT buffer. The diluted phage supernatant was transferred to plates coated with human VEGF, HER2, human DR5, human insulin, neutravidin, human IGF-1, HGH, or BSA and incubated for one hour with gentle shaking at room temperature. The plates were washed with PBS including 0.05% Tween 20 and were incubated for 30 minutes with horseradish peroxidase/anti-M13 antibody conjugate (diluted 1:5000 in PT buffer) (Pharmacia). The plates were washed, developed with tetramethylbenzidine (TMB) substrate (Kirkegaard and Perry Laboratories) and quenched with 1.0 M $H_3PO_4$. Absorbance was determined spectrophotometrically at 450 nm. Weak cross-reactivity was defined as a signal between 0.2-2.0 and strong cross-reactivity was defined as a signal above 2.0. The results for the SX-surface clones are shown in FIG. 24B. As shown in FIG. 27, of the SX-surface clones isolated, the S:R and S:W clones displayed the greatest average non-specific binding (0.5-0.6 OD and approximately 4.0 OD, respectively, at 450 nm by ELISA assay), while the S:Y and S:F clones each displayed similar low levels of average non-specific binding (0-0.1 OD at 450 nm by ELISA assay).

A competitive phage ELISA was also used to estimate the binding affinities of HER2-binding phage-displayed Fabs. Phage were produced in a 96-well format as described above, and phage supernatants were serially diluted in PBT buffer, then incubated on plates coated with HER2 for 15 minutes. The plates were washed with PBS including 0.05% Tween 20 and were incubated for 30 minutes with horseradish peroxidase/anti-M13 antibody conjugate (diluted 1:5000 in PT buffer) (Pharmacia). The plates were washed, developed with tetramethylbenzidine (TMB) substrate (Kirkegaard and Perry Laboratories) and quenched with 1.0 M $H_3PO_4$. Absorbance was measured spectrophotometrically at 450 nm to determine the phage concentration giving ~50% of the signal at saturation. A fixed, sub-saturating concentration of phage was diluted two fold in PBT buffer or PBT buffer containing two-fold serial dilutions of HER2 protein from 250 nM HER2 to 0.12 nM HER2. The mixtures were incubated for one hour with gentle shaking at room temperature, transferred to plates coated with HER2 and the plates were incubated for 15 minutes. The plates were washed and treated exactly as above. The binding affinities were estimated as $IC_{50}$ values (defined as the concentration of antigen that blocked 50% of the phage binding to the immobilized antigen). The results are shown in FIG. 24B.

Based on this analysis, the analysis of HER2-binding clones from the SXH3 library (Example 6), and the YSGR-A-D library (Example 1), soluble Fab proteins from three clones (clone nos. 42 (YSGR-A) and B11 (SXH3) and G54 (SX-surface)) were purified and subjected to surface plasmon resonance analysis of binding to human HER2. BIAcore® data was obtained according to Chen et al., J. Mol. Biol. (1999), 293(4): 865-81. Briefly, binding affinities of the purified Fabs for human HER2 were calculated from association and dissociation rate constants measured using a BIAcore®-A100 surface plasmon resonance system (BIACORE, Inc., Piscataway, N.J.). HER2 was covalently coupled to a biosensor chip at two different concentrations using N-ethyl-N'-(3-dimethylaminopropyl)-carbodiimide hydrochloride (EDC) and N-hydroxysuccinimide (NHS) according to the supplier's (BIAcore, Inc., Piscataway, N.J.) instructions. HER2 was buffer-exchanged into 10 mM sodium acetate, pH 5.0 and diluted to approximately 2.5 or 5.0 μg/ml. Aliquots of HER2 were injected at a flow rate of 5 μL/min to achieve approximately 50-170 response units (RU) of coupled protein. A solution of 1 M ethanolamine was injected as a blocking agent. For kinetics measurements, twofold serial dilutions of each Fab were injected in HBT at 25° C. at a flow rate of 10 μL/minute over each flow cell. The $k_{on}$ and $k_{off}$ values were determined from the binding curves using the BIAevaluation software package (BIACORE, Inc., Piscataway, N.J.) using two-spot global fitting and combining the data from both flow cells. The equilibrium dissociation constant, $K_D$, was calculated as $K_{off}/k_{on}$. The BIAcore® data is summarized in FIGS. 26A and B. Clone B11 had a $k_a$ of $1.9 \times 10^6$ $M^{-1}s^{-1}$, a $k_d$ of $1.7 \times 10^{-3}$ $s^{-1}$, and a $K_D$ of 890 pM. Rmax1 for the clone B11 experiments was 19 RU, and Rmax2 for the clone B11 experiments was 29 RU. (FIG. 26A) Clone G54 had a $k_a$ of $2.0 \times 10^5$ $M^{-1}s^{-1}$, a $k_d$ of $2.2 \times 10^{-3}$ $s^{-1}$, and a $K_D$ of 11 nM. $R_{max1}$ for the clone G54 experiments was 21 RU and $R_{max2}$ for the clone G54 experiments was 34 RU. (FIG. 26A) Clone YSGR-A-42 had a $k_a$ of $2.7 \times 10^6$ $M^{-1}s^{-1}$, a $k_d$ of $1.5 \times 10^{-3}$ $s^{-1}$, and a $K_D$ of 570 pM. Rmax1 for the clone 42 experiments was 25 RU, and $R_{max2}$ for the clone 42 experiments was 38 RU. (FIG. 26B) The tryptophan-containing clone (B11) had a faster $k_{on}$ and correspondingly smaller $K_D$ than the tyrosine-containing clone (G54).

To study binding of anti-HER2 antibodies to HER2 expressed on mammalian cells, the binding of purified Fab protein of clones 42 (YSGR-A), B11 (SXH3), G54 (SX-surface), and G37 (SX-surface) to NR6 fibroblast cells overexpressing HER2 (NR6-HER2) was studied by flow cytometry. One million NR6-HER2 cells were incubated with 10 μg/ml Fab for 1 hour, followed by incubation with an Alexa488-conjugated murine anti-human IgG antibody for 1 hour. As a negative control, Fab binding to non-expressing NR6 cells was studied. As a positive control, 4D5 Fab was used. As demonstrated in FIG. 27, clones 42, B11, G54, and G37 bind specifically to Her2 on NR6 cells.

A competitive ELISA was used to test binding competition with Herceptin and Omnitarg and between several HER2 clones in IgG format (see FIG. 28 for the CDR sequences of the relevant clones). Biotinylated HER2 protein was serially diluted from 200 nM to 0.39 nM in PBT buffer, then incubated on plates coated with purified IgG proteins for 15 minutes. The plates were washed with PBS containing 0.05% Tween 20, and were incubated for 30 minutes with horseradish peroxidase/anti-M13 antibody conjugate (diluted 1:5000 in PT buffer) (Pharmacia). The plates were washed, developed with tetramethylbenzidine (TMB) substrate (Kirkegaard and Perry Laboratories) and quenched with 1.0 M $H_3PO_4$. Absorbance was measured spectrophotometrically at 450 nm to determine the biotinylated HER2 concentration giving around 50% of the signal at saturation. A fixed, sub-saturating concentration of biotinylated HER2 was diluted two-fold in PBT buffer or PBT buffer containing 100 nM purified IgG proteins. The mixtures were incubated for one hour with gentle shaking at room temperature, transferred to plates coated with IgG proteins, and the plates were incubated for 15 minutes. The plates were washed and treated as above. As shown in FIG. 29, none of the HER2-binding IgGs blocked binding of biotinylated HER2 to either Omnitarg or Herceptin. The IgGs did block binding between each other in two groups. One group made up of clones B11, G37, G54, and YSGR-A-42 compete for the same epitope and blocked binding to biotinylated HER2 that had been previously incubated with any of those clones. A second group made up of clones YSGR-A-27, B27, G43, and YSGR-D-104 compete for the same epitope on HER2 and blocked binding to biotinylated HER2. Group one clones are all higher-affinity binders than the group two clones.

All publications (including patents and patent applications) cited herein are hereby incorporated in their entirety by reference.

TABLE 1

Human DR5-ECD polypeptide
(SEQ ID NO:595)
MSALLILALVGAAVADYKDDDDKLSALITQQDLAPQQRVAPQQKRSSPSE
GLCPPGHHISEDGRDCISCKYGQDYSTHWNDLLFCLRCTRCDSGEVELSP
CTTTRNTVCQCEEGTFREEDSPEMCRKCRTGCPRGMVKVGDCTPWSDIEC
VHKESGTKHSGEAPAVEETVTSSPGTPASPCSLS Human DR5 Polypeptide
(SEQ ID NO:604)
meqrgqnapa asgarkrhgp gpreargarp glrvpktlvl
vvaavlllvs aesalitqqd lapqqraapq qkrsspsegl
cppghhised grdcisckyg qdysthwndl lfclrctrcd
sgevelspct ttrntvcqce egtfreedsp emcrkcrtgc
prgmvkvgdc tpwsdiecvh kesgiiigvt vaavvlivav
fvcksllwkk vlpylkgics ggggdpervd rssqrpgaed
nvlneivsil qptqvpeqem evqepaeptg vnmlspgese
hllepaeaer sqrrrllvpa negdptetlr qcfddfadlv TABLE 1-continued pfdsweplmr klglmdneik vakaeaaghr dtlytmlikw
vnktgrdasv htlldaletl gerlakqkie dhllssgkfm
ylegnadsal s MURINE DR5 ECD
(SEQ ID NO:605)
GLQRPEESPSRGPCLAGQYLSEGNCKPCREGIDYTSHSNHSLDSCILCTV
CKEDKVVETRCNITTNTVCRCKPGTFEDKDSPEICQSCSNCTDGEEELTS
CTPRENRKCVSKTAWASWHK Apo-2L polypeptide sequence
(SEQ ID NO:606)
  1 MetAlaMetMetGluValGlnGlyGlyProSerLeuGlyGln
    ThrCysValLeuIleValIlePheThrValLeuLeuGlnSer
    LeuCys 31 ValAlaValThrTyrValTyrPheThrAsnGluLeuLysGln
    MetGlnAspLysTyrSerLysSerGlyIleAlaCysPheLeu
    LysGlu 61 AspAspSerTyrTrpAspProAsnAspGluGluSerMetAsn
    SerProCysTrpGlnValLysTrpGlnLeuArgGlnLeuVal
    ArgLys 91 MetIleLeuArgThrSerGluGluThrIleSerThrValGln
    GluLysGlnGlnAsnIleSerProLeuValArgGluArgGly
    ProGln 121 ArgValAlaAlaHisIleThrGlyThrArgGlyArgSerAsn
    ThrLeuSerSerProAsnSerLysAsnGluLysAlaLeuGly
    ArgLys 151 IleAsnSerTrpGluSerSerArgSerGlyHisSerPheLeu
    SerAsnLeuHisLeuArgAsnGlyGluLeuValIleHisGlu
    LysGly 181 PheTyrTyrIleTyrSerGlnThrTyrPheArgPheGlnGlu
    GluIleLysGluAsnThrLysAsnAspLysGlnMetValGln
    TyrIle 211 TyrLysTyrThrSerTyrProAspProIleLeuLeuMetLys
    SerAlaArgAsnSerCysTrpSerLysAspAlaGluTyrGly
    LeuTyr 241 SerIleTyrGlnGlyGlyIlePheGluLeuLysGluAsnAsp
    ArgIlePheValSerValThrAsnGluHisLeuIleAspMet
    AspHis 271 GluAlaSerPhePheGlyAlaPheLeuValGly Apo-2L Sequence of Amino Acids 114-281
(SEQ ID NO:607)
VRERGPQRVA AHITGTRGRS NTLSSPNSKN EKALGRKINS
WESSRSGHSF LSNLHLRNGE LVIHEKGFYY IYSQTYFRFQ
EEIKENTKND KQMVQYIYKY TSYPDPILLM KSARNSCWSK
DAEYGLYSIY QGGIFELKEN DRIFVSVTNE HLIDMDHEAS
FFGAFLVG

We claim:

1. A polypeptide that binds to human DR5, the polypeptide comprising an immunoglobulin heavy chain variable domain, and an immunoglobulin light chain variable domain, wherein, in the heavy chain variable domain:
   (i) CDRH1 comprises an amino acid sequence GFYISSSSIH (SEQ ID NO:531);
   (ii) CDRH2 comprises an amino acid sequence SISPSSG-STYYADSVKG (SEQ ID NO:548); and
   (iii) CDRH3 comprises an amino acid sequence YRSYR-YGSYYGSYGFDY (SEQ ID NO:565);
and in the light chain variable domain:
   (iv) CDRL1 comprises an amino acid sequence RASQD-VNTAVA (SEQ ID NO:29);
   (v) CDRL2 comprises an amino acid sequence SASSLYS (SEQ ID NO:30); and
   (vi) CDRL3 comprises an amino acid sequence QQYYYSPST (SEQ ID NO:514).

2. The polypeptide of claim 1, wherein the polypeptide is an antibody.

3. The polypeptide of claim 1 which is a single chain Fv.

4. The polypeptide of claim 1 which is a Fab polypeptide.

5. The polypeptide of claim 1 which is a fully human polypeptide.

6. A polypeptide of claim 1, further comprising framework regions FR1, FR2, FR3, and/or FR4 for an polypeptide variable domain corresponding to the CDRH1, CDRH2, CDRH3, and/or CDRL3, wherein the framework regions are obtained from a single polypeptide template.

7. The polypeptide of claim 6, wherein each of the framework regions comprises an amino acid sequence corresponding to the framework region amino acid sequences of polypeptide 4D5 (SEQ ID NOs: 1 and 2).

8. The polypeptide of claim 6, wherein the polypeptide comprises framework regions corresponding to the amino acid sequences of a 4D5 antibody framework regions (SEQ ID NOS: 14-17 and 18-21).

9. An polypeptide according to claim 1, further comprising a dimerization domain linked to the C-terminal region of a heavy chain polypeptide variable domain.

10. The polypeptide according to claim 9, wherein the dimerization domain comprises a leucine zipper domain or a sequence comprising at least one cysteine residue.

11. The polypeptide of claim 9, wherein the dimerization domain comprises a hinge region from an polypeptide and leucine zipper.

12. The polypeptide according to claim 9, wherein the dimerization domain is a single cysteine.

13. A fusion polypeptide comprising an polypeptide according to claim 1, wherein an polypeptide variable domain is fused to at least a portion of a viral coat protein.

14. The fusion polypeptide of claim 13, wherein the viral coat protein is selected from the group consisting of protein pIII, major coat protein pVIII, Soc, Hoc, gpD, pv1, and variants thereof.

15. The fusion polypeptide of claim 14, further comprising a dimerization domain between the variable domain and the viral coat protein.

16. The fusion polypeptide of claim 13, further comprising a peptide tag.

17. The fusion polypeptide of claim 16, wherein the peptide tag is selected from the group consisting of gD, c-myc, poly-his, a fluorescence protein, and B-galactosidase.

18. A composition comprising a polypeptide of claim 1 and a carrier.

* * * * *